(12) United States Patent
Hrdlicka

(10) Patent No.: US 9,885,082 B2
(45) Date of Patent: Feb. 6, 2018

(54) EMBODIMENTS OF A PROBE AND METHOD FOR TARGETING NUCLEIC ACIDS

(75) Inventor: Patrick Jerzy Hrdlicka, Moscow, ID (US)

(73) Assignee: University of Idaho, Moscow, ID (US)

( * ) Notice: Subject to any disclaimer, the term of this patent is extended or adjusted under 35 U.S.C. 154(b) by 620 days.

(21) Appl. No.: 14/233,375

(22) PCT Filed: Jul. 19, 2012

(86) PCT No.: PCT/US2012/047442
§ 371 (c)(1),
(2), (4) Date: Mar. 12, 2014

(87) PCT Pub. No.: WO2013/013068
PCT Pub. Date: Jan. 24, 2013

(65) Prior Publication Data
US 2014/0220573 A1    Aug. 7, 2014

Related U.S. Application Data

(60) Provisional application No. 61/542,044, filed on Sep. 30, 2011, provisional application No. 61/509,336, filed on Jul. 19, 2011.

(51) Int. Cl.
C12Q 1/68     (2006.01)
C07H 21/00   (2006.01)
C07H 19/06   (2006.01)

(52) U.S. Cl.
CPC ........... *C12Q 1/6876* (2013.01); *C07H 19/06* (2013.01); *C07H 21/00* (2013.01); *C12Q 1/689* (2013.01);
(Continued)

(58) Field of Classification Search
CPC ............................. C12Q 1/6876; C07H 21/00
(Continued)

(56) References Cited

U.S. PATENT DOCUMENTS 5,514,786 A    5/1996  Cook et al.
5,623,068 A    4/1997  Reddy et al.
(Continued)

FOREIGN PATENT DOCUMENTS

EP    1 334 109       5/2006
JP    2000-032999    2/2000
(Continued)

OTHER PUBLICATIONS

Stratagene Catalog, 1988, p. 39.*
(Continued)

*Primary Examiner* — Jezia Riley
(74) *Attorney, Agent, or Firm* — Klarquist Sparkman, LLP

(57) ABSTRACT

Disclosed embodiments concern a probe comprising one or more pairs of monomers capable of targeting a nucleic acid target. The pair of monomers may be arranged in a manner that promotes thermoinstability of the probe complex, thus producing a probe capable of locating and/or detecting a target. The probe also may comprise one or more natural or non-natural nucleotides capable of Watson-Crick base pairing with an isosequential nucleic acid target. Particular disclosed embodiments concern a method of using the disclosed probe to target nucleic acids. In particular disclosed embodiments, the probe may be incubated with a target nucleic acid and then be detected.

32 Claims, 26 Drawing Sheets

(52) U.S. Cl.
CPC ......... *C12Q 1/6879* (2013.01); *C12Q 1/6886* (2013.01); *Y10T 436/143333* (2015.01)

(58) Field of Classification Search
USPC .......................................... 536/23.1; 435/6.1
See application file for complete search history.

(56) References Cited

U.S. PATENT DOCUMENTS

| | | | |
|---|---|---|---|
| 5,892,024 | A | 4/1999 | Chaturvedula et al. |
| 7,002,006 | B2 | 2/2006 | Song et al. |
| 7,037,654 | B2 | 5/2006 | Chenna et al. |
| 7,053,207 | B2 | 5/2006 | Wengel |
| 7,084,125 | B2 | 8/2006 | Wengel |
| 7,202,036 | B2 | 4/2007 | Cai et al. |
| 7,276,599 | B2 | 10/2007 | Moore et al. |
| 7,282,575 | B2 | 10/2007 | Ikeda et al. |
| 7,572,582 | B2 | 8/2009 | Wengel et al. |
| 7,575,863 | B2 | 8/2009 | Chen et al. |
| 7,741,294 | B1 | 6/2010 | Benner |
| 7,803,580 | B2 | 9/2010 | Millar |
| 8,057,997 | B2 | 11/2011 | Seela et al. |
| 8,133,984 | B2 | 3/2012 | Christensen |
| 8,153,365 | B2 | 4/2012 | Wengel et al. |
| 8,518,908 | B2 | 8/2013 | Hrdlicka et al. |
| 2003/0198982 | A1 | 10/2003 | Seela et al. |
| 2004/0142946 | A1 | 7/2004 | Chattopadhyaya |
| 2004/0219565 | A1 | 11/2004 | Kauppinen et al. |
| 2005/0026192 | A1 | 2/2005 | Moore et al. |
| 2005/0053939 | A1 | 3/2005 | Chenna et al. |
| 2005/0266418 | A1 | 12/2005 | Chen et al. |
| 2005/0287566 | A1 | 12/2005 | Wengel et al. |
| 2007/0117144 | A1 | 5/2007 | Kauppinen et al. |
| 2010/0210712 | A1 | 8/2010 | Hansen et al. |
| 2010/0223691 | A1 | 9/2010 | Bundock |
| 2010/0273999 | A1 | 10/2010 | Jung et al. |
| 2010/0311059 | A1 | 12/2010 | Didion et al. |
| 2010/0317004 | A1 | 12/2010 | Bunce et al. |
| 2011/0021365 | A1 | 1/2011 | Seela et al. |
| 2011/0137010 | A1 | 6/2011 | Srivastava et al. |
| 2011/0287415 | A1 | 11/2011 | Fan et al. |
| 2012/0040857 | A1 | 2/2012 | Kingston et al. |
| 2012/0295862 | A1 | 11/2012 | Hdrlicka et al. |
| 2013/0337581 | A1 | 12/2013 | Hdrlicka et al. |

FOREIGN PATENT DOCUMENTS

| | | |
|---|---|---|
| WO | WO 2000/056748 | 9/2000 |
| WO | WO 2002/012263 | 2/2002 |
| WO | WO 2003/039523 | 5/2003 |
| WO | WO 2003/052132 | 6/2003 |
| WO | WO 2003/052133 | 6/2003 |
| WO | WO 2003/052134 | 6/2003 |
| WO | WO 2007/104318 | 9/2007 |
| WO | WO 2008/061311 | 5/2008 |
| WO | WO 2009/064115 | 5/2009 |
| WO | WO 2009/079456 | 6/2009 |
| WO | WO 2010/003420 | 1/2010 |
| WO | WO 2011/032034 | 3/2011 |
| WO | WO 2011/103468 | 8/2011 |
| WO | WO 2011/117353 | 9/2011 |

OTHER PUBLICATIONS

Kalra et al., "DNA and LNA oligonucleotides containing N2'-functionalised derivatives of 2'-amino-2'deoxyuridine," *Bioorganic & Medicinal Chemistry* 16:3166-3169, Apr. 2006.
Printz et al., "Optimizing the Stacking Moiety and Linker of 2'-Acylamido Caps of DNA Duplexes with 3'-Terminal Adenine Residues," *J. Comb. Chem.* 9:306-320, Feb. 2007.
Karmakar et al., "High-Affinity DNA Targeting Using Readily Accessible Mimics of N2'-Functionalized 2'-Amino-α-L-LNA," *The Journal of Organic Chemistry* 76:7119-7131, Aug. 2011.

Sau et al., "C2'-Pyrene-Functionalized Triazole-Linked DNA: Universal DNA/RNA Hybridization Probes," *The Journal of Organic Chemistry* 77:5-16, Nov. 2012.
Supplementary European Search Report, dated Jan. 30, 2015, from European Patent Application No. 12814839.2 (9 pages).
Fonvielle et al., "Decoding the Logic of the tRNA Regiospecificity of Nonribosomal FemX$_{Wv}$ Aminoacyl Transferase," *Angew. Chem. Int. Ed.* 49:5115-5119, 2010.
Fukuda et al., "Duplex formation of multiple pyrene-modified RNAs," *Nucleic Acids Symposium Series* 3:133-134, Sep. 27, 2009.
Gupta et al., "Synthesis and Biophysical Studies of Coronene Functionalized 2'-Amino-LNA: A Novel Class of Fluorescent Nucleic Acids," *Bioconjugate Chem.* 21:513-520, 2010.
Holt, "M.truncatula DNA sequence from clone MTH2-22115 on chromosome 3, complete sequence," GenBank No. CT030234, http://www.ncbi.nlm.nih.gov/nuccore/89145300, downloaded Dec. 11, 2012.
Hrdlicka et al., "Targeting of mixed sequence double stranded DNA using pyrene-functionalized 2'-amino-α-L -LNA," *Chem. Commun.* 34:4279-4281, 2005.
International Search Report from International Application No. PCT/US2012/047442, dated Jan. 25, 2013.
Kalra et al., "Conformationally controlled high-affinity targeting of RNA or DNA by novel 2'-amino-DNA/LNA mixmers and pyrenyl-functionalized 2'-amino-DNA," *Org. Biomol. Chem.* 2:2885-2887, Sep. 14, 2004.
Kumar et al., "2'-N-(Pyren-1-yl)acetyl-2'-Amino-α-L-LNA: Synthesis and Detection of Single Nucleotide Mismatches in DNA and RNA Targets," *ChemBioChem* 8:1122-1125, 2007.
Kumar et al., "Synthesis and Biophysical Studies of N2'-Functionalized 2'Amino-α-L-LNA," *Nucleosides, Nucleotides, and Nucleic Acids* 26:1403-1405, 2007.
Kumar et al., "Nucleic Acid Structural Engineering Using Pyrene-Functionalized 2'-Amino-α-K-LNA Monomers and Abasic Sites," *J. Org. Chem.* 73:7060-7066, Aug. 19, 2008.
Kumar et al., "Functionalized 2'-Amino-α-L -LNA—Directed Positioning of Intercalators for DNA Targeting," *J. Org. Chem.* 74(3):1070-1081, Dec. 24, 2008.
Kumar et al., "Parallel RNA-strand recognition by 2'-Amino-β-L -LNA," *Bioorganic & Medicinal Chemistry Letters* 19:2396-2399, Mar. 24, 2009.
Marahara et al., "Detection of Acceptor Sites for Antisense Oligonucleotides on Native Folded RNA by Fluorescence Spectroscopy," *Bioorganic & Medicinal Chemistry* 11:2783-2790, 2003.
Marahara et al., "Detection of acceptor sites for antisense oligonucleotides on native folded RNA by fluorescence-labeled oligonucleotide," *Nucleic Acids Research Supplement* 3:73-74, 2003.
Mayer-Enthart et al., "Helical self-assembled chromophore clusters based on DNA-like architecture," *Tetrahedron* 63:3434-3439, Feb. 3, 2007.
Nakamura et al., "Pyrene aromatic arrays on RNA duplexes as helical templates," *Organic & Biomolecular Chemistry* 5:1945-1951, May 18, 2007.
Oeda et al., "Microwave-Assisted Synthesis of 2'-O-Aryluridine Derivatives," *Organic Letters* 11(4):5582-5585, Nov. 13, 2009.
Østergaard et al., "Novel insights into the use of Glowing LNA as nucleic acid detection probes—Influence of labeling density and nucleobases," *Bioorganic & Medicinal Chemistry Letters* 20:7265-7268, 2010.
Sakamoto et al., "Solid-phase detection of RNA using bispyrene-modified RNA probe," *Nucleic Acids Symposium Series* 50:215-216, 2006.
Sakamoto et al., "Microarray-based label-free detection of RNA using bispyrene-modified 2'-O-methyl oligoribonucleotide as capture and detection probe," *Bioorganic & Medicinal Chemistry Letters* 18:2590-2590, 2008.
Sekine et al., "Synthesis and hybridization properties of 2'-O-methylated oligoribonucleotides incorporating 2'-O-naphthyluridines," *Organic & Biomolecular Chemistry* 9:210/218, 2011.
Umemoto et al., "Sensitive SNP Dual-Probe Assays Based on Pyrene-Functionalized 2'-Amino-LNA: Lessons to be Learned," *ChemBioChem* 8:2240-2248, 2007.

(56) References Cited

OTHER PUBLICATIONS

Yamana et al., "Synthesis of Oligonucleotide Derivatives with Pyrene Group at Sugar Fragment," *Tetrahedron Letters* 32(44):6347-6350, 1991.

Yamana et al., "2'-Pyrene modified oligonucleotide provides a highly sensitive fluorescent probe of RNA," *Nucleic Acids Research* 27(11):2387-2392, 1999.

* cited by examiner universal hybridization
via base-flipping

Lane  1    2    3    4    5    6    7

Lane    1    2    3    4    5    6

EMBODIMENTS OF A PROBE AND METHOD FOR TARGETING NUCLEIC ACIDS

CROSS REFERENCE TO RELATED APPLICATIONS

This application is the U.S. National Stage of International Application No. PCT/US2012/047442, filed Jul. 19, 2012, which was published in English under PCT Article 21(2), which claims the benefit of the earlier filing dates of U.S. provisional application No. 61/509,336, filed on Jul. 19, 2011, and U.S. provisional application No. 61/542,044, filed on Sep. 30, 2011, both of which prior applications are incorporated herein by reference in their entirety.

ACKNOWLEDGMENT OF GOVERNMENT SUPPORT

This invention was made with government support under R01 GM088697 awarded by the National Institute of General Medical Sciences, under P20 RR016448 awarded by the National Institute of Health, and under a grant awarded by INBRE-Institute of Translational Health Sciences. The government has certain rights in the invention.

FIELD

Disclosed herein are embodiments of a probe capable of targeting nucleic acids and particular sequences thereof. Also disclosed are methods for using the disclosed probe to target nucleic acids and sequences thereof.

BACKGROUND

The use of short exogenous antisense oligonucleotides (ONs) or siRNA to silence gene expression on an RNA level has become an immensely popular approach to study fundamental functions of genes, to detect genes of interest, and to design new drugs against diseases of genetic origin. For development of high impact therapeutics with broad application, strategies that directly target the gene offer a powerful alternative to conventional therapies.

Progress in sequence-selective targeting of double stranded DNA (dsDNA) has been accomplished with minor groove binding polyamides or by DNA triple-helix-based approaches using modified oligonucleotides or helix-invading peptide nucleic acids (PNAs). However, the utility of these methods is limited by the sequence-dependent microstructure of the minor groove of DNA duplexes (polyamides), by target sequence restrictions (triplex-based approaches), or by the necessity of non-physiological salt concentrations (PNAs). An attractive alternative approach was introduced with pseudo-complementary DNA (pcDNA), i.e., DNA duplexes containing modified purine and pyrimidines that do not form stable base pairs with each other, while allowing hybridization to natural complementary DNA. pcDNA is able to strand invade blunt ended duplexes containing terminal mixed sequence target regions and this strategy has been extended into pseudo-complementary PNA (pcPNA), which has been used to target mixed sequence internal target regions of double stranded DNA. Unfortunately, the positively charged lysine residues commonly used to increase pcPNA solubility and binding affinity may lead to self-inhibitory effects of strand invasion at high probe concentrations. The requirement for low salt concentrations during pcPNA-mediated strand invasion of mixed sequence dsDNA is a limitation for all experiments in biological media and for numerous biotechnological applications. Development of alternative strategies for sequence selective recognition of dsDNA at physiologically relevant salt concentrations is therefore highly desirable.

SUMMARY

Particular disclosed embodiments concern a probe, comprising: a pair of monomers comprising a first monomer having a formula

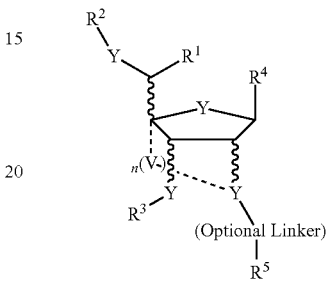

where each Y independently is selected from carbon, oxygen, sulfur, a triazole, and $NR^b$, wherein $R^b$ is selected from hydrogen, aliphatic, aryl, heteroaliphatic, and heteroaryl; V is selected from carbon, oxygen, sulfur, and $NR^b$; n ranges from 0 to 4; $R^1$ and $R^2$ are selected from hydrogen, aliphatic, aryl, and a heteroatom-containing moiety; $R^3$ is a heteroatom-containing functional group; $R^4$ is selected from any natural or non-natural nucleobase; $R^5$ is selected from any aromatic moiety suitable for intercalating within a nucleic acid; "optional linker" is selected from alkyl, amide, carbamate, carbonate, urea, and combinations thereof; a second monomer having a formula

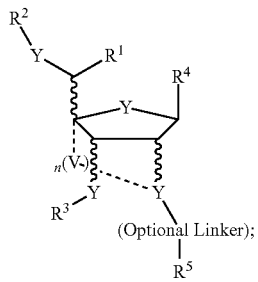

and at least one nucleotide selected from a natural nucleotide, a non-natural nucleotide, and combinations thereof, wherein the at least one nucleotide typically is coupled to the first and/or second monomer at $R^2$ and/or $R^3$ by a phosphate group.

In particular disclosed embodiments, the heteroatom-containing functional group is selected from ether ($R^aOR^b$), hydroxyl ($R^aOH$), silyl ether ($R^aR^bR^cSiOR^d$), phosphine ($PR^aR^bR^c$), thiol ($R^aSH$), thioether/sulfide ($R^aSR^b$), disulfide ($R^aSSR^b$), isothiocyanate ($R^aNCS$), isocyanate ($R^aNCO$), amine ($NH_2$, $NHR^a$, $NR^aR^b$), amide ($R^aNR^bC(O)R^c$), ester ($R^aOC(O)R^b$), halogen (I, Br, Cl, F), carbonate ($R^aOC(O)OR^b$), carboxyl ($R^aC(O)OH$), carboxylate ($R^aCOO^-$), ester ($R^aC(O)OR^b$), ketone ($R^aC(O)R^b$), phosphate ($R^aOP(O)OH_2$), phosphoryl ($R^aP(O)(OH)_2$), sulfinyl ($R^aS(O)R^b$), sulfonyl ($R^aSO_2R^b$), carbonothioyl ($R^aC(S)R^b$ or R$^a$C(S)H), sulfino (R$^a$S(O)OH), sulfo (R$^a$SO$_3$H), amide (R$^a$C(O)NR$^b$R$^c$), azide (N$_3$), nitrile (R$^a$CN), isonitrile (R$^a$N$^+$C$^-$), and nitro (R$^a$NO$_2$); R$^a$ represents the remaining monomer structure, which is attached to the abovementioned functional groups at the position indicated; and R$^b$, R$^c$, and R$^d$ independently are hydrogen, aliphatic, aryl, heteroaliphatic, heteroaryl, and any combination thereof. In certain embodiments, R$^2$ and R$^3$ independently are selected from a heteroatom functional group comprising phosphorous, sulfur, nitrogen, oxygen, selenium, and/or a metal, more typically R$^2$ and R$^3$ independently are selected from a phosphate group of the natural nucleotide, non-natural nucleotide, synthetic nucleotides, or combinations thereof. In particular disclosed embodiments, R$^4$ is selected from adenine, guanine, cytosine, uracil, thymine, or any derivative thereof and the intercalator is an aromatic hydrocarbon or an aromatic heterocycle. In particular disclosed embodiments, the intercalator is a hydrocarbon selected from pyrene, coronene, perylene, anthracene, naphthalene and functionalized derivatives thereof; or may be an aromatic heterocycle selected from a porphyrin, nucleobase, metal chelator, azapyrene, thiazole orange, indole, pyrrole, and derivatives thereof.

Certain disclosed embodiments concern a probe having at least one monomer, and typically two or more monomers. The monomers are generally incorporated within oligonucleotide strands, and can be located anywhere in the oligonucleotide strand, including the first position, the last position, and anywhere in between, and preferably are arranged in a final structure in an interstrand zipper arrangement, such as a +1 zipper arrangement, as discussed in more detail below. Certain disclosed embodiments concern probes wherein either the first monomer or the second monomer has a formula

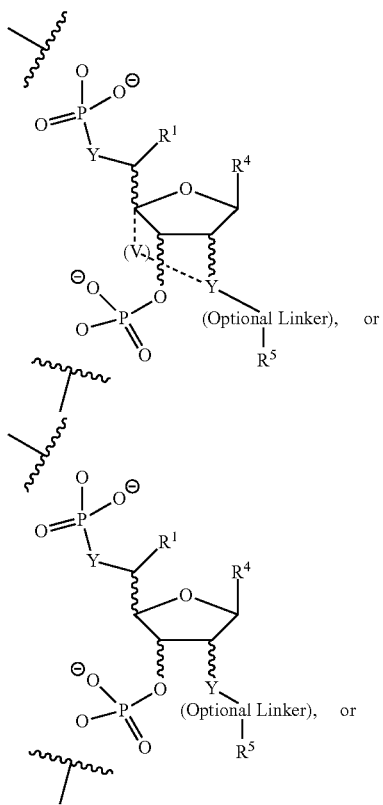

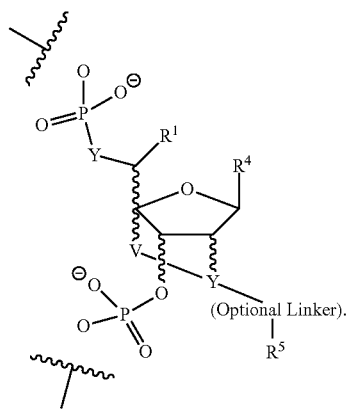

In certain disclosed embodiments, either the first monomer or the second monomer has a formula

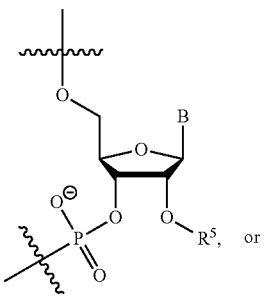

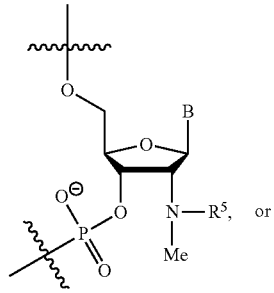

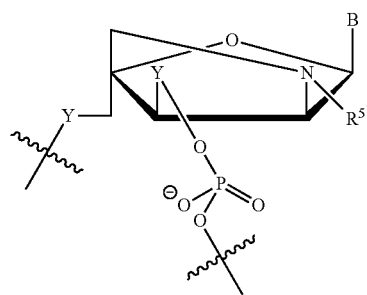

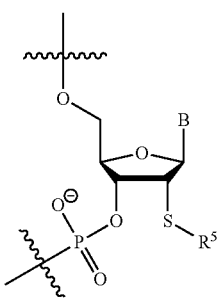
wherein B is selected from uracil, guanine, cytosine, adenine, thymine, 2-thiouracil, 2,6-diaminopurine, inosine, 3-pyrrolo-[2,3-d]-pyrimidine-2-(3H)-one or derivatives thereof.
Particular disclosed embodiments of the probe comprise monomers having any one of the following structures:
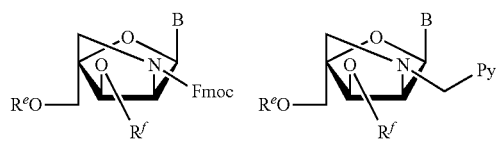
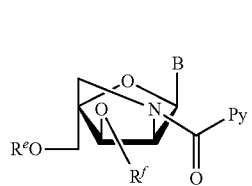
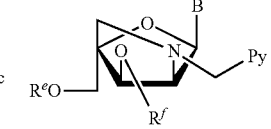
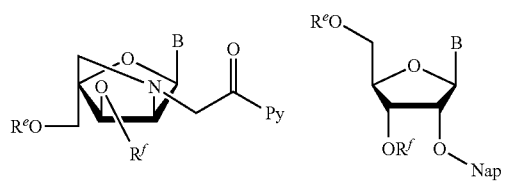
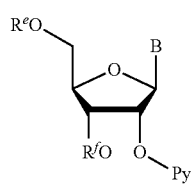
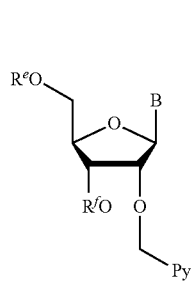
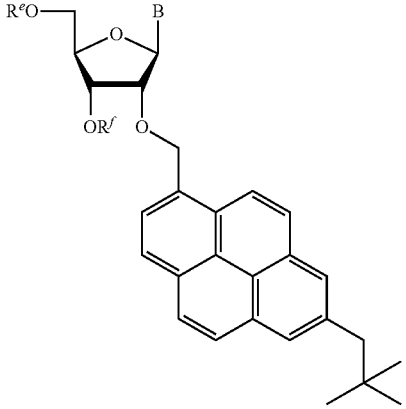
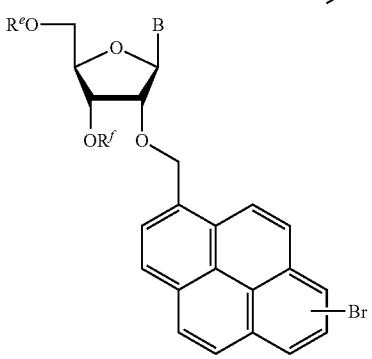
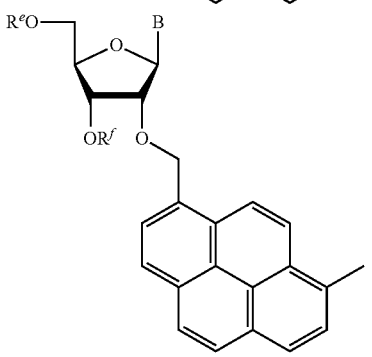
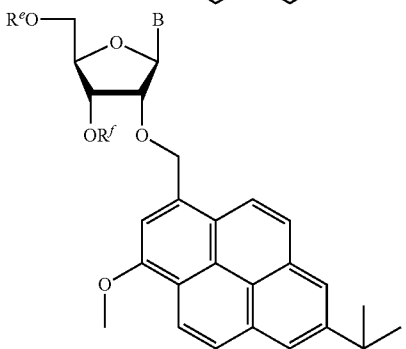
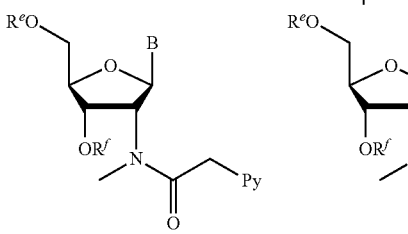

-continued

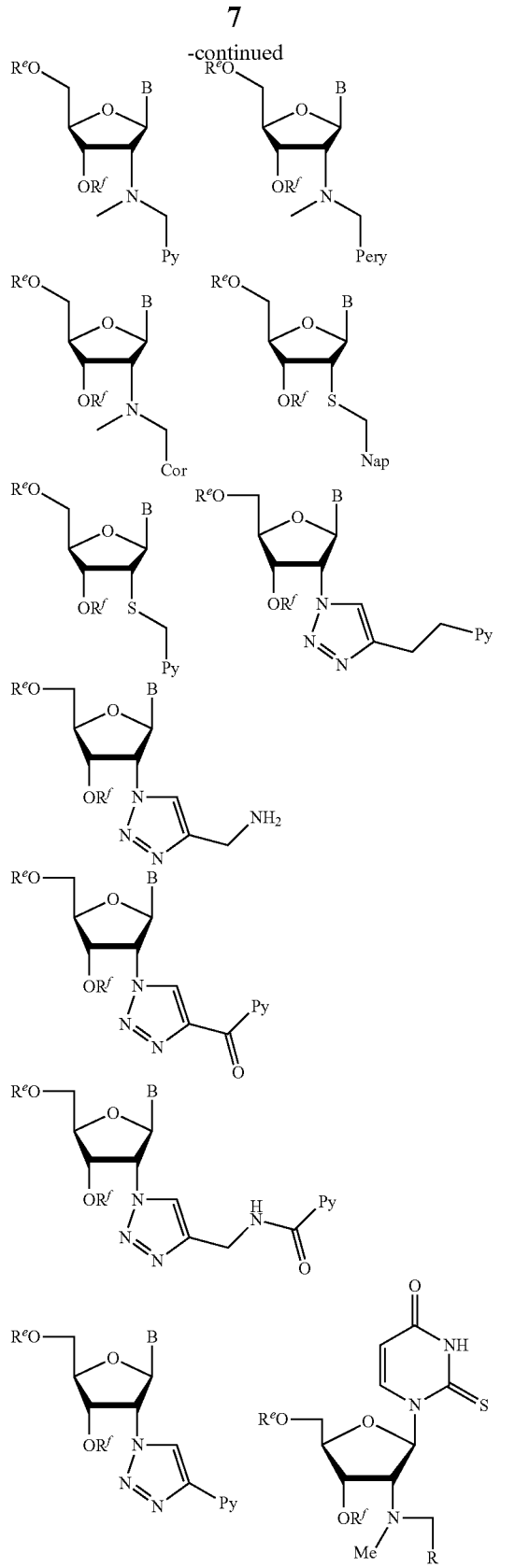

wherein B is selected from uracil, guanine, cytosine, adenine, thymine, 2-thiouracil, 2,6-diaminopurine, inosine, 3-pyrrolo-[2,3-d]-pyrimidine-2-(3H)-one or derivatives thereof, $R^e$ is H, DMTr, or phosphate, such as provided by a phosphodiester bond in an oligonucleotide and $R^f$ is H, $(N(i\text{-}Pr)_2)P(OCH_2CH_2CN)$, or phosphate, such as provided by a phosphodiester bond in an oligonucleotide; Nap refers to napthyl, such as 2-napthyl, Cor to coronenyl, such as coronen-1-yl, Py to pyrenyl, such as pyren-1-yl, pyren-2-yl and pyren-4-yl and Pery to peryleneyl, such as to perylene-3-yl.

In particular disclosed embodiments, the at least one natural nucleotide may be selected from adenine, guanine, cytosine, uracil, thymine and derivatives thereof, and the at least one non-natural nucleobase may be selected from C5-functionalized pyrimidines, C6-functionalized pyrimidines, C7-functionalized 7-deazapurines, C8-functionalized purines, 2-thiouracil, 2,6-diaminopurine, inosine, 3-pyrrolo-[2,3-d]-pyrimidine-2-(3H)-one or derivatives thereof. In certain disclosed embodiments, the probe comprises at least one natural nucleotide, unnatural nucleotide, and combinations thereof, which are selected to substantially match at least one nucleotide of a corresponding nucleic acid sequence.

Particular disclosed embodiments concern a probe having the following formula:

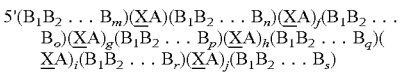

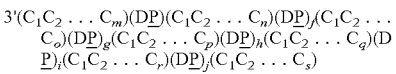

wherein $B_1$, $B_2$ and $B_{m-s}$ may be any natural or non-natural nucleotide, wherein m-s ranges from zero to about 28; f, g, h, i and j range from 0 to 10, more likely 0 to 5, and typically 0 to 3; X is the first monomer; A is the complement Watson-Crick base pairing nucleotide of P; C is any natural or non-natural nucleotide capable of Watson-Crick base pairing with any one of $B_1$, $B_2$ and $B_{m-s}$; P is the second monomer, and D is the complement Watson-Crick base pairing nucleotide of X. In certain disclosed embodiments, the probe is selected to recognize a predetermined sequence of a nucleic acid target, which may be single-stranded or double-stranded, more commonly double-stranded. In certain disclosed embodiments, the probe may additionally comprise one or more monomers at any given position that do not participate in base pairing, such as the following structures, wherein $R^e$ is H, DMTr, or phosphate, such as provided by a phosphodiester bond in an oligonucleotide and $R^f$ is H, $(N(i\text{-}Pr)_2)P(OCH_2CH_2CN)$, or phosphate, such as provided by a phosphodiester bond in an oligonucleotide, and $R^g$ and $R^h$ are, by way of example and without limitation, independently selected from hydrogen, aliphatic, particularly alkyl, such as C1-C10 alkyl, cyclic, heterocyclic, aromatic, heteroaromatic, amides, and carbamates.

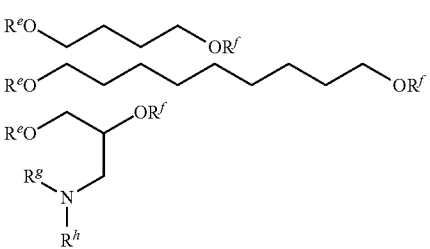

Particular disclosed embodiments concern a probe wherein the first monomer and the second monomer are arranged in a manner that substantially weakens the duplex's thermal stability. In particular disclosed embodiments, the probe may have a thermal melting temperature which is comparable (slightly lower, similar or slightly higher) to that of a corresponding (i.e., isosequential) unmodified nucleic acid duplex, which typically does not comprise a monomer having the formulas disclosed herein. The probe may comprise a pair of monomers wherein the first monomer and the second monomer are arranged in a +n or −n interstrand zipper orientation, wherein n ranges from 0 to about 10, more typically from 0 to about 2, more typically the first monomer and the second monomer are arranged in a +n orientation, wherein n is 1. The probe may also comprise one or more additional pairs of monomers; a signal generating moiety capable of being detected, selected from a fluorophore, a member of a specific binding pair (e.g. biotin), a nanoparticle, a signal quenching moiety, such as a quencher of fluorescence (e.g., Black Hole Quencher); permanent or inducible crosslinking reagents (such as psoralen) capable of forming bonds between the probe and nucleic acids, proteins, sugars, lipids and other biomolecules; a nucleic acid cargo (e.g., single-stranded DNA, single-stranded RNA, double-stranded DNA, double-stranded RNA, plasmid, gene); and combinations thereof. In particular disclosed embodiments, the secondary entity facilitates cell-uptake and/or cellular compartmentalization and includes peptides [NLS, CPP, KDEL], and small molecules with nuclear affinity (e.g. Hoechst-type dyes, ethidium, acridine and thiazole orange). The probe may be used in solution, on a solid surface (e.g. multi-well plates; noble metal surfaces, such as electrodes), or in combination with a colloidal material and/or nanomaterials (e.g. gold nanoparticles, quantum dots).

Certain disclosed embodiments concern a method for detecting a target, comprising: selecting a probe comprising a monomer having a formula

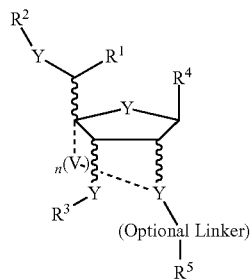

where each Y independently is selected from oxygen, sulfur, and $NR^b$, wherein $R^b$ is selected from hydrogen, aliphatic, aryl, heteroaliphatic, and heteroaryl; V is selected from carbon, oxygen, sulfur, and $NR^b$; n ranges from 0 to 4; $R^1$ and $R^2$ are selected from hydrogen, aliphatic, aryl, and a heteroatom-containing moiety; $R^3$ is a heteroatom-containing functional group; $R^4$ is selected from any natural or non-natural nucleobase; $R^5$ is selected from any functional group suitable for coupling to or associating with a nucleic acid and at least one natural nucleotide, unnatural nucleotide, and combinations thereof; exposing a nucleic acid target to the probe; and detecting the probe. In particular disclosed embodiments of the method, the probe is selected to substantially match a region of the target nucleic acid, particularly double stranded nucleic acid target regions, which may or may not comprise one or more polypurine stretches; more typically the nucleic acid is a mixed sequence of nucleotides, structured nucleic acid, particularly double-stranded nucleic acid sequences (dsDNA), even more particularly double stranded DNA, such as by way of example a mixed-sequence, hairpin DNA targets, PCR amplicons, genomic DNA, etc. which are isosequential with the probe. In particular disclosed embodiments, exposing the target to the probe comprises incubating the probe with the nucleic acid target. In certain disclosed embodiments, the nucleic acid target is incubated with an excess, such as about a 5-fold excess of the probe up to at least about a 5,000-fold excess of the probe, more typically up to about a 500-fold excess of the probe, and even more typically about a 5-fold excess of the probe to about a 200-fold excess of the probe. In particular disclosed embodiments, the probe and probe-target (recognition) complex, is detected by fluorescence spectroscopy, electrophoresis, absorption spectroscopy, fluorescence microscopy, flow cytometer, and combinations thereof.

A person of ordinary skill in the art will appreciate that the target sequences for disclosed probe embodiments can vary. For certain disclosed embodiments, the method is particularly useful for gender determination in mammals. For example, the method can be used for gender determination of ungulates and ruminates, particularly bovines, equines or porcines. For other embodiments, the target is isosequential (relative to a probe) to double stranded DNA target regions, including stems of molecular beacons, target regions embedded within PCR amplicons, target regions embedded within circular or linearized plasmids, target regions embedded within genomic DNA, and target regions embedded within microorganisms. The target also can be selected from a nucleic acid sequence associated with a proliferative disorder, such as B cell and T cell leukemias, lymphomas, breast cancer, colon cancer, and neurological cancers. In yet other embodiments, the target is selected from a virus or other microorganism and the probe is used to detect and/or identify the microorganism.

Kids comprising a nucleic acid probe also are disclosed. Such kits typically comprise a probe comprising at least one disclosed monomer, and may comprise at least one bulge monomer. Such kits also may include a sequence selected from SEQ ID NOs. 1-254. Certain kit embodiments are particularly useful for gender determination in mammals.

The foregoing and other objects, features, and advantages of the invention will become more apparent from the following detailed description, which proceeds with reference to the accompanying figures.

SEQUENCE LISTING

Figure 1:
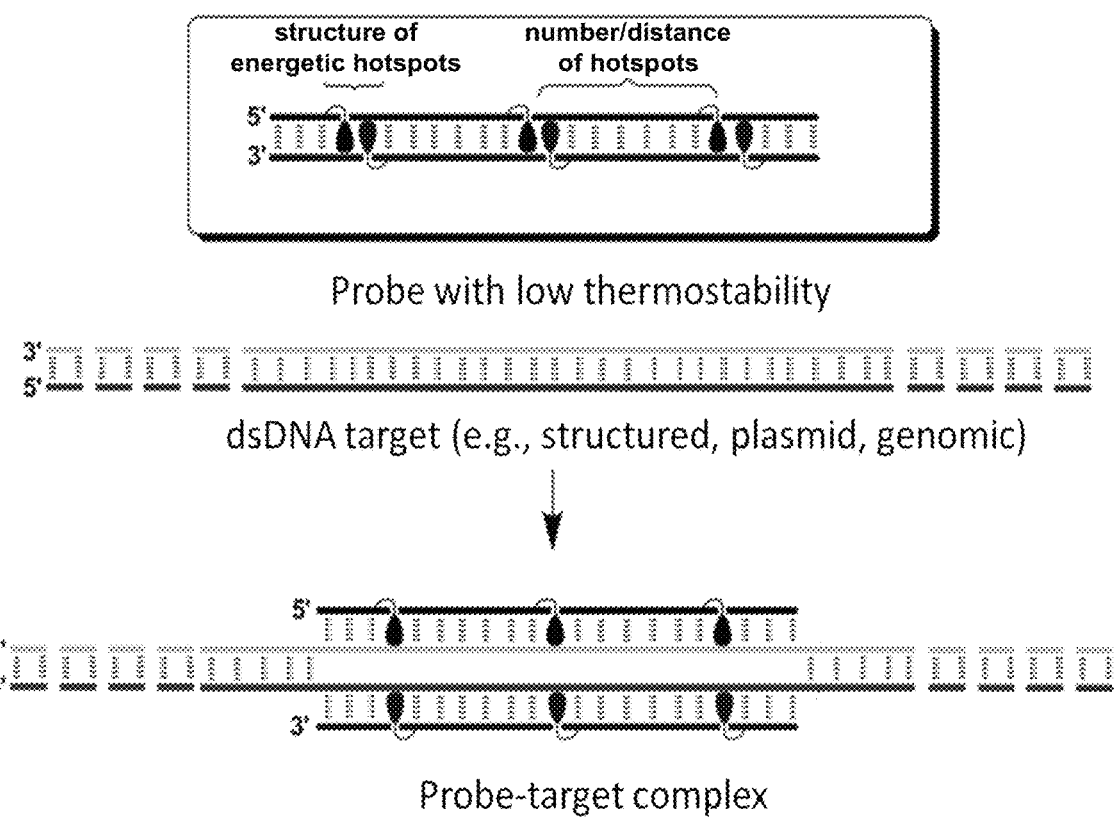
FIG. 1 is a schematic diagram that illustrates a particular embodiment of a method for detecting a target using the disclosed probe.

The nucleic acid sequences listed in the accompanying sequence listing are shown using standard letter abbreviations for nucleotide bases, as defined in 37 C.F.R. 1.822. Only one strand of each nucleic acid sequence is shown, but the complementary strand is understood as included by any reference to the displayed strand. In the accompanying sequence listing:

SEQ ID NOs: 1-4, 11 and 240-245 are nucleotide sequences of structured dsDNA targets with isosequential or non-isosequential stem regions.

SEQ ID NOs: 5-10, 12-239, 246-251, 254, and 255-264 are nucleotide sequences of oligonucleotide probes and target regions.

SEQ ID NOs: 252 and 253 are nucleotide sequences of double-stranded probes containing a non-pairing bulge.

DETAILED DESCRIPTION

I. Terms

Unless otherwise noted, technical terms are used according to conventional usage. Definitions of common terms in molecular biology may be found in Benjamin Lewin, *Genes VII*, published by Oxford University Press, 2000 (ISBN 019879276X); Kendrew et al. (eds.), *The Encyclopedia of Molecular Biology*, published by Blackwell Publishers, 1994 (ISBN 0632021829); and Robert A. Meyers (ed.), *Molecular Biology and Biotechnology: a Comprehensive Desk Reference*, published by Wiley, John & Sons, Inc., 1995 (ISBN 0471186341); and other similar references.

As used herein, the singular terms "a," "an," and "the" include plural referents unless context clearly indicates otherwise. Similarly, the word "or" is intended to include "and" unless the context clearly indicates otherwise. Also, as used herein, the term "comprises" means "includes." Hence "comprising A or B" means including A, B, or A and B.

A wavy line ("⌇") indicates a bond disconnection. A dashed line ("---") illustrates that a bond may be formed at a particular position.

All nucleotide sizes or amino acid sizes, and all molecular weight or molecular mass values, given for nucleic acids or polypeptides or other compounds are approximate, and are provided for description.

Although methods and materials similar or equivalent to those described herein can be used in the practice or testing of the present disclosure, suitable methods and materials are described below.

All publications, patent applications, patents, and other references mentioned herein are incorporated by reference in their entirety. In case of conflict, the present specification, including explanations of terms, will control. In addition, the materials, methods, and examples are illustrative only and not intended to be limiting.

In order to facilitate review of the various examples of this disclosure, the following explanations of specific terms are provided:

Aliphatic: Any open or closed chain molecule, excluding aromatic compounds, containing only carbon and hydrogen atoms which are joined by single bonds (alkanes), double bonds (alkenes), or triple bonds (alkynes). This term encompasses substituted aliphatic compounds, saturated aliphatic compounds, and unsaturated aliphatic compounds.

Analog, Derivative or Mimetic: An analog is a molecule that differs in chemical structure from a parent compound, for example a homolog (differing by an increment in the chemical structure, such as a difference in the length of an alkyl chain), a molecular fragment, a structure that differs by one or more functional groups, a change in ionization. Structural analogs are often found using quantitative structure activity relationships (QSAR), with techniques such as those disclosed in Remington (*The Science and Practice of Pharmacology*, 19th Edition (1995), chapter 28). A derivative is a biologically active molecule derived from the base structure. A mimetic is a molecule that mimics the activity of another molecule, such as a biologically active molecule. Biologically active molecules can include chemical structures that mimic the biological activities of a compound.

Aromatic: A term describing conjugated rings having unsaturated bonds, lone pairs, or empty orbitals, which exhibit a stabilization stronger than would be expected by the stabilization of conjugation alone. It can also be considered a manifestation of cyclic delocalization and of resonance.

Aryl: A substantially hydrocarbon-based aromatic compound, or a radical thereof (e.g. $C_6H_5$) as a substituent bonded to another group, particularly other organic groups, having a ring structure as exemplified by benzene, naphthalene, phenanthrene, anthracene, etc. This term also encompasses substituted aryl compounds.

Aryl alkyl: A compound, or a radical thereof ($C_7H_7$ for toluene) as a substituent bonded to another group, particularly other organic groups, containing both aliphatic and aromatic structures.

Complementary: The natural binding of polynucleotides under permissive salt and temperature conditions by base-pairing. Complementarity may exist when only some of the nucleic acids bind, or when total complementarity exists between the nucleic acids.

Conjugating, joining, bonding or linking: Joining one molecule to another molecule to make a larger molecule. For example, making two polypeptides into one contiguous polypeptide molecule, or covalently attaching a hapten or other molecule to a polypeptide, such as an scFv antibody. In the specific context, the terms include reference to joining a ligand, such as an antibody moiety, to an effector molecule. The linkage can be either by chemical or recombinant means. "Chemical means" refers to a reaction between the antibody moiety and the effector molecule such that there is a covalent bond formed between the two molecules to form one molecule.

Coupled: The term "coupled" means joined together, either directly or indirectly. A first atom or molecule can be directly coupled or indirectly coupled to a second atom or molecule. A secondary antibody provides an example of indirect coupling. Coupling can occur via covalent, non-covalent, and ionic bond formation.

Derivative: In chemistry, a derivative is a compound that is derived from a similar compound or a compound that can be imagined to arise from another compound, for example, if one atom is replaced with another atom or group of atoms. The latter definition is common in organic chemistry. In biochemistry, the word is used for compounds that at least theoretically can be formed from the precursor compound.

Deviation from additivity (DA): The DA value for a probe ONX:ONY is defined as: $DA_{ONX:ONY} = \Delta T_m$ (ONX:ONY)−[$\Delta T_m$ (ONX:DNA X)+$\Delta T_m$ (DNA Y:ONY)], where ONX:ONY is a double-stranded probe with certain interstrand zipper arrangements of disclosed monomers and 'DNA X' and 'DNA Y' are the complementary single-stranded nucleic acid targets of ONX and ONY, respectively. The term "Thermal advantage" is significantly related to DA, i.e., TA=−DA.

Displace (ment) (ed): A reaction in which an atom, radical, or molecule (anionic or neutral) replaces another in a compound.

Double Stranded Nucleic Acid: An oligonucleotide containing a region of two or more nucleotides having a double stranded motif.

Epitope: An antigenic determinant. These are particular chemical groups or contiguous or non-contiguous peptide sequences on a molecule that are antigenic, that is, that elicit a specific immune response.

Fluorescence: The emission of light by a substance that has absorbed light or other electromagnetic radiation of a different wavelength.

Fluorophore: A functional group of a molecule which causes the molecule to be fluorescent. Typically, the functional group can absorb energy of a specific wavelength and re-emit energy at a different (but equally specific) wavelength.

Human epidermal growth factor receptor (Her) family: A family of structurally related proteins, including at least Her1, Her2, Her3 and Her4 (aka EGFR1, EGFR2, EGFR3 and EGFR4, respectively, or ErbB-1, ErbB-2, ErbB-3 and ErbB-4, respectively). Her1, Her2 and Her4 are receptor tyrosine kinases; although Her3 shares homology with Her1, Her2 and Her4, Her3 is kinase inactive. Included in the Her family is p95, a truncated form of Her2 lacking portions of the Her2 extracellular domain (see, e.g., Arribas et al., *Cancer Res.*, 71:1515-1519, 2011; Molina et al., *Cancer Res.*, 61:4744-4749, 2001).

The human epidermal growth factor family of receptors mediate cell growth and are disregulated in many types of cancer. For example Her1 and Her2 are upregulated in many human cancers, and their excessive signaling may be critical factors in the development and malignancy of these tumors. See, e.g., Herbst, *Int. J. Radiat. Oncol. Biol. Phys.*, 59:21-6, 2004; Zhang et al., *J. Clin. Invest.* 117 (8): 2051-8, 2007. Receptor dimerization is essential for Her pathway activation leading to receptor phosphorylation and downstream signal transduction. Unlike Her1, -3 and -4, Her2 has no known ligand and assumes an open conformation, with its dimerization domain exposed for interaction with other ligand-activated Her receptors.

Approximately 30% of breast cancers have an amplification of the Her2 gene or overexpression of its protein product. Her2 overexpression also occurs in other cancer types, such as ovarian cancer, stomach cancer, and biologically aggressive forms of uterine cancer, such as uterine serous endometrial carcinoma. See, e.g., Santin et al., *Int. J. Gynaecol. Obstet.*, 102 (2): 128-31, 2008. Her2-containing homo- and hetero-dimers are transformation competent protein complexes. Trastuzumab, a humanized antibody that prevents Her2 homodimerization is used to treat certain Her2 overexpressing cancers, including breast cancer. Additionally, the level of Her2 expression in cancer tissue is predictive of patient response to Her2 therapeutic antibodies (e.g., Trastuzumab). Because of its prognostic role as well as its ability to predict response to Trastuzumab, tumors (e.g., tumors associated with breast cancer) are routinely checked for overexpression of Her2.

The Her pathway is also involved in ovarian cancer pathogenesis. Many ovarian tumor samples express all members of the Her family. Co-expression of Her1 and Her2 is seen more frequently in ovarian cancer than in normal ovarian epithelium, and overexpression of both receptors correlates with poor prognosis. Preferred dimerization with Her2 (Her1/Her2, Her2/Her3) and subsequent pathway activation via receptor phosphorylation have also been shown to drive ovarian tumor cell proliferation, even in the absence of Her2 overexpression. Pertuzumab, a humanized antibody that prevents Her2 dimerization (with itself and with Her3) has been shown to provide therapeutic benefit to patients with Her2 and/or Her3 expressing ovarian cancer. Examples of Her1 amino acid sequence include NCBI/Genbank accession Nos. NP_005219.2, CAA25240.1, AAT52212.1, AAZ66620.1, BAF83041.1, BAH11869.1, ADZ75461.1, ADL28125.1, BAD92679.1, AAH94761.1. Examples of, Her2, amino acid sequences include NCBI/Genbank accession BAJ17684.1, P04626.1, AAI67147.1, NP_001005862.1, NP_004439.2, AAA75493.1, AAO18082.1. Examples of Her3 amino acid sequences include NCBI/Genbank accession Nos. NP_001973.3, P21860.1, AAH82992.1, AAH02706.1, AAA35979.1.

Examples of Her4 amino acid sequences include NCBI/Genbank accession Nos., AAI43750, Q15303.1, NP_005226.1, NP_001036064.1, AAI43748.1.

Heteroaliphatic: An aliphatic group, which contains one or more atoms other than carbon and hydrogen, such as, but not limited to, oxygen, sulfur, nitrogen, phosphorus, chlorine, fluorine, bromine, iodine, and selenium.

Homology: As used herein, "homology" refers to a degree of complementarity. Partial homology or complete homology can exist. Partial homology involves a nucleic acid sequence that at least partially inhibits an identical sequence from hybridizing to a target nucleic acid.

Homopolymer: This term refers to a polymer formed by the bonding together of multiple units of a single type of molecular species, such as a single monomer (for example, an amino acid).

Interstrand Zipper Nomenclature (+1/−1, etc. . . . ): The "interstrand zipper arrangement" nomenclature is used to describe relative arrangement between two monomers positioned on opposing strands in a duplex. The number 'n' describes the distance measured in number of base pairs and has a positive value if a monomer is shifted toward the 5'-side of its own strand relative to a second reference monomer on the other strand. Conversely, n has a negative value if a monomer is shifted toward the 3'-side of its own strand relative to a second reference monomer on the other strand.

Isolated: An "isolated" microorganism (such as a virus, bacterium, fungus, or protozoan) has been substantially separated or purified away from microorganisms of different types, strains, or species. Microorganisms can be isolated by a variety of techniques, including serial dilution and culturing.

An "isolated" biological component (such as a nucleic acid molecule, protein or organelle) has been substantially separated or purified away from other biological components in the cell of the organism in which the component naturally occurs, such as other chromosomal and extra-chromosomal DNA and RNA, proteins, and organelles. Nucleic acids and proteins that have been "isolated" include nucleic acids and proteins purified by standard purification methods. The term also embraces nucleic acids and proteins prepared by recombinant expression in a host cell, as well as chemically synthesized nucleic acids or proteins, or fragments thereof.

Leaving Group: A molecular fragment that departs with a pair of electrons after heterolytic bond cleavage. Leaving groups can be anions or neutral molecules. Common anionic leaving groups can include halides, such as Cl$^-$, Br$^-$, and I$^-$, and sulfonate esters, such as para-toluenesulfonate (TsO$^-$), trifluoromethanesulfonate (TfO$^-$), Common neutral molecule leaving groups can include $H_2O$, $NH_3$, alcohols, and gases ($N_2$, $O_2$, $CO_2$, CO, and $SO_2$).

Lewis acid: A chemical substance that can accept a pair of electrons from a Lewis base, B, which acts as an electron-pair donor, forming an adduct, AB as given by the following: A+:B→A−B.

Linker: As used herein, a linker is a molecule or group of atoms positioned between two moieties.

Lower alkyl: Any aliphatic chain that contains 1-10 carbon atoms.

Modified: As used herein, "modified" refers to an oligonucleotide that has a non-natural composition, in that it comprises one or more synthetic nucleobases which can pair with a natural base.

Molecule of interest or Target: A molecule for which the presence, location and/or concentration is to be determined.

Nucleobase: As used herein, "nucleobase" includes naturally occurring nucleobases as well as non-natural nucleobases. A person of ordinary skill in the art will recognize that "nucleobase" encompasses purine and pyrimidine derivatives, as well as heterocyclic derivatives and tautomers thereof.

Nucleophile: A reagent that forms a chemical bond to its reaction partner (the electrophile) by donating both bonding electrons. A molecule or ion with a free pair of electrons can act as nucleophile.

Nucleotide: Phosphorylated nucleosides are "nucleotides," which are the molecular building-blocks of DNA and RNA.

Nucleoside: A glycoside of a heterocyclic base. The term "nucleoside" is used broadly as to include non-naturally occurring nucleosides, naturally occurring nucleosides as well as other nucleoside analogues. Illustrative examples of nucleosides are ribonucleosides comprising a ribose moiety as well as deoxyribo-nucleosides comprising a deoxyribose moiety. With respect to the bases of such nucleosides, it should be understood that this may be any of the naturally occurring bases, e.g. adenine, guanine, cytosine, thymine, and uracil, as well as any modified variants thereof or any possible unnatural bases.

Oligonucleotide: A plurality of joined nucleotides joined by native phosphodiester bonds. An oligonucleotide is a polynucleotide of between at least 2 and about 300 nucleotides in length. Typically, an oligonucleotide is a polynucleotide of between about 5 and about 50 nucleotides. An oligonucleotide analog refers to moieties that function similarly to oligonucleotides but have non-naturally occurring portions. For example, oligonucleotide analogs can contain non-naturally occurring portions, such as altered sugar moieties or inter-sugar linkages, such as a phosphorothioate oligodeoxynucleotide. Functional analogs of naturally occurring polynucleotides can bind to RNA or DNA, and include locked nucleic acid (LNA) and peptide nucleic acid (PNA) molecules.

Pharmaceutically acceptable salt: Pharmaceutically acceptable salts are more soluble in aqueous solutions than the corresponding free acids and bases from which the salts are produced; however, salts having lower solubility than the corresponding free acids and bases from which the salts are produced may also be formed. Pharmaceutically acceptable salts are typically counterbalanced with an inorganic base, organic base, or basic amino acid if the salts are positively charged; or the salt is counterbalanced with an inorganic acid, organic acid, or acidic amino acid if they are negatively charged. Pharmaceutically acceptable salts can also be zwitterionic in form. Salts can be formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. Other elements capable of forming salts are well-known to those of ordinary skill in the art, e.g. all elements from the main groups I to V of the Periodic Table of the Elements, as well as the elements from the subgroups I to VIII. Any chemical compound recited in this specification may alternatively be administered as a pharmaceutically acceptable salt thereof. "Pharmaceutically acceptable salts" are also inclusive of the free acid, base, and. Descriptions of suitable pharmaceutically acceptable salts can be found in *Handbook of Phar-* maceutical Salts, Properties, Selection and Use, Wiley VCH (2002), which we herein incorporate by reference.

Polypeptide: A polymer in which the monomers are amino acid residues that are joined together through amide bonds. When the amino acids are α-amino acids, either the L-optical isomer or the D-optical isomer can be used. The terms "polypeptide" or "protein" as used herein are intended to encompass any amino acid sequence and include modified sequences such as glycoproteins. The term "polypeptide" is specifically intended to cover naturally occurring proteins, as well as those which are recombinantly or synthetically produced.

The term "residue" or "amino acid residue" includes reference to an amino acid that is incorporated into a protein, polypeptide, or peptide.

Protecting Group: A moiety that can be introduced into a molecule by chemical modification of a functional group. Protecting groups often are used to protect one functional group in order to obtain chemoselectivity in a chemical reaction with a different functional group. Suitable protecting groups are well known to those of ordinary skill in the art and can include aryl groups, aliphatic groups, heteroaliphatic groups, heteroaryl groups.

Protein: A molecule, particularly a polypeptide, comprised of amino acids.

Purified: The term "purified" does not require absolute purity; rather, it is intended as a relative term. Thus, for example, a purified compound is one that is isolated in whole or in part from other contaminants. Generally, substantially purified peptides, proteins, conjugates, oligonucleotides, or other active compounds for use within the disclosure comprise more than 80% of all macromolecular species present in a preparation prior to admixture or formulation of the peptide, protein, conjugate or other active compound with a pharmaceutical carrier, excipient, buffer, absorption enhancing agent, stabilizer, preservative, adjuvant or other co-ingredient in a complete pharmaceutical formulation for therapeutic administration. More typically, the peptide, protein, conjugate or other active compound is purified to represent greater than 90%, often greater than 95% of all macromolecular species present in a purified preparation prior to admixture with other formulation ingredients. In other cases, the purified preparation may be essentially homogeneous, wherein other macromolecular species are not detectable by conventional techniques.

Quantum Yield: A measure of the efficiency of the fluorescence process. The "quantum yield" of a radiation-induced process indicates the number of times that a defined event occurs per photon absorbed by the system.

Reactive Groups: Formulas throughout this application refer to "reactive groups," which can be any of a variety of groups suitable for undergoing a chemical transformation as described herein. For example, the reactive group might be an amine-reactive group, such as an isothiocyanate, an isocyanate, an acyl azide, an NHS ester, an acid chloride, such as sulfonyl chloride, aldehydes and glyoxals, epoxides and oxiranes, carbonates, arylating agents, imidoesters, carbodiimides, anhydrides, and combinations thereof. Suitable thiol-reactive functional groups include haloacetyl and alkyl halides, maleimides, aziridines, acryloyl derivatives, arylating agents, thiol-disulfide exchange reagents, such as pyridyl disulfides, TNB-thiol, and disulfide reductants, and combinations thereof. Suitable carboxylate-reactive functional groups include diazoalkanes, diazoacetyl compounds, carbonyldiimidazole compounds, and carbodiimides. Suitable hydroxyl-reactive functional groups include epoxides and oxiranes, carbonyldiimidazole, N,N'-disuccinimidyl carbonates or N-hydroxysuccinimidyl chloroformates, periodate oxidizing compounds, enzymatic oxidation, alkyl halogens, and isocyanates. Aldehyde and ketone-reactive functional groups include hydrazines, Schiff bases, reductive amination products, Mannich condensation products, and combinations thereof. Active hydrogen-reactive compounds include diazonium derivatives, Mannich condensation products, iodination reaction products, and combinations thereof. Photoreactive chemical functional groups include aryl azides, halogenated aryl azides, benzophonones, diazo compounds, diazirine derivatives, and combinations thereof.

Sample: A biological specimen from a subject, such as might contain genomic DNA, RNA (including mRNA), protein, or combinations thereof. Examples include, but are not limited to, peripheral blood, urine, saliva, tissue biopsy, surgical specimen, amniocentesis samples and autopsy material.

Single nucleotide polymorphism: A nucleic acid sequence variation occurring when a single nucleotide in the genome (or other shared sequence) differs between members of a species or paired chromosomes in an individual. For example, two sequenced nucleic acid fragments from different individuals, AAGCCTA to AAGCTTA, contain a difference in a single nucleotide.

Substantially complementary: As used herein, "substantially complementary refers to the oligonucleotides of the disclosed methods that are at least about 50% homologous to target nucleic acid sequence they are designed to detect, more preferably at least about 60%, more preferably at least about 70%, more preferably at least about 80%, more preferably at least about 90%, more preferably at least about 90%, more preferably at least about 95%, most preferably at least about 99%.

Thermal advantage: Thermal Advantage (TA) is defined as TA (ONX:ONY)≡$T_m$ (ONX:DNA X)+$T_m$ (DNA Y:ONY)−$T_m$ (ONX:ONY)−Tm (DNA X: DNA Y), where ONX:ONY is a double-stranded probe with certain interstrand zipper arrangements of disclosed monomers, ONX: DNA X and DNA Y:ONY are the duplexes between individual probe strands and nucleic acid targets, and DNA X: DNA Y is the double-stranded nuclei acid target. A large, positive TA-value signifies significant potential for probe ONX:ONY to target DNA X:DNA Y. The term "Deviation from Additivity" is significantly related to 'TA' by the equation: TA=−DA (highly positive TA or highly negative DA values demonstrate significant targeting potential).

Transition metal: Any of the metallic elements within Groups 3 to 12 in the Periodic Table that have an incomplete inner electron shell and that serve as transitional links between the most and the least electropositive in a series of elements.

II. Introduction

Disclosed herein is a probe for targeting nucleic acids and particular sequences thereof. In particular disclosed embodiments, the probe comprises one or more pairs of monomers capable of intercalating with one or more nucleic acid targets. In particular disclosed embodiments, the probe comprises one or more pairs of monomers comprising a first monomer and a second monomer arranged on opposite nucleic acid strands. Certain disclosed embodiments concern a probe wherein one or more monomers are arranged in a manner that promotes thermal instability of the probe and increases the probe's ability to detect a target.

III. Embodiments of Disclosed Probes

A. Monomers

In particular disclosed embodiments, the disclosed probe may comprise one or more monomers capable of coupling with a nucleic acid. In particular disclosed embodiments, each monomer independently may have a Formula 1, illustrated below.

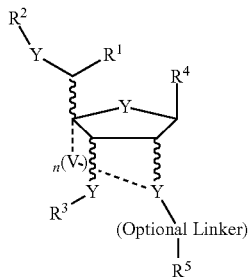

Formula 1

With reference to Formula 1, each Y may independently be selected from oxygen, sulfur, a triazole, oxazole, tetrazole, isoxazole, and $NR^b$, wherein $R^b$ is selected from hydrogen, aliphatic, aryl, heteroaliphatic, and heteroaryl, and V may be selected from carbon, oxygen, sulfur, and $NR^b$, wherein $R^b$ is as previously recited. The variable "n" may range from 0 to 4; more typically, n is 1 or zero. A person of ordinary skill in the art will recognize that when n is 1 or greater, V may or may not be bound to Y, as indicated by the dashed line connecting these two variables in Formula 1. $R^1$ may be selected from hydrogen, aliphatic, such as alkyl, more typically lower alkyl, such as methyl, ethyl, propyl, butyl, etc., alkenyl, alkynyl, aryl, aryl aliphatic, such as aryl alkyl, and a heteroatom-containing moiety. The heteroatom-containing moiety may be selected from, but not limited to, ether ($R^aOR^b$), hydroxyl ($R^aOH$), silyl ether ($R^aR^bR^cSiOR^d$), phosphine ($PR^aR^bR^c$), thiol ($R^aSH$), thioether/sulfide ($R^aSR^b$), disulfide ($R^aSSR^b$), isothiocyanate ($R^aNCS$), isocyanate ($R^aNCO$), amine ($NH_2$, $NHR^a$, $NR^aR^b$), amide ($R^aNR^bC(O)R^c$), ester ($R^aOC(O)R^b$), halogen (I, Br, Cl, F), carbonate ($R^aOC(O)OR^b$), carboxyl ($R^aC(O)OH$), carboxylate ($R^aCOO^-$), ester ($R^aC(O)OR^b$), ketone ($R^aC(O)R^b$), phosphate ($R^aOP(O)OH_2$), phosphoryl ($R^aP(O)(OH)_2$), sulfinyl ($R^aS(O)R^b$), sulfonyl ($R^aSO_2R^b$), carbonothioyl ($R^aC(S)R^b$ or $R^aC(S)H$), sulfino ($R^aS(O)OH$), sulfo ($R^aSO_3H$), amide ($R^aC(O)NR^bR^b$), azide ($N_3$), nitrile ($R^aCN$), isonitrile ($R^aN^+C^-$), and nitro ($R^aNO_2$). With reference to all the heteroatom-containing moieties disclosed herein, $R^a$ represents the remaining monomer structure, which is attached to the abovementioned functional groups at the position indicated for $R^1$; and $R^b$, $R^c$, and $R^d$ independently are hydrogen, aliphatic, aryl, heteroaliphatic, heteroaryl, and any combination thereof. The optional linker may be selected from alkyl, amide, carbamate, carbonate, urea, and combinations thereof.

$R^2$ may be selected from hydrogen, aliphatic, aryl, and any one of the heteroatom-containing moieties described herein. In particular embodiments, $R^2$ may be selected from a protecting group known to those of ordinary skill in the art, such as, but not limited to, 4,4'-dimethoxytrityl, trityl, 9-arylthioxanthenyl, mesyl (Ms), tosyl (Ts), besoyl (Bs), trifluoromethane ($CF_3$), and trifluoromethanesulfonyl. In certain disclosed embodiments, $R^2$ may be one or more nucleotides or monomers.

$R^3$ typically may be a heteroatom-containing functional group. In particular disclosed embodiments, the heteroatom may be selected from phosphorous, sulfur, nitrogen, oxygen, selenium, and/or a metal. Certain disclosed embodiments utilize $R^3$ substituents having a formula

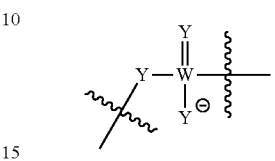

where Y is selected from oxygen, sulfur, $NR^b$ where $R^b$ is selected from hydrogen, aliphatic, aryl, heteroaliphatic, heteroaryl, and W is selected from phosphorus, SH, or SeH. Certain species of $R^3$ substituents include, without limitation, the following:

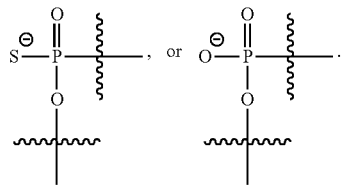 [SMILES: *OP(*)(=O)[S-] ; *OP(*)(=O)[O-]]

In other disclosed embodiments, $R^3$ has a formula

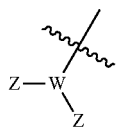

where W is phosphorus, and each Z independently is selected from ether, thioether, hydroxyl, and $NR^b_2$. In particular disclosed embodiments, $R^3$ may be

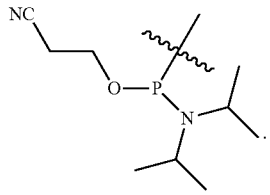 [SMILES: *P(OCCC#N)N(C(C)C)C(C)C]

$R^4$ may be selected from any natural or non-natural nucleobase. In particular disclosed embodiments, $R^4$ is a natural nucleobase selected from uracil, adenine, thymine, cytosine, guanine. A person of ordinary skill in the art will recognize that $R^4$ may also be any non-natural, or synthetically developed nucleobase including those presently known or developed in the future. In particular disclosed embodiments, $R^4$ may be selected from C-5 functionalized pyrimidines, C6-functionalized pyrimidines, C7-functionalized 7-deazapurines, C8-functionalized purines, 2,6-diaminopurine, 2-thiouracil, 4-thiouracil, deoxyinosine and 3-(2'-deoxy-β-D-ribofuranosyl)pyrrolo-[2,3-d]-pyrimdine-2-(3H)-one.

R[5] may be an intercalator capable of intercalating within a nucleic acid. In particular disclosed embodiments, R[5] may be any moiety capable of intercalating with single stranded nucleic acids, double stranded nucleic acids, and/or triple stranded nucleic acids. In particular disclosed embodiments, R[5] may be a planar moiety capable of maintaining a flat orientation when inserted into a nucleic acid. R[5] may be a hydrocarbon selected from pyrene, coronene, perylene, anthracene, naphthalene, and functionalized derivatives thereof; or an aromatic heterocycle, such as a porphyrin, a nucleobase (such as pyrimidines, purines, size-expanded nucleobases), a metal chelator (such as phenanthroline, DPPZ), an azapyrene, thiazole orange, ethidium, a diazobenzene, an indole, a pyrrole, benzimidizoles, and modified analogs thereof. R[5] may be modified to include various aliphatic, aryl, or heteroatom-containing functional groups.

Particular disclosed embodiments concern a probe comprising one or more monomers selected from any one of Formulas 3-5.

In certain disclosed embodiments, the probe may comprise one or more monomers having any one of Formulas 6 and 7. With reference to Formulas 6 and 7, B may be selected from uracil, adenine, thymine, guanine, cytosine and 2-thiouracil with or without common protecting groups, and R[5] may be selected from napth-2-yl, pyren-1-yl, coronen-1-yl, CH$_2$-pyren-1-yl, CH$_2$-coronen-1-yl, CO-pyren-1-yl, COCH$_2$-pyren-1-yl, CH$_2$-perylen-3-yl; CH$_2$-1-(7-neopentylpyrenyl), CH$_2$-1-(6-bromopyrenyl), CH$_2$-1-(8-bromopyrenyl), CH$_2$-1-(8-methylpyrenyl), CH$_2$-1-(7-tert-butyl-3-methoxypyrenyl), CH$_2$-pyren-2-yl and CH$_2$-pyren-4-yl.

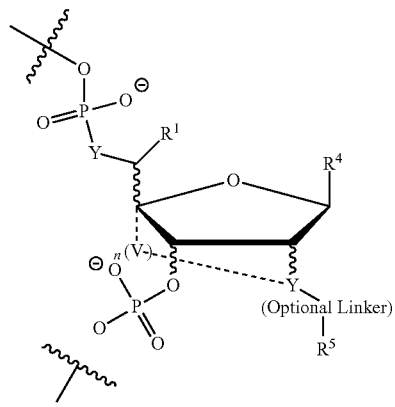

Formula 3

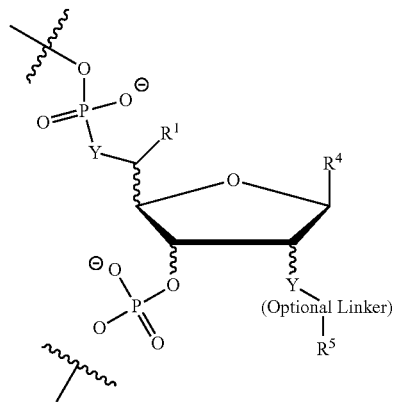

Formula 4

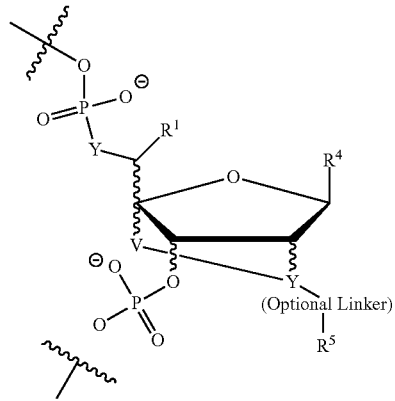

Formula 5

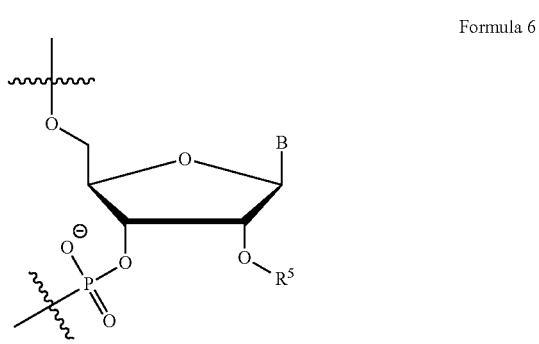

Formula 6

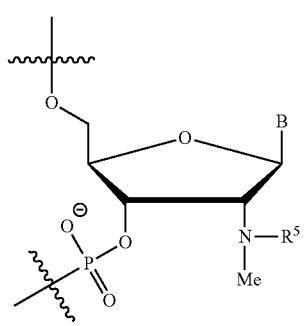

Formula 7

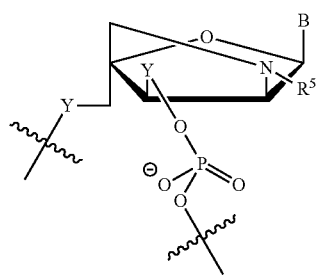

Formula 8

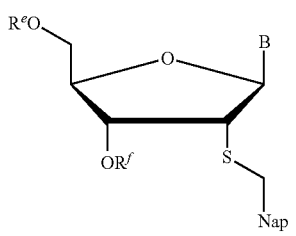

Formula 9

Exemplary working embodiments include the following compounds:

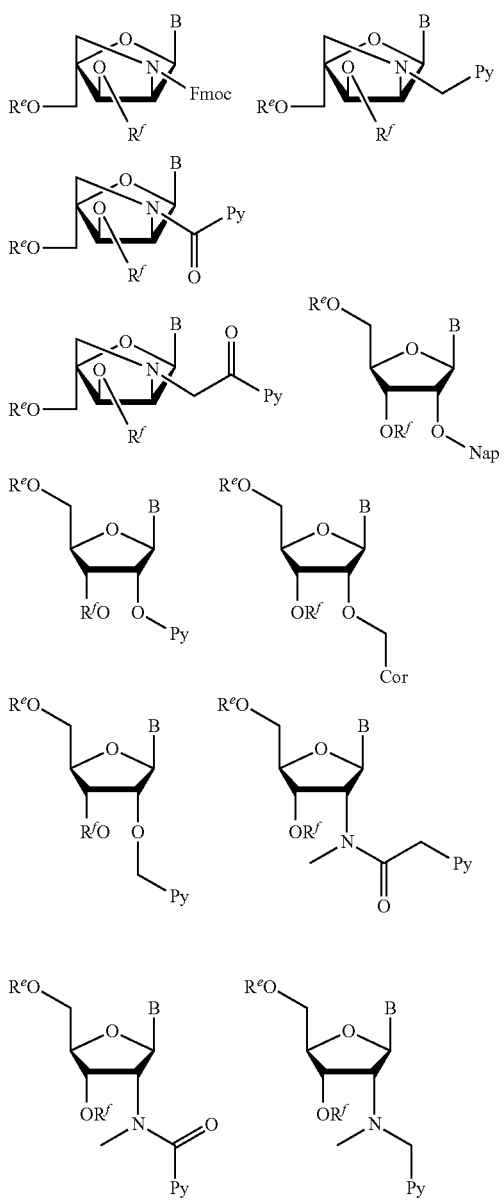
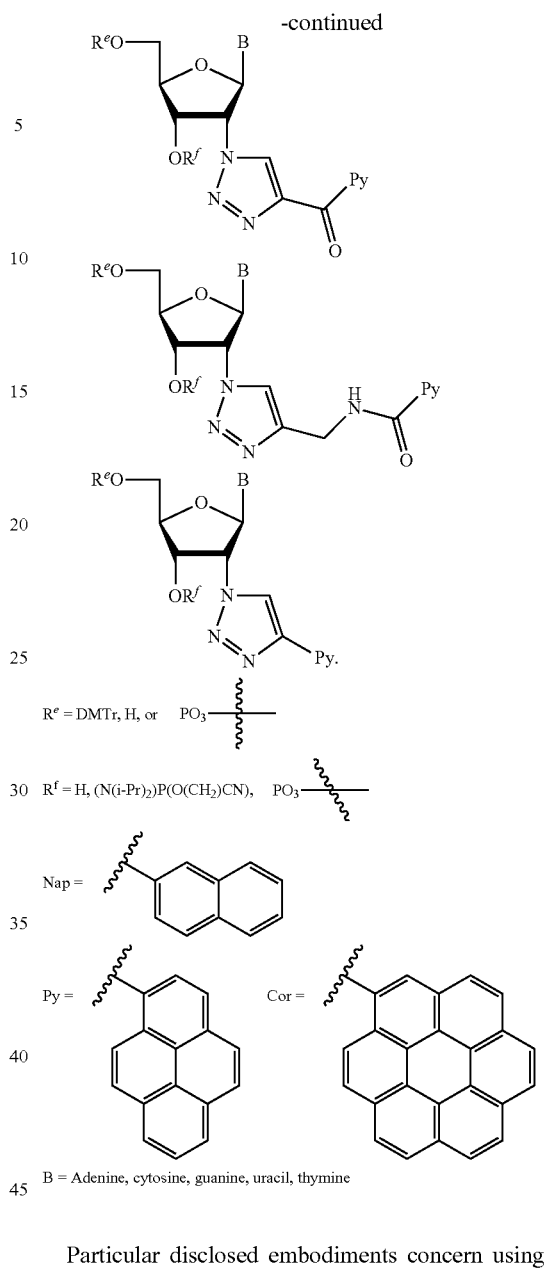
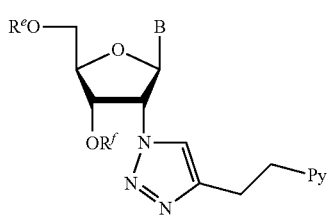
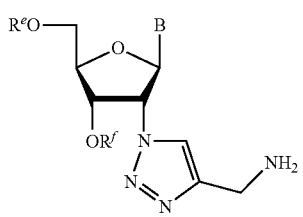

Particular disclosed embodiments concern using one or more monomers that do not participate in base pairing when either forming the probe or when the probe is reacted with a target. The monomers that do not participate in base pairing are herein referred to as "bulge monomers." In particular disclosed embodiments, the bulge monomers may comprise one or more aliphatic, abasic sites, heteroalkyl groups, natural/modified nucleotides, and combinations thereof. One or more of the bulge monomers may be included in the probe.

B. Single-Stranded Probe Precursor

Particular disclosed embodiments concern a single-stranded probe precursor wherein one or more of the disclosed monomers are contained within a single-stranded oligonucleotide. In certain disclosed embodiments, the single-stranded probe precursor may comprise one or more monomers arranged sequentially or in a manner wherein one or more natural or non-natural nucleotides are located between two or more monomers.

In particular disclosed embodiments, a single-stranded probe may serve as a precursor to a duplex comprising one or more of the disclosed monomers, or it may be used in the disclosed method discussed herein. Certain disclosed embodiments concern a single-stranded probe having a general Formula 9, illustrated below. The disclosed single-stranded probe precursor may comprise locked monomers, unlocked monomers, or combinations thereof.

$$5'(B_1B_2 \ldots B_m)(\underline{X}A)(B_1B_2 \ldots B_n)_f(\underline{X}A)(B_1B_2 \ldots B_o)(\underline{X}A)_g(B_1B_2 \ldots B_p)(\underline{X}A)_h(B_1B_2 \ldots B_q)(\underline{X}A)_i(B_1B_2 \ldots B_r)(XV)_j(B_1B_2 \ldots B_s)$$ Formula 9

With reference to Formula 9, $B_1B_2$, $B_{m-s}$, may be any natural or non-natural nucleotide presently known or discovered in the future, wherein m-s may range from zero to about 28. In particular disclosed embodiments, f, g, h, i and j may range from 0 to 10, more typically 0 to 5, and even more typically 0 to 1. Each X independently may be selected from any of the disclosed monomers and A may be a Watson-Crick base pairing nucleotide, or derivative thereof, which is capable of coupling with a complementary Watson-Crick base pairing nucleotide, or derivative thereof, in a target. In particular disclosed embodiments, each X independently may be a monomer having any one of formulas 1-7 and A may be selected from uracil, adenine, guanine, thymine, cytosine, and derivatives thereof. In particular disclosed embodiments, the single-stranded probe precursor may have a Formula 9 wherein the variables are defined according to any one of the following: m=2, n=5, o=p=q=r=s=0, f=g=h=i=j=0, $\underline{X}$ is any one of the disclosed monomers comprising a uracil nucleobase, and A is adenin-9-yl DNA nucleotide; m=4, n=3, o=p=q=r=s=0, f=g=h=i=j=0, $\underline{X}$ is any one of the disclosed monomers comprising a uracil nucleobase, and A is adenin-9-yl DNA nucleotide; m=2, n=9, o=p=q=r=s=0, f=g=h=i=j=0, $\underline{X}$ is any one of the disclosed monomers comprising a uracil nucleobase, and A is adenin-9-yl DNA nucleotide; m=4, n=7, o=p=q=r=s=0, f=g=h=i=j=0, $\underline{X}$ is any one of the disclosed monomers comprising a uracil nucleobase, and A is adenin-9-yl DNA nucleotide; m=6, n=5, o=p=q=r=s=0, f=g=h=i=j=0, $\underline{X}$ is any one of the disclosed monomers comprising a uracil nucleobase, and A is adenin-9-yl DNA nucleotide; m=8, n=3, o=p=q=r=s=0, f=g=h=i=j=0, $\underline{X}$ is any one of the disclosed monomers comprising a uracil nucleobase, and A is adenin-9-yl DNA nucleotide; m=2, n=0, o=7, p=q=r=s=0, f=1, g=h=i=j=0, $\underline{X}$ is any one of the disclosed monomers comprising a uracil nucleobase, and A is adenin-9-yl DNA nucleotide; m=2, n=2, o=5, p=q=r=s=0, f=1, g=h=i=j=0, $\underline{X}$ is any one of the disclosed monomers comprising a uracil nucleobase, and A is adenin-9-yl DNA nucleotide; m=2, n=4, o=3, p=q=r=s=0, f=1, g=h=i=j=0, $\underline{X}$ is any one of the disclosed monomers comprising a uracil nucleobase, and A is adenin-9-yl DNA nucleotide; m=2, n=o=p=q=r=s=0, f=g=h=1, i=j=0, $\underline{X}$ is any one of the disclosed monomers comprising a uracil nucleobase, and A is adenin-9-yl DNA nucleotide; m=2, n=13, o=p=q=r=s=0, f=g=h=i=j=0, $\underline{X}$ is any one of the disclosed monomers comprising a uracil nucleobase, and A is adenin-9-yl DNA nucleotide; m=2, n=0, o=11, p=q=r=s=0, f=1, g=h=i=j=0, $\underline{X}$ is any one of the disclosed monomers comprising a uracil nucleobase, and A is adenin-9-yl DNA nucleotide; m=2, n=7, o=4, p=q=r=s=0, f=1, g=h=i=j=0, $\underline{X}$ is any one of the disclosed monomers comprising a uracil nucleobase, and A is adenin-9-yl DNA nucleotide; m=4, n=3, o=p=q=r=s=0, f=g=h=i=j=0, $\underline{X}$ is any one of the disclosed monomers comprising an adenine nucleobase, and A is thymin-1-yl DNA nucleotide; m=4, n=3, o=p=q=r=s=0, f=g=h=i=j=0, $\underline{X}$ is any one of the disclosed monomers comprising a cytosine nucleobase, and A is guanin-9-yl DNA nucleotide; m=4, n=3, o=p=q=r=s=0, f=g=h=i=j=0, $\underline{X}$ is any one of the disclosed monomers comprising a guanine nucleobase, and A is cytosin-1-yl DNA nucleotide; m=4, n=3, o=p=q=r=s=0, f=g=h=i=j=0, $\underline{X}$ is any one of the disclosed monomers comprising an adenine nucleobase, and A is a guanin-9-yl DNA nucleotide; and m=4, n=3, o=p=q=r=s=0, f=g=h=i=j=0, $\underline{X}$ is any one of the disclosed monomers comprising an cytosine nucleobase, and A is an adenin-9-yl DNA nucleotide.

One or more bulge monomers also may be inserted at any position within a single stranded or double stranded probe. Probes may be additionally modified with one or more non-pairing modifications (a non-pairing modification is anything that can be incorporated internally within an oligonucleotide), which serves to decrease the thermostability of the probe, which facilitates the dsDNA-recognition reaction. The following provides examples of structures of non-pairing bulges that have been incorporated into disclosed probe embodiments.

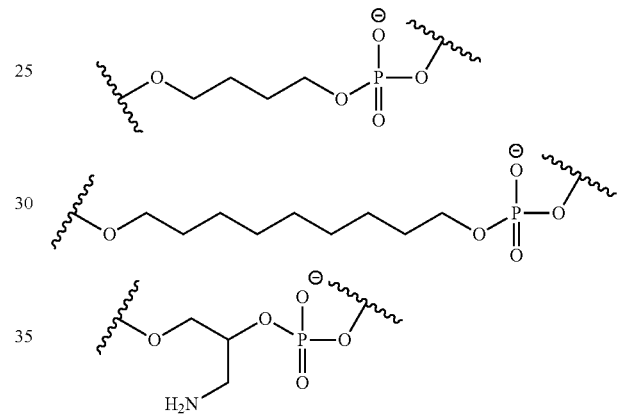

C. Probe Duplex

Particular disclosed embodiments concern a probe that can be used to identify, locate, bind, and/or modify a target. The probe may be a duplex comprising two strands of oligonucleotides comprising one or more pairs of the disclosed monomers. In particular disclosed embodiments, the one or more pairs of the disclosed monomers are arranged in a manner that substantially decrease the duplex's thermal stability, thereby providing the probe with the ability to bind to the target. Without being limited to a single theory of operation, it is currently believed that arranging the monomers in the particular manner disclosed herein provides the probe with sufficient energy to dissociate (or denature) into two strands that then couple with the target (FIG. 1).

Figure 2:
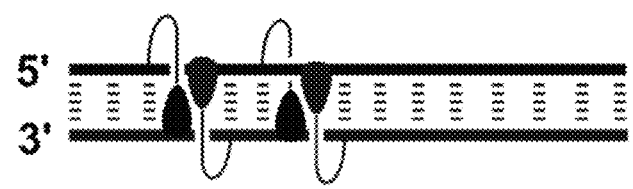
FIG. 2 is an image of an embodiment of the disclosed probe.

The probe may comprise more than one pairs of monomers; for example, the probe may comprise anywhere from 1 pair of monomers to about 5 pairs of monomers. In particular disclosed embodiments, a pair of monomers can comprise two monomers, having any of the formulas disclosed herein, that are located on opposite strands of the probe (e.g. opposite strands of the duplex). In particular disclosed embodiments, a first monomer may be positioned at any location on one of the probe strands, with the second monomer of the pair being positioned at a particular location relative to the first monomer on the other probe strand. Certain disclosed embodiments concern a probe having one or more pairs of monomers arranged in a (+/−)n zipper arrangement, wherein n can range from 0 to about 10; more typically from 0 to about 3; even more typically from at least 1 to about 2. Particular disclosed embodiments concern a probe having at least one pair of monomers arranged in a +n zipper arrangement. Without being limited to a particular theory of operation, it currently is believed that certain arrangements of the interstrand monomers result in destabilization of the probe, such as illustrated in FIGS. 1-2. In particular disclosed embodiments, the pair of monomers may be arranged in a −n zipper arrangement Exemplary embodiments of the disclosed probe typically comprise a pair of monomers comprising a first monomer and a second monomer arranged in a (+1) interstrand zipper arrangement. Other exemplary embodiments concern a probe comprising two pairs of monomers, with the first monomer and the second monomer of each pair being arranged in a (+1) interstrand zipper arrangement and each pair of monomers being separated by at least 0 to about 10 natural or non-natural nucleotides or bulge monomers.

Particular disclosed embodiments of the probe may have a Formula 10, illustrated below. The disclosed probe may comprise locked monomers, unlocked monomers, and combinations thereof.

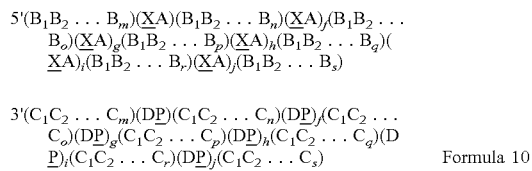

$5'(B_1B_2 \ldots B_m)(\underline{X}A)(B_1B_2 \ldots B_n)(\underline{X}A)_f(B_1B_2 \ldots B_o)(\underline{X}A)_g(B_1B_2 \ldots B_p)(\underline{X}A)_h(B_1B_2 \ldots B_q)(\underline{X}A)_i(B_1B_2 \ldots B_r)(\underline{X}A)_j(B_1B_2 \ldots B_s)$ $3'(C_1C_2 \ldots C_m)(D\underline{P})(C_1C_2 \ldots C_n)(D\underline{P})_f(C_1C_2 \ldots C_o)(D\underline{P})_g(C_1C_2 \ldots C_p)(D\underline{P})_h(C_1C_2 \ldots C_q)(D\underline{P})_i(C_1C_2 \ldots C_r)(D\underline{P})_j(C_1C_2 \ldots C_s)$ Formula 10

With reference to Formula 10, $B_1, B_2 \ldots B_{m-s}$ may be any natural or non-natural nucleotide, presently known or discovered in the future, wherein m-s may range from zero to about 28. In particular disclosed embodiments, f, g, h, i and j may range from 0 to 1,000, such as 0 to 900, such as 0 to 800, such as 0 to 700, such as 0 to 600, such as 0 to 500, such as 0 to 400, such as 0 to 300, such as 0 to 200, such as 0 to 100, such as 0 to 50, typically 0 to 10, and even more typically 0-5 $\underline{X}$ may be selected from any of the disclosed monomers and A may be a Watson-Crick base pairing nucleotide, or derivative thereof, or another disclosed monomer, which is capable of coupling with a complementary Watson-Crick base pairing nucleotide, or derivative thereof, in a target. In particular disclosed embodiments, $\underline{X}$ may be a monomer having any one of Formulas 1-7, and A may be selected from nucleotides with uracil, adenine, guanine, thymine or cytosine nucleobases, or nucleotides with pseudocomplementary nucleobases (e.g., 2-thiouracil, 2,6-diaminopurine, inosine, 3-pyrrolo-[2,3-d]-pyrimidine-2-(3H)-one). C may be any natural or non-natural nucleotide, presently known or discovered in the future, that is capable of Watson-Crick base pairing with any one of $B_1, B_2 \ldots B_{m-s}$. "B" and "C" also can be pseudocomplementary base pairs that do not form strong (or any base pairs); $\underline{P}$ may be selected from any of the disclosed monomers, and D may be a Watson-Crick base pairing nucleotide, or derivative thereof, or another disclosed monomer, which is capable of coupling with a complementary Watson-Crick base pairing nucleotide, or derivative thereof, in a target. In particular disclosed embodiments, $\underline{P}$ may be a monomer having any one of Formulas 1-7, and D may be selected from uracil, adenine, guanine, thymine, and cytosine.

Particular disclosed embodiments concern a probe having a Formula 10, wherein the variables are defined according to any one of the following: m=2, n=5, o=p=q=r=s=0, f=g=h=i=j=0, $\underline{X}=\underline{P}$ are monomers with a uracil nucleobase, and V=Y are adenin-9-yl DNA nucleotide; m=4, n=3, o=p=q=r=s=0, f=g=h=i=j=0, $\underline{X}=\underline{P}$ are monomers with a uracil nucleobase, and V=Y are adenin-9-yl DNA nucleotide; m=2, n=9, o=p=q=r=s=0, f=g=h=i=j=0, $\underline{X}=\underline{P}$ are monomers with a uracil nucleobase, and V=Y are adenin-9-yl DNA nucleotide; m=4, n=7, o=p=q=r=s=0, f=g=h=i=j=0, $\underline{X}=\underline{P}$ are monomers with a uracil nucleobase, and V=Y are adenin-9-yl DNA nucleotide; m=6, n=5, o=p=q=r=s=0, f=g=h=i=j=0, $\underline{X}=\underline{P}$ are monomers with a uracil nucleobase, and V=Y are adenin-9-yl DNA nucleotide; m=8, n=3, o=p=q=r=s=0, f=g=h=i=j=0, $\underline{X}=\underline{P}$ are monomers with a uracil nucleobase, and V=Y are adenin-9-yl DNA nucleotide; m=2, n=0, o=7, p=q=r=s=0, f=1, g=h=i=j=0, $\underline{X}=\underline{P}$ are monomers with a uracil nucleobase, and V=Y are adenin-9-yl DNA nucleotide; m=2, n=2, o=5, p=q=r=s=0, f=1, g=h=i=j=0, $\underline{X}=\underline{P}$ are monomers with a uracil nucleobase, and V=Y are adenin-9-yl DNA nucleotide; m=2, n=4, o=3, p=q=r=s=0, f=1, g=h=i=j=0, $\underline{X}=\underline{P}$ are monomers with a uracil nucleobase, and V=Y are adenin-9-yl DNA nucleotide; m=2, n=o=p=q=r=s=0, f=g=h=1, i=j=0, $\underline{X}=\underline{P}$ are monomers with a uracil nucleobase, and V=Y are adenin-9-yl DNA nucleotide; m=2, n=13, o=p=q=r=s=0, f=g=h=i=j=0, $\underline{X}=\underline{P}$ are monomers with a uracil nucleobase, and V=Y are adenin-9-yl DNA nucleotide; m=2, n=0, o=11, p=q=r=s=0, f=1, g=h=i=j=0, $\underline{X}=\underline{P}$ are monomers with a uracil nucleobase, and V=Y are adenin-9-yl DNA nucleotide; m=2, n=7, o=4, p=q=r=s=0, f=1, g=h=i=j=0, $\underline{X}=\underline{P}$ are monomers with a uracil nucleobase, and V=Y are adenin-9-yl DNA nucleotide; m=4, n=3, o=p=q=r=s=0, f=g=h=i=j=0, $\underline{X}=\underline{P}$ are monomers with an adenine nucleobase, and V=Y are thymin-1-yl DNA nucleotide; m=4, n=3, o=p=q=r=s=0, f=g=h=i=j=0, $\underline{X}=\underline{W}$ are monomers with a cytosine nucleobase, and V=Y are guanin-9-yl DNA nucleotide; m=4, n=3, o=p=q=r=s=0, f=g=h=i=j=0, $\underline{X}=\underline{W}$ are monomers with a guanine nucleobase, and V=Y are cytosin-1-yl DNA nucleotide; m=4, n=3, o=p=q=r=s=0, f=g=h=i=j=0, $\underline{X}$ is a monomer with an adenine nucleobase, $\underline{W}$ is a monomer with a cytosine nucleobase, Y is a thymin-1-yl DNA nucleotide and V is a guanin-9-yl DNA nucleotide; m=4, n=3, o=p=q=r=s=0, f=g=h=i=j=0, $\underline{X}$ is a monomer with a cytosine nucleobase, $\underline{W}$ is a monomer with a thymine nucleobase, Y is a guanin-9-yl DNA nucleotide and V is an adenin-9-yl DNA nucleotide.

Figure 3A:
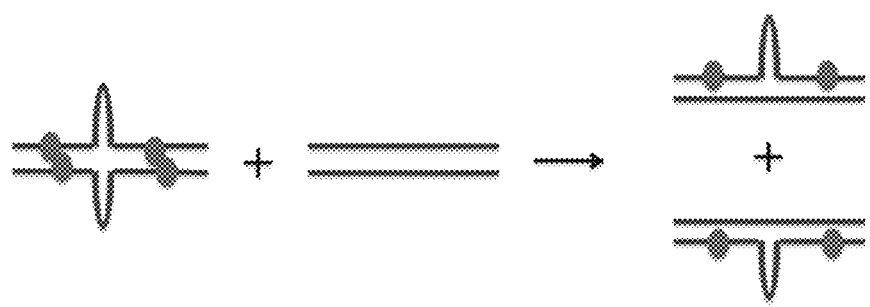
FIG. 3A is a schematic drawing illustrating the concept of using bulge monomers.

FIGS. 3A and B illustrates the concept of using bulge monomers. With reference to FIGS. 3A and B green denotes disclosed the intercalator-functionalized monomers; red represents a non-nucleosidic linker. One or more bulge monomers can be added to any of the embodiments defined by the above formula.

Exemplary embodiments of the disclosed probe are provided in Table 1. A person of ordinary skill in the art will recognize that any of the disclosed embodiments of the probe can be made from two single-stranded precursors that are combined (hybridized) to form the probe. The embodiments disclosed in Table 1 concern a probe wherein $\underline{X}$ is a monomer disclosed herein and $R^4$ is defined as a uracil or thymine nucleobase; however a person of ordinary skill in the art would recognize that any of the disclosed monomers may be used.

TABLE 1

Exemplary Embodiments of Certain Disclosed Probes and Corresponding Target

| Probe | Target region |
|---|---|
| 5'-d(GTG A$\underline{X}$A TGC) | 5'-GTG ATA TGC |
| 3'-d(CAC TA$\underline{X}$ ACG | 3'-CAC TAT ACG |

TABLE 1-continued

Exemplary Embodiments of Certain Disclosed Probes and Corresponding Target

| Probe | Target region |
|---|---|
| 5'-d(GGX ATA TAT AGG C) (SEQ ID NO: 12)<br>3'-d(CCA XAT ATA TCC G) (SEQ ID NO: 13) | 5'-GGT ATA TAT AGG C (SEQ ID NO: 34)<br>3'-CCA TAT ATA TCC G (SEQ ID NO: 35) |
| 5'-d(GGT AXA TAT AGG C) (SEQ ID NO: 14)<br>3'-d(CCA TAX ATA TCC G) (SEQ ID NO: 15) | 5'-GGT ATA TAT AGG C (SEQ ID NO: 34)<br>3'-CCA TAT ATA TCC G (SEQ ID NO: 35) |
| 5'-d(GGT ATA XAT AGG C) (SEQ ID NO: 16)<br>3'-d(CCA TAT AXA TCC G) (SEQ ID NO: 17) | 5'-GGT ATA TAT AGG C (SEQ ID NO: 34)<br>3'-CCA TAT ATA TCC G (SEQ ID NO: 35) |
| 5'-d(GGT ATA TAX AGG C) (SEQ ID NO: 18)<br>3'-d(CCA TAT ATA XCC G) (SEQ ID NO: 10) | 5'-GGT ATA TAT AGG C (SEQ ID NO: 34)<br>3'-CCA TAT ATA TCC G (SEQ ID NO: 35) |
| 5'-d(GGX AXA TAT AGG C) (SEQ ID NO: 20)<br>3'-d(CCA XAX ATA TCC G) (SEQ ID NO: 21) | 5'-GGT ATA TAT AGG C (SEQ ID NO: 34)<br>3'-CCA TAT ATA TCC G (SEQ ID NO: 35) |
| 5'-d(GGX ATA XAT AGG C) (SEQ ID NO: 22)<br>3'-d(CCA XAT AXA TCC G) (SEQ ID NO: 23) | 5'-GGT ATA TAT AGG C (SEQ ID NO: 34)<br>3'-CCA TAT ATA TCC G (SEQ ID NO: 35) |
| 5'-d(GGX ATA TAX AGG C) (SEQ ID NO: 24)<br>3'-d(CCA XAT ATA XCC G) (SEQ ID NO: 25) | 5'-GGT ATA TAT AGG C (SEQ ID NO: 34)<br>3'-CCA TAT ATA TCC G (SEQ ID NO: 35) |
| 5'-d(G GXA XAT AAG CAG C) (SEQ ID NO: 26)<br>3'-d(C CAX AX A TTC GTC G) (SEQ ID NO: 27) | 5'-G GTA TAT AAG CAG C (SEQ ID NO: 36)<br>3'-C CAT ATA TTC GTC G (SEQ ID NO: 37) |
| 5'-GGT AXA XAT AGG C (SEQ ID NO: 28)<br>3'-CCA TAX AXA TCC G (SEQ ID NO: 29) | 5'-GGT ATA TAT AGG C (SEQ ID NO: 34)<br>3'-CCA TAT ATA TCC G (SEQ ID NO: 35) |
| 5'-GGT ATA XAX AGG C (SEQ ID NO: 30)<br>3'-CCA TAT AXA XCC G (SEQ ID NO: 31) | 5'-GGT ATA TAT AGG C (SEQ ID NO: 34)<br>3'-CCA TAT ATA TCC G (SEQ ID NO: 35) |
| 5'-GGX AXA XAG AGG C (SEQ ID NO: 32)<br>3'-CCA XAX AXA XCC G (SEQ ID NO: 33) | 5'-GGT ATA TAT AGG C (SEQ ID NO: 34)<br>3'-CCA TAT ATA TCC G (SEQ ID NO: 35) |

Additional exemplary embodiments are disclosed in Table 2. The embodiments disclosed in Table 2 concern a probe wherein the monomer in each strand (e.g. the strands designated as 5' and 3') may have any one of formulas 1-7, wherein the R⁴ moiety is selected from adenine (A), cytosine (C), guanine (G), uracil (U), or thymine (T).

TABLE 2

Exemplary Embodiments of Certain Disclosed Probes and Corresponding Target Regions

| Probe | Target region |
|---|---|
| 5'-d(GTG AAT TGC)<br>3'-d(CAC TTA ACG) | 5'-GTG AAT TGC<br>3'-CAC TTA ACG |
| 5'-d(GTG AAG TGC)<br>3'-d(CAC TTC ACG) | 5'-GTG AAG TGC<br>3'-CAC TTC ACG |
| 5'-d(GTG AAC TGC)<br>3'-d(CAC TTG ACG) | 5'-GTG AAC TGC<br>3'-CAC TTG ACG |
| 5'-d(GTG ACG TGC)<br>3'-d(CAC TGC ACG) | 5'-GTG ACG TGC<br>3'-CAC TGC ACG |
| 5'-d(GTG ACC TGC)<br>3'-d(CAC TGG ACG) | 5'-GTG ACC TGC<br>3'-CAC TGG ACG |
| 5'-d(GTG ACA TGC)<br>3'-d(CAC TGT ACG) | 5'-GTG ACA TGC<br>3'-CAC TGT ACG |
| 5'-d(GTG AGC TGC)<br>3'-d(CAC TCG ACG) | 5'-GTG AGC TGC<br>3'-CAC TCG ACG |
| 5'-d(GTG AGA TGC)<br>3'-d(CAC TCT ACG) | 5'-GTG AGA TGC<br>3'-CAC TCT ACG |
| 5'-d(GTG ATT TGC)<br>3'-d(CAC TAA ACG) | 5'-GTG ATT TGC<br>3'-CAC TAA ACG |
| 5'-d(GTG ATA TGC)<br>3'-d(CAC TAT ACG) | 5'-GTG ATA TGC<br>3'-CAC TAT ACG |

Additional working embodiments of probes are provided below in Table 3 with 0-arrangements.

TABLE 3

Working Embodiments of Probes with 0-Arrangement

| Probe | Target Region |
|---|---|
| 5'-GGT ATA TAT AGG C (SEQ ID NO: 12)<br>3'-CCA TAT ATA TCC G (SEQ ID NO: 39) | 5'-GGT ATA TAT AGG C (SEQ ID NO: 34)<br>3'-CCA TAT ATA TCC G (SEQ ID NO: 35) |
| 5'-GGT ATA TAT AGG C (SEQ ID NO: 14)<br>3'-CCA TAT ATA TCC G (SEQ ID NO: 41) | 5'-GGT ATA TAT AGG C (SEQ ID NO: 34)<br>3'-CCA TAT ATA TCC G (SEQ ID NO: 35) |
| 5'-GGT ATA TAT AGG C (SEQ ID NO: 16)<br>3'-CCA TAT ATA TCC G (SEQ ID NO: 43) | 5'-GGT ATA TAT AGG C (SEQ ID NO: 34)<br>3'-CCA TAT ATA TCC G (SEQ ID NO: 35) |
| 5'-GGT ATA TAT AGG C (SEQ ID NO: 18)<br>3'-CCA TAT ATA TCC G (SEQ ID NO: 45) | 5'-GGT ATA TAT AGG C (SEQ ID NO: 34)<br>3'-CCA TAT ATA TCC G (SEQ ID NO: 35) |
| 5'-GGT ATA TAT AGG C (SEQ ID NO: 20)<br>3'-CCA TAT ATA TCC G (SEQ ID NO: 47) | 5'-GGT ATA TAT AGG C (SEQ ID NO: 34)<br>3'-CCA TAT ATA TCC G (SEQ ID NO: 35) |
| 5'-GGT ATA TAT AGG C (SEQ ID NO: 22)<br>3'-CCA TAT ATA TCC G (SEQ ID NO: 49) | 5'-GGT ATA TAT AGG C (SEQ ID NO: 34)<br>3'-CCA TAT ATA TCC G (SEQ ID NO: 35) |
| 5'-GGT ATA TAT AGG C (SEQ ID NO: 24)<br>3'-CCA TAT ATA TCC G (SEQ ID NO: 51) | 5'-GGT ATA TAT AGG C (SEQ ID NO: 34)<br>3'-CCA TAT ATA TCC G (SEQ ID NO: 35) |
| 5'-GGT ATA TAT AGG C (SEQ ID NO: 28) | 5'-GGT ATA TAT AGG C (SEQ ID NO: 34) |

TABLE 3-continued

Working Embodiments of Probes with 0-Arrangement

| Probe | Target Region |
|---|---|
| 3'-CCA TAT ATA TCC G (SEQ ID NO: 53) | 3'-CCA TAT ATA TCC G (SEQ ID NO: 35) |
| 5'-GGT ATA TAT AGG C (SEQ ID NO: 30) 3'-CCA TAT ATA TCC G (SEQ ID NO: 55) | 5'-GGT ATA TAT AGG C (SEQ ID NO: 34) 3'-CCA TAT ATA TCC G (SEQ ID NO: 35) |
| 5'-GGT ATA TAT AGG C (SEQ ID NO: 32) 3'-CCA TAT ATA TCC G (SEQ ID NO: 57) | 5'-GGT ATA TAT AGG C (SEQ ID NO: 34) 3'-CCA TAT ATA TCC G (SEQ ID NO: 35) |

Tables 4-6 outline additional working embodiments of certain exemplary probes targeting different DNA regions, i.e., second insulin [INSB], PPAR gamma and CEBP promotors.

TABLE 4

Probes Targeting Second Insulin Promoter [INSB]

| Probe | Target region |
|---|---|
| 5'-G GTA TAT AAG CAG CAC A (SEQ ID NO: 58) 3'-C CAT ATA TTC GTC GTG T (SEQ ID NO: 59) | 5'-G GTA TAT AAG CAG CAC A (SEQ ID NO: 66) 3'-C CAT ATA TTC GTC GTG T (SEQ ID NO: 67) |
| 5'-G GTA TAT AAG CAG CAC A (SEQ ID NO: 60) 3'-C CAT ATA TTC GTC GTG T (SEQ ID NO: 61) | 5'-G GTA TAT AAG CAG CAC A (SEQ ID NO: 66) 3'-C CAT ATA TTC GTC GTG T (SEQ ID NO: 67) |
| 5'-AGG AAG GTA TAT AAG CA (SEQ ID NO: 62) 3'-TCC TTC CAT ATA TTC GT (SEQ ID NO: 63) | 5'-AGG AAG GTA TAT AAG CA (SEQ ID NO: 68) 3'-TCC TTC CAT ATA TTC GT (SEQ ID NO: 69) |
| 5'-ACT ATA GAA TAC TCA AG (SEQ ID NO: 64) 3'-TGA TAT CTT ATG AGT TC (SEQ ID NO: 65) | 5'-ACT ATA GAA TAC TCA AG (SEQ ID NO: 70) 3'-TGA TAT CTT ATG AGT TC (SEQ ID NO: 71) |

TABLE 5

Additional Examples of Probes for PPAR Gamma

| Probe | Target region |
|---|---|
| 5'-CCC ACG TTA GCA GTT (SEQ ID NO: 72) 3'-GGG TGC AATCGT CAA (SEQ ID NO: 73) | 5'-CCC ACG TTA GCA GTT (SEQ ID NO: 86) 3'-GGG TGC AAT CGT CAA (SEQ ID NO: 87) |
| 5'-CCC ACG TTA GCA GTT (SEQ ID NO: 74) 3'-GGG TGC AAT CGT CAA (SEQ ID NO: 75) | 5'-CCC ACG TTA GCA GTT (SEQ ID NO: 86) 3'-GGG TGC AAT CGT CAA (SEQ ID NO: 87) |
| 5'-AGA CAA AAC ACC AGT (SEQ ID NO: 76) 3'-TCT GTT TTG TGG TCA (SEQ ID NO: 77) | 5'-AGA CAA AAC ACC AGT (SEQ ID NO: 88) 3'-TCT GTT TTG TGG TCA (SEQ ID NO: 89) |
| 5'-AGA CAA AAC ACC AGT (SEQ ID NO: 78) 3'-TCT GTT TTG TGG TCA (SEQ ID NO: 79) | 5'-AGA CAA AAC ACC AGT (SEQ ID NO: 88) 3'-TCT GTT TTG TGG TCA (SEQ ID NO: 89) |

TABLE 5-continued

Additional Examples of Probes for PPAR Gamma

| Probe | Target region |
|---|---|
| 5'-CTA CAT TGT CTC GCC (SEQ ID NO: 80) 3'-GAT GTA ACA GAG CGG (SEQ ID NO: 81) | 5'-CTA CAT TGT CTC GCC (SEQ ID NO: 90) 3'-GAT GTA ACA GAG CGG (SEQ ID NO: 91) |
| 5'-CTA CAT TGT CTC GCC (SEQ ID NO: 82) 3'-GAT GTA ACA GAG CGG (SEQ ID NO: 83) | 5'-CTA CAT TGT CTC GCC (SEQ ID NO: 90) 3'-GAT GTA ACA GAG CGG (SEQ ID NO: 91) |
| 5'-CGT CAT CGT GCT CGC (SEQ ID NO: 84) 3'-GCA GTA GCA CGA GCG (SEQ ID NO: 85) | 5'-CGT CAT CGT GCT CGC (SEQ ID NO: 93) 3'-GCA GTA GCA CGA GCG (SEQ ID NO: 93) |

TABLE 6

Additional Examples of Probes for CEBP

| Probe | Target region |
|---|---|
| 5'-CGG ACC ACG TGT GTG (SEQ ID NO: 94) 3'-GCC TGG TGC ACA CAC (SEQ ID NO: 95) | 5'-CGG ACC ACG TGT GTG (SEQ ID NO: 106) 3'-GCC TGG TGC ACA CAC (SEQ ID NO: 107) |
| 5'-CGG ACC ACG TGT GTG (SEQ ID NO: 96) 3'-GCC TGG TGC ACA CAC (SEQ ID NO: 97) | 5'-CGG ACC ACG TGT GTG (SEQ ID NO: 106) 3'-GCC TGG TGC ACA CAC (SEQ ID NO: 107) |
| 5'-GTC AGT GGG CGT TGC (SEQ ID NO: 98) 3'-CAG TCA CCC GCA ACG (SEQ ID NO: 99) | 5'-GTC AGT GGG CGT TGC (SEQ ID NO: 108) 3'-CAG TCA CCC GCA ACG (SEQ ID NO: 109) |
| 5'-GTC AGT GGG CGT TGC (SEQ ID NO: 100) 3'-CAG TCA CCC GCA ACG (SEQ ID NO: 101) | 5'-GTC AGT GGG CGT TGC (SEQ ID NO: 108) 3'-CAG TCA CCC GCA ACG (SEQ ID NO: 109) |
| 5'-CCT CTA TAA AAG CGG (SEQ ID NO: 102) 3'-GGA GAT ATT TTC GCC (SEQ ID NO: 103) | 5'-CCT CTA TAA AAG CGG (SEQ ID NO: 110) 3'-GGA GAT ATT TTC GCC (SEQ ID NO: 111) |
| 5'-CCT CTA TAA AAG CGG (SEQ ID NO: 104) 3'-GGA GAT ATT TTC GCC (SEQ ID NO: 105) | 5'-CCT CTA TAA AAG CGG (SEQ ID NO: 110) 3'-GGA GAT ATT TTC GCC (SEQ ID NO: 111) |

Additional working embodiments of probes that may be used for gender determination in animals, more commonly, in bovine, are shown in Table 7, where Cy3 is a Cy3 fluorophore; underlined A/C/G/T are monomers; and underlined B is a bulged (non-pairing) monomer.

TABLE 7

Bovine Series

| Probe | Target Region |
|---|---|
| 5'-AGC CCT GTG CCC TG (SEQ ID NO: 112) 3'-TCG GGA CAC GGG AC (SEQ ID NO: 113) | 5'-AGC CCT GTG CCC TG (SEQ ID NO: 130) 3'-TCG GGA CAC GGG AC (SEQ ID NO: 131) |
| 5'-CCT GTG CCC TG (SEQ ID NO: 114) 3'-GGA CAC GGG AC (SEQ ID NO: 115) | 5'-CCT GTG CCC TG (SEQ ID NO: 132) 3'-GGA CAC GGG AC (SEQ ID NO: 133) |

TABLE 7-continued

Bovine Series

| Probe | Target Region |
|---|---|
| 5'-CCT GTG CCC TG (SEQ ID NO: 116)<br>3'-GGA CAC GGG AC (SEQ ID NO: 117) | 5'-CCT GTG CCC TG (SEQ ID NO: 132)<br>3'-GGA CAC GGG AC (SEQ ID NO: 133) |
| 5'-AGC CCT GTG CCC TG (SEQ ID NO: 118)<br>3'-TCG GGA CAC GGG AC (SEQ ID NO: 119) | 5'-AGC CCT GTG CCC TG (SEQ ID NO: 130)<br>3'-TCG GGA CAC GGG AC (SEQ ID NO: 131) |
| 5'-CTG AAGC CCT GTG CCC TG (SEQ ID NO: 120)<br>3'-GAG TCG GGA CAC GGG AC (SEQ ID NO: 121) | 5'-CTG AGC CCT GTG CCC TG (SEQ ID NO: 134)<br>3'-GAG TCG GGA CAC GGG AC (SEQ ID NO: 135) |
| 5'-AGC CCT GTG CCC TG (SEQ ID NO: 122)<br>3'-TCG GGA CAC GGG AC (SEQ ID NO: 123) | 5'-AGC CCT GTG CCC TG (SEQ ID NO: 130)<br>3'-TCG GGA CAC GGG AC (SEQ ID NO: 131) |
| 5'-Cy3 AGC CCT GTG B CCC TG (SEQ ID NO: 124)<br>3'-TCG GGA CAC B GGG AC Cy3 (SEQ ID NO: 125) | 5'-AGC CCT GTG CCC TG (SEQ ID NO: 130)<br>3'-TCG GGA CAC GGG AC (SEQ ID NO: 131) |
| 5'Cy3 AGC CCT GTG BCCC TG (SEQ ID NO: 126)<br>3'-TCG GGA CAC GGG AC Cy3 (SEQ ID NO: 127) | 5'-AGC CCT GTG CCC TG (SEQ ID NO: 130)<br>3'-TCG GGA CAC GGG AC (SEQ ID NO: 131) |
| 5'-Cy3 AGC CCT GTG CCC TG (SEQ ID NO: 128)<br>3'-TCG GGA CAC B GGG AC Cy3 (SEQ ID NO: 129) | 5'-AGC CCT GTG CCC TG (SEQ ID NO: 130)<br>3'-TCG GGA CAC GGG AC (SEQ ID NO: 131) |

IV. Targets

Figure 18:
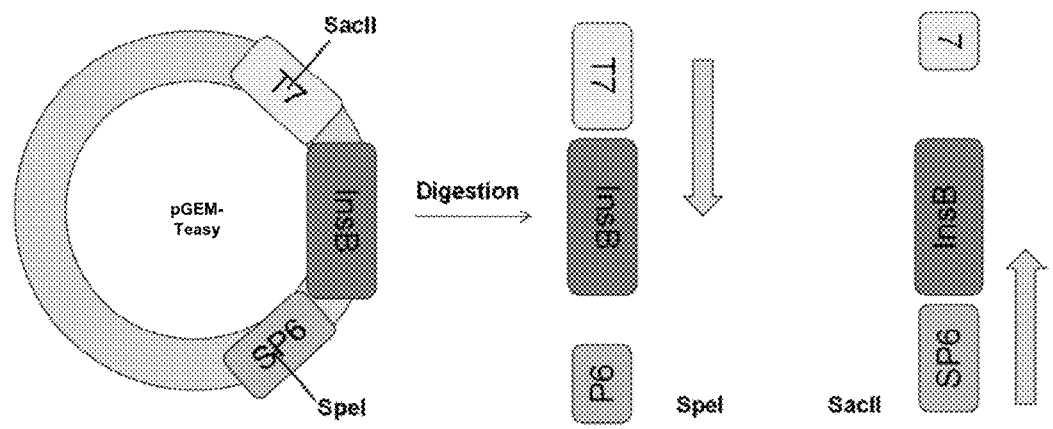
FIG. 18 is a schematic drawing of a target used in an exemplary method of using a disclosed probe.
Figure 19:
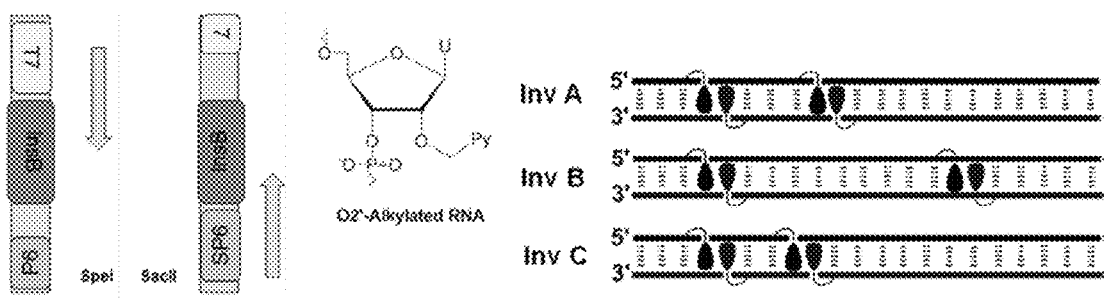
FIG. 19 is a schematic drawing of a target and exemplary embodiments of the disclosed probe used in an exemplary method of using the probe.
Figure 20:
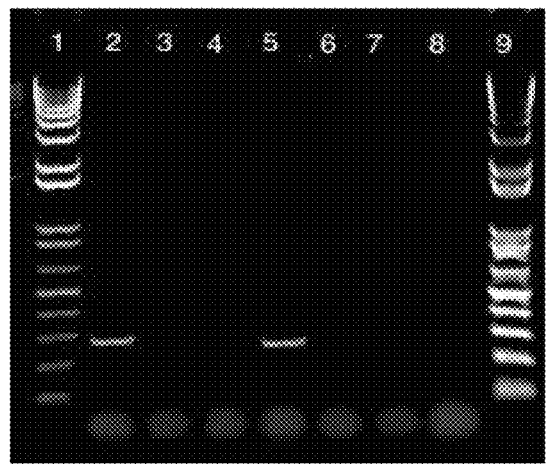
FIG. 20 is an image of a gel obtained using gel electrophoresis analysis of different exemplary embodiments of the probe and their ability to bind to a particular target.
Figure 21:
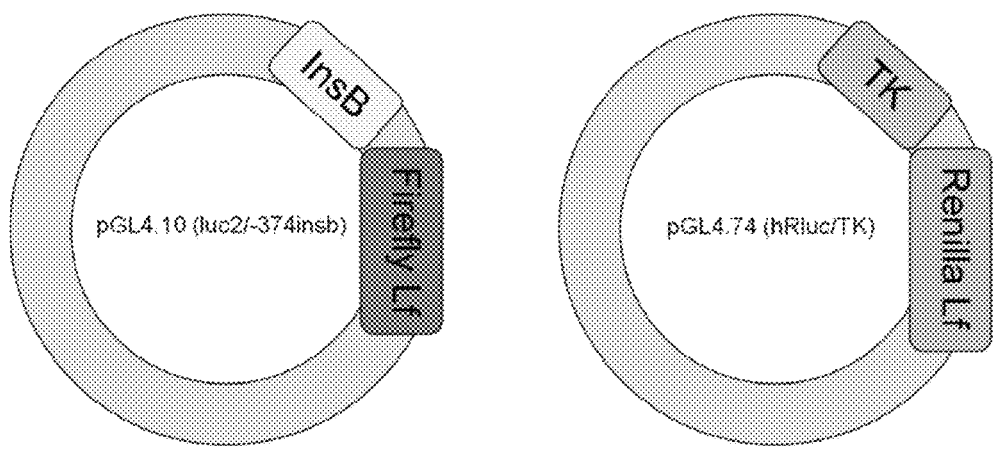
FIG. 21 is schematic drawing of a target used to analyze the ability of the disclosed probe to suppress gene expression.
Figure 22:
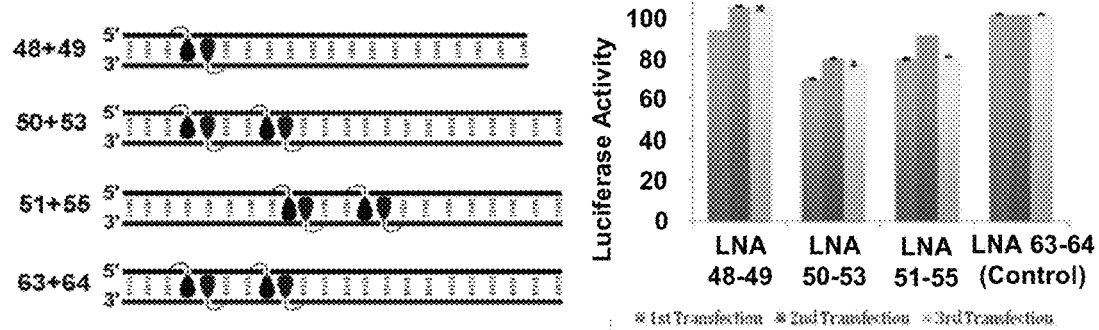
FIG. 22 is schematic drawing of exemplary embodiments of disclosed probes and the results obtained using such probes to suppress gene expression in a particular target.
Figure 23:
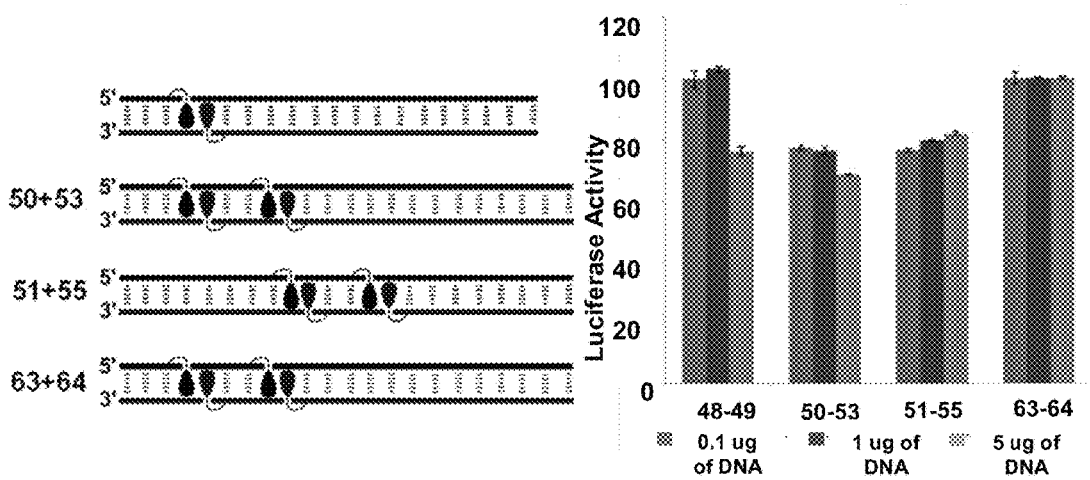
FIG. 23 is schematic drawing of the results obtained from a dose-dependent study using exemplary embodiments of the disclosed probe and a particular target.

Particular disclosed embodiments concern targeting and binding to a particular target using the disclosed probe. In particular disclosed embodiments, the target may be a nucleic acid, such as, but not limited to, single-stranded DNA (and derivatives thereof), double-stranded DNA (and derivatives thereof), and any combinations thereof. Particular disclosed embodiments concern targeting isosequential (relative to the probe) double stranded DNA target regions, including: stems of molecular beacons, target regions embedded within PCR amplicons, target regions embedded within circular or linearized plasmids, target regions embedded within genomic DNA (crude, purified, cell culture, in vivo, embryos, etc.), target regions embedded within microorganisms, and the like. This list of targets is meant to be exemplary and is not intended to be limiting. In particular disclosed embodiments, the target may be selected by identifying an RNA target, such as those pursued in antisense/siRNA/anti-miRNA clinical trials and pre-clinical trials (e.g. those used in modulation of gene expression and/or identification of biomarkers) and design a target comprising the corresponding DNA to this particular RNA target. Solely by way of example, specific targets include linearized plasmids (e.g. against T7 promotor, as illustrated by FIGS. 18-20); circular plasmids (e.g. against insulin B promotor in circular plasmids, as illustrated by FIGS. 21-23); genomic DNA; structured dsDNA targets (FIGS. 24-26 and FIGS. 30-42).

A target nucleic acid sequence can vary substantially in size. Without limitation, the nucleic acid sequence can have a variable number of nucleic acid residues. For example a target nucleic acid sequence can have at least about 2 nucleic acid residues, typically at least about 10 nucleic acid residues, or at least about 20, 30, 50, 100, 150, 500, 1000 residues.

In specific, non-limiting examples, a protein is produced by a target nucleic acid sequence (e.g., genomic target nucleic acid sequence) associated with a neoplasm (for example, a cancer). Numerous chromosome abnormalities (including translocations and other rearrangements, amplification or deletion) have been identified in neoplastic cells, especially in cancer cells, such as B cell and T cell leukemias, lymphomas, breast cancer, colon cancer, neurological cancers and the like. Therefore, in some examples, at least a portion of a protein is produced by a nucleic acid sequence (e.g., genomic target nucleic acid sequence) that is amplified or deleted in at least a subset of cells in a sample.

Oncogenes are known to be responsible for several human malignancies. For example, chromosomal rearrangements involving the SYT gene located in the breakpoint region of chromosome 18q1.2 are common among synovial sarcoma soft tissue tumors. The t(18q1.2) translocation can be identified, for example, using the disclosed probe. In other examples, a protein produced from a nucleic acid sequence (e.g., genomic target nucleic acid sequence) is selected that is a tumor suppressor gene that is deleted (lost) in malignant cells. In particular disclosed embodiments, this type of target may also be detected, identified, the expression of the gene reduced and/or the gene modified using disclosed probe embodiments. For example, the p16 region (including D9S1749, D9S1747, p16(INK4 Å), p14(ARF), D9S1748, p15(INK4B), and D9S1752) located on chromosome 9p21 is deleted in certain bladder cancers. Chromosomal deletions involving the distal region of the short arm of chromosome 1 (that encompasses, for example, SHGC57243, TP73, EGFL3, ABL2, ANGPTL1, and SHGC-1322), and the pericentromeric region (e.g., 19p13-19q13) of chromosome 19 (that encompasses, for example, MAN2B1, ZNF443, ZNF44, CRX, GLTSCR2, and GLTSCR1) are characteristic molecular features of certain types of solid tumors of the central nervous system.

The aforementioned examples are provided solely for purpose of illustration and are not intended to be limiting. Numerous other cytogenetic abnormalities that correlate with neoplastic transformation and/or growth are known to those of ordinary skill in the art. Target proteins that are produced by nucleic acid sequences (e.g., genomic target nucleic acid sequences), which have been correlated with neoplastic transformation and which are useful in the disclosed methods, also include the EGFR gene (7p12; e.g., GENBANK™ Accession No. NC_000007, nucleotides 55054219-55242525), the C-MYC gene (8q24.21; e.g., GENBANK™ Accession No. NC_000008, nucleotides 128817498-128822856), D5S271 (5p15.2), lipoprotein lipase (LPL) gene (8p22; e.g., GENBANK™ Accession No. NC_000008, nucleotides 19841058-19869049), RB1 (13q14; e.g., GENBANK™ Accession No. NC_000013, nucleotides 47775912-47954023), p53 (17p13.1; e.g., GENBANK™ Accession No. NC_000017, complement, nucleotides 7512464-7531642)), N-MYC (2p24; e.g., GENBANK™ Accession No. NC_000002, complement, nucleotides 151835231-151854620), CHOP (12q13; e.g., GENBANK™ Accession No. NC_000012, complement, nucleotides 56196638-56200567), FUS (16p11.2; e.g., GENBANK™ Accession No. NC_000016, nucleotides 31098954-31110601), FKHR (13p14; e.g., GENBANK™ Accession No. NC_000013, complement, nucleotides 40027817-40138734), as well as, for example: ALK (2p23;

e.g., GENBANK™ Accession No. NC_000002, complement, nucleotides 29269144-29997936), Ig heavy chain, CCND1 (11q13; e.g., GENBANK™ Accession No. NC_000011, nucleotides 69165054.69178423), BCL2 (18q21.3; e.g., GENBANK™ Accession No. NC_000018, complement, nucleotides 58941559-59137593), BCL6 (3q27; e.g., GENBANK™ Accession No. NC_000003, complement, nucleotides 188921859-188946169), MALF1, AP1 (1p32-p31; e.g., GENBANK™ Accession No. NC_000001, complement, nucleotides 59019051-59022373), TOP2A (17q21-q22; e.g., GENBANK™ Accession No. NC_000017, complement, nucleotides 35798321-35827695), TMPRSS (21q22.3; e.g., GENBANK™ Accession No. NC_000021, complement, nucleotides 41758351-41801948), ERG (21q22.3; e.g., GENBANK™ Accession No. NC_000021, complement, nucleotides 38675671-38955488); ETV1 (7p21.3; e.g., GENBANK™ Accession No. NC_000007, complement, nucleotides 13897379-13995289), EWS (22q12.2; e.g., GENBANK™ Accession No. NC_000022, nucleotides 27994271-28026505); FLI1 (11q24.1-q24.3; e.g., GENBANK™ Accession No. NC_000011, nucleotides 128069199-128187521), PAX3 (2q35-q37; e.g., GENBANK™ Accession No. NC_000002, complement, nucleotides 222772851-222871944), PAX7 (1p36.2-p36.12; e.g., GENBANK™ Accession No. NC_000001, nucleotides 18830087-18935219), PTEN (10q23.3; e.g., GENBANK™ Accession No. NC_000010, nucleotides 89613175-89716382), AKT2 (19q13.1-q13.2; e.g., GENBANK™ Accession No. NC_000019, complement, nucleotides 45431556-45483036), MYCL1 (1p34.2; e.g., GENBANK™ Accession No. NC_000001, complement, nucleotides 40133685-40140274), REL (2p13-p12; e.g., GENBANK™ Accession No. NC_000002, nucleotides 60962256-61003682) and CSF1R (5q33-q35; e.g., GENBANK™ Accession No. NC_000005, complement, nucleotides 149413051-149473128).

In other examples, a target protein is selected from a virus or other microorganism associated with a disease or condition. Detection of the virus- or microorganism-derived target nucleic acid sequence (e.g., genomic target nucleic acid sequence) in a cell or tissue sample is indicative of the presence of the organism. The disclosed probe may be used to detect and/or identify these types of targets. Also, a gene encoding a critical enzyme for the survival of a microorganism can be targeted by disclosed probe embodiments, which can cause the death of the microorganism. For example, the target protein can be selected from the genome of an oncogenic or pathogenic virus, a bacterium or an intracellular parasite (such as *Plasmodium falciparum* and other *Plasmodium* species, *Leishmania* (sp.), *Cryptosporidium parvum*, *Entamoeba histolytica*, and *Giardia lamblia*, as well as *Toxoplasma, Eimeria, Theileria*, and *Babesia* species).

In some examples, the target protein is produced from a nucleic acid sequence (e.g., genomic target nucleic acid sequence) from a viral genome. Exemplary viruses and corresponding genomic sequences may selected from the following (GENBANK™ RefSeq Accession No. in parentheses): human adenovirus A (NC_001460), human adenovirus B (NC_004001), human adenovirus C(NC_001405), human adenovirus D (NC_002067), human adenovirus E (NC_003266), human adenovirus F (NC_001454), human astrovirus (NC_001943), human BK polyomavirus (V01109; GI:60851) human bocavirus (NC_007455), human coronavirus 229E (NC_002645), human coronavirus HKU1 (NC_006577), human coronavirus NL63 (NC_005831), human coronavirus OC43 (NC_005147), human enterovirus A (NC_001612), human enterovirus B (NC_001472), human enterovirus C(NC_001428), human enterovirus D (NC_001430), human erythrovirus V9 (NC_004295), human foamy virus (NC_001736), human herpesvirus 1 (Herpes simplex virus type 1) (NC_001806), human herpesvirus 2 (Herpes simplex virus type 2) (NC_001798), human herpesvirus 3 (Varicella zoster virus) (NC_001348), human herpesvirus 4 type 1 (Epstein-Barr virus type 1) (NC_007605), human herpesvirus 4 type 2 (Epstein-Barr virus type 2) (NC_009334), human herpesvirus 5 strain AD169 (NC_001347), human herpesvirus 5 strain Merlin Strain (NC_006273), human herpesvirus 6A (NC_001664), human herpesvirus 6B (NC_000898), human herpesvirus 7 (NC_001716), human herpesvirus 8 type M (NC_003409), human herpesvirus 8 type P (NC_009333), human immunodeficiency virus 1 (NC_001802), human immunodeficiency virus 2 (NC_001722), human metapneumovirus (NC_004148), human papillomavirus-1 (NC_001356), human papillomavirus-18 (NC_001357), human papillomavirus-2 (NC_001352), human papillomavirus-54 (NC_001676), human papillomavirus-61 (NC_001694), human papillomavirus-cand90 (NC_004104), human papillomavirus RTRX7 (NC_004761), human papillomavirus type 10 (NC_001576), human papillomavirus type 101 (NC_008189), human papillomavirus type 103 (NC_008188), human papillomavirus type 107 (NC_009239), human papillomavirus type 16 (NC_001526), human papillomavirus type 24 (NC_001683), human papillomavirus type 26 (NC_001583), human papillomavirus type 32 (NC_001586), human papillomavirus type 34 (NC_001587), human papillomavirus type 4 (NC_001457), human papillomavirus type 41 (NC_001354), human papillomavirus type 48 (NC_001690), human papillomavirus type 49 (NC_001591), human papillomavirus type 5 (NC_001531), human papillomavirus type 50 (NC_001691), human papillomavirus type 53 (NC_001593), human papillomavirus type 60 (NC_001693), human papillomavirus type 63 (NC_001458), human papillomavirus type 6b (NC_001355), human papillomavirus type 7 (NC_001595), human papillomavirus type 71 (NC_002644), human papillomavirus type 9 (NC_001596), human papillomavirus type 92 (NC_004500), human papillomavirus type 96 (NC_005134), human parainfluenza virus 1 (NC_003461), human parainfluenza virus 2 (NC_003443), human parainfluenza virus 3 (NC_001796), human parechovirus (NC_001897), human parvovirus 4 (NC_007018), human parvovirus B19 (NC_000883), human respiratory syncytial virus (NC_001781), human rhinovirus A (NC_001617), human rhinovirus B (NC_001490), human spumaretrovirus (NC_001795), human T-lymphotropic virus 1 (NC_001436), human T-lymphotropic virus 2 (NC_001488).

In certain examples, the target protein is produced from a nucleic acid sequence (e.g., genomic target nucleic acid sequence) from an oncogenic virus, such as Epstein-Barr Virus (EBV) or a Human Papilloma Virus (HPV, e.g., HPV16, HPV18). In other examples, the target protein produced from a nucleic acid sequence (e.g., genomic target nucleic acid sequence) is from a pathogenic virus, such as a Respiratory Syncytial Virus, a Hepatitis Virus (e.g., Hepatitis C Virus), a Coronavirus (e.g., SARS virus), an Adenovirus, a Polyomavirus, a Cytomegalovirus (CMV), or a Herpes Simplex Virus (HSV). Other targets contemplated by the present disclosure include Her1, Her2, Her3 and Her4 (e.g. EGFR1, EGFR2, EGFR3 and EGFR4, respectively, or ErbB-1, ErbB-2, ErbB-3 and ErbB-4, respectively).

V. Method of Making Monomers

Particular disclosed embodiments concern a method of making the disclosed monomers. In certain disclosed embodiments, the method may concern synthesizing locked monomers (e.g. monomers having Formulas 1, 2, or 3); and in other disclosed embodiments, the method may concern synthesizing unlocked monomers (e.g. monomers having Formulas 1, 2, or 4).

In particular disclosed embodiments, the monomer may be a locked monomer, which may be synthesized from a precursor 2 using the synthetic sequence illustrated in Scheme 1.

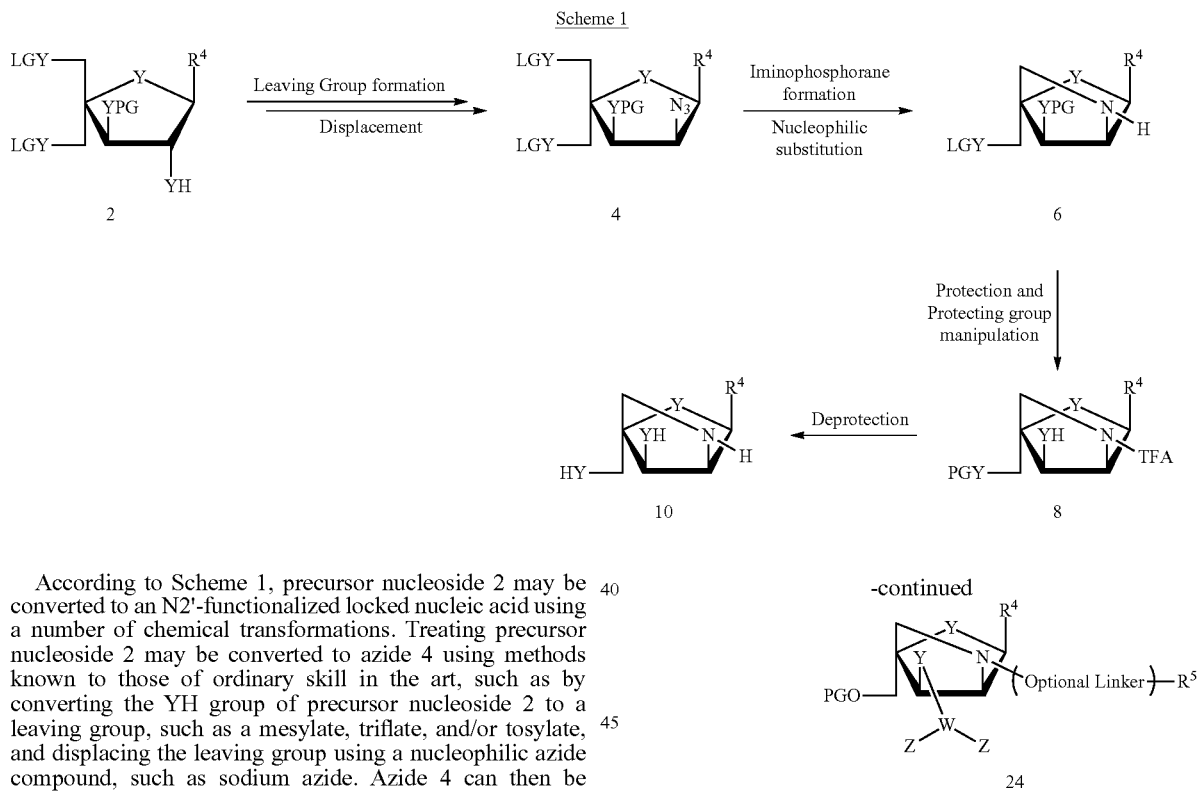

According to Scheme 1, precursor nucleoside 2 may be converted to an N2'-functionalized locked nucleic acid using a number of chemical transformations. Treating precursor nucleoside 2 may be converted to azide 4 using methods known to those of ordinary skill in the art, such as by converting the YH group of precursor nucleoside 2 to a leaving group, such as a mesylate, triflate, and/or tosylate, and displacing the leaving group using a nucleophilic azide compound, such as sodium azide. Azide 4 can then be converted to locked nucleoside 6 using a tandem Staudinger reaction (iminophosphorane formation)/intramolecular nucleophilic substitution sequence. Protection and protecting group manipulation of N2' nucleoside 6 followed by deprotection ultimately provides locked nucleoside 10 in a number of steps.

In particular disclosed embodiments, the locked nucleoside 10 may be converted to a monomer suitable for implementation into the disclosed probe. Scheme 2 illustrates the conversion of locked nucleoside 10 to such a monomer.

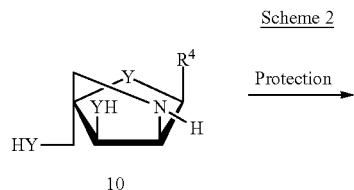

With reference to Scheme 2, the locked nucleoside 10 can be converted to protected nucleoside 20. N2' functionalization of protected nucleoside 20 using a variety of substituents can carried out using conditions known to a person of ordinary skill in the art as being suitable for coupling an amine with various functional groups. These conditions include, for example, reductive amination with aromatic aldehydes (ArCHO) using trisacetoxyborohydride or acylation using aromatic carboxylic acids (ArCOOH) using 1-ethyl-3-(3-dimethylaminopropyl)carbodiimide (EDC) or 2-(1H-7-azobenzotriazol-1-yl)-1,1,3,3-tetramethyluronium hexafluorophosphate methanaminium (HATU) as a coupling reagent. N2' functionalized nucleoside 22 can comprise an optional linker and an $R^5$ moiety selected from any of the $R^5$ moieties disclosed herein. After functionalization of the YH group of N2' functionalized nucleoside 22 using methods known to those having ordinary skill in the art, such as by base-mediated substitution, a monomer 24 can be made. Monomer 24 is suited for further incorporation into a nucleic acid sequence.

An exemplary method of making the disclosed monomers is illustrated below in Schemes 3 and 4. See, N. K. Andersen, J. Wengel and P. J. Hrdlicka, "N2'-Functionalized 2'-Amino-α-L-LNA Adenine Derivatives—Efficient Targeting of Single Stranded DNA," *Nucleosides Nucleotides Nucleic Acids*, 2007, 26, 1415-1417, which is incorporated herein by reference.

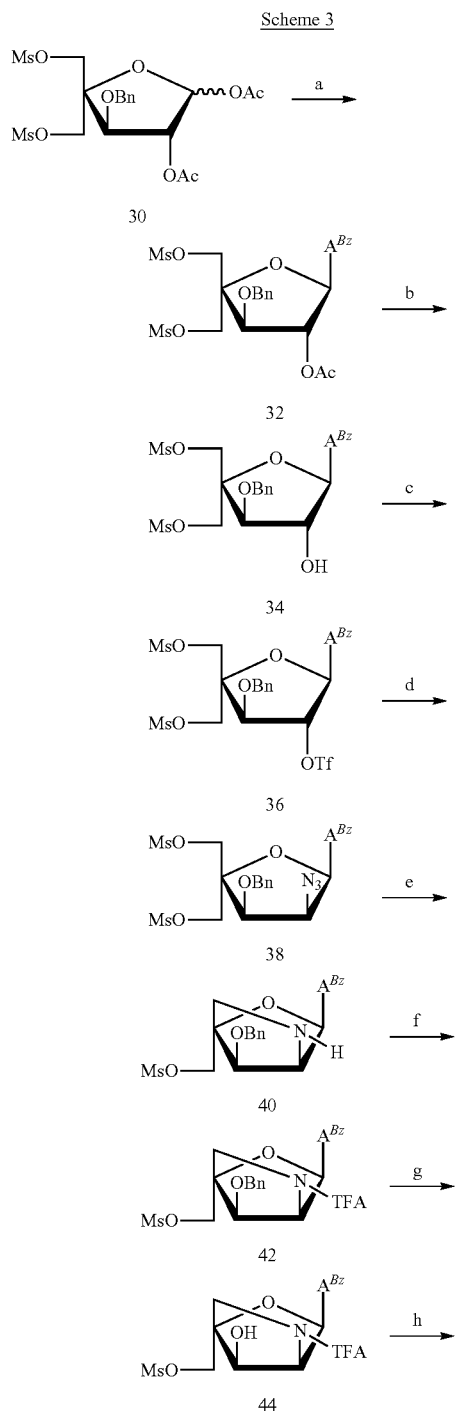

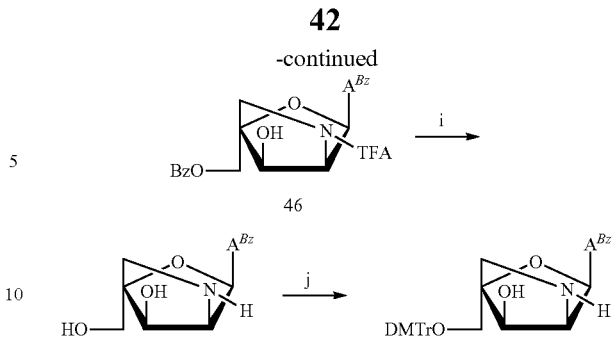

Reagents and conditions: a) BSA, TMSOTf, $A^{Bz}$, an. 1,2-DCE, reflux 70 h; b) 1) Guanidinium nitrate, NaOMe, MeOH, DCM, 30 min, rt. or 2) ½ sat. NH$_3$/MeOH, 0° C., 1.5 h; c) (CF$_3$SO$_2$)$_2$O pyridine, an. DCM -78° C., 3 h; d) NaN$_3$, 15-C-5, an. DMF, 40° C., 16 h; e) 2M aq. NaOH, PMe$_3$, THF, rt. 16 h; f) (CF$_3$CO)$_2$O, an. pyridine, an CH$_2$Cl$_2$, 0° C., 2 h; g) BCl$_3$, an. CH$_2$Cl$_2$, -78° C. to rt., 17 h; h) NaOBz, 15-crown-5, an. DMF, 90° C., 5 h,; i) 2M aq NaOH, 1,4-diooxane/water, 0° C., 2 h; j) DMTrCl, an. pyridine, 0° C. to rt., 23 h. Key: $A^{Bz}$ = 6-N-benzoyl-adenine. 1,2-DCE = 1,2-dichloroethane According to Scheme 3, conversion of diacetate 30 to the desired β-nucleoside 32 was carried out using a one-pot reaction, under modified Vorbrüggen conditions, with in-situ persilylation of the benzoyl protected adenine nucleobase using N,O-bis(trimethylsilyl)acetamide (BSA) and TMSOTf at reflux in 1,2-dichloroethane. Nucleoside 32 was then subjected to chemoselective O2'-deacetylation using half saturated methanolic ammonia to afford nucleoside 34. Nucleoside 34 was reacted with trifluoromethanesulfonic anhydride to facilitate formation of the O2'-triflate 36 which was subsequently without intermediate purification treated with sodium azide and 15-crown-5 in anhydrous DMF to afford azide 38. IR spectroscopy verified the presence of the azide functionality (sharp band at 2115 cm$^{-1}$) and provided along with NMR and HRMS-MALDI, evidence for the proposed structure of azide 38. Azide 38 was converted into the desired bicyclic nucleoside 40 in 80% yield using a one-pot tandem Staudinger/intramolecular nucleophilic substitution reaction. Protecting nucleoside 40 with a trifluoroacetyl group using trifluoroacetic anhydride in anhydrous dichloromethane and anhydrous pyridine facilitated formation of nucleoside 42 in 70% yield. Nucleoside 42 was subsequently subjected to benzylic ether cleavage conditions using BCl$_3$ in anhydrous dichloromethane affording debenzylated nucleoside 44 in yields of 65-87%. Debenzylation was followed by exchanging the methanesulfonyl protecting group at C-5' with a benzoyl protecting group. The reaction was carried out under anhydrous conditions using sodium benzoate and 15-crown-5 in DMF affording nucleoside 46 in isolated yields of 70-83%. Subjecting nucleoside 46 to sodium hydroxide in water and 1,4-dioxane cleaved both the 5'-benzoyl and trifluoroacetic acid protecting groups. Purification of the amino diol afforded target nucleoside 48 in 60-80% isolated yield. The hydroxyl group of nucleoside 48 was subsequently protected at the 5'-position by 4,4'-dimethoxytrityl (DMTr) to afford the DMTr-protected nucleoside 50.

Scheme 4 illustrates an exemplary method of converting a DMTr-protected nucleoside 50 to different exemplary embodiments of the disclosed monomers.

Scheme 4

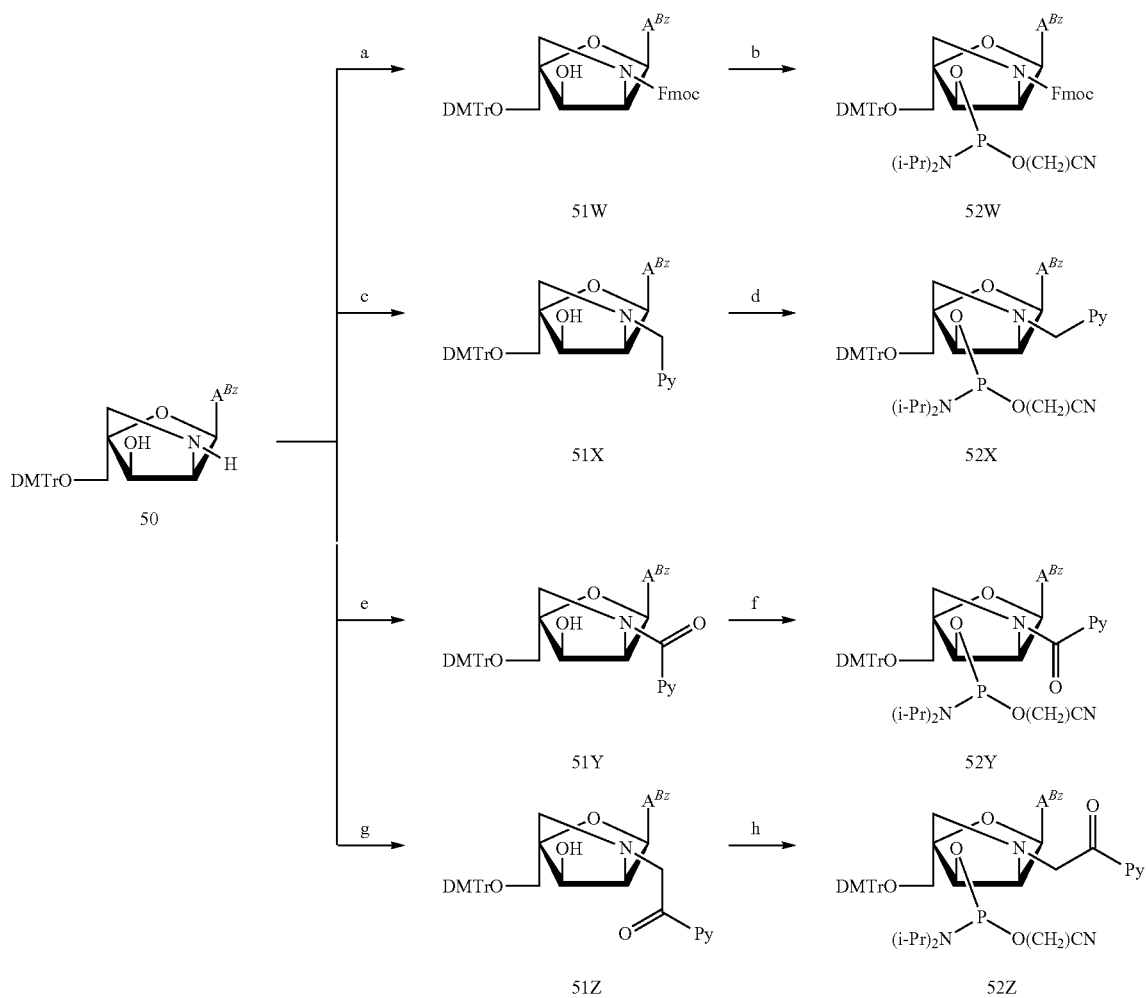

Reagents and conditions: a) Fmoc-Cl, an. pyridine, rt. 6 h, 51%; b) 2-cyanoethyl-N-N'-(diisopropyl)-phosphoamidochloridite, N-methylimidazole, DIPEA, CH$_2$Cl$_2$, rt, 4 h, 47%;
c) 1-pyrenecarboxaldehyde, NaBH(OAc)$_3$, 1,2-DCE, rt., 17 h, 68%.; d) 2-cyanoethyl-N,N'-(diisopropyl)-phosphoamidochloridite, 20% DIPEA in CH$_2$Cl$_2$, rt. 21 h, 51%;
e) 1-pyrenecarboxylic acid, EDC•HCl, CH$_2$Cl$_2$, rt. 45 h, 64%, or 1-pyrenecarboxylic acid, HATU, DIPEA, DMF, 0° C. to rt, 5 h, 74%; f) 2-cyanoethyl-N,N'-(diisopropyl)-phosphoamidchloridite, 20% DIPEA in CH$_2$Cl$_2$, rt. 22 h, 67%; g) 1-pyreneacetic acid, EDC•HCl, CH$_2$Cl$_2$, rt, 3.5 h, 79%; h) 2-cyanoethyl-N,N'-(diisopropyl)-phosphoamidchloridite, DIPEA, CH$_2$Cl$_2$, rt, 71%.

According to Scheme 4, monomer 51W was synthesized from nucleoside 50 using 9-fluorenylmethoxycarbonyl chloride (Fmoc-Cl) in anhydrous pyridine at 0° C. for 6 h, and isolated in 51% yield. Nucleoside 51W was converted into the corresponding amidite 52W for use during oligonucleotide synthesis using 2-cyanoethyl-N,N'-(diisopropyl)-phosphoramidochloridite and diisopropylethylamine in anhydrous dichloromethane.

Pyrenylmethyl derivative 51X was synthesized from nucleoside 50 via reductive amination, using pyrene carboxaldehyde and sodium triacetoxy borohydride in 1,2-dichloroethane at room temperature for 24 h, and was isolated in 60% yield. The functionalized nucleoside 51X was converted into the corresponding amidite 52X for use during oligonucleotide synthesis, using 2-cyanoethyl-N,N'-(diisopropyl)-phosphoramidochloridite and 20% diisopropylethylamine in anhydrous dichloromethane.

The amide bond of 51Y was formed via a 1-ethyl-3-(3-dimethyl-amino-propyl)-carbodiimide hydrochloride (EDC.HCl) mediated coupling. The reaction was performed by dissolving bicyclic nucleoside 50 in anhydrous dichloromethane and adding pyrenecarboxylic acid and EDC.HCl. The reaction mixture was stirred at room temperature for 45 h. The reaction mixture was subsequently subjected to standard aqueous workup and purification, isolating nucleoside 51Y in 64% yield. Nucleoside 51Y was converted into the corresponding phosphoramidite 52Y using 2-cyanoethyl-N,N'-(diisopropyl)-phosphoramidochloridite and 20% diisopropylethylamine in anhydrous dichloromethane.

In addition, bicyclic nucleoside 50 was converted to monomer 51Z by adding pyrenecarboxylic acid and EDC.HCl. The reaction mixture was stirred at room temperature for 2.5 h and was subjected to standard aqueous workup and purification, isolating nucleoside 51Z in 79% yield. Nucleoside 51Z was converted into the corresponding phosphoramidite 52Z using 2-cyanoethyl-N,N'-(diisopropyl)-phosphoramidochloridite and diisopropylethylamine in anhydrous dichloromethane.

Also disclosed are embodiments wherein the R$^4$ moiety is selected to be thymine. An exemplary method for synthesizing monomers having $R^4$=thymine is illustrated below in Scheme 5. See, T. S. Kumar, A. S. Madsen, M. E. Østergaard, S. P. Sau, J. Wengel and P. J. Hrdlicka*, "Functionalized 2'-Amino-α-L-LNA—Directed Positioning of Intercalators for DNA Targeting", *J. Org. Chem.* 2009, 74, 1070-1081, which is incorporated herein by reference.

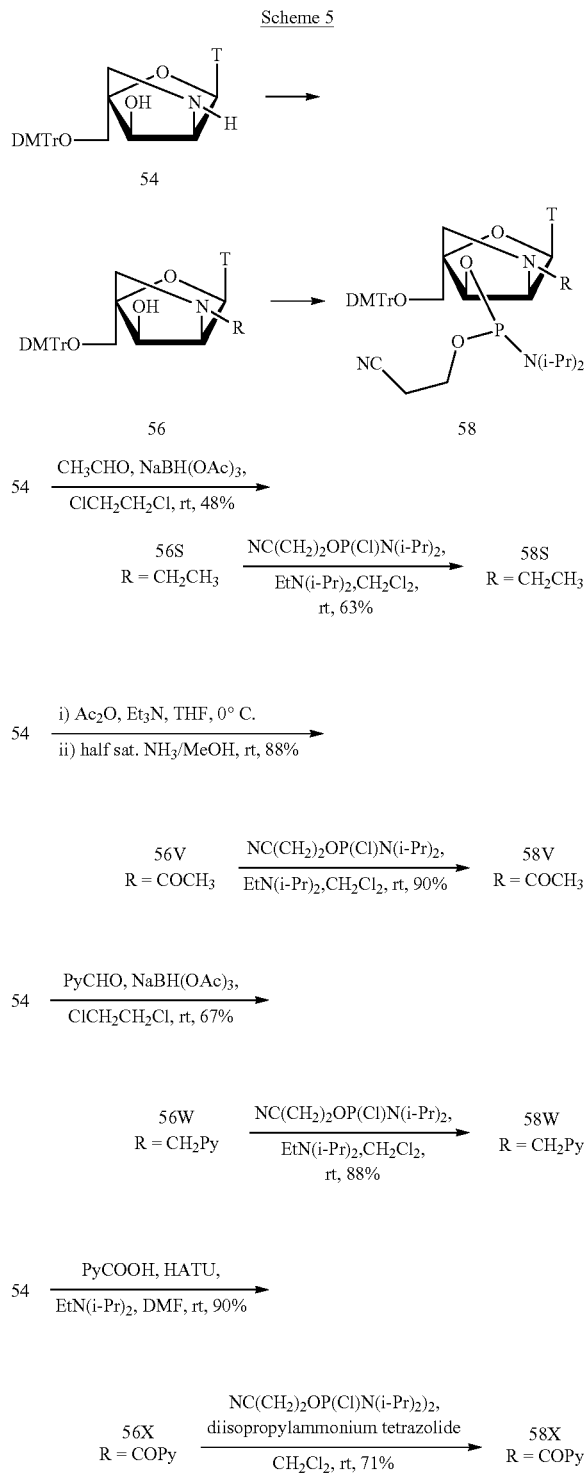

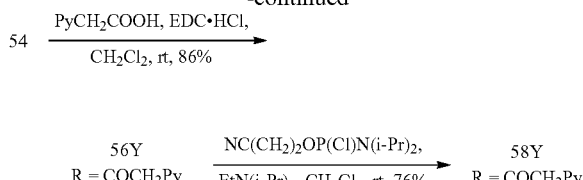

With reference to Scheme 5, O5'-tritylated bicyclic nucleoside 54, which may be obtained from commercially available diacetone-α-D-glucose in 5% overall yield over seventeen steps involving eight chromatographic purification steps, was used as a suitable starting material for the synthesis of N2'-functionalized 2'-amino-α-L-LNA phosphoramidites 58Q-58Z. The disclosed monomers are selected to probe the available structural space in nucleic acids and fall into two groups based on the nature of the N2'-moiety (e.g. monomers with small non-aromatic units [monomers 58Q, 58S, and 58V] or with aromatic units [monomers 58W-58Z]). Sodium triacetoxyborohydride mediated reductive amination of secondary amine 54 with acetaldehyde or 1-pyrenecarbaldehyde provided tertiary amines 56S and 56W in 48% and 67% yield, respectively. Chemoselective N-acylation of amino alcohol 54 was achieved using two different strategies. Treatment of amino alcohol 54 with slight excess of acetic anhydride followed by selective O3'-deacylation using dilute methanolic ammonia provided nucleoside 56V in excellent 88% yield over two steps. EDC-mediated coupling of amino alcohol 54 with 1-pyrenylcarboxylic acid, 1-pyrenylacetic acid or 4-(1-pyrenyl)butyric acid afforded nucleosides 56X, 56Y and 56Z in 62%, 86% and 63% yield, respectively. A HATU-mediated coupling procedure were used in order to improve the yield of 56X to 90%. Disappearance of $^1$H NMR signals of the exchangeable 3'-OH protons upon $D_2O$ addition confirmed the N2'-functionalized constitution of nucleosides 56S-56Z, which subsequently were converted to the corresponding phosphoramidites 58S-58Z using 2-cyanoethyl N,N'-(diisopropyl)-phosphoramidochloridite and diisopropylethyl amine (Hünig's base). While amidites 58S-58Y were obtained in good to excellent yields (60-90%), 58Z is obtained in 36% yield. The yield of 58X was improved using bis-(N,N-diisopropylamino)-2-cyanoethoxyphosphine in dichloromethane with diisopropylammonium tetrazolide as an activator.

Other disclosed embodiments concern unlocked monomers and a method of making these monomers. In particular disclosed embodiments, the unlocked monomers may be made in approximately three steps from a particular compound. A particular disclosed embodiment of a method of making the unlocked monomers is illustrated in Scheme 6.

Scheme 6

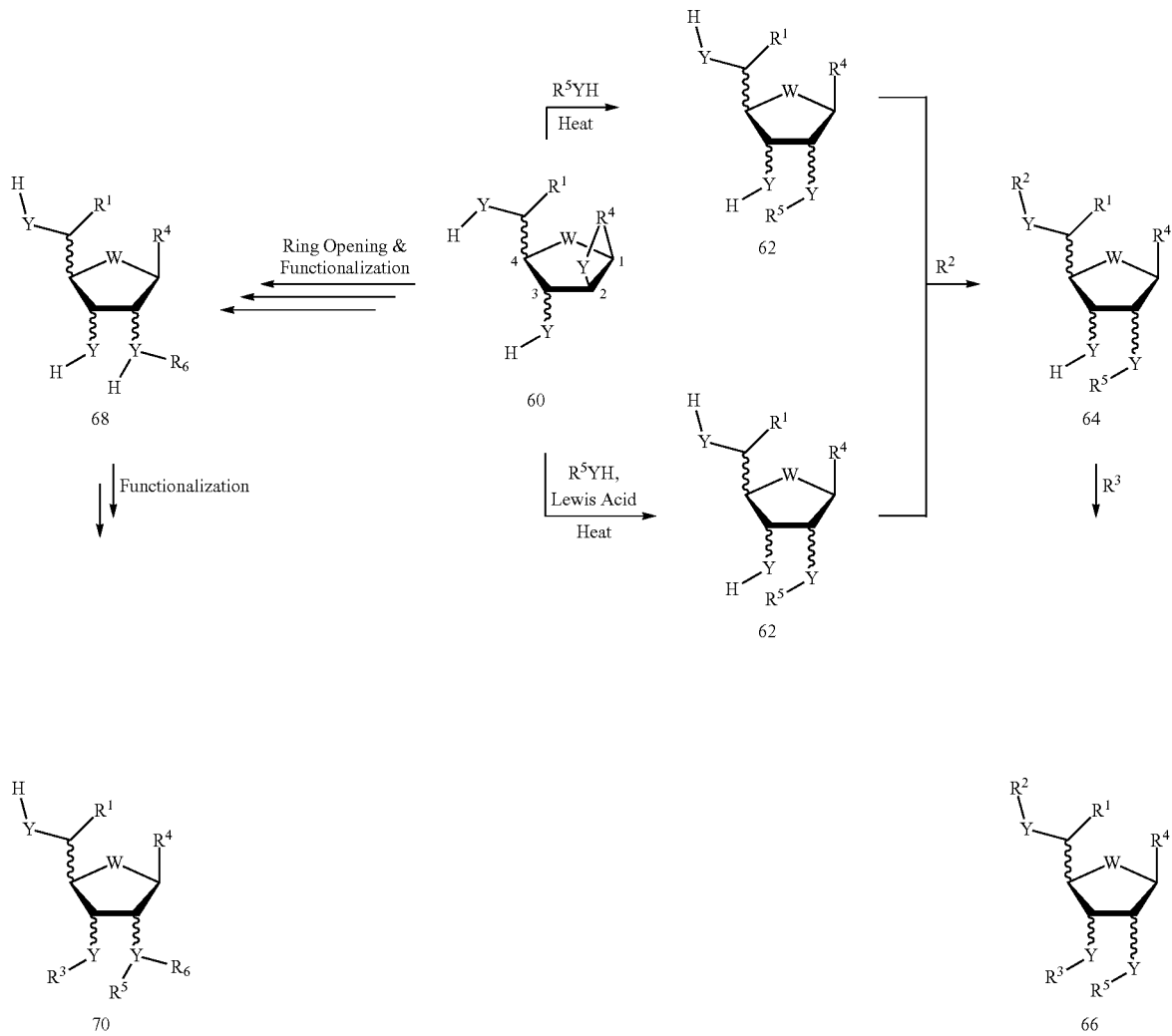

According to Scheme 6, bicyclic nucleoside 60 may be converted to nucleoside 62 via methods known to those of ordinary skill in the art, such as Lewis acid-mediated ring-opening and/or heat-catalyzed nucleophilic addition. In particular disclosed embodiments, an alcohol, thiol, or amine may be used to open the ring illustrated in Scheme 6. These reagents may be combined with a Lewis acid, such as a borane, and heat to facilitate functionalization and conversion of the bicyclic nucleoside 60 into nucleoside 62. Subsequently, nucleoside 62 can be converted to protected nucleoside 64, which may then be further protected to produce monomer 66. Also according to Scheme 6, nucleoside 62 may be converted to a compound having a di-functionalized Y2' moiety at the C2' position, such as compound 68, which can be made by methods known in the art, such as via ring-opening and functional group manipulation. In order to make monomer 70, compound 68 can be exposed to coupling conditions known to those of ordinary skill in the art, such as, but not limited to activated couplings and base mediated couplings. In particular disclosed embodiments, activating agents, such as N-ethyl-N'-(3-dimethylaminopropyl)carbodiimide (EDC), 1-ethyl-3-(3-dimethylaminopropyl)carbodiimide hydrochloride (EDCI), dicyclohexylcarbodiimide (DCC), carbonyl diimidazole (CDI), 1-hydroxybenzotriazole (HOBt), 1-hydroxy-7-azabenzotriazole (HOAt), and o-(7-azabenzotriazol-1-yl)-N,N,N',N'-tetramethyluronium hexafluorophosphate (HATU) may be used in the activated coupling. In certain disclosed embodiments, coupled nucleosides may also be obtained by treating nucleoside 68 with a base, such as an aliphatic amine base (e.g. triethylamine, 1,8-diazabicycloundec-7-ene, 1,4-diazabicyclo[2.2.2]octane, and diisopropylethylamine), and an electrophile, such as a compound comprising an $R^4$ moiety and a leaving group, wherein the leaving group may be selected from a halide, a mesylate, a triflate, and a tosylate. Monomer 70 is made via base-mediated functionalization. In certain embodiments, an optional linker is inserted between Y and $R^5$ and/or $R^6$.

Sulfur analogs can be used in the general approach illustrated in Scheme 6. An example of this approach is illustrated below in Scheme 6A where a sulfur nucleophile is introduced using a nucleophile $R^5YH$ and a base (e.g., NaH).

Scheme 6A

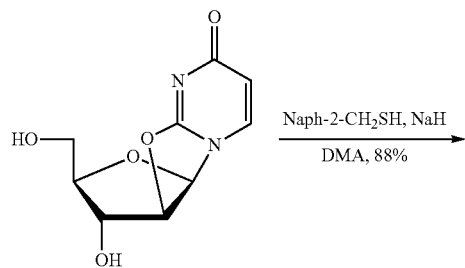

Naph-2-CH₂SH, NaH
─────────────────→
DMA, 88%

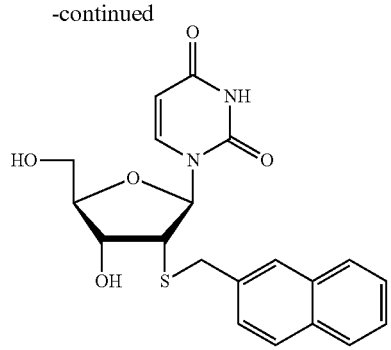

In particular disclosed embodiments, the monomer may be synthesized using the methods illustrated in Scheme 7, below. A person of ordinary skill in the art will recognize that the methods of Scheme 7 are exemplary only and are not intended to be limiting.

Scheme 7A

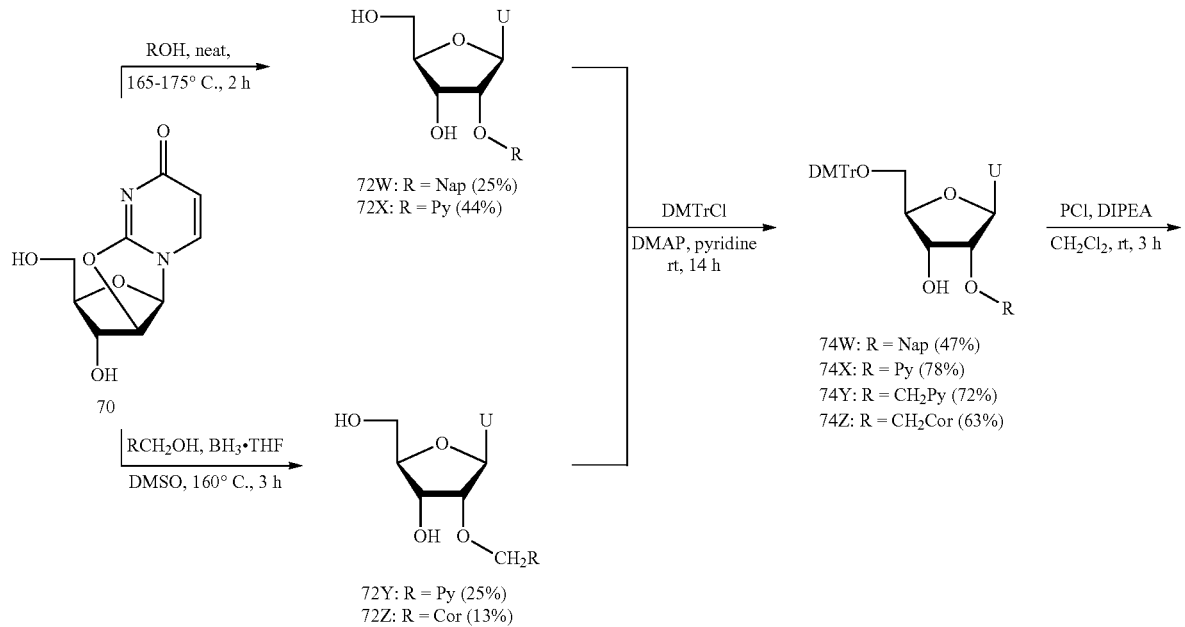

72W: R = Nap (25%)
72X: R = Py (44%)

72Y: R = Py (25%)
72Z: R = Cor (13%)

74W: R = Nap (47%)
74X: R = Py (78%)
74Y: R = CH₂Py (72%)
74Z: R = CH₂Cor (63%)

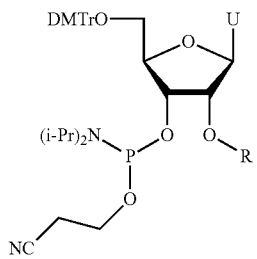

76W: R = Nap (74%)
76X: R = Py (76%)
76Y: R = CH₂Py (76%)
76Z: R = CH₂Cor (78%)

According to Scheme 7A, 2,2'-anhydrouridine 70 is treated with neat phenols, such as 2-naphtol and 1-pyrenol, to afford O2'-arylated uredines 72W and 72X in 25% and 44% yield, respectively. This method was adapted in order to obtain nucleosides 72Y and 72Z by treating bicyclic nucleoside 70 with tris(pyrene-1-ylmethyl) or tris(coronene-1-ylmethyl)borate—generated in situ upon addition of pyren-1-ylmethanol or coronen-1-ylmethanol to borane. This modification afforded nucleosides 72Y and 72Z in reproducible yields. Subsequent O5'-dimethoxytritylation afforded nucleosides 74W-74Z in 47-78% yield, which upon treatment with 2-cyanoethyl-N,N-diisopropylchlorophosphoramidite (PCl-reagent) and diisopropylethylamine (Hünig's base) provided target phosphoramidites 76W-76Z in 74-78% yield (Scheme 7).

Scheme 7B provides additional examples of monomers obtained via this method.

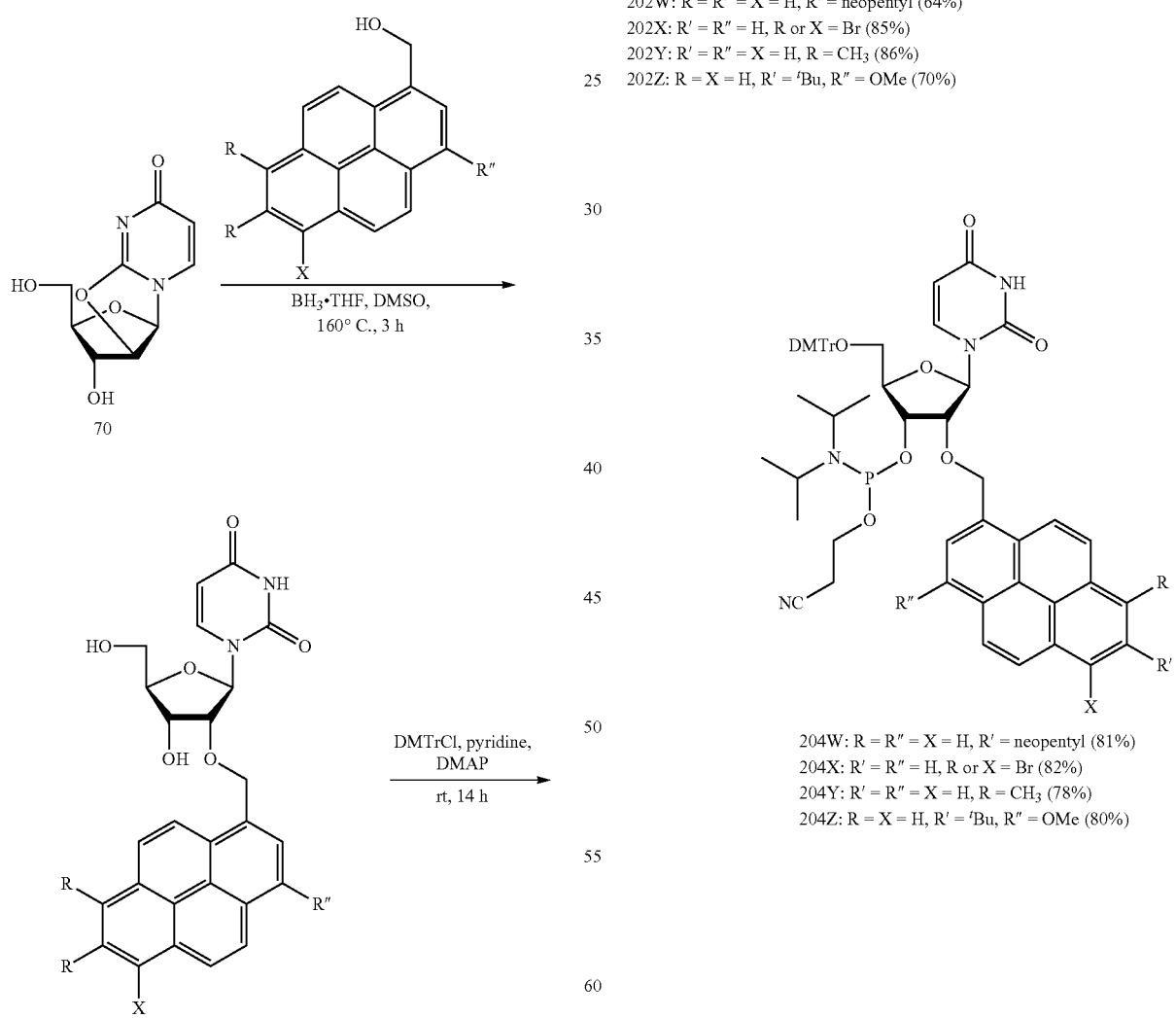

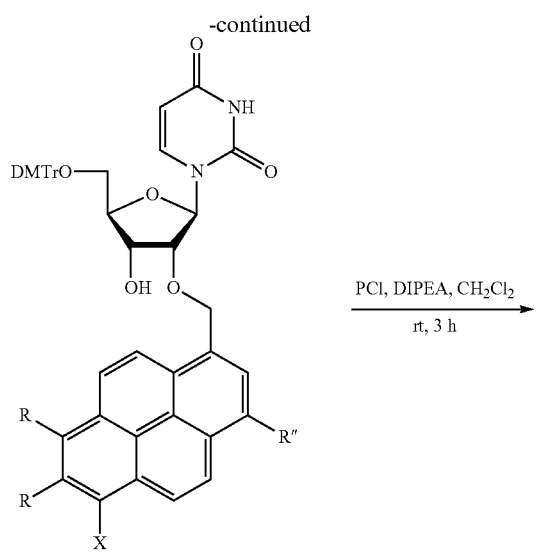

202W: R = R'' = X = H, R' = neopentyl (64%)
202X: R' = R'' = H, R or X = Br (85%)
202Y: R' = R'' = X = H, R = CH$_3$ (86%)
202Z: R = X = H, R' = $^t$Bu, R'' = OMe (70%)

204W: R = R'' = X = H, R' = neopentyl (81%)
204X: R' = R'' = H, R or X = Br (82%)
204Y: R' = R'' = X = H, R = CH$_3$ (78%)
204Z: R = X = H, R' = $^t$Bu, R'' = OMe (80%)

Other particular disclosed embodiments of making the disclosed monomers are illustrated in Schemes 8 and 9. With reference to Scheme 8, and concerning the exemplary conversion of 128 to 130W, certain embodiments used O2' alkylation, typically using a haloalkane and base, such as arylmethylhalide and sodium hydride.

Scheme 8
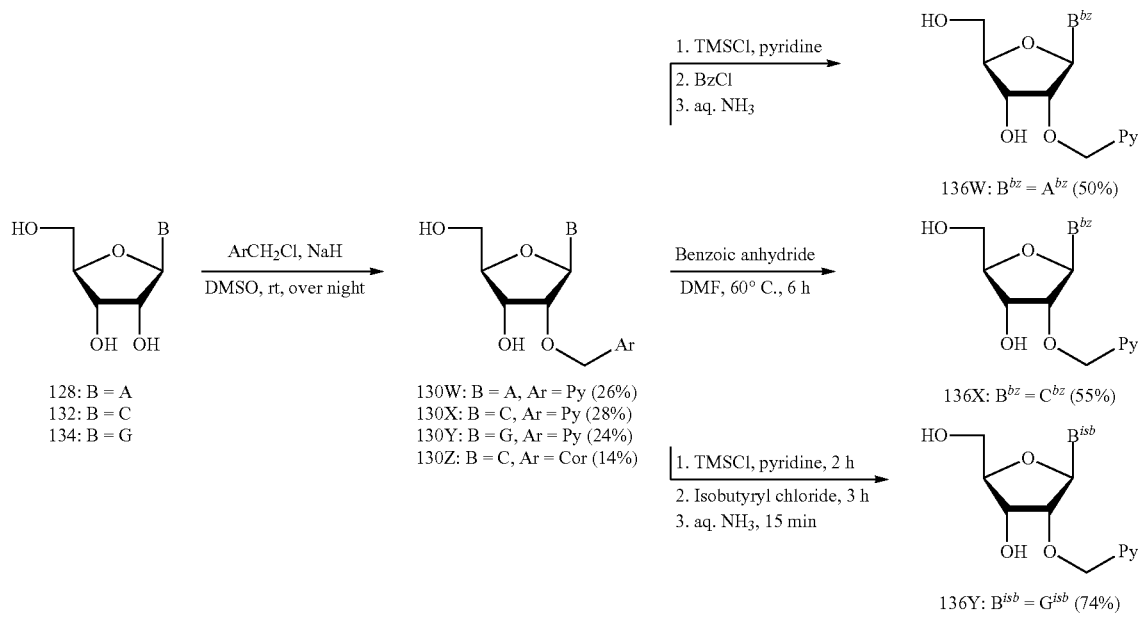
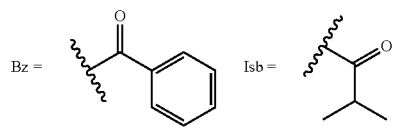
Scheme 9
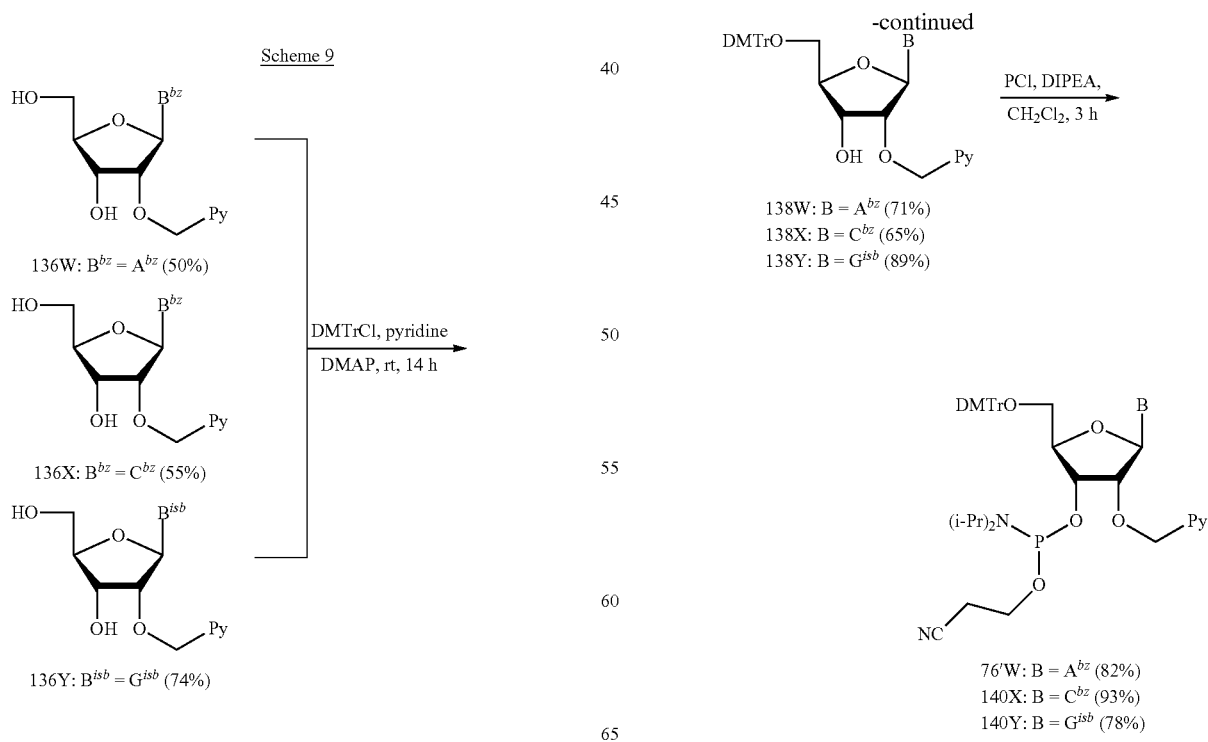

Exemplary embodiments of the disclosed monomer may also be obtained using the methods illustrated in Scheme 10. According to Scheme 10, methylamine nucleoside 80 (made from 5'-O-dimethoxytrityl-2,2'-anhydrouridine in ~73% yield over three steps) may undergo direct N2'-alkylation using pyren-1-ylmethyl chloride afforded the desired product 82Q in 46% yield. Interestingly, reductive amination of 80 using 1-pyrenecarbaldehyde and sodium triacetoxyborohydride or sodium cyanoborohydride failed to afford 82Q in acceptable yields due to prominent formation of the corresponding cyclic N2',O3'-hemiaminal ether. While formation of this byproduct was avoided by prior protection of the O3'-position of 80 as a TBDMS-ether, the increased steric bulk resulted in low yields during the subsequent reductive amination.

Still with reference to Scheme 10 HATU-mediated coupling between nucleoside 80 and 1-pyrenecarboxylic acid afforded N2'-acylated nucleoside 82S in 78% yield, while EDC-mediated coupling between nucleoside 80 and 1-pyreneacetic acid furnished 82V in 83% yield. Subsequent O3'-phosphitylation of 82Q/82S/82V using similar conditions as for the synthesis of 76W-76Z afforded phosphoramidites 84Q/84S/84V only in moderate yields (42-57%), presumably due to the increased steric bulk at the N2'-position.

With reference to Scheme 11 reductive amination of 220 using an aromatic aldehyde (e.g., 1-pyrenecarbaldehyde, 3-perylenecarbaldehyde or 1-coronencarbaldehyde) affords 222 in 43-95% yield. Subsequent N-methylation of 222 via reductive amination affords 224 in 89-99% yield (note 224X=82Q & 226X=84Q). Subsequent O3'-phophitylation (e.g., using cyanoethyl N,N-diisopropyl-chloro-phosphoramidite, i.e., PCl-reagent) provides 226 in 62-90% yield.

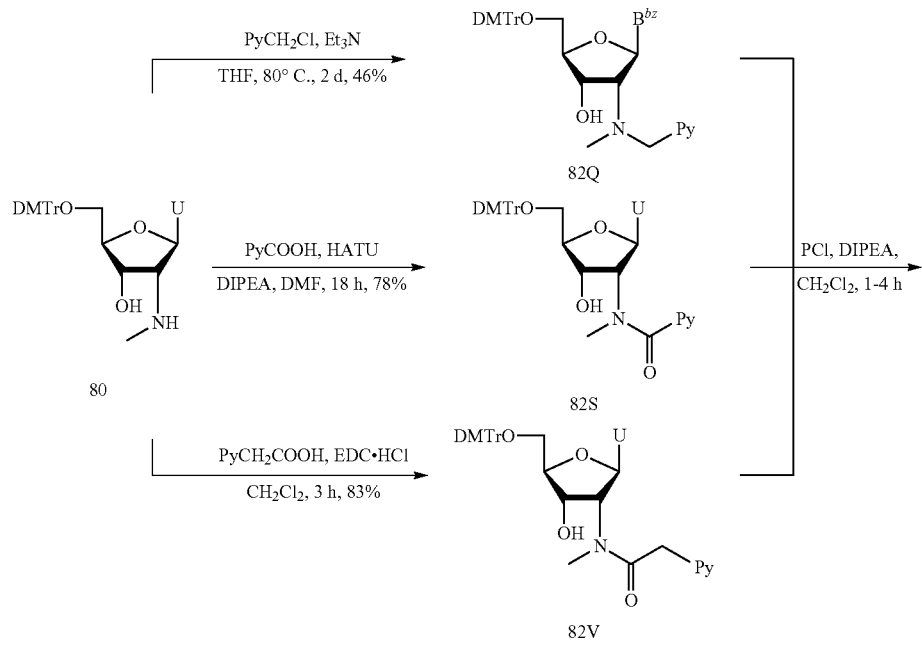

Scheme 10

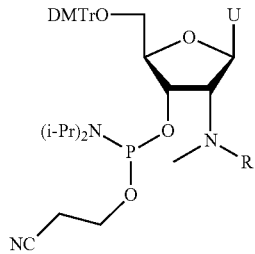

84Q: R = CH$_2$Py (57%)
84S: R = COPy (49%)
84V: R = COCH$_2$Py (42%)

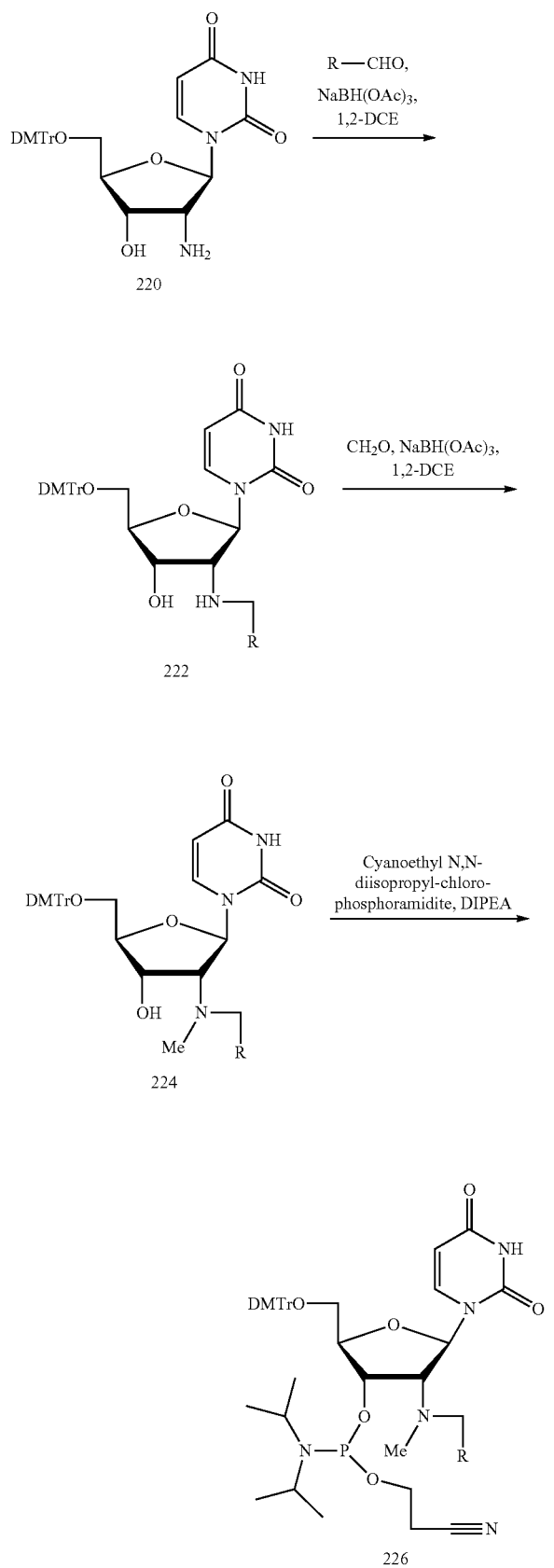
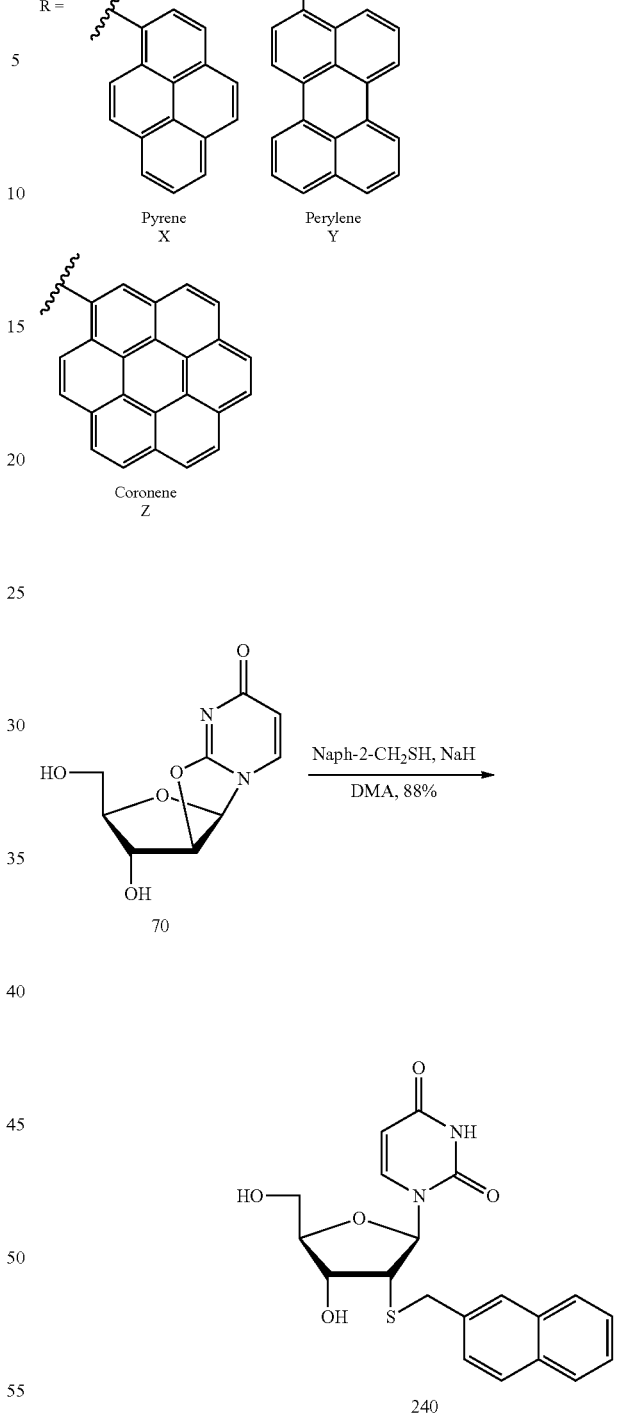

Other disclosed embodiments concern monomers comprising a triazole moiety, wherein the triazole moiety allows the nucleoside to be coupled with a variety of $R^5$ moieties. Schemes 12 and 13 illustrate an exemplary embodiment of making a monomer comprising a triazole moiety. Scheme 12 illustrates an exemplary method for making the necessary coupling reagents used in producing the triazole moieties, and Scheme 13 illustrates how these coupling reagents are ultimately used in triazole synthesis.

Scheme 12

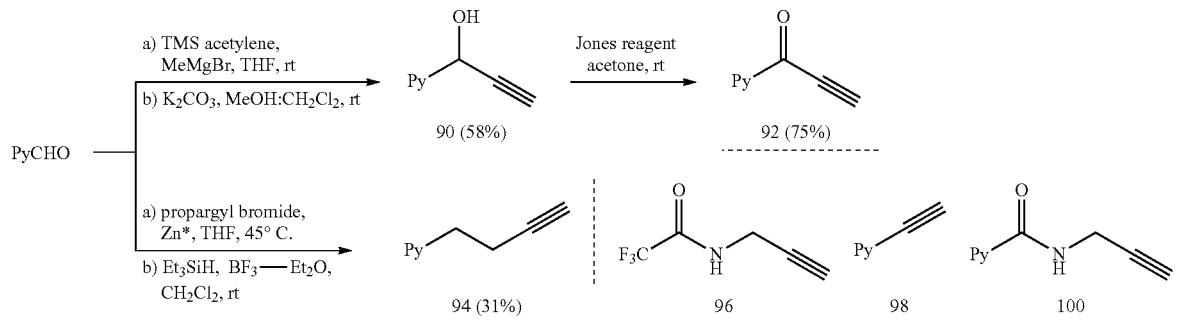

With reference to Scheme 12, 2,2,2-trifluoro-N-(prop-2-ynyl)acetamide 96, 1-ethynylpyrene 98 and N-(prop-2-ynyl)pyrene-1-carboxamide 100 were prepared according to methods readily known in the art. In contrast, 1-(pyren-1-yl)-prop-2-yn-1-one 92 and 4-(pyren-1-yl)-but-1-yne 94 were obtained via substantially different methods. According to Scheme 12, nucleophilic addition of MgC≡CTMS (generated in situ from trimethylsilylacetylene and MeMgBr in THF) to pyrene-1-carboxaldehyde followed by desilylation using potassium carbonate provided 90 in 58% yield. Subsequent Jones oxidation afforded 92 in 75% yield. Similarly, nucleophilic addition of HC≡CCH$_2$ZnBr (generated in situ from propargyl bromide and activated zinc in THF) to pyrene-1-carboxaldehyde, followed by deoxygenation of the resultant homopropargyl alcohol using trifluoroboron etherate and triethylsilane, afforded 94 in 31% yield.

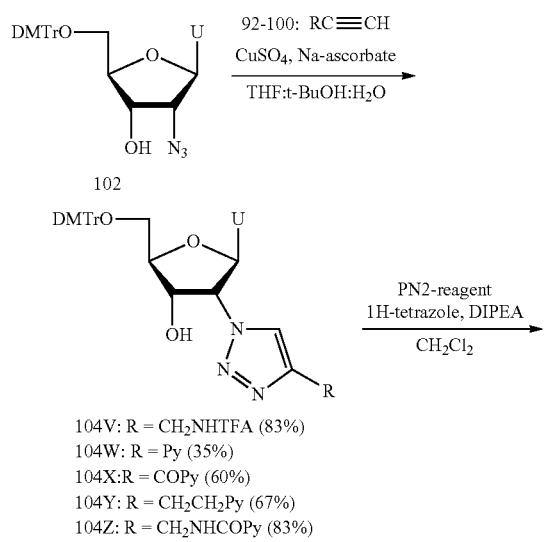

Scheme 13

104V: R = CH$_2$NHTFA (83%)
104W: R = Py (35%)
104X: R = COPy (60%)
104Y: R = CH$_2$CH$_2$Py (67%)
104Z: R = CH$_2$NHCOPy (83%)

-continued

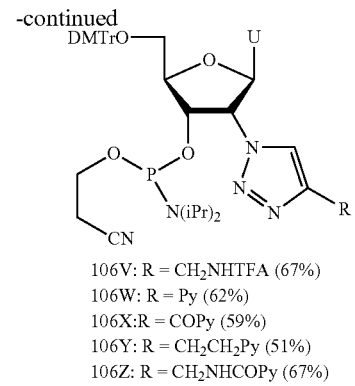

106V: R = CH$_2$NHTFA (67%)
106W: R = Py (62%)
106X: R = COPy (59%)
106Y: R = CH$_2$CH$_2$Py (51%)
106Z: R = CH$_2$NHCOPy (67%)

With reference to Scheme 13, room temperature reactions between 102 and terminal alkynes 92-100 provided the corresponding triazoles 104V-104Z in robust yields (60-83%), except for the reaction involving 1-ethynylpyrene 98, which required heating (75° C.) to afford nucleoside 104W in 35% yield (Scheme 2). Nucleosides 104V-104Z were subsequently converted into phosphoramidites 106V-106Z (51-67% yield) using 2-cyanoethyl-N,N,N',N'-tetraisopropylphosphordiamidite (PN2-reagent) and 1H-tetrazole as an activator.

Other disclosed embodiments concern monomers comprising pseudocomplimentary nucleobases (n particular those involving C2-thiouracil as the nucleobase moiety). With reference to Scheme 14, protecting group manipulations on nucleoside 82Q (=224X) converted it to nucleoside 260 in 55% yield. Base-mediated anhydronucleoside formation and nucleophilic cleavage hereof, provided 262 in 52% yield. O5'-protection hereof provided 264, which upon treatment with a sulphur source produced 2-thiouracil derivative 266. Subsequent O3'-phosphitylation using standard conditions, afforded amidite 268 as a suitable building block for oligonucleotide synthesis.

Scheme 14

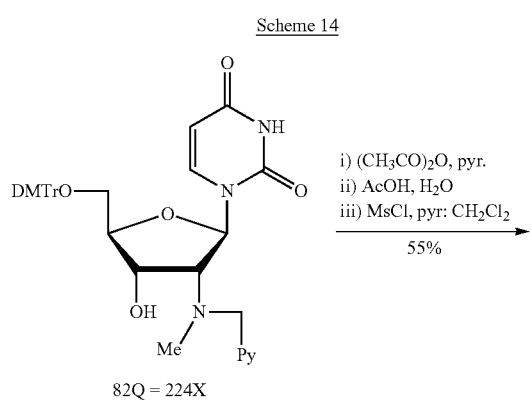

82Q = 224X

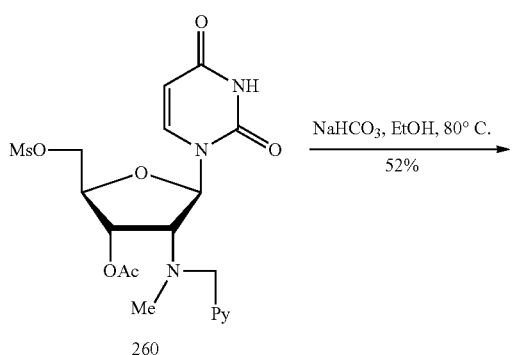

260

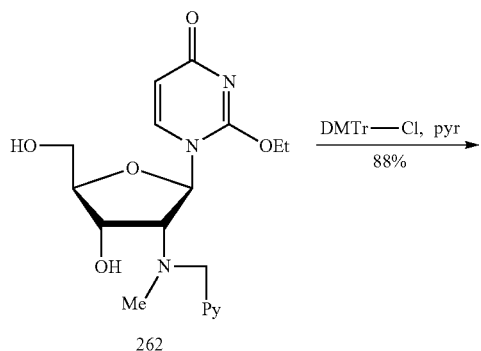

262

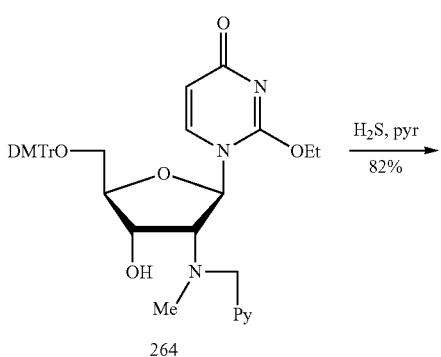

264

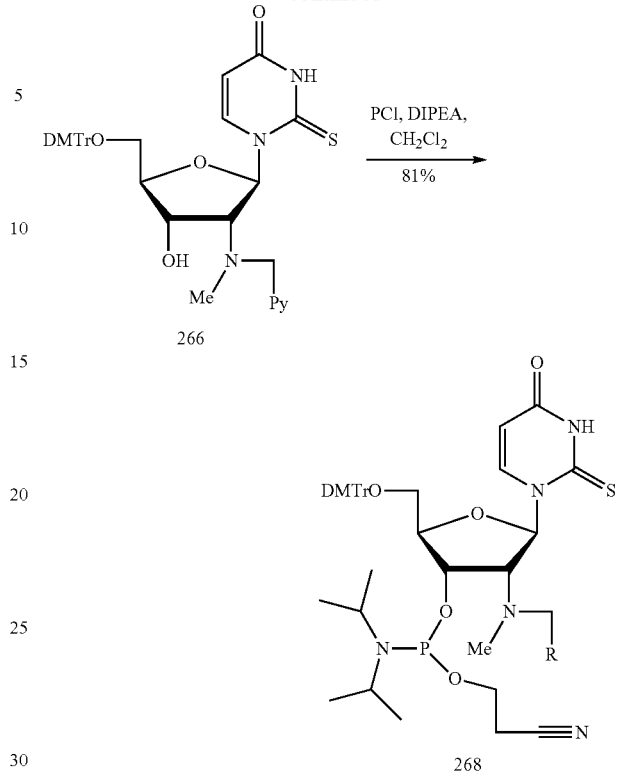

266

268

VI. Method of Making Disclosed Probe Embodiments

Disclosed embodiments concern a method of making a probe capable of recognizing a target, particularly a double stranded DNA target. In particular disclosed embodiments, the probe is a nucleic acid duplex that comprises at least one pair of monomers that are capable of reducing the thermal stability of the duplex and thus promote dissociation of two strands of the duplex.

In certain disclosed embodiments, the probe may be able to identify an isosequential nucleic acid sequence. For example, the probe may be made by first identifying a desired target, such as a particular nucleic acid sequence, and then constructing the probe to be a complement to such sequence by developing a probe having nucleotides capable of Watson-Crick base pairing with the target. The probe may be modified with at least one pair of monomers, whereas the isosequential target lacks such a modification.

In particular disclosed embodiments, the probe is constructed by converting one or more of the monomers disclosed herein to an oligonucleotide, wherein the monomer is coupled with one or more natural or non-natural nucleobases to form a modified oligonucleotide. The probe may be designed as a double stranded DNA probe (e.g. monomers and natural and/or non-natural nucleobases bound together via phosphate moieties), a double stranded phosphorothioate-DNA probe (e.g. monomers and natural and/or non-natural nucleobases bound together via one or more phosphorothioate moieties), a triazole-linked DNA or RNA probe, an unmodified RNA probe, modified RNA probe and/or other non-natural DNA/RNA strands now known or hereafter discovered or made.

Scheme 14 illustrates a particular disclosed embodiment of a method for making the probe. According to Scheme 14, a monomer may be incorporated into an oligonucleotide using methods known to a person of ordinary skill in the art, such as by using a nucleic acid synthesizer. With reference to Scheme 15, monomer 110 may be converted into oligonucleotide 112, wherein the wavy lines indicate the position at which one or more natural or non-natural nucleotides and/or additional identical or different monomers may be coupled. The transformation illustrated in Scheme 14 can be obtained by any methods known to those of ordinary skill in the art, such as by using an activator, such as an imidazole, triazole, or tetrazole compound, and an oxidant, such as iodine or a peroxide compound. Particular embodiments utilize dicyanoimidazole as the activator. Examples of peroxide compounds include, but are not limited to, hydrogen peroxide or tert-butyl hydrogen peroxide.

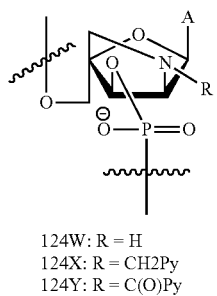

124W: R = H
124X: R = CH2Py
124Y: R = C(O)Py

Scheme 15

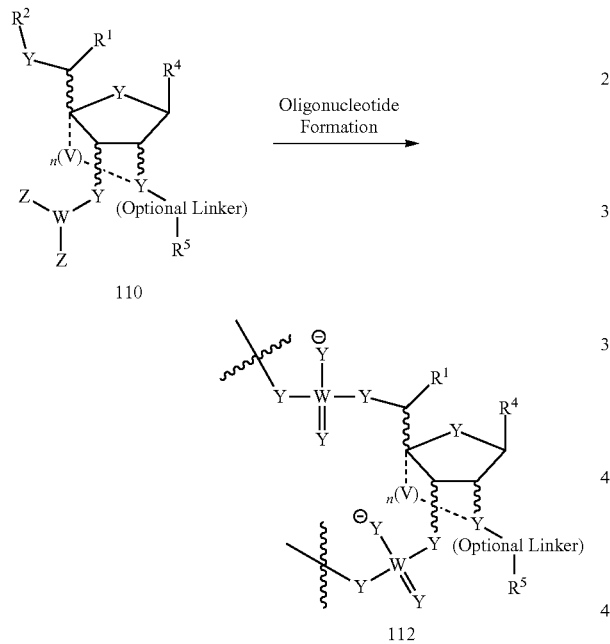

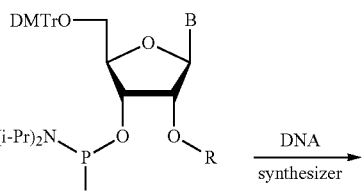

58′W: R = CH₂Py
58′X: R = C(O)Py
58′Y: R = C(O)CH₂Py
58′Z: R = C(O)CH₂CH₂CH₂Py

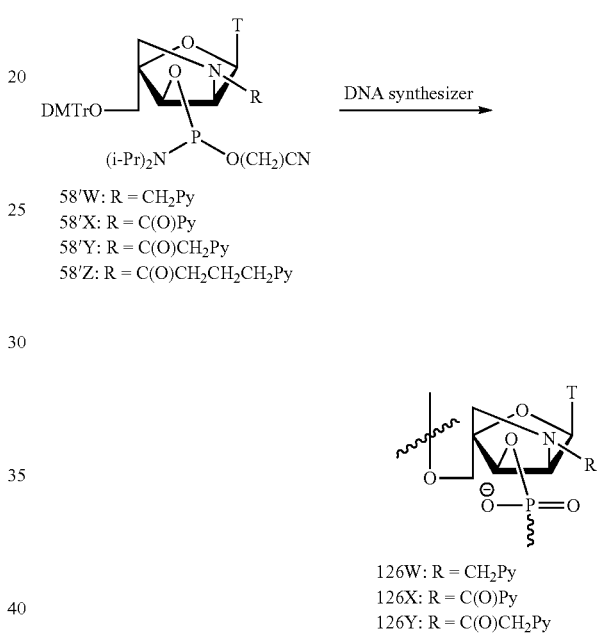

126W: R = CH₂Py
126X: R = C(O)Py
126Y: R = C(O)CH₂Py
126Z: R = C(O)CH₂CH₂CH₂Py

Particular disclosed embodiments may concern making the disclosed probe according to the method illustrated in Scheme 16.

Scheme 16

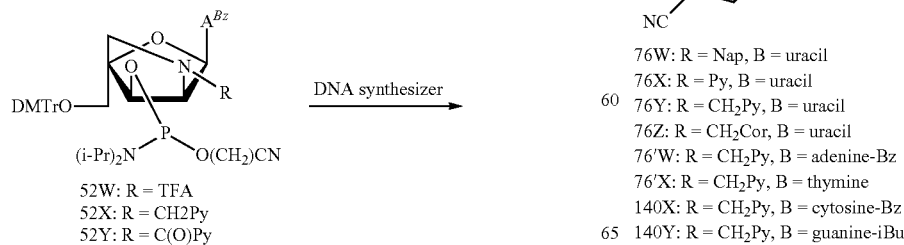

52W: R = TFA
52X: R = CH₂Py
52Y: R = C(O)Py

76W: R = Nap, B = uracil
76X: R = Py, B = uracil
76Y: R = CH₂Py, B = uracil
76Z: R = CH₂Cor, B = uracil
76′W: R = CH₂Py, B = adenine-Bz
76′X: R = CH₂Py, B = thymine
140X: R = CH₂Py, B = cytosine-Bz
140Y: R = CH₂Py, B = guanine-iBu

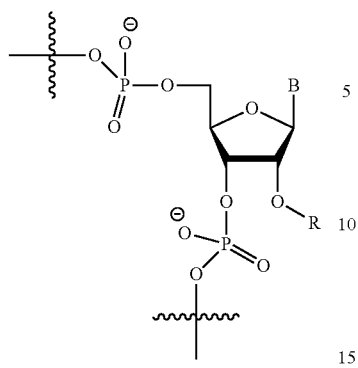

120W: R = Nap, B = uracil
120X: R = Py, B = uracil
120Y: R = CH$_2$Py, B = uracil
120Z: R = CH$_2$Cor, B = uracil
120'W: R = CH$_2$Py, B = adenine
120'X: R = CH$_2$Py, B = thymine
140'X: R = CH$_2$Py, B = cytosine
140'Y: R = CH$_2$Py, B = guanine

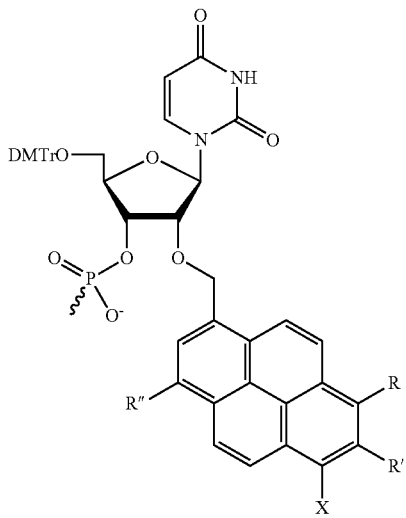

Monomer 208W: R = R″ = X = H, R′ = neopentyl
Monomer 208X: R′ = R″ = H, R or X = Br
Monomer 208Y: R′ = R″ = X = H, R = CH$_3$
Monomer 208Z: R = X = H, R′ = $^t$Bu, R″ = OMe

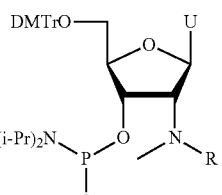

84Q: R = CH$_2$Py
84S: R = COPy
84V: R = COCH$_2$Py

→ DNA synthesizer

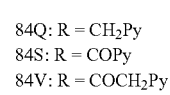
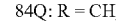
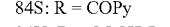

204W: R = R″ = X = H, R′ = neopentyl
204X: R′ = R″ = H, R or X = Br
204Y: R′ = R″ = X = H, R = CH$_3$
204Z: R = X = H, R′ = $^t$Bu, R″ = OMe → DNA synthesizer

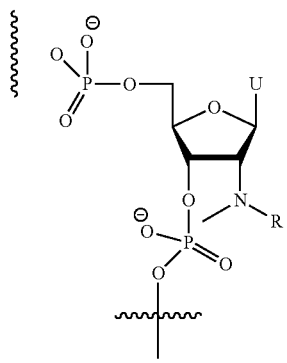

120Q: R = CH$_2$Py
120S: R = COPy
120V: R = COCH$_2$Py

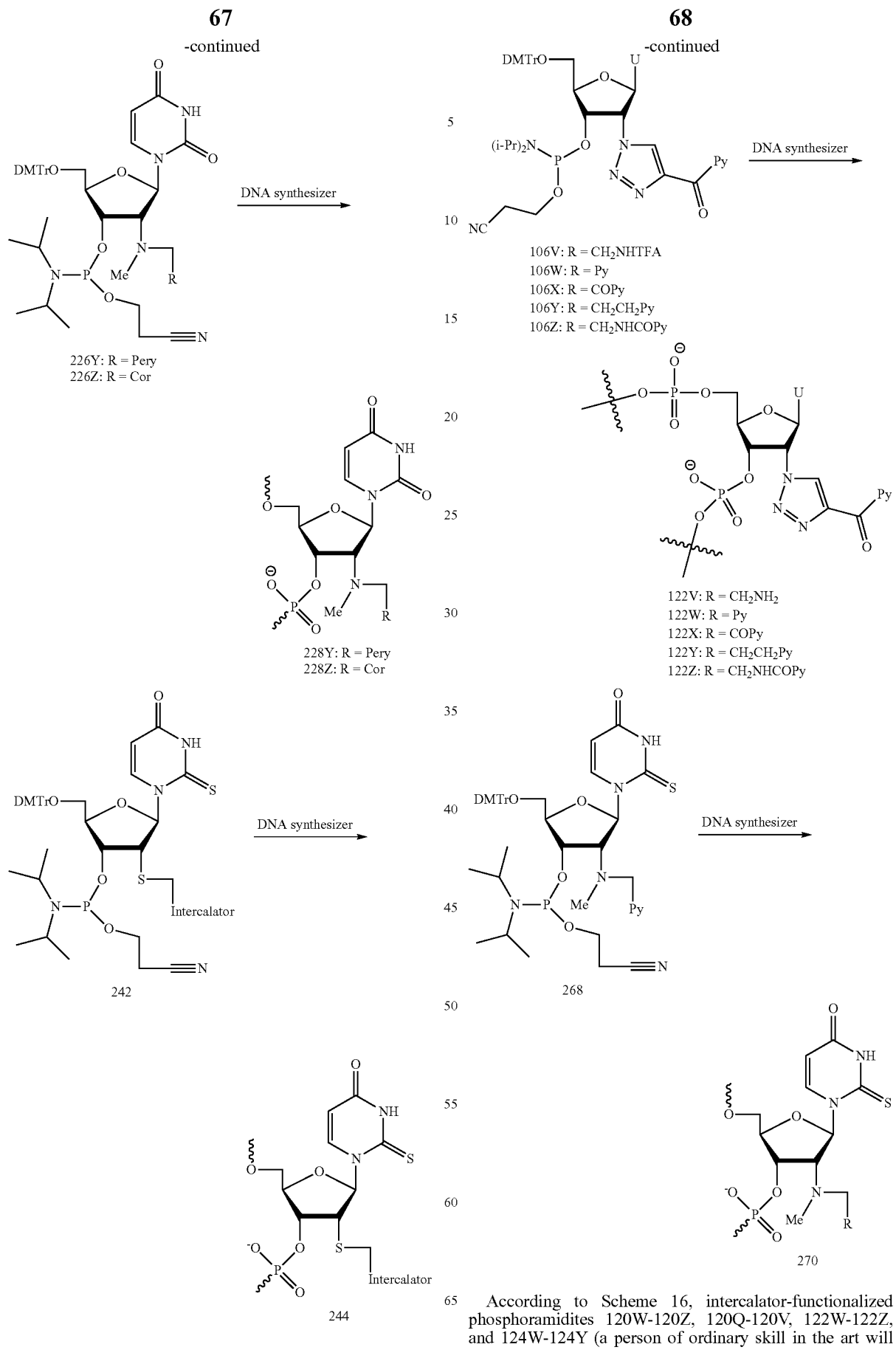
According to Scheme 16, intercalator-functionalized phosphoramidites 120W-120Z, 120Q-120V, 122W-122Z, and 124W-124Y (a person of ordinary skill in the art will realize that this can apply to all disclosed monomer embodiments) were incorporated into oligonucleotides via machine-assisted solid-phase DNA synthesis using an activator, such as an activator selected from 4,5-dicyanoimidazole and 5-(bis-3,5-trifluoromethylphenyl)-1H-tetrazole, for time periods ranging from about 1 minute to about 40 minutes; more typically from about 10 minutes to about 35 minutes.

Particular embodiments concern probes simultaneously comprising one or more of the disclosed monomers and one or more non-pairing or bulge monomers. According to Scheme 17 below, non-pairing or bulge monomers 402-4, 402-9 and 402-N were incorporated into oligonucleotides via machine-assisted solid-phase DNA synthesis as recommended by commercial vendors and/or in an equivalent manner as described for the disclosed intercalator-functionalized monomers.

(126X>126Y>>126Z); still without being limited to one operation of theory, monomers with acyl linkers seem preferred over those with alkyl linkers (126X>126W). Significantly similar trends seem to be observed for ONs modified with N2'-pyrene-functionalized 2'-amino-α-L-LNA adenine monomers 124X and 124Y (Table 9).

Control ONs that are singly modified with 2'-oxy-α-L-LNA thymine monomer O (i.e., without an intercalator) only display moderately increased thermal affinity toward DNA complements (see Table 8). ONs modified with unfunctionalized 2'-amino-α-L-LNA thymine monomer N (i.e., without an intercalator) also display low thermal affinity toward DNA (see Table 8). This suggests that the intercalators of the disclosed monomers have stabilizing roles.

Without being limited to a single theory, it is currently believed that the observed trends in DNA duplex thermo- Scheme 17

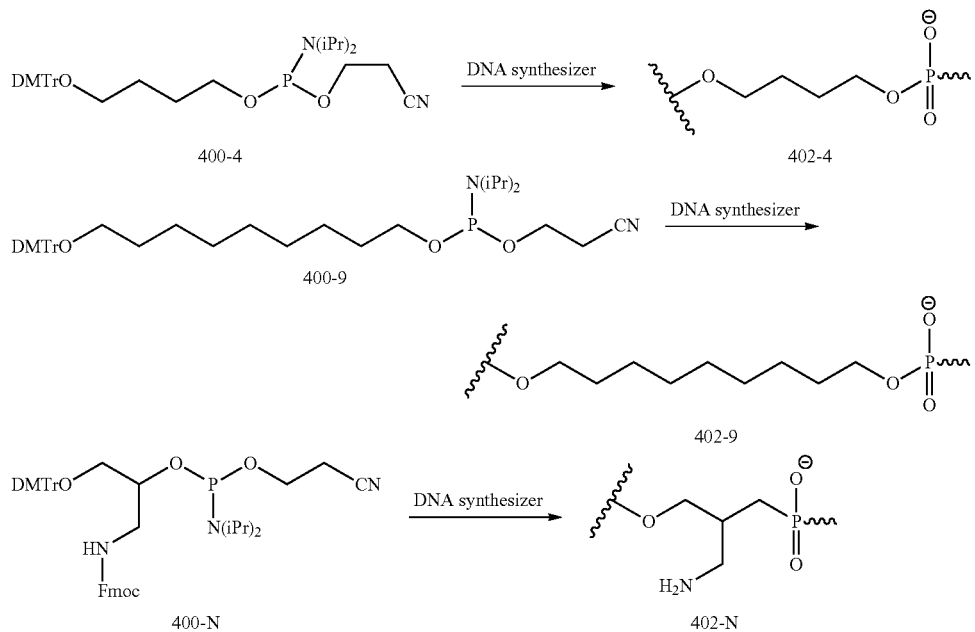

Figure 4:
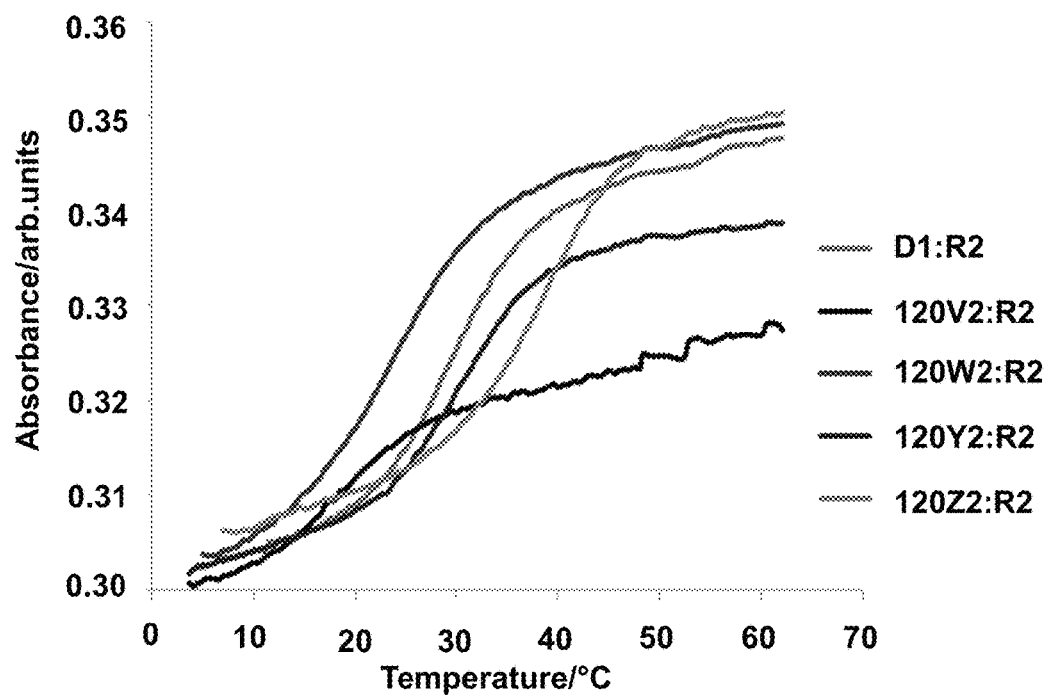
FIG. 4 is an image of a thermal denaturation curve between an exemplary embodiment of disclosed probes and a nucleic acid target illustrating characteristics of duplexes between one of the (two) probe strands and one of the (two) target strands.
Figure 5:
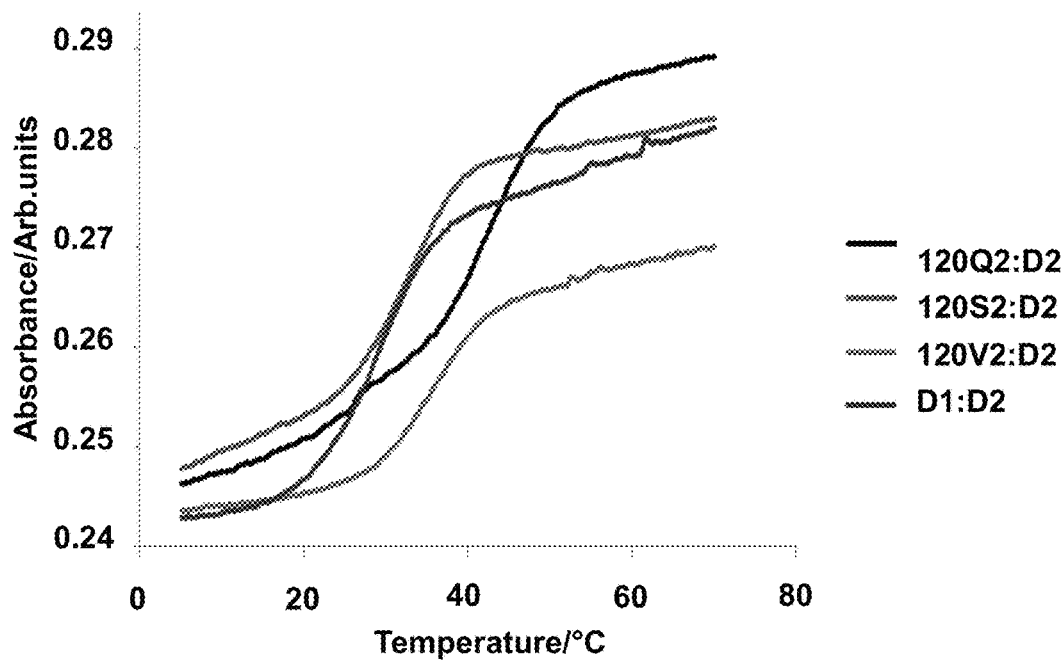
FIG. 5 is an image of a thermal denaturation curve between an exemplary embodiments of disclosed probes and a nucleic acid target illustrating characteristics of duplexes between one of the (two) probe strands and one of the (two) target strands.
Figure 6:
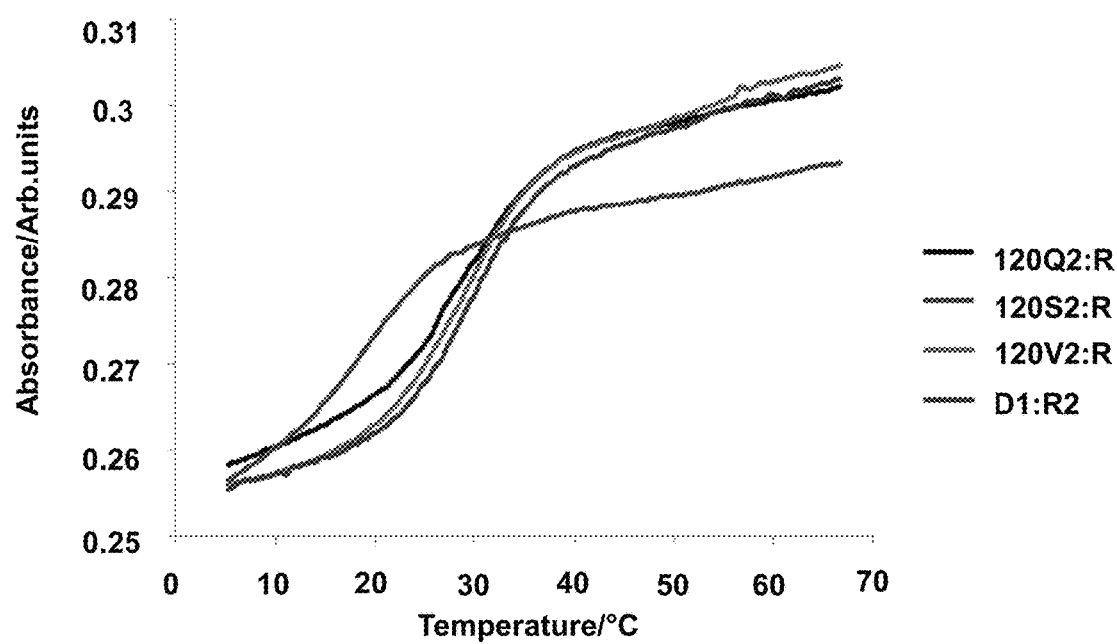
FIG. 6 is an image of a thermal denaturation curve between an exemplary embodiment of disclosed probes and a nucleic acid target illustrating characteristics of duplexes between one of the (two) probe strands and one of the (two) target strands.

In order to determine the efficiency of probes disclosed herein, the thermal affinity of the probe toward complementary DNA or RNA targets can be evaluated via UV thermal denaturation experiments using medium salt buffers that mimic physiological ionic strengths ([Na$^+$]=110 mM, Tables 8 and 9). In particular disclosed embodiments, denaturation curves may display sigmoidal monophasic transitions, such as those exemplary embodiments illustrated in FIGS. 4-5. Changes in thermal denaturation temperatures (T$_m$-values) of modified duplexes are discussed relative to T$_m$-values of unmodified reference duplexes, unless otherwise mentioned.

Certain embodiments entail single-stranded probes comprising the disclosed monomers. It currently is believed that certain disclosed monomers result in significantly increased thermal affinity toward single-stranded nucleic acid targets, more commonly single-stranded DNA. For example, 9-mer oligonucleotides (ONs), which are modified with locked monomers 126W-Z, display extraordinary thermal affinity toward complementary DNA relative to unmodified ONs (ΔT$_m$ up to +19.5° C., Table 8).

Without being limited to one theory of operation, incorporation of monomers with short linkers appears to result in greater duplex stabilization than monomers with long linkers stabilization of probes comprising monomers 120Q-120V indicate that monomers where the intercalator moiety is attached via N2'-alkyl linkers are preferred over those with N2'-alkanoyl linkers (compare ΔT$_m$/mod for 120S1-120S5=−6.0 to +4.0° C. with data for 120Q1-120Q5, Table 8) and that extending the N2'-alkanoyl linker between the furanose and intercalator moiety as in oligonucleotides modified with 2'-N-(pyren-1-ylmethycarbonyl)-2'-aminouridine monomer 120V, partially reverses the detrimental effects of N2'-acylation on DNA duplex thermostability (monomer 120S→monomer 120V, ΔT$_m$/mod=−0.5 to +6.5° C., Table 8). Also, without being limited to a single theory of operation, it is currently believed that the rigid 2'-N-alkanoyl linker positions the intercalator in an unsuitable position for affinity-enhancing intercalation and/or that increased solvation of the linker stabilizes the single-stranded state rendering hybridization less energetically favorable.

Without being limited to a single theory of operation, it is currently believed that the observed trends in DNA affinity of ONs modified with unlocked monomers, such as monomer 120Q or 120Y are substantially similar to those obtained with locked monomers, such as 126W-126Z (Table 8). Significantly similar trend is observed for probes modified with monomers 120'W and 124X bearing adenines as nucleobases (Table 9).

TABLE 8

ΔT$_m$ values of duplexes between probes comprised of certain disclosed monomers and complementary DNA.[a]

| | | | | | | 66 T$_m$/° C. | | | | | |
|---|---|---|---|---|---|---|---|---|---|---|---|
| ON Duplex | B = | O | N | 126W | 126X | 126Y | 126Z | 120Q | 120S | 120V | 120Y |
| B1 5'-GBG ATA TGC<br>D2 3'-CAC TAT ACG | | +2.5 | −2.0 | +7.0 | +10.0 | +10.5 | +0.5 | +5.0 | −6.0 | −0.5 | +5.0 |
| B2 5'-GTG ABA TGC<br>D2 3'-CAC TAT ACG | | +6.0 | +0.5 | +14.0 | +19.0 | +15.5 | +6.0 | +14.0 | +3.0 | +6.0 | +12.5 |
| B3 5'-GTG ATA BGC<br>D2 3'-CAC TAT ACG | | +3.0 | −1.0 | +10.5 | +14.0 | +11.5 | — | — | — | — | +8.0 |
| D1 5'-GTG ATA TGC<br>B4 3'-CAC BAT ACG | | +3.5 | −0.5 | +6.5 | +10.5 | +10.0 | +0.5 | +1.5 | −6.0 | +1.0 | +3.5 |
| D1 5'-GTG ATA TGC<br>B5 3'-CAC TAB ACG | | +8.0 | +2.5 | +15.5 | +19.5 | +16.5 | +6.5 | +13.0 | +4.0 | +6.5 | +11.5 |

[a]ΔT$_m$ = change in T$_m$ values relative to unmodified reference duplex D1:D2 (T$_m$ = 29.5° C.); T$_m$ values determined as the first derivative maximum of denaturation curves (A$_{260}$ vs T) recorded in medium salt buffer ([Na$^+$] = 110 mM, [Cl$^−$] = 100 mM, pH 7.0 (NaH$_2$PO$_4$/Na$_2$HPO$_4$)), using 1.0 μM of each strand. T$_m$ values are averages of at least two measurements within 1.0° C.; A = adenin-9-yl DNA monomer, C = cytosin-1-yl DNA monomer, G = guanin-9-yl DNA monomer, T = thymin-1-yl DNA monomer. "—" = not determined.

TABLE 9

T$_m$ Values of Duplexes Between Probes Comprised of Certain Disclosed Monomers and Complementary DNA[a]

| | | | ΔT$_m$/° C. | | |
|---|---|---|---|---|---|
| ON | Duplex | B = | 124X | 124Y | 120'W |
| B6 | 5'-GTG BTA TGC<br>3'-CAC TAT ACG | | +5.0 | +11.0 | +4.5 |
| B7 | 5'-GTG ATB TGC<br>3'-CAC TAT ACG | | +7.0 | +14.0 | +8.5 |
| D1<br>B8 | 5'-GTG ATA TGC<br>3'-CAC TBT ACG | | +6.5 | +11.5 | +8.5 |
| D1<br>B9 | 5'-GTG ATA TGC<br>3'-CAC TAT BCG | | +5.5 | +12.0 | +6.5 |

[a]ΔT$_m$ = change in T$_m$ values relative to unmodified reference duplex D1:D2 (T$_m$ = 29.5° C.); see Table 8 for experimental conditions.

TABLE 10

T$_m$ Values of Duplexes Between Probes Comprised of Certain Disclosed Monomers and Complementary DNA[a]

| | | | | T$_m$ [ΔT$_m$/mod] (° C.) | | |
|---|---|---|---|---|---|---|
| ON | Duplex | B = | T | 120W | 120X | 120Z |
| B1<br>D2 | 5'-GBG ATA TGC<br>3'-CAC TAT ACG | | 29.5 | 21.5<br>[−8.0] | 26.5<br>[−3.0] | 34.0<br>[+4.5] |
| B2<br>D2 | 5'-GTG ABA TGC<br>3'-CAC TAT ACG | | 29.5 | 24.5<br>[−5.0] | 33.5<br>[+4.0] | 49.5<br>[+20.0] |
| B3<br>D2 | 5'-GTG ATA BGC<br>3'-CAC TAT ACG | | 29.5 | 24.5<br>[−5.0] | 26.0<br>[−3.5] | 40.5<br>[+11.0] |
| D1<br>B4 | 5'-GTG ATA TGC<br>3'-CAC BAT ACG | | 29.5 | 16.5<br>[−13.0] | 26.0<br>[−3.5] | 36.0<br>[+6.5] |
| D1<br>B5 | 5'-GTG ATA TGC<br>3'-CAC TAB ACG | | 29.5 | 24.5<br>[−5.0] | 30.5<br>[+1.0] | 45.5<br>[+16.0] |
| D1<br>B6 | 5'-GTG ATA TGC<br>3'-CAC BAB ACG | | 29.5 | ND | 25.5<br>[−2.0] | 47.0<br>[+8.8] |
| B7<br>D2 | 5'-GBG ABA BGC<br>3'-CAC TAT ACG | | 29.5 | ND | 25.5<br>[−1.3] | ND |

[a]ΔT$_m$ = change in T$_m$ values relative to unmodified reference duplex D1:D2 (T$_m$ = 29.5° C.); see Table 8 above for experimental conditions.

In particular disclosed embodiments, the results of thermal DNA affinity of other monomers may vary from ΔT$_m$/mod=−13.0° C. to +20.0° C. (Table 10). Also suggested by these results is the theory that increasing the intercalator surface area leads to additional increases in DNA duplex thermostability (compare data for probes comprising monomers 120Y and 120Z, Tables 8 and 10) and that shortening the linker between the furanose and intercalator moiety results in markedly lower DNA-affinity (compare data for probes comprising monomers 120Y and 120X, Tables 8 and 10). Furthermore, it is currently believed that concomitant reduction in aromatic surface area results in additionally decreased DNA duplex thermostability (compare data for probes comprising monomers 120X and 120W, Table 10).

Certain embodiments entail double-stranded probes with interstrand zipper arrangements of disclosed monomers such as those shown in Table 11, which result in destabilization of the probe. The impact on duplex thermostability upon hybridization of two single-stranded probes that are each modified with one or more of the disclosed monomers can be additive, more-than-additive or less-than-additive relative to the correspondingly singly modified duplexes. This can be readily assessed by the term 'deviation from additivity' (DA) for a probe ONX:ONY, defined as:

$$DA_{ONX:ONY}=\Delta T_m(ONX:ONY)-[\Delta T_m(ONX:DNA\ X)+\Delta T_m(DNA\ Y:ONY)]$$

where ONX:ONY is a duplex with an interstrand monomer arrangement and 'DNA X' and 'DNA Y' are the complementary DNA of ONX and ONY, respectively. It follows that DA~0° C. for additive impacts, DA>>0° C. for more-than-additive impacts, and DA<<0° C. for less-than-additive impacts (see also definitions). The term thermal advantage, TA, is strongly related to DA, i.e., TA=−DA (see also definitions). Double-stranded probes may display a largely positive TA (or largely negative DA). This energy difference between probe-target duplexes on one side and double-stranded nucleic acid targets (more commonly dsDNA) and probes on the other side, may provide the driving force for recognition of double-stranded target regions (more commonly dsDNA target regions), via the method shown in FIG. 1.

Particular embodiments entail double-stranded probes with +1 interstrand zipper arrangements (see also definitions) of disclosed monomers as shown in Tables 11 and 12, which display significant dsDNA-targeting potential as evidenced by the highly negative DA-values (DA between −40° C. and −12° C.). Other embodiments entail double-stranded probes with +2 zipper arrangements of intercalator-modified monomers, which also display negative DA-values, although the values are generally less prominent than probes with +1 zipper monomer arrangements. Probes with other interstrand zipper arrangements (e.g., +4, −1 and −3) display less regular and/or prominent dsDNA-targeting potential as indicated by DA-values ranging from moderately negative to moderately positive (DA between −8.5° C. and +4° C.). Without being limited to a single theory of operation, probes with +1 interstrand arrangements of disclosed monomers display significant potential for targeting of isosequential dsDNA regions, and enable targeting of isosequential double-stranded nucleic acid regions, more commonly double-stranded DNA, via the method outlined in FIG. 1.

Control duplexes with two conventional 2'-oxy-α-L-LNA thymine monomer O or 2'-amino-α-L-LNA thymine monomer N in +1 arrangements, display DA values ~0° C. This implies that the dsDNA-targeting potential is generated by the active involvement of the intercalators moieties.

TABLE 11

$\Delta T_m$ And DA Values for Double-Stranded Probes with Certain Interstrand Zipper Arrangements of Disclosed Monomers[a]

| ON | Zipper | Duplex | B = | O | N | 126W | 126X | 126Y | 126Z | 120Q | 120S | 120V | 120Y |
|---|---|---|---|---|---|---|---|---|---|---|---|---|---|
| B1 | +4 | 5'-GBG ATA TGC | | +11.0 | +1.0 | +25.0 | +28.5 | +26.0 | +8.5 | +19.5 | −3.5 | +9.0 | +16.5 |
| B5 | | 3'-CAC TAB ACG | | [+0.5] | [+0.5] | [+2.5] | [−1.0] | [−1.0] | [+1.5] | [+1.5] | [−5.5] | [+3.0] | [0.0] |
| B1 | +2 | 5'-GBG ATA TGC | | +8.0 | −1.5 | 0.0 | +6.5 | +12.5 | −1.0 | −1.5 | −17.5 | −2.0 | −6.0 |
| B4 | | 3'-CAC BAT ACG | | [+2.0] | [+1.0] | [−13.5] | [−14.0] | [−8.0] | [−2.0] | [−8.0] | [−5.5] | [−2.5] | [−14.5] |
| B2 | +1 | 5'-GTG ABA TGC | | +16.0 | −5.5 | +2.5 | −1.5 | +1.0 | −5.5 | −2.0 | −10.0 | +0.5 | −2.0 |
| B5 | | 3'-CAC TAB ACG | | [+2.0] | [−8.5] | [−27.0] | [−40.0] | [−31.0] | [−18.0] | [−29.0] | [−17.0] | [−12.0] | [−26.0] |
| B2 | −1 | 5'-GTG ABA TGC | | +7.0 | −5.5 | +15.5 | +26.0 | +26.5 | +9.5 | +13.0 | −8.5 | +5.5 | +10.5 |
| B4 | | 3'-CAC BAT ACG | | [+2.5] | [−5.5] | [−5.0] | [−3.5] | [+1.0] | [+3.0] | [−2.5] | [−5.5] | [−2.5] | [−5.5] |
| B3 | −1 | 5'-GTG ATA BGC | | +8.5 | −2.5 | +18.0 | +25.0 | +29.5 | — | — | — | — | — |
| B5 | | 3'-CAC TAB ACG | | [−2.5] | [−4.0] | [−8.0] | [−8.5] | [+1.5] | | | | | |
| B3 | −3 | 5'-GTG ATA BGC | | +8.0 | −2.5 | +18.0 | +28.5 | +22.0 | — | — | — | — | — |
| B4 | | 3'-CAC BAT ACG | | [+1.5] | [−1.0] | [+1.0] | [+4.0] | [+0.5] | | | | | |

[a]$\Delta T_m$ = change in $T_m$ values relative to unmodified reference DNA duplex D1:D2 ($T_m$ = 29.5° C.); see Table 8 for experimental conditions.

TABLE 12

$\Delta T_m$ And DA Values for Double-Stranded Probes with Certain Interstrand Zipper Arrangements of Disclosed Monomers.[a]

| ON | Zipper | Duplex | B = | 124X | 124Y | 120'W |
|---|---|---|---|---|---|---|
| B6 | +3 | 5'-GTG BTA TGC | | +12.0 | +13.0 | +10.0 |
| B9 | | 3'-CAC TAT BCG | | [+1.5] | [−10.0] | [−1.0] |
| B6 | +1 | 5'-GTG BTA TGC | | −7.0 | −8.0 | −7.5 |
| B8 | | 3'-CAC TBT ACG | | [−18.5] | [−30.5] | [−20.5] |
| B7 | +1 | 5'-GTG ATB TGC | | −5.0 | −7.0 | −7.0 |
| B9 | | 3'-CAC TAT BCG | | [−17.5] | [−33.0] | [−22.0] |
| B7 | −1 | 5'-GTG ATB TGC | | +14.0 | +23.5 | +15.0 |
| B8 | | 3'-CAC TBT ACG | | [+0.5] | [−2.0] | [−2.0] |

[a]$\Delta T_m$ = change in $T_m$ values relative to unmodified reference duplex D1:D2 ($T_m$ = 29.5° C.); see Table 8 for experimental conditions.

Certain embodiments entail double-stranded probes with 'mixed' interstrand arrangements of disclosed monomers. Double-stranded probes with 'mixed' interstrand arrangements of 124X and 124Y are one representative example of this embodiment (e.g., one strand modified with 2'-amino- α-L-LNA monomer 124X, the other strand modified with 2'-amino-α-L-LNA monomer 124Y, Table 13). Significantly negative DA values are observed for these double-stranded probes. For example, probes with 'mixed' +1 zippers display DA values between −19.5° C. and −23.0° C. (Table 13). Without being limited to a single operation of theory, probes with +1 zippers composed of different monomers, display significant dsDNA-targeting potential and enable targeting of dsDNA-regions as described in FIG. 1.

TABLE 13

$\Delta T_m$ And DA Values for Double-Stranded Probes with 'Mixed' Interstrand Arrangements of Monomer 124X and Monomer 124Y[a]

| ON | Zipper | Duplex | $\Delta T_m$[DA]/° C. |
|---|---|---|---|
| 124X6 | +3 | 5'-GTG KTA TGC | +13.0 |
| 124Y9 |  | 3'-CAC TAT LCG | [−4.0] |
| 124Y6 | +3 | 5'-GTG LTA TGC | +11.0 |
| 124X9 |  | 3'-CAC TAT KCG | [−5.5] |
| 124X6 | +1 | 5'-GTG KTA TGC | −3.0 |
| 124Y8 |  | 3'-CAC TLT ACG | [−19.5] |
| 124Y6 | +1 | 5'-GTG LTA TGC | −4.0 |
| 124X8 |  | 3'-CAC TKT ACG | [−21.5] |
| 124X7 | +1 | 5'-GTG ATK TGC | −4.0 |
| 124Y9 |  | 3'-CAC TAT LCG | [−23.0] |
| 124Y7 | +1 | 5'-GTG ATL TGC | 0.0 |
| 124X9 |  | 3'-CAC TAT KCG | [−19.5] |
| 124X7 | −1 | 5'-GTG ATK TGC | +22.0 |
| 124Y8 |  | 3'-CAC TLT ACG | [+3.5] |
| 124Y7 | −1 | 5'-GTG ATL TGC | +18.0 |
| 124X8 |  | 3'-CAC TKT ACG | [−2.5] |

[a]$\Delta T_m$ = change in $T_m$ values relative to unmodified reference duplex D1:D2 ($T_m$ = 29.5° C.); see Table 8 for experimental conditions.

Certain embodiments entail double-stranded probes where one strand is modified with one or more monomers comprising a thymine nucleobase, and the other strand is modified is with one or more monomers comprising an adenine nucleobase. Particular embodiments of a double-stranded probe where one strand is modified with a thymine monomer (126W or 126X) and the other strand is modified is with an adenine monomer (124X or 124Y) are given in (Tables 14-17). Probes with 0 or +2 interstrand monomer arrangements generally display significantly negative DA-values (DA-values between −22° C. to −10° C.), indicating significant potential for targeting of double-stranded nucleic acid targets, more commonly dsDNA, via the method shown in FIGS. 1-2. Probes with −2 interstrand arrangements display DA-values ~0° C. Without being limited to a single theory of operation, probes with 0, +1 or +2 interstrand zipper arrangements of disclosed monomers may display significant potential for targeting of double-stranded nucleic acids, more commonly dsDNA, and may enable targeting of dsDNA as shown FIG. 1.

TABLE 14

$\Delta T_m$ And DA Values for Selected Double-Stranded Probes with 'Mixed' Interstrand Zippers Comprised of Monomer 126W And Monomer 124X[a]

| ON | Zipper | Duplex | $\Delta T_m$[DA]/° C. |
|---|---|---|---|
| 126W2 | +2 | 5'-GTG A(126W)A TGC | +9.5 |
| 124X9 |  | 3'-CAC TAT (126X)CG | [−10.0] |
| 124X6 | 0 | 5'-GTG (126X)TA TGC | −4.0 |
| 126W4 |  | 3'-CAC (126W)AT ACG | [−15.5] |
| 126W2 | 0 | 5'-GTG A(126W)A TGC | 0.0 |
| 124X8 |  | 3'-CAC T(126X)T ACG | [−20.5] |
| 126W3 | 0 | 5'-GTG ATA (126W)GC | −4.5 |
| 124X9 |  | 3'-CAC TAT (126X)CG | [−20.5] |
| 126W3 | −2 | 5'-GTG ATA (126W)GC | +17.5 |
| 124X8 |  | 3'-CAC T(126X)T ACG | [+0.5] |
| 124X7 | −2 | 5'-GTG AT(126X) TGC | +14.5 |
| 126W4 |  | 3'-CAC (126W)AT ACG | [+1.0] |

[a]$\Delta T_m$ = change in $T_m$ values relative to unmodified reference duplex D1:D2 ($T_m$ = 29.5° C.); see Table 8 for experimental conditions.

TABLE 15

$\Delta T_m$ And DA Values for Selected DNA Duplexes with 'Mixed' Interstrand Zippers Comprised of Monomer 126X And Monomer 124Y[a]

| ON | Zipper | Duplex | $\Delta T_m$[DA]/° C. |
|---|---|---|---|
| 126X2 | +2 | 5'-GTG A(126X)A TGC | +12.0 |
| 124Y9 |  | 3'-CAC TAT (124Y)CG | [−19.0] |
| 124Y6 | 0 | 5'-GTG (124Y)TA TGC | +11.5 |
| 126X4 |  | 3'-CAC (126X)AT ACG | [−10.0] |
| 126X2 | 0 | 5'-GTG A(126X)A TGC | +12.5 |
| 124Y8 |  | 3'-CAC T(124Y)T ACG | [−18.0] |
| 126X3 | 0 | 5'-GTG ATA (126X)GC | +6.5 |
| 124Y9 |  | 3'-CAC TAT (124Y)CG | [−19.5] |
| 126X3 | −2 | 5'-GTG ATA (126X)GC | +24.5 |
| 124Y8 |  | 3'-CAC T(124Y)T ACG | [−1.0] |

[a]$\Delta T_m$ = change in $T_m$ values relative to unmodified reference duplex D1:D2 ($T_m$ = 29.5° C.); see Table 8 for experimental conditions.

TABLE 16

$\Delta T_m$ and DA Values for Selected DNA Duplexes with 'Mixed' Interstrand Zippers Comprised of Monomer 126X) and Monomer 124X[a]

| ON | Zipper | Duplex | $\Delta T_m$[DA]/° C. |
|---|---|---|---|
| 126X2 | +2 | 5'-GTG A(126X)A TGC | +12.0 |
| 124X9 |  | 3'-CAC TAT (124X)CG | [−12.5] |
| 124X6 | 0 | 5'-GTG (124X)TA TGC | −2.0 |
| 126X4 |  | 3'-CAC (126X)AT ACG | [−17.5] |
| 126X2 | 0 | 5'-GTG A(126X)A TGC | +6.0 |
| 124X8 |  | 3'-CAC T(124X)T ACG | [−19.5] |
| 124X7 | 0 | 5'-GTG AT(124X) TGC | +6.0 |
| 126X5 |  | 3'-CAC TA(126X) ACG | [−20.5] |
| 126X3 | −2 | 5'-GTG ATA (126X)GC | +21.5 |
| 124X8 |  | 3'-CAC T(124X)T ACG | [+1.0] |

TABLE 16-continued

ΔT$_m$ and DA Values for Selected DNA
Duplexes with 'Mixed' Interstrand Zippers
Comprised of Monomer 126X) and Monomer 124X$^a$

| ON | Zipper | Duplex | ΔT$_m$[DA]/° C. |
|---|---|---|---|
| 124X7 | −2 | 5'-GTG AT(124X) TGC | +19.5 |
| 126X4 | | 3'-CAC (126X)AT ACG | [+2.0] |

$^a$ΔT$_m$ = change in T$_m$ values relative to unmodified reference duplex D1:D2 (T$_m$ = 29.5° C.); see Table 8 for experimental conditions.

TABLE 17

ΔT$_m$ And DA Values for Selected DNA
Duplexes with 'Mixed' Interstrand Zippers
Comprised of Monomer 126W and Monomer 124Y$^a$

| ON | Zipper | Duplex | ΔT$_m$[DA]/° C. |
|---|---|---|---|
| 126W2 | +2 | 5'-GTG A(126W)A TGC | +11.0 |
| 124Y9 | | 3'-CAC TAT (124Y)CG | [−15.0] |
| 126W3 | 0 | 5'-GTG ATA (126W)GC | +0.5 |
| 124Y9 | | 3'-CAC TAT (124Y)CG | [−22.0] |
| 126W3 | −2 | 5'-GTG ATA (126W)GC | +24.0 |
| 124Y8 | | 3'-CAC T(124Y)T ACG | [+2.0] |

$^a$ΔT$_m$ = change in T$_m$ values relative to unmodified reference duplex D1:D2 (T$_m$ = 29.5° C.); see Table 8 for experimental conditions.

Additional embodiments include double-stranded probes with +1 interstrand zipper arrangements of monomers 208W-Z (Table 18).

TABLE 18

Thermal Denaturation Properties and dsDNA-Targeting
Potential of Certain Disclosed Probes

| B = | 5'-GTG ATA TGC 3'-CAC TAT ACG T$_m$ (° C.) | 5'-GTG ABA TGC 3'-CAC TAB ACG T$_m$ [ΔT$_m$] (° C.) | 5'-GTG ABA TGC 3'-CAC TAT ACG T$_m$ [ΔT$_m$] (° C.) | 5'-GTG ATA TGC 3'-CAC TAB ACG T$_m$ [ΔT$_m$] (° C.) | TA ° C. |
|---|---|---|---|---|---|
| 120Y | 29.5 | 27.5 [−2.0] | 42.0 [+12.5] | 41.0 [+11.5] | +26.0 |
| 208W | 29.5 | 25.0 [−4.5] | 40.0 [+10.5] | 38.0 [+8.5] | +23.5 |
| 208X | 29.5 | 27.0 [−2.5] | 45.0 [+15.5] | 45.0 [+15.5] | +33.5 |
| 208Y | 29.5 | 29.0 [−0.5] | 46.5 [+17.0] | 45.5 [+16.0] | +33.5 |
| 208Z | 29.5 | 22.0 [−7.5] | 36.0 [+6.5] | 35.0 [+5.5] | +19.5 | see Table 8 for experimental conditions.

With reference to Table 18 above, thermal denaturation temperatures for model DNA duplex target (column 2 of 6), probe (column 3 of 6), probe-target duplex involving upper (column 4 of 6) or lower probe strand (column 5 of 6) are given. Thus, probes with +1 interstrand zipper arrangement of the monomers (column 3) display similar or lower thermostability than model DNA duplex target (column 2; note negative delta Tm values in column 3), while probe-target duplexes (columns 4 and 5) may be greatly stabilized (note highly positive delta Tm values). Without being limited to a single theory of operation, probes with +1 interstrand arrangements of monomers 120Y/208X/208Y/208Z display significantly positive thermal advantage (TA) values and, thus, significant potential for targeting of double-stranded nucleic acid targets, more commonly dsDNA, via the method outlined in FIGS. 1-2.

Additional particular embodiments entailing double-stranded probes with +1 interstrand zipper arrangements of certain disclosed monomers are given below in Table 19. Without being limited to a single theory of operation, probes with +1 interstrand arrangements of monomers 228X-Z display significantly positive thermal advantage (TA) values and, thus, significant potential for targeting of double-stranded nucleic acid targets, more commonly dsDNA, via the method outlined in FIGS. 1-2.

TABLE 19

Exemplary Embodiments of Double-stranded Probes
with +1 Interstrand Zipper Arrangements Comprising
Certain Disclosed Monomers

| Sequence | Probe T$_m$ [° C.] | Upper probe strand vs DNA T$_m$ [° C.] | Lower probe strand vs DNA T$_m$ [° C.] | dsDNA target T$_m$ [° C.] | TA [° C.] |
|---|---|---|---|---|---|
| 5'-GTG A(228X)A TGC 3'-CAC TA(228X) ACG | 29.5 | 43.5 | 42.5 | 29.5 | +27.0 |
| 5'-GTG A(228Y)A TGC 3'-CAC TA(228Y) ACG | 32.5 | 48.0 | 51.5 | 29.5 | +37.5 |

TABLE 19-continued

Exemplary Embodiments of Double-stranded Probes
with +1 Interstrand Zipper Arrangements Comprising
Certain Disclosed Monomers

| Sequence | Probe T$_m$ [° C.] | Upper probe strand vs DNA T$_m$ [° C.] | Lower probe strand vs DNA T$_m$ [° C.] | dsDNA target T$_m$ [° C.] | TA [° C.] |
|---|---|---|---|---|---|
| 5'-GTG A(228Z)A TGC | 41.0 | 50.5 | 49.5 | 29.5 | +29.5 |

TABLE 19-continued

Exemplary Embodiments of Double-stranded Probes with +1 Interstrand Zipper Arrangements Comprising Certain Disclosed Monomers

| Sequence | Probe $T_m$ [° C.] | Upper probe strand vs DNA $T_m$ [° C.] | Lower probe strand vs DNA $T_m$ [° C.] | dsDNA target $T_m$ [° C.] | TA [° C.] |
|---|---|---|---|---|---|
| 3'-CAC TA(228Z) ACG | | | | | | see Table 8 above for experimental conditions.

Additional examples of working embodiments of probes based on monomer 120Y are provided below in Table 20. Table 20 provides thermal denaturation temperatures for a model DNA duplex target (column 6 of 7), probe (column 5 of 7), probe-target duplexes [i.e., model products from dsDNA recognition] involving upper (column 3 of 7) or lower probe strand (column 4 of 7). Probes with one +1 interstrand zipper arrangement of the monomers (first four entries) display similar or lower thermostability than unmodified dsDNA (representing the target; note negative delta Tm values in column 5), while probe-target duplexes (columns 3 and 4) display far greater stabilization (note highly positive delta Tm values). As previously indicated, probes with other interstrand arrangements may display less positive (or even negative) TA values and may therefore display less dsDNA-targeting potential (i.e., entriesin this Table). Probes with two or more +1 interstrand arrangements of the disclosed monomers (bottom six entries), may display very high TA-values, suggesting significant potential for targeting of double-stranded targets, more commonly, dsDNA target regions, via the method shown in FIGS. 1-2.

TABLE 20

Exemplary Probes Based on Monomer 120Y (=T)

| Probe | Zipper | Upper probe strand vs DNA $T_m[\Delta T_m]$ (° C.) | Lower probe strand vs DNA $T_m[\Delta T_m]$ (° C.) | Probe $T_m[\Delta T_m]$ (° C.) | dsDNA target $T_m$ (° C.) | TA (° C.) |
|---|---|---|---|---|---|---|
| 5'-GGT ATA TAT AGG C (SEQ ID NO: 38) 3'-CCA TAT ATA TCC G (SEQ ID NO: 136) | +1 | 44.5 [+7.0] | 47.5 [+10.0] | 36.5 [−1.0] | 37.5 | +18.0 |
| 5'-GGT ATA TAT AGG C (SEQ ID NO: 40) 3'-CCA TAT ATA TCC G (SEQ ID NO: 137) | +1 | 47.5 [+10.0] | 48.5 [+11.0] | 36.5 [−1.0] | 37.5 | +22.0 |
| 5'-GGT ATA TAT AGG C (SEQ ID NO: 42) 3'-CCA TAT ATA TCC G (SEQ ID NO: 138) | +1 | 48.5 [+11.0] | 47.5 [+10.0] | 36.5 [−1.0] | 37.5 | +22.0 |
| 5'-GGT ATA TAT AGG C (SEQ ID NO: 44) 3'-CCA TAT ATA TCC G (SEQ ID NO: 139) | +1 | 47.5 [+10.0] | 46.5 [+9.0] | 35.5 [−2.0] | 37.5 | +21.0 |
| 5'-GGT ATA TAT AGG C (SEQ ID NO: 38) 3'-CCA TAT ATA TCC G (SEQ ID NO: 137) | +3 | 44.5 [+7.0] | 48.5 [+11.0] | 54.0 [+16.5] | 37.5 | +1.5 |
| 5'-GGT ATA TAT AGG C (SEQ ID NO: 38) 3'-CCA TAT ATA TCC G (SEQ ID NO: 138) | +5 | 44.5 [+7.0] | 47.5 [+10.0] | 55.0 [+17.5] | 37.5 | −0.5 |
| 5'-GGT ATA TAT AGG C (SEQ ID NO: 38) 3'-CCA TAT ATA TCC G (SEQ ID NO: 139) | +7 | 44.5 [+7.0] | 46.5 [+9.0] | 53.0 [+15.5] | 37.5 | +0.5 |
| 5'-GGT ATA TAT AGG C (SEQ ID NO: 40) 3'-CCA TAT ATA TCC G (SEQ ID NO: 138) | +3 | 47.5 [+10.0] | 47.5 [+10.0] | 57.0 [+19.5] | 37.5 | +0.5 |
| 5'-GGT ATA TAT AGG C (SEQ ID NO: 40) 3'-CCA TAT ATA TCC G (SEQ ID NO: 136) | −1 | 47.5 [+10.0] | 47.5 [+10.0] | 53.0 [+15.5] | 37.5 | +4.5 |

TABLE 20-continued

Exemplary Probes Based on Monomer 120Y (=T)

| Probe | Zipper | Upper probe strand vs DNA $T_m[\Delta T_m]$(° C.) | Lower probe strand vs DNA $T_m[\Delta T_m]$(° C.) | Probe $T_m[\Delta T_m]$(° C.) | dsDNA target $T_m$ (° C.) | TA (° C.) |
|---|---|---|---|---|---|---|
| 5'-GGT ATA TAT AGG C (SEQ ID NO: 40)<br>3'-CCA TAT ATA TCC G (SEQ ID NO: 139) | +5 | 47.5 [+10.0] | 46.5 [+9.0] | 56.0 [+18.5] | 37.5 | +0.5 |
| 5'-GGT ATA TAT AGG C (SEQ ID NO: 42)<br>3'-CCA TAT ATA TCC G (SEQ ID NO: 139) | +3 | 48.5 [+11.0] | 46.5 [+9.0] | 56.0 [+18.5] | 37.5 | +1.5 |
| 5'-GGT ATA TAT AGG C (SEQ ID NO: 42)<br>3'-CCA TAT ATA TCC G (SEQ ID NO: 137) | -1 | 48.5 [+11.0] | 48.5 [+11.0] | 55.0 [+17.5] | 37.5 | +4.5 |
| 5'-GGT ATA TAT AGG C (SEQ ID NO: 42)<br>3'-CCA TAT ATA TCC G (SEQ ID NO: 136) | -3 | 48.5 [+11.0] | 47.5 [+10.0] | 57.0 [+19.5] | 37.5 | +1.5 |
| 5'-GGT ATA TAT AGG C (SEQ ID NO: 44)<br>3'-CCA TAT ATA TCC G (SEQ ID NO: 138) | -1 | 47.5 [+10.0] | 47.5 [+10.0] | 54.0 [+16.5] | 37.5 | +3.5 |
| 5'-GGT ATA TAT AGG C (SEQ ID NO: 44)<br>3'-CCA TAT ATA TCC G (SEQ ID NO: 137) | -3 | 47.5 [+10.0] | 48.5 [+11.0] | 57.0 [+19.5] | 37.5 | +1.5 |
| 5'-GGT ATA TAT AGG C (SEQ ID NO: 44)<br>3'-CCA TAT ATA TCC G (SEQ ID NO: 136) | -5 | 47.5 [+10.0] | 47.5 [+10.0] | 57.0 [+19.5] | 37.5 | +0.5 |
| 5'-GGT ATA TAT AGG C (SEQ ID NO: 46)<br>3'-CCA TAT ATA TCC G (SEQ ID NO: 140) | 2x + 1 | 51.5 [+14.0] | 55.5 [+18.0] | 40.0 [+2.5] | 37.5 | +29.5 |
| 5'-GGT ATA TAT AGG C (SEQ ID NO: 48)<br>3'-CCA TAT ATA TCC G (SEQ ID NO: 141) | 2x + 1 | 53.5 [+16.0] | 56.5 [+19.0] | 49.0 [+11.5] | 37.5 | +23.5 |
| 5'-GGT ATA TAT AGG C (SEQ ID NO: 50)<br>3'-CCA TAT ATA TCC G (SEQ ID NO: 142) | 2x + 1 | 52.5 [+15.0] | 55.5 [+18.0] | 49.0 [+11.5] | 37.5 | +21.5 |
| 5'-GGT ATA TAT AGG C (SEQ ID NO: 52)<br>3'-CCA TAT ATA TCC G (SEQ ID NO: 143) | 2x + 1 | 55.5 [+18.0] | 55.5 [+18.0] | 45.0 [+7.5] | 37.5 | +28.5 |
| 5'-GGT ATA TAT AGG C (SEQ ID NO: 54)<br>3'-CCA TAT ATA TCC G (SEQ ID NO: 144) | 2x + 1 | 54.5 [+17.0] | 54.5 [+17.0] | 47.5 [+10.0] | 37.5 | +24.0 |
| 5'-GGT ATA TAT AGG C (SEQ ID NO: 56)<br>3'-CCA TAT ATA TCC G (SEQ ID NO: 145) | 4x + 1 | 65.5 [+28.0] | 67.5 [+30.0] | 50.0 [+12.5] | 37.5 | +45.5 |

"].

Particular embodiments concern probes with 0-arrangements of disclosed monomers, in some particular cases, monomers 120Y and 120"W. Such probes may display variable TA values ranging from −1° C. to +27° C., demonstrating that said probes may display significant potential for targeting of double-stranded nucleic acid targets, more commonly dsDNA targets, via the method outlined in FIGS. 1-2.

[product from dsDNA recognition] involving upper (column 2 of 6) or lower probe strand (column 3 of 6). Probes with one or more +1 interstrand zipper arrangement of the monomers display variable thermostability (ranging from strongly destabilized to moderately stabilized relative to unmodified dsDNA (note delta Tm values from −18 to +8 C, column 4). Probe-target duplexes (columns 2 and 3) are greatly stabilized (note highly positive delta Tm values). All probes

TABLE 21

Thermal Denaturation Properties of Certain Probes with 0-Zipper Interstrand Arrangements Where T is 120Y and A is 120'W

| Probe | Upper probe strand vs DNA $T_m[\Delta T_m]$(° C.) | Lower probe strand vs DNA $T_m[\Delta T_m]$(° C.) | Probe $T_m[\Delta T_m]$(° C.) | dsDNA target $T_m$ (° C.) | TA (° C.) |
|---|---|---|---|---|---|
| 5'-GGT ATA TAT AGG C (SEQ ID NO: 38) 3'-CCA TAT ATA TCC G (SEQ ID NO: 255) | 44.5 [+7.0] | 34.0 [−3.5] | 38.0 [+0.5] | 37.5 | +3.0 |
| 5'-GGT ATA TAT AGG C (SEQ ID NO: 40) 3'-CCA TAT ATA TCC G (SEQ ID NO: 256) | 47.5 [+10.0] | 31.0 [−6.5] | 40.0 [+2.5] | 37.5 | +1.0 |
| 5'-GGT ATA TAT AGG C (SEQ ID NO: 42) 3'-CCA TAT ATA TCC G (SEQ ID NO: 257) | 48.5 [+11.0] | 31.0 [−6.5] | 40.0 [+2.5] | 37.5 | +2.0 |
| 5'-GGT ATA TAT AGG C (SEQ ID NO: 44) 3'-CCA TAT ATA TCC G (SEQ ID NO: 258) | 47.5 [+10.0] | 31.0 [−6.5] | 40.0 [+2.5] | 37.5 | +1.0 |
| 5'-GGT ATA TAT AGG C (SEQ ID NO: 46) 3'-CCA TAT ATA TCC G (SEQ ID NO: 259) | 51.5 [+14.0] | 27.0 [−10.5] | 41.0 [+3.5] | 37.5 | ±0 |
| 5'-GGT ATA TAT AGG C (SEQ ID NO: 48) 3'-CCA TAT ATA TCC G (SEQ ID NO: 260) | 53.5 [+16.0] | 26.0 [−11.5] | 41.0 [+3.5] | 37.5 | +1.0 |
| 5'-GGT ATA TAT AGG C (SEQ ID NO: 50) 3'-CCA TAT ATA TCC G (SEQ ID NO: 261) | 52.5 [+15.0] | 26.0 [−11.5] | 42.0 [+4.5] | 37.5 | −1.0 |
| 5'-GGT ATA TAT AGG C (SEQ ID NO: 52) 3'-CCA TAT ATA TCC G (SEQ ID NO: 262) | 55.5 [+18.5] | 26.0 [−11.5] | 42.0 [+4.5] | 37.5 | +2.0 |
| 5'-GGT ATA TAT AGG C (SEQ ID NO: 54) 3'-CCA TAT ATA TCC G (SEQ ID NO: 263) | 54.5 [+17.5] | 26.0 [−11.5] | 42.0 [+4.5] | 37.5 | +1.0 |
| 5'-GGT ATA TAT AGG C (SEQ ID NO: 56) 3'-CCA TAT ATA TCC G (SEQ ID NO: 264) | 65.5 [+28.0] | 43.0 [+5.5] | 44.0 [+6.5] | 37.5 | +27.0 |

Tables 22-24 outline thermal denaturation properties of additional working embodiments of yet further probes comprising unlocked monomers targeting different DNA regions, i.e., second insulin [INSB], PPAR gamma and CEBP promotors). Yet again, the following thermal denaturation temperatures are given: model DNA duplex target (column 5 of 6), probe (column 4 of 6), probe-target duplex display positive thermal advantage (TA). Probes with two or more +1 interstrand monomers arrangements display larger TA values (and thus, greater dsDNA-targeting potential) than probes with a single +1 interstrand monomers arrangement. Without being limited to a single theory of operation, probes with more than one +1 zipper arrangement of monomers facilitate dsDNA-targeting.

TABLE 22

Probes Targeting Second Insulin Promoter [INSB] Where Y = 120Y and X = 120Q

| Probe | Upper probe strand vs DNA $T_m[\Delta T_m]$ (° C.) | Lower probe strand vs DNA $T_m[\Delta T_m]$ (° C.) | Probe $T_m[\Delta T_m]$ (° C.) | DNA target duplex $T_m$ (° C.) | TA (° C.) |
|---|---|---|---|---|---|
| 5'-G GYA TAT AAG CAG CAC A (SEQ ID NO: 146)<br>3'-C CAY ATA TTC GTC GTG T (SEQ ID NO: 147) | 58.5 [+6.5] | 60.5 [+8.5] | 56.0 [+4.0] | 52.0 | +11.0 |
| 5'-G GYA YAT AAG CAG CAC A (SEQ ID NO: 148)<br>3'-C CAY AYA TTC GTC GTG T (SEQ ID NO: 149) | 64.5 [+12.5] | 65.5 [+13.5] | 60.0 [+8.0] | 52.0 | +18.0 |
| 5'-AGG AAG GYA YAT AAG CA (SEQ ID NO: 150)<br>3'-TCC TTC CAY AYA TTC GT (SEQ ID NO: 151) | 61.5 [+12.0] | 64.0 [+14.5] | 53.0 [+3.5] | 49.5 | +23.0 |
| 5'-ACY AYA GAA TAC TCA AG (SEQ ID NO: 152)<br>3'-TGA YAY CTT ATG AGT TC (SEQ ID NO: 153) | 57.5 [+12.5] | 56.5 [+11.5] | 48.0 [+3.0] | 45.0 | +21.0 |
| 5'-G GXA TAT AAG CAG CAC A (SEQ ID NO: 154)<br>3'-C CAX ATA TTC GTC GTG T (SEQ ID NO: 155) | 60.5 [+8.5] | 62.5 [+10.5] | 54.0 [+2.0] | 52.0 | +17.0 |
| 5'-G GXA XAT AAG CAG CAC A (SEQ ID NO: 156)<br>3'-C CAX AXA TTC GTC GTG T (SEQ ID NO: 157) | 65.0 [+13.0] | 66.0 [+14.0] | 56.0 [+4.0] | 52.0 | +23.0 |
| 5'-AGG AAG GXA XAT AAG CA (SEQ ID NO: 158)<br>3'-TCC TTC CAX AXA TTC GT (SEQ ID NO: 159) | 62.0 [+12.5] | 64.0 [+14.5] | 49.0 [−0.5] | 49.5 | +27.5 |
| 5'-ACX AXA GAA TAC TCA AG (SEQ ID NO: 160)<br>3'-TGA XAX CTT ATG AGT TC (SEQ ID NO: 161) | 58.5 [+13.5] | 57.0 [+12.0] | 44.0 [−1.0] | 45.0 | +26.5 |

TABLE 23

Additional Examples of probes for PPAR Gamma Where T = 120Y; A = 120'W; and C = 140'X

| Probe | Upper probe strand vs DNA $T_m[\Delta T_m]$ (° C.) | Lower probe strand vs DNA $T_m[\Delta T_m]$ (° C.) | Probe $T_m[\Delta T_m]$ (° C.) | dsDNA target $T_m$ (° C.) | TA (° C.) |
|---|---|---|---|---|---|
| 5'-CCC ACG TTA GCA GTT (SEQ ID NO: 72)<br>3'-GGG TGC AAT CGT CAA (SEQ ID NO: 73) | 69.0 [+12.0] | 68.0 [+11.0] | 54.0 [−3.0] | 57.0 | +26.0 |
| 5'-CCC ACG TTA GCA GTT (SEQ ID NO: 74)<br>3'-GGG TGC AAT CGT CAA (SEQ ID NO: 75) | 71.0 [+14.0] | 68.0 [+11.0] | 57.0 [±0] | 57.0 | +25.0 |
| 5'-AGA CAA AAC ACC AGT (SEQ ID NO: 76)<br>3'-TCT GTT TTG TGG TCA (SEQ ID NO: 77) | 65.0 [+12.0] | 60.0 [+7.0] | 54.0 [+1.0] | 53.0 | +18.0 |
| 5'-AGA CAA AAC ACC AGT (SEQ ID NO: 78)<br>3'-TCT GTT TTG TGG TCA (SEQ ID NO: 79) | 65.0 [+12.0] | 58.0 [+5.0] | 46.0 [−7.0] | 53.0 | +24.0 |

TABLE 23-continued

Additional Examples of probes for PPAR Gamma
Where T = 120Y; A = 120'W; and C = 140'X

| Probe | Upper probe strand vs DNA $T_m[\Delta T_m]$ (° C.) | Lower probe strand vs DNA $T_m[\Delta T_m]$ (° C.) | Probe $T_m[\Delta T_m]$ (° C.) | dsDNA target $T_m$ (° C.) | TA (° C.) |
|---|---|---|---|---|---|
| 5'-CTA CAT TGT CTC GCC (SEQ ID NO: 80) 3'-GAT GTA ACA GAG CGG (SEQ ID NO: 81) | 66.0 [+10.0] | 69.0 [+13.0] | 56.0 [±0] | 56.0 | +23.0 |
| 5'-CTA CAT TGT CTC GCC (SEQ ID NO: 82) 3'-GAT GTA ACA GAG CGG (SEQ ID NO: 83) | 64.0 [+8.0] | 68.0 [+12.0] | 59.0 [+3.0] | 56.0 | +17.0 |
| 5'-CGT CAT CGT GCT CGC (SEQ ID NO: 84) 3'-GCA GTA GCA CGA GCG (SEQ ID NO: 85) | 73.0 [+9.0] | 75.0 [+11.0] | 62.0 [−2.0] | 64.0 | +22.0 |

TABLE 24

Additional Examples of Probes for CEBP
Where T = 120Y; A = 120'W; C = 140'X; and G = 140'Y

| Probe | Upper probe strand vs DNA $T_m[\Delta T_m]$ (° C.) | Lower probe strand vs DNA $T_m[\Delta T_m]$ (° C.) | Probe $T_m[\Delta T_m]$ (° C.) | dsDNA target $T_m$ (° C.) | TA (° C.) |
|---|---|---|---|---|---|
| 5'-CGG ACC ACG TGT GTG (SEQ ID NO: 94) 3'-GCC TGG TGC ACA CAC (SEQ ID NO: 95) | 67.5 [+6.0] | 68.5 [+7.0] | 46.5 [−15.0] | 61.5 | +28.0 |
| 5'-CGG ACC ACG TGT GTG (SEQ ID NO: 96) 3'-GCC TGG TGC ACA CAC (SEQ ID NO: 97) | 69.5 [+8.0] | 70.0 [+8.5] | 44.5 [−17.0] | 61.5 | +33.5 |
| 5'-GTC AGT GGG CGT TGC (SEQ ID NO: 98) 3'-CAG TCA CCC GCA ACG (SEQ ID NO: 99) | 70.5 [+9.5] | 73.0 [+11.5] | 61.5 [±0] | 61.5 | +20.5 |
| 5'-GTC AGT GGG CGT TGC (SEQ ID NO: 100) 3'-CAG TCA CCC GCA ACG (SEQ ID NO: 101) | 74.5 [+13.0] | 70.5 [+9.0] | 60.5 [−1.0] | 61.5 | +23.0 |
| 5'-CCT CTA TAA AAG CGG (SEQ ID NO: 102) 3'-GGA GAT ATT TTC GCC (SEQ ID NO: 103) | 64.5 [+14.0] | 62.5 [+12.0] | 59.5 [+9.0] | 50.5 | +17.0 |
| 5'-CCT CTA TAA AAG CGG (SEQ ID NO: 104) 3'-GGA GAT ATT TTC GCC (SEQ ID NO: 105) | 63.5 [+13.0] | 64.5 [+14.0] | 47.5 [−3.0] | 50.5 | +30.0 |

The following Tables 25-27 describe the thermal denaturation properties of probes that may be used for gender determination of individual cells or multicellular assemblies from certain animals and humans; more commonly somatic cells, sperm cells or embryos from certain animals and humans; even more commonly, somatic cells, sperm cells or embryos from bovine.

As before, probes display thermostabilities that range from significantly lower to moderately higher than corresponding unmodified double-stranded DNA targets (note delta Tm values from −13 C to +9; column 4), while probe-target duplexes (column 2 and 3) are significantly more thermostable (range from +5 to +24 C). Accordingly, all of the probes (which have between two to five +1 zipper monomer arrangements) display significantly positive TA-values suggesting significant potential for targeting of double-stranded nucleic acid targets, more commonly dsDNA.

TABLE 25

Thermal Denaturation Properties of Exemplary Probes
Where T = 120Y; A = 120'W; C = 140'X and G = 140'Y

| Probe | Upper probe strand vs DNA $T_m[\Delta T_m]$ (° C.) | Lower probe strand vs DNA $T_m[\Delta T_m]$ (° C.) | Probe $T_m[\Delta T_m]$ (° C.) | dsDNA target $T_m$ (° C.) | TA (° C.) |
|---|---|---|---|---|---|
| 5'-AGC CCT GTG CCC TG (SEQ ID NO: 112) 3'-TCG GGA CAC GGG AC (SEQ ID NO: 113) | 69.5 [+9.0] | 74.5 [+14.0] | 58.0 [−2.5] | 60.5 | +25.5 |
| 5'-CCT GTG CCC TG (SEQ ID NO: 114) 3'-GGA CAC GGG AC (SEQ ID NO: 115) | 59.5 [+9.0] | 65.5 [+15.0] | 48.0 [−2.5] | 50.5 | +26.5 |
| 5'-CCT GTG CCC TG (SEQ ID NO: 116) 3'-GGA CAC GGG AC (SEQ ID NO: 117) | 59.0 [+8.5] | 64.0 [+13.5] | 47.0 [−3.5] | 50.5 | +25.5 |
| 5'-AGC CCT GTG CCC TG (SEQ ID NO: 118) 3'-TCG GGA CAC GGG AC (SEQ ID NO: 119) | 69.5 [+9.0] | 75.5 [+15.0] | 61.5 [+1.0] | 60.5 | +23.0 |
| 5'-CTG AGC CCT GTG CCC TG (SEQ ID NO: 120) 3'-GAG TCG GGA CAC GGG AC (SEQ ID NO: 121) | 74.0 [+8.0] | 78.0 [+12.0] | 57.0 [−9.0] | 66.0 | +29.0 |
| 5'-AGC CCT GTG CCC TG (SEQ ID NO: 122) 3'-TCG GGA CAC GGG AC (SEQ ID NO: 123) | 70.0 [+9.5] | 80.0 [+19.5] | 60.0 [−0.5] | 60.5 | +29.5 |

Yet another working example of a particular embodiment is provided in Table 26 below, which shows thermal denaturation properties and TA-values for probes modified with unlocked monomer 120Q. Similar patters as seen for other disclosed monomers are observed, i.e., probes display relatively low thermostability while probe-target duplexes are significantly more thermostable. Probes containing one or more +1 zipper arrangement of unlocked monomer 120Q therefore display significantly positive TA-values and therefore significant potential for targeting of double-stranded nucleic acid targets, more commonly dsDNA targets.

TABLE 26

Thermal Denaturation Properties and TA-Values for Probes
Modified with Unlocked Monomer 120Q

| Probe | TA (° C.) | Probe Tm (° C.) | 'upper' probe strand vs DNA Tm (° C.) | 'lower' probe strand vs DNA Tm (° C.) | Target DNA Tm (° C.) |
|---|---|---|---|---|---|
| 5'-GG120Q ATA TAT AGG C (SEQ ID NO: 162) 3'-CCA 120Q AT ATA TCC G (SEQ ID NO: 163) | 22.0 | 33.5 | 45.5 | 47.5 | 37.5 |
| 5'-GGX 120Q A120Q A TAT AGG C (SEQ ID NO: 164) 3'-CCA 120Q A120Q ATA TCC G (SEQ ID NO: 165) | 25.0 | 43.5 | 51.5 | 54.5 | 37.5 |
| 5'-GG120Q A120Q A 120Q A120Q AGG C (SEQ ID NO: 166) 3'-CCA 120Q A120Q A120Q A 120Q CC G (SEQ ID NO: 167) | 56.5 | 39.5 | 66.5 | 67 | 37.5 |

Particular embodiments entail double-stranded probes with certain zipper arrangements of monomers comprising so-called pseudo-complementary nucleobases (e.g., such as 2-thiouracil, 2,6-diamonopurines, inosine and pyrrolo-[2,3-d]-pyrimidine-2-(3H)-one), more commonly, +1 zipper arrangements of monomers comprising pseudo-complementary nucleobases, even more commonly, +1 zipper arrangements of monomers such as 270. Examples of working examples of these particular embodiments are given in Table 27 below.

Further particular embodiments entail double-stranded probes with certain zipper arrangements (more commonly +1 zippers) of monomers comprising nucleobases where, in addition, the nucleotide opposite of the disclosed monomer comprising a pseudo-complementary nucleobase, is a nucleotide or disclosed monomer comprising a pseudo-complementary nucleobase (e.g., such as 2-thiouracil, 2,6-diamonopurines, inosine and pyrrolo-[2,3-d]-pyrimidine-2-(3H)-one). For a representative working examples, please see entries 2 and 4 in Table 29 below, where D is a DNA monomer with a 2,6-diaminopurine nucleobase (i.e., 2,6-diaminopurine-2'-deoxyriboside). With reference to Table 27 below, it observed that double-stranded probes with −1 or +1 zipper arrangements of monomer 270 display positive TA-values, and therefore significant potential for targeting of double-stranded nucleic acid targets via the method disclosed in FIGS. 1-2, more commonly, dsDNA. With further reference to Table 27 below, it is observed that double-stranded probes with −1 or +1 zipper arrangements of monomer 270, where, in addition, the nucleotide opposite of monomer 270 is D display positive TA-values, and therefore significant potential for targeting of double-stranded nucleic acid targets via the method disclosed in FIGS. 1-2, more commonly, dsDNA.

where "L" denotes the non-pairing monomer; in particular working examples, L is selected from monomers 402-4, 402-9 and 402-N. With reference to Table 28 below, "4", "9" and "N" denotes a single incorporation of 402-4, 402-9 and 402-N, respectively. "444", "999" and "NNN" denotes three consecutive incorporations of 402-4, 402-9 and 402-N, respectively. Still with reference to Table 28 below, "Up", "down" and "both" in the third column, denotes whether bulged monomer(s) were included only in the upper probe strand, only in the lower probe strand or in both probe strands, respectively.

With continued reference to the data in Table 28 below, introduction of one or two non-pairing bulges into double-stranded probes, greatly reduces probe thermostability relative to corresponding to double-stranded probes that do not contain non-pairing bulges, denoted control probes (note, Tm values for probes are lower than the 60.5° C. observed for the control probe [i.e., bulge=none] shown in the first entry, column 3). While the stability of the probe-target duplexes also is decreased relative to the control probe (note that Tm values in column 4 and 5 are similar or lower than the Tm values in column 3), probes comprising one or two non-pairing bulges display positive TA-values; in the working examples shown below, several of the probes comprising one or two non-pairing bulges display significantly similar or larger TA-values than the control probe shown in entry 1, suggesting significant potential for targeting of double-stranded nucleic acid targets via the method disclosed in FIGS. 1-2, more commonly dsDNA.

TABLE 27

Double-Stranded Probes with −1 Or +1 Zipper Arrangements of Monomer 270

| Probe | dsDNA target $T_m$ [° C.] | Upper probe strand vs DNA $T_m$ [° C.] | Lower probe strand vs DNA $T_m$ [° C.] | Probe $T_m$ [° C.] | TA |
|---|---|---|---|---|---|
| 5'-GTG A(270)A TGC<br>3'-CAC TA$\underline{S}$ ACG | 29.5 | 41.0 | 40.5 | 28.5 | +23.5 |
| 5'-GTG A(270)$\underline{D}$ TGC<br>3'-CAC T$\underline{D}$(270) ACG | 29.5 | 45.0 | 45.0 | 29.5 | +31.0 |
| 5'-GTG A(270)A TGC<br>3'-CAC (270)AT ACG | 29.5 | 41.0 | 32.0 | 39.5 | +4.0 |
| 5'-GTG $\underline{D}$(270)A TGC<br>3'-CAC (270)$\underline{D}$T ACG | 29.5 | 42.5 | 33.0 | 29.0 | +17.0 |

Figure 3B:
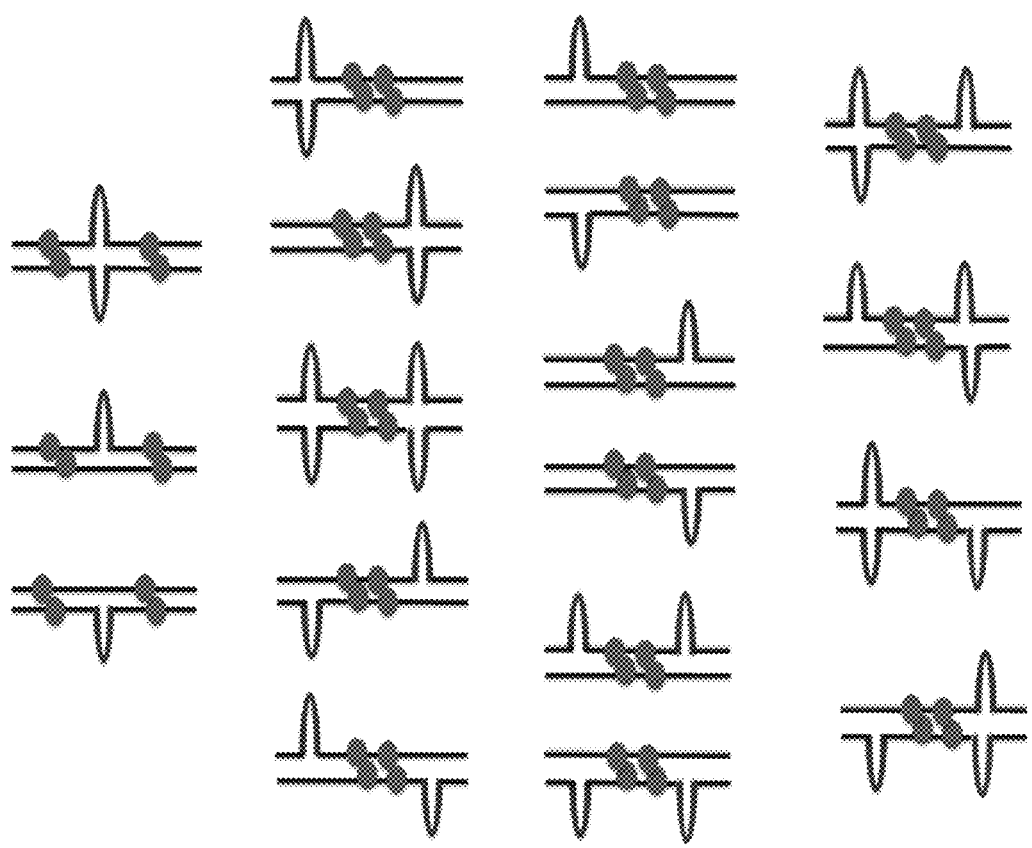
FIG. 3B is a schematic drawing illustrating probes with two +1 interstrand arrangements of disclosed monomers (green) and one to four non-pairing bulged monomers (red loop), such as 402-4, 402-N and 402-9.

Particular embodiments entail double-stranded probes simultaneously comprising one or more arrangements of disclosed monomers and one or more non-pairing monomers (FIG. 3b). Working examples of such embodiments are provided below. Table 28 concerns thermal hybridization properties and dsDNA-targeting potential of 18-mer probes containing non-pairing bulges with a general structure:

(SEQ ID NO: 223)
5'-GG(120Y) GGT CAA L CTA TC(120Y) GGA (SEQ ID NO: 253)
3'-CCA (140'X)CA GGT L GAT AGA (140'X)CT

TABLE 28

Thermal Denaturation Properties and TA-Values of Duplexes Involving Probes Comprising Non-Pairing Monomers

| Used bulge | Strand(s) with Bulge(s) | Probe $T_m$ [° C.] | Upper probe strand vs DNA $T_m$ [° C.] | Lower probe strand vs DNA $T_m$ [° C.] | TA [° C.] |
|---|---|---|---|---|---|
| None | — | 60.5 | 68.5 | 65.5 | 14.5 |
| 4 | Up | 47.5 | 60.0 | 65.5 | 19.0 |
|  | Down | 51.5 | 68.5 | 58.0 | 16.0 |
|  | Both | 40.5 | 60.0 | 58.0 | 18.5 |

TABLE 28-continued

Thermal Denaturation Properties and TA-Values of Duplexes Involving Probes Comprising Non-Pairing Monomers

| Used bulge | Strand(s) with Bulge(s) | Probe $T_m$ [° C.] | Upper probe strand vs DNA $T_m$ [° C.] | Lower probe strand vs DNA $T_m$ [° C.] | TA [° C.] |
|---|---|---|---|---|---|
| 9 | Up | 45.0 | 55.5 | 65.5 | 17.0 |
|   | Down | 46.5 | 55.0 | 68.5 | 19.0 |
|   | Both | 44.5 | 55.5 | 53.5 | 5.5 |
| N | Up | 54.0 | 64.5 | 65.5 | 17.0 |
|   | Down | 58.0 | 68.5 | 63.0 | 14.5 |
|   | Both | 52.0 | 64.5 | 63.0 | 16.5 |
| 444 | Up | 39.0 | 53.5 | 65.5 | 22.0 |
|   | Down | 44.0 | 68.5 | 53.0 | 18.5 |
|   | Both | 37.0 | 53.0 | 53.5 | 10.5 |
| 999 | Up | 43.0 | 56.0 | 65.5 | 19.5 |
|   | Down | 44.0 | 68.5 | 53.0 | 18.5 |
|   | Both | 44.0 | 53.0 | 56.0 | 6.0 |
| NNN | Up | 47.5 | 59.0 | 65.5 | 18.0 |
|   | Down | 52.0 | 68.5 | 58.0 | 15.5 |
|   | Both | 41.0 | 59.0 | 58.0 | 17.0 |

Further working examples of this embodiment are shown in Table 29 below, which illustrates the thermal hybridization properties and dsDNA-targeting potential of 13-mer double-stranded probes comprising monomer 120Y (=T) and non-pairing monomer 402-9 (=9). Introduction of one or two non-pairing monomer 402-9 near the termini of the probes, results in greatly reduced probe thermostability (note that all Tm values are lower than the 45 C observed for the control probe shown in the first entry, column 2). While the stability of the probe-target duplexes also is decreased relative to the control probe (note that Tm values in columns 3 and 4 are the same or lower than the Tm value in column 3 of entry 1), all probe except for one, positive TA-values. Without being limited to a theory or operation, this suggests that probes with one or more bulges toward probe termini, display significant potential for targeting of double-stranded nucleic acid targets, more commonly dsDNA, via the method shown in FIGS. 1-2.

TABLE 29

Thermal Hybridization Properties and dsDNA-Targeting Potential of 13-Mer Double-Stranded Probes Comprising Monomer 120Y

| Sequence | Probe | Upper probe strand vs DNA | Lower probe strand vs DNA | TA (° C.) |
|---|---|---|---|---|
| 5'-GGT ATA TAT AGG C (SEQ ID NO: 52)<br>3'-CCA TAT ATA TCC G (SEQ ID NO: 143) | 45.0 | 55.5 | 55.5 | 28.5 |
| 5'-GG-9-T ATA TAT AGG C (SEQ ID NO: 168)<br>3'-CC-9-A TAT ATA TCC G (SEQ ID NO: 169) | <15 | 44.0 | 46.5 | 38.0 |
| 5'-GGT ATA TAT AG-9-G C (SEQ ID NO: 170)<br>3'-CCA TAT ATA TC-9-C G (SEQ ID NO: 171) | <15 | 44.5 | 43.5 | 35.5 |
| 5'-GG-9-T ATA TAT AG-9-G C (SEQ ID NO: 172)<br>3'-CC-9-A TAT ATA TC-9-C G (SEQ ID NO: 173) | <15 | <15 | <15 | -22.5 |
| 5'-GG-9-T ATA TAT AGG C (SEQ ID NO: 168)<br>3'-CCA TAT ATA TC-9-C G (SEQ ID NO: 171) | 28.5 | 44.0 | 43.5 | 21.5 |
| 5'-GGT ATA TAT AG-9-G C (SEQ ID NO: 170)<br>3'-CC-9-A TAT ATA TCC G (SEQ ID NO: 169) | 32.5 | 44.5 | 46.5 | 21.0 |
| 5'-GG-9-T ATA TAT AGG C (SEQ ID NO: 168)<br>3'-CCA TAT ATA TCC G (SEQ ID NO: 143) | 31.5 | 44.0 | 55.5 | 30.5 |
| 5'-GGT ATA TAT AG-9-G C (SEQ ID NO: 170)<br>3'-CCA TAT ATA TCC G (SEQ ID NO: 143) | 33.0 | 44.5 | 55.5 | 29.5 |

TABLE 29-continued

Thermal Hybridization Properties and dsDNA-Targeting Potential of 13-Mer Double-Stranded Probes Comprising Monomer 120Y

| Sequence | Probe | Upper probe strand vs DNA | Lower probe strand vs DNA | TA (° C.) |
|---|---|---|---|---|
| 5'-GGT ATA TAT AGG C (SEQ ID NO: 52)<br>3'-CC-9-A TAT ATA TCC G (SEQ ID NO: 169) | 35.0 | 55.5 | 46.5 | 29.5 |
| 5'-GGT ATA TAT AGG C (SEQ ID NO: 52)<br>3'-CCA TAT ATA TC-9-C G (SEQ ID NO: 171) | 28.5 | 55.5 | 43.5 | 33.0 |
| 5'-GG-9-T ATA TAT AG-9-G C (SEQ ID NO: 172)<br>3'-CCA TAT ATA TCC G (SEQ ID NO: 143) | <15 | <15 | 55.5 | 18.0 |
| 5'-GGT ATA TAT AGG C (SEQ ID NO: 52)<br>3'-CC-9-A TAT ATA TC-9-C G (SEQ ID NO: 173) | <15 | 55.5 | <15 | 18.0 |
| 5'-GG-9-T ATA TAT AG-9-G C (SEQ ID NO: 172)<br>3'-CC-9-A TAT ATA TCC G (SEQ ID NO: 169) | <15 | <15 | 46.5 | 9.0 |
| 5'-GG-9-T ATA TAT AG-9-G C (SEQ ID NO: 172)<br>3'-CCA TAT ATA TC-9-C G (SEQ ID NO: 171) | <15 | <15 | 43.5 | 6.0 |
| 5'-GG-9-T ATA TAT AGG C (SEQ ID NO: 168)<br>3'-CC-9-A TAT ATA TC-9-C G (SEQ ID NO: 173) | <15 | 44.0 | <15 | 6.5 |
| 5'-GGT ATA TAT AG-9-G C (SEQ ID NO: 170)<br>3'-CC-9-A TAT ATA TC-9-C G (SEQ ID NO: 173) | <15 | 44.5 | <15 | 7.0 |

TABLE 30

Thermal Denaturation Properties of exemplary probes Where T = 120Y; A = 120'W; C = 140'X and G = 140'Y

| Probe | dsDNA target Tm (° C.) | Upper probe strand vs DNA Tm (° C.) | Lower probe strand vs DNA Tm (° C.) | Probe Tm (° C.) | TA (° C.) |
|---|---|---|---|---|---|
| 5'-Cy3 AGC CCT GTG 9 CCC TG (SEQ ID NO: 234)<br>3'-TCG GGA CAC 9 GGG AC Cy3 (SEQ ID NO: 235) | 60.5 | 51.5 | 57.5 | 26.5 | 22 |
| 5'-Cy3 AGC CCT GTG 4 CCC TG (SEQ ID NO: 236)<br>3'-TCG GGA CAC 4 GGG AC Cy3 (SEQ ID NO: 237) | 60.5 | 61.5 | 62.5 | 34.5 | 29 |
| 5'-Cy3 AGC CCT GTG N CCC TG (SEQ ID NO: 238)<br>3'-TCG GGA CAC N GGG AC Cy3 (SEQ ID NO: 239) | 60.5 | 67 | 70 | 45.5 | 31 |

TABLE 30-continued

Thermal Denaturation Properties of exemplary probes
Where T = 120Y; A = 120'W; C = 140'X and G = 140'Y

| Probe | dsDNA target Tm (° C.) | Upper probe strand vs DNA Tm (° C.) | Lower probe strand vs DNA Tm (° C.) | Probe Tm (° C.) | TA (° C.) |
|---|---|---|---|---|---|
| 5'-Cy3 AGC CC<u>T</u> GTG 9 CC<u>C</u> TG (SEQ ID NO: 234)<br>3'-T<u>C</u>G GGA <u>C</u>AC GGG <u>A</u>C Cy3 (SEQ ID NO: 119) | 60.5 | 51.5 | 74 | 29.5 | 35.5 |
| 5'-Cy3 AGC CC<u>T</u> GTG CC<u>C</u> TG (SEQ ID NO: 1248)<br>3'-T<u>C</u>G GGA <u>C</u>AC 9 GGG <u>A</u>C Cy3 (SEQ ID NO: 235) | 60.5 | 69.5 | 57.5 | 32.5 | 34 |
| 5'-Cy3 AGC CC<u>T</u> GTG 4 CC<u>C</u> TG (SEQ ID NO: 236)<br>3'-T<u>C</u>G GGA <u>C</u>AC GGG <u>A</u>C Cy3 (SEQ ID NO: 119) | 60.5 | 61.5 | 74 | 50.5 | 24.5 |
| 5'-Cy3 AGC CC<u>T</u> GTG CC<u>C</u> TG (SEQ ID NO: 1248)<br>3'-T<u>C</u>G GGA <u>C</u>AC 4 GGG <u>A</u>C Cy3 (SEQ ID NO: 237) | 60.5 | 69.5 | 62.5 | 41.5 | 30 |
| 5'-Cy3 AGC CC<u>T</u> GTG <u>N</u> CC<u>C</u> TG (SEQ ID NO: 238)<br>3'-T<u>C</u>G GGA <u>C</u>AC GGG <u>A</u>C Cy3 (SEQ ID NO: 119) | 60.5 | 67 | 74 | 60 | 20.5 |
| 5'-Cy3 AGC CC<u>T</u> GTG CC<u>C</u> TG (SEQ ID NO: 1248)<br>3'-T<u>C</u>G GGA <u>C</u>AC <u>N</u> GGG <u>A</u>C Cy3 (SEQ ID NO: 239) | 60.5 | 69.5 | 70 | 47 | 32 |

Table 30 above shows additional working examples of this embodiment. Hybridization properties and dsDNA-targeting potential of probes comprising non-pairing monomers 4 (402-4), 9 (402-9) or N (402-N) bulges designed for sexing of bovine cells are shown in Table 30 where <u>A</u> = 120'W, <u>C</u> = 140'X, <u>G</u> = 140'Y, and <u>T</u> = 120Y.

VII. Method of Using Disclosed Probe Embodiments

In particular disclosed embodiments, the disclosed probe is capable of associating with a target. The disclosed probe comprises at least one pair of monomers that are arranged in a +/−n zipper arrangement, which allows the monomers to affect the thermostability of the probe. Certain zipper arrangements, i.e., −1, 0, +1 and +2 zipper arrangements but more commonly +1 zipper arrangements provides the probe with sufficient thermodynamic instability to cause the two strands of the probe duplex to dissociate in the presence of a significantly complementary double-stranded nucleic acid target, more commonly dsDNA, and thereby associate with a target nucleic acid. In particular disclosed embodiments, the two separated strands of the probe will partake in Watson-Crick base pairing with the nucleotides of the target nucleic acid, more commonly the two strands of a dsDNA. In particular disclosed embodiments, the probe may be used in diagnostic techniques, such as identification of biomarkers, oncogenes, gender-specific genes, etc., and/or direct detection of double-stranded DNA in living cells, embryos, organs and tissues and/or induction of site-specific mutagenesis, recombination or repair of genomic DNA and site-specific modulation of gene expression (i.e. up- or down regulation). The probe is not limited to use in these techniques, as this list is meant only to be exemplary and not limiting. In particular disclosed embodiments, the probe may be pre-annealed using methods known to those of ordinary skill in the art. The pre-annealed probe may then be added to a target, such as a double stranded DNA target.

Particular disclosed embodiments concern using the disclosed probe to inhibit transcription. The disclosed probe may be designed to have at least one pair of monomers. In particular disclosed embodiments, the probe is designed to have two pairs of monomers, wherein the two pairs may be identical or different, and are separated by zero or more natural or non-natural nucleotides, such as disclosed monomers herein. In particular disclosed embodiments, a pair of monomers comprises at least two unlocked or locked monomers functionalized with an intercalator and arranged in a +1 zipper arrangement.

The probe may be designed to target a particular isosequential nucleic acid target—whether synthetic or biological, such as any of those disclosed herein. In certain disclosed embodiments, the nucleic acid target may be the SP6 and T7 promoters on PGEM-Teasy plasmids that may or may not overlap with a transcription start site. With reference to this particular disclosed embodiment, the pGEM-T-Easy vector containing insb-cDNA was linearized with either SpeI or SacII and used for in vitro transcription reactions to synthesize cRNA driven by T7 or SP6 promoters, respectively (FIG. 18). The linearized plasmids were incubated with dsDNA-targeting agents as follows: either positive control (commercial Zorro LNA), targeting the SP6 promoter, or the disclosed probe selected to target the SP6 or T7 promoter (FIG. 19). Following incubation to facilitate binding of the positive control and the probe, in vitro transcription was initiated by incubating with ribonucleotide triphosphates, buffer, and T7 or SP6 polymerases. cRNA products were reverse transcribed to cDNA. Primers designed to detect a 240 base insert amplicon were used in end-point PCR and the product was resolved by gel electrophoresis. The results of this particular disclosed embodiment are illustrated in FIG. 20 wherein lanes 1 and 9 illustrate the DNA ladder (100 bp increments); lane 2 illustrates the T7-driven product formed in SpeI digested plasmid in the absence of either the control or the probe; lane 3 illustrates the SacII digested plasmid, which does not yield T7-driven product; lane 4 illustrates that a particular embodiment of the probe binds to the T7 promoter and prevents formation of T7-driven product in SpeI digested plasmid; and lane 5 illustrates that the SP6-driven product is formed in SacII digested plasmid in the absence of a either the positive control or the probe. Also referring to FIG. 20, lanes 6-8 illustrate that Zorro LNA (ln 6), one embodiment of the disclosed probe (ln 7) or a different embodiment of the disclosed probe (ln 8) bind to the SP6 promoter and prevent formation of SP6-driven product in SacII treated plasmid. Other targets are contemplated by the disclosed method, such as gene knockdown in live cell lines targeting chromosomal progesterone receptor, estrogen receptors, and any other biologically relevant targets. In particular disclosed embodiments, the disclosed probe may be used for animal sexing, such as sexing of ungulates, ruminates, and more particularly bovines, equines and porcines, as the probe may be designed to selectively targeting gender-specific DNA regions. Examples of gender-specific DNA regions are known in the art. See, for example, WO 2009079456 and Brown, Kim H., Irvin R. Schultz, J. G. Cloud, and James J. Nagler (2008) "Aneuploid Sperm Formation in Rainbow Trout Exposed to the Environmental Estrogen 17a-ethynylestradiol PNAS (USA), 105:19786-19791, both of which are incorporated herein by reference. In particular disclosed embodiments, the probe may be designed to comprise one or more pairs of the disclosed monomers and have a sequence of nucleotides that is isosequential with a particular gene of a target cell that is specific for certain genetic traits, such as gender. In certain disclosed embodiments, the probe comprises one or more pairs of disclosed monomers selected from embodiments of monomers disclosed herein, such as those of Scheme 16, and may contain zero or more non-pairing monomers such as 402-4, 402-9 or 402-9. In particular disclosed embodiments, the probe may be used to determine the gender of animals and cells (in particular sperm cells), organs, tissues and embryos thereof. Particular embodiments enable gender determination of unadulterated early-stage embryos from animals used in food production and sport breeding.

In another disclosed embodiment of using the disclosed probe, a transfected plasmid in-cell assay was performed. Beta TC-6 cells (ATCC, CRL-11506) were co-transfected with [pGL4.10 (luc2/−374insb)] and an internal transfection control vector [pGL4.74 (hRluc/TK)] (FIG. 21). A probe comprising at least one pair of locked monomers targeting the insb promoter was transfected 24 h after plasmid co-transfection. In this particular disclosed embodiment, 2 µg of the probe per well was used (6-well plate format). The cells were harvested 24 h after probe addition (90-100% confluency) and assayed for Firefly and Renilla luciferase (enzyme) activity using a dual luciferase assay system (Promega) to determine the efficacy and specificity of probe-mediated antigene activity. Firefly luciferase activity was normalized to Renilla luciferase activity to correct for transfection variation. Normalized Firefly luciferase activity is expressed relative to a scrambled control probe. Experiments conducted in triplicate were replicated on three independent occasions. For the dose-response study, cells were transfected in triplicate with 0.1, 1.0 or 5.0 µg the particular probe per well. With reference to this transfection study and FIG. 22, a particular embodiment of the probe (i.e. a probe comprising only one pair of locked monomers) did not show a detectable decrease in luciferase activity. Two different probes comprising more than one pair of locked monomers did display an effect (10-30% reduction in luciferase activity). Also explored were dose-dependent studies, which illustrated that particular embodiments of the probe displayed efficacy at the highest dose, particular embodiments displayed dose-response effect, and other embodiments displayed evidence of inversed efficacy with increasing dose. These results are illustrated in FIG. 23.

Figure 24:
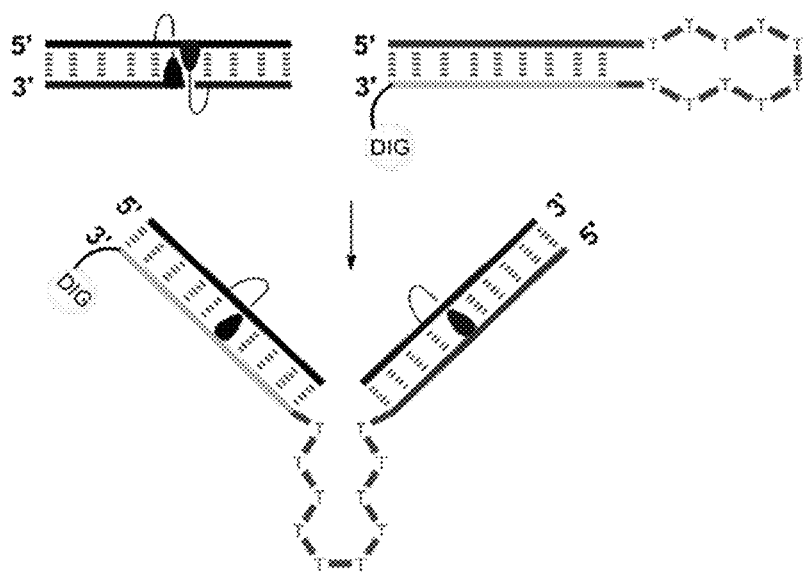
FIG. 24 is schematic drawing of an exemplary embodiment wherein the probe is used to target a mixed-sequence, structured nucleic acid target.

In particular disclosed embodiments, the probe may be used to target an isosequential double-stranded DNA duplex or structured analogs hereof. For example, two strands of an isosequential target duplex may be connected through a linker, such as a polynucleotide, to produce a duplex having a hairpin configuration (FIG. 24). In exemplary embodiments, the linker comprises ten thymidines, with the stem of the hairpin target being the primary region recognized by the probe. In particular disclosed embodiments, the nucleic acid target may or may not comprise one or more polypurine units. In certain disclosed embodiments, the intramolecular nature of the target duplex of the hairpin structure increases the $T_m$ value of the duplex, rendering it a more challenging target than linear dsDNA targets. The ability of the probe to recognize and invade (or associate with) the complex may be analyzed using an electrophoretic mobility shift assay.

Figure 25:
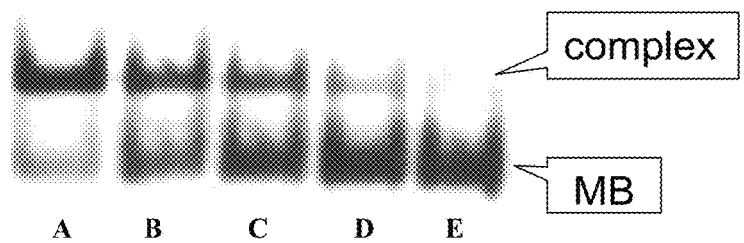
FIG. 25 is an image of a gel obtained from gel electrophoresis analysis of an exemplary embodiment of the disclosed probe illustrating its ability to complex with a mixed-sequence, structured nucleic acid target.

In exemplary embodiments, the ability of a (+1) interstrand zipper probe comprising at least one pair of monomers was used to target a hairpin target. According to FIG. 25, hairpin invasion by the disclosed probe resulted in a probe-target complex having a slower migration rate, such as that illustrated in lanes A-D of FIG. 25. As illustrated in FIG. 25, the concentration of the probe added to the target, affects the ability of the probe-target complex to be formed. In particular disclosed embodiments, an excess of about 5-fold to about 500-fold of the disclosed probe may result in probe-target complex formation; even more typically, an excess of from about 5-fold to about 50-fold of the disclosed probe will result in significant probe-target complex formation. According to FIG. 25, lanes A-E represent samples in which a varying excess of the probe is used, with lane A representing a 500-fold excess of the probe, lane B representing a 100-fold excess of the probe, lane C representing a 50-fold excess of the probe, lane D representing a 10-fold excess of the probe, and lane E representing a 5-fold excess of the probe. In particular disclosed embodiments, any of the disclosed monomers may be incorporated into the probe.

Figure 30:
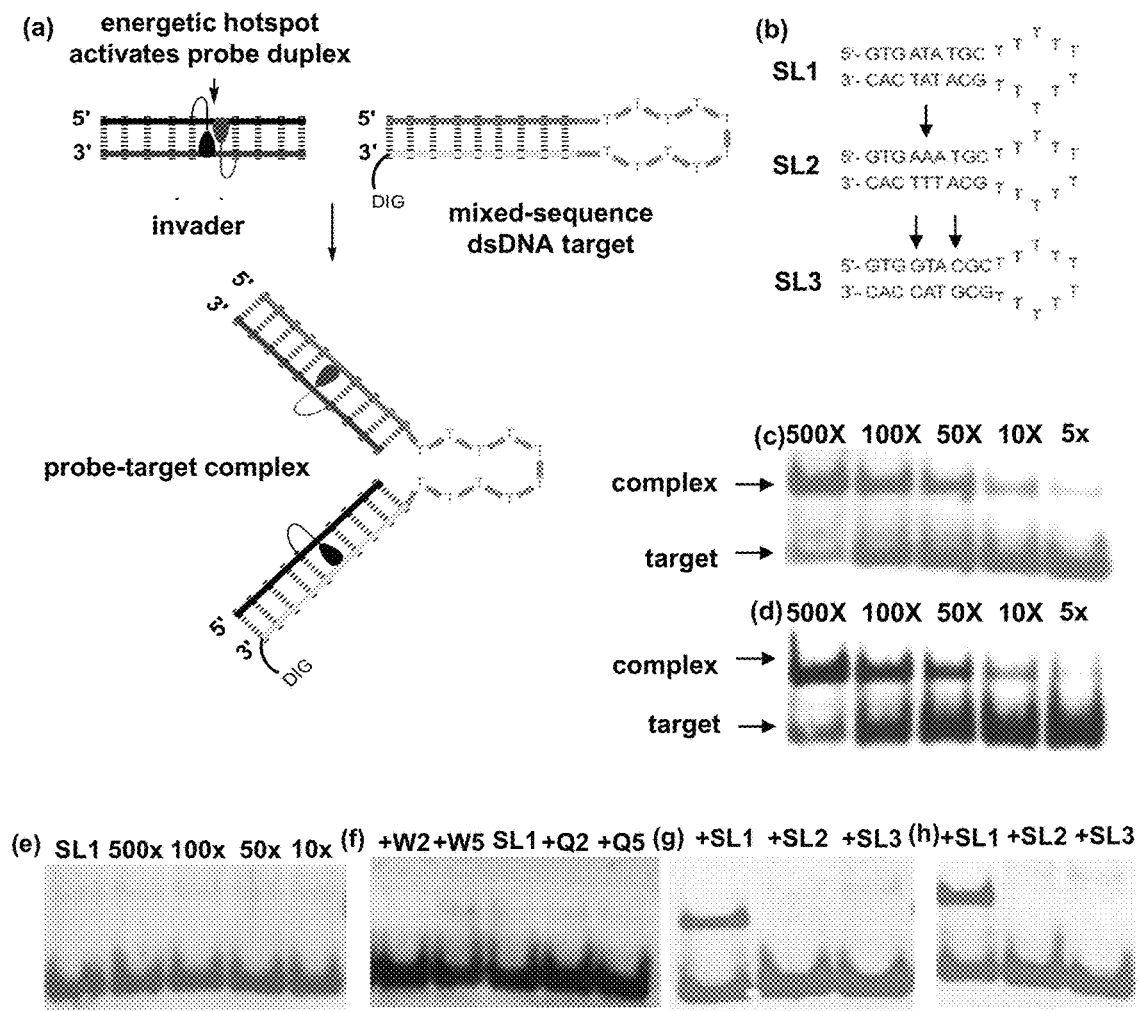
FIG. 30 illustrates recognition of structured dsDNA targets by probes using electrophoretic mobility shift assays: (a) schematic illustration of recognition process; (b) structures of dsDNA-targets with isosequential (SL1) or non-isosequential (SL2 and SL3) stem regions (arrows denote deviation points); (c), (d) and (e) recognition of SL1 using escalating excess of 126W2:126W5, 120Q2:120Q5 or D1:D2, respectively; (f) incubation of SL1 with 100-fold excess of single-stranded 126W2, 126W5, 120Q2 or 120Q5; (g) and (h) incubation of SL1-SL3 with 100-fold excess of 126W2:126W5 or 120Q2:120Q5, respectively. Probe-target incubation: 3 hours at 20° C.; 15% non-denaturing PAGE; DIG: digoxigenin.

In exemplary embodiments, monomers 124X, 124Y, 126W, 126X, 126Y, 126Z, 120Q, 120S, 120V, 120Y, and 120'W were used to form a (+1) interstrand zipper within the probe. Working examples of these embodiments are given in FIG. 30. Thus, probes with +1 arrangements of the disclosed monomers, recognize a structured and digoxigenin-labeled dsDNA target comprised of an isosequential double-stranded target region, which is linked on one side by a single-stranded $T_{10}$ loop (SL1, FIG. 30b). The unimolecular nature of this target (SL) structures leads to extensive thermostabilization of the double-stranded region [$T_m$ (SL1)=56.0° C. vs $T_m$ (D1:D2)=29.5° C.]. Incubation of 126W2:126W5 with the structured dsDNA target SL1 (3 h at 20° C.) results in the formation of a recognition complex with lower electrophoretic mobility on 15% non-denaturing PAGE gels than SL1 (FIG. 30c). A clear dose-response trend is observed; a trace of complex formation is observed when 5-fold excess of 126W2:126W5 is used, while a 100-fold excess of 126W2:126W5 results in ~48% recognition (FIG. 30c; Table 31, where for all except 124X and 120'W the probe is:

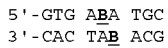

5'-GTG A<u>B</u>A TGC
3'-CAC TA<u>B</u> ACG where <u>B</u> is the disclosed monomer. For all 124X and 120'W the probe is:

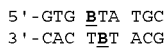

Figure 31:
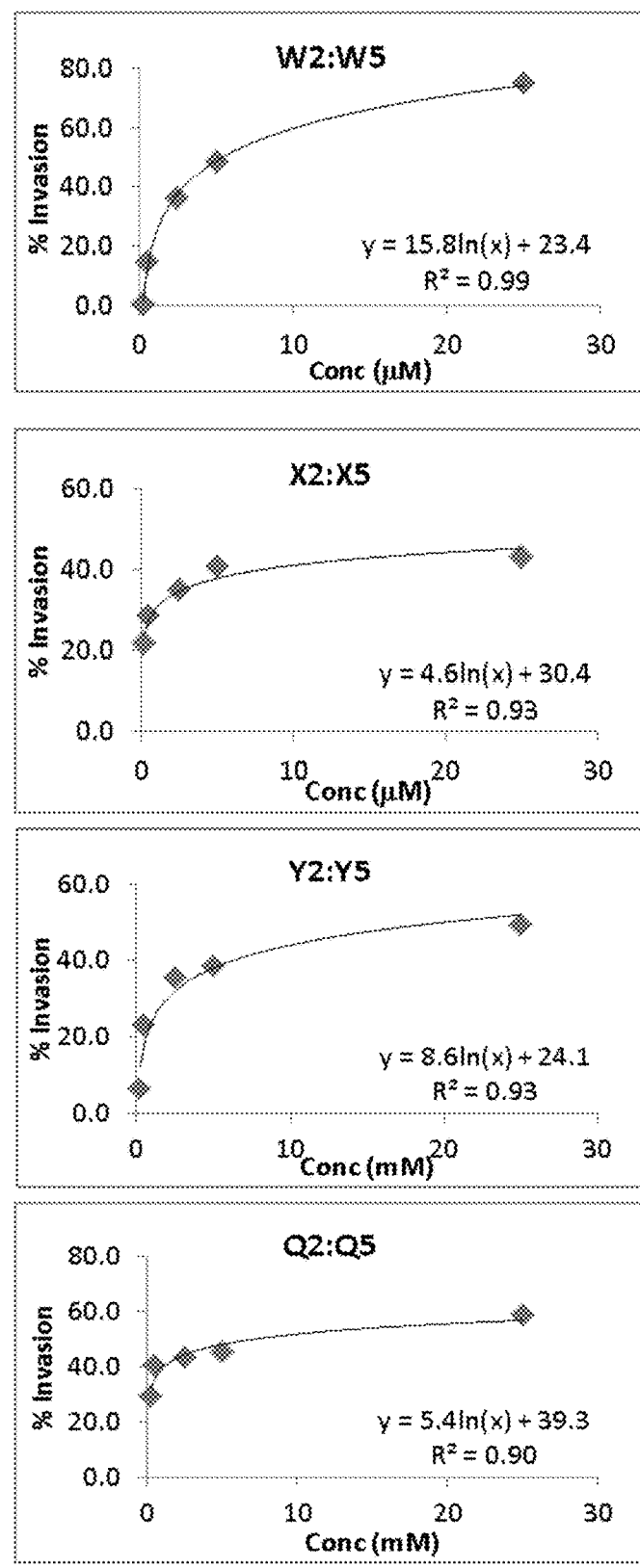
FIG. 31 are dose-response curves for recognition of structured dsDNA SL1 by the following probes (top to bottom): 126W2:126W5, 126X2:126X5, 126Y2:126Y5, 120Q2:120Q5, 120Y2:120Y5 (P2:P5), 124X6:124X8 (K6:K8) and 120'W6:120'W8 (M6:M8). For experimental conditions see FIG. 30. Dose response curves are fitted to a logarithmic equation.
Figure 31:
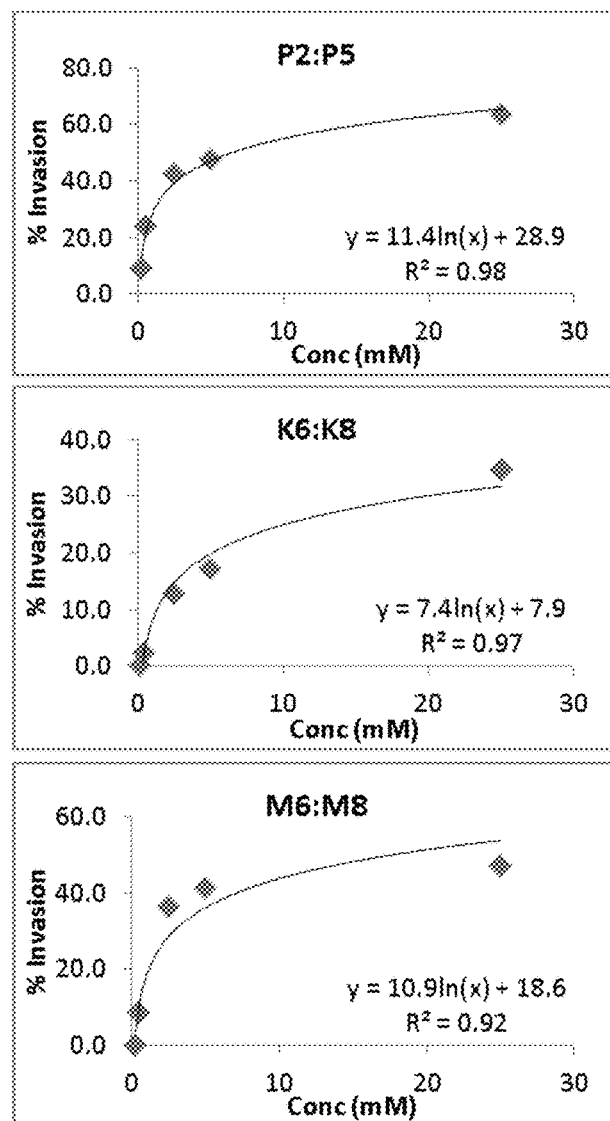

5'-GTG <u>B</u>TA TGC
3'-CAC T<u>B</u>T ACG where <u>B</u> is the disclosed monomer; FIG. 31). Similar results are observed for probe 120Q2:120Q5 (FIG. 30 D, Table 31, FIG. 31) and all other evaluated probes (Table 31, FIG. 31), except for 120S2:120 S5 and 120V2:120 V5 (Table 31). This includes probes with +1 interstrand arrangements of locked thymine monomers 126X and 126Y, unlocked uracil-based monomers 120Y and 120Q, and adenine-based monomers 124X and 120'W. Thus, in exemplary embodiments, monomers 120S and 120V did not produce a probe-target complex, and monomer 124X was found to be less efficient to invade the hairpin duplex, while the other monomers exhibited substantial probe-target complex formation. Without being limited to a single theory of operation, it is currently believed that the reactivity of monomers 120S, 120V and 124X could be attributed to formation of less thermally stable probe-target duplexes. In exemplary embodiments, the hairpin invasion reached a saturation point at 25 μM of the probe, wherein about 50% to about 75% of the hairpin was targeted. Additional results of the percentage of hairpin invasion using 5 μM of the probe are summarized in Table 31, below.

TABLE 31

Efficiency of Hairpin Invasion by Various Invader Duplex at 100 Fold Excess of Probe[a]

| Monomer | % of invasion |
|---|---|
| 126W | 48 |
| 126X | 40 |
| 126Y | 38 |
| 120Q | 45 |
| 120S | <5 |
| 120V | <5 |
| 120Y | 47 |
| 124X | 17 |
| 120'W | 41 |

[a]average of three independent measurements

Figure 26:
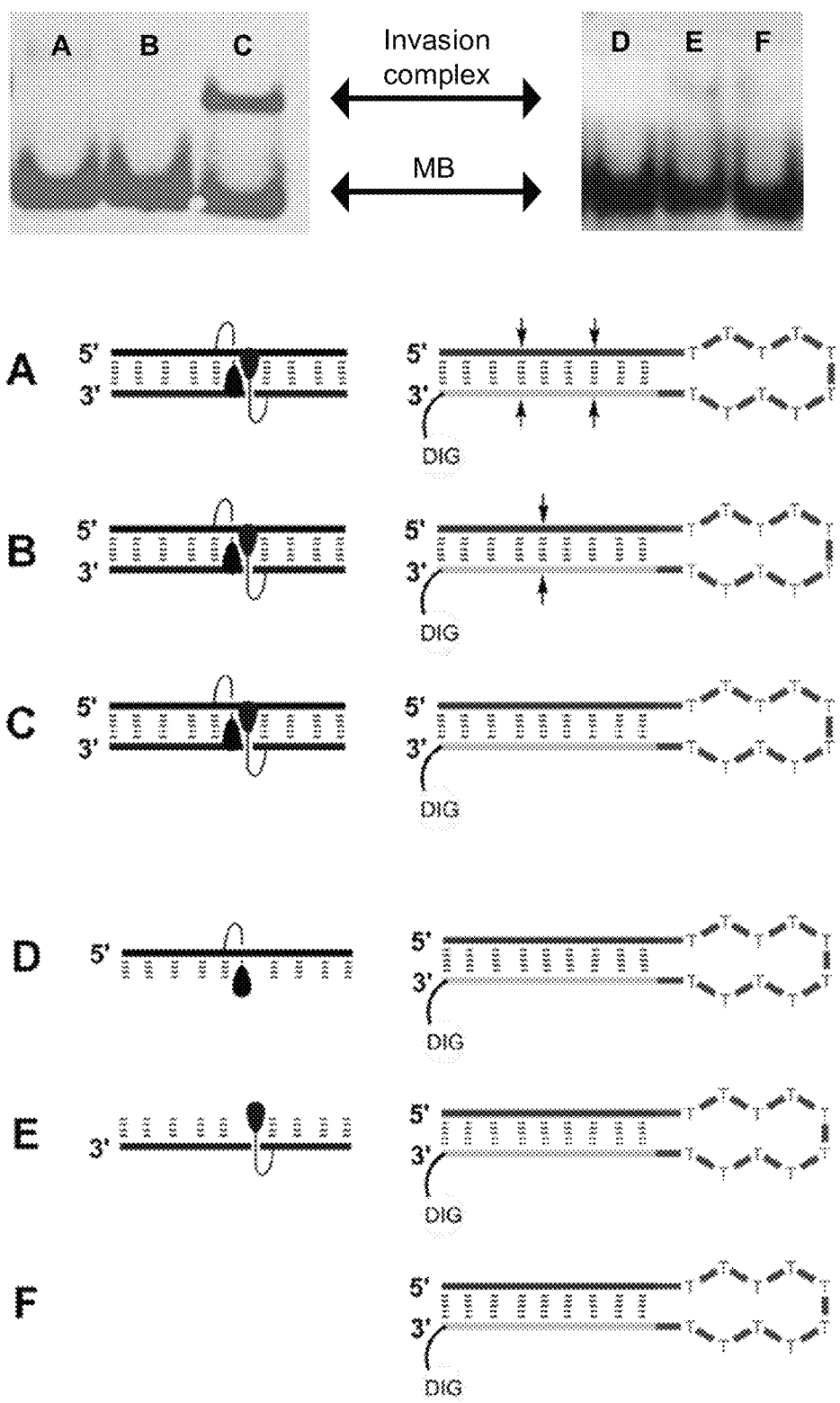
FIG. 26 is an image of the results obtained using a variety of exemplary embodiments of the disclosed probes as well as embodiments used as controls (e.g. single-stranded probe precursor and a control with no probe) to target and form a complex with a mixed-sequence, structured nucleic acid target.

In particular disclosed embodiments, the ability of the disclosed probe to invade, or associate with, the target may be evaluated by comparing its reactivity with that of control probes. For example, incubation of the mixed-sequence hairpin target with an unmodified isosequential DNA duplex did not show any complex formation, even with up to a 500-fold excess of the unmodified DNA duplex. In addition, incubation of the hairpin target with the either single-stranded probe precursor that comprises a double-stranded probe did not exhibit substantial complex formation (FIGS. 26 D & E). Furthermore, the sequence specificity of the probe may be determined by methods known to those of ordinary skill in the art. In exemplary embodiments, singly and doubly mutated, but perfectly base paired hairpins were targeted. In these particular embodiments, the probe-target complex was not observed, even at a 100-fold (5 uM) excess of the probe, thereby demonstrating high target specificity (FIGS. 26 A & B).

Figure 32:
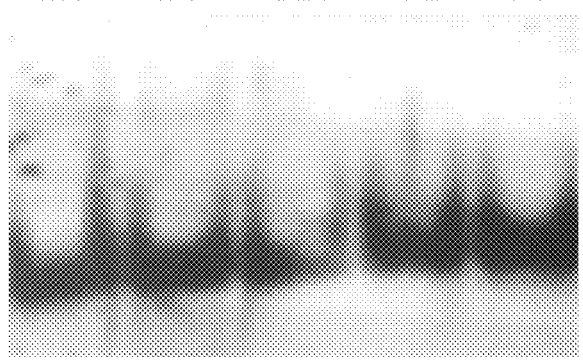
FIG. 32 illustrates the results of a control experiment. Incubation of SL1 with 100-fold excess of single-stranded 120'W6 (M6), 120'W8 (M8), 120Y2 (P2) or 120Y5 (P5). For experimental conditions and sequence of SL1, see FIG. 30.
Figure 33:
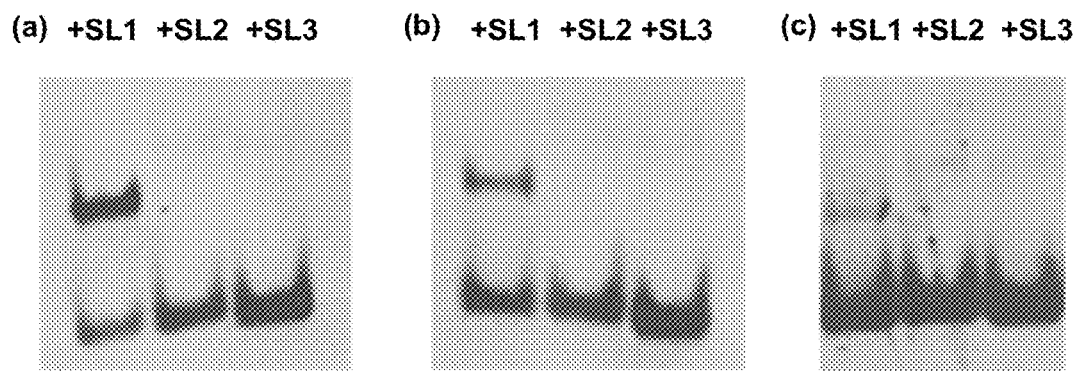
FIG. 33 illustrates the results of a control experiment. Incubation of SL1-SL3 with 100-fold excess of a) 126X2:126×5, b) 126Y2:126Y5 or c) 124X6:124X8. For experimental conditions and sequence of SL1-SL3, see FIG. 30.

Specific examples of control experiments were performed to validate the approach and evaluate the binding specificity (FIG. 30e-h): a) addition of up to 500-fold excess of unmodified DNA duplex D1:D2 to the structured DNA target SL1 (3 hours, 20° C.) fails to produce a recognition complex, which underlines the critical role of +1 interstrand arrangements of the disclosed monomers for dsDNA-targeting (FIG. 30e); b) addition of 100-fold excess of single-stranded 126W2/126W5/120Q2/120Q5/120P2/120P5/120'W6/120'W8 to structured DNA target SL1 (3 hours, 20° C.) fails to yield a recognition complex, which demonstrates that both strands of a probe enable dsDNA-recognition (FIG. 30f; FIG. 32); and c) addition of 100-fold excess of probes 126W2:126W5, 120Q2:120Q5, 126X2:126X5, 120Y2:120Y5 or 124X6:124X8 to structured DNA targets SL2 or SL3 (3 h, 20° C.) featuring fully base-paired but non-isosequential stem regions [one or two base pair deviations relative to probes; $T_m$ (SL2)=57.0° C.; $T_m$ (SL3)=64.5° C.], failed to form a recognition complex, which demonstrated that the approach is very specific (FIGS. 30g and 30h; FIG. 33).

VIII. Working Examples

General Experimental Section:

Unless otherwise noted, reagents and solvents were commercially available, of analytical grade and used without further purification. Petroleum ether of the distillation range 60-80° C. was used. Solvents were dried over activated molecular sieves: acetonitrile and THF (3 Å); $CH_2Cl_2$, 1,2-dichloroethane, N,N'-diisopropylethylamine and anhydrous DMSO (4 Å). Water content of "anhydrous" solvents was verified on Karl-Fisher apparatus. Reactions were conducted under argon whenever anhydrous solvents were used. Reactions were monitored by TLC using silica gel coated plates with a fluorescence indicator ($SiO_2$-60, F-254) which were visualized a) under UV light and/or b) by dipping in 5% conc. $H_2SO_4$ in absolute ethanol (v/v) followed by heating. Silica gel column chromatography was performed with Silica gel 60 (particle size 0.040-0.063 mm) using moderate pressure (pressure ball). Evaporation of solvents was carried out under reduced pressure at temperatures below 45° C. After column chromatography, appropriate fractions were pooled, evaporated and dried at high vacuum for at least 12 h to give the obtained products in high purity (>95%) as ascertained by 1D NMR techniques. Chemical shifts of $^1H$ NMR (500 MHz), $^{13}C$ NMR (125.6 MHz), and/or $^{31}P$ NMR (121.5 MHz) are reported relative to deuterated solvent or other internal standards (80% phosphoric acid for $^{31}P$ NMR). Exchangeable (ex) protons were detected by disappearance of signals upon $D_2O$ addition. Assignments of NMR spectra are based on 2D spectra (HSQC, COSY) and DEPT-spectra. Quaternary carbons are not assigned in $^{13}C$ NMR but verified from HSQC and DEPT spectra (absence of signals). MALDI-HRMS spectra of compounds were recorded on a Q-TOF mass spectrometer using 2,5-dihydroxybenzoic acid (DHB) as a matrix and polyethylene glycol (PEG 600) as an internal calibration standard.

9-[2-O-Acetyl-3-O-benzyl-5-O-methanesulfonyl-4-C-methanesulfonyloxy-methyl]-α-L-threo-pento-furanosyl-6-N-benzoyladenine (32)

Benzoylated adenine (28.6 g, 120 mmol) and coupling sugar 30 α/β (40.6 g, 80 mmol) were co-evaporated with 1,2-DCE (2×150 mL), redissolved in anhydrous 1,2-DCE (270 mL), and BSA (49.2 mL, 0.20 mol) was added. The heterogeneous mixture was heated at reflux until becoming homogeneous. After cooling to rt. TMSOTf (43.1 mL, 0.24 mol) was added and the reaction mixture heated at reflux for 70 h. After cooling to rt. the mixture was poured into sat. aq. NaHCO$_3$/crushed ice (500 mL, 1:1, v/v). To control effervescence additional crushed ice (400 mL) was added, and the mixture was stirred for 30 min during which a precipitate was formed. The precipitate was removed by filtration and the filtrate was washed with CH$_2$Cl$_2$ (1.5 L). The combined organic phase was washed with sat. aq. NaHCO$_3$ (2×500 mL) and the aqueous phase back-extracted with CH$_2$Cl$_2$ (2×500 mL). The organic phase was evaporated to afford a crude yellow foam, which was purified by silica gel column chromatography (0-10% i-PrOH in CH$_2$Cl$_2$, v/v) to afford target nucleoside 32 as a white foam (38.3 g, 70%). R$_f$=0.4 (5% MeOH in CH$_2$Cl$_2$, v/v). MALDI-HRMS m/z 712.1380 ([M+Na]$^+$, C$_{29}$H$_{31}$N$_5$O$_{11}$S$_2$.Na$^+$ Calc. 712.1354); $^1$H NMR (300 MHz, CDCl$_3$) δ 8.97 (s, 1H), 8.81 (s, 1H), 8.37 (s, 1H), 8.03 (d, 2H, J=8.1 Hz), 7.50-7.65 (m, 5), 7.29-7.38 (m, 5H), 6.45 (d, 1H, J=2.6 Hz), 5.95 (t, 1H, J=2.4 Hz), 4.78-4.82 (d, J=11.7 Hz, 1H), 4.63-4.67 (m, 3H), 4.38-4.43 (m, 4H), 3.28-3.32 (d, 1H, J=10.6 Hz), 3.0 (s, 3H), 2.96 (s, 3H), 2.16 (s, 3H); $^{13}$C NMR (75.5 MHz, CDCl$_3$) δ 169.5, 164.6, 152.9 (A$^{Bz}$), 151.6, 149.7, 141.2 (A$^{Bz}$), 135.7, 133.4, 132.8, 128.9, 128.8, 128.7, 128.6, 128.5, 128.4, 128.0, 127.8, 123.0, 87.3 (C1'), 86.0 (C4'), 81.3 (C3'), 79.4 (C2'), 73.3 (CH$_2$-Ph), 67.4 (C5'), 65.5 (C5''), 37.7 (OMs), 37.6 (OMs), 20.7 (Ac).

9-(3-O-Benzyl-5-O-methanesulfonyl-4-C-methane-sulfonyloxymethyl-α-L-threo-pentofuranosyl)-6-N-benzoyladenine (34)

Small Scale Procedure Using Guanidinium Nitrate.

A stock solution of guanidine/guanidinium nitrate (G/GHNO$_3$) was prepared according to the published procedure by dissolving guanidinium nitrate (4.91 g, 40.2 mmol) in a mixture of MeOH:CH$_2$Cl$_2$ (450 mL, 9:1, v/v) and adding NaOMe (0.24 g, 4.5 mmol). Fully protected nucleoside 32 (4.66 g, 6.7 mmol) was dissolved in an aliquot of the prepared G/GHNO$_3$ solution (450 mL) and the mixture was stirred at rt. for 30 min whereupon sat. aq. NH$_4$Cl (200 mL) was added, resulting in formation of a white precipitate. The formed precipitate was filtered off and washed repeatedly with CH$_2$Cl$_2$ until sugar residues were undetectable in the filtrate by TLC. The filtrate was concentrated under reduced pressure, the aqueous phase washed with CH$_2$Cl$_2$ (5×200 mL) and the combined organic phase evaporated, affording a yellowish solid. The crude solid was purified by silica gel column chromatography (0-4% MeOH in CH$_2$Cl$_2$, v/v) affording alcohol 34 (3.84 g, 88%) as a white foam. R$_f$: 0.5 (10% MeOH in CH$_2$Cl$_2$, v/v).

Large Scale Method Using ½ Sat. Methanolic Ammonia.

Fully protected nucleoside 32 (30.42 g, 44 mmol) was dissolved in MeOH (706 mL) and the solution cooled to 0° C., whereupon sat. methanolic ammonia (353 mL) was added. The reaction mixture was stirred at rt. for 2.5 h whereupon the mixture was evaporated and the obtained residue co-evaporated with abs. EtOH:toluene (2×500 mL, 1:1, v/v). The solid residue was purified by silica gel column chromatography (0-2.5% MeOH in CH$_2$Cl$_2$, v/v) affording target alcohol 34 as a white foam (23.81 g, 84%). R$_f$: 0.5 (10% MeOH in CH$_2$Cl$_2$, v/v). MALDI-HRMS m/z 670.1234 ([M+Na]$^+$, C$_{27}$H$_{29}$N$_5$O$_{10}$S$_2$.Na$^+$ Calc. 647.1248); $^1$H NMR (300 MHz, CDCl$_3$) δ 9.21 (s, 1H), 8.47 (s, 1H), 8.29 (s, 1H), 7.97 (d, 2H, J=7.7 Hz), 7.61-7.32 (m, 9H), 6.11 (d, 1H, J=6.2 Hz), 5.28 (d, 1H, J=9.2 Hz), 4.96 (d, 1H, J=11.7 Hz), 4.75 (d, 1H, J=11.3 Hz), 4.61 (d, 1H, J=10.6 Hz), 4.45-4.25 (m, 4H), 3.03 (s, 3H), 2.90 (s, 3H). $^{13}$C NMR (75.5 MHz, CDCl$_3$) δ165.2, 152.4 (A$^{Bz}$), 151.1, 148.6, 141.9 (A$^{Bz}$), 136.8, 133.2, 133.0, 128.9, 128.6, 128.3, 127.8, 121.7, 87.6 (C1'), 83.0 (C4'), 81.9 (C3'), 78.6 (C2'), 73.2 (CH$_2$-Ph), 68.4 (C5'), 68.2 (C5''), 37.7 (OMs), 37.4 (OMs).

1-(2-Azido-3-O-benzyl-4-C-methanesulfonyloxym-ethyl-5-O-methanesulfonyl-2-deoxy-α-L-erythro-pentofuranosyl)-6-benzoyl-adenine-9-yl (36, 38)

Alcohol 34 (18.6 g, 30 mmol) was co-evaporated with pyridine (50 mL), and subsequently dissolved in an. CH$_2$Cl$_2$ (200 mL). The mixture was then cooled to −78° C., and pyridine (7.3 mL, 90 mmol) and trifluoromethanesulfonyl anhydride (9.90 mL, 60 mmol) was added. The mixture was stirred for 3 h during which it was allowed to heat to rt. Hereafter crushed ice (50 mL) was added. The organic phase was washed with sat. aq. NaHCO$_3$ (2×50 mL), evaporated to dryness and co-evaporated with abs. EtOH (2×50 mL) affording a crude yellowish/brown solid which was used in the next step without further purification. The crude solid, tentatively assigned as triflate derivative 36, was dissolved in DMF (300 mL), and NaN$_3$ (19.6 g, 0.3 mol) and 15-crown-5 (6.0 mL, 30.2 mmol) was added. The reaction mixture was stirred at rt. for 15 h, where analytical TLC showed approximately 50% conversion. Subsequently the mixture was heated to 50° C. for 8 h, whereupon analytical TLC showed full conversion. After cooling to rt., the mixture was filtered to remove excess NaN$_3$. The filtrate was washed repeatedly with EtOAc and the combined organic phase was concentrated under reduced pressure. The concentrated mixture was taken up in brine (200 mL) and EtOAc (200 mL). The phases were separated and the aqueous phase extracted with EtOAc (4×100 mL). The combined organic phase was evaporated under reduced pressure affording a crude dark brown solid. The crude solid was then purified by silica gel column chromatography (0-90% EtOAc in petroleum ether, v/v) affording azide 38 (17.9 g, 89% over 2 steps) as a white solid. R$_f$: 0.4 (EtOAc). IR: 2115.6 cm$^{-1}$ (—N$_3$). MALDI-HRMS m/z 695.1295 ([M+Na]$^+$, C$_{27}$H$_{28}$N$_8$O$_9$S$_2$.Na$^+$ Calc. 695.1313); $^1$H NMR (300 MHz, DMSO-d$_6$) δ11.30 (s, 1H, NH, ex), 8.79 (s, 1H, A$^{Bz}$), 8.54 (s, 1H, A$^{Bz}$), 8.05 (d, 2H, J=7.0 Hz, Bz), 7.53-7.67 (m, 3H, Bz), 7.35-7.47 (m, 5H, Bn), 6.74 (d, 1H, J=4.4 Hz, H-1'), 5.20 (t, 1H, J=4.8 Hz, H-2'), 4.89 (d, 1H, J=5.1 Hz, H-3'), 4.79-4.83 (d, 1H, J=11.7 Hz, H-5'$_a$), 4.74-4.78 (d, 1H, J=11.7 Hz, H-5'$_b$), 4.69-4.72 (d, 1H, J=11.4 Hz, CH$_2$-Ph), 4.47-4.51 (d, 1H, J=11.4 Hz, CH$_2$-Ph), 4.42 (s, 2H, H-5''), 3.28 (s, 3H, OMs), 3.24 (s, 3H, OMs). $^{13}$C NMR (75.5 MHz, DMSO-d$_6$) δ151.9 (A$^{Bz}$), 150.4, 142.7 (A$^{Bz}$), 136.9, 133.2, 132.5, 128.5, 128.0, 81.9 (C1'), 81.7 (C3'), 80.1 (C2'), 73.5 (CH$_2$-Ph), 68.3 (C5'), 61.9 (C5''), 36.98 (OMs), 36.94 (OMs).

(1R,3R,4S,7R)-3-(6-Benzoyladenine-9-yl)-7-benzy-loxy-1-methanesulfonyloxy-methyl-2-oxa-5-azabi-cyclo[2.2.1]heptane (40)

Azide derivative 38 (35.18 g, 51.8 mmol) was dissolved in THF (500 mL) cooled to 0° C. and aq. NaOH (2M, 38.9 mL, 77.8 mmol) and trimethylphosphine (1M in THF, 77.8 mL, 77.8 mmol) was added. The reaction mixture was stirred for 21 h during which it was allowed to heat to rt. subsequently, the reaction mixture was evaporated to dryness. The resulting crude residue was taken up in brine (200 mL) and EtOAc (200 mL), and the aqueous phase washed with MeOH:CH$_2$Cl$_2$ (3×200 mL, 2:8, v/v). The combined organic phases was evaporated to dryness and the crude purified by silica gel column chromatography (0-5% MeOH in CH$_2$Cl$_2$, v/v) affording bicyclic nucleoside 40 as a yellow/brown solid (24.2 g, 85%). R$_f$: 0.3 (EtOAc). MALDI-HRMS m/z 573.1517 ([M+Na]$^+$, C$_{26}$H$_{26}$N$_6$O$_6$S.Na Calc. 573.1527); $^{13}$C NMR data is not in accordance with previous data. The corrected data are given here. $^1$H NMR (500 MHz, DMSO-d$_6$) δ 11.20 (s, 1H, NH, ex), 8.77 (s, 1H, A$^{Bz}$), 8.73 (s, 1H, A$^{Bz}$), 8.06 (d, 2H, J=7.0 Hz, Bz), 7.53-7.67 (m, 3H, Bz), 7.29-7.47 (m, 5H, Ph), 6.52 (d, 1H, J=1.8 Hz, H-1'), 4.72-4.76 (d, 1H, J=11.7 Hz, CH$_2$Ph), 4.62-4.67 (d, 1H, J=11.7 Hz, CH$_2$Ph), 4.57-4.60 (d, 1H, J=11.7 Hz, H-5$_a$'), 4.49-4.53 (d, 1H, J=11.7 Hz, H-5$_b$'), 4.44 (s, 1H, H-3'), 3.92 (m, 1H, H-2'), 3.24-3.30 (m, 1H, H5$_a$" overlap with H$_2$O) 3.23 (s, 3H, OMs), 3.10-3.13 (d, 1H, J=9.89 Hz, H-5$_b$"). $^{13}$C NMR (125 MHz, DMSO-d$_6$) δ 165.5, 152.0, 151.4 (A$^{Bz}$), 150.0, 143.1 (A$^{Bz}$), 137.8, 133.3, 132.3 (Ar), 128.4 (Ar), 128.2 (Ar), 127.6 (Ar), 127.5 (Ar), 125.0, 87.1, 84.3 (C-1'), 80.3 (C-3'), 71.0 (CH$_2$-Ph), 66.8 (C-5'), 59.8 (C-2'), 51.1 (C-5"), 36.8 (Ms).

(1R,3R,4S,7R)-3-(6-Benzoyladenine-9-yl)-7-benzyloxy-1-methanesulfonyloxy-methyl-5-trifluoroacetyl-2-oxa-5-azabicyclo[2.2.1]heptane (42)

Amine derivative 40 (8.68 g, 15.8 mmol) was co-evaporated with pyridine (2×20 mL) and dissolved in anhydrous CH$_2$Cl$_2$ (200 mL). Anhydrous pyridine (5.09 mL, 63 mmol) was added, the mixture cooled to 0° C., and trifluoroacetic acid anhydride (4.45 mL, 31.5 mmol) was added. The reaction mixture was stirred for 2 h whereupon crushed ice (50 mL) was added. The organic phase was washed with sat. aq. NaHCO$_3$ (2×50 mL), and the aqueous phase was back-extracted with CH$_2$Cl$_2$ (2×100 mL) and MeOH:CH$_2$Cl$_2$ (100 mL, 2:8, v/v). The combined organic phase was evaporated to dryness and co-evaporated with toluene (50 mL) and once with abs. EtOH:toluene (50 mL, 1:1, v/v). The crude residue was purified by silica gel column chromatography (0-100% EtOAc in petroleum ether, v/v) affording the fully protected nucleoside 42 as a white foam (6.27 g, 62%). R$_f$: 0.5 (10% MeOH:EtOAc, v/v). Physical data for the mixture of rotamers: MALDI-HRMS m/z 647.1541 ([M+H]$^+$, C$_{28}$H$_{25}$F$_3$N$_6$O$_7$S.H Calc. 647.1530); $^1$H NMR (500 MHz, DMSO-d$_6$) δ11.21 (s, 0.5H, NH, ex), 11.19 (s, 0.5H, NH, ex), 8.78 (s, 0.5H, A$^{Bz}$), 8.76 (s, 0.5H, A$^{Bz}$), 8.64 (s, 0.5H, A$^{Bz}$), 8.60 (s, 0.5H, A$^{Bz}$), 8.05 (d, 2H, J=7.0 Hz, Bz), 7.52-7.67 (m, 3H, Bz), 7.31-7.41 (m, 5H, Ph), 6.83 (d, 0.5H, J=1.1 Hz, H-1'), 6.80 (d, 0.5H, J=1.1 Hz, H-1'), 5.26 (s, 0.5H, H-2'), 5.17 (s, 0.5H, H-2'), 4.84 (s, 1H, H-3'), 4.82 (s, 0.5H, H-3'), 4.62-4.79 (m, 4H, CH$_2$Ph, H5"), 4.53 (d, 0.5H, J=10.6 Hz, H-5'), 4.35 (d, 0.5H, J=12.1 Hz, H-5'), 4.07 (d, 0.5H, J=10.6 Hz, H-5'), 3.90 (d, 0.5H, J=12.1 Hz, H-5'), 3.28 (s, 3H, OMs). $^{13}$C NMR (125 MHz, DMSO-d$_6$) δ165.5, 155.2 (q, J=36.6 Hz, COCF$_3$), 154.8 (q, J=36.6 Hz, COCF$_3$), 151.8 (A$^{Bz}$), 151.6 (A$^{Bz}$), 151.5, 150.3, 150.26, 141.2 (A$^{Bz}$), 141.0 (A$^{Bz}$), 137.1, 137.0, 133.2, 132.4 (Ar), 128.4 (Ar), 128.38 (Ar), 128.36 (Ar), 128.32 (Ar), 127.9 (Ar), 127.8 (Ar), 127.5 (Ar), 125.4, 125.2, 115.5 (q, J=288 Hz, CF$_3$), 115.2 (q, J=288 Hz, CF$_3$), 86.15 (C-4'), 86.14 (C-4'), 84.9 (C-1'), 84.8 (C-1'), 83.9 (C-2'), 79.1 (C-3'), 77.4 (C-3'), 71.6 (CH$_2$Ph), 65.3 (C-5"), 65.0 (C-5"), 63.0 (C-2'), 61.4 (C-2'), 53.2 (C-5'), 53.07 (C-5') 53.05 (C-5'), 37.0 (OMs). $^{19}$F NMR (376 MHz, DMSO-d$_6$) δ −71.3, −72.1.

(1R,3R,4S,7R)-3-(6-Benzoyladenine-9-yl)-7-hydroxy-1-methanesulfonyloxy-methyl-5-trifluoroacetyl-2-oxa-5-azabicyclo[2.2.1]heptane (44)

Fully protected nucleoside 42 (19.63 g, 30.4 mmol) was co-evaporated with 1,2-DCE (3×100 mL) and dissolved in anhydrous CH$_2$Cl$_2$ (610 mL). The solution was cooled to −78° C., followed by addition of BCl$_3$ (1M solution in hexanes, 370 mL, 370 mmol). The reaction mixture was stirred for 17 h during which it was allowed to heat to rt. The reaction mixture was subsequently cooled to 0° C. and crushed ice (800 mL) was added. The phases were separated and the organic phase was washed with sat. aq. NaHCO$_3$ (2×300 mL). The aqueous phase was back-extracted with EtOAc (4×500 mL), and the combined organic phase was evaporated under reduced pressure. The resulting residue was purified using silica gel column chromatography (0-20% MeOH in CH$_2$Cl$_2$, v/v) affording target alcohol 44 as a white solid (14.65 g, 87%). R$_f$: 0.3 (50% acetone in CH$_2$Cl$_2$, v/v). Physical data for the mixture of rotamers: MALDI-HRMS m/z 579.0871 ([M+Na]$^+$, C$_{21}$H$_{19}$F$_3$N$_6$O$_7$S.Na Calc. 579.0880); $^1$H NMR (300 MHz, DMSO-d$_6$) δ11.21 (s, 1H, NH, ex), 8.76 (s, 0.5H, A$^{Bz}$), 8.75 (s, 0.5H, A$^{Bz}$), 8.61 (s, 0.5H, A$^{Bz}$), 8.56 (s, 0.5H, A$^{Bz}$), 8.04 (d, 2H, J=7.7 Hz, Bz), 7.51-7.67 (m, 3H, Bz), 6.83 (d, 0.5, J=1.37 Hz, H-1'), 6.80 (d, 0.5H, J=1.37 Hz, H-1'), 6.73 (d, 0.5H, J=4.12 Hz, 3'-OH, ex), 6.69 (d, 0.5H, J=4.12 Hz, 3'-OH, ex), 4.91 (br s, 0.5H, H-2'), 4.81 (d, 0.5H, J=4.12 Hz, H-3'), 4.76 (d, 0.5H, J=4.12 Hz, H-3'), 4.70 (br s, 0.5H, H-2'), 4.60-4.67 (m, 2H, H-5"), 4.46 (d, 0.5H, J=10.3 Hz, H-5'), 4.26 (d, 0.5H, J=11.7 Hz, H-5'), 4.03 (d, 0.5H, J=10.3 Hz, H-5'), 3.86 (d, 0.5H, J=11.7 Hz, H-5'), 3.29 (s, 3H, OMs); $^{13}$C NMR (75.5 MHz, DMSO-d$_6$) δ165.5, 155.3 (q, J=36.6 Hz, COCF$_3$), 155.1 (q, J=36.6 Hz, COCF$_3$), 151.7 (A$^{Bz}$), 151.5 (A$^{Bz}$), 150.3, 150.2, 141.2 (A$^{Bz}$), 141.0 (A$^{Bz}$), 133.3, 132.4, 128.4, 125.4, 125.2, 115.5 (q, J=288 Hz, CF$_3$), 115.2 (q, J=288 Hz, CF$_3$), 87.0 (C-4'), 85.7 (C-4'), 84.7 (C-1'), 83.8 (C-1'), 72.5 (C-3'), 70.6 (C-3'), 65.7 (C-5"), 65.4 (C-5"), 65.3 (C-2'), 63.6 (C-2'), 52.7 (C-5'), 52.6 (C-5'), 36.97 (OMs). $^{19}$F NMR (376 MHz, DMSO-d$_6$) δ−71.1, −72.1.

(1S,3R,4S,7R)-3-(6-Benzoyladenin-9-yl)-1-benzoylmethyl-7-hydroxy-5-trifluoro-acetyl-2-oxa-5-azabicyclo[2.2.1]heptane (46)

Alcohol 44 (5.8 g, 10.4 mmol) was dissolved in DMF (100 mL) whereupon NaOBz (2.99 g, 20.8 mmol) and 15-crown-5 (2.07 mL, 10.4 mmol) were added. The mixture was heated to 90° C. and stirred for 5 h, then allowed to cool to rt. and stirred for an additional 18 h. Subsequently the mixture was concentrated in-vaccuo and taken up in EtOAc and brine. The phases were separated and the aqueous phase extracted with EtOAc (4×200 mL). The combined organic phase was evaporated under reduced pressure affording a dark brown solid material which was purified by silica gel column chromatography (0-3.5% i-PrOH in CHCl$_3$, v/v) to afford target benzoyl protected alcohol 46 (5.05 g, 83%) as a white foam. R$_f$=0.4 (10% i-PrOH in CHCl$_3$, v/v). Physical data for the mixture of rotamers: MALDI-HRMS m/z 605.1337 ([M+Na]$^+$, C$_{27}$H$_{21}$F$_3$N$_6$O$_6$.Na Calc. 605.1367); $^1$H NMR (300 MHz, DMSO-d$_6$) δ11.18 (br s, 1.7H, NH$_{a,b}$, ex), 8.77 (s, 1H, A$^{Bz}$$_a$), 8.76 (s, 0.7H, A$^{Bz}$$_b$), 8.67 (s, 0.7H, A$^{Bz}{}_b$), 8.63 (s, 1H, A$^{Bz}{}_b$), 8.09-8.18 (m, 4H, Bz), 8.02-8.09 (m, 4H, Bz), 7.51-7.76 (m, 13.5H, Bz), 6.89 (d, 1H, J=1.65 Hz, H1'$_a$), 6.86 (d, 0.7H, J=1.65 Hz, H1'$_b$), 6.67 (d, 1H, J=4.12 Hz, 3'-OH$_a$, ex), 6.63 (d, 0.7H, J=4.12 Hz, 3'-OH$_b$, ex), 4.89-4.96 (m, 2.4H, H3'$_{a,b}$, H2'$_b$), 4.74-4.82 (dd, 2H, J=6.04 Hz, J=12.65 Hz, H5"$_a$), 4.68-4.72 (m, 1H, H2'$_a$), 4.58-4.66 (dd, 1.4H, J=6.04 Hz, J=12.65 Hz, H5"$_b$), 4.55 (d, 0.7H, J=10.7 Hz, H5'$_b$), 4.38 (d, 1H, J=11.53 Hz, H5'$_a$), 4.10 (d, 0.7H, J=10.7 Hz, H5'$_b$), 3.93 (d, 1H, J=11.53 Hz, H5'$_a$). $^{13}$C NMR (75.5 MHz, DMSO-d$_6$) δ166.5, 165.3, 155.1 (q, COCF$_3$), 151.9 (A$^{Bz}$), 151.7 (A$^{Bz}$), 151.1, 140.3 (A$^{Bz}$), 140.1 (A$^{Bz}$), 134.5, 134.4, 133.5 (Bz), 131.9 (Bz), 129.55 (Bz), 129.54 (Bz), 129.18, 129.17, 128.7 (Bz), 128.4 (Bz), 128.2 (Bz), 125.4, 125.2, 115.5 (q, CF$_3$), 87.3 (C-4'), 86.0 (C-4'), 84.4 (C-1'$_b$), 83.6 (C-1'$_a$), 72.9 (C-3'$_a$), 71.0 (C-3'$_b$), 65.3 (C-2'$_b$), 63.6 (C-2'$_a$), 60.7 (C-5"$_a$), 60.2 (C-5"$_b$), 53.0 (C-5'$_a$), 52.9 (C-5'$_b$). $^{19}$F NMR (376 MHz, DMSO-d$_6$) δ−71.1, −72.0.

(1S,3R,4S,7R)-3-(6-Benzoyladenin-9-yl)-7-hydroxy-1-hydroxymethyl-2-oxa-5-azabicyclo[2.2.1]heptane (48)

Alcohol 46 (3.41 g, 5.85 mmol) was dissolved in 1,4-dioxane:H$_2$O (225 mL, 2:1, v/v) and cooled to 0° C., whereafter aq. NaOH (2M, 17.5 mL, 35 mmol) was added. The reaction mixture was stirred for 2 h, whereupon sat. aq. NH$_4$Cl (25 mL) was added, and the mixture was then evaporated to dryness. The resulting crude was adsorbed on silica gel and purified by silica gel column chromatography (0-20% MeOH in CH$_2$Cl$_2$, v/v) to afford target amino diol 48 as a white solid (1.33 g, 60%). R$_f$=0.4 (20% MeOH in CH$_2$Cl$_2$, v/v). MALDI-HRMS m/z 405.1294 ([M+Na]$^+$, C$_{18}$H$_{18}$N$_6$O$_4$.Na$^+$ Calc. 405.1282); $^1$H NMR (300 MHz, DMSO-d$_6$) δ 11.17 (br s, 1H, NH, ex), 8.73 (s, 1H, A$^{Bz}$), 8.71 (s, 1H, A$^{Bz}$), 8.05 (d, 2H, J=8.1 Hz, Bz), 7.49-7.67 (m, 3H, Bz), 6.44 (d, 1H, J=1.92 Hz, H-1'), 5.70 (d, 1H, J=4.0 Hz, 3'OH, ex), 4.82 (t, 1H, J=5.5 Hz, 5'-OH, ex), 4.30 (d, 1H, J=4.0 Hz, H-3'), 3.69 (d, 2H, J=5.5 Hz, H-5'), 3.51 (s, 1H, H-2'), 3.15 (d, 1H, J=10.6 Hz, H$_a$-5"), 2.96 (d, 1H, J=10.6 Hz, H$_b$-5"); $^{13}$C NMR (75.5 MHz, DMSO-d$_6$) δ165.5 (C=O), 152.0, 151.2 (A$^{Bz}$), 149.8, 143.2 (A$^{Bz}$), 133.3, 132.3 (Bz), 128.4 (Bz), 125.2, 91.3 (C-4'), 83.9 (C-1'), 73.4 (C-3'), 62.2 (C-5"), 58.3 (C-2'), 50.6 (C-5').

(1R,3R,4R,7R)-3-(6-Benzoyladenin-9-yl)-7-hydroxy-1-(4,4'-dimethoxytrityloxy-methyl)-2-oxa-5-azabicyclo[2.2.1]heptane (50)

Diol 48 (2.47 g, 6.5 mmol) was co-evaporated with anhydrous pyridine (2×50 mL), redissolved in anhydrous pyridine (130 mL) and cooled to 0° C. DMTrCl (3.25 g, 2.7 mmol) was added, and the reaction mixture stirred for 23 h during which it was allowed to heat to rt. Subsequently MeOH (20 mL) was added, and the mixture was diluted with EtOAc (200 mL) and washed with sat. aq. NaHCO$_3$ (2×20 mL). After separating the two phases, the aqueous phase was back-extracted with EtOAc (4×50 mL), and the combined organic phase was evaporated to dryness. The resulting residue was purified by silica gel column chromatography (0-8% MeOH and 1% pyridine in CH$_2$Cl$_2$, v/v) and the resulting product was co-evaporated with abs. EtOH:Toluene (2×50 mL, 1:1, v/v) affording nucleoside 50 as a white solid (1.51 g, 34%). R$_f$: 0.2 (7% MeOH in CH$_2$Cl$_2$, v/v). MALDI-HRMS m/z 707.2609 ([M+Na]$^+$, C$_{39}$H$_{36}$N$_6$O$_4$.Na$^+$ Calc. 707.2589). $^1$H NMR (500 MHz, DMSO-d$_6$) δ 11.15 (br s, 1H, NH, ex), 8.78 (s, 1H, A$^{Bz}$), 8.73 (s, 1H, A$^{Bz}$), 8.06 (d, 2H, J=7 Hz, Bz), 7.52-7.69 (m, 3H, Bz), 7.18-7.46 (m, 9H, DMTr), 6.86-6.93 (m, 4H, DMTr), 6.54 (d, 1H, J=1.92 Hz, H-1'), 5.66 (d, 1H, J=4.67 Hz, 3'-OH, ex), 4.39 (d, 1H, J=4.94 Hz, H-3'), 3.74 (s, 6H, 2×OMe), 3.48-3.51 (m, 1H, H-2'), 3.31 (d, 1H, J=10.7 Hz, H-5'$_a$), 3.26 (d, 1H, J=10.7 Hz, H-5'$_b$), 3.16-3.21 (m, 2H, H-5"$_a$,b), 2.89 (br s, 1H, 2'-NH, ex). $^{13}$C NMR (125 MHz, DMSO-d$_6$) δ165.5, 158.0, 152.2, 151.3 (A$^{Bz}$), 149.9, 144.8, 143.3 (A$^{Bz}$), 135.5, 135.4, 133.4, 132.3 (Ar), 129.7 (Ar), 129.68 (Ar), 128.4 (Ar), 128.39 (Ar), 127.8 (Ar), 127.7 (Ar), 126.5 (Ar), 125.1, 113.1 (Ar), 89.6 (C4'), 85.1 (C1'), 84.0, 74.0 (C-3'), 62.2 (C-2'), 61.2 (C5"), 54.9 (OMe), 51.2 (C5').

*A trace impurity of pyridine was identified in $^{13}$C NMR (149.5 ppm).

(1S,3R,4S,7R)-3-(6-benzoyladenin-9-yl)-7-hydroxy-1-(4,4'-dimethoxytrityl-oxy-methyl)-5-(9'-fluorenyl-methoxycarbonyl)-2-oxa-5-azabicyclo[2.2.1]heptane 51W Amino Alcohol 50 (200 mg, 0.29 mmol) was co-evaporated in anhydrous pyridine (2×2 mL) and re-dissolved in anhydrous pyridine (1.5 mL). This was cooled to 0° C. whereupon 9'-fluorenylmethyl chloroformate (100 mg, 0.38 mmol) was added and allowed to reach rt while stirring for 6 h. It was then diluted with EtOAc (30 mL) and washed with sat. aq. NaHCO$_3$ (30 mL). The aqueous phase was back-extracted with EtOAc (25 mL) and the combined organic phases were evaporated to dryness and co-evaporated with 2:1 EtOH:Toluene (2×6 mL). The resulting crude was purified by silica gel column chromatography (30-100% EtOAc in Petroleum Ether, v/v) to afford target nucleoside 51W as a white foam (136 mg, 51%). R$_f$=0.4 (EtOAc). Physical data for the mixture of rotamers: MALDI-HRMS m/z 929.3241 ([M+Na]$^+$, C$_{54}$H$_{46}$N$_6$O$_8$.Na$^+$ Calc. 929.3269); $^1$H NMR (300 MHz, DMSO-d$_6$) δ11.29 (br s, 2H, ex), 8.74 (s, 1H, A$^{Bz}$), 8.72 (s, 1H, A$^{Bz}$), 8.55 (s, 1H, A$^{Bz}$), 8.49 (s, 1H, A$^{Bz}$), 8.02-8.08 (m, 4H, Bz), 7.77-7.88 (m, 6H, Bz), 7.09-7.69 (m, 40H, DMT, Fmoc), 6.90-6.95 (m, 8H, DMT), 6.80 (d, 1H, J=1.65 Hz, H-1'), 6.73 (d, 1H, J=1.65 Hz, H-1'), 6.25 (d, 1H, J=4.39 Hz, 3'-OH, ex), 6.22 (d, 1H, J=4.39 Hz, 3'-OH, ex), 4.50 (br s, 1H, H-2'), 4.45 (br s, 1H, H-2'), 4.22 (d, 1H, J=6.86, CH$_2$Fmoc), 4.15 (d, 1H, J=6.86, CH$_2$Fmoc), 3.87 (d, 1H, J=6.86, CH$_2$Fmoc), 3.83 (d, 1H, J=6.86, CH$_2$Fmoc), 3.73-3.76 (m, 14H, OCH$_3$, CH (Fmoc)), 3.70 (d, 1H, J=10.5 Hz, H-5'), 3.62 (d, 1H, J=10.5 Hz, H-5'), 3.34-3.43 (m, 6H, H-5", H-5'). $^{13}$C NMR (75.5 MHz, DMSO-d$_6$) δ 165.6, 158.1, 154.7, 154.6, 151.8 (A$^{Bz}$), 151.5 (A$^{Bz}$), 150.3, 150.2, 144.7, 143.7, 143.6, 143.5, 142.8, 141.3 (A$^{Bz}$), 141.2 (A$^{Bz}$), 140.6, 140.4, 140.3, 135.3, 135.2, 133.3, 132.4, 129.7, 128.8, 128.4, 127.9, 127.7, 127.6, 127.5, 127.2, 127.1, 126.9, 126.7, 125.4, 125.2, 125.1, 124.9, 124.6, 121.3, 119.98, 113.2, 88.9 (C-4'), 88.4 (C-4'), 85.4 (C-(Ph)$_3$, DMT), 84.9 (C-1'), 84.7 (C-1'), 72.5 (C-3'), 72.0 (C-3'), 66.7 (CH$_2$-fmoc), 63.9 (C-2'), 63.4 (C-2'), 60.6 (C-5"), 60.56 (C-5"), 54.96 (OCH$_3$), 52.7 (C-5'), 52.6 (C-5'), 46.4 (CH, fmoc), 45.9 (CH, fmoc).

FMOC Protected Nucleoside Phosphoramidite 52W:

Nucleoside 51W (225 mg, 0.25 mmol) was co-evaporated with an. 1,2-DCE (2×4 mL) and re-dissolved in anhydrous CH$_2$Cl$_2$ (3.5 mL). Anhydrous DIPEA (195 µL, 1.12 mmol) and N-methylimidazole (16 µL, 0.20 mmol) were added followed by dropwise addition of 2-cyanoethyl-N,N'-(diisopropyl)-phosphoramidochloridite (111 µL, 0.50 mmol). The reaction mixture stirred at rt. for 4 h whereupon the crude was evaporated to dryness and the resulting residue was purified by silica gel column chromatography (0-2% MeOH in CH$_2$Cl$_2$, v/v, initially built in 0.5% Et$_3$N) and precipitated from CH$_2$C$_2$/Petroleum Ether to afford target amidite 52W as a white foam (126 mg, 46%). Physical data for the mixture of rotamers: R$_f$=0.5 (5% MeOH in CH$_2$Cl$_2$, v/v); HiResESI m/z 1129.4356 ([M+Na]$^+$, C$_{63}$H$_{63}$N$_8$O$_9$P.Na$^+$ Calc. 1129.4348); $^{31}$P NMR (121 MHz, CDCl$_3$) δ 150.32, 150.26, 150.12, 149.48.

(1R,3R,4S,7R)-3-(6-Benzoyladenin-9-yl)-7-hydroxy-1-(4,4'-dimethoxytrityl-oxy-methyl)-5-(pyren-1-yl)methyl-2-oxa-5-azabicyclo[2.2.1]heptane (51X)

Nucleoside 50 (300 mg, 0.44 mmol) was co-evaporated with anhydrous 1,2-DCE (2×10 mL), suspended in anhydrous CH$_2$Cl$_2$ (4.4 mL), and pyrenecarboxaldehyde (171 mg, 0.74 mmol) and NaBH(OAc)$_3$ (186 mg, 0.88 mmol) was added. The resulting suspension was stirred at rt. for 17 h whereupon sat. aq. NaHCO$_3$ (4 mL) was added and the mixture subsequently diluted with CH$_2$Cl$_2$ (20 mL). The two phases were separated and the organic phase was washed with sat. aq. NaHCO$_3$ (20 mL). The resulting aqueous phase was back-extracted with EtOAc (2×20 mL). The combined organic phase was evaporated to dryness, and the resulting residue was purified by silica gel column chromatography (0-99% EtOAc and 1% pyridine in petroleum ether, v/v) affording target nucleoside 51X as a white foam (268 mg, 68%). R$_f$=0.4 (EtOAc). MALDI-HRMS m/z 921.3326 ([M+Na]$^+$, C$_{56}$H$_{46}$N$_6$O$_6$.Na$^+$ Calc. 921.3371). $^1$H NMR (300 MHz, DMSO-d$_6$) δ11.13 (s, 1H, NH, ex), 8.46 (s, 1H, A$^{Bz}$), 8.36 (s, 1H, A$^{Bz}$), 7.89-8.16 (m, 12H, Ar), 7.51-7.76 (m, 9H, Ar), 7.12-7.36 (m, 14H, Ar), 6.82 (s, 3H, DMT), 6.78 (s, 3H, DMT), 6.42 (s, 1H, H-1'), 6.07 (s, 1H, 3'-OH, ex), 4.66 (d, 1H, J=12.5 Hz, CH$_2$Py), 4.51 (s, 1H, H-3'), 4.45 (d, 1H, J=12.5 Hz, CH$_2$Py), 3.64 (s, 6H, 2×OMe), 3.57 (s, 1H, H-2'), 3.42 (d, 1H, J=9.6 Hz, H-5'), 3.17 (d, 1H, J=9.6 Hz, H-5'). The signals from H-5"$_{A+B}$ were not identifiable due to signal overlap with water; $^{13}$C NMR (75.5 MHz, CDCl$_3$) δ164.1, 158.6, 151.3 (A$^{Bz}$), 150.5, 149.6, 148.3, 144.4, 141.8 (A$^{Bz}$), 136.1, 135.5, 135.4, 133.7, 132.6, 132.3, 131.1, 130.7, 130.5, 130.0, 129.1, 128.7, 128.0, 127.8, 127.6, 127.2, 127.1, 127.0, 126.8, 125.7, 125.0, 124.8, 124.6, 124.4, 124.1, 123.8, 122.9, 122.6, 113.2 (DMT), 90.2 (C-4') 86.5 (C-(Ph)$_3$ DMT), 86.1 (C-1'), 65.2 (C-3'), 61.2 (C-2'), 59.2 (C-5"), 57.6 (C-5'), 55.2 (OCH$_3$), 29.6 (CH$_2$Py).

(1S,3R,4R,7S)-3-(6-Benzoyladenin-9-yl)-7-[2-cyanothoxy(diisopropylamino)-phosphinoxy]-1-(4,4'-dimethoxytrityloxymethyl)-5-(pyren-1-yl)methyl-2-oxa-5-azabicyclo[2.2.1]heptane (52X)

Nucleoside 51X (220 mg, 0.24 mmol) was co-evaporated with 1,2-DCE (2×10 mL), dissolved in 20% DIPEA in anhydrous CH$_2$Cl$_2$ (4.4 mL, v/v) and 2-cyanoethyl-N,N'-(diisopropyl)-phosphoramidochloridite (0.12 mL, 0.54 mmol) was added. The reaction mixture was stirred at rt. for 21 h, whereupon additional 2-cyanoethyl-N,N'-(diisopropyl)-phosphoramidochloridite (0.05 mL, 0.06 mmol) was added. The reaction mixture was then stirred for 4 h followed by addition of abs. EtOH (2 mL). Subsequently the mixture was diluted with CH$_2$Cl$_2$ (10 mL) and the organic phase was washed sequentially with sat. aq. NaHCO$_3$ (10 mL) and brine (10 mL). After separation of the two phases the organic phase was evaporated to dryness and the resulting residue purified by silica gel column chromatography (0-60% EtOAc and 1% pyridine in petroleum ether, v/v). The resulting product was co-evaporated with abs. EtOH: toluene (2×10 mL, 1:1, v/v) affording a white solid which was then precipitated from HPLC-grade EtOAc/n-hexane affording pure amidite 52X as a white solid (136 mg, 51%). R$_f$: 0.7 (5% MeOH in CH$_2$Cl$_2$, v/v). HiResESI m/z 1099.4642 ([M+Na]$^+$, C$_{65}$H$_{63}$N$_8$O$_7$P.Na$^+$ Calc. 1099.4630). $^{31}$P NMR (121 MHz, CDCl$_3$) δ151.3, 149.0.

(1S,3R,4S,7R)-3-(6-Benzoyladenin-9-yl)-7-hydroxy-1-(4,4'-dimethoxytrityl-oxy-methyl)-5-(pyren-1-yl)carbonyl-2-oxa-5-azabicyclo[2.2.1]heptane (51Y)

Amino alcohol 50 (407 mg, 0.59 mmol) was co-evaporated with anhydrous 1,2-DCE (2×10 mL), dissolved in anhydrous CH$_2$Cl$_2$ (11.9 mL), and 1-ethyl-3-(3-dimethylaminopropyl)carbodiimide hydrochlorid (EDC. HCl, 226 mg, 1.19 mmol) and 1-pyrenylcarboxylic acid (293 mg, 1.19 mmol) was added. The reaction mixture was stirred at rt. for 45 h, whereafter it was diluted with CH$_2$Cl$_2$ (50 mL) and washed with water (20 mL). The two phases were separated and the aqueous phase back-extracted with CH$_2$Cl$_2$ (3×50 mL). The combined organic phase was evaporated under reduced pressure and the resulting residue was purified by silica gel column chromatography (0-99% EtOAc and 1% pyridine in petroleum, v/v). The resulting product was co-evaporated with abs. EtOH:toluene (2×50 ml, 1:1, v/v) affording target nucleoside 51Y as a yellow solid (343 mg, 64%). Physical data for the mixture of rotamers: R$_f$: 0.5 (5% MeOH: CH$_2$Cl$_2$, v/v); MALDI-HRMS m/z 935.3138 ([M+Na]$^+$, C$_{56}$H$_{44}$N$_6$O$_7$.Na$^+$ Calc. 935.3164). Unknown impurity is identified at 6.22 ppm in $^1$H-NMR. $^1$H NMR (300 MHz, DMSO-d$_6$) δ11.21 (s, 1H, NH, ex), 11.20 (s, 1H, NH, ex), 8.55 (s, 1H, A$^{Bz}$), 8.53 (s, 1H, A$^{Bz}$), 8.45 (s, 1H, A$^{Bz}$), 8.40 (s, 1H, A$^{Bz}$), 7.97-8.23 (m, 10H, Ar), 7.56-7.84 (m, 7H, Ar), 7.18-7.44 (m, 10H, Ar), 7.09 (s, 1H, Ar), 7.06 (s, 1H, Ar), 6.82-6.90 (m, 4H, DMTr), 6.50 (d, 1H, J=2.2 Hz, H-1'), 6.40 (d, 1H, J=1.8 Hz, H-1'), 6.15 (d, 1H, J=4.0 Hz, 3'-OH, ex), 6.07 (d, 1H, J=3.7 Hz, 3'-OH, ex), 4.42-4.77 (m, 4H, H-3', H-5'), 3.73 (s, 12H, 2×OMe), 3.66 (s, 2H, H-2'), 3.41-3.44 (d, 1H, J=13.6 Hz, H-5"$_a$), 3.15-3.20 (d, 2H, J=13.6 Hz, H-5"$_b$); $^{13}$C NMR (75.5 MHz, DMSO-d$_6$) δ165.5, 157.9, 157.7, 151.7, 150.98, 149.8, 148.2, 144.7, 142.8, 140.1, 135.4, 135.3, 133.5, 133.1, 132.3, 130.5, 130.2, 129.9, 129.6, 128.8, 128.6, 128.4, 127.8, 127.6, 127.5, 127.3, 127.2, 126.9, 126.5, 126.3, 125.9, 125.5, 124.9, 124.8, 124.78, 124.2, 123.8, 123.7, 123.1, 113.1, 112.7, 92.0, 90.3, 85.1, 84.7, 79.8, 75.3, 74.7, 66.4, 61.2, 59.1, 58.6, 58.3, 58.2, 54.6.

(1S,3R,4S,7R)-3-(6-Benzoyladenin-9-yl)-7-hydroxy-1-(4,4'-dimethoxytrityl-oxy-methyl)-5-(pyren-1-yl)carbonyl-2-oxa-5-azabicyclo[2.2.1]heptanes (51Y)

Pyrene-1-carboxylic acid (127 mg, 0.50 mmol), 2-(1H-7-Azabenzotriazol-1-yl)-1,1,3,3-tetramethyluronium hexafluorophosphate (HATU, 166 mg, 0.44 mmol), and diisopropylethylamine (DIPEA, 0.15 mL, 0.87 mmol) were dissolved in anhydrous DMF (3 mL) and allowed to stir at rt for 1 h then cooled to 0° C. Amino alcohol 50 (230 mg, 0.34 mmol) was co-evaporated with anhydrous 1,2-DCE (2×3 mL) and redissolved in anhydrous DMF (3 mL) and added to the cooled reaction mixture. After 5 h stirring, the mixture was diluted with EtOAc (30 mL) and washed with water (3×20 mL). The organic layer was evaporated to dryness and the resulting crude purified by silica gel column chromatography (0-4% MeOH in CH$_2$Cl$_2$, v/v) affording compound 51Y as a white solid (227 mg, 74%). Physical data for the mixture of rotamers: R$_f$: 0.5 (5% MeOH: CH$_2$Cl$_2$, v/v); MALDI-HRMS m/z 935.3138 ([M+Na]$^+$, $C_{56}H_{44}N_6O_7\cdot Na^+$ Calc. 935.3164). $^1$H NMR (500 MHz, DMSO-$d_6$) δ 11.32 (br s, 1.3H, NH, ex), 8.85 (s, 0.3H, $A^{Bz}$), 8.79 (s, 1.3H, $A^{Bz}$), 8.75 (s, 0.3H, $A^{Bz}$), 8.02-8.39 (m, 13.7H, Ar), 7.82 (m, 0.6H, Ar), 7.49-7.75 (m, 6H, Ar), 7.10-7.42 (m, 9.7H, Ar), 6.93-6.98 (m, 4H, DMT$_a$), 6.92 (d, 0.3H, J=1.92 Hz, H-1'$_b$), 6.72-6.78 (m, 1.2H, DMT$_b$), 6.54 (d, 0.3H, J=3.57 Hz, 3'-OH$_b$, ex), 6.48 (d, 1H, J=4.94 Hz, 3'-OH$_a$, ex), 6.44 (s, 1H, H-1'$_a$), 5.22 (s, 0.3H, H-2'$_b$), 4.87 (d, 0.3H, J=3.56 Hz, H-3'$_b$), 4.61 (d, 1H, J=5.21 Hz, H-3'$_a$), 4.36 (d, 1H, J=12.08 Hz, H-5'$_a$) 4.02 (d, 1H, J=12.08 Hz, H-5'$_a$), 3.77 (s, 7H, 2×(OCH$_3$)$_a$, H-2'$_a$), 3.69 (d, 0.3H, J=10.43 Hz, H-5'$_b$), 3.66 (s, 1H, (OCH$_3$)$_b$), 3.64 (s, 1H, (OCH$_3$)$_b$), 3.47 (s, 2H, H5"$_a$), 3.39 (d, 0.3H, J=10.43 Hz, H-5'$_b$), 3.18 (s, 0.6H, H-5"$_b$). $^{13}$C NMR (125 MHz, DMSO-$d_6$) δ 169.5, 169.1, 165.8, 165.6, 158.0, 157.9, 152.0, 151.6, 151.23, 151.21, 150.3, 144.7, 144.5, 141.5 ($A^{Bz}$), 141.4 ($A^{Bz}$), 135.4, 135.2, 135.15, 135.11, 133.48, 132.5 (Ar), 132.4 (Ar), 131.3, 130.9, 130.6, 130.5, 130.4, 130.1, 129.9 (Ar), 129.8 (Ar), 129.7 (Ar), 129.6 (Ar), 128.8 (Ar), 128.7, 128.6 (Ar), 128.5 (Ar), 128.49 (Ar), 128.47 (Ar), 128.2 (Ar), 128.1 (Ar), 127.9 (Ar), 127.8 (Ar), 127.7 (Ar), 127.6 (Ar), 127.1 (Ar), 126.9 (Ar), 126.7 (Ar), 126.6 (Ar), 126.5 (Ar), 125.9 (Ar), 125.8 (Ar), 125.6 (Ar), 125.5 (Ar), 124.8 (Ar), 124.2 (Ar), 124.0, 123.9 (Ar), 123.5, 123.3, 123.1, 113.2 (DMT), 113.06 (DMT), 113.04 (DMT), 88.7 (C-4'$_a$), 88.5 (C-4'$_b$), 85.4 (C-(Ph)$_3$, DMT$_a$), 85.3 (C-(Ph)$_3$, DMT$_b$), 85.0 (C-1'$_b$), 84.7 (C-1'$_a$), 72.5 (C-3'$_a$), 71.8 (C-3'$_b$), 65.6 (C-2'$_b$), 62.8 (C-2'$_a$), 60.5 (C-5"$_a$), 60.0 (C-5"$_b$), 55.0 (OCH$_3$), 54.8 (OCH$_3$), 54.0 (C-5'$_b$), 52.2 (C-5'$_a$).

(1S,3R,4S,7R)-3-(6-Benzoyladenin-9-yl)-7-[2-cyanothoxy(diisopropylamino)-phosphinoxy]-1-(4,4'-dimethoxytrityloxymethyl)-5-(pyren-1-yl)carbonyl-2-oxa-5-azabicyclo[2.2.1]heptane (52Y)

Nucleoside 51Y (300 mg, 0.33 mmol) was co-evaporated with 1,2-DCE (2×5 mL), dissolved in anhydrous CH$_2$Cl$_2$ (2.7 mL) and anhydrous DIPEA (0.66 ml), and 2-cyanoethyl-N,N'-(diisopropyl)-phosphoramidochloridite (0.11 mL, 0.5 mmol) was added. The reaction mixture stirred at rt. for 22 h. whereafter abs. EtOH (2 mL) was added. The mixture was subsequently taken up in CH$_2$Cl$_2$ (50 mL) and washed with sat. aq. NaHCO$_3$ (50 mL) and brine (50 mL). The combined aqueous phase was back-extracted with CH$_2$Cl$_2$ (2×20 ml) and the combined organic phase was evaporated under reduced pressure. The resulting residue was purified by silica gel column chromatography (0-99% EtOAc and 1% pyridine in petroleum ether, v/v) and the resulting product co-evaporated with abs. EtOH:toluene (2×50 ml, 1:1, v/v) and precipitated from HPLC-grade EtOAc/n-hexane to afford target amidite 52Y as a white foam (247 mg, 67%). Physical data for the mixture of rotamers: R$_f$=0.5 (EtOAc); HiResESI m/z 1113.4462 ([M+Na]$^+$, $C_{65}H_{61}N_8O_8P\cdot Na^+$ Calc. 1113.4422); $^{31}$P NMR (121 MHz, CDCl$_3$) δ152.3, 151.8, 150.2.

(1S,3R,4S,7R)-3-(6-Benzoyladenin-9-yl)-7-hydroxy-1-(4,4'-dimethoxytrityl-oxy-methyl)-5-(pyren-1-yl)acetyl-2-oxa-5-azabicyclo[2.2.1]heptane 51Z Amino alcohol 50 (250 mg, 0.37 mmol) was co-evaporated with anhydrous 1,2-DCE (2×5 mL), dissolved in anhydrous CH$_2$Cl$_2$ (10 mL), and 1-ethyl-3-(3-dimethylaminopropyl)carbodiimide hydrochlorid (EDC.HCl, 108 mg, 0.55 mmol) and 1-pyreneacetic acid (145 mg, 0.55 mmol) was added. The reaction mixture was stirred at rt. for 2.5 h, whereafter it was diluted with CH$_2$Cl$_2$ (20 mL) and washed with water (2×10 mL). The two phases were separated and the aqueous phase back-extracted with CH$_2$Cl$_2$ (10 mL). The combined organic phase was evaporated under reduced pressure and the resulting residue was purified by silica gel column chromatography (0-4% MeOH in CH$_2$Cl$_2$, v/v) affording target nucleoside 51Z as a white solid (266 mg, 79%). Physical data for the mixture of rotamers: R$_f$: 0.5 (10% MeOH:CH$_2$Cl$_2$, v/v); MALDI-HRMS m/z 949.3321 ([M+Na]$^+$, $C_{57}H_{46}N_6O_7\cdot Na^+$ Calc. 949.3320). $^1$H NMR (500 MHz, DMSO-$d_6$) δ 11.29 (br s, 1.5H, NH, ex), 8.96 (s, 1H, $A^{Bz}$), 8.73 (s, 0.5H, $A^{Bz}{}_b$), 8.71 (s, 1H, $A^{Bz}{}_a$), 8.55 (s, 0.5H, $A^{Bz}{}_b$), 7.92-8.33 (m, 16H, Py, Bz), 7.83 (m, 1H, Py, Bz), 7.60-7.79 (m, 4.5H, Py, Bz), 7.44-7.54 (m, 3.5H, DMT), 7.20-7.40 (m, 10.5H, DMT), 6.88-6.98 (m, 6H, DMT), 6.82 (d, 0.5H, J=1.65 Hz, H-1'$_b$), 6.79 (d, 1H, J=1.37 Hz, H-1'$_a$), 6.31 (d, 0.5H, J=4.39 Hz, 3'-OH$_b$, ex), 6.19 (d, 1H, J=4.39 Hz, 3'-OH$_a$, ex), 5.07 (s, 0.5H, H-2'$_b$), 4.71-4.74 (m, 1.5H, H-2'$_a$, H-3'$_b$), 4.67 (d, 1H, J=10.43, H-5'$_{1a}$), 4.63 (d, 1H, J=4.39 Hz, H-3'$_a$), 4.57 (d, 1H, J=16.2 Hz, CH$_2$Py$_a$), 4.38 (d, 1H, J=10.2 Hz, CH$_2$Py$_a$), 4.11 (d, 0.5H, J=16.2 Hz, CH$_2$Py$_b$), 3.95-4.04 (m, 1.5H, H-5'$_{1b}$, H-5'$_{2a}$), 3.66-3.77 (m, 9.5H, OCH$_3$, H-5'$_{2b}$), 3.34-3.51 (m, 3.5H, H-5"$_{a,b}$, CH$_2$Py$_b$). $^{13}$C NMR (125 MHz, DMSO-$d_6$) δ 172.7, 169.8, 169.6, 165.5, 165.4, 158.1, 158.0, 151.9, 151.7 ($A^{Bz}$), 151.5, 151.4 ($A^{Bz}$), 150.5, 150.2, 144.7, 144.6, 141.7 ($A^{Bz}$), 141.5 ($A^{Bz}$), 135.5, 135.2, 133.5, 133.4, 132.5, 130.8, 130.7, 130.6, 130.3, 130.2, 130.1, 129.9, 129.88, 129.82, 129.78, 129.77, 129.74, 129.68, 129.67, 129.66, 129.62, 129.4, 129.2, 128.9, 128.8, 128.7, 128.6, 128.5, 128.5, 128.2, 127.8, 127.77, 127.72, 127.4, 127.3, 127.27, 127.25, 127.1, 126.9, 126.8, 126.7, 126.6, 126.2, 126.0, 125.9, 125.4, 125.3, 125.2, 125.0, 124.9, 124.8, 124.76, 124.72, 124.6, 124.5, 124.4, 124.3, 124.0, 123.9, 123.8, 123.78, 123.76, 123.72, 123.6, 123.2, 113.2 (DMT), 89.0 (C-4'), 88.4 (C-4'), 85.47 (C-(Ph)$_3$), 85.40 (C-(Ph)$_3$), 84.7 (C-1'$_a$), 84.6 (C-1'$_b$), 72.9 (C-3'$_b$), 72.0 (C-3'$_a$), 64.5 (C-2'$_b$), 61.8 (C-2'$_a$), 60.9 (C-5"$_a$), 60.8 (C-5"$_b$), 55.0 (OCH$_3$), 54.8 (OCH$_3$), 52.8 (C-5'$_a$), 52.3 (C-5'$_b$), 38.7, 37.8 (CH$_2$Py$_a$), 37.7 (CH$_2$Py$_b$). *Trace impurities of residual 1-pyreneacetic acid were identified in $^{13}$CNMR (C=O at 172 ppm, CH$_2$ at 38.7 ppm, plus extra pyrene peaks, couples to impurities in HNMR (4.35 ppm is extra CH$_2$Py peak that couples to 38.7 in HSQC).

(1S,3R,4S,7R)-3-(6-Benzoyladenin-9-yl)-7-[2-cyanothoxy(diisopropylamino)-phosphinoxy]-1-(4,4'-dimethoxytrityloxymethyl)-5-(pyren-1-yl)acetyl-2-oxa-5-azabicyclo[2.2.1]heptane (52Z)

Nucleoside 51Z (235 mg, 0.25 mmol) was co-evaporated with an. 1,2-DCE (2×5 mL) and re-dissolved in anhydrous CH$_2$Cl$_2$ (5 mL). Anhydrous DIPEA (220 μL, 1.27 mmol) was added followed by dropwise addition of 2-cyanoethyl-N,N'-(diisopropyl)-phosphoramidochloridite (115 μL, 0.51 mmol). The reaction mixture stirred at rt. for 22 h. whereafter abs. EtOH (1 mL) was added. The crude was evaporated to dryness and the resulting residue was purified by silica gel column chromatography (0-2% MeOH in CH$_2$Cl$_2$, v/v) and precipitated from CH$_2$Cl$_2$/Petroleum Ether to afford target amidite 52Z as a white foam (203 mg, 71%). Physical data for the mixture of rotamers: R$_f$=0.6 (5% MeOH in CH$_2$Cl$_2$, v/v); MALDI-HRMS m/z 1149.4358 ([M+Na]$^+$, $C_{66}H_{63}N_8O_8P\cdot Na^+$ Calc. 1149.4399); $^{31}$P NMR (121 MHz, CDCl$_3$) δ 150.39, 150.31, 150.26, 148.09.

Synthesis of Probes with Locked Monomers 124W-124Y:

Syntheses of probes containing incorporations of locked phosphoramidites 52W, 52X, and 52Y were performed on an automated DNA synthesizer (0.2 μmol scale) using the following hand coupling conditions (activator; coupling time; approximate coupling yield): Monomer 124W (pyridinium hydrochloride; 30 min; ~82%), monomers 124X and 124Y (pyridinium hydrochloride; 15 min; ~95%). The probes were deprotected using 32% aq. NH$_3$ at 55° C. for 2 h. Purification of probes (till at least 75% purity) was performed by RP-HPLC (DMT-ON), followed by detritylation (80% aq. AcOH, 20 min) and precipitation (abs. EtOH, −18° C., 12 h). RP-HPLC purification of oligonucleotides was performed using a Waters Prep LC 4000 system equipped with an Xterra MS C18-column (10 μm, 300 mm×7.8 mm). A representative RP-HPLC gradient protocol for purification of oligonucleotides with DMT-ON is to use an isocratic hold of 100% A-buffer for 5 min followed by a linear gradient to 55% B-buffer over 75 min at a flow rate of 1.0 mL/min (A-buffer: 95% 0.1 M NH$_4$HCO$_3$, 5% CH$_3$CN; B-buffer: 25% 0.1 M NH$_4$HCO$_3$, 75% CH$_3$CN). The composition of the probes was verified by MALDI-MS analysis (Table 32) whereas the purity (>80%, unless stated otherwise) was verified by ion-exchange HPLC using a LaChrom L-7000 system (VWR International) equipped with a GenPak Fax column (100 mm×4.6 mm). A representative protocol involves the use of an isocratic hold of 95% A-buffer for 5 min, followed by a linear gradient to 70% B-buffer over 41 min at a flow rate of 0.75 mL/min (A-buffer: 25 mM Tris-Cl, 1 mM EDTA, pH 8.0; B-buffer: 1 M NaCl).

TABLE 32

MS-data of representative single-stranded probe modified with adenine monomers 124X (=K) or 124Y (=L).[a]

| ONs | Sequence | Calc. m/z | Found m/z |
|---|---|---|---|
| 124X6 | 5'-GTG KTA TGC | 2995 | 2995 |
| 124X7 | 5'-GTG ATK TGC | 2995 | 2993 |
| 124X8 | 3'-CAC TKT ACG | 2924 | 2923 |
| 124X9 | 3'-CAC TAT KCG | 2924 | 2923 |
| 124Y6 | 5'-GTG LTA TGC | 3009 | 3008 |
| 124Y7 | 5'-GTG ATL TGC | 3009 | 3009 |
| 124Y8 | 3'-CAC TLT ACG | 2937 | 2937 |
| 124Y9 | 3'-CAC TAT LCG | 2937 | 2936 |

Thermal Affinity of Probes Modified with Monomers 124W/X/Y:

The thermal affinity of probes toward complementary DNA or RNA targets and of probe duplexes was evaluated via UV thermal denaturation experiments ([Na$^+$]=110 mM, Tables 33 and 34. Changes in thermal denaturation temperatures (T$_m$-values) of modified duplexes are discussed relative to T$_m$-values of unmodified reference duplexes, unless otherwise stated. Single-stranded probes that are modified with monomer 124W show similar thermal affinity toward single-stranded DNA as toward single-stranded RNA targets. Single-stranded probes that are modified with 124X and 124Y show higher thermal affinity toward single-stranded DNA than toward single-stranded RNA targets (Tables 33 and 34). This DNA selectivity makes these monomers useful as probes for targeting double stranded DNA.

TABLE 33

T$_m$-Values of Duplexes Between B6-B11 and Complementary DNA Targets[a]

| | | | | T$_m$ [ΔT$_m$/mod] (° C.) | | |
|---|---|---|---|---|---|---|
| ON | Duplex | B = | T | 124W | 124X | 124Y |
| B6 D2 | 5'-GTG BTA TGC 3'-CAC TAT ACG | | 27.5 | 27.0 [−0.5] | 32.5 [+5.0] | 38.5 [+11.0] |
| B7 D2 | 5'-GTG ATB TGC 3'-CAC TAT ACG | | 27.5 | 28.0 [+0.5] | 34.5 [+7.0] | 41.5 [+14.0] |
| B10 D2 | 5'-GTG BTB TGC 3'-CAC TAT ACG | | 27.5 | 26.5 [−0.5] | 32.5 [+2.5] | 41.0 [+6.8] |
| D1 B8 | 5'-GTG ATA TGC 3'-CAC TBT ACG | | 27.5 | 27.5 [+0.0] | 34.0 [+6.5] | 39.0 [+11.5] |
| D1 B9 | 5'-GTG ATA TGC 3'-CAC TAT BCG | | 27.5 | 27.5 [+0.0] | 33.0 [+5.5] | 29.5 [+12.0] |
| D1 B11 | 5'-GTG ATA TGC 3'-CAC TBT BCG | | 27.5 | 25.5 [−1.0] | 32.5 [+2.5] | 41.0 [+6.8] |

[a]ΔT$_m$ = change in T$_m$'s relative to unmodified reference duplex; T$_m$'s determined as the maximum of the first derivative of melting curves (A$_{260}$ vs 7) recorded in medium salt buffer ([Na$^+$] = 110 mM, [Cl$^-$] = 100 mM. pH 7.0 (NaH$_2$PO$_4$/Na$_2$HPO$_4$)), using 1.0 μM of each strand. T$_m$'s are averages of at least two measurements within 1.0° C.; A = adenin-9-yl DNA monomer, C = cytosin-1-yl DNA monomer, G = guanin-9-yl DNA monomer, T = thymin-1-yl DNA monomer.
ND = not determined.

TABLE 34

T$_m$-Values of Duplexes Between B6-B11 and Complementary RNA Targets[a]

| | | | | T$_m$ [ΔT$_m$/mod] (° C.) | | |
|---|---|---|---|---|---|---|
| ON | Duplex | B = | T | 124W | 124X | 124Y |
| B6 R2 | 5'-GTG BTA TGC 3'-CAC UAU ACG | | 26.0 | 27.0 [+1.0] | 25.0 [−1.0] | 27.5 [+1.5] |
| B7 R2 | 5'-GTG ATB TGC 3'-CAC UAU ACG | | 26.0 | 27.0 [+1.0] | 27.0 [+1.0] | 31.0 [+5.0] |
| B10 R2 | 5'-GTG BTB TGC 3'-CAC UAU ACG | | 26.0 | 27.5 [+0.8] | 24.5 [−0.8] | 30.5 [+2.3] |
| R1 B8 | 5'-GUG AUA UGC 3'-CAC TBT ACG | | 26.0 | 25.5 [−0.5] | 24.0 [−2.0] | 27.0 [+1.0] |
| R1 B9 | 5'-GUG AUA UGC 3'-CAC TAT BCG | | 26.0 | 28.0 [+2.0] | 27.0 [+1.0] | 31.0 [+5.0] |

TABLE 34-continued $T_m$-Values of Duplexes Between B6-B11 and Complementary RNA Targets[a]

| ON | Duplex | B = | T | 124W | 124X | 124Y |
|---|---|---|---|---|---|---|
| R1 | 5'-GUG AUA | | 26.0 | 28.0 | 24.5 | 31.5 |
| B11 | UGC | | | [+1.0] | [-0.8] | [+2.8] |
| | 3'-CAC TBT | | | | | |
| | BCG | | | | | |

[a]For conditions of thermal denaturation experiments, see Table 33.

The Watson-Crick specificity of single-stranded probes modified with monomers 124W, 124X and 124Y (B8-series) was evaluated using DNA (Table 35) or RNA targets (Table 36) that contain mismatched nucleobases opposite to the modification sites. All monomers show excellent discrimination in terms of $T_m$.

TABLE 35

Discrimination of Mismatched DNA Targets By Probes Modified with Monomers 124W-Y[a]

DNA: 5'-GTG ABA TGC

| | | | $T_m$ [° C.] | $\Delta T_m$ [° C.] | | |
|---|---|---|---|---|---|---|
| ON | Sequence | B = | T | A | C | G |
| D2 | 3'-CAC TAT ACG | | 27.5 | -21.0 | -16.5 | -7.5 |
| 124W8 | 3'-CAC T124WT ACG | | 27.5 | -20.0 | -17.0 | -16.0 |
| 124X8 | 3'-CAC T124XT ACG | | 34.0 | -15.5 | -7.0 | -14.5 |
| 124Y8 | 3'-CAC T124YT ACG | | 39.0 | -21.0 | -11.0 | -13.5 |

[a]For conditions of thermal denaturation experiments, see Table 33 above. $T_m$-values of fully matched duplexes are shown in bold. $\Delta T_m$ = change in $T_m$ relative to fully matched DNA:DNA duplex.

TABLE 36

Discrimination of Mismatched RNA Targets by Probes Modified with Monomers 124W-Y.[a]

RNA: 5'-GUG ABA UGC

| | | | $T_m$ [° C.] | $\Delta T_m$ [° C.] | | |
|---|---|---|---|---|---|---|
| ON | Sequence | B = | T | A | C | G |
| D1 | 3'-CAC TAT ACG | | 26.0 | -16.0 | -15.5 | -11.0 |
| 124W8 | 3'-CAC T124WT ACG | | 25.5 | -13.5 | -13.0 | -11.5 |
| 124X8 | 3'-CAC T124XT ACG | | 24.0 | -10.5 | -8.0 | -10.0 |
| 124Y8 | 3'-CAC T124YT ACG | | 27.0 | -11.0 | -11.0 | -8.5 |

[a]For conditions of thermal denaturation experiments, see Table 33 above. $T_m$-values of fully matched duplexes are shown in bold. $\Delta T_m$ = change in $T_m$ relative to fully matched RNA:DNA duplex.

The specificity of doubly-modified single-stranded probes against centrally mismatched DNA targets was also evaluated (Table 37). Decreased mismatch discrimination compared to unmodified reference strand D1 was observed.

TABLE 37

Discrimination of Mismatched DNA Targets by Probes Modified with Monomers 124X/Y[a]

DNA: 3'-CAC TBT ACG

| | | | $T_m$ [° C.] | $\Delta T_m$ [° C.] | | |
|---|---|---|---|---|---|---|
| ON | Sequence | B = | A | T | C | G |
| D1 | 5'-GTG ATA TGC | | 27.5 | -16.5 | -16.5 | -8.0 |
| 124X10 | 5'-GTG 124XT124X TGC | | 32.5 | +2.0 | +2.0 | +0.5 |
| 124Y10 | 5'-GTG 124YT124Y TGC | | 41.0 | -2.0 | -5.0 | -2.0 |

[a]For conditions of thermal denaturation experiments, see Table 33 above. $T_m$-values of fully matched duplexes are shown in bold. $\Delta T_m$ = change in $T_m$ relative to fully matched DNA:DNA duplex. ND = not determined Absorption maxima in the 300-400 nm region for single-stranded probes modified with monomers 124X and 124Y in the presence or absence of complementary DNA/RNA targets are given below (Table 38).

TABLE 38

Absorption Maxima in The 300-400 Nm Region for Single-Stranded Probes Modified with Monomers 124X And 124Y in The Presence or Absence of Complementary DNA/RNA Targets.[a]

$\lambda_{max}[\Delta\lambda_{max}]$ (nm)

| | | | 124X | | | 124Y | | |
|---|---|---|---|---|---|---|---|---|
| ON | Sequence | B = | ss | +DNA | +RNA | ss | +DNA | +RNA |
| B6 | 5'-GTG BTA TGC | | 348 | 350 [+2] | 350 [+2] | 349 | 352 [+3] | 351 [+2] |
| B7 | 5'-GTG ATB TGC | | 348 | 350 [+2] | 349 [+1] | 349 | 353 [+4] | 351 [+2] |
| B10 | 5'-GTG BTB TGC | | 347 | 349 [+2] | 348 [+1] | 349 | 351 [+2] | 351 [+2] |
| B8 | 3'-CAC TBT ACG | | 348 | 350 [+2] | 348 [+0] | 347 | 353 [+6] | 352 [+5] |

TABLE 38-continued

Absorption Maxima in The 300-400 Nm Region for Single-Stranded Probes Modified with Monomers 124X And 124Y in The Presence or Absence of Complementary DNA/RNA Targets.[a]

| ON Sequence | B = | 124X | | | 124Y | | |
|---|---|---|---|---|---|---|---|
| | | ss | +DNA | +RNA | ss | +DNA | +RNA |
| B9 3'-CAC TAT BCG | | 348 | 350 [+2] | 350 [+2] | 350 | 351 [+1] | 350 [+0] |
| B11 3'-CAC TBT BCG | | 348 | 350 [+2] | 348 [+0] | 348 | 352 [+4] | 353 [+5] |

$\lambda_{max}[\Delta\lambda_{max}]$ (nm)

[a]Measurements were performed using a spectrophotometer and quartz optical cells with a 1.0 cm path length. Buffer conditions are as for thermal denaturation experiments.

General Protocol for Coupling Between 1 and Phenols (ArOH) to Prepare 72W/72X (Description for ~1.33 mmol Scale):

The appropriate phenol and 2,2'-anhydrouridine 70 were placed in a sealed pressure tube (specific quantities of substrates and reagents given below) and heated (165° C. for 72W; 175° C. for 72X) until analytical TLC indicated full conversion (~2 h). The resulting crude was purified by silica gel column chromatography (2-4% MeOH in CH$_2$Cl$_2$, v/v) to afford nucleoside 72W/72X (yields specified below).

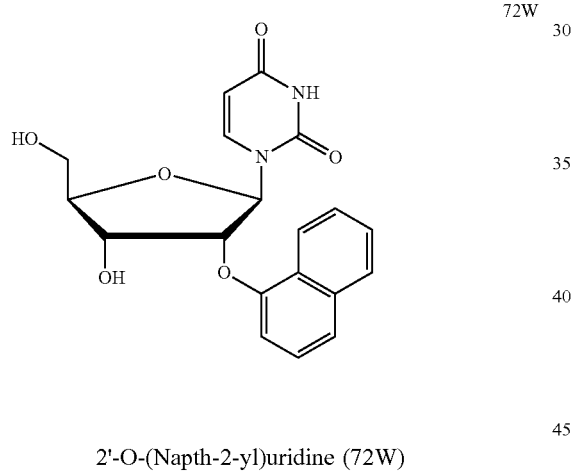

2'-O-(Napth-2-yl)uridine (72W)

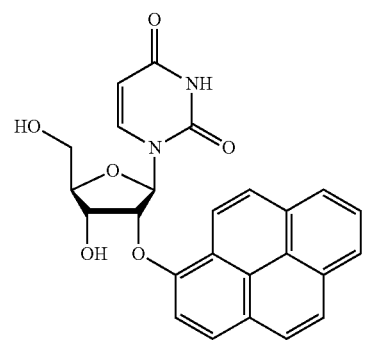

2'-O-(Pyren-1-yl)uridine (72X)

A mixture of 2,2'-anhydrouridine 70 (1.00 g, 4.42 mmol) and 2-napthol (2.40 g, 22.1 mmol) were reacted and purified as described above to afford nucleoside 72W (0.41 g, 25%) as a light brown solid. R$_f$: 0.4 (10% MeOH in CH$_2$Cl$_2$, v/v); MALDI-HRMS m/z 393.1039 ([M+Na]$^+$, C$_{19}$H$_{18}$N$_2$O$_6$.Na$^+$, Calc. 393.1057); $^1$H NMR (DMSO-d$_6$) δ 11.34 (s, 1H, ex, NH), 8.03 (1H, d, J=8.1 Hz, H6), 7.82-7.85 (ap d, 2H, Nap), 7.73-7.75 (1H, d, J=8.3 Hz, Nap), 7.44-7.48 (ap t, 1H, Nap), 7.41 (d, 1H, J=2.5 Hz, Nap), 7.34-7.37 (ap t, 1H, Nap), 7.23-7.25 (dd, 1H, J=9.1 Hz, J=2.5 Hz, Nap), 6.14 (d, 1H, J=4.9 Hz, H1'), 5.68 (d, 1H, J=8.1 Hz, H5), 5.46 (d, 1H, ex, J=6.4 Hz, 3'-OH), 5.25 (t, 1H, ex, J=5.2 Hz, 5'-OH), 5.02 (ap t, 1H, H2'), 4.43-4.46 (m, 1H, H3'), 4.02-4.05 (m, 1H, H4'), 3.74-3.78 (m, 1H, H5'), 3.65-3.69 (m, 1H, H5'); $^{13}$C NMR (DMSO-d$_6$) δ 162.9, 155.4, 150.5, 140.4 (C6), 133.9, 129.2 (Nap), 128.7, 127.4 (Nap), 126.6 (Nap), 126.4 (Nap), 123.8 (Nap), 118.9 (Nap), 108.9 (Nap), 102.0 (C5), 86.4 (C1'), 85.2 (C4'), 79.3 (C2'), 68.2 (C3'), 60.4 (C5').

A mixture of 2,2'-anhydrouridine 70 (0.30 g, 1.33 mmol) and 1-pyrenol[19] (0.86 g, 3.97 mmol) were reacted and purified as described above to afford nucleoside 72X (0.26 g, 44%) as a pale yellow solid. R$_f$: 0.4 (10% MeOH in CH$_2$Cl$_2$, v/v); MALDI-HRMS m/z 467.1217 ([M+Na]$^+$, C$_{25}$H$_{20}$N$_2$O$_6$.Na$^+$, Calc. 467.1214); $^1$H NMR (DMSO-d$_6$) δ 11.36 (s, 1H, ex, NH), 8.45 (d, 1H, J=9.3 Hz, Py), 8.20-8.24 (m, 3H, Py), 8.14 (d, 1H, J=9.3 Hz, Py), 7.99-8.09 (m, 4H, H6, Py), 7.86 (1H, d, J=8.5 Hz, Py), 6.35 (d, 1H, J=4.6 Hz, H1'), 5.68 (d, 1H, J=8.2 Hz, H5), 5.63 (br s, 1H, ex, 3'-OH), 5.30 (br s, 1H, ex, 5'-OH), 5.22-5.25 (ap t, 1H, H2'), 4.55-4.56 (m, 1H, H3'), 4.19-4.21 (m, 1H, H4'), 3.81-3.84 (ap d, 1H, H5'), 3.72-3.75 (ap d, 1H, H5'); $^{13}$C NMR (DMSO-d$_6$) δ 162.9, 151.7, 150.5, 140.3 (C6), 131.0, 130.9, 127.1 (Py), 126.4 (Py), 125.6 (Py), 125.2, 125.0 (Py), 124.8 (Py), 124.5 (Py), 124.3 (Py), 123.9, 121.1 (Py), 120.1, 111.9 (Py), 102.0 (C5), 86.6 (C1'), 85.4 (C4'), 80.9 (C2'), 68.5 (C3'), 60.4 (C5').

General Protocol for Coupling Between 1 and Arylmethyl Alcohol (ArCH$_2$OH) for the Preparation of 72Y/72Z (Description for ~44.2 mmol Scale):

The appropriate aromatic alcohol (ArCH$_2$OH), NaHCO$_3$ and 1.0M BH$_3$ in THF were placed in a pressure tube, suspended in anhydrous DMSO and stirred under an argon atmosphere at rt until effervescence ceased (~10 min). At this point, 2,2'-anhydrouridine 70 was added (specific quantities of substrates and reagents given below), the pressure tube was purged with argon and sealed, and the reaction was heated at ~160° C. until analytical TLC indicated full conversion (~3 h). At this point, the reaction mixture was poured into water (200 mL), stirred for 30 min and diluted with EtOAc (500 mL). The organic phase was washed with water (4×200 mL), evaporated to dryness, and the resulting crude purified by silica gel column chromatography (2-4%, MeOH in CH$_2$Cl$_2$, v/v) to afford a residue, which was precipitated from cold acetone to obtain nucleosides 72Y/72Z (yields specified below).

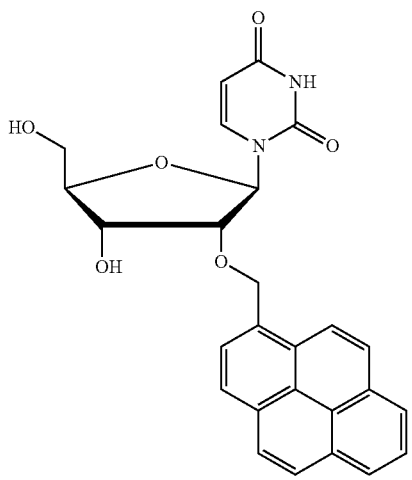

2'-O-(Pyren-1-yl-methyl)uridine (72Y)

2,2'-Anhydrouridine 70 (10.00 g, 44.2 mmol), pyren-1-ylmethanol (20.5 g, 88.4 mmol), NaHCO$_3$ (0.73 g. 8.80 mmol), 1.0 M BH$_3$ in THF (24.5 mL, 22.0 mmol) and anhydrous DMSO (40 mL) were mixed, reacted, worked up, and purified as described above to afford nucleoside 72Y (5.04 g, 25%) as a white solid. R$_f$: 0.4 (10% MeOH in CH$_2$Cl$_2$, v/v); MALDI-HRMS m/z 458.1480 ([M]$^+$, C$_{26}$H$_{22}$N$_2$O$_6$$^+$, Calc. 458.1472); $^1$H NMR (DMSO-d$_6$): δ 11.29 (s, 1H, ex, NH), 8.37-8.39 (d, 1H, J=9.3 Hz, Py), 8.29-8.31 (m, 2H, Py), 8.24-8.26 (d, 1H, J=7.7 Hz, Py), 8.17-8.19 (m, 3H, Py), 8.06-8.12 (m, 2H, Py), 7.82 (d, 1H, J=8.4 Hz, H6), 6.04 (d, 1H, J=5.1 Hz, H1'), 5.43-5.50 (m, 2H, H5, CH$_2$Py), 5.37 (d, 1H, ex, J=5.7 Hz, 3'-OH), 5.28-5.30 (d, 1H, J=12.0 Hz, CH$_2$Py), 5.11 (t, 1H, ex, J=4.9 Hz, 5'-OH), 4.26-4.31 (m, 1H, H3'), 4.18-4.21 (m, 1H, H2'), 3.96-3.97 (m, 1H, H4'), 3.64-3.68 (m, 1H, H5'), 3.59-3.62 (m, 1H, H5'); $^{13}$C NMR (DMSO-d$_6$) δ 162.9, 150.6, 140.1 (C6), 131.4, 130.7, 130.2, 128.7, 127.4 (Py), 127.3 (Py), 127.0 (Py), 126.2 (Py), 125.3 (Py), 124.5 (Py), 124.0 (Py), 123.8, 123.5 (Py), 101.7 (C5), 86.2 (C1'), 85.4 (C4'), 80.9 (C2'), 69.8 (CH$_2$Py), 68.5 (C3'), 60.6 (C5').

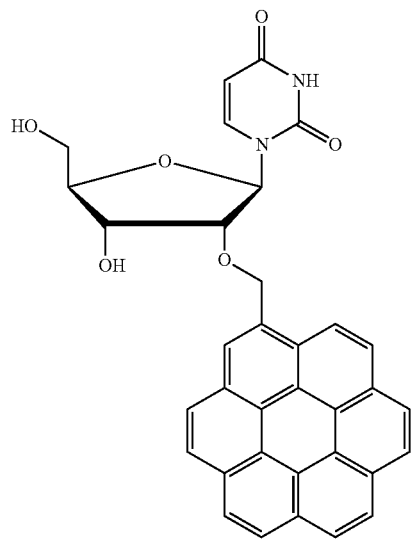

2'-O-(Coronen-1-yl-methyl)uridine (72Z)

2,2'-Anhydrouridine 70 (1.40 g, 6.19 mmol), coronen-1-ylmethanol (4.08 g, 12.4 mmol), NaHCO$_3$ (0.104 g. 1.24 mmol), 1.0 M BH$_3$ in THF (3.5 mL, 3.1 mmol) and anhydrous DMSO (40 mL) were mixed, reacted, worked up and purified as described above with a minor modification. The precipitate that formed upon pouring the reaction mixture into water was collected by filtration, washed with water (3×100 mL) and purified by column chromatography to afford nucleoside 72Z (450 mg, 13%) as a pale yellow solid. R$_f$: 0.4 (10% MeOH in CH$_2$Cl$_2$, v/v); MALDI-HRMS m/z 579.1537 ([M+Na]$^+$, C$_{34}$H$_{24}$N$_2$O$_6$.Na$^+$, Calc. 579.1532); $^1$H NMR (DMSO-d$_6$) δ 11.30 (br d, ex, 1H, J=1.9 Hz, NH), 9.13-9.15 (d, 1H, J=8.7 Hz, Cor), 8.93-9.03 (m, 10H, Cor), 7.82 (d, 1H, J=8.0 Hz, H6), 6.18 (d, 1H, J=4.9 Hz, H1'), 5.85-5.88 (d, 1H, J=12.1 Hz, CH$_2$Cor), 5.67-5.69 (d, 1H, J=12.1 Hz, CH$_2$Cor), 5.52 (d, 1H, ex, J=5.5 Hz, 3'-OH), 5.38 (dd, 1H, J=8.0 Hz, 1.9 Hz, H5), 5.11 (ap t, 1H, ex, 5'-OH), 4.37-4.43 (m, 2H, H2', H3'), 4.03-4.06 (m, 1H, H4'), 3.63-3.71 (m, 2H, H5'); $^{13}$C NMR (DMSO-d$_6$) δ 162.9, 150.6, 140.1 (C6), 132.1, 128.2, 128.1, 127.9, 127.4, 126.5, 126.23 (Cor), 126.20 (Cor), 126.1 (Cor), 126.0 (Cor), 122.5 (Cor), 121.8, 121.5, 121.4, 121.23, 121.17, 101.7 (C5), 86.3 (C1'), 85.5 (C4'), 81.1 (C2'), 70.7 (CH$_2$Cor), 68.6 (C3'), 60.6 (C5'). General DMTr-Protection Protocol for the Preparation of 74W-74Z (Description for ~2.2 mmol Scale):

The appropriate nucleoside 72 (specific quantities given below) was co-evaporated twice with anhydrous pyridine (15 mL) and redissolved in anhydrous pyridine. To this was added 4,4'-dimethoxytritylchloride (DMTrCl) and N,N-dimethyl-4-aminopyridine (DMAP), and the reaction mixture was stirred at rt until TLC indicated complete conversion (~14 h). The reaction mixture was diluted with CH$_2$Cl$_2$ (70 mL) and the organic phase sequentially washed with water (2×70 mL) and sat. aq. NaHCO$_3$ (2×100 mL). The organic phase was evaporated to near dryness and the resulting crude co-evaporated with absolute EtOH and toluene (2:1, v/v, 3×6 mL) and purified by silica gel column chromatography (0-5%, MeOH in CH$_2$Cl$_2$, v/v) to afford nucleoside 74 (yields specified below).

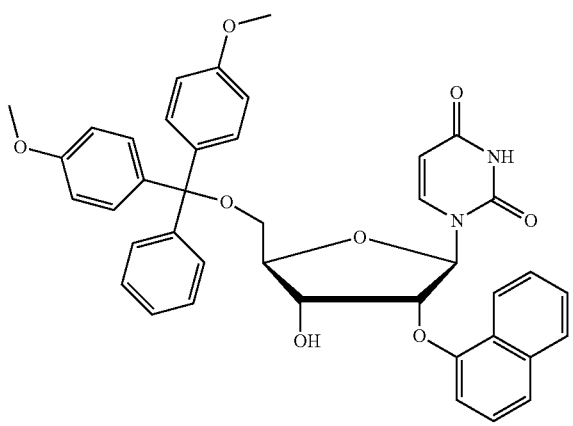

2'-O-(Napth-2-yl)-5'-O-(4,4'-dimethoxytrityl)uridine
(74W)

Nucleoside 72W (150 mg, 0.40 mmol), DMTrCl (240 mg, 0.60 mmol) and DMAP (~6 mg) in anhydrous pyridine (7 mL) were mixed, reacted, worked up and purified as described above to afford nucleoside 74W (120 mg, 47%) as a pale yellow foam. $R_f$: 0.6 (5%, MeOH in $CH_2Cl_2$, v/v); MALDI-HRMS m/z 695.2379 ([M+Na]$^+$, $C_{40}H_{36}N_2O_8$·Na$^+$, Calc. 695.2364); $^1$H NMR (DMSO-d$_6$) δ 11.40 (d, 1H, ex, J=2.1 Hz, NH), 7.83-7.86 (m, 3H, H6, Nap), 7.68 (d, 1H, J=8.2 Hz, Nap), 7.24-7.45 (m, 13H, DMTr, Nap), 6.90-6.92 (d, 4H, J=7.1 Hz, DMTr), 6.06 (d, 1H, J=3.2 Hz, H1'), 5.51 (d, 1H, ex, J=7.1 Hz, 3'-OH), 5.38-5.40 (m, 1H, H5), 5.12-5.14 (m, 1H, H2'), 4.51-4.55 (m, 1H, H3'), 4.14-4.17 (m, 1H, H4'), 3.75 (s, 6H, 2×CH$_3$O), 3.32-3.41 (m, 2H, H5'); $^{13}$C NMR (DMSO-d$_6$) δ 162.9, 158.1, 155.5, 150.3, 144.6, 140.6 (C6), 135.4, 135.2, 133.9, 129.8 (Ar), 129.1 (Nap), 128.8, 127.9 (Ar), 127.7 (Ar), 127.5 (Nap), 126.8 (Ar), 126.6 (Nap), 126.4 (Ar), 123.8 (Ar), 119.0 (Ar), 113.2 (Ar), 109.0 (Ar), 101.8 (C5), 87.6 (C1'), 85.9, 82.6 (C4'), 79.1 (C2'), 68.5 (C3'), 62.7 (C5'), 55.0 (CH$_3$O).

74X

2'-O-(Pyren-1-yl)-5'-O-(4,4'-dimethoxytrityl)uridine
(74X)

Nucleoside 72X (230 mg, 0.52 mmol), DMTrCl (0.30 g, 0.78 mmol) and DMAP (~9 mg) in anhydrous pyridine (8 mL) were mixed, reacted, worked up and purified as described above to afford nucleoside 74X (0.30 g, 78%) as a light yellow foam. $R_f$: 0.6 (5%, MeOH in $CH_2Cl_2$, v/v); MALDI-HRMS m/z 769.2504 ([M+Na]$^+$, $C_{46}H_{38}N_2O_8$·Na$^+$, Calc. 769.2520); $^1$H NMR (DMSO-d$_6$): δ 11.32 (s, 1H, ex, NH), 8.49 (d, 1H, J=9.2 Hz, Py), 8.20-8.24 (m, 3H, Py), 8.14 (d, 1H, J=9.2 Hz, Py), 8.08-8.10 (d, 1H, J=9.1 Hz, Py), 7.99-8.04 (m, 2H, Py), 7.86-7.89 (m, 2H, H6, Py), 7.43-7.45 (m, 2H, DMTr), 7.24-7.36 (m, 7H, DMTr), 6.90-6.92 (m, 4H, DMTr), 6.25 (d, 1H, J=3.2 Hz, H1'), 5.69 (d, 1H, ex, J=6.8 Hz, 3'-OH), 5.38 (d, 1H, J=8.2 Hz, H5), 5.35-5.37 (m, 1H, H2'), 4.61-4.65 (m, 1H, H3'), 4.34-4.37 (m, 1H, H4'), 3.74 (s, 6H, 2×CH$_3$O), 3.46-3.50 (m, 1H, H5'), 3.38-3.41 (m, 1H, H5'); $^{13}$C NMR (DMSO-d$_6$) δ 162.9, 158.1, 151.7, 150.3, 144.6, 140.5 (C6), 135.4, 135.1, 131.1, 131.0, 129.78 (DMTr), 129.76 (DMTr), 127.9 (DMTr), 127.1 (Py), 126.8 (DMTr), 126.4 (Py), 125.6 (Py), 125.3, 125.1 (Py), 124.9, 124.5 (Py), 124.3 (Py), 124.0, 121.2 (Py), 120.1, 113.2 (DMTr), 112.3 (Py), 101.7 (C5), 87.8 (C1'), 85.9, 82.7 (C4'), 80.7 (C2'), 68.7 (C3'), 62.7 (C5'), 55.0 (CH$_3$O).

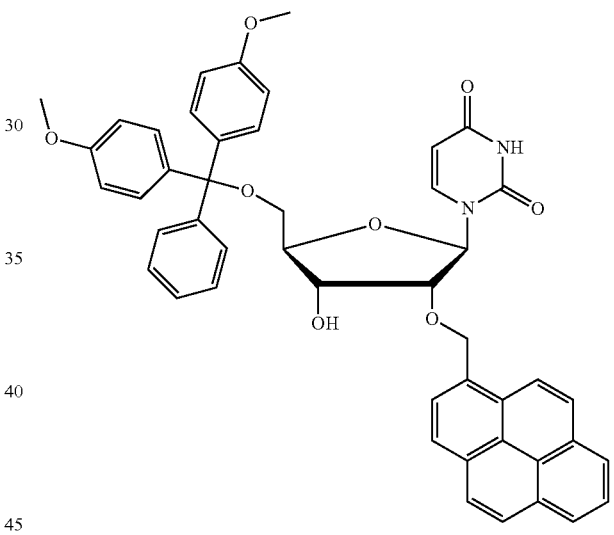

2'-O-(Pyren-1-yl-methyl)-5'-O-(4,4'-dimethoxytrityl)uridine (74Y)

Nucleoside 72Y (1.02 g, 2.20 mmol), DMTrCl (1.29 g, 3.30 mmol) and DMAP (~18 mg) in anhydrous pyridine (20 mL) were mixed, reacted, worked up and purified as described above to afford 74Y(1.20 g, 72%) as pale yellow foam. $R_f$: 0.6 (5%, MeOH in $CH_2Cl_2$, v/v); MALDI-HRMS m/z 783.2698 ([M+Na]$^+$, $C_{47}H_{40}N_2O_8$·Na$^+$, Calc. 783.2677); $^1$H NMR (DMSO-d$_6$) δ 11.36 (d, 1H, ex, J=1.9 Hz, NH), 8.41-8.43 (d, 1H, J=9.3 Hz, Py), 8.30-8.32 (m, 2H, Py), 8.14-8.25 (m, 5H, Py), 8.07-8.10 (t, 1H, J=7.7 Hz, Py), 7.63 (d, 1H, J=8.1 Hz, H6), 7.17-7.34 (m, 9H, DMTr), 6.82-6.86 (m, 4H, DMTr), 6.02 (d, 1H, J=3.9 Hz, H1'), 5.48-5.50 (d, 1H, J=12.1 Hz, CH$_2$Py), 5.45 (d, 1H, ex, J=6.3 Hz, 3'-OH), 5.36-5.38 (d, 1H, J=12.1 Hz, CH$_2$Py), 5.13 (dd, 1H, J=8.1 Hz, 1.9 Hz, H5), 4.34-4.38 (m, 1H, H3'), 4.21-4.24 (m, 1H, H2'), 4.05-4.09 (m, 1H, H4'), 3.71 (s, 3H, CH$_3$O), 3.69 (s, 3H, CH$_3$O), 3.20-3.24 (m, 2H, H5'); $^{13}$C NMR (DMSO-d$_6$) δ 162.8, 158.08, 158.06, 150.4, 144.5, 140.0 (C6), 135.3, 135.0, 131.3, 130.7, 130.2, 129.71 (DMTr), 129.66 (DMTr), 128.7, 127.8 (DMTr), 127.6 (DMTr), 127.4 (Py), 127.3 (Py), 127.0 (Py), 126.7 (DMTr), 126.2 (Py), 125.3 (Py), 124.5 (Py), 124.0, 123.8, 123.4 (Py), 113.20 (DMTr), 113.17 (DMTr), 101.4 (C5), 87.1 (C1'), 85.9, 83.1 (C4'), 80.6 (C2'), 69.9 (CH$_2$Py), 68.7 (C3'), 62.8 (C5'), 55.0 (CH$_3$O).

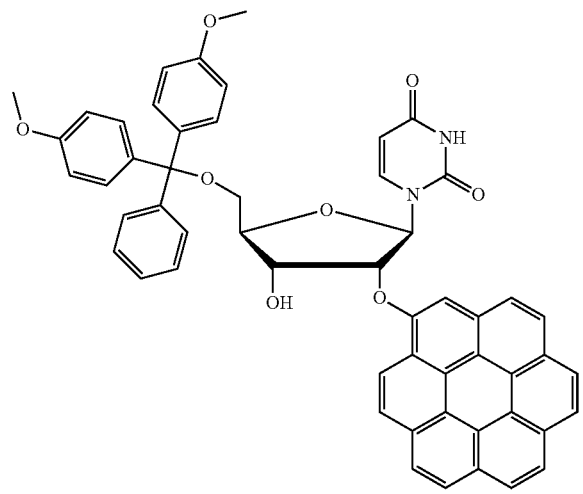

74Z

2'-O-(Coronen-1-yl-methyl)-5'-O-(4,4'-dimethoxytrityl)uridine (74Z)

Nucleoside 72Z (250 mg, 0.45 mmol), DMTrCl (262 mg, 0.67 mmol) and DMAP (~15 mg) in anhydrous pyridine (6 mL) were mixed, reacted, worked up and purified as described above to afford nucleoside 74Z (245 mg 63%) as a yellow foam. R$_f$: 0.6 (5%, MeOH in CH$_2$Cl$_2$, v/v); MALDI-HRMS m/z 881.2824 ([M+Na]$^+$, C$_{55}$H$_{42}$N$_2$O$_8$·Na$^+$, Calc. 881.2839); $^1$H NMR (DMSO-d$_6$) δ 11.40 (br d, 1H, ex, J=1.9 Hz, NH), 9.14-9.16 (d, 1H, J=8.8 Hz, Cor), 8.96-9.02 (m, 9H, Cor), 8.88-8.90 (d, 1H, J=8.5 Hz, Cor), 7.63 (d, 1H, J=8.1 Hz, H6), 7.29-7.31 (d, 2H, J=7.4 Hz, DMTr), 7.11-7.22 (m, 7H, DMTr), 6.74-6.79 (m, 4H, DMTr), 6.18 (d, 1H, J=4.1 Hz, H1'), 5.87-5.90 (d, 1H, J=12.6 Hz, CH$_2$Cor), 5.75-5.78 (d, 1H, J=12.6 Hz, CH$_2$Cor), 5.59 (d, 1H, ex, J=6.3 Hz, 3'-OH), 5.06 (dd, 1H, J=8.1 Hz, 1.9 Hz, H5), 4.46-4.50 (m, 1H, H3'), 4.40-4.43 (m, 1H, H2'), 4.15-4.18 (m, 1H, H4'), 3.63 (s, 3H, CH$_3$O), 3.58 (s, 3H, CH$_3$O), 3.32-3.34 (m, 1H, H5'), 3.25-3.27 (m, 1H, H5'); $^{13}$C NMR (DMSO-d$_6$) δ 162.8, 158.02, 157.97, 150.4, 144.4, 140.0 (C6), 135.3, 135.0, 132.2, 129.7 (DMTr), 129.6 (DMTr), 128.3, 128.2, 128.0, 127.7 (DMTr), 127.59 (DMTr), 127.56, 126.61 (DMTr), 126.59, 126.41 (Cor), 126.36 (Cor), 126.3 (Cor), 126.23 (Cor), 126.21, 126.19, 126.1 (Cor), 122.6 (Cor), 121.9, 121.6, 121.5, 121.4, 121.35, 121.28, 113.13 (DMTr), 113.09 (DMTr), 101.4 (C5), 87.1 (C1'), 85.9, 83.2 (C4'), 80.7 (C2'), 70.7 (CH$_2$Cor), 68.8 (C3'), 62.8 (C5'), 54.9 (CH$_3$O), 54.8 (CH$_3$O).

General Phosphitylation Protocol for the Preparation of 4W-4Z (Description for ~1 Mmol Scale):

The appropriate nucleoside 74 (specific quantities of substrates and reagents given below) was co-evaporated with anhydrous 1,2-dicholoroethane (4 mL) and redissolved in anhydrous CH$_2$Cl$_2$. To this was added N,N-diisopropylethylamine (DIPEA) and 2-cyanoethyl-N,N-diisopropylchlorophosphoramidite (PCl-reagent) and the reaction mixture was stirred at rt until TLC indicated complete conversion (~3 h), whereupon abs. EtOH (2 mL) and CH$_2$Cl$_2$ (20 mL) were sequentially added to the solution. The organic phase was washed with sat. aq. NaHCO$_3$ (10 mL), evaporated to near dryness, and the resulting residue purified by silica gel column chromatography (40-70% EtOAc in petroleum ether, v/v) to afford the corresponding phosphoramidite 76 (yields specified below).

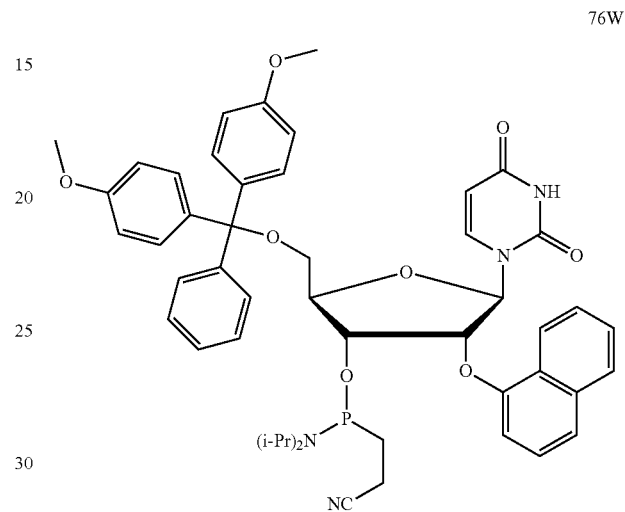

76W

2'-O-(Napth-2-yl)-3'-O—(N,N-diisopropylamino-2-cyanoethoxyphosphinyl)-5'-O-(4,4'-dimethoxytrityl) uridine (76W)

Nucleoside 74W (100 mg, 0.15 mmol), DIPEA (106 µL, 0.59 mmol) and PCl-reagent (66 µL, 0.23 mmol) in anhydrous CH$_2$Cl$_2$ (1.5 mL) were mixed, reacted, worked up and purified as described above to afford phosphoramidite 76W (95 mg, 74%) as a white foam. R$_f$: 0.8 (5% MeOH in CH$_2$Cl$_2$, v/v); MALDI-HRMS m/z 895.3462 ([M+Na]$^+$, C$_{49}$H$_{53}$N$_4$O$_9$P·Na$^+$, Calc. 895.3448); $^{31}$P NMR (CDCl$_3$) δ 151.0, 150.9.

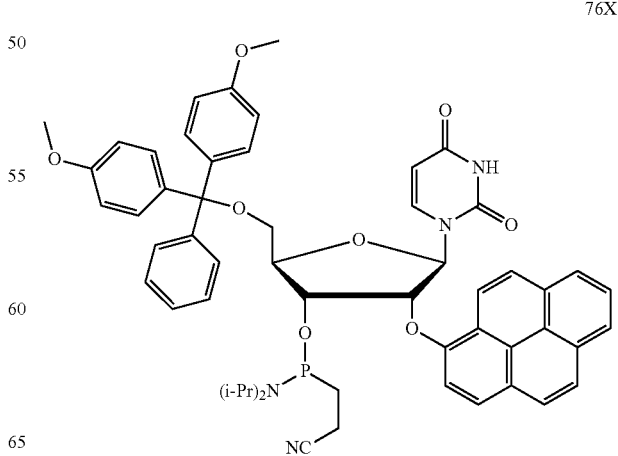

76X

3'-O—(N,N-Diisopropylamino-2-cyanoethoxyphosphinyl)-2'-O-(pyren-1-yl)-5'-O-(4,4'-dimethoxytrityl) uridine (76X)

Nucleoside 74X (0.28 g, 0.38 mmol), DIPEA (268 µL, 1.50 mmol) and PCl-reagent (167 µL, 0.75 mmol) in anhydrous $CH_2Cl_2$ (2.5 mL) were mixed, reacted, worked up and purified as described above to afford phosphoramidite 76X (0.27 g, 76%) as a white foam. $R_f$: 0.8 (5% MeOH in $CH_2Cl_2$, v/v); MALDI-HRMS m/z 969.3608 ([M+Na]$^+$, $C_{55}H_{55}N_4O_9P.Na^+$, Calc. 969.3604); $^{31}P$ NMR (CDCl$_3$) δ 149.8, 149.4.

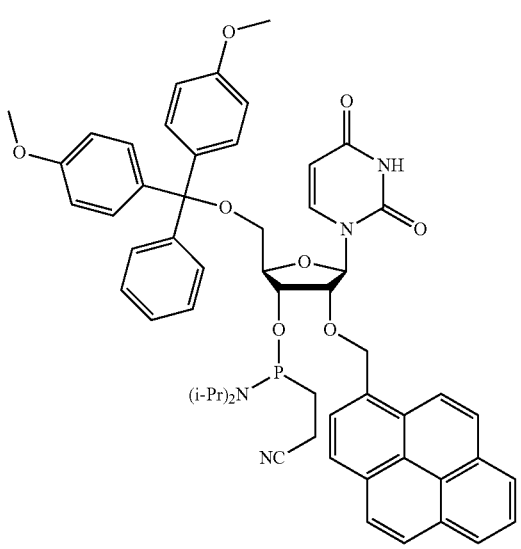

3'-O—(N,N-Diisopropylamino-2-cyanoethoxyphosphinyl)-2'-O-(pyren-1-yl-methyl)-5'-O-(4,4'-dimethoxytrityl)uridine (76Y)

Nucleoside 74Y (0.58 g, 0.76 mmol), DIPEA (0.53 mL, 3.05 mmol) and PCl-reagent (340 µL, 1.53 mmol) in anhydrous $CH_2Cl_2$ (5 mL) were mixed, reacted, worked up and purified as described above to afford phosphoramidite 76Y (0.56 g, 76%) as a white foam. $R_f$: 0.8 (5% MeOH in $CH_2Cl_2$, v/v); MALDI-HRMS m/z 983.3767 ([M+Na]$^+$, $C_{56}H_{57}N_4O_9P.Na^+$, Calc. 983.3761); $^{31}P$ NMR (CDCl$_3$) δ 150.3, 150.2.

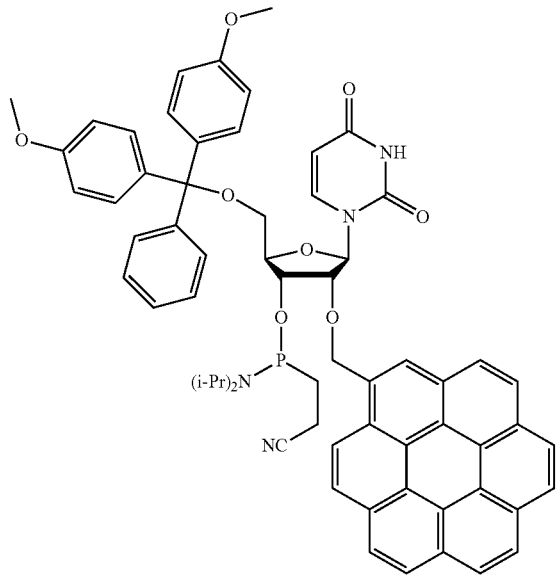

2'-O-(Coronen-1-yl-methyl)-3'-O—(N,N-diisopropylamino-2-cyanoethoxyphosphinyl)-5'-O-(4,4'-dimethoxytrityl)uridine (76Z)

Nucleoside 74Z (240 mg, 0.28 mmol), DIPEA (200 µL, 1.11 mmol) and PCl-reagent (125 µL, 0.56 mmol) in anhydrous $CH_2Cl_2$ (6 mL) were mixed, reacted, worked up and purified as described above to afford phosphoramidite 76Z (230 mg, 78%) as a light yellow foam. $R_f$: 0.8 (5% MeOH in $CH_2Cl_2$, v/v); MALDI-HRMS m/z 1081.3864 ([M+Na]$^+$, $C_{64}H_{59}N_4O_9P.Na^+$, Calc. 1081.3917); $^{31}P$ NMR (CDCl$_3$) δ 150.2.

7-neopentylpyrene-1-ylmethyl alcohol

Pyrene (2.0 g, 9.9 mmol) was added into anhydrous $CH_2Cl_2$ containing a mixture of anhydrous $AlCl_3$ (1.3 g, 9.0 mmol) and 2,2,2-trimethylacetylchloride (0.97 mL, 7.9 mmol) at 0° C. The yellow crude product was purified using silica gel column chromatography to afford 7-(2,2,2-trimethylacetyl)pyrene (1.4 g, 50%) as a bright yellow solid. This intermediate was then reduced to 7-neopentylpyrene (1.4 g, 98%) in the presence of trifluoroacetic acid (3.6 mL, 49 mmol) and triethylsilane (4.7 mL, 29.0 mmol). $R_f$: 0.8 (10% EtOAc in petroleum ether, v/v). To a stirred solution of 7-neopentylpyrene (0.9 g, 3.3 mmol) and dichloromethylmethylether (0.4 mL, 4.3 mmol) in anhydrous $CH_2Cl_2$ (20 mL) at 0° C. was added a solution of titaniumtetrachloride (0.7 mL, 6.3 mmol). The mixture was poured into a large amount of ice water and extracted with $CH_2Cl_2$. The crude was purified by silica gel column chromatography (40% benzene in petroleum ether, v/v) to afford 7-neopentylpyrene-1-carboxaldehyde (0.9 g, 91%) as a yellow solid. This intermediate was then reduced to 7-neopentylpyrene-1-ylmethylalcohol (0.9 g, 99%) using sodium borohydride (0.1 g, 2.66 mmol) in tetrahydrofuran (50 mL).

6/8-bromopyrene-1-ylmethylalcohol

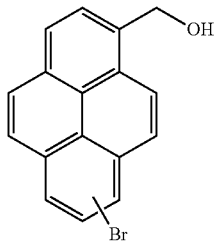

To a solution of 1-bromopyrene (2.6 g, 9.25 mmol) and dichloromethylmethylether (1.08 mL, 12.0 mmol) in anhydrous CH$_2$Cl$_2$ (60 mL) at 0° C. was added a solution of titaniumtetrachloride (1.98 mL, 17.5 mmol). The mixture was poured into a large amount of ice water and extracted with CH$_2$Cl$_2$. The crude was purified by silica gel column chromatography (40% benzene in petroleum ether, v/v) to afford a mixture of 6- and 8-bromopyrene-1-carboxaldehyde (1.4 g, 49%) as a yellow solid. This intermediate was then reduced to a mixture of 6- and 8-bromopyrene-1-ylmethylalcohol (1.4 g, 99%) as using sodium borohydride (0.17 g, 4.53 mmol) in tetrahydrofuran (80 mL).

8-methylpyrene-1-ylmethylalcohol

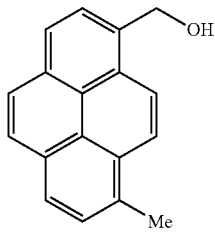 [SMILES: Cc1ccc2ccc3ccc(CO)c4ccc1c2c34]

To a stirred solution of 1-methylpyrene (4.3 g, 19.8 mmol) and dichloromethylmethylether (2.34 mL, 25.8 mmol) in anhydrous CH$_2$Cl$_2$ (150 mL) at 0° C. was added a solution of titaniumtetrachloride (4.26 mL, 37.7 mmol). The mixture was poured into a large amount of ice water and chromatography (40% benzene in petroleum ether, v/v) to afford 8-methylpyrene-1-carboxaldehyde (4.0 g, 83%) as a yellow solid. This intermediate was then reduced to 8-methylpyrene-1-ylmethylalcohol (4.0 g, 99%) in the presence of sodium borohydride (0.74 g, 19.6 mmol) in tetrahydrofuran (100 mL).

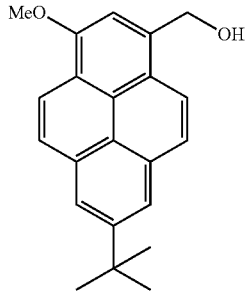 [SMILES: COc1cc(CO)c2ccc3cc(C(C)(C)C)cc4ccc1c2c34]

7-tert-Butyl-3-methoxypyrene-1-ylmethylalcohol 7-tert-butyl-3-methoxypyrene-1-carboxaldehyde (obtained as described in: Yamoto et al. *Organic Preparation and Procedure International.* 1997, 29, 3) was reduced to 7-tert-butyl-3-methoxypyrene-1-ylmethylalcohol (2.1 g, 99%) using sodium borohydride (0.26 g, 6.94 mmol) in tetrahydrofuran (30 mL).

General Protocol for Coupling Between O2,O2'-Anhydronucleoside 70 and Arylmethyl Alcohol (ArCH$_2$OH) for the preparation of 200W-Z (description for ~44.2 mmol scale).

The appropriate aromatic alcohol (ArCH$_2$OH), NaHCO$_3$ and 1.0M BH$_3$ in THF were placed in a pressure tube, suspended in anhydrous DMSO and stirred under an argon atmosphere at room temperature until effervescence ceased (~10 min). At this point, nucleoside 70 was added (specific quantities of substrates and reagents given below), the pressure tube was purged with argon and sealed, and the reaction was heated at ~160° C. until analytical TLC indicated full conversion (~3 h). At this point, the reaction mixture was poured into water (200 mL), stirred for 30 min and diluted with EtOAc (500 mL). The organic phase was washed with water (4×200 mL), evaporated to dryness, and the resulting crude purified by silica gel column chromatography (2-4%, MeOH in CH$_2$Cl$_2$, v/v) to afford a residue, which was precipitated from cold acetone to obtain nucleosides 200 (yields specified below).

2'-O-(7-neopentylpyrene-1-ylmethyl)uridine (200W)

Nucleoside 70 (0.40 g, 1.8 mmol), 7-neopentylpyrene-1-ylmethanol (1.07 g, 3.5 mmol), NaHCO$_3$ (0.03 g. 0.35 mmol), 1.0 M BH$_3$ in THF (0.9 mL, 0.9 mmol) and anhydrous DMSO (3 mL) were mixed, reacted, worked up, and purified as described above to nucleoside 200W (0.18 g, 20%) as a white solid. R$_f$: 0.4 (10% MeOH in CH$_2$Cl$_2$, v/v).

2'-O-(6/8-bromopyrene-1-ylmethyl)uridine (200X)

Nucleoside 70 (0.7 g, 3.1 mmol), 6/8-bromopyrene-1-ylmethanol (1.9 g, 6.2 mmol), NaHCO$_3$ (0.05 g. 0.62 mmol), 1.0 M BH$_3$ in THF (1.6 mL, 1.55 mmol) and anhydrous DMSO (10 mL) were mixed, reacted, worked up, and purified as described above to afford nucleoside 200X (0.28 g, 17%) as a white solid. R$_f$: 0.4 (10% MeOH in CH$_2$Cl$_2$, v/v).

2'-O-(8-methylpyrene-1-ylmethyl)uridine (200Y)

Nucleoside 70 (2.0 g, 8.84 mmol), 8-methylpyrene-1-ylmethanol (4.3 g, 17.7 mmol), NaHCO$_3$ (0.15 g. 1.77 mmol), 1.0 M BH$_3$ in THF (4.9 mL, 4.42 mmol) and anhydrous DMSO (10 mL) were mixed, reacted, worked up, and purified as described above to afford nucleoside 200Y (0.87 g, 20%) as a white solid. R$_f$: 0.4 (10% MeOH in CH$_2$Cl$_2$, v/v).

2'-O-(3-methoxy-7-tert-butylpyrene-1-ylmethyl)uridine (200Z)

Nucleoside 70 (0.36 g, 1.57 mmol), 3-methoxy-7-tertiarbutylypyrene-1-ylmethanol (1.0 g, 3.14 mmol), NaHCO$_3$ (26.0 mg. 0.31 mmol), 1.0 M BH$_3$ in THF (0.8 mL, 0.78 mmol) and anhydrous DMSO (8 mL) were mixed, reacted, worked up, and purified as described above to afford nucleoside 200Z (0.2 g, 21%) as a white solid. R$_f$: 0.4 (10% MeOH in CH$_2$Cl$_2$, v/v).

General DMTr-Protection Protocol for the Preparation of 202V-Z (Description for ~2.2 Mmol Scale).

The appropriate nucleoside 200 (specific quantities of substrates and reagents given below) was co-evaporated twice with anhydrous pyridine (15 mL) and redissolved in anhydrous pyridine. To this was added 4,4'-dimethoxytrityl-chloride (DMTrCl) and N,N-dimethyl-4-aminopyridine (DMAP), and the reaction mixture was stirred at room temperature until TLC indicated complete conversion (~14 h). The reaction mixture was diluted with $CH_2Cl_2$ (70 mL) and the organic phase sequentially washed with water (2×70 mL) and sat. aq. $NaHCO_3$ (2×100 mL). The organic phase was evaporated to near dryness and co-evaporated with absolute EtOH and toluene (2:1, v/v, 3×6 mL) and the resulting crude purified by silica gel column chromatography (0-5%, MeOH in $CH_2Cl_2$, v/v) to afford nucleosides 202 (yields specified below).

5'-O-(4,4'-dimethoxytrityl)-2'-O-(7-neopentylpyrene-1-ylmethyl)uridine (202W)

Nucleoside 200W (0.13 g, 0.25 mmol), DMTrCl (0.14 g, 0.37 mmol) and DMAP (~1 mg) in anhydrous pyridine (3 mL) were mixed, reacted, worked up and purified as described above to afford 202W (0.13 g, 64%) as pale yellow foam. $R_f$: 0.6 (5%, MeOH in $CH_2Cl_2$, v/v).

5'-O-(4,4'-dimethoxytrityl)-2'-O-(6/8-bromopyrene-1-ylmethyl)uridine (202X)

Nucleoside 200X (0.21 g, 0.39 mmol), DMTrCl (0.23 g, 0.58 mmol) and DMAP (~2 mg) in anhydrous pyridine (7 mL) were mixed, reacted, worked up and purified as described above to afford 202X (0.28 g, 85%) as pale yellow foam. $R_f$: 0.6 (5%, MeOH in $CH_2Cl_2$, v/v).

5'-O-(4,4'-dimethoxytrityl)-2'-O-(8-methylpyrene-1-ylmethyl)uridine (202Y)

Nucleoside 200Y (0.7 g, 1.48 mmol), DMTrCl (0.86 g, 2.20 mmol) and DMAP (~4 mg) in anhydrous pyridine (10 mL) were mixed, reacted, worked up and purified as described above to afford 202Y (0.9 g, 78%) as pale yellow foam. $R_f$: 0.6 (5%, MeOH in $CH_2Cl_2$, v/v).

5'-O-(4,4'-dimethoxytrityl)-2'-O-(pyrene-1-ylmethyl)uridine (202Z)

Nucleoside 200Z (0.18 g, 0.33 mmol), DMTrCl (0.19 g, 0.49 mmol) and DMAP (~2 mg) in anhydrous pyridine (7 mL) were mixed, reacted, worked up and purified as described above to afford 202Z (0.2 g, 70%) as pale yellow foam. $R_f$: 0.6 (5%, MeOH in $CH_2Cl_2$, v/v).

General Phosphitylation Protocol for the Preparation of 204V-Z (Description for ~1 Mmol Scale).

The appropriate nucleoside 202 (specific quantities of substrates and reagents are given below) was co-evaporated with anhydrous 1,2-dicholoroethane (4 mL) and redissolved in anhydrous $CH_2Cl_2$. To this was added DIPEA and 2-cyanoethyl-N,N-diisopropylchlorophosphoramidite (PCl-reagent) and the reaction mixture was stirred at rt until TLC indicated complete conversion (~3 h), whereupon abs. EtOH (2 mL) and $CH_2Cl_2$ (20 mL) were sequentially added to the solution. The organic phase was washed with sat. aq. $NaHCO_3$ (10 mL), evaporated to near dryness, and the resulting residue purified by silica gel column chromatography (40-70% EtOAc in petroleum ether, v/v) to afford the corresponding phosphoramidite 204 (yields specified below)

5'-O-(4,4'-dimethoxytrityl)-2'-O-(7-neopentylpyrene-1-ylmethyl)uridine-3'-O-(2-cyanoethyl)-N,N-diisopropylphosphoramidite (204W)

Nucleoside 202W (0.11 g, 0.13 mmol), DIPEA (0.1 mL, 0.53 mmol) and PCl-reagent (60 µL, 0.26 mmol) in anhydrous $CH_2Cl_2$ (3 mL) were mixed, reacted, worked up and purified as described above to afford phosphoramidite 204W (0.11 g, 81%) as a white foam. $R_f$: 0.8 (5% MeOH in $CH_2Cl_2$, v/v).

5'-O-(4,4'-dimethoxytrityl)-2'-O-(6/8-bromopyrene-1-ylmethyl)uridine-3'-O-(2-cyanoethyl)-N,N-diisopropylphosphoramidite (204X)

Nucleoside 202X (0.25 g, 0.29 mmol), DIPEA (021 mL, 1.19 mmol) and PCl-reagent (133 µL, 0.59 mmol) in anhydrous $CH_2Cl_2$ (5 mL) were mixed, reacted, worked up and purified as described above to afford phosphoramidite 204X (0.26 g, 82%) as a white foam. $R_f$: 0.8 (5% MeOH in $CH_2Cl_2$, v/v).

5'-O-(4,4'-dimethoxytrityl)-2'-O-(8-methylpyrene-1-ylmethyl)uridine-3'-O-(2-cyanoethyl)-N,N-diisopropylphosphoramidite (204Y)

Nucleoside 202Y (0.65 g, 0846 mmol), DIPEA (0.59 mL, 3.35 mmol) and PCl-reagent (374 µL, 1.77 mmol) in anhydrous $CH_2Cl_2$ (10 mL) were mixed, reacted, worked up and purified as described above to afford phosphoramidite 204Y (0.6 g, 78%) as a white foam. $R_f$: 0.8 (5% MeOH in $CH_2Cl_2$, v/v)

5'-O-(4,4'-dimethoxytrityl)-2'-O-(3-methoxy-7-tertiarybutylpyrene-1-ylmethyl)uridine-3'-O-(2-cyanoethyl)-N,N-diisopropylphosphoramidite (204Z)

Nucleoside 202Z (0.15 g, 0.18 mmol), DIPEA (126 µL, 0.71 mmol) and PCl-reagent (79 µL, 0.35 mmol) in anhydrous $CH_2Cl_2$ (5 mL) were mixed, reacted, worked up and purified as described above to afford phosphoramidite 204Z (0.15 g, 80%) as a white foam. $R_f$: 0.8 (5% MeOH in $CH_2Cl_2$, v/v).

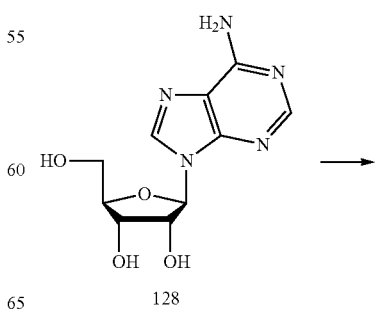

128

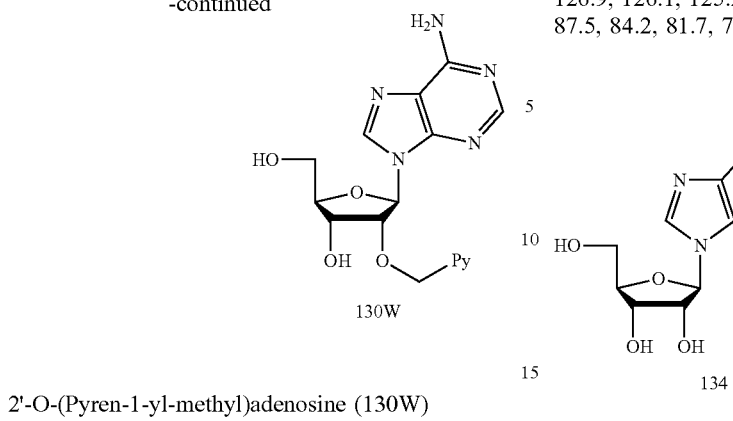

2'-O-(Pyren-1-yl-methyl)adenosine (130W)

An adenosine-functionalized nucleoside 128 (1.60 g, 5.98 mmol), pyren-1-ylmethylchloride (1.0 g, 3.9 mmol), NaH (0.36 g, 14.9 mmol), and anhydrous DMSO (30 mL) were mixed, reacted, worked up, and purified as described above to afford nucleoside 2W (0.48 g, 17%) as a pale yellow solid. $R_f$ 0.29 (10% MeOH in $CH_2Cl_2$, v/v); MALDI-HRMS m/z 504.1649 ([M+Na]$^+$, $C_{27}H_{23}N_5O_4$·Na$^+$, Calcd 504.1642); $^1$HNMR (DMSO-d$_6$) δ 8.32 (s, 1H, adenine), 7.95-8.29 (m, 10H, pyrene, adenine), 7.27 (s, 2H, NH$_2$), 6.14 (d, 1H, H1', J=6.3 Hz), 5.48 (d, 1H, ex, J=5.1 Hz, 3'-OH), 5.39-5.45 (m, 2H, CH$_2$-Py, 5'-OH (ex)), 5.17-5.20 (d, 1H, J=11.7 Hz, CH$_2$Py), 4.81 (t, 1H, J=5.1 Hz, 11.1 Hz, H2'), 4.50-4.54 (m, 1H, H3'), 4.08-4.11 (m, 1H, H4'), 3.68-3.75 (m, 1H, H5'), 3.57-3.65 (m, 1H, H5'); $^{13}$C NMR (DMSO-d$_6$) δ 156.1, 152.3, 148.9, 139.6, 131.2, 130.6, 130.6, 130.1, 128.7, 127.2, 127.2, 127.0, 126.1, 125.2, 125.2, 124.3, 123.8, 123.7, 123.3, 119.3, 86.7, 86.1, 80.8, 69.9, 69.1, 61.5.

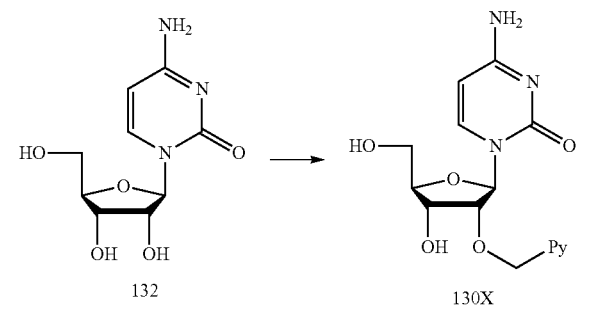

2'-O-(Pyren-1-yl-methyl)cytidine (130X)

Cytidine 132 (10.0 g, 41.1 mmol), pyren-1-ylmethylchloride (6.8 g, 27.1 mmol), NaH (2.47 g, 102.8 mmol), and anhydrous DMSO (150 mL) were mixed, reacted, worked up, and purified as described above to afford nucleoside 130X (3.5 g, 19%) as a pale yellow solid. $R_f$ 0.3 (10% MeOH in $CH_2Cl_2$, v/v); MALDI-HRMS m/z 480.1532 ([M+Na]$^+$, $C_{26}H_{23}N_3O_5$·Na$^+$, Calcd 480.1529); $^1$HNMR (DMSO-d$_6$) δ 8.06-8.49 (m, 9H, Py), 7.90 (d, 1H, cytosine), 7.15 (s, 2H, NH$_2$), 6.08 (d, 1H, H1'), 5.67 (d, 1H, cytosine), 5.41-5.43 (d, 1H, CH2Py), 5.24 (d, 1H, CH$_2$Py), 5.22 (d, 1H, 3'-OH), 5.07-5.11 (m, 1H, 5'-OH), 4.18-4.22 (m, 1H, H3'), 4.06-4.11 (m, 1H, H2'), 3.93-3.95 (m, 1H, H4'), 3.53-3.74 (m, 2H, H5'); $^{13}$C NMR (DMSO-d$_6$) δ 165.6, 155.1, 141.0, 131.6, 130.7, 130.5, 130.2, 128.6, 127.4, 127.3, 127.2, 126.9, 126.1, 125.2, 124.5, 123.9, 123.8, 123.6, 93.8, 89.7, 87.5, 84.2, 81.7, 77.2, 72.9, 69.7, 68.2, 60.1.

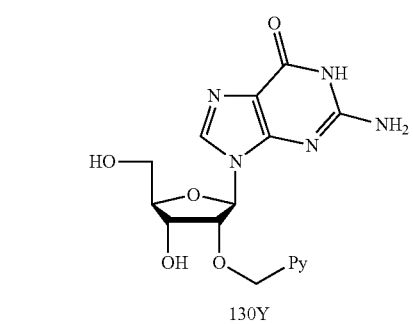

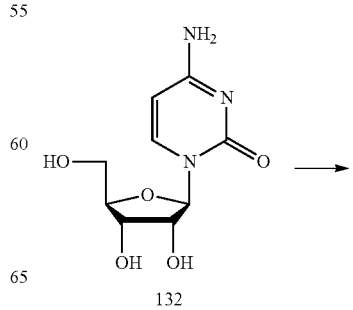

2'-O-(Pyren-1-yl-methyl)guanosine (130Y)

Guanosine 134 (3.0 g, 10.6 mmol), pyren-1-ylmethylchloride (1.86 g, 7.4 mmol), NaH (0.64 g, 26.5 mmol), and anhydrous DMSO (50 mL) were mixed, reacted, worked up, and purified as described above to afford nucleoside 130Y (0.90 g, 17%) as a white solid. $R_f$ 0.29 (10% MeOH in $CH_2Cl_2$, v/v); MALDI-HRMS m/z 520.1608 ([M+Na]$^+$, $C_{27}H_{23}N_5O_5$·Na$^+$, Calcd 520.1591); $^1$HNMR (DMSO-d$_6$) 10.6 (s, 1H, NH), 8.0-8.35 (m, 9H, Py), 7.97 (s, 1H, H7-adenine), 6.37 (s, 2H, NH$_2$), 5.97 (d, 1H, H1'), 5.40-5.43 (dd, 2H, CH$_2$Py), 5.20 (d, 1H, ex, 3'-OH), 5.08 (t, 1H, ex, 5'-OH), 4.61-4.63 (m, 1H, H2'), 4.44-4.46 (m, 1H, H3'), 4.00-4.02 (m, 1H, H4'), 3.60-3.68 (m, 2H, H5'); $^{13}$C NMR (DMSO-d$_6$) δ 156.6, 153.6, 151.1, 135.2, 131.2, 130.6, 130.2, 128.7, 127.3, 127.0, 126.2, 125.2, 125.1, 124.4, 123.8, 123.7, 123.5, 116.7, 86.1, 84.5, 81.3, 69.8, 69.0, 61.3

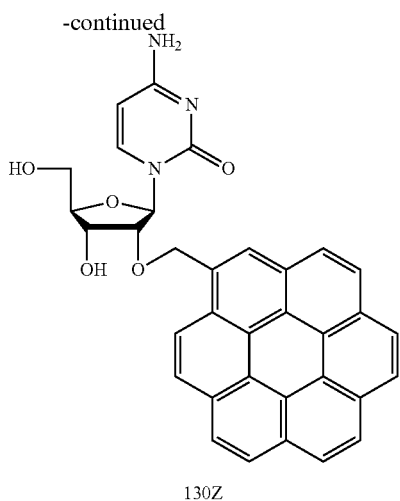

2'-O-(Coronen-1-yl-methyl)cytidine (130Z)

Cytidine 132 (0.70 g, 2.88 mmol), coronen-1-ylmethyl-chloride (0.66 g, 1.99 mmol), NaH (0.17 g, 7.19 mmol), and anhydrous DMSO (20 mL) were mixed, reacted, worked up, and purified as described above to afford nucleoside 130Z (0.16 g, 10%) as a pale yellow solid. $R_f$ 0.3 (10% MeOH in $CH_2Cl_2$, v/v); MALDI-HRMS m/z 578.1679 ([M+Na]$^+$, $C_{34}H_{25}N_3O_5 \cdot Na^+$, Calcd 578.1686); $^1$H-NMR (DMSO-$d_6$) δ 9.01-9.17 (m, 11H, Cor), 7.94 (d, 1H, cytosine), 7.20 (s, 2H, NH$_2$), 6.08 (d, 1H, H1'), 5.85 (d, 1H, cytosine), 5.68-5.78 (m, 2H, CH$_2$Cor), 5.22 (d, 1H, 3'-OH), 5.07-5.11 (m, 1H, 5'-OH), 4.18-4.22 (m, 1H, H3'), 4.13-4.15 (m, 1H, H2'), 3.90-3.93 (m, 1H, H4'), 3.58-3.88 (m, 2H, H5').

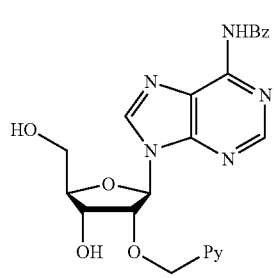

2'-O-(Pyren-1-yl-methyl)-N-benzoyl-adenosine (136W)

Nucleoside 130W (0.40 g, 0.83 mmol) was dried by co-evaporation with pyridine (5 mL) and re-dissolved in anhydrous pyridine (10 mL) followed by addition of trimethylsilyl chloride (0.42 mL, 3.32 mmol). After stirring for 30 min at rt, benzoyl chloride (0.14 mL, 1.25 mmol) was added and the mixture was stirred for additional 5 h. Aqueous NH$_3$ (28%, 10 mL) was added and stirred for additional 1 h and the reaction mixture was concentrated to near dryness. The residual material was re-dissolved in $CH_2Cl_2$ (150 mL) and washed with water (2×75 mL). The organic phase was evaporated to near dryness and the product was purified by silica gel column chromatography (1-3% MeOH in $CH_2Cl_2$, v/v), to afford nucleoside 136W (0.245 g, 50%) as pale yellow solid. $R_f$ 0.56 (10% MeOH in $CH_2Cl_2$, v/v); MALDI-HRMS m/z 608.1910 ([M+Na]$^+$, $C_{34}H_{27}N_5O_5 \cdot Na^+$, calcd 608.1904); $^1$H NMR (DMSO-$d_6$) δ 11.09 (s, 1H, amide), 8.62 (s, 1H, adenine), 8.57 (s, 1H, adenine), 7.99-8.28 (m, 11H, benzoyl, Py), 7.56-7.70 (m, 3H, benzoyl), 6.25 (d, 1H, H1', J=6 Hz), 5.58 (d, 1H, J=5.1 Hz, ex, 3'-OH), 5.46-5.50 (d, 1H, J=11.4 Hz, CH$_2$Py), 5.17-5.24 (m, 2H, 1 ex, 5'-OH, CH$_2$Py), 4.86 (m, 1H, H2'), 4.52-4.57 (m, 1H, H3'), 4.10-11 (m, 1H, H4'), 3.59-3.74 (m, 2H, H5'). $^{13}$C NMR (DMSO-$d_6$) δ 165.4, 151.8, 151.4, 150.2, 142.77, 133.4, 132.4, 131.1, 131.1, 130.7, 130.6, 130.1, 128.7, 128.4, 128.4, 128.1, 127.4, 127.3, 127.2, 127.1, 126.1, 125.6, 125.2, 125.2, 124.3, 123.8, 123.7, 123.3, 86.6, 85.9, 80.8, 70.1, 69.0, 61.3.

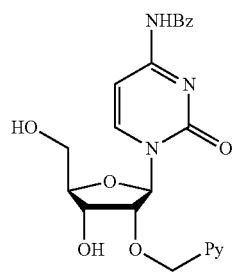

2'-O-(Pyren-1-yl-methyl)-N-benzoyl-cytidine (136X)

Benzoic anhydride (1.68 g, 7.45 mmol) was added to the solution of nucleoside 130X (3.1 g, 6.77 mmol) in anhydrous DMF (100 mL). The reaction mixture was stirred at 60° C. until TLC indicated complete conversion (~6 h). The reaction mixture was diluted with $CH_2Cl_2$ (150 mL), and the organic phase was sequentially washed with water (2×60 mL) and satd aq NaHCO$_3$ (2×100 mL). The organic phase was dried over Na$_2$SO$_4$, evaporated to near dryness, and the resulting crude was purified by silica gel column chromatography (0-2%, MeOH in $CH_2Cl_2$, v/v) to afford nucleoside 136X (2.1 g, 55%) as pale yellow solid. $R_f$ 0.6 (10% MeOH in $CH_2Cl_2$, v/v); MALDI-HRMS m/z 584.1785 ([M+Na]$^+$, $C_{33}H_{27}N_3O_6 \cdot Na^+$, calcd 584.1790); $^1$HNMR (DMSO-$d_6$) δ 11.16 (s, 1H, amide), 8.15-8.45 (m, 9H, Py), 8.00-8.03 (m, 3H, benzoyl, cytosine), 7.62-7.66 (m, 1H, benzoyl), 7.52-7.55 (m, 2H, benzoyl), 7.44 (d, 1H, cytosine), 6.13 (d, 1H, H1'), 5.43-5.53 (dd, 2H, CH$_2$Py), 5.30 (d, 1H, ex, 3'-OH), 5.19 (t, 1H, 5'-OH), 4.24-4.27 (m, 1H, H3'), 4.17-4.18 (m, 1H, H2'), 4.02-4.04 (m, 1H, H4'), 3.76-3.80 (m, 1H, H5'), 3.63-3.67 (m, 1H, H5'); $^{13}$C NMR (DMSO-$d_6$) δ 167.2, 162.9, 154.5, 144.8, 133.1, 132.7, 132.6, 131.8, 131.5, 130.6, 130.3, 130.2, 129.2, 128.7, 128.4, 127.4, 127.3, 126.2, 125.2, 124.5, 123.9, 123.7, 123.6, 96.0, 88.1, 84.7, 82.6, 81.7, 76.3, 73.0, 69.9, 67.8, 59.7

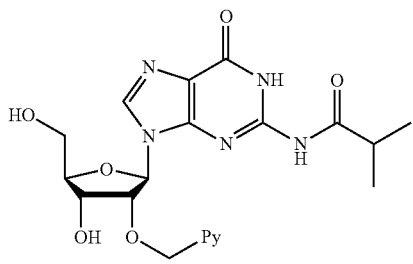

2'-O-(Pyren-1-yl-methyl)-N-isobutyryl-guanosine (136Y)

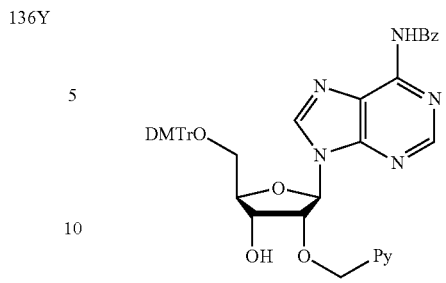

5'-O-(4,4'-dimethoxytrityl)-2'-O-(Pyren-1-yl-methyl)-N-benzoyl-adenosine (138W)

Trimethylsilyl chloride (0.5 mL, 3.92 mmol) was added to a solution of nucleoside 130Y (0.26 g, 0.52 mmol), which was dried by coevaporation with pyridine three times, in pyridine (6 mL). After stirring 2 h at rt, isobutyrylchloride (0.15 ml, 1.57 mmol) was added drop wise at 0° C. for 10 min. Water (2 mL) was added to the reaction mixture at 0° C. and stirred for another 10 min. The solution was stirred for another 5 min at rt, and aq $NH_3$ (28%, 5 mL) was added to the solution. After stirring for another 15 min at room temperature, the solution was concentrated to near dryness. The residual material was re-dissolved in $CH_2Cl_2$ (100 mL) and washed with water (2×60 mL). The organic phase was dried over $Na_2SO_4$, evaporated to near dryness and the crude was purified by silica gel column chromatography (1-3% MeOH in $CH_2Cl_2$, v/v), to afford nucleoside 136Y (0.220 g, 74%) as pale yellow solid. $R_f$ 0.56 (10% MeOH in $CH_2Cl_2$, v/v); MALDI-HRMS m/z 590.2008 ([M+Na]$^+$, $C_{31}H_{29}N_5O_6$.Na$^+$, calcd 590.2010); $^1$HNMR (DMSO-d$_6$) 11.8 (s, 1H, amide), 11.3 (s, 1H, NH), 8.01-8.27 (m, 9H, Py), 7.95 (s, 1H, H7-guanine), 5.93 (d, 1H, H1'), 5.43-5.46 (m, 2H, 1 ex, 3'-OH, CH$_2$Py), 5.20 (d, 1H, ex, 3'-OH), 5.06-5.16 (m, 2H, 1 ex, 5'-OH, CH$_2$Py), 4.65-4.67 (m, 1H, H2'), 4.45-4.48 (m, 1H, H3'), 4.01-4.03 (m, 1H, H4'), 3.61-3.66 (m, 2H, H5'), 2.56-2.61 (m, 1H, isobutyryl), 1.00-1.04 (dd, 6H, isobutyryl); $^{13}$C NMR (DMSO-d$_6$) δ 179.8, 154.5, 148.5, 147.8, 137.2, 131.1, 130.6, 130.1, 128.7, 127.3, 127.1, 127.0, 126.1, 125.2, 125.1, 124.3, 123.8, 123.6, 123.5, 86.5, 84.6, 81.6, 70.2, 69.2, 61.3, 34.5, 18.7, 18.6

General DMTr-Protection Protocol for the preparation of 138W-138Y

[Description for ~3.6 mmol Scale]: The appropriate nucleoside 136 (specific quantities given below) was coevaporated twice with anhydrous pyridine (15 mL) and redissolved in anhydrous pyridine. To this were added 4,4'-dimethoxytritylchloride (DMTrCl) and N,N-dimethyl-4-aminopyridine (DMAP), and the reaction mixture was stirred at rt until TLC indicated complete conversion (~14 h). The reaction mixture was diluted with $CH_2Cl_2$ (100 mL), and the organic phase was sequentially washed with water (2×50 mL) and satd aq NaHCO$_3$ (2×100 mL). The organic phase was evaporated to near dryness, and the resulting crude coevaporated with absolute EtOH and toluene (2:1, v/v, 3×10 mL) and purified by silica gel column chromatography (0-5%, MeOH in $CH_2Cl_2$, v/v) to afford nucleoside 138 (yields specified below).

Nucleoside 136W (0.24 g, 0.41 mmol), DMTrCl (0.27 g, 0.70 mmol), and DMAP (~12 mg) in anhydrous pyridine (6 mL) were mixed, reacted, worked up, and purified as described above to afford nucleoside 138W (0.3 g, 71%) as a pale yellow foam. $R_f$ 0.78 (10% MeOH in $CH_2Cl_2$, v/v); MALDI-HRMS m/z 910.3225 ([M+Na]$^+$, $C_{55}H_{45}N_5O_7$.Na$^+$, calcd 910.3211); $^1$H NMR (DMSO-d$_6$) δ 11.12 (s, 1H, amide), 8.50 (s, 1H, adenine), 8.46 (s, 1H, adenine), 8.00-8.29 (m, 11H, benzoyl, Py), 7.64-7.69 (m, 1H, benzoyl), 7.55-7.60 (m, 2H, benzoyl), 7.35 (d, 2H, J=9 Hz, DMTr), 7.14-7.27 (m, 7H, DMTr), 6.81 (d, 4H, J=8.4 Hz, DMTr), 6.27 (d, 1H, J=5.7 Hz, H1'), 5.56 (d, 1H, ex, J=5.7 Hz, 3'-OH), 5.50 (d, 1H, J=11.7 Hz, CH$_2$Py), 5.28 (d, 1H, J=11.7 Hz, CH$_2$Py), 4.97-5.00 (m, 1H, H2'), 4.61-4.65 (m, 1H, H3'), 4.20-4.24 (m, 1H, H4'), 3.70 (s, 6H, 2×CH$_3$O), 3.26-3.28 (m, 2H, H5'). $^{13}$C NMR (DMSO-d$_6$) δ 165.5, 158.0, 151.8, 151.3, 150.3, 144.7, 135.5, 135.4, 133.4, 132.4, 131.1, 131.1, 130.7, 130.6, 130.1, 129.6, 129.6, 128.8, 128.7, 128.4, 128.4, 128.1, 128.1, 127.7, 127.6, 127.4, 127.3, 127.2, 127.1, 126.6, 126.1, 125.7, 125.2, 124.3, 123.9, 123.7, 123.3, 113.1, 86.3, 85.5, 84.2, 79.8, 70.1, 69.2, 63.5, 54.9.

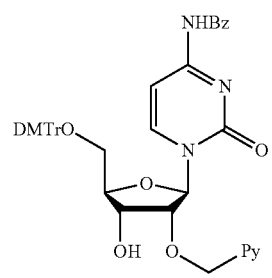

5'-O-(4,4'-dimethoxytrityl)-2'-O-(Pyren-1-yl-methyl)-N-benzoyl-cytidine (138X)

Nucleoside 136X (2.0 g, 3.56 mmol), DMTrCl (2.07 g, 5.34 mmol), and DMAP (~20 mg) in anhydrous pyridine (50 mL) were mixed, reacted, worked up, and purified as described above to afford nucleoside 138X (2.0 g, 65%) as a pale yellow foam. $R_f$ 0.78 (10% MeOH in $CH_2Cl_2$, v/v); MALDI-HRMS m/z 886.3087 ([M+Na]$^+$, $C_{54}H_{45}N_3O_8$.Na$^+$, calcd 886.3098); $^1$HNMR (DMSO-d$_6$) δ 11.22 (s, 1H, amide), 847-8.49 (d, 1H, Py), 8.21-8.30 (m, 6H, H6 and Py), 8.16 (s, 2H, Py), 8.00-8.05 (m, 3H, benzoyl and Py), 7.63-7.65 (m, 1H, benzoyl), 7.52-7.55 (m, 2H, benzoyl), 7.24-7.39 (m, 9H, DMTr), 7.04 (d, 1H, H5), 6.86-6.90 (m, 4H, DMTr), 6.15 (d, 1H, H1'), 5.56 (bs, 2H, CH$_2$Py), 5.37 (d, 1H, ex, 3'-OH), 4.41-4.45 (m, 1H, H3'), 4.16-4.20 (m, 2H, H2' and H4'), 3.73 (bs, 6H, 2×CH$_3$O), 3.38-3.41 (m, 1H, H5'), 3.29-3.34 (m, 1H, H5'); $^{13}$C NMR (DMSO-d$_6$) δ 167.1, 163.1, 158.1, 154.3, 144.3, 135.5, 135.1, 133.1, 132.6, 131.4, 130.6, 130.2, 129.7, 129.6, 128.7, 128.4, 127.8, 127.7, 127.5, 127.2, 127.8, 126.1, 125.2, 124.5, 123.9, 123.8, 123.6, 113.2, 96.0, 88.7, 85.9, 82.3, 81.5, 69.9, 68.0, 61.8, 54.9.

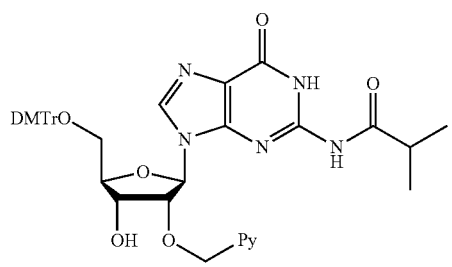

138Y

5'-O-(4,4'-dimethoxytrityl)-2'-O-(Pyren-1-yl-methyl)-N-isobutyryl-guanosine (138Y)

Nucleoside 136Y (0.20 g, 0.35 mmol), DMTrCl (0.20 g, 0.53 mmol), and DMAP (~10 mg) in anhydrous pyridine (5 mL) were mixed, reacted, worked up, and purified as described above to afford nucleoside 138Y (0.27 g, 89%) as a pale yellow foam. R$_f$ 0.8 (10% MeOH in CH$_2$Cl$_2$, v/v); MALDI-HRMS m/z 892.3325 ([M+Na]$^+$, C$_{52}$H$_{47}$N$_5$O$_8$.Na$^+$, calcd 892.3317); $^1$HNMR (DMSO-d$_6$) 11.8 (s, 1H, amide), 11.3 (s, 1H, NH), 8.25-8.32 (m, 3H, Py), 7.99-8.15 (m, 7H, H7-guanine and Py), 7.32-7.34 (m, 2H, DMTr), 7.18-7.25 (m, 7H, DMTr), 6.79-6.82 (m, 4H, DMTr), 5.97 (d, 1H, H1'), 5.46-5.51 (m, 2H, 1 ex, 3'-OH, CH$_2$Py), 5.22-5.25 (d, 1H, CH$_2$Py), 4.71-4.73 (m, 1H, H2'), 4.45-4.48 (m, 1H, H3'), 4.11-4.13 (m, 1H, H4'), 3.70-3.71 (bd, 6H, 2×CH$_3$O), 3.18-3.28 (m, 2H, H5'), 2.59-2.65 (m, 1H, isobutyryl), 1.04-1.06 (dd, 6H, isobutyryl); $^{13}$C NMR (DMSO-d$_6$) δ 179.8, 158.0, 154.5, 148.5, 147.8, 144.6, 137.1, 135.4, 135.3, 131.12, 130.7, 130.6, 130.1, 129.6, 128.7, 127.7, 127.6, 127.3, 127.2, 127.1, 127.0, 126.6, 126.1, 125.2, 125.1, 124.4, 123.8, 123.7, 123.4, 120.1, 113.1, 85.6, 85.0, 84.2, 80.8, 70.3, 69.3, 63.9, 54.9, 34.6, 18.7, 18.6.

General Phosphitylation Protocol:

[Description for ~2.3 mmol Scale] The appropriate nucleoside (specific quantities of substrates and reagents given below) was co-evaporated twice with anhydrous 1,2-dicholoroethane (20 mL) and redissolved in anhydrous CH$_2$Cl$_2$ (25 mL). To this was added N,N-diisopropylethylamine (DIPEA) and 2-cyanoethyl-N,N-diisopropylchlorophosphoramidite (PCl-reagent) and the reaction mixture was stirred at rt until TLC indicated complete conversion (~3 h), whereupon abs. EtOH (4 mL) and CH$_2$Cl$_2$ (50 mL) were sequentially added to the solution. The organic phase was washed with sat. aq. NaHCO$_3$ (20 mL), evaporated to near dryness, and the resulting residue purified by silica gel column chromatography (40-70% EtOAc in petroleum ether, v/v) to afford the corresponding phosphoramidite (yields specified below).

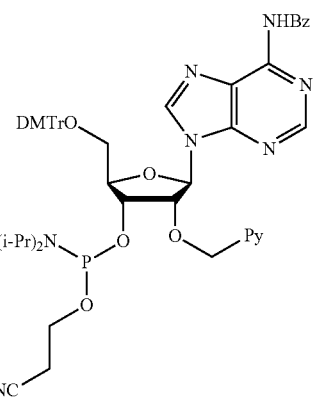

76'W

3'-O—(N,N-Diisopropylamino-2-cyanoethoxyphosphinyl)-2'-O-(pyren-1-yl-methyl)-5'-O-(4,4'-dimethoxytrityl)-N-benzoyl-adenosine (76'W)

Nucleoside 138W (0.25 g, 0.28 mmol), DIPEA (74 μL, 0.43 mmol) and PCl-reagent (95 μL, 0.43 mmol) in anhydrous CH$_2$Cl$_2$ (6 mL) were mixed, reacted, worked up and purified as described above to afford phosphoramidite 76'W (0.26 g, 82%) as a white foam. R$_f$ 0.75 (5% MeOH in CH$_2$Cl$_2$, v/v); MALDI-HRMS m/z 1110.4295 ([M+Na]$^+$, C$_{64}$H$_{62}$N$_7$O$_8$P.Na$^+$, Calcd 1110.4289); $^{31}$P NMR (CDCl$_3$) δ 150.7, 150.8.

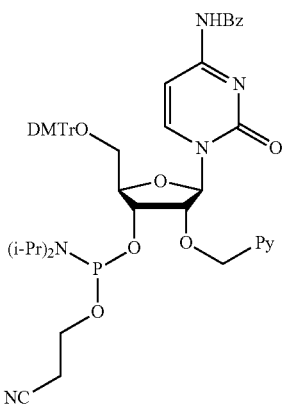

140X

3'-O—(N,N-Diisopropylamino-2-cyanoethoxyphosphinyl)-2'-O-(pyren-1-yl-methyl)-5'-O-(4,4'-dimethoxytrityl)-N-benzoyl-cytidine (140X)

Nucleoside 138X (2.0 g, 2.31 mmol), DIPEA (1.65 mL, 9.26 mmol) and PCl-reagent (1.03 mL, 4.63 mmol) in anhydrous CH$_2$Cl$_2$ (25 mL) were mixed, reacted, worked up and purified as described above to afford phosphoramidite 140X (2.3 g, 93%) as a white foam. R$_f$ 0.67 (5% MeOH in CH$_2$Cl$_2$, v/v); MALDI-HRMS m/z 1086.4183 ([M+Na]$^+$, C$_{63}$H$_{62}$N$_5$O$_9$P.Na$^+$, Calcd 1086.4177); $^{31}$P NMR (CDCl$_3$) δ 149.7, 150.1.

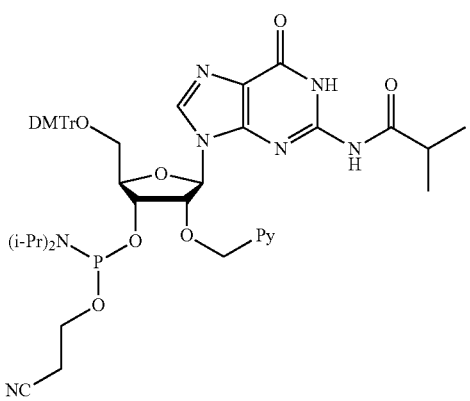

3'-O—(N,N-Diisopropylamino-2-cyanoethoxyphosphinyl)-2'-O-(pyren-1-yl-methyl)-5'-O-(4,4'-dimethoxytrityl)-N-isobutyryl-guanosine (140Y)

Nucleoside 138Y (0.26 g, 0.29 mmol), DIPEA (213 µL, 1.19 mmol) and PCl-reagent (133 µL, 0.59 mmol) in anhydrous $CH_2Cl_2$ (7 mL) were mixed, reacted, worked up and purified as described above to afford phosphoramidite 140Y (0.25 g, 78%) as a white foam. $R_f$: 0.7 (5% MeOH in $CH_2Cl_2$, v/v); MALDI-HRMS m/z 1092.4389 ([M+Na]$^+$, $C_{61}H_{64}N_7O_9P\cdot Na^+$, Calcd 1092.4395); $^{31}$P NMR ($CDCl_3$) δ 150.3, 150.4.

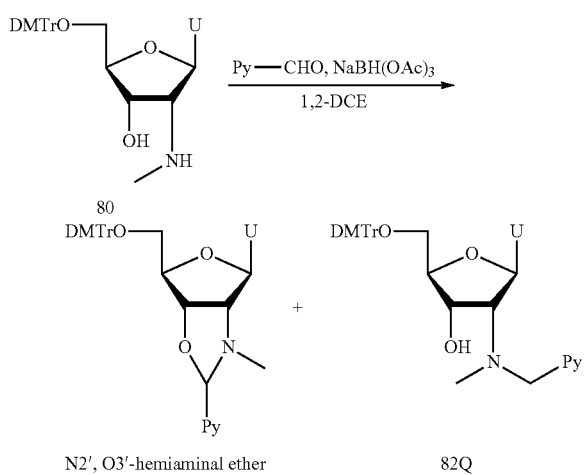

Cyclic N2',O3'-hemiaminal ether

The structure of the cyclic N2',O3'-hemiaminal ether byproduct (Scheme 15) is supported by the following $^1$H NMR observations (500 MHz, DMSO-$d_6$, results not shown): a) appearance of the hemiaminal ether proton as a singlet at 6.07 ppm; b) absence of an exchangeable signal corresponding to a 3'-OH group, c) absence of a signal corresponding to a $CH_2$-group linking the O2'-position and the pyrene moiety, and, d) appearance of the H1'-signal as a singlet at 6.13 ppm indicating formation of a restricted North type furanose conformation unlike what is observed for 6Q (H1' signal appearing as a doublet at 6.43 ppm, J=8.2 Hz). Despite formation of a new stereocenter, we only observed one set of signals, suggesting that only one of the diastereomers of the cyclic N2',O3'-hemiaminal ether byproduct is formed.

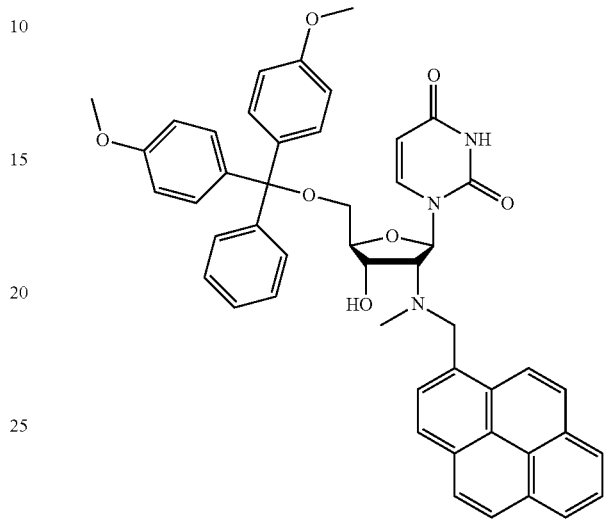

2'-Amino-2'-deoxy-2'-N-methyl-2'-N-(pyren-1-yl-methyl)-5'-O-(4,4'-dimethoxytrityl)uridine (82Q)

Nucleoside 80 (200 mg, 0.36 mmol) was co-evaporated with anhydrous 1,2-dichloroethane (2×4 mL) and redissolved in anhydrous THF (5 mL). Pyrene-1-ylmethylchloride (205 mg, 0.37 mmol) and triethylamine (0.52 mL, 3.73 mmol) were added and the reaction mixture was heated at reflux for two days, whereupon the solvent was evaporated off. The crude residue was taken up in a mixture $CHCl_3$ and sat. aq. $NaHCO_3$ (50 mL, 3:2, v/v) and the layers were separated. The aqueous phase was extracted with $CHCl_3$ (2×20 mL) and the combined organic phase was evaporated to dryness. The resulting residue was purified by silica gel column chromatography (0-1.25% MeOH/$CH_2Cl_2$, v/v) to afford nucleoside 82Q as a yellow foam (129 mg, 46%). $R_f$: 0.5 (60%, EtOAc in petroleum ether, v/v); MALDI-HRMS m/z 774.3156 ([M+H]$^+$ $C_{48}H_{43}N_3O_7\cdot H^+$, Calc 774.3174); $^1$H NMR (DMSO-$d_6$) δ 11.41 (d, 1H, ex, J=1.7 Hz, NH), 8.50 (d, 1H, J=9.1 Hz, Py), 8.01-8.29 (m, 8H, Py), 7.63 (d, 1H, J=8.2 Hz, H6), 7.20-7.38 (m, 9H, DMTr), 6.85-6.89 (m, 4H, DMTr), 6.43 (d, 1H, J=8.2 Hz, H1'), 5.56 (d, 1H, ex, J=5.2 Hz, 3'-OH), 5.43 (dd, 1H, J=8.3 Hz, 1.7 Hz, H5), 4.41-4.50 (m, 3H, $CH_2$Py, H3'), 4.06-4.08 (m, 1H, H4'), 3.71 (s, 3H, $CH_3$O), 3.70 (s, 3H, $CH_3$O), 3.44-3.48 (dd, 1H, J=8.3 Hz, 8.1 Hz, H2'), 3.28-3.31 (m, 1H, H5', overlap with $H_2$O), 3.16-3.20 (dd, 1H, J=10.6 Hz, 3.6 Hz, H5'), 2.33 (s, 3H, $CH_3$N); $^{13}$C NMR (DMSO-$d_6$) δ 162.7, 158.08, 158.07, 150.6, 144.5, 140.2 (C6), 135.4, 135.1, 132.7, 130.7, 130.3, 130.2, 129.71 (DMTr), 129.67 (DMTr), 129.2, 128.0 (Py), 127.8 (DMTr), 127.6 (DMTr), 127.3 (Py), 126.9 (Py), 126.8 (Py), 126.7 (DMTr), 126.1 (Py), 125.01, 124.98 (Py), 124.4 (Py), 124.1, 124.0 (Py), 123.9, 113.20 (DMTr), 113.17 (DMTr), 102.1 (C5), 85.9, 85.1 (C4'), 83.4 (C1'), 71.3 (C3'), 67.8 (C2'), 64.1 (C5'), 57.4 ($CH_2$Py), 55.0 ($CH_3$O), 38.6 ($CH_3$N).

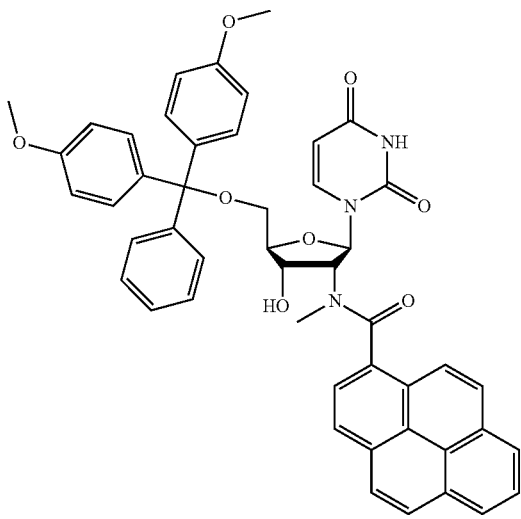

2'-Amino-2'-deoxy-2'-N-methyl-2'-N-(pyren-1-yl-carbonyl)-5'-O-(4,4'-dimethoxytrityl)uridine (82S)

Nucleoside 80 (150 mg, 0.27 mmol) was co-evaporated with anhydrous 1,2-dichloroethane (2×5 mL), dissolved in anhydrous DMF (4.5 mL) and added to a pre-stirred (1 h at rt) solution of 1-pyrenecarboxylic acid (100 mg, 0.40 mmol), O-(7-azabenzotriazole-1-yl)-N,N,N',N'-tetramethyluronium hexafluorophosphate (HATU, 125 mg, 0.32 mmol) and DIPEA (0.12 mL, 0.70 mmol) in anhydrous DMF (4.5 mL). The reaction mixture was stirred for 17 h, whereupon it was diluted with EtOAc (50 mL) and sequentially washed with sat. aq. NaHCO$_3$ (20 mL) and H$_2$O (2×20 mL). The organic phase was evaporated to dryness and the resulting residue purified by silica gel column chromatography (0-2% MeOH in CH$_2$Cl$_2$, v/v) to afford nucleoside 82S as a white foam (164 mg, 78%). R$_f$=0.4 (5% MeOH in CH$_2$Cl$_2$, v/v). MALDI-HRMS m/z 788.2985 ([M+H]$^+$, C$_{48}$H$_{41}$N$_3$O$_8$.H$^+$, calc. 788.2966); $^1$H NMR (CDCl$_3$) δ 8.65 (br s, 1H, NH, ex), 7.97-8.28 (m, 9H, Py), 7.85 (d, 1H, J=8.3 Hz, H6), 7.20-7.44 (m, 9H, DMTr), 6.80-6.90 (m, 4H, DMTr), 6.78 (d, 1H, J=6.0 Hz, H1'), 5.42-5.48 (m, 1H, H5), 4.80-4.90 (m, 2H, H2', H3'), 4.28-4.43 (m, 1H, H4'), 3.77 (s, 6H, CH$_3$O), 3.48-3.63 (m, 2H, H5'), 2.98 (s, 3H, NCH$_3$), traces of a second rotamer are observed; $^{13}$C NMR (CDCl$_3$) δ 174.4, 162.9, 159.0, 150.5, 144.5, 140.0 (C6), 135.6, 135.5, 132.3, 131.4, 131.0, 130.44 (DMTr), 130.42 (DMTr), 129.4 (Py), 128.7 (Py), 128.5 (DMTr), 128.3 (DMTr), 127.4, 126.7 (Py), 126.1 (Py), 126.0 (Py), 125.0 (Py), 124.8, 124.7, 124.3 (Py), 113.6 (DMTr), 113.3 (DMTr), 103.2 (C5), 87.3, 86.6 (C4'), 85.3 (C1'), 71.8 (C3'/C2'), 65.8 (C2'/C3'), 63.0 (C5'), 55.5 (CH$_3$O), 38.5 (NCH$_3$). A trace impurity of grease was observed at 29.9 ppm.

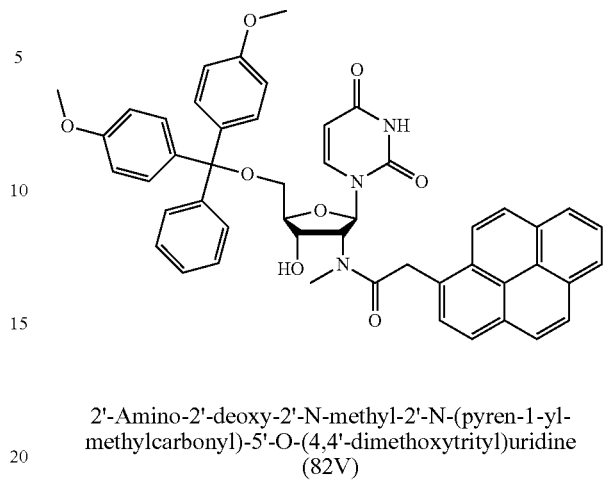

2'-Amino-2'-deoxy-2'-N-methyl-2'-N-(pyren-1-yl-methylcarbonyl)-5'-O-(4,4'-dimethoxytrityl)uridine (82V)

Nucleoside 80 (158 mg, 0.28 mmol) was co-evaporated with 1,2-dichloroethane (2×5 mL) and subsequently dissolved in anhydrous CH$_2$Cl$_2$ (8 mL). To this was added 1-ethyl-3-(3-dimethylamino-propyl) carbodiimide hydrochloride (EDC.HCl, 73 mg, 0.38 mmol) and pyrene-1-ylacetic acid (108 mg, 0.41 mmol). The reaction mixture was stirred under argon at rt for 3 h whereupon the reaction mixture was diluted with CH$_2$Cl$_2$ (30 mL) and sequentially washed with sat. aq. NaHCO$_3$ (20 mL) and H$_2$O (3×15 mL). The organic phase was evaporated to dryness and the resulting residue was purified by silica gel column chromatography (0-3% i-PrOH/CH$_2$Cl$_2$, v/v) to afford a rotameric mixture (2:5 by $^1$HNMR) of nucleoside 82V (187 mg, 83%) as a brown foam. R$_f$: 0.5 (5%, i-PrOH in CH$_2$Cl$_2$, v/v); MALDI-HRMS m/z 801.3078 ([M]$^+$, C$_{49}$H$_{43}$N$_3$O$_8$, calc. 801.3045); $^1$H NMR (DMSO-d$_6$) δ 11.52 (d, 1H, J=1.7 Hz, NH$_{(A)}$), 11.46 (d, 0.4H, J=1.7 Hz, NH$_{(B)}$), 8.05-8.31 (m, 11.2H, Py$_{(A)}$+Py$_{(B)}$), 7.89 (d, 1H, J=7.8 Hz, Py$_{(A)}$), 7.82 (d, 0.4H, J=7.8 Hz, Py$_{(B)}$), 7.67-7.70 (m, 1.4H, H6$_{(A)}$+H6$_{(B)}$), 7.13-7.43 (m, 12.6H, DMT$_{(A+B)}$), 6.78-6.87 (m, 5.6H, DMT$_{(A+B)}$), 6.42 (d, 1H, J=8.0 Hz, H1'$_{(A)}$), 6.31 (d, 0.4H, J=5.5 Hz, H1'$_{(B)}$), 5.92 (d, 0.4H, ex, J=4.9 Hz, 3'-OH$_{(B)}$), 5.76 (d, 1H, ex, J=4.9 Hz, 3'-OH$_{(A)}$), 5.38 (dd, 1H, J=8.2 Hz, 1.7 Hz, H5$_{(A)}$), 5.33 (dd, 0.4H, J=8.2 Hz, 1.7 Hz, H5$_{(B)}$), 5.11-5.17 (m, 1H, H2'$_{(A)}$), 4.80-4.86 (m, 0.4H, H2'$_{(B)}$), 4.58-4.63 (d, 1H, J=16.5 Hz, CH$_2$Py$_{(A)}$), 4.51-4.56 (d, 0.4H, J=16.5 Hz, CH$_2$Py(B)), 4.37-4.49 (m, 2.4H, 1×CH$_2$Py$_{(A)}$, H3'$_{(A)}$, H3'$_{(B)}$), 4.30-4.37 (d, 0.4H, J=16.5 Hz, CH$_2$Py(B)), 4.10-4.16 (m, 1.4H, H4'$_{(A)}$+H4'$_{(B)}$), 3.68 (s, 2.4H, CH$_3$O (B)), 3.64 (s, 3H, CH$_3$O$_{(A)}$), 3.62 (s, 3H, CH$_3$O$_{(A)}$), 3.35-3.37 (m, 0.4H, H5'$_{(B)}$), 3.32 (s, 3H, CH$_3$N$_{(A)}$), 3.29-3.32 (m, 1H, H5'$_{(A)}$, overlap with H$_2$O), 3.23-3.27 (dd, 0.4H, J=10.6 Hz, 2.6 Hz, H5'$_{(B)}$), 3.15-3.19 (dd, 1H, J=10.6 Hz, 2.6 Hz, H5'$_{(A)}$), 3.03 (s, 1.2H, CH$_3$N$_{(B)}$); $^{13}$C NMR (DMSO-d$_6$) δ 172.2, 172.1, 162.81, 162.78, 158.06, 158.03, 158.02, 150.5, 150.4, 144.6, 144.3, 140.2 (C6$_{(B)}$), 140.1 (C6$_{(A)}$), 135.4, 135.3, 135.2, 135.0, 130.7, 130.62, 130.56, 130.3, 130.2, 129.71 (DMTr), 129.69 (DMTr), 129.1, 128.1 (Py-CH$_A$), 127.9 (Py-CH$_B$), 127.8 (DMTr), 127.73 (DMTr), 127.70 (DMTr), 127.3 (Py), 127.14 (Py), 127.10 (Py), 126.73 (Py), 126.66 (DMTr), 126.1 (Py), 125.1 (Py), 125.0 (Py), 124.9 (Py), 124.5 (Py), 124.1, 124.0, 123.85 (Py), 123.76 (Py), 113.2 (DMTr), 113.1 (DMTr), 102.2 (C5$_{(A)}$), 102.0 (C5$_{(B)}$), 85.9, 85.7, 85.5 (C1'$_{(B)}$), 85.2 (C4'$_{(A)}$), 84.8 (C4'$_{(B)}$), 83.2 (C1'$_{(A)}$), 70.5 (C3'$_{(A)}$), 69.3 (C3'$_{(B)}$), 63.8 (C5'$_{(A)}$), 63.7 (C5'$_{(B)}$), 62.1 (C2'$_{(B)}$), 59.0 (C2'$_{(A)}$), 54.92 (CH$_3$O$_{(B)}$), 54.87 (CH$_3$O$_{(B)}$), 54.85 (CH$_3$O$_{(A)}$), 54.82 (CH$_3$O$_{(A)}$), 38.1 (CH$_2$Py$_{(A)}$), 37.8 (CH$_2$-Py$_{(B)}$), 34.2 (CH$_3$N$_{(A)}$), 31.4 (CH$_3$N$_{(B)}$).

84Q

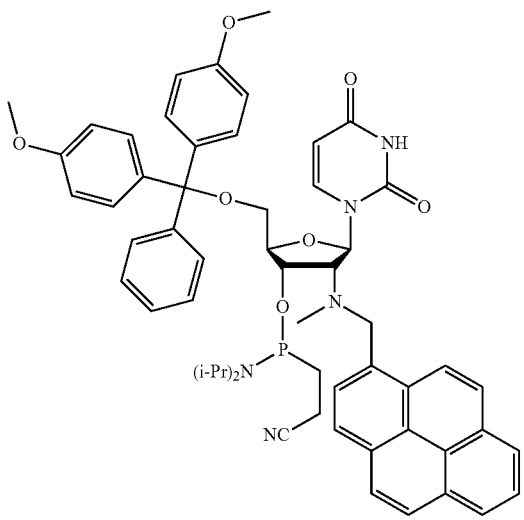

2'-Amino-2'-deoxy-2'-N-methyl-2'-N-(pyren-1-yl-methyl)-3'-O—(N,N-diisopropylamino-2-cyanoethoxyphosphinyl)-5'-O-(4,4'-dimethoxytrityl)uridine (84Q)

Nucleoside 82Q (135 mg, 0.18 mmol) was co-evaporated with CH$_3$CN (2×4 mL) and redissolved in anhydrous CH$_3$CN (2.5 mL). To this was added DIPEA (153 µL, 0.87 mmol) and PCl-reagent (78 µL, 0.35 mmol). The reaction mixture was stirred at rt for 4 h, whereupon it was cooled on an ice bath and abs. EtOH (3 mL) was added. The solvent was evaporated off and the resulting residue purified by silica gel column chromatography (0-40% EtOAc in petroleum ether, v/v; column built in 0.5% Et$_3$N) to afford nucleoside 84Q as a white foam (97 mg, 57%). R$_f$: 0.3 (40% EtOAc in petroleum ether, v/v); MALDI-HRMS m/z 996.4046 ([M+Na]$^+$, C$_{57}$H$_{60}$N$_5$O$_8$P.Na$^+$, Calc. 996.4077); $^{31}$P NMR (CDCl$_3$) δ 151.0, 149.8.

84S

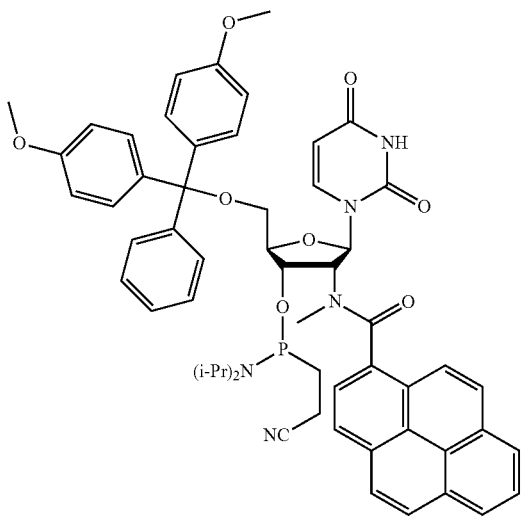

2'-Amino-2'-deoxy-2'-N-methyl-3'-O—(N,N-diisopropylamino-2-cyanoethoxyphosphinyl)-2'-N-(pyren-1-yl-carbonyl)-5'-O-(4,4'-dimethoxytrityl)uridine (84S)

Nucleoside 82S (219 mg, 0.28 mmol) was co-evaporated with anhydrous 1,2-dicholoroethane (2×2 mL) and redissolved in anhydrous CH$_2$Cl$_2$ (2 mL). To this was added DIPEA (58 µL, 0.33 mmol) followed by dropwise addition of PCl-reagent (74 µL, 0.33 mmol). After stirring at rt for 2 h, CH$_2$Cl$_2$ (10 mL) was added and the reaction mixture stirred for additional 10 min whereupon the solvent was evaporated under reduced pressure. The resulting residue was purified by silica gel column chromatography (1$^{st}$ column: 0-40% EtOAc in petroleum ether, v/v; 2$^{nd}$ column: 0-4% MeOH in CH$_2$Cl$_2$, v/v) to afford a rotameric mixture of phosphoramidite 84S as a white foam (138 mg, 49%). R$_f$: 0.8 (5% MeOH in CH$_2$Cl$_2$, v/v); MALDI-HRMS m/z 1010.3865 ([M+Na]$^+$, C$_{57}$H$_{58}$N$_5$O$_9$P.Na$^+$, Calc. 1010.3870); $^{31}$P NMR (CDCl$_3$) δ 151.8, 151.2, 150.8.

84V

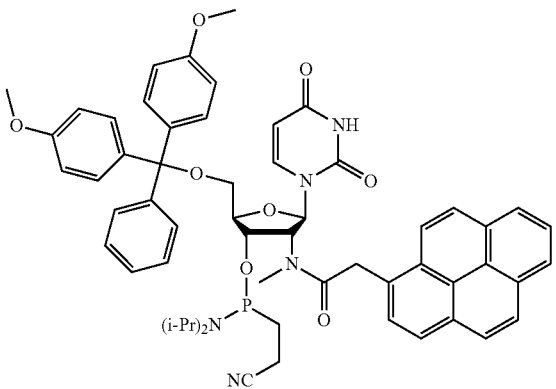

2'-Amino-2'-deoxy-2'-N-methyl-3'-O—(N,N-diisopropylamino-2-cyanoethoxyphosphinyl)-2'-N-(pyren-1-yl-methylcarbonyl)-5'-O-(4,4'-dimethoxytrityl)uridine (84V)

Nucleoside 82V (0.30 g, 0.37 mmol) was co-evaporated with anhydrous 1,2-dicholoroethane (2×3 mL) and redissolved in anhydrous CH$_2$Cl$_2$ (4 mL). To this was added DIPEA (0.32 mL, 1.84 mmol) followed by dropwise addition of PCl-reagent (0.16 mL, 0.74 mmol). After stirring for 1.5 h at rt, CH$_2$Cl$_2$ (10 mL) was added and the reaction mixture stirred for additional 10 min whereupon the solvent was evaporated under reduced pressure. The resulting residue was purified by silica gel column chromatography (0-60% EtOAc in petroleum ether, v/v) to afford phosphoramidite 84V as a bright yellow foam (153 mg, 42%). R$_f$: 0.4 (60% EtOAc in petroleum ether, v/v); MALDI-HRMS m/z 1024.4037 ([M+Na]$^+$, C$_{58}$H$_{60}$N$_5$O$_9$P.Na$^+$, Calc. 1024.4026); $^{31}$P NMR (CDCl$_3$) δ 150.6, 150.5.

General procedure for 222: Coevaporated starting material (1 mmol) in anhydrous 1,2-dichloroethane (2×5 mL) and redissolved in anhydrous 1,2-dichloroethane (5 mL). To this was added NaBH(OAc)$_3$ (1.5-7 eq) and RCHO (1.5 eq). Allowed to stir at rt under an argon atmosphere for 5-22 h whereupon the reaction mixture was diluted with CH$_2$Cl$_2$ (50 mL) washed with sat. aq. NaHCO$_3$ (2×30 mL) and H$_2$O (30 mL). Back-extracted aqueous phase with CH$_2$Cl$_2$ (2×20 mL), dried over Na$_2$SO$_4$ and evaporated to dryness. The crude was then purified via silica gel column chromatography isolate products (43-95%).

General procedure for synthesis of 224: Coevaporated starting material (1 mmol) in anhydrous 1,2-dichloroethane (2×10 mL) and redissolved in anhydrous 1,2-dichloroethane (10 mL). To this was added NaBH(OAc)$_3$ (10 eq) and CH$_2$O (1.5 eq) and was stirred at rt under argon atmosphere for 4-7 h whereupon the reaction mixture was diluted with CH$_2$Cl$_2$ (50 mL) washed with sat. aq. NaHCO$_3$ (2×30 mL) and the aqueous back-extracted with CH$_2$Cl$_2$ (2×20 mL), dried over Na$_2$SO$_4$ and evaporated to dryness. The crude was then purified via silica gel column chromatography isolate products (89-99%).

General procedure for synthesis of 226: Coevaporated starting material (1 mmol) in anhydrous 1,2-dichloroethane (10 mL) and redissolved in an. CH$_2$Cl$_2$ (10 mL). To this was added DIPEA (4-5 eq) followed by dropwise addition of "PCl" reagent (2-3 eq) and allowed to stir under argon atmosphere at rt for 2-4 h whereupon the reaction mixture was quenched with cold EtOH (1 mL) and evaporated to dryness. The crude was purified by silica gel column chromatography and precipitated in CH$_2$Cl$_2$ and petroleum ether to afford the desired phosphoramidite (62-90%).

Synthesis of 240. Naphthy-2-methylthiol (616 mg, 3.53 mmol) and sodium hydride (42 mg, 1.77 mmol) were dissolved in an. DMA (3 mL) and stirred under argon atm for 10 min whereupon O2,O2'-anhydrouridine 70 (200 mg, 0.88 mmol) was added. After stirring for 48 h, the reaction mixture was diluted with EtOAc (30 mL), neutralized with acetic acid (1 drop) and washed with H$_2$O (2×15 mL). The aqueous was back-extracted with CH$_2$Cl$_2$ (3×15 mL) and the organic layers evaporated to dryness. The crude product was purified by silica gel column chromatography (0-7% MeOH/CH$_2$Cl$_2$, v/v) to give nucleoside 240 (311 mg, 88%). R$_f$=0.3 (10% MeOH in CH$_2$Cl$_2$); $^1$H NMR (DMSO-d$_6$) 11.33 (br s, 1H, NH, ex), 7.77-7.89 (m, 3H, Ar), 7.61-7.68 (m, 2H, Ar), 7.39-7.54 (m, 3H, Ar, H6), 6.09 (d, 1H, J=8.23 Hz, H1'), 5.65 (d, 1H, J=5.21 Hz, ex, 3'-OH), 5.34 (d, 1H, J=7.96 Hz, H5), 5.05 (t, 1H, J=5.21, ex, 5'-OH), 4.15-4.20 (m, 1H, H3'), 3.81-3.94 (m, 3H, SCH$_2$, H4'), 3.50-3.58 (m, 2H, H5'), 3.36 (dd, 1H, J=8.5 Hz, 5.5 Hz, H2').

Synthesis and purification of single-stranded probes modified with monomers 120W/X/Y/Z, 120Q/S/V, 120'W, 120'X, 140'X, 140'Y, 208W/X/Y/Z, 228Y/Z and 244:

Synthesis of modified probes was performed on a DNA synthesizer using 0.2 μmol scale succinyl linked LCAA-CPG (long chain alkyl amine controlled pore glass) columns with a pore size of 500 Å. Standard protocols for incorporation of DNA phosphoramidites were used. A ~50-fold molar excess of modified phosphoramidites in anhydrous acetonitrile (at 0.05 M) was typically used during hand-couplings (performed to conserve material) except with 76Z (~70-fold molar excess in anhydrous CH$_2$Cl$_2$, at 0.07M). Moreover, extended oxidation (45 s) and coupling times were typically used (0.01 M 4,5-dicyanoimidazole as activator, 15 min for monomers 84V/76W/76Y, 35 min for monomer 76Z; 0.01 M 5-(bis-3,5-trifluoromethylphenyl)-1H-tetrazole [Activator 42], 15 min for monomers 84Q/84S/84V). Probes modified with monomers 120'W, 120'X, 140'X, 140'Y, 208W/X/Y/Z, 228Y/Z and 244, were made in an equivalent manner. Cleavage from solid support and removal of protecting groups was typically accomplished upon treatment with 32% aq. ammonia (55° C., 24 h). Purification of all modified oligonucleotides was performed to minimum 80% purity using either of two methods: a) overall synthesis yield>80%: cleavage of DMT using 80% aq. AcOH, followed by precipitation from acetone (−18° C. for 12-16 h) and washing with acetone, or b) overall synthesis yield<80%: purification of oligonucleotides by RP-HPLC as described below, followed by detritylation and precipitation.

Purification of the crude oligonucleotides was performed on a HPLC system equipped with an XTerra MS C18 pre-column (10 μm, 7.8×10 mm) and a XTerra MS C18 column (10 μm, 7.8×150 mm). The identity of synthesized oligonucleotides was established through MALDI-MS/MS analysis (Table 35-36) recorded in positive ions mode on a Quadrupole Time-Of-Flight Tandem Mass Spectrometer equipped with a MALDI source using anthranilic acid as a matrix (Tables 39-51), while purity (>80%) was verified by RP-HPLC running in analytical mode.

TABLE 39

MALDI-MS of Representative Single-Stranded Probes Modified with Monomers 120W/X/Y/Z

| ONs | Sequence | Calc. m/z [M] | Found m/z [M + H] |
|---|---|---|---|
| 120W1 | 5'-G120W G ATA TGC | 2880 | 2881 |
| 120W2 | 5'-GTG A120WA TGC | 2880 | 2881 |
| 120W3 | 5'-GTG ATA 120WGC | 2880 | 2881 |
| 120W4 | 3'-CAC 120WAT ACG | 2809 | 2810 |
| 120W5 | 3'-CAC TA120W ACG | 2809 | 2810 |
| 120X1 | 5'-G120XG ATA TGC | 2954 | 2955 |
| 120X2 | 5'-GTG A120XA TGC | 2954 | 2955 |
| 120X3 | 5'-GTG ATA 120XGC | 2954 | 2955 |
| 120X4 | 3'-CAC 120XAT ACG | 2883 | 2884 |
| 120X5 | 3'-CAC TA120XACG | 2883 | 2884 |
| 120X6 | 3'-CAC 120XA120XACG | 3085 | 3086 |
| 120X7 | 5'-G120XG A120XA 120XGC | 3358 | 3359 |
| 120Y1 | 5'-G120YG ATA TGC | 2968 | 2969 |
| 120Y2 | 5'-GTG A120YA TGC | 2968 | 2969 |
| 120Y3 | 5'-GTG ATA 120YGC | 2968 | 2969 |
| 120Y4 | 3'-CAC 120YAT ACG | 2897 | 2898 |
| 120Y5 | 3'-CAC TA120Y ACG | 2897 | 2898 |
| 120Y6 | 3'-CAC 120YA120Y ACG | 3113 | 3114 |
| 120Y7 | 5'-G120YG A120YA 120YGC | 3400 | 3401 |
| 120Z1 | 5'-G120ZG ATA TGC | 3066 | 3067 |
| 120Z2 | 5'-GTG A120ZA TGC | 3066 | 3067 |
| 120Z3 | 5'-GTG ATA 120ZGC | 3066 | 3067 |
| 120Z4 | 3'-CAC 120ZAT ACG | 2995 | 2996 |
| 120Z5 | 3'-CAC TA120Z ACG | 2995 | 2996 |
| 120Z6 | 3'-CAC 120ZA120Z ACG | 3309 | 3310 |
| 120Z7 | 5'-G120ZG A120ZA 120ZGC | 3694 | 3695 |

TABLE 40

MALDI-MS of Representative Single-Stranded Probes Modified with Monomers 120Q/S/V

| ONs | Sequence | Calc. m/z [M] | Found m/z [M + H] |
|---|---|---|---|
| 120Q1 | 5'-G120QG ATA TGC | 2982 | 2983 |
| 120Q2 | 5'-GTG A120QA TGC | 2982 | 2983 |
| 120Q4 | 3'-CAC 120QAT ACG | 2911 | 2912 |
| 120Q5 | 3'-CAC TA120Q ACG | 2911 | 2912 |
| 120Q6 | 3'-CAC 120QA120Q ACG | 3140 | 3141 |
| 120S1 | 5'-G120SG ATA TGC | 2996 | 2997 |
| 120S2 | 5'-GTG A120SA TGC | 2996 | 2997 |
| 120S4 | 3'-CAC 120SAT ACG | 2925 | 2926 |
| 120S5 | 3'-CAC TA120S ACG | 2925 | 2926 |
| 120S6 | 3'-CAC 120SA120S ACG | 3168 | 3169 |

TABLE 40-continued

MALDI-MS of Representative Single-Stranded Probes Modified with Monomers 120Q/S/V

| ONs | Sequence | Calc. m/z [M] | Found m/z [M + H] |
|---|---|---|---|
| 120V1 | 5'-G120VG ATA TGC | 3009 | 3010 |
| 120V2 | 5'-GTG A120VA TGC | 3009 | 3010 |
| 120V4 | 3'-CAC 120VAT ACG | 2938 | 2939 |
| 120V5 | 3'-CAC TA120V ACG | 2938 | 2939 |
| 120V6 | 3'-CAC 120VA120VACG | 3195 | 3196 |

TABLE 41

MS-Data of Representative Single-Stranded Probes Modified with Monomer 120'W (=M).[a]

| ONs | Sequence | Calc. m/z | Found m/z |
|---|---|---|---|
| 120'W6 | 5'-GTG MTA TGC | 2984 | 2984 |
| 120'W7 | 5'-GTG ATM TGC | 2984 | 2984 |
| 120'W8 | 3'-CAC TMT ACG | 2913 | 2913 |
| 120'W9 | 3'-CAC TAT MCG | 2913 | 2914 |

TABLE 42

MS-Data of Representative Single-Stranded Probes Modified with Monomer 208W/X/Y/Z[a]

| ONs | expected mass | observed mass [M + H] |
|---|---|---|
| 5'-GTG A(208W)A TGC | 3038 | 3039 |
| 3'-CAC TA(208W) ACG | 2967 | 2968 |
| 5'-GTG A(208X)A TGC | 3046 | 3046 |
| 3'-CAC TA(208X) ACG | 2975 | 2975 |
| 5'-GTG A(208Y)A TGC | 2982 | 2983 |
| 3'-CAC TA(208Y) ACG | 2911 | 2912 |
| 5'-GTG A(208Z)A TGC | 3054 | 3056 |
| 3'-CAC TA(208Z) ACG | 2983 | 2984 |

TABLE 43

MS-Data of Representative Single-Stranded Probes Modified with Monomer 228Y/Z[a]

| Probe | Calc [M] | Found [M + 1] |
|---|---|---|
| 5'-GTG A(228Y)A TGC | 3031.6 | 3032.4 |
| 3'-CAC TA(228Y) ACG | 2960.6 | 2961.4 |
| 5'-GTG A(228Z)A TGC | 3079.6 | 3079.6 |
| 3'-CAC TA(228Z) ACG | 3008.6 | 3010.5 |

TABLE 44

MS-Data of Additional Single-Stranded Probes Modified with Monomer 120Y

| Probes | Expected mass | Observed [M + H] |
|---|---|---|
| 5'-GG(120Y) ATA TAT AGG C (SEQ ID NO: 38) | 4227 | 4228 |
| 3'-CCA (120Y)AT ATA TCC G (SEQ ID NO: 136) | 4107 | 4108 |
| 5'-GGT A(120Y)A TAT AGG C (SEQ ID NO: 40) | 4227 | 4228 |
| 3'-CCA TA(120Y) ATA TCC G (SEQ ID NO: 137) | 4107 | 4108 |
| 5'-GGT ATA (120Y)AT AGG C (SEQ ID NO: 42) | 4227 | 4228 |
| 3'-CCA TAT A(120Y)A TCC G (SEQ ID NO: 138) | 4107 | 4108 |
| 5'-GGT ATA TA(120Y) AGG C (SEQ ID NO: 44) | 4227 | 4228 |
| 3'-CCA TAT ATA (120Y)CC G (SEQ ID NO: 139) | 4107 | 4108 |
| 5'-GG(120Y) A(120Y)A TAT AGG C (SEQ ID NO: 46) | 4443 | 4444 |
| 3'-CCA (120Y)A(120Y) ATA TCC G (SEQ ID NO: 140) | 4323 | 4324 |
| 5'-GG(120Y) ATA (120Y)AT AGG C (SEQ ID NO: 48) | 4443 | 4444 |
| 3'-CCA (120Y)AT A(120Y)A TCC G (SEQ ID NO: 141) | 4323 | 4324 |
| 5'-GG(120Y) ATA TA(120Y) AGG C (SEQ ID NO: 50) | 4443 | 4444 |
| 3'-CCA (120Y)AT ATA (120Y)CC G (SEQ ID NO: 142) | 4323 | 4324 |
| 5'-GGT A(120Y)A (120Y)AT AGG C (SEQ ID NO: 52) | 4443 | 4444 |
| 3'-CCA TA(120Y) A(120Y)A TCC G (SEQ ID NO: 143) | 4323 | 4324 |
| 5'-GGT ATA (120Y)A(120Y) AGG C (SEQ ID NO: 54) | 4443 | 4444 |
| 3'-CCA TAT A(120Y) A(120Y)CC G (SEQ ID NO: 144) | 4323 | 4324 |
| 5'-GG(120Y) A(120Y)A (120Y)A(120Y) AGG C (SEQ ID NO: 56) | 4875 | 4876 |
| 3'-CCA (120Y)A(120Y) A(120Y)A (120Y)CC G (SEQ ID NO: 145) | 4755 | 4757 |

TABLE 45

MS-Data of Additional Single-Stranded Probes Modified with Monomer 120'W

| Probe | Expected mass | Observed Mass [M + H] |
|---|---|---|
| 3'-CC(120'W) TAT ATA TCC G (SEQ ID NO: 255) | 4121 | 4122 |
| 3'-CCA T(120'W)T ATA TCC G (SEQ ID NO: 256) | 4121 | 4122 |
| 3'-CCA TAT (120'W)TA TCC G (SEQ ID NO: 257) | 4121 | 4122 |
| 3'-CCA TAT AT(120'W) TCC G (SEQ ID NO: 258) | 4121 | 4123 |
| 3'-CC(120'W) T(120'W)T ATA TCC G (SEQ ID NO: 259) | 4351 | 4352 |
| 3'-CC(120'W) TAT (120'W)TA TCC G (SEQ ID NO: 260) | 4351 | 4352 |

TABLE 45-continued

MS-Data of Additional Single-Stranded Probes Modified with Monomer 120'W

| Probe | Expected mass | Observed Mass [M + H] |
|---|---|---|
| 3'-CC(120'W) TAT AT(120'W) TCC G (SEQ ID NO: 261) | 4351 | 4353 |
| 3'-CCA T(120'W)T (120'W)TA TCC G (SEQ ID NO: 262) | 4351 | 4353 |
| 3'-CCA TAT (120'W)T(120'W) TCC G (SEQ ID NO: 263) | 4351 | 4352 |
| 3'-CC(120'W) T(120'W)T (120'W)T(120'W) TCC G (SEQ ID NO: 264) | 4812 | 4813 |

TABLE 46

MS-Data of Even Further Additional Single-Stranded Probes Modified with Monomer 120Y

| Probe | Expected mass | Observed Mass [M + H] |
|---|---|---|
| 5'-G-G(120Y)A-TAT-AAG-CAG-CAC-A (SEQ ID NO: 146) | 5440 | 5441 |
| 3'-C-CA(120Y)-ATA-TTC-GTC-GTG-T (SEQ ID NO: 59) | 5364 | 5365 |
| 5'-G-G(120Y)A-(120Y)AT-AAG-CAG-CAC-A (SEQ ID NO: 148) | 5657 | 5658 |
| 3'-C-CA(120Y)-A(120Y)A-TTC-GTC-GTG-T (SEQ ID NO: 61) | 5580 | 5582 |
| 5'-AGG-AAG-G(120Y)A-(120Y)AT-AAG-CA (SEQ ID NO: 150) | 5721 | 5722 |
| 3'-TCC-TTC-CA(120Y)-A(120Y)A-TTC-GT (SEQ ID NO: 63) | 5515 | 5516 |
| 5'-G-G(120Y)A-(120Y)AT-AAG-CAG-C (SEQ ID NO: 60) | 4741 | 4742 |
| 3'-C-CA(120Y)-A(120Y)A-TTC-GTC-G (SEQ ID NO: 181) | 4643 | 4684 |
| 5'-AC(120Y)-A(120Y)A-GAA-TAC-TCA-AG (SEQ ID NO: 152) | 5616 | 5617 |
| 3'-TGA-(120Y)A(120Y)-CTT-ATG-AGT-TC (SEQ ID NO: 153) | 5620 | 5621 |
| 5'-AC(120Y)-A(120Y)A-GAA-TAC-TC (SEQ ID NO: 182) | 4660 | 4661 |
| 3'-TGA-(120Y)A(120Y)-CTT-ATG-AG (SEQ ID NO: 183) | 4722 | 4723 |

TABLE 47

MS-Data of Even Further Single-Stranded Probes Modified with Monomer 120Q

| Probe | Calc [M] | Found [M + H] |
|---|---|---|
| 5'-GG(120Q) ATA TAT AGG C (SEQ ID NO: 184) | 4240.8 | 4242.5 |
| 3'-CCA (120Q)AT ATA TCC G (SEQ ID NO: 185) | 4120.8 | 4122.6 |

TABLE 47-continued

MS-Data of Even Further Single-Stranded Probes Modified with Monomer 120Q

| Probe | Calc [M] | Found [M + H] |
|---|---|---|
| 5'-GG(120Q) A(120Q)A TAT AGG C (SEQ ID NO: 186) | 4469.9 | 4471.5 |
| 3'-CCA (120Q)A(120Q) ATA TCC G (SEQ ID NO: 187) | 4349.9 | 4351.6 |
| 5'-GGT A(120Q)A (120Q)AT AGG C (SEQ ID NO: 188) | 4469.9 | 4471.9 |
| 3'-CCA TA(120Q) A(120Q)A TCC G (SEQ ID NO: 189) | 4349.9 | 4351.4 |
| 5'-GG(120Q) A(120Q)A (120Q)A(120Q) AGG C (SEQ ID NO: 190) | 4928.1 | 4929.7 |
| 3'-CCA (120Q)A(120Q) A(120Q)A (120Q)CC G (SEQ ID NO: 251) | 4808.1 | 4810.5 |

TABLE 48

MS-Data of Yet Even Further Additional Single-Stranded Probes Modified with Monomer 120Q

| Probe | Expected mass | Observed Mass [M + H] |
|---|---|---|
| 5'-G-G(120Q)A-TAT-AAG-CAG-CAC-A (SEQ ID NO: 154) | 5454 | 5455 |
| 3'-C-CA(120Q)-ATA-TTC-GTC-GTG-T (SEQ ID NO: 155) | 5377 | 5378 |
| 5'-G-G(120Q)A-(120Q)AT-AAG-CAG-CAC-A (SEQ ID NO: 156) | 5683 | 5684 |
| 3'-C-CA(120Q)-A(120Q)A-TTC-GTC-GTG-T (SEQ ID NO: 157) | 5607 | 5608 |
| 5'-AGG-AAG-G(120Q)A-(120Q)AT-AAG-CA (SEQ ID NO: 158) | 5747 | 5749 |
| 3'-TCC-TTC-CA(120Q)-A(120Q)A-TTC-GT (SEQ ID NO: 159) | 5542 | 5543 |
| 5'-AC(120Q)-A(120Q)A-GAA-TAC-TCA-AG (SEQ ID NO: 160) | 5642 | 5646 |
| 3'-TGA-(120Q)A(120Q)-CTT-ATG-AGT-TC (SEQ ID NO: 161) | 5646 | 5648 |

TABLE 49

MS-Data of Even Further Additional Single-Stranded Probes Modified with Monomer 120Y, 120'W and 140'X

| Probe | Expected mass | Observed Mass [M + H] |
|---|---|---|
| 5'-CC(140'X) ACG T(120Y)A GCA GTT (SEQ ID NO: 72) | 4971 | 4973 |
| 3'-GGG (120Y)GC AA(120Y) CGT CAA (SEQ ID NO: 73) | 5046 | 5047 |
| 5'-CCC ACG T(120Y)A G(140'X)A GTT (SEQ ID NO: 74) | 4971 | 4972 |
| 3'-GGG TGC AA(120Y) CG(120Y) CAA (SEQ ID NO: 75) | 5046 | 5047 |

TABLE 49-continued

MS-Data of Even Further Additional Single-Stranded Probes Modified with Monomer 120Y, 120'W and 140'X

| Probe | Expected mass | Observed Mass [M + H] |
|---|---|---|
| 5'-AGA CAA AA(140'X) AC(140'X) AGT (SEQ ID NO: 76) | 5020 | 5021 |
| 3'-TCT GTT TTG (120Y)GG (120Y)CA (SEQ ID NO: 77) | 5009 | 5010 |
| 5'-AGA (140'X)AA AA(140'X) ACC AGT (SEQ ID NO: 78) | 5020 | 5021 |
| 3'-TCT G(120Y)T TTG (120Y)GG TCA (SEQ ID NO: 79) | 5009 | 5011 |
| 5'-CTA (140'X)AT (120Y)GT CTC GCC (SEQ ID NO: 80) | 4922 | 4923 |
| 3'-GAT G(120Y)A A(140'X)A GAG CGG (SEQ ID NO: 81) | 5109 | 5110 |
| 5'-CTA C(120'W)T (120Y)GT CTC GCC (SEQ ID NO: 82) | 4922 | 4923 |
| 3'-GAT GT(120'W) A(140'X)A GAG CGG (SEQ ID NO: 83) | 5123 | 5124 |
| 5'-CGT (140'X)AT CG(120Y) GCT CGC (SEQ ID NO: 84) | 4963 | 4965 |
| 3'-GCA G(120Y)A GCA (140'X)GA GCG (SEQ ID NO: 85) | 5070 | 5071 |

TABLE 50

MS-Data of Yet Even Further Additional Single-Stranded Probes Modified with Monomers 120Y, 120'W, 140'X and 140'Y

| Probes | Expected mass | Observed Mass [M + H] |
|---|---|---|
| 5'-CGG ACC ACG (120Y)G(120Y) GTG (SEQ ID NO: 94) | 5038 | 5040 |
| 3'-GCC TGG TGC A(140'X)A (140'X)AC (SEQ ID NO: 95) | 4995 | 4996 |
| 5'-CGG AC(140'X) ACG TG(120Y) GTG (SEQ ID NO: 96) | 5052 | 5053 |
| 3'-GCC TGG (120Y)GC ACA (140'X)AC (SEQ ID NO: 97) | 4981 | 4982 |
| 5'-GT(140'X) AG(120Y) GGG CGT TGC (SEQ ID NO: 98) | 5083 | 5084 |
| 3'-CAG (120Y)CA (140'X)CC GCA ACG (SEQ ID NO: 99) | 4950 | 4951 |
| 5'-GT(140'X) AG(120Y) GGG CG(120Y) TGC (SEQ ID NO: 100) | 5299 | 5299 |
| 3'-CAG (120Y)CA (140'X)CC GCA (120'W)CG (SEQ ID NO: 101) | 5181 | 5182 |
| 5'-CCT C(120Y)A (120Y)AA AAG CGG (SEQ ID NO: 102) | 4990 | 4991 |
| 3'-GGA GA(120Y) A(120Y)T TTC GCC (SEQ ID NO: 103) | 5012 | 5013 |
| 5'-CC(120Y) C(120Y)A (120Y)AA AAG CGG (SEQ ID NO: 104) | 5206 | 5208 |
| 3'-GGA (140'Y)A(120Y) A(120Y)T TTC GCC (SEQ ID NO: 105) | 5242 | 5244 |

TABLE 51

MS-Data of Yet Even Further More Additional Single-Stranded Probes Modified with Monomer 120Y, 120'W, 140'X and 140'Y

| 5'-Cy3 labeled probes | Expected mass | Observed mass [M + H] |
|---|---|---|
| 5'-AGC CC(120Y) G(120Y)G CCC TG (SEQ ID NO: 112) | 5522 | 5523 |
| 3'-TCG GGA (140'X)A(140'X) GGG AC (SEQ ID NO: 113) | 5495 | 5496 |
| 5'-CC(120Y) G(120Y)G CCC TG (SEQ ID NO: 114) | 5390 | 5391 |
| 3'-GGA (140'X)A(140'X) GGG AC (SEQ ID NO: 115) | 6075 | 6076 |
| 5'-CC(120Y) GTG CC(140'X) TG (SEQ ID NO: 116) | 5713 | 5714 |
| 3'-GGA (140'X)AC GGG (120'W)C (SEQ ID NO: 117) | 5922 | 5923 |
| 5'-(120'W)GC CC(120Y) GTG CC(140'X) TG (SEQ ID NO: 118) | 5508 | 5509 |
| 3'-T(140'X)G GGA (140'X)AC GGG (120'W)C (SEQ ID NO: 119) | 6520 | 5621 |
| 5'-C(120Y)G (120'W)GC CC(120Y) G(120Y)G CCC (120Y)G-3' (SEQ ID NO: 120) | 6697 | 6696 |
| 3'-GA(140'Y) T(140'X)G GGA (140'X)A(140'X) GGG A(140'X)-5' (SEQ ID NO: 121) | 6940 | 6941 |
| 5'-(120'W)GC CC(120Y) G(120Y)G CCC (120Y)G-3' (SEQ ID NO: 122) | 5599 | 5600 |
| 3'-T(140'X)G GGA (140'X)A(140'X) GGG A(140'X)-5' (SEQ ID NO: 123) | 5739 | 5740 |

Thermal Denaturation Studies involving probes modified with 120W/X/Y/Z, 120Q/S/V, 120'W, 120'X, 140'X, 140'Y, 208W/X/Y/Z, 228Y/Z and 244:

Concentrations of oligonucleotides were estimated using the following extinction coefficients for DNA (OD/μmol): G (12.01), A (15.20), T (8.40), C (7.05); for RNA (OD/μmol): G (13.70), A (15.40), U (10.00), C (9.00); for fluorophores (OD/μmol): naphthalene (3.75), pyrene (22.4), and coronene (36.0). Each strand was thoroughly mixed and denatured by heating to 70-85° C. followed by cooling to the starting temperature of the experiment. Quartz optical cells with a path length of 1.0 cm were used. Thermal denaturation temperatures ($T_m$ values [° C.]) of duplexes (1.0 M final concentration of each strand) were measured on a UV/VIS spectrophotometer equipped with a 12-cell Peltier temperature controller and determined as the maximum of the first derivative of the thermal denaturation curve ($A_{260}$ VS. 7) recorded in medium salt buffer ($T_m$ buffer: 100 mM NaCl, 0.1 mM EDTA, and pH 7.0 adjusted with 10 mM $Na_2HPO_4$ and 5 mM $Na_2HPO_4$). The temperature of the denaturation experiments ranged from at least 15° C. below $T_m$ to 20° C. above $T_m$ (although not below 1° C.). A temperature ramp of 0.5° C./min was used in all experiments. Reported $T_m$-values are averages of two experiments within ±1.0° C.

In particular disclosed embodiments, single-stranded probes modified with monomers 120W/X/Y/Z or 120 Q/S/V, display varying trends in thermal affinity toward complementary RNA ($\Delta T_m$/mod=-12.0° C. to +10.5° C., Table 52 Substantial DNA-selectivity, defined as $\Delta\Delta T_m$ (DNA-RNA)=$\Delta T_m$ (vs DNA)-$\Delta T_m$ (vs RNA)>0° C., is observed for these probes (Table 53). The DNA-selectivity of probes modified with unlocked monomers 120Y and 120Z is especially pronounced and comparable to that of probes modified with locked monomer 126W (Table 53). This suggests that interesting DNA-targeting applications are possible. DNA-selective hybridization is typically observed for oligonucleotides modified with intercalating moieties, since intercalation favors the less compressed helix geometry of DNA:DNA duplexes. In contrast, the majority of probes modified with monomers 120X or 120W display much lower DNA selectivity, indicating that intercalative binding modes are less prominent than in probes modified with monomer 120Y and 120Z (Table 53).

acid targets with mismatched nucleotides opposite of the monomer-incorporation site. Certain disclosed embodiments concern using single-stranded probes and their ability to associate with DNA (Table 54) or RNA targets (Table 55) comprising mismatched nucleotides opposite of the incorporation site.

The B2-series probes generally displayed reduced DNA target specificity relative to reference strand D1. For example, 120Y2 and 120Z2 discriminate dT-mismatches very poorly relative to D1 (compare $\Delta T_m$-values for D1/120Y2/120Z2 against targets with a dT-mismatch, Table

TABLE 52

$T_m$-Values of Duplexes between Probe Modified with Monomers 120W/X/Y/Z/Q/S/V Or 126W and Complementary RNA Targets

| | | | | $T_m$ [$\Delta T_m$/mod] (° C.) | | | | | | |
|---|---|---|---|---|---|---|---|---|---|---|
| ON Duplex | | B = | T | 120W | 120X | 120Y | 120Z | 120Q | 120S | 120V | 126W |
| B1 5'-GBG ATA TGC<br>R2 3'-CAC UAU ACG | | | 26.5 | 21.0<br>[−5.5] | 22.5<br>[−4.0] | 24.5<br>[−2.0] | 21.5<br>[−5.0] | 22.0<br>[−4.5] | 14.0<br>[−12.5] | 20.0<br>[−6.5] | 27.0<br>[+0.5] |
| B2 5'-GTG ABA TGC<br>R2 3'-CAC UAU ACG | | | 26.5 | 16.0<br>[−10.5] | 22.5<br>[−4.0] | 30.5<br>[+4.0] | 37.0<br>[+10.5] | 29.0<br>[+2.5] | 18.0<br>[−8.5] | 28.0<br>[+1.5] | 31.5<br>[+5.0] |
| B3 5'-GTG ATA BGC<br>R2 3'-CAC UAU ACG | | | 26.5 | 18.0<br>[−8.5] | 14.5<br>[−12.0] | 26.5<br>[±0.0] | 30.5<br>[+4.0] | ND | ND | ND | 28.0<br>[+1.5] |
| R1 5'-GUG AUA UGC<br>B4 3'-CAC BAT ACG | | | 24.5 | 16.5<br>[−8.0] | 16.5<br>[−8.0] | 20.0<br>[−4.5] | 22.5<br>[−2.0] | 17.5<br>[−7.0] | 9.0<br>[−15.5] | 16.0<br>[−8.5] | 23.5<br>[−1.0] |
| R1 5'-GUG AUA UGC<br>B5 3'-CAC TAB ACG | | | 24.5 | 19.5<br>[−5.0] | 21.5<br>[−3.0] | 27.0<br>[+2.5] | 30.5<br>[+6.0] | 27.0<br>[+2.5] | 16.0<br>[−8.5] | 26.5<br>[+2.0] | 32.0<br>[+7.5] |
| R1 5'-GUG AUA UGC<br>B6 3'-CAC BAB ACG | | | 24.5 | ND | 14.5<br>[−5.0] | 24.0<br>[−0.3] | 11.0<br>[−6.8] | 20.0<br>[−2.3] | ND | 19.0<br>[−2.8] | ND |
| B7 5'-GBG ABA BGC<br>D2 3'-CAC UAU ACG | | | 26.5 | ND | 15.5<br>[−3.7] | 27.5<br>[+0.3] | ND | ND | ND | ND | ND |

TABLE 53

DNA-Selectivity of Probes Modified With Monomers 120W/X/Y/Z/Q/S/V or 126W

| | | | $\Delta\Delta T_m$ (DNA-RNA) [° C.] | | | | | | |
|---|---|---|---|---|---|---|---|---|---|
| ON Duplex | | B = | 120W | 120X | 120Y | 120Z | 120Q | 120S | 120V | 126W |
| B1 5'-GBG ATA TGC<br>D2 3'-CAC TAT ACG | | | −2.5 | +1.0 | +7.0 | +9.5 | +9.5 | +6.5 | +6.0 | +6.5 |
| B2 5'-GTG ABA TGC<br>D2 3'-CAC TAT ACG | | | +5.5 | +8.0 | +8.5 | +9.5 | +11.5 | +11.5 | +4.5 | +9.0 |
| B3 5'-GTG ATA BGC<br>D2 3'-CAC TAT ACG | | | +3.5 | +8.5 | +8.0 | +7.0 | ND | ND | ND | +9.0 |
| D1 5'-GTG ATA TGC<br>B4 3'-CAC BAT ACG | | | +5.0 | +4.5 | +8.0 | +8.5 | +8.5 | +9.5 | +9.5 | +7.5 |
| D1 5'-GTG ATA TGC<br>B5 3'-CAC TAB ACG | | | 0 | +4.0 | +9.0 | +10.0 | +10.5 | +12.5 | +4.5 | +8.0 |
| D1 5'-GTG ATA TGC<br>B6 3'-CAC BAB ACG | | | ND | +6.0 | +14.5 | +31.0 | +18.5 | ND | +13.0 | ND |
| B7 5'-GBG ABA BGC<br>D2 3'-CAC TAT ACG | | | ND | +7.0 | +20.5 | ND | ND | ND | ND | ND |

[a]DNA selectivity defined as $\Delta\Delta T_m$ (DNA-RNA) = $\Delta T_m$ (vs DNA) − $\Delta T_m$ (vs RNA).

The Watson-Crick specificity the disclosed probes may also be determined. In particular disclosed embodiments, modified oligonucleotides may be evaluated using nucleic acid targets with mismatched nucleotides opposite of the monomer-incorporation site. Certain disclosed embodiments concern using single-stranded probes and their ability to associate with DNA (Table 54) or RNA targets (Table 55) comprising mismatched nucleotides opposite of the incorporation site.

X) while dC- and dG-mismatches almost are as efficiently discriminated as with D1. Particular disclosed embodiments of oligonucleotides comprising locked monomers had a similar specificity profile but discriminated the dT-mismatch even more poorly. Interestingly, 120Q2 displays substantially better discrimination of dC- and dT-mismatches than 120Y2, 120Z2 and 126W2 rendering it as the most specific of the high-affinity DNA-targeting modifications. In particular disclosed embodiments, even minor changes in linker chemistry and length have marked influence on target specificity. For example, 120S2 displays similar DNA target specificity as 120Y2/120Z2/126W2, while 120V2 discriminates DNA mismatches more poorly. Similarly, 120W2 exhibits very poor target specificity, while 120X2 displays much higher target specificity than 120W2 or 120Y2 (Table 54).

TABLE 54

Discrimination of Mismatched DNA Targets by the B2-series of Single-stranded Probes.[a]

| | | | DNA: 3'-CAC TBT ACG | | | |
|---|---|---|---|---|---|---|
| | | | $T_m$ [° C.] | $\Delta T_m$ [° C.] | | |
| ON | Sequence | B = | A | C | G | T |
| D1 | 5'-GTG ATA TGC | | 29.5 | −16.5 | −9.5 | −17.0 |
| 120W2 | 5'-GTG A(120W)A TGC | | 24.5 | −11.0 | +2.0 | −3.5 |
| 120X2 | 5'-GTG A(120X)A TGC | | 33.5 | <−23.5 | −7.0 | −13.0 |
| 120Y2 | 5'-GTG A(120Y)A TGC | | 42.0 | −13.0 | −5.0 | −6.5 |
| 120Z2 | 5'-GTG A(120Z)A TGC | | 49.0 | −13.5 | −6.0 | −7.0 |
| 120Q2 | 5'-GTG A(120Q)A TGC | | 43.5 | −22.0 | −3.5 | −12.0 |
| 120S2 | 5'-GTG A(120S)A TGC | | 32.5 | −11.5 | −9.0 | −8.5 |
| 120V2 | 5'-GTG A(120V)A TGC | | 35.5 | −11.5 | +1.5 | −3.5 |
| 126W2 | 5'-GTG A(126W)A TGC | | 43.5 | −12.5 | −5.5 | −3.5 |

[a]For conditions of thermal denaturation experiments, see Table 33 above. $T_m$-values of fully matched duplexes are shown in bold. $\Delta T_m$ = change in $T_m$ relative to fully matched DNA:DNA duplex.

TABLE 55

Discrimination of Mismatched RNA Targets by the B2-Series of Single-Stranded Probes[a]

| | | | RNA: 3'-CAC UBU ACG | | | |
|---|---|---|---|---|---|---|
| | | | $T_m$ [° C.] | $\Delta T_m$ [° C.] | | |
| ON | Probe | B = | A | C | G | U |
| D1 | 5'-GTG ATA TGC | | 26.5 | <−16.5 | −4.5 | <−16.5 |
| 120W2 | 5'-GTG A(120W)A TGC | | 16.0 | −1.0 | +0.5 | +6.0 |
| 120X2 | 5'-GTG A(120X)A TGC | | 22.5 | −11.5 | −5.0 | <−12.5 |
| 120Y2 | 5'-GTG A(120Y)A TGC | | 31.0 | −17.5 | −3.5 | −9.5 |
| 120Z2 | 5'-GTG A(120Z)A TGC | | 37.0 | −12.0 | −9.0 | −13.0 |
| 120Q2 | 5'-GTG A(120Q)A TGC | | 29.0 | −16.5 | −0.5 | −13.0 |
| 120S2 | 5'-GTG A(120S)A TGC | | 18.0 | <−8.5 | −6.0 | −6.0 |
| 120V2 | 5'-GTG A(120V)A TGC | | 28.0 | −16.5 | −1.0 | −7.5 |
| 126W2 | 5'-GTG A(126W)A TGC | | 31.5 | −12.0 | −1.0 | −4.5 |

[a]For conditions of thermal denaturation experiments, see Table 33 above. $T_m$-values of fully matched duplexes are shown in bold. $\Delta T_m$ = change in $T_m$ relative to fully matched DNA:RNA duplex.

Figure 8:
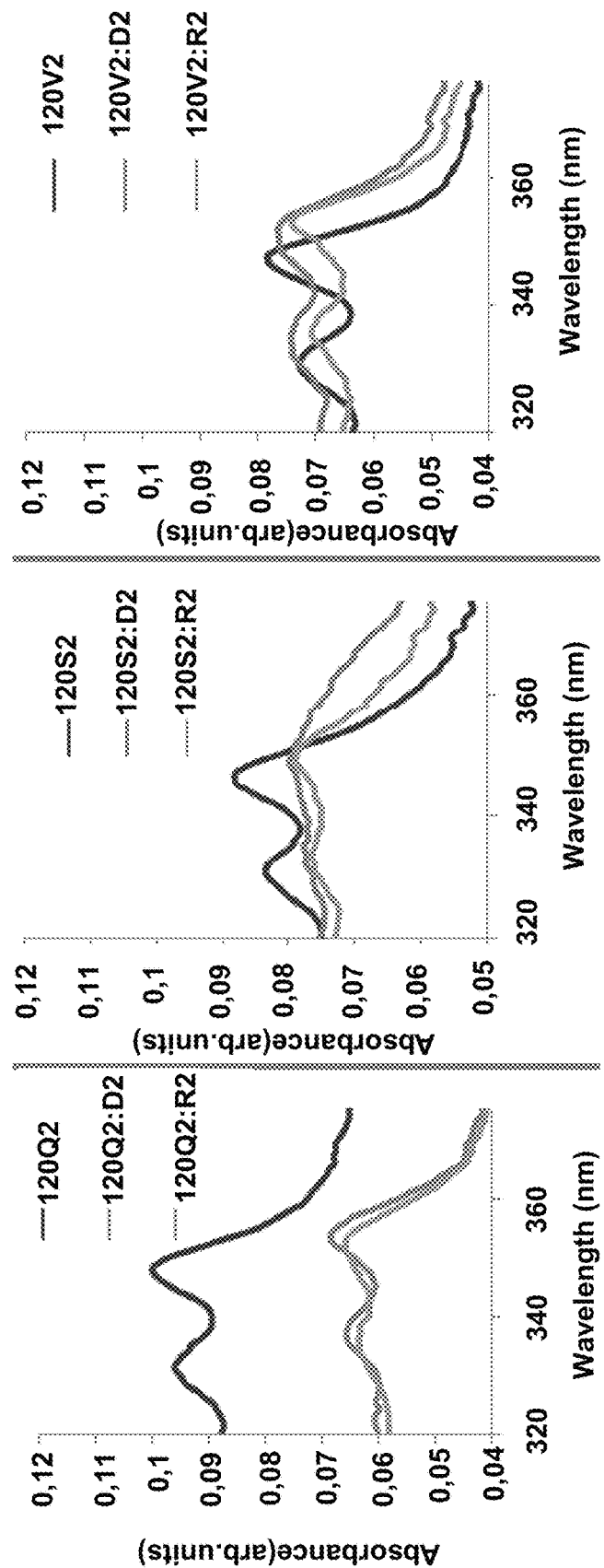
FIG. 8 are absorption spectra obtained from an exemplary probe embodiment and the duplexes formed with a nucleic acid targets.
Figure 9:
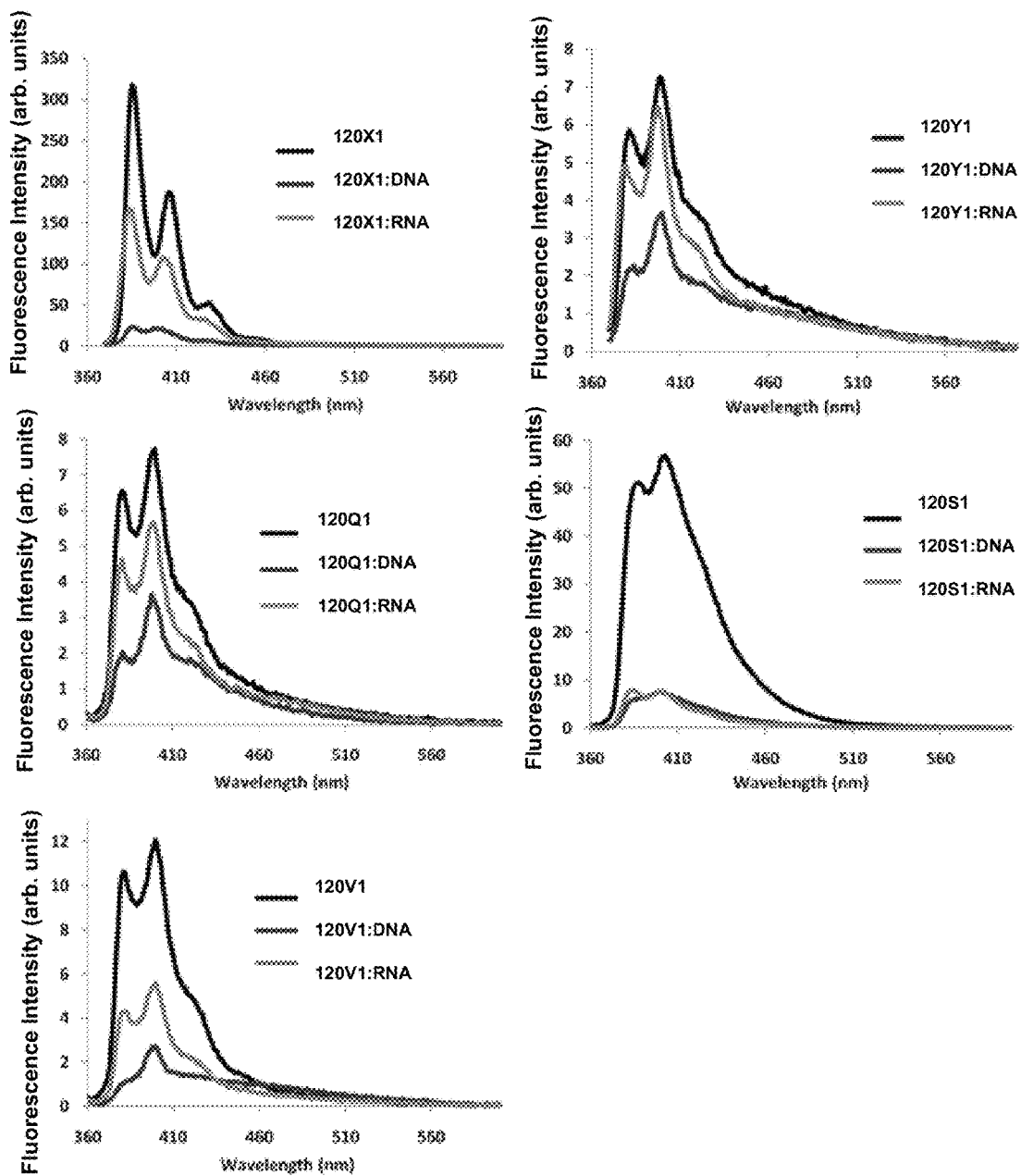
FIG. 9 are fluorescence emission spectra of an exemplary probe embodiment in the presence or absence of a nucleic acid target.
Figure 10:
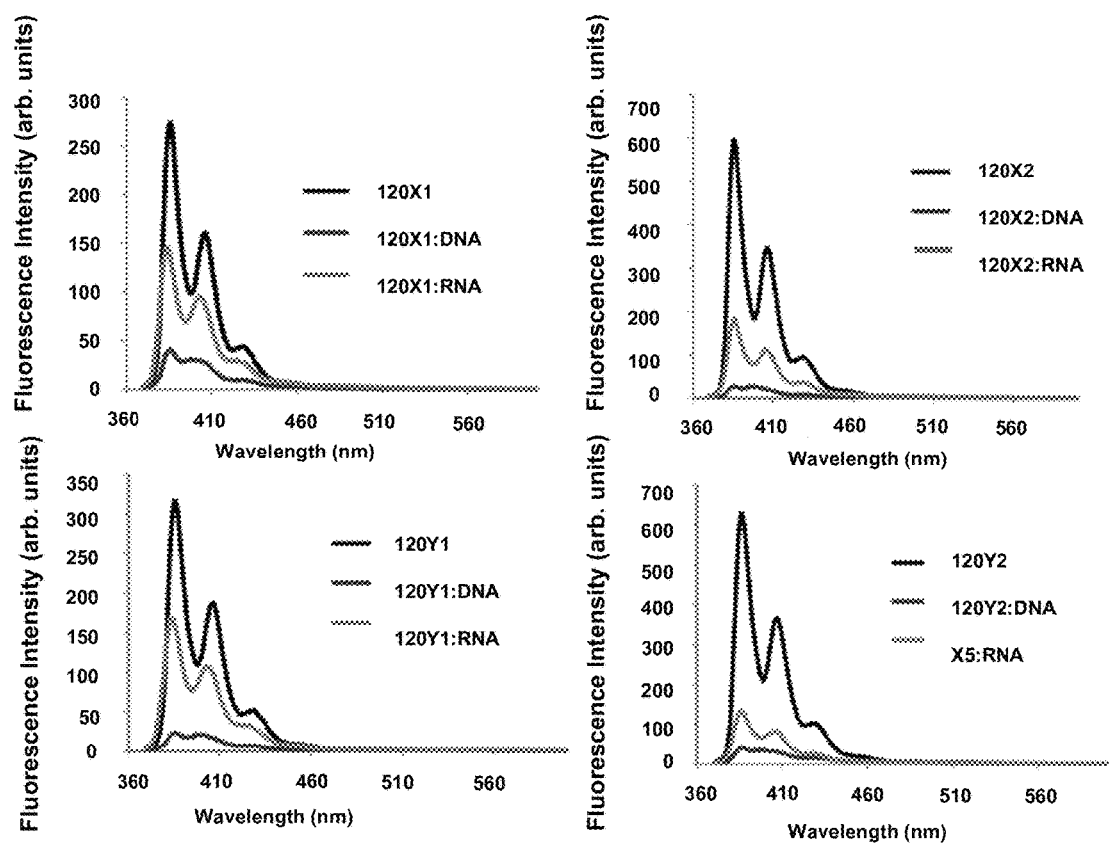
FIG. 10 are fluorescence emission spectra of an exemplary probe embodiment in the presence or absence of a nucleic acid target.
Figure 11:
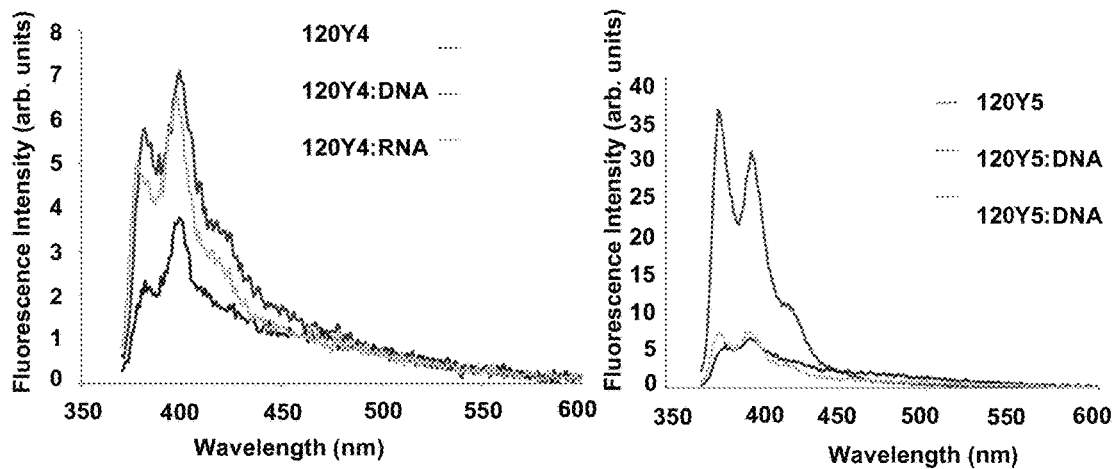
FIG. 11 are fluorescence emission spectra of an exemplary probe embodiment in the presence or absence of a nucleic acid target.
Figure 12:
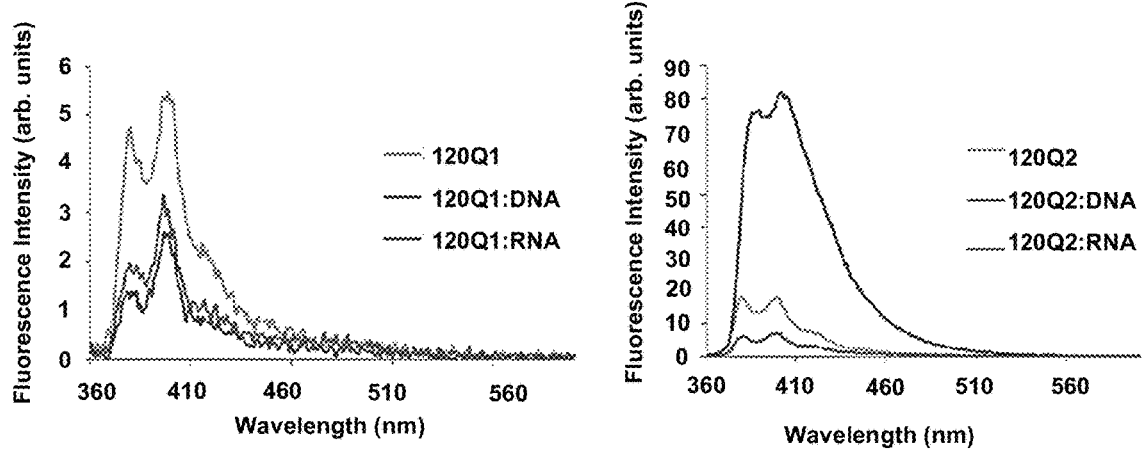
FIG. 12 are fluorescence emission spectra of an exemplary probe embodiment in the presence or absence of a nucleic acid target.
Figure 13:
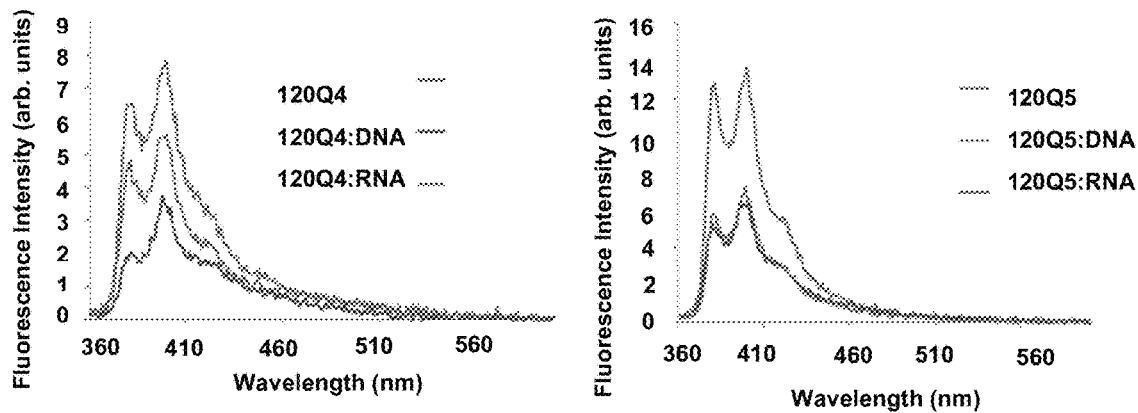
FIG. 13 are fluorescence emission spectra of an exemplary probe embodiment in the presence or absence of a nucleic acid target.
Figure 14:
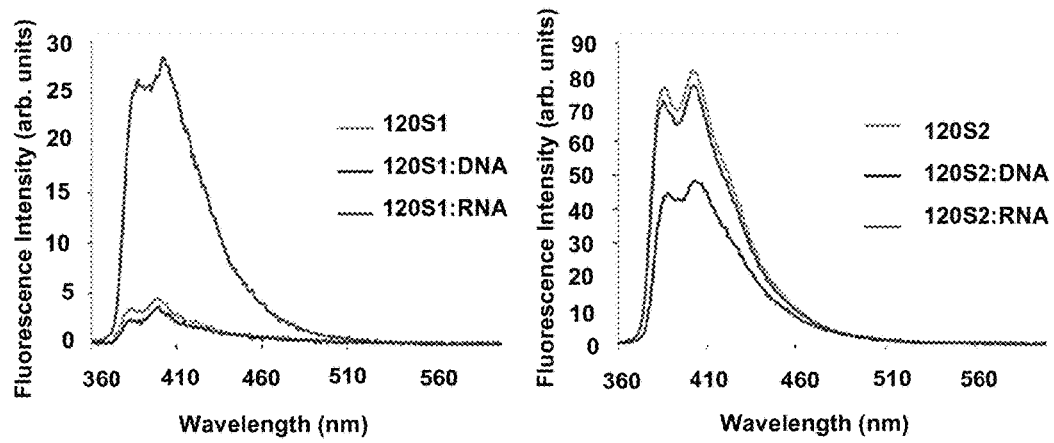
FIG. 14 are fluorescence emission spectra of an exemplary probe embodiment in the presence or absence of a nucleic acid target.
Figure 15:
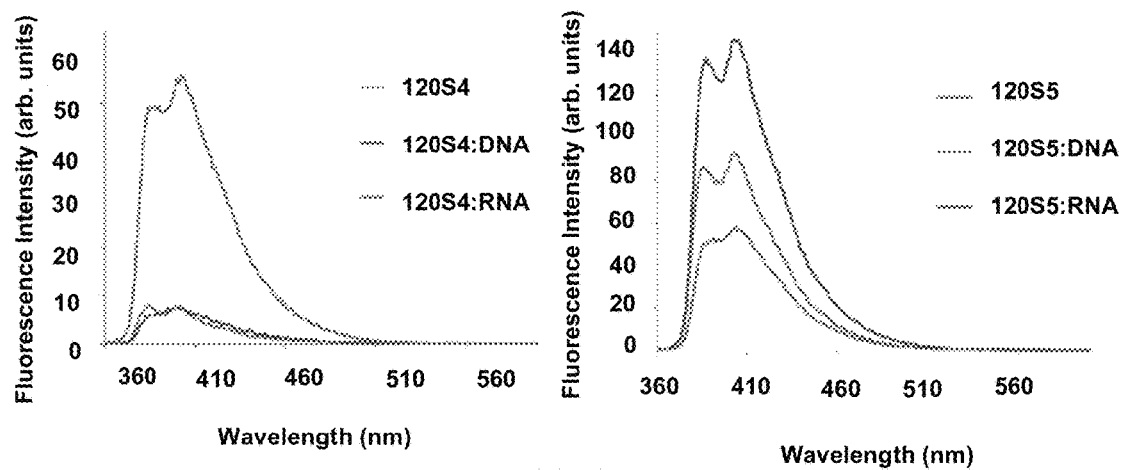
FIG. 15 are fluorescence emission spectra of an exemplary probe embodiment in the presence or absence of a nucleic acid target.
Figure 16:
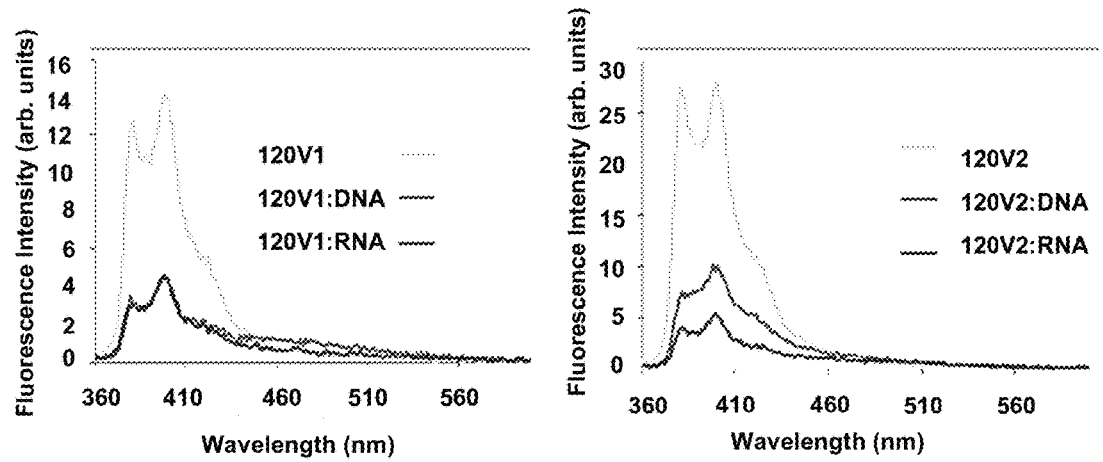
FIG. 16 are fluorescence emission spectra of an exemplary probe embodiment in the presence or absence of a nucleic acid target.
Figure 17:
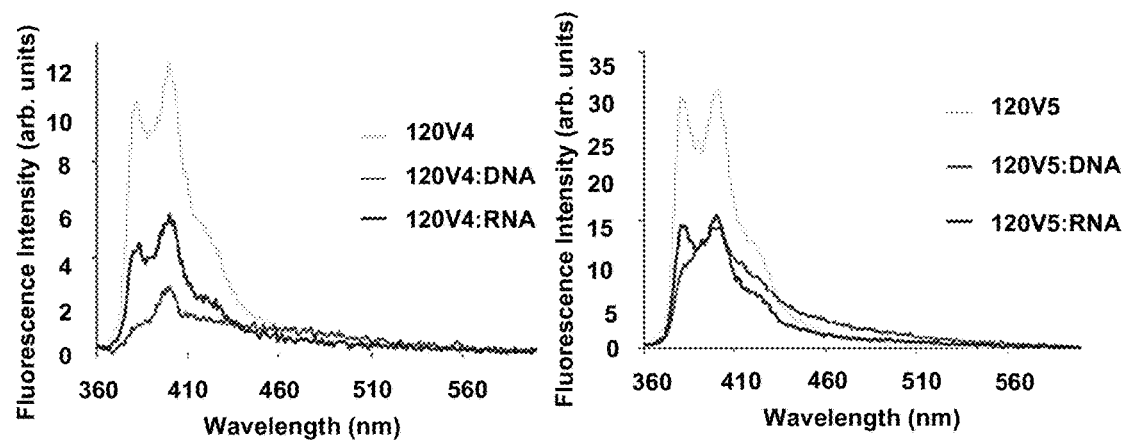
FIG. 17 are fluorescence emission spectra of an exemplary probe embodiment in the presence or absence of a nucleic acid target.

In other disclosed embodiments, the specificity of oligonucleotides with two modifications positioned as next-nearest neighbors (B6-series) were evaluated against nucleic acid (e.g. DNA) targets with a single central mismatched nucleotide opposite of the central 2'-deoxyadenosine residue (Table 56). Interestingly, this probe design generally resulted in improved mismatch discrimination relative to reference strand D2; A- and G-mismatches are particularly efficiently discriminated.

the intercalator (e.g. pyrene) moieties and/or presence of a matched or mismatched target. A person of ordinary skill in the art will recognize that intercalation of pyrene moieties is known to induce bathochromic shifts of pyrene absorption peaks. Particular embodiments of the disclosed probe, such as those modified with monomers 120Q/120S/120Y, display significant bathochromic shifts upon hybridization with nucleic acid (e.g. DNA) targets (average $\Delta\lambda_{max}$=2.8-5.0 nm vs 2.5 nm, respectively, Table 58 and FIG. 8. Hybridization

TABLE 56

Discrimination of Mismatched DNA Targets by B6-Series and Reference Strands[a]

| | | | DNA: 5'-GTG ABA ACG | | | |
|---|---|---|---|---|---|---|
| | | | $T_m$ [° C.] | $\Delta T_m$ [° C.] | | |
| ON | Sequence | B = | T | A | C | G |
| D2 | 3'-CAC TAT ACG | | 29.5 | -17.0 | -15.5 | -9.0 |
| 120X6 | 3'-CAC (120X)A(120X) ACG | | 25.5 | <-15.5 | -14.0 | -14.5 |
| 120Y6 | 3'-CAC (120Y)A(120Y) ACG | | 43.5 | -24.0 | -17.0 | -14.0 |
| 120Z6 | 3'-CAC (120Z)A(120Z) ACG | | 47.0 | -19.5 | -13.0 | -11.0 |
| 120Q6 | 3'-CAC (120Q)A(120Q) ACG | | 43.5 | -21.5 | -10.5 | -13.5 |
| 120V6 | 3'-CAC (120V)A(120V) ACG | | 37.0 | -14.5 | -13.5 | -11.0 |

[a]For conditions of thermal denaturation experiments, see Table 33 above. $T_m$-values of fully matched duplexes are shown in bold. $\Delta T_m$ = change in $T_m$ relative to fully matched DNA:DNA duplex.

Figure 7:
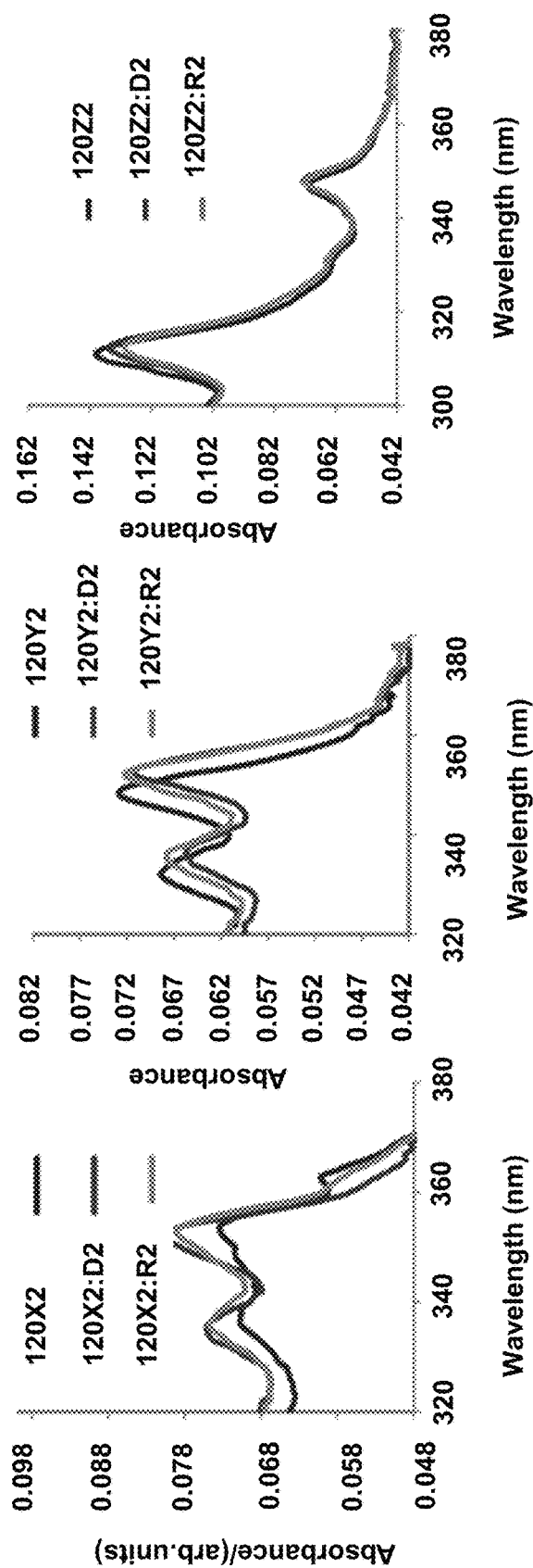
FIG. 7 are absorption spectra obtained from an exemplary embodiment and duplexes formed with a nucleic acid target.

In particular disclosed embodiments, the fluorescence characteristics of the disclosed probe can be examined, wherein an observed optical signal provides information regarding the probe and/or target. In particular disclosed embodiments, absorption and steady state fluorescence emission spectra of a probe comprising one or more of the disclosed monomers, such as monomers 120Q/120S/120V/120X/120Y, in the presence or absence of complementary or mismatched nucleic acid targets (e.g. DNA/RNA) were recorded to gain additional insight into the binding modes of with complementary RNA leads to smaller bathochromic shifts (average $\Delta\lambda_{max}$=2.0-4.5 nm, Table 58). Probes 120X1-120X5 display distinctly smaller hybridization-induced bathochromic shifts than the other pyrene-functionalized oligonucleotides (average $\Delta\lambda_{max}$~0.6 nm, Table 57 and FIG. 7), which substantiates the trends from thermal denaturation studies indicating that intercalation of the pyrene moiety is a less important binding mode for monomer 120X.

TABLE 57

Absorption Maxima in the 320-360 Nm Region for Probes Modified with Monomers 120X-120Z Or 126W in the Presence or Absence of Complementary DNA/RNA Targets[a]

| | | | $\lambda_{max}[\Delta\lambda_{max}]$ (nm) | | | | | | | | | | |
|---|---|---|---|---|---|---|---|---|---|---|---|---|---|
| | | | 120X | | | 120Y | | | 120Z | | | 126W | | |
| ON | Sequence | B = | ss | +DNA | +RNA | ss | +DNA | +RNA | ss | +DNA | +RNA | ss | +DNA | +RNA |
| B1 | 5'-GBG ATA TGC | | 349 | 352[+3] | 351[+2] | 350 | 353[+3] | 352[+2] | 347 | 348[+1] | 348[+1] | 348 | 350[+2] | 349[+1] |
| B2 | 5'-GTG ABA TGC | | 353 | 352[-1] | 352[±0] | 348 | 353[+5] | 352[+4] | 347 | 348[+1] | 348[+1] | 347 | 351[+4] | 349[+2] |
| B3 | 5'-GTG ATA BGC | | 352 | 352[±0] | 352[±0] | 350 | 353[+3] | 352[+2] | 348 | 348[±0] | 348[±0] | 348 | 351[+3] | 350[+2] |
| B4 | 3'-CAC BAT ACG | | 350 | 352[+2] | 352[+2] | 350 | 352[+2] | 352[+2] | 347 | 348[+1] | 348[+1] | 348 | 350[+2] | 348[±0] |
| B5 | 3'-CAC TAB ACG | | 353 | 352[-1] | 352[-1] | 349 | 353[+4] | 352[+3] | 347 | 348[+1] | 347[±0] | 348 | 350[+2] | 349[+1] |

[a]Measurements were performed at room temperature (monomer 126W), 10° C. (monomer 120Z) and 7° C. (monomer 120X and 120Y) using a spectrophotometer and quartz optical cells with a 1.0 cm path length. Buffer conditions are as for thermal denaturation experiments. Values in italics are for duplexes with low thermostability (partial duplex dissociation at experimental temperature possible).

TABLE 58

Absorption Maxima in the 320-360 Nm Region for Probes Modified with Monomers 120Q/120S/120V in ihe Presence or Absence of Complementary DNA/RNA Targets[a]

| | | | \multicolumn{3}{c}{$\lambda_{max}[\Delta\lambda_{max}]$ (nm)} | | | | | | | | |
|---|---|---|---|---|---|---|---|---|---|---|---|---|
| | | | \multicolumn{3}{c}{120Q} | \multicolumn{3}{c}{120S} | \multicolumn{3}{c}{120V} | \multicolumn{3}{c}{126W} |
| ON | Sequence | B = | ss | +DNA | +RNA | ss | +DNA | +RNA | ss | +DNA | +RNA | ss | +DNA | +RNA |
| B1 | 5'-GBG ATA TGC | | 349 | 353[+4] | 351[+2] | 347 | 351[+4] | 348[+1] | 348 | 352[+4] | 352[+4] | 348 | 350[+2] | 349[+1] |
| B2 | 5'-GTG ABA TGC | | 348 | 353[+5] | 351[+3] | 346 | 349[+3] | 349[+3] | 347 | 352[+5] | 353[+6] | 347 | 351[+4] | 349[+2] |
| B4 | 3'-CAC BAT ACG | | 349 | 354[+5] | 349[±0] | 348 | 350[+2] | 348[±0] | 349 | 353[+4] | 352[+3] | 348 | 350[+2] | 348[±0] |
| B5 | 3'-CAC TAB ACG | | 348 | 354[+6] | 352[+4] | 346 | 348[+2] | 350[+4] | 347 | 352[+5] | 352[+5] | 348 | 350[+2] | 349[+1] |

[a]Measurements were performed at 5° C.

Steady-State Fluorescence Emission Spectra:

Steady-state fluorescence emission spectra of oligonucleotides modified with pyrene-functionalized monomers 120Q/120S/120V/120X/120Y and the corresponding duplexes with complementary DNA/RNA targets were recorded in non-deoxygenated thermal denaturation buffer (each strand 1.0 µM) and obtained as an average of five scans using an excitation wavelength of $\lambda_{ex}$=350 nm, excitation slit 5.0 nm, emission slit 2.5 nm and a scan speed of 600 nm/min (FIGS. 9-17). Experiments were determined at 5° C. to ascertain maximal hybridization of probes to DNA/RNA targets. Solutions were heated to 80° C. followed by cooling to 5° C. over 10 min.

The steady-state fluorescence emission spectra ($\lambda_{ex}$=350 nm; $\lambda_{em}$=360-600 nm; T=5° C.) display the two expected vibronic bands I and III at $\lambda_{em}$=382±3 nm and 402±3 nm, respectively, as well as a small shoulder at ~420 nm (FIGS. 9-17). Hybridization of oligonucleotides modified with monomers 120Q/120S/120V/120X/120Y with complementary targets, and DNA in particular, results in reduced fluorescence emission intensity (FIGS. 9-17). This trend is indicative of pyrene intercalation as nucleobase moieties are known to quench pyrene fluorescence via photoinduced electron transfer (PET) with guanine and cytosine moieties being the strongest quenchers. In agreement with this, duplexes involving the 120Y/120Q/120V-series (intercalation, important binding mode) display far lower emission intensity than those involving the 120X-series (intercalation, less important binding mode).

On balance, the data from the thermal denaturation and optical spectroscopy studies (DNA-selectivity; mismatch discrimination; UV-vis; fluorescence) suggest that intercalation of the attached hydrocarbon is a possible binding mode for all studied monomers. Intercalation is least important for monomers 120W and 120X, while being a dominant binding mode for monomers 120Y, 120Z and 120Q.

Additional Working Examples of Embodiments Involving Probes Modified with Monomers 228Y/Z.

Particular embodiments involve probes modified with monomers 228Y and 228Z. With reference to Table 59 below, it is observed that single-stranded probes modified with monomers 228Y and 228Z display significantly increased thermal affinity toward nucleic acid targets, more commonly single-stranded DNA. This property will facilitate targeting of double-stranded nucleic acid targets, more commonly dsDNA, via the approach shown in FIG. 1.

TABLE 59

Additional Examples of Thermal Denaturation Temperatures of DNA Duplexes Modified with Monomers 228Y or 228Z

| | | $T_m$ ($\Delta T_m$/mod) | |
|---|---|---|---|
| Sequence | B = | 228Y | 228Z |
| 5'-GTG ABA TGC<br>3'-CAC TAT ACG | | 48.0<br>(+18.5) | 50.5<br>(+21.0) |
| 5'-GTG ATA TGC<br>3'-CAC TAB ACG | | 51.5<br>(+22.0) | 49.5<br>(+20.0) |
| 5'-GTG ATA TGC<br>3'-CAC BAT ACG | | 41.0<br>(+11.5) | 37.0<br>(+7.5) |
| 5'-GBG ATA TGC<br>3'-CAC TAT ACG | | 41.0<br>(+11.5) | 37.0<br>(+7.5) |
| 5'-GTG ATA TBC<br>3'-CAC TAT ACG | | 45.5<br>(+16.0) | 43.5<br>(+14.0) |
| 5'-GTG ATA TGC<br>3'-CAC BAB ACG | | 54.0<br>(+12.3) | 54.0<br>(+12.3) |

Particular embodiments involve double-stranded probes with certain interstrand zipper arrangements of monomers 228Y and/or 228Z. With reference to Table 60 below, it is observed that double-stranded probes +1 and +2 interstrand zipper arrangements display relatively low thermostability, which coupled with the high DNA affinity that each probe strands displays (Table 59), results in pronounced potential for targeting of double-stranded nucleic acid targets, more commonly dsDNA via the method outlined in FIG. 1.

TABLE 60

Additional Examples of Double-Stranded Probes with Various Interstrand Zipper Arrangements of Monomer 228Y or 228Z

| | | $T_m$ ($\Delta T_m$/mod) | |
|---|---|---|---|
| Sequence | B = | 228Y | 228Z |
| 5'-GTG ABA TGC<br>3'-CAC TAB ACG | | 32.5<br>(+1.5) | 41.0<br>(+5.8) |
| 5'-GTG ABA TGC<br>3'-CAC BAT ACG | | 29.5<br>(±0) | 62.5<br>(+16.5) |
| 5'-GBG ATA TGC<br>3'-CAC BAT ACG | | 34.5<br>(+2.5) | 43.5<br>(+6.8) |

TABLE 60-continued

Additional Examples of Double-Stranded
Probes with Various Interstrand Zipper
Arrangements of Monomer 228Y or 228Z

| Sequence | B = | $T_m$ ($\Delta T_m$/mod) 228Y | 228Z |
|---|---|---|---|
| 5'-GBG ATA TGC<br>3'-CAC TAB ACG | | 54.0<br>(+12.3) | 61.5<br>(+16.0) |

General Click Reaction Protocol for Preparation of 104V-104Z (Description for ~6 Mmol Scale):

5'-O-Dimethoxytrityl-2'-azido-2'-deoxyuridine 102 and the appropriate alkyne 92-100 were added to a mixture of THF/t-BuOH/H$_2$O (3:1:1, v/v/v) along with sodium ascorbate and CuSO$_4$.5H$_2$O (reagent quantities, and solvent volumes are specified below). The reaction mixture was stirred under a nitrogen atmosphere until analytical TLC indicated full conversion (reaction times and temperatures specified below) whereupon it was diluted with EtOAc (10 mL). The organic phase was successively washed with sat. aq. NaHCO$_3$ (20 mL) and brine (20 mL), dried over anhydrous Na$_2$SO$_4$ and evaporated to dryness. The resulting crude was purified by silica column chromatography (eluent specified below) to afford the corresponding nucleoside 2 (yield specified below).

1-(Pyren-1-yl)-prop-2-yn-1-ol (90)

Trimethylsilylacetylene (1.0 mL, 7.00 mmol) was added to MeMgBr in THF (1M, 4.0 mL, 4.00 mmol) under an argon atmosphere and stirred at rt for 1 h. At this point, pyrene-1-carboxaldehyde (0.70 g, 3.00 mmol) was added and the reaction mixture was stirred at rt for another 2 h. Sat. aq. NH$_4$Cl (~1 mL) was added and the mixture was extracted with EtOAc (2×20 mL). The combined organic phase was dried over Na$_2$SO$_4$ and evaporated to dryness. The resulting crude [assumed to be 1-(pyren-1-yl)-3-trimethylsilyl-prop-2-yn-1-ol] was dissolved in CH$_2$Cl$_2$ and MeOH (10 mL, 1:1, v/v) and stirred with K$_2$CO$_3$ (0.50 g, 3.62 mmol) at rt for 2 h. The reaction mixture was then diluted with CH$_2$Cl$_2$ (10 mL) and successively washed with brine (20 mL) and water (20 mL). The organic phase was dried over Na$_2$SO$_4$ and evaporated to dryness. The resulting crude was purified by silica gel column chromatography (0-50% EtOAc in petroleum ether, v/v) to afford 90 (0.47 g, 58%) as a white solid material. R$_f$=0.3 (25% EtOAc in petroleum ether, v/v); ESI-HRMS m/z 279.0783 ([M+Na]$^+$, C$_{19}$H$_{12}$O.Na$^+$, calc 279.0780); $^1$H NMR (DMSO-d$_6$) δ8.59 (d, 1H, J=10.0 Hz, Py), 8.35-8.29 (m, 4H, Py), 8.26 (d, 1H, J=10.0 Hz, Py), 8.20-8.16 (m, 2H, Py), 8.09 (t, 1H, J=7.5 Hz, Py), 6.41-6.39 (d, 1H, ex, J=5.0 Hz, OH), 6.34-6.31 (dd, 1H, J=5.0 Hz, 2.5 Hz, HC(OH)), 3.60 (d, 1H, J=2.5 Hz, HC≡C); $^{13}$C NMR (DMSO-d$_6$) δ135.0, 130.7, 130.5, 130.1, 127.34, 127.31 (Py), 127.28 (Py), 127.25 (Py), 126.2 (Py), 125.3 (Py), 125.2 (Py), 124.65 (Py), 124.59 (Py), 124.1, 123.8, 123.7 (Py), 85.5, 76.6 (HC≡C), 60.8 (HC(OH)).

1-(Pyren-1-yl)-prop-2-yn-1-one (92)

The Jones reagent (2.67 M CrO$_3$ in 3M H$_2$SO$_4$, 1.0 mL, 2.67 mmol) was added to a solution of alcohol 90 (180 mg, 0.67 mmol) in acetone (10 mL), and the reaction mixture was stirred under an ambient atmosphere at rt for 2 h, whereupon it was diluted with EtOAc (20 mL), neutralized by drop-wise addition of 6M NaOH (1.0 mL) under stirring, and sequentially washed with water (30 mL) and sat. aq. NaHCO$_3$ (30 mL). The organic phase was dried over Na$_2$SO$_4$, evaporated to dryness, and the resulting crude purified by silica gel column chromatography (0-20% EtOAc in petroleum ether, v/v) to furnish 92 (130 mg, 75%) as a brightly yellow solid material. R$_f$=0.6 (50% EtOAc in petroleum ether, v/v); ESI-HRMS m/z 277.0626 ([M+Na]$^+$, C$_{19}$H$_{10}$O.Na$^+$, calc 277.0624); $^1$H NMR (CDCl$_3$) δ9.48 (d, 1H, J=10.0 Hz), 8.94 (d, 1H, J=8.0 Hz), 8.28-8.23 (m, 3H), 8.19-8.14 (m, 2H), 8.07-8.02 (m, 2H), 3.53 (s, 1H); $^{13}$C NMR (CDCl$_3$) δ179.3, 135.8, 132.2 (Py), 131.31, 131.25 (Py), 131.14, 131.05 (Py), 130.6, 128.4, 127.35 (Py), 127.29 (Py), 127.1 (Py), 126.8 (Py), 124.97 (Py), 124.96, 124.95, 124.2 (Py), 124.1, 82.6, 80.1 (HC≡C).

4-(Pyren-1-yl)-but-1-yne (94)

An oven-dried flask was charged with pyrene-1-carboxaldehyde (230 mg, 1.00 mmol) and activated zinc (100 mg, 1.50 mmol) and placed under an argon atmosphere. Anhydrous THF (5 mL) and propargyl bromide (0.20 mL, 1.79 mmol) were added and the reaction mixture was stirred at 45° C. for 4 h. Sat. aq. NH$_4$Cl (1 mL) was added and the mixture was extracted with EtOAc (2×20 mL). The organic phase was washed with brine (20 mL) and evaporated to dryness. The resulting crude was purified by silica gel column chromatography (0-30% EtOAc in petroleum ether, v/v) to afford a crude white solid material (145 mg), which $^1$H NMR suggested to be a ~9:1 mixture of the desired 1-(pyren-1-yl)-but-3-yn-1-ol and the corresponding allene isomer. Et$_3$SiH (0.20 mL, 1.25 mmol) and boron trifluoride etherate (0.20 mL, 1.62) were added to a solution of the crude mixture in CH$_2$Cl$_2$ (5 mL), which then was stirred at rt for 1 h. The reaction mixture was diluted with CH$_2$Cl$_2$ (20 mL) and sat. aq. NaHCO$_3$ (2 mL), and successively washed with brine (20 mL) and water (20 mL). The organic phase was dried over Na$_2$SO$_4$, evaporated to dryness under reduced pressure, and the resulting crude purified by silica gel column chromatography (0-3% EtOAc in petroleum ether, v/v) to afford 94 (80 mg, 31%) as a white solid material. R$_f$=0.5 (5% EtOAc in petroleum ether, v/v); ESI-HRMS m/z 277.0973 ([M+Na]$^+$, C$_{20}$H$_{14}$.Na$^+$, calc 279.0988); $^1$H NMR (CDCl$_3$) δ8.27-8.25 (d, 1H, J=9.5 Hz, Py), 8.17-8.14 (m, 2H, Py), 8.12-8.10 (m, 2H, Py), 8.01 (ap s, 2H), 8.00-7.96 (t, 1H, J=8.0 Hz, Py), 7.92-7.90 (d, 1H, J=7.5 Hz, Py), 3.59 (t, 2H, J=7.7 Hz, CH$_2$CH$_2$C≡CH), 2.72 (dt, 2H, J=7.7 Hz, 2.5 Hz, CH$_2$C≡CH), 2.03 (t, 1H, J=2.5 Hz, HC≡C); $^{13}$C NMR (CDCl$_3$) δ134.7, 131.6, 131.1, 130.5, 128.9, 127.8 (Py), 127.7 (Py), 127.5 (Py), 127.1 (Py), 126.1 (Py), 125.31, 125.27 (Py), 125.2, 125.1 (Py), 125.0 (Py), 123.2 (Py), 84.0, 69.6 (HC≡C), 32.8 (CH$_2$CH$_2$C≡CH), 21.0 (CH$_2$C≡CH).

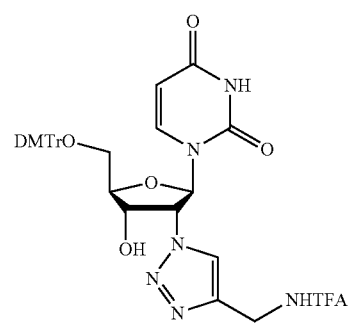

104V

5'-O-(4,4'-Dimethoxytrityl)-2'-C-[4-(2,2,2-trifluoro-acetamidomethyl)-1H-1,2,3-triazol-1-yl]-2'-deoxyuridine (104V)

Nucleoside 102 (0.40 g, 0.70 mmol), 2,2,2-trifluoro-N-(prop-2-ynyl)acetamide Av (105 mg, 0.70 mmol), sodium ascorbate (70 mg, 0.35 mmol), CuSO$_4$.5H$_2$O (5 mg, 0.02 mmol) and THF/t-BuOH/H$_2$O (5 mL) were mixed, reacted (14 h at rt), worked up and purified (50-100% EtOAc in petroleum ether, v/v) as described above except that the organic phase was successively washed with brine and water. Nucleoside 104V (0.42 g, 83%) was obtained as a yellow solid material. R$_f$=0.3 (80% EtOAc in petroleum ether, v/v); MALDI-HRMS m/z 745.2225 ([M+Na]$^+$, C$_{35}$H$_{34}$F$_3$N$_6$O$_8$.Na$^+$, calc 745.2204); $^1$H NMR (DMSO-d$_6$) δ11.40 (d, 1H, ex, J=2.0 Hz, H3), 10.02 (t, 1H, J=6.0 Hz, NHCOCF$_3$), 8.01 (s, 1H, Tz), 7.81 (d, 1H, J=8.0 Hz, H6), 7.43-7.22 (m, 9H, DMTr), 6.93-6.88 (m, 4H, DMTr), 6.42 (d, 1H, J=4.5 Hz, H1'), 5.79 (d, 1H, ex, J=6.0 Hz, 3'-OH), 5.50 (dd, 1H, J=7.0 Hz, 4.5 Hz, H2'), 5.45 (dd, 1H, J=8.0 Hz, 2.0 Hz, H5), 4.52 (m, 1H, H3'), 4.47 (d, 2H, J=5.5 Hz, CH$_2$NHCO), 4.24-4.20 (m, 1H, H4'), 3.75 (s, 6H, CH$_3$O), 3.38-3.30 (m, 2H, H5'—partial overlap with H$_2$O); $^{13}$C NMR (DMSO-d$_6$) δ162.8, 158.09, 158.08, 156.2 (q, $^{1,3}J_{CF}$=36 Hz, COCF$_3$), 150.1, 144.6, 142.4, 140.5 (C6), 135.3, 135.1, 129.7 (DMTr), 127.8 (DMTr), 127.7 (DMTr), 126.7 (DMTr), 124.5 (Tz), 115.8 (q, J$_{CF}$=288 Hz, CF$_3$), 113.2 (DMTr), 101.9 (C5), 87.1 (C1'), 85.8, 83.2 (C4'), 68.8 (C3'), 64.5 (C2'), 62.8 (C5'), 55.0 (CH$_3$O), 34.5 (CH$_2$NHCO); $^{19}$F-NMR (DMSO-d$_6$) δ−74.2.

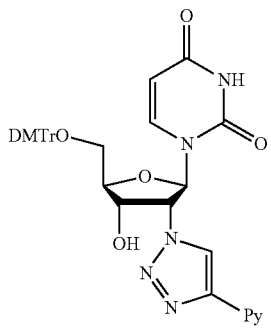

104W

5'-O-(4,4'-Dimethoxytrityl)-2'-C-[4-(pyrene-1-yl)-1H-1,2,3-triazol-1-yl]-2'-deoxyuridine (104W)

Nucleoside 102 (0.28 g, 0.49 mmol), 1-ethynylpyrene 98 (130 mg, 0.58 mmol), sodium ascorbate (200 mg, 1.00 mmol), CuSO$_4$.5H$_2$O (25 mg, 0.10 mmol) and THF/t-BuOH/H$_2$O (10 mL) were mixed, reacted (7 h at 75° C.), worked up and purified (40-70% EtOAc in petroleum ether, v/v) as described above to provide nucleoside 104W (140 mg, 35%) as an off-white solid material. R$_f$=0.5 (80% EtOAc in petroleum ether, v/v); MALDI-HRMS m/z 820.277 ([M+Na]$^+$, C$_{48}$H$_{39}$N$_5$O$_7$.Na$^+$, calc 820.274); $^1$H NMR (DMSO-d$_6$) δ11.46 (d, 1H, ex, J=1.5 Hz, NH), 8.87 (d, 1H, J=9.0 Hz, Py), 8.80 (s, 1H, Tz), 8.41-8.33 (m, 4H, Py), 8.27 (d, 1H, J=9.2 Hz, Py), 8.26-8.22 (m, 2H, Py); 8.12 (t, 1H, J=7.5 Hz, Py), 7.91 (d, 1H, J=8.0 Hz, H6), 7.48-7.20 (m, 9H, DMTr), 6.96-6.90 (m, 4H, DMTr), 6.65 (d, 1H, J=5.0 Hz, H1'), 5.95 (d, 1H, ex, J=6.0 Hz, 3'-OH), 5.69 (dd, 1H, J=7.0 Hz, 5.0 Hz, H2'), 5.54 (dd, 1H, J=8.0 Hz, 1.5 Hz, H5), 4.69-4.64 (m, 1H, H3'), 4.40-4.36 (m, 1H, H4'), 3.76 (s, 6H, CH$_3$O), 3.46-3.36 (m, 2H, H5'); $^{13}$C NMR (DMSO-d$_6$) δ162.9, 158.2, 150.3, 145.7, 144.7, 140.8 (C6), 135.4, 135.2, 130.9, 130.6, 130.3, 129.78 (DMTr), 129.76 (DMTr), 128.0 (Py), 127.9 (DMTr), 127.73 (DMTr), 127.67 (Py), 127.5, 127.3 (Py), 127.0 (Py), 126.8 (DMTr), 126.4 (Py), 125.7 (Tz), 125.5 (Py), 125.16, 125.15 (Py), 125.09 (Py), 124.8 (Py), 124.3, 123.9, 113.3 (DMTr), 102.1 (C5), 87.4 (C1'), 85.9, 83.4 (C4'), 69.1 (C3'), 64.9 (C2'), 63.1 (C5'), 55.0 (CH$_3$O).

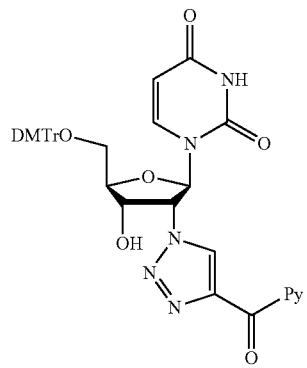

104X

5'-O-(4,4'-Dimethoxytrityl)-2'-C-[4-(pyrene-1-ylcarbonyl)-1H-1,2,3-triazol-1-yl]-2'-deoxyuridine (104X)

Nucleoside 102 (0.28 g, 0.49 mmol), 1-(pyren-1-yl)-prop-2-yn-1-one 92 (140 mg, 0.55 mmol), sodium ascorbate (200 mg, 1.00 mmol), CuSO$_4$.5H$_2$O (25 mg, 0.10 mmol) and THF/t-BuOH/H$_2$O (10 mL) were mixed, reacted (5 h at rt), worked up and purified (40-90% EtOAc in petroleum ether, v/v) as described above to provide nucleoside 104X (0.25 g, 60%) as yellow solid material. R$_f$=0.4 (80% EtOAc in petroleum ether, v/v); MALDI-HRMS m/z 848.267 ([M+Na]$^+$, C$_{49}$H$_{39}$N$_5$O$_8$.Na$^+$, calc 848.270); $^1$H NMR (DMSO-d$_6$) δ11.46 (br s, 1H, ex, NH), 8.96 (s, 1H, Tz), 8.51-8.28 (m, 8H, Py), 8.17 (t, 1H, J=7.5 Hz, Py), 7.83 (d, 1H, J=8.0 Hz, H6), 7.44-7.21 (m, 9H, DMTr), 6.93-6.88 (m, 4H, DMTr), 6.55 (d, 1H, J=5.0 Hz, H1'), 5.90 (d, 1H, ex, J=5.0 Hz, 3'-OH), 5.68 (dd, 1H, J=7.0 Hz, 5.0 Hz, H2'), 5.53 (dd, 1H, J=8.0 Hz, 2.0 Hz, H5), 4.64-4.58 (m, 1H, H3'), 4.31-4.26 (m, 1H, H4'), 3.74 (s, 6H, CH$_3$O), 3.40-3.30 (m, 2H, H5'); $^{13}$C NMR (DMSO-d$_6$) δ188.3, 162.9, 158.1, 150.2, 147.2, 144.6, 140.8 (C6), 135.4, 135.2, 133.0, 131.8, 131.5 (Tz), 130.6, 130.0, 129.74 (DMTr), 129.72 (DMTr), 129.4 (Py), 129.1 (Py), 128.9, 127.9, 127.84 (DMTr), 127.80 (Py), 127.7 (DMTr), 127.2 (Py), 126.8 (Py), 126.7 (DMTr), 126.5 (Py), 126.1 (Py), 124.01 (Py), 123.98 (Py), 123.8, 123.5, 113.2 (DMTr), 102.0 (C5), 87.4 (C1'), 85.8, 83.3 (C4'), 69.0 (C3'), 65.0 (C2'), 63.0 (C5'), 55.0 (CH$_3$O).

165

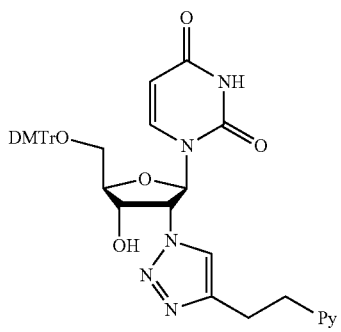

104Y

5'-O-(4,4'-Dimethoxytrityl)-2'-C-[4-{2-(pyrene-1-yl)ethyl}-1H-1,2,3-triazol-1-yl]-2'-deoxyuridine (104Y)

Nucleoside 102 (0.34 g, 0.60 mmol), 4-(pyren-1-yl)-but-1-yne 94 (160 mg, 0.63 mmol), sodium ascorbate (0.25 g, 1.25 mmol), CuSO$_4$.5H$_2$O (31 mg, 0.12 mmol) and THF/t-BuOH/H$_2$O (10 mL) were mixed, reacted (2 h at rt), worked up and purified (50-100% EtOAc in petroleum ether, v/v) as described above to provide nucleoside 104Y (0.33 g, 67%) as a white solid material. R$_f$=0.3 (80% EtOAc in petroleum ether, v/v); MALDI-HRMS m/z 848.3046 ([M+Na]$^+$, C$_{50}$H$_{43}$N$_5$O$_7$.Na$^+$, calc 848.3055); $^1$H NMR (DMSO-d$_6$) δ11.44 (s, 1H, ex, NH), 8.40 (d, 1H, J=9.0 Hz, Py), 8.30-8.19 (m, 4H, Py), 8.13 (ap s, 2H, Py), 8.06 (t, 1H, J=8.0 Hz, Py), 8.01 (s, 1H, Tz), 7.95 (d, 1H, J=8.0 Hz, Py), 7.82 (d, 1H, J=8.0 Hz, H6), 7.44-7.41 (m, 2H, DMTr), 7.36-7.23 (m, 7H, DMTr), 6.94-6.90 (m, 4H, DMTr), 6.44 (d, 1H, J=5.0 Hz, H1'), 5.79 (d, 1H, ex, J=6.0 Hz, 3'-OH), 5.49-5.45 (m, 2H, H5, H2'), 4.54-4.49 (m, 1H, H3'), 4.27-4.22 (m, 1H, H4'), 3.75 (s, 6H, CH$_3$O), 3.72-3.66 (m, 2H, CH$_2$CH$_2$), 3.40-3.30 (m, 2H, H5'), 3.19-3.14 (m, 2H, CH$_2$CH$_2$); $^{13}$C NMR (DMSO-d$_6$) δ162.8, 158.12, 158.11, 150.2, 145.8, 144.6, 140.5 (C6), 135.6, 135.4, 135.1, 130.8, 130.3, 129.7 (DMTr), 129.4, 128.0, 127.8 (DMTr), 127.7 (DMTr), 127.5 (Py), 127.4 (Py), 127.3 (Py), 126.7 (DMTr), 126.5 (Py), 126.1 (Py), 124.93 (Py), 124.88 (Py), 124.8 (Py), 124.2, 124.1, 123.4 (Tz), 123.2 (Py), 113.2 (DMTr), 102.0 (C5), 87.1 (C1'), 85.9, 83.3 (C4'), 68.9 (C3'), 64.3 (C2'), 62.9 (C5'), 55.0 (CH$_3$O), 32.6 (CH$_2$CH$_2$), 27.3 (CH$_2$CH$_2$).

166

5'-O-(4,4'-Dimethoxytrityl)-2'-C-[4-(pyrene-1-yl)carboxamidomethyl-1H-1,2,3-triazol-1-yl]-2'-deoxyuridine (104Z)

Nucleoside 102 (0.40 g, 0.70 mmol), N-(prop-2-ynyl)pyrene-1-carboxamide 100 (200 mg, 0.71 mmol), sodium ascorbate (50 mg, 0.25 mmol), CuSO$_4$.5H$_2$O (5 mg, 0.02 mmol) and THF/t-BuOH/H$_2$O (5 mL) were mixed, reacted (8 h at rt), worked up and purified (50-100% EtOAc in petroleum ether, v/v) as described above except that the organic phase was successively washed with brine and water. Nucleoside 104Z (0.49 g, 83%) was obtained a yellow solid material. R$_f$=0.2 (EtOAc); MALDI-HRMS m/z 877.2979 ([M+Na]$^+$, C$_{50}$H$_{42}$N$_6$O$_8$.Na$^+$, calc 877.2956); $^1$H NMR (DMSO-d$_6$) δ11.43 (s, 1H, ex, H3), 9.26 (t, 1H, ex, J=6.0 Hz, NHCO), 8.53-8.52 (d, 1H, J=9.5 Hz, Ar), 8.36-8.34 (m, 3H, Ar), 8.27-8.22 (m, 3H, Ar), 8.17-8.11 (m, 3H, Ar, Tz), 7.85 (d, 1H, J=8.5 Hz, H6), 7.44-7.43 (m, 2H, DMTr), 7.35-7.24 (m, 7H, DMTr), 6.93-6.89 (m, 4H, DMTr), 6.50 (d, 1H, J=4.7 Hz, H1'), 5.87 (d, 1H, ex, J=5.5 Hz, 3'-OH), 5.56 (dd, 1H, J=7.0 Hz, 4.7 Hz, H2'), 5.47 (d, 1H, J=8.0 Hz, H5), 4.71 (d, 2H, J=6.0 Hz, CH$_2$NHCO), 4.58-4.54 (m, 1H, H3'), 4.30-4.25 (m, 1H, H4'), 3.75 (s, 6H, CH$_3$O), 3.41-3.32 (m, 2H, H5'); $^{13}$C NMR (DMSO-d$_6$) δ168.8, 162.9, 158.13, 158.12, 150.2, 144.7, 144.6, 140.5 (C6), 135.4, 135.2, 131.6, 131.5, 130.7, 130.2, 129.8 (DMTr), 128.3 (Ar), 128.1 (Ar), 127.9 (DMTr), 127.8, 127.7 (DMTr), 127.1 (Ar), 126.8 (DMTr), 126.5 (Ar), 125.7 (Ar), 125.5 (Ar), 125.2 (Ar), 124.7 (Ar), 124.3 (Ar), 124.2 (Tz), 123.7, 123.6, 113.2 (DMTr), 102.0 (C5), 87.1 (C1'), 85.9, 83.3 (C4'), 69.0 (C3'), 64.5 (C2'), 62.9 (C5'), 55.0 (CH$_3$O), 35.0 (CH$_2$NHCO).

General Phosphitylation Protocol for Preparation of 106V-106Z (Description for ~3 Mmol Scale):

The appropriate nucleoside 104 was co-evaporated with anhydrous CH$_2$Cl$_2$ (5 mL) and redissolved in anhydrous CH$_2$Cl$_2$ (reagent quantities and solvent volumes are specified below). To this was added N,N-diisopropylethylamine (DIPEA), 0.45 M tetrazole in CH$_3$CN and 2-cyanoethyl-N,N,N',N'-tetraisopropylphosphordiamidite (PN2-reagent). The reaction mixture was stirred at rt until analytical TLC indicated complete conversion (reaction time specified below) whereupon cold abs. EtOH (0.5 mL) was added. The reaction mixture was evaporated to dryness and the resulting residue was purified by silica gel column chromatography (eluent specified below). The crude material was triturated from cold petroleum ether to afford phosphoramidite 106 (yields specified below).

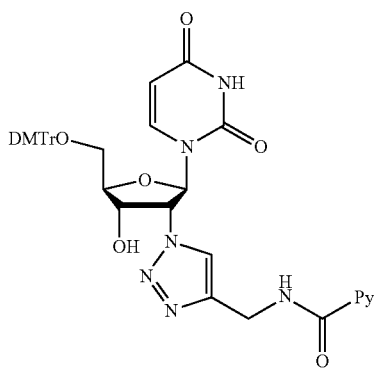

104Z

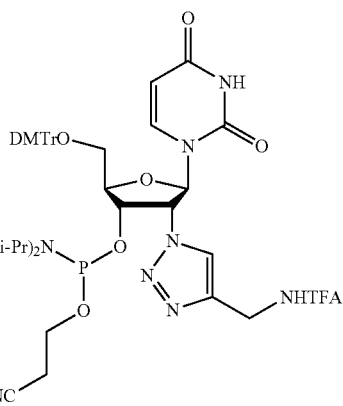

106V

3'-O—(N,N-Diisopropylamino-2-cyanoethoxyphosphinyl)-5'-O-(4,4'-dimethoxytrityl)-2'-C-[4-(2,2,2-trifluoroacetamidomethyl)-1H-1,2,3-triazol-1-yl]-2'-deoxyuridine (106V)

Nucleoside 104V (0.29 g, 0.40 mmol), DIPEA (0.10 mL, 0.57 mmol), tetrazole in CH$_3$CN (0.45 M, 1.0 mL, 0.45 mmol), PN2-reagent (0.15 mL, 0.46 mmol) and anhydrous CH$_2$Cl$_2$ (1 mL) were mixed, reacted (3 h), worked up and purified (50-90% EtOAc in petroleum ether, v/v) as described above except that: a) the reaction mixture was extracted with EtOAc (5 mL) after addition of EtOH, followed by drying of the organic phase over anhydrous Na$_2$SO$_4$ and evaporation to dryness under reduced pressure and b) trituration was not performed. Phosphoramidite 106V (0.24 g, 67%) was obtained as a white solid material. R$_f$=0.3 (5% MeOH in CH$_2$Cl$_2$, v/v); MALDI-HRMS m/z 945.3322 ([M+Na]$^+$, C$_{44}$H$_{50}$F$_3$N$_8$O$_9$.Na$^+$, calc 945.3283); $^{31}$P NMR (CDCl$_3$) δ152.0, 149.8; $^{19}$F NMR (CDCl$_3$) δ−75.7.

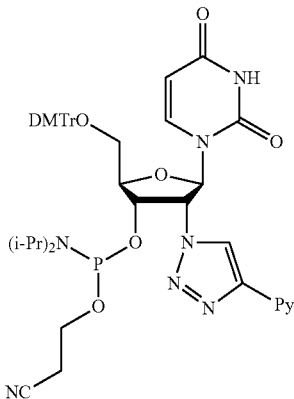

3'-O—(N,N-Diisopropylamino-2-cyanoethoxyphosphinyl)-5'-O-(4,4'-dimethoxytrityl)-2'-C-[4-(pyrene-1-yl)-1H-1,2,3-triazol-1-yl]-2'-deoxyuridine (106W)

Nucleoside 104W (230 mg, 0.29 mmol), DIPEA (0.10 mL, 0.57 mmol), tetrazole in CH$_3$CN (0.45 M, 1.0 mL, 0.45 mmol), PN2-reagent (0.20 mL, 0.62 mmol) and anhydrous CH$_2$Cl$_2$ (2 mL) were mixed, reacted (4 h), worked up and purified (0-4% MeOH/CH$_2$Cl$_2$, v/v) as described above to afford 106W (180 mg, 62%) as a white powder. R$_f$=0.35 (5% MeOH in CH$_2$Cl$_2$, v/v); MALDI-HRMS m/z 1020.3855 ([M+Na]$^+$, C$_{57}$H$_{56}$N$_7$O$_8$P.Na$^+$, calc 1020.3826); $^{31}$P NMR (CDCl$_3$) δ152.0, 150.5.

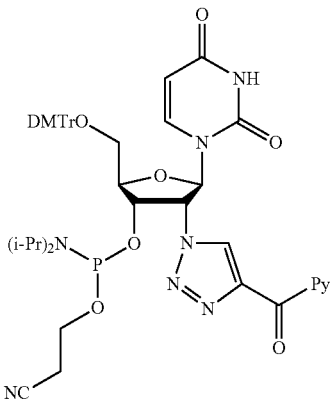

3'-O—(N,N-Diisopropylamino-2-cyanoethoxyphosphinyl)-5'-O-(4,4'-dimethoxytrityl)-2'-C-[4-(pyrene-1-ylcarbonyl)-1H-1,2,3-triazol-1-yl]-2'-deoxyuridine (106X)

Nucleoside 104X (150 mg, 0.18 mmol), DIPEA (0.10 mL, 0.57 mmol), tetrazole in CH$_3$CN (0.45 M, 0.6 mL, 0.27 mmol), PN2-reagent (0.12 mL, 0.37 mmol) and anhydrous CH$_2$Cl$_2$ (2 mL) were mixed, reacted (3.5 h), worked up and purified (0-4% MeOH/CH$_2$Cl$_2$, v/v) as described above to afford 106X (110 mg, 59%) as a yellow solid material. R$_f$=0.4 (5% MeOH in CH$_2$Cl$_2$, v/v); MALDI-HRMS m/z 1048.3779 ([M+Na]$^+$, C$_{58}$H$_{56}$N$_7$O$_9$P.Na$^+$, calc 1048.3775); $^{31}$P NMR (CDCl$_3$) δ152.4, 150.9.

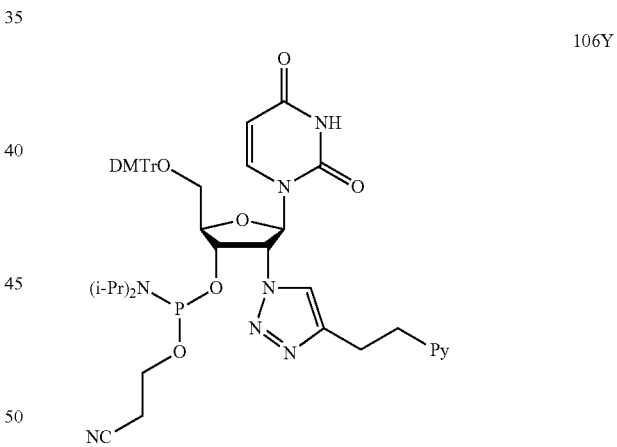

3'-O—(N,N-Diisopropylamino-2-cyanoethoxyphosphinyl)-5'-O-(4,4'-dimethoxytrityl)-2'-C-[4-{2-(pyrene-1-yl)ethyl}-1H-1,2,3-triazol-1-yl]-2'-deoxyuridine (106Y)

Nucleoside 104Y (0.33 g, 0.40 mmol), DIPEA (0.10 mL, 0.57 mmol), tetrazole in CH$_3$CN (0.45 M, 1.5 mL), PN2-reagent (0.25 mL, 0.78 mmol) and anhydrous CH$_2$Cl$_2$ (2 mL) were mixed, reacted (3.5 h), worked up and purified (0-4% MeOH/CH$_2$Cl$_2$, v/v) as described above to afford 106Y (210 mg, 51%) as a white powder. R$_f$=0.45 (5% MeOH in CH$_2$Cl$_2$, v/v); MALDI-HRMS m/z 1048.4147 ([M+Na]$^+$, C$_{59}$H$_{60}$N$_7$O$_8$P.Na$^+$, calc 1048.4139); $^{31}$P NMR (CDCl$_3$) δ151.6, 150.6.

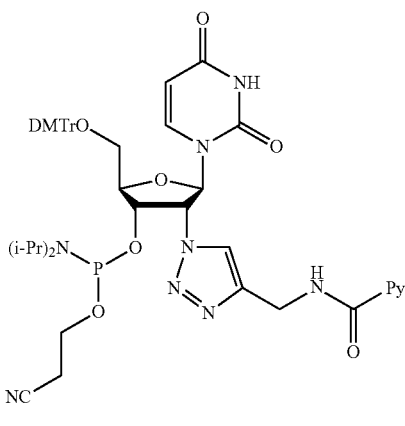

3'-O—(N,N-Diisopropylamino-2-cyanoethoxyphosphinyl)-5'-O-(4,4'-dimethoxytrityl)-2'-C-[4-(pyrene-1-yl)carboxamidomethyl-1H-1,2,3-triazol-1-yl]-2'-deoxyuridine (106Z)

Nucleoside 104Z (0.36 g, 0.42 mmol), DIPEA (0.10 mL, 0.57 mmol), tetrazole in $CH_3CN$ (0.45 M, 1.0 mL, 0.45 mmol), PN2-reagent (0.15 mL, 0.46 mmol) and anhydrous $CH_2Cl_2$ (1 mL) were mixed, reacted (3 h), worked up and purified (50-90% EtOAc in petroleum ether, v/v) as described above except that: a) the reaction mixture was extracted with EtOAc (5 mL) after addition of EtOH, followed by drying of the organic phase over anhydrous $Na_2SO_4$ and evaporation to dryness under reduced pressure and b) trituration was not performed. Phosphoramidite 106Z (0.28 g, 67%) was obtained as a white solid material. $R_f$=0.3 (5% MeOH in $CH_2Cl_2$, v/v); MALDI-HRMS m/z 1077.3984 ($[M+Na]^+$, $C_{59}H_{59}N_8O_9P.Na^+$, calc 1077.4035); $^{31}P$ NMR ($CDCl_3$) δ151.9, 150.1.

Synthesis and purification of single-stranded probes modified with monomers 122V/W/X/Y/Z:

Synthesis of modified oligodeoxyribonucleotides was performed on an Expedite 8909 DNA Synthesizer using 0.2 μmol scale succinyl linked LCAA-CPG (long chain alkyl amine controlled pore glass) columns with a pore size of 500 Å. Standard protocols for incorporation of DNA phosphoramidites were used. A ~50-fold molar excess of modified phosphoramidites in anhydrous acetonitrile (at 0.05 M) was used during hand-couplings using the conditions specified in the main manuscript. Moreover, extended oxidation (45 s) was employed during hand-couplings. Cleavage from solid support and removal of protecting groups was accomplished upon treatment with 32% aq. ammonia (55° C., 20 h). Purification of all modified oligonucleotides was performed by ion-pair reverse phase HPLC as described below followed by detritylation (80% aq. AcOH) and precipitation from acetone (−18° C. for 12-16 h).

Purification of crude oligonucleotides was performed on a Varian Prostar HPLC system equipped with an XTerra MS C18 pre-column (10 μm, 7.8×10 mm) and an XTerra MS C18 column (10 μm, 7.8×150 mm) using a 0.05 mM TEAA (triethylammonium acetate) buffer—25% water/acetonitrile (v/v) gradient. The identity of synthesized oligonucleotides was established through MALDI-MS/MS analysis recorded in positive ions mode on a Quadrupole Time-Of-Flight Tandem Mass Spectrometer (Q-TOF Premiere) equipped with a MALDI source (Waters Micromass LTD., U.K) using anthranilic acid as a matrix (Table 61, while purity (>80%) was verified by RP-HPLC running in analytical mode.

TABLE 61

MALDI-Tof MS-Analysis of Single-Stranded Probes Modified with 122W/X/Y/Z

| Sequence | Calc. $(M + H)^+$ | Expt. $(M + H)^+$ |
|---|---|---|
| 5'-CGCAA A122WA AACGC (SEQ ID NO: 191) | 4188.8 | 4188.9 |
| 5'-CGCAA C122WC AACGC (SEQ ID NO: 192) | 4140.8 | 4140.9 |
| 5'-CGCAA G122WG AACGC (SEQ ID NO: 193) | 4220.8 | 4220.8 |
| 5'-CGCAA T122WT AACGC (SEQ ID NO: 194) | 4170.8 | 4170.8 |
| 5'-GCGTT 122WAT TTGCG (SEQ ID NO: 195) | 4223.8 | 4223.8 |
| 5'-GCGTT TA122W TTGCG (SEQ ID NO: 196) | 4223.8 | 4223.9 |
| 5'-GCGTT 122WA122W TTGCG (SEQ ID NO: 197) | 4476.8 | 4477.0 |
| 5'-CGCAA A122XA AACGC (SEQ ID NO: 198) | 4216.8 | 4216.9 |
| 5'-CGCAA C122XC AACGC (SEQ ID NO: 199) | 4168.8 | 4169.0 |
| 5'-CGCAA G122XG AACGC (SEQ ID NO: 200) | 4248.8 | 4248.8 |
| 5'-CGCAA T122XT AACGC (SEQ ID NO: 201) | 4198.8 | 4198.9 |
| 5'-GCGTT 122XAT TTGCG (SEQ ID NO: 202) | 4251.8 | 4251.9 |
| 5'-GCGTT TA122X TTGCG (SEQ ID NO: 203) | 4251.8 | 4251.9 |
| 5'-GCGTT 122XA122X TTGCG (SEQ ID NO: 204) | 4532.8 | 4532.9 |
| 5'-CGCAA A122YA AACGC (SEQ ID NO: 205) | 4216.8 | 4216.9 |
| 5'-CGCAA C122YC AACGC (SEQ ID NO: 206) | 4168.8 | 4169.0 |
| 5'-CGCAA G122YG AACGC (SEQ ID NO: 207) | 4248.8 | 4248.9 |
| 5'-CGCAA T122YT AACGC (SEQ ID NO: 208) | 4198.8 | 4198.9 |
| 5'-GCGTT 122YAT TTGCG (SEQ ID NO: 209) | 4251.8 | 4251.9 |
| 5'-GCGTT TA122Y TTGCG (SEQ ID NO: 210) | 4251.8 | 4251.9 |
| 5'-GCGTT 122YA122Y TTGCG (SEQ ID NO: 211) | 4532.9 | 4533.1 |
| 5'-CGCAA A122ZA AACGC (SEQ ID NO: 212) | 4245.8 | 4245.9 |
| 5'-CGCAA C122ZC AACGC (SEQ ID NO: 213) | 4197.8 | 4197.9 |

TABLE 61-continued

MALDI-Tof MS-Analysis of Single-Stranded Probes Modified with 122W/X/Y/Z

| Sequence | Calc. (M + H)+ | Expt. (M + H)+ |
|---|---|---|
| 5'-CGCAA G122ZG AACGC (SEQ ID NO: 214) | 4277.8 | 4278.1 |
| 5'-CGCAA T122ZT AACGC (SEQ ID NO: 215) | 4227.8 | 4227.9 |
| 5'-GCGTT 122ZAT TTGCG (SEQ ID NO: 216) | 4280.8 | 4280.9 |
| 5'-GCGTT TA122Z TTGCG (SEQ ID NO: 217) | 4280.8 | 4280.8 |
| 5'-GCGTT 122ZA122Z TTGCG (SEQ ID NO: 218) | 4590.9 | 4590.9 |
| 5'-GTG ATA 122VGC | 2835.5 | 2835.9 |
| 5'-GTG A122VA TGC | 2835.5 | 2835.9 |
| 5'-G122VG ATA TGC | 2835.5 | 2835.8 |
| 5'-GTG ATA 122ZGC | 3063.6 | 3063.9 |
| 5'-GTG A122ZA TGC | 3063.6 | 3063.9 |
| 5'-G122ZG ATA TGC | 3063.6 | 3063.8 |

Thermal Denaturation Studies involving probes modified with monomers 122V/W/X/Y/Z:

Concentrations of oligonucleotides were estimated using the following extinction coefficients (OD/µmol): dG (12.01), dA (15.20), dT (8.40), dC (7.05); rG (13.70), rA (15.40), rU (10.00), rC (9.00); 122V (19.96), 122W (31.08), 122X (35.60), 122Y (27.62) and 122Z (30.95) [values for monomers 122V-122Z were estimated through $A_{260}$ measurements of the corresponding phosphoramidites in 1% aq. DMSO solutions]. Each strand was thoroughly mixed and denatured by heating to 80-85° C. followed by cooling to the starting temperature of the experiment. Quartz optical cells with a path length of 10 mm were used. Thermal denaturation temperatures ($T_m$ values [° C.]) of duplexes (1.0 µM final concentration of each strand) were measured on a Cary 100 UV/VIS spectrophotometer equipped with a 12-cell Peltier temperature controller and determined as the maximum of the first derivative of the thermal denaturation curve ($A_{260}$ VS. T) recorded in medium salt buffer ($T_m$-buffer: 100 mM NaCl, 0.1 mM EDTA, and pH 7.0 adjusted with 10 mM $Na_2HPO_4$ and 5 mM $Na_2HPO_4$). The temperature of the denaturation experiments ranged from at least 20° C. below $T_m$ to 20° C. above $T_m$. A temperature ramp of 0.5° C./min was used in all experiments. Reported $T_m$-values are averages of two experiments within ±1.0° C.

Certain embodiments pertain probes modified with monomers 122W/X/Y/Z. Thermal denaturation studies for duplexes between such probes and matched or mismatched DNA targets are disclosed in Tables 62 and 63. The examples provided therein, demonstrate that probes modified with monomers 122W/X/Y/Z, display universal thermal hybridization properties, i.e., they display significantly similar thermal affinity toward matched and mismatched nucleic acid targets, more commonly single-stranded nucleic acid targets, even more commonly single-stranded DNA and/or single-stranded RNA.

TABLE 62

$T_m$-Values of Duplexes Between Probes Modified with Monomers 122W/X/Y/Z and Complementary or Centrally Mismatched DNA Targets[a]

| Probe | $T_m$ ($\Delta T_m$) [° C.] B = A | Mismatch $\Delta T_m$ [° C.] C | G | T |
|---|---|---|---|---|
| 5'-CGCAA ATA AACGC (SEQ ID NO: 198) | 48.5 | -10.0 | -5.0 | -9.0 |
| 5'-CGCAA CTC AACGC (SEQ ID NO: 199) | 55.5 | -13.5 | -9.5 | -9.0 |
| 5'-CGCAA GTG AACGC (SEQ ID NO: 200) | 55.5 | -13.0 | -9.5 | -10.0 |
| 5'-CGCAA TTT AACGC (SEQ ID NO: 201) | 48.5 | -11.0 | -9.0 | -11.0 |
| 5'-CGCAA A(122W)A AACGC (SEQ ID NO: 191) | 48.0 (-0.5) | +1.0 | +1.5 | +1.5 |
| 5'-CGCAA C(122W)C AACGC (SEQ ID NO: 192) | 53.5 (-2.0) | +0.5 | +2.0 | +2.5 |
| 5'-CGCAA G(122W)G AACGC (SEQ ID NO: 193) | 51.5 (-4.0) | +1.0 | -4.5 | 0.0 |
| 5'-CGCAA T(122W)T AACGC (SEQ ID NO: 194) | 47.0 (-1.5) | +2.5 | -0.5 | +2.0 |
| 5'-CGCAA A(122X)A AACGC (SEQ ID NO: 191) | 46.5 (-2.0) | +1.0 | +0.5 | +1.0 |
| 5'-CGCAA C(122X)C AACGC (SEQ ID NO: 192) | 52.0 (-3.5) | -1.5 | 0.0 | -0.5 |
| 5'-CGCAA G(122X)G AACGC (SEQ ID NO: 193) | 52.5 (-3.0) | +0.5 | -7.0 | -0.5 |
| 5'-CGCAA T(122X)T AACGC (SEQ ID NO: 194) | 44.5 (-4.0) | +1.0 | -1.0 | 0.0 |
| 5'-CGCAA A(122Y)A AACGC (SEQ ID NO: 191) | 49.5 (+1.0) | +1.5 | 0.0 | +1.0 |
| 5'-CGCAA C(122Y)C AACGC (SEQ ID NO: 192) | 50.5 (-5.0) | -5.0 | -1.0 | -2.5 |
| 5'-CGCAA G(122Y)G AACGC (SEQ ID NO: 193) | 53.0 (-2.5) | +1.5 | -3.5 | +0.5 |
| 5'-CGCAA T(122Y)T AACGC (SEQ ID NO: 194) | 44.5 (-4.0) | -2.0 | -2.0 | -1.5 |
| 5'-CGCAA A(122Z)A AACGC (SEQ ID NO: 191) | 47.0 (-1.5) | -5.5 | -2.5 | -4.0 |
| 5'-CGCAA C(122Z)C AACGC (SEQ ID NO: 192) | 51.5 (-4.0) | -6.5 | -1.0 | -4.0 |
| 5'-CGCAA G(122Z)G AACGC (SEQ ID NO: 193) | 52.0 (-3.5) | -2.0 | -6.0 | -4.0 |

TABLE 62-continued

T$_m$-Values of Duplexes Between Probes Modified with Monomers 122W/X/Y/Z and Complementary or Centrally Mismatched DNA Targets[a]

| Probe | T$_m$ (ΔT$_m$) [° C.] B = A | Mismatch ΔT$_m$ [° C.] C | G | T |
|---|---|---|---|---|
| 5'-CGCAA T(122Z)T AACGC (SEQ ID NO: 194) | 45.5 (-3.0) | -4.5 | -5.0 | -4.0 |

[a]T$_m$'s determined as maximum of the first derivative of denaturation curves (A$_{260}$ vs T) recorded in T$_m$-buffer ([Na$^+$] = 110 mM, [Cl$^-$] = 100 mM, pH 7.0 (NaH$_2$PO$_4$/Na$_2$HPO$_4$)) using 1.0 µM of each strand. T$_m$'s are averages of at least two measurements within 1.0° C. "ΔT$_m$" = change in T$_m$ relative to unmodified reference duplex. "Mismatch ΔT$_m$" = change in T$_m$ relative to fully matched duplex (B = A). "Avg Mismatch ΔT$_m$ seq" = average of all three "Mismatch ΔT$_m$"-values for a given probe. "Avg Mismatch ΔT$_m$ series" = average of all twelve "Mismatch ΔT$_m$"-values of all four studied sequences within a monomer series. "±" denotes standard deviation. DNA targets: 3'-GCGTT TBT TTGCG, 3'-GCGTT GBG TTGCG, 3'-GCGTT CBC TTGCG and 3'-GCGTT ABA TTGCG.

TABLE 63

Additional T$_m$-Values of Duplexes Between Probes Modified with Monomers 122W/X/Y/Z and Complementary or Centrally Mismatched DNA Targets.[a]

| Probe | DNA: 5'-CGCAA ABA AACGC T$_m$ (ΔT$_m$) [° C.] B = T | Mismatch ΔT$_m$ [° C.] A | C | G |
|---|---|---|---|---|
| 3'-GCGTT TAT TTGCG (SEQ ID NO: 219) | 48.5 | -10.0 | -10.0 | -5.5 |
| 3'-GCGTT TA122W TTGCG (SEQ ID NO: 196) | 46.5 (-2.0) | -17.0 | -9.0 | -12.0 |
| 3'-GCGTT 122WAT TTGCG (SEQ ID NO: 195) | 41.0 (-7.5) | -11.5 | -10.0 | -5.5 |
| 3'-GCGTT 122WA122W TTGCG (SEQ ID NO: 197) | 35.0 (-13.5) | nt | -3.5 | Nt |
| 3'-GCGTT TA122X TTGCG (SEQ ID NO: 196) | 44.0 (-4.5) | -9.0 | -7.5 | -5.0 |
| 3'-GCGTT 122XAT TTGCG (SEQ ID NO: 195) | 42.0 (-6.5) | -10.5 | -11.5 | -6.0 |
| 3'-GCGTT 122XA122X TTGCG (SEQ ID NO: 197) | 36.5 (-12.0) | -2.5 | -4.5 | +0.5 |
| 3'-GCGTT TA122Y TTGCG (SEQ ID NO: 196) | 40.0 (-8.5) | -7.0 | -7.0 | -5.0 |
| 3'-GCGTT 122YAT TTGCG (SEQ ID NO: 195) | 42.5 (-6.0) | -6.0 | -2.5 | -7.0 |
| 3'-GCGTT 122YA122Y TTGCG (SEQ ID NO: 197) | 34.5 (-14.0) | -4.5 | -3.5 | -4.5 |
| 3'-GCGTT TA122Z TTGCG (SEQ ID NO: 196) | 42.5 (-6.0) | -7.0 | -8.5 | -7.5 |
| 3'-GCGTT 122ZAT TTGCG (SEQ ID NO: 195) | 44.0 (-4.5) | -11.5 | -12.0 | -9.0 |
| 3'-GCGTT 122ZA122Z TTGCG (SEQ ID NO: 197) | 39.5 (-9.0) | -2.5 | -0.5 | -3.5 |

[a]Conditions and definitions as described in footnote of Table above.
"nt" = no transition.

Steady-State Fluorescence Emission Spectra Involving Probes Modified with Monomers 122V/W/X/Y/Z:

Spectra of oligonucleotides modified with pyrene-functionalized monomers 122W/122X/122Y/122Z and the corresponding duplexes with complementary or mismatched DNA/RNA targets were recorded in non-deoxygenated thermal denaturation buffer (each strand 1.0 µM) using an excitation wavelength of $\lambda_{ex}$=350 nm for 122W/122Y/122Z or $\lambda_{ex}$=400 nm for 122X, excitation slit 5.0 nm, emission slit 5.0 nm and a scan speed of 600 nm/min. Experiments were performed at ambient temperature (~20° C.).

Determination of Quantum Yields Involving Probes Modified with Monomers 122V/W/X/Y/Z:

Relative fluorescence emission quantum yields ($\Phi_F$) of modified nucleic acids (SSP or duplex) were determined using the following equation: $\Phi_F$ (NA)=[$\Phi_F$ (std)/α(std)]×[IFI (NA)/A$_{ex}$ (NA)]×[n(NA)/n(std)]$^2$ where $\Phi_F$ (std) is the fluorescence emission quantum yield of standard; α(std) is the slope of the integrated fluorescence intensity vs. optical intensity plot made for the standard; IFI (NA) is the integrated fluorescence intensity ($\lambda_{em}$=360-510 nm for monomer 122W/122Y/122Z; $\lambda_{em}$=425-625 nm for monomer 122X; $\lambda_{em}$=360-600 nm for standards); $A_{ex}$ (NA) is the optical density of the sample at the utilized excitation wavelength ($\lambda_{ex}$=350 nm for monomer 122W/122Y/122Z; $\lambda_{ex}$=400 nm for monomer 122X; $\lambda_{ex}$=350 nm for standards; optical densities of all solutions at the excitation wavelengths were between 0.01 and 0.10); n(NA) and n(std) are refractive indexes of solvents used for sample and standard respectively ($n_{water}$=1.33, $n_{ethanol}$=1.36, and $n_{cyclohexane}$=1.43).

The validity of this method under our experimental set-up was ascertained by determining the quantum yield of anthracene in ethanol with respect to 9,10-diphenylanthracene in cyclohexane ($\Phi_F$=0.86). The measured value of $\Phi_F$=0.28 is in excellent agreement with the reported value of ($\Phi_F$=0.27). Subsequently, the literature value for anthracene in ethanol was used as the standard for determination of quantum yields of SSPs and duplexes.

Optical Spectroscopy Studies Involving Probes Modified with Monomers 122V/W/X/Y/Z.

Figure 27:
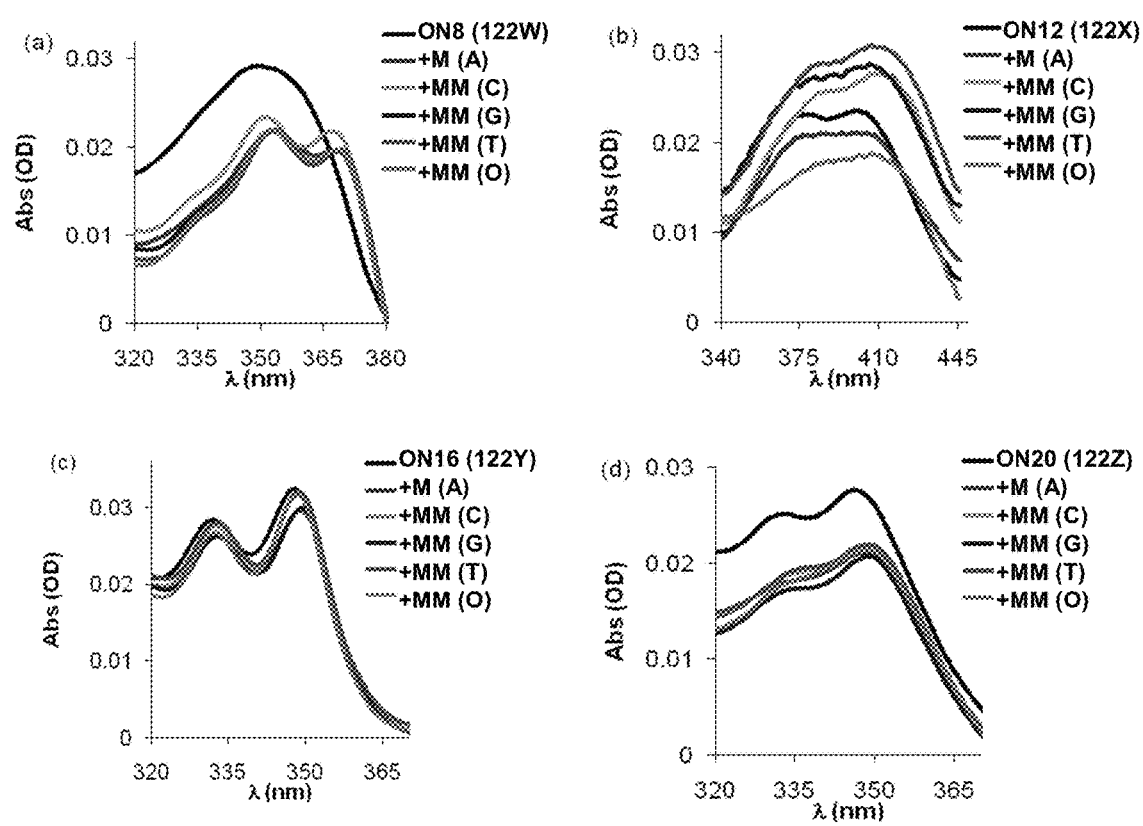
FIG. 27 are absorption spectra obtained using exemplary embodiments of a disclosed probe comprising a triazole moiety.

UV-Vis absorption spectra of oligonucleotides modified with monomers 122W-122Z were recorded in absence or presence of complementary or centrally mismatched DNA targets, in order to gain additional insights into the mechanism that governs the observed universal hybridization characteristics (FIG. 27); hybridization-induced intercalation of pyrene moieties is known to induce subtle bathochromic shifts.

Single-stranded probes modified with monomer 122W display a single unstructured maximum in the pyrene region ($\lambda_{max}$~351 nm, FIG. 27), while duplexes with complementary, mismatched or abasic DNA targets display two resolved maxima at ~351 nm and ~365 nm. The lack of defined peaks for the single stranded probes (SSPs) precludes analysis of bathochromic shifts. Single-stranded probes modified with monomer 122X display two broad and virtually equally intense peaks which renders exact determination of absorption maxima unfeasible ($\lambda_{max}$~385 nm and ~415 nm, FIG. 27). Hybridization with complementary DNA results in subtle bathochromic shifts, while more pronounced shifts are observed upon hybridization with mismatched or abasic DNA. The pyrene maxima are red-shifted relative to those of unconjugated pyrenes chromophores, which suggests electronic coupling between the pyrene and triazole moieties. Single-stranded probes modified with monomer 122Y or monomer 122Z), on the other hand, have structured absorption spectra with two maxima in the 'normal' region (i.e., $\lambda_{max}$~333/348 nm and ~332/346 nm, respectively, FIG. 27). Hybridization of these probes with complementary, mismatched or abasic DNA target strands results in subtle bathochromic shifts ($\Delta\lambda_{max}$ between +1 and +3 nm, FIG. 27, Table 64. Thus, the absorption data are consistent with the hypothesis that the pyrene moieties of monomers 122W-122Z intercalate into the duplex core upon hybridization with DNA targets.

TABLE 64

Pyrene Absorption Maxima of Oligonucleotides Modified With 122Y or 122Z in the Absence (SSP) or Presence of Matched (M) or Centrally Mismatched (MM) DNA Targets.[a]

| Sequence | SSP | +M (A) | +MM (C) | +MM (G) | +MM (T) |
|---|---|---|---|---|---|
| | | $\lambda_{max}$/nm ($\lambda_{max}$) | | | |
| 5'-CGCAA A(122Y)A AACGC (SEQ ID NO: 191) | 348 | 349 (+1) | 349 (+1) | 349 (+1) | 349 (+1) |
| 5'-CGCAA C(122Y) C AACGC (SEQ ID NO: 199) | 347 | 349 (+2) | 349 (+2) | 350 (+3) | 350 (+3) |
| 5'-CGCAA G(122Y) G AACGC (SEQ ID NO: 200) | 348 | 349 (+1) | 349 (+1) | 349 (+1) | 349 (+1) |
| 5'-CGCAA T(122Y) T AACGC (SEQ ID NO: 201) | 346 | 349 (+3) | 349 (+3) | 349 (+3) | 349 (+3) |
| 5'-CGCAA A(122Z)A AACGC (SEQ ID NO: 191) | 346 | 348 (+2) | 349 (+3) | 349 (+3) | 349 (+3) |
| 5'-CGCAA C (122Z)C AACGC (SEQ ID NO: 199) | 346 | 349 (+3) | 349 (+3) | 349 (+3) | 347 (+1) |
| 5'-CGCAA G (122Z)G AACGC (SEQ ID NO: 200) | 347 | 348 (+1) | 350 (+3) | 349 (+2) | 350 (+3) |
| 5'-CGCAA T (122Z)T AACGC (SEQ ID NO: 201) | 346 | 348 (+2) | 348 (+2) | 349 (+3) | 349 (+3) |

[a]Recorded in Tm-buffer at T = 20° C. using 1.0 µM of each strand.
SSP = single-stranded probe. Nucleotide opposite of modification is mentioned in parenthesis.
"M" = matched,
"MM" = mismatched.

Figure 28:
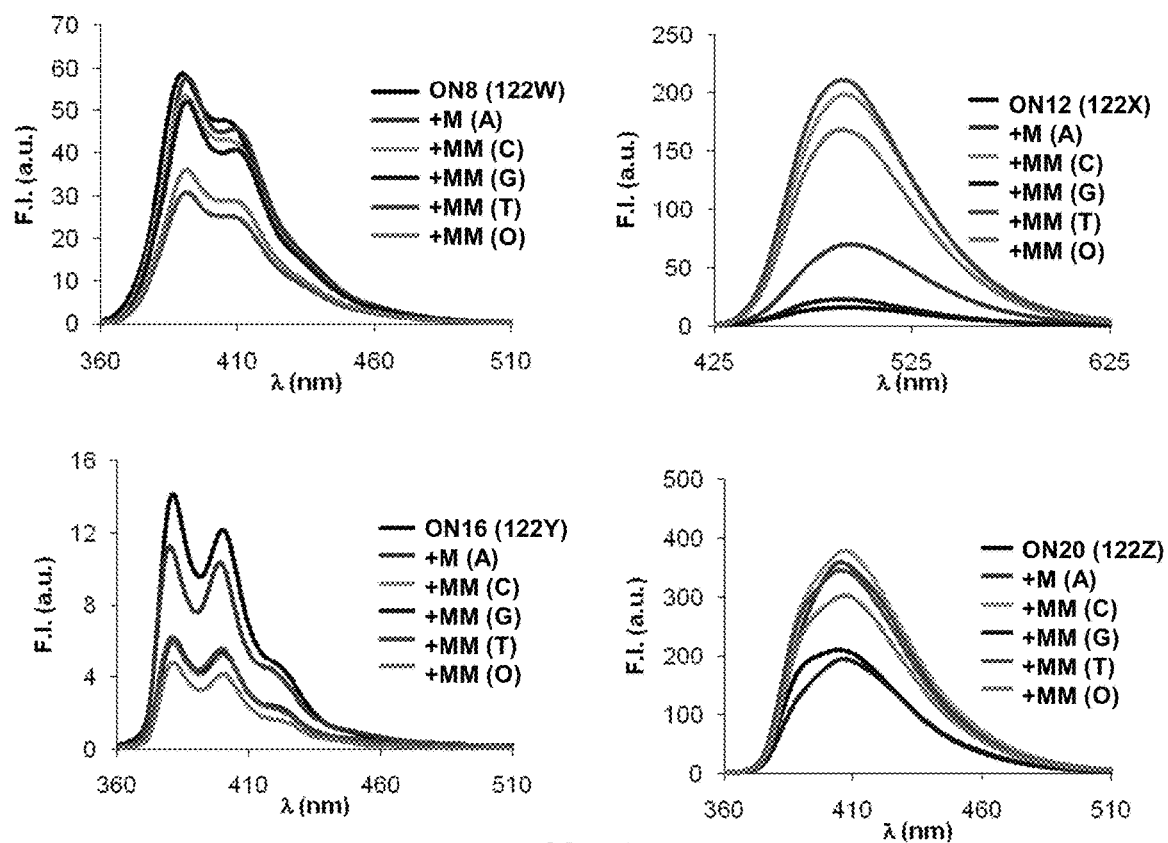
FIG. 28 are steady-state fluorescence emission spectra obtained using exemplary embodiments of a disclosed probe comprising a triazole moiety.

Next, steady-state fluorescence emission spectra and fluorescence emission quantum yields were determined for oligonucleotides modified with 122W/X/Y/Z in absence or presence of complementary or centrally mismatched DNA targets (FIG. 28 and Table 65).

Single-stranded probes modified with monomer 122W display two structured emission peaks at $\lambda_{em}$~390 nm and 405 nm (FIG. 28). The single-stranded probe with a central A122WA-context has higher fluorescence quantum yield than SSPs in other contexts ($\Phi_F$=0.27 vs 0.07/0.05/0.05, Table 65). The spectra of the corresponding duplexes with complementary DNA have a similar shape and sequence dependency, affirming that the pyrene moiety is in close contact with the neighboring nucleobases (FIG. 28, Table 65). The extensive decreases in fluorescence quantum yield (Table 65) upon hybridization with matched or mismatched DNA targets further corroborate this hypothesis. The probe with T122WT-context exhibits considerably smaller changes, presumably since the fluorophore interacts with the neighboring and only weakly quenching adenine moieties upon target binding (FIG. 28).

Fluorescence emission spectra of single-stranded probes modified with monomer 122X and the corresponding duplexes with complementary or mismatched DNA targets display broad and unstructured emission peaks with maxima at $\lambda_{em}$~490 nm (FIG. 28). SSPs are strongly quenched with the probe having the G(122X)G-context) displaying the lowest intensity ($\Phi_F$<0.04, Table 65). Quantum yields are markedly increased upon hybridization of the probes with A(122X)A- and T(122X)T-sequence contexts with complementary/mismatched DNA targets (Table 65). In contrast, probes with C(122X)C- and G(122X)G-sequence contexts display hybridization-induced decreases in fluorescence intensity (Table 65). One interpretation of these observations is that the conjugated pyrene moiety of monomer 122X intercalates into the base stack where it is quenched by neighboring cytosine and guanine moieties (but not quenched by adenine and thymine moieties.

The fluorescence emission spectra of single-stranded probes modified with monomer 122Y and the corresponding duplexes with matched or mismatched DNA targets, display two well-resolved pyrene peaks at $\lambda_{em}$~380 nm and 400 nm, with an additional shoulder at $\lambda_{em}$~420 nm (FIG. 28). Very low quantum yields are observed ($\Phi_F$<0.03, Table 65), except for the single-stranded probe with A(122Y)A sequence context. Hybridization of single-stranded probes modified with monomer 122Y with complementary or mismatched DNA targets generally results in decreased fluorescence intensity, which is consistent with an intercalating binding mode for the pyrene moiety.

The fluorescence emission spectra of single-stranded probes modified with monomer 122Z the corresponding duplexes with matched or mismatched DNA targets display an unstructured peak at $\lambda_{em}$~410 nm with a weaker shoulder at $\lambda_{em}$~390 nm (FIG. 28). The quantum yields of SSPs range from moderate to high and closely align with the previously discussed quenching trends of nucleobases ($\Phi_F$=0.05-0.58, Table 65). Hybridization with matched or mismatched DNA targets generally results in decreases or minor increases in quantum yields and intensity (Table 65).

TABLE 65

Relative Fluorescence Emission Quantum Yield ($\Phi_F$) of Single-Stranded Probes Modified with Monomer 122W/X/Y/Z in the Absence (SSP) or Presence of Matched (M) or Centrally Mismatched (MM) DNA Targets.[a]

| Sequence | $\Phi_F$ | | | | |
|---|---|---|---|---|---|
| | SSP | +M (A) | +MM (C) | +MM (G) | +MM (T) |
| 5'-CGCAA A(122W)A AACGC (SEQ ID NO: 191) | 0.27 | 0.08 | 0.09 | 0.06 | 0.08 |
| 5'-CGCAA C(122W)C AACGC (SEQ ID NO: 192) | 0.07 | 0.02 | 0.02 | 0.02 | 0.01 |
| 5'-CGCAA G(122W)G AACGC (SEQ ID NO: 193) | 0.05 | 0.03 | 0.01 | 0.02 | 0.01 |
| 5'-CGCAA T(122W)T AACGC (SEQ ID NO: 194) | 0.05 | 0.07 | 0.06 | 0.06 | 0.04 |
| 5'-CGCAA A(122X)A AACGC (SEQ ID NO: 191) | 0.02 | 0.25 | 0.33 | 0.10 | 0.25 |
| 5'-CGCAA C(122X)C AACGC (SEQ ID NO: 192) | 0.02 | <0.01 | <0.01 | <0.01 | <0.01 |
| 5'-CGCAA G(122X)G AACGC (SEQ ID NO: 193) | <0.01 | <0.01 | <0.01 | <0.01 | <0.01 |
| 5'-CGCAA T(122X)T AACGC (SEQ ID NO: 194) | 0.04 | 0.16 | 0.35 | 0.04 | 0.32 |
| 5'-CGCAA A(122Y)A AACGC (SEQ ID NO: 191) | 0.09 | 0.02 | 0.02 | 0.02 | 0.03 |
| 5'-CGCAA C(122Y)C AACGC (SEQ ID NO: 192) | 0.01 | 0.02 | <0.01 | <0.01 | <0.01 |
| 5'-CGCAA G(122Y)G AACGC (SEQ ID NO: 193) | 0.03 | 0.01 | 0.01 | 0.01 | <0.01 |
| 5'-CGCAA T(122Y)T AACGC (SEQ ID NO: 194) | 0.01 | <0.01 | <0.01 | <0.01 | <0.01 |
| 5'-CGCAA A(122Z)A AACGC (SEQ ID NO: 191) | 0.58 | 0.52 | 0.78 | 0.29 | 0.79 |

TABLE 65-continued

Relative Fluorescence Emission Quantum Yield ($\Phi_F$)
of Single-Stranded Probes Modified with Monomer
122W/X/Y/Z in the Absence (SSP) or Presence of Matched
(M) or Centrally Mismatched (MM) DNA Targets.[a]

| | $\Phi_F$ | | | | |
|---|---|---|---|---|---|
| Sequence | SSP | +M (A) | +MM (C) | +MM (G) | +MM (T) |
| 5'-CGCAA C(122Z)C AACGC (SEQ ID NO: 192) | 0.24 | 0.15 | 0.17 | 0.15 | 0.19 |
| 5'-CGCAA G(122Z)G AACGC (SEQ ID NO: 193) | 0.05 | 0.04 | 0.02 | 0.02 | 0.03 |
| 5'-CGCAA T(122Z)T AACGC (SEQ ID NO: 194) | 0.27 | 0.57 | 0.58 | 0.31 | 0.52 |

[a]Relative to quantum yield of anthracene in ethanol (0.27). Recorded in $T_m$-buffer at T = 20° C. using 1.0 μM concentration of each strand and $\lambda_{ex}$ = 350 nm and $\lambda_{em}$ = 360-510 nm (monomers 122W, 122Y and 122Z) or $\lambda_{ex}$ = 400 nm and $\lambda_{em}$ = 425-625 nm (monomer 122X). Nucleotide opposite of modification is mentioned in parenthesis.

Figure 29:
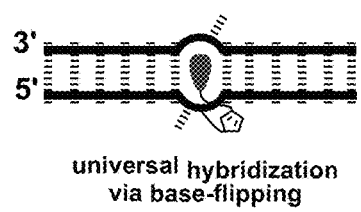
FIG. 29 is schematic drawing illustrating a putative mechanism of the disclosed probe wherein universal hybridization occurs.

Very similar quantum yields are observed for the four duplexes between a particular probe and matched/mismatched DNA targets Collectively, these observations indicate a) that the fluorophore is in a similar electronic environment within the duplex core regardless of the nucleotide opposite of the monomer, and b) that the opposing nucleotide is not strongly involved in base pairing and possibly even pushed into an extrahelical position (FIG. 29). Along the lines, it is interesting to note that placement of pyrene-functionalized C-glycosides in DNA duplexes opposite of abasic sites, which are generated via enzyme-mediated extrahelical flipping of the opposing nucleotide, is known to be stabilizing.

Universal Hybridization—RNA Targets:

A representative subset of modified oligonucleotides (TBT/CBT-contexts) was studied with respect to thermal denaturation, absorption and fluorescence properties with complementary/mismatched RNA targets. Briefly described: a) incorporation of monomer 122W or 122X into oligonucleotides results in similar decreases in thermal affinity toward complementary RNA as toward DNA, while oligonucleotides modified with monomers 122Y or 122Z are more destabilizing (Table 66); b) oligonucleotides modified with monomers 122W or 122X display robust universal hybridization characteristics (compare 'mismatch $\Delta T_m$'-values for ON6/ON8/ON12 and ON2/ON4, Table 66), while oligonucleotides modified with monomers 122Y or 122Z do not; c) pyrene absorption spectra of duplexes between modified oligonucleotides and complementary or centrally mismatched RNA targets are very similar to those of the corresponding DNA duplexes; and d) hybridization of modified oligonucleotides to RNA targets results in very similar changes in fluorescence intensity as with DNA targets.

Thus, the results indicate that the universal RNA hybridization characteristics of oligonucleotides modified with monomer 122W/122X also are be governed by a similar mechanism as universal DNA hybridization (FIG. 29).

TABLE 66

$T_m$-Values of Duplexes Between Centrally Modified
Oligonucleotides and Complementary or Centrally
Mismatched RNA Targets.[a]

| | | | Mismatch $\Delta T_m$ [° C.] | | |
|---|---|---|---|---|---|
| ON Sequence | B = | $T_m$ ($\Delta T_m$) [° C.] A | C | G | U |
| 2 5'-CGCAA CTC AACGC (SEQ ID NO: 192) | | 51.5 | -15.5 | -3.0 | -13.5 |
| 4 5'-CGCAA TTT AACGC (SEQ ID NO: 194) | | 40.5 | -19.0 | -3.5 | -17.0 |
| 6 5'-CGCAA C122WC AACGC (SEQ ID NO: 192) | | 47.0 (-4.5) | +1.0 | +0.0 | +0.5 |
| 8 5'-CGCAA T122WT AACGC (SEQ ID NO: 194) | | 42.0 (+1.5) | +3.0 | +0.5 | +1.5 |
| 12 5'-CGCAA T122XT AACGC (SEQ ID NO: 201) | | 38.0 (-2.5) | +1.0 | +0.0 | +1.0 |
| 14 5'-CGCAA C122YC AACGC (SEQ ID NO: 206) | | 43.5 (-8.0) | -2.0 | -5.0 | -4.0 |
| 16 5'-CGCAA T122YT AACGC (SEQ ID NO: 208) | | 36.0 (-4.5) | +1.5 | -1.0 | -1.0 |

TABLE 66-continued $T_m$-Values of Duplexes Between Centrally Modified Oligonucleotides and Complementary or Centrally Mismatched RNA Targets.[a]

| ON Sequence | B = | $T_m$ ($\Delta T_m$) [° C.] A | Mismatch $\Delta T_m$ [° C.] | | |
|---|---|---|---|---|---|
| | | | C | G | U |
| 18 5'-CGCAA C122ZC AACGC (SEQ ID NO: 213) | | 44.5 (−7.0) | −3.0 | −8.0 | −7.0 |
| 20 5'-CGCAA T122ZT AACGC (SEQ ID NO: 215) | | 36.5 (−4.0) | −12.0 | −7.5 | −13.0 |

[a]RNA targets: 3'-GCGUU GBG UUGCG and 3'-GCGUU ABA UUGCG.

Synthesis of 260.

Co-evaporated 82Q (3.40 g, 4.39 mmol) with anhydrous 1,2-dicholoethane (2×30 mL), redissolved in anhydrous pyridine (55 mL) and cooled to 0° C. Dimethylaminopyridine (DMAP, 55 mg, 0.44 mmol) was added followed by dropwise addition of acetic anhydride (1.25 mL, 13.18 mmol). After stirring at rt for 12 h, the reaction mixture was diluted with EtOAc (150 mL) and washed with H$_2$O (80 mL) and sat. aq. NaHCO$_3$ (80 mL). The product was co-evaporated with EtOH:toluene (2:1, 3×30 mL) and suspended in AcOH:H$_2$O (4:1, 55 mL) and stirred overnight. The reaction mixture was then evaporated to dryness and purified via silica gel column chromatography (0-5% MeOH/CH$_2$Cl$_2$, v/v). The appropriate fractions were pooled and evaporated to dryness. The product was then coevaporated in anhydrous pyridine:CH$_2$Cl$_2$ (1:1, 2×30 mL), redissolved in pyridine:CH$_2$Cl$_2$ (1:1, 44 mL) and cooled to −20° C. Methanesulfonyl chloride (MsCl, 0.75 mL, 9.62 mmol) was added dropwise over 30 min and allowed to stir at −20° C. for 2 h whereupon the crude was diluted with CH$_2$Cl$_2$ (80 mL) and washed with sat. aq. NaHCO3 (50 mL). The aqueous layer was back-extracted with CH$_2$Cl$_2$ (3×15 mL) and the organic layers were evaporated to dryness via co-evaporation with EtOH: toluene (2:1, 3×30 mL). The crude was purified by silica gel column chromatography (0-3% MeOH/CH$_2$Cl$_2$, v/v) to afford nucleoside 260 (1.43 g, 55%) as a white foam. R$_f$: 0.4 (5%, MeOH in CH$_2$Cl$_2$, v/v); MALDI-HRMS m/z 614.1600 ([M+Na]$^+$, C$_{30}$H$_{29}$N$_3$O$_8$S.Na$^+$, Calc. 614.1568); $^1$H NMR (DMSO-d$_6$) δ 11.48 (d, 1H, ex, J=2.20 Hz, NH), 8.03-8.36 (m, 8H, py), 7.93 (d, 1H, J=7.96 Hz, py), 7.73 (d, 1H, J=8.23 Hz, H6), 6.39 (d, 1H, J=7.41 Hz, H1'), 5.67 (dd, 1H, J=2.20 Hz, 8.23 Hz, H5), 5.39 (dd, 1H, J=3.57 Hz, 6.56 Hz, H3'), 4.33-4.38 (m, 5H, CH$_2$Py, H4', H5'), 3.83 (dd, 1H, J=6.59 Hz, 7.41 Hz, H2'), 3.20 (s, 3H, CH$_3$ (Ms)), 2.33 (s, 3H, NCH$_3$), 2.13 (s, 3H, CH$_3$ (Ac)); $^{13}$C NMR (DMSO-d$_6$) δ 169.7, 162.7, 150.5, 140.6 (C6), 131.9, 130.7, 130.3, 130.2, 129.1, 127.7 (py), 127.3 (py), 127.0 (py), 126.8 (py), 126.1 (py), 125.1 (py), 124.4 (py), 124.2, 123.8, 123.7 (py), 102.6 (C5), 83.7 (C5), 79.9 (C4'), 71.7 (C3'), 69.1 (C5'), 64.9 (C2'), 57.5 (CH$_2$Py), 37.7 (NCH$_3$), 36.8 (CH$_3$, Ms), 20.9 (CH$_3$, Ac).

Synthesis of 262.

Nucleoside 260 (770 mg, 1.30 mmol) was coevaporated in anhydrous 1,2-dicholoethane (3×6 mL) and suspended in absolute EtOH (25 mL) whereupon NaHCO$_3$ (275 mg, 3.25 mmol) was added and the suspension was heated to reflux under Argon atmosphere for 4 days. The reaction mixture was then diluted with CH$_2$Cl$_2$ and the salts were filtered and washed with CH$_2$Cl$_2$. The CH$_2$Cl$_2$ layer was evaporated to dryness and purified via silica gel column chromatography (0-7% MeOH/CH$_2$Cl$_2$, v/v) to afford nucleoside 262 (338 mg, 52%) as a white foam. R$_f$: 0.3 (10%, MeOH in CH$_2$Cl$_2$, v/v); MALDI-HRMS m/z 522.1985 ([M+Na]$^+$, C$_{29}$H$_{29}$N$_3$O$_5$.Na$^+$, Calc. 522.1999); $^1$H NMR (DMSO-d$_6$) δ 8.40 (d, 1H, J=9.33 Hz, Py), 8.24-8.29 (m, 2H, Py), 8.21 (d, 1H, J=7.96 Hz, Py), 8.13-8.16 (m, 2H, Py), 8.05-8.11 (m, 2H, Py), 7.97 (d, 1H, J=7.96 Hz, Py), 7.92 (d, 1H, J=7.68 Hz, H6), 6.34 (d, 1H, J=8.51 Hz, H1'), 5.82 (d, 1H, J=7.68 Hz, H5), 5.53 (d, 1H, ex, J=4.94 Hz, 3'-OH), 5.11 (t, 1H, ex, J=5.21 Hz, 5'-OH), 4.42-4.52 (m, 3H, CH$_2$Py, H3'), 4.11-4.28 (m, 2H, CH$_2$CH$_3$), 3.97-4.02 (m, 1H, H4'), 3.57-3.63 (m, 2H, H5'), 3.47 (dd, 1H, J=5.21 Hz, 8.51 Hz, H2'), 2.36 (s, 3H, NCH$_3$), 1.07 (t, 3H, J=7.14 Hz, CH$_2$CH$_3$); $^{13}$C NMR (DMSO-d$_6$) δ 169.3, 155.0, 138.1 (C6), 132.7, 130.7, 130.3, 130.1, 129.0, 127.5 (Py), 127.3 (Py), 126.9 (Py), 126.8 (Py), 126.1 (Py), 125.02 (Py), 125.00 (Py), 124.4 (Py), 124.1, 123.8, 123.6 (Py), 108.4 (C5), 87.6 (C4'), 85.0 (C1'), 71.2 (C3'), 68.8 (C2'), 64.2 (CH$_2$, OEt), 61.7 (C5'), 57.1 (CH$_2$Py), 39.0 (NCH$_3$), 13.6 (CH$_3$, OEt).

Synthesis of 264.

Compound 262 (315 mg, 0.63 mmol) was coevaporated with anhydrous 1,2-dicholoethane (2×5 mL) and redissolved in anhydrous pyridine (6 mL). Added DMTr-Cl (260 mg, 0.76 mmol) and DMAP (8 mg, 0.06 mmol) and let stir at ambient temperature for 14 h whereupon the crude mixture was diluted with CHCl$_3$ (80 mL) and washed with sat. aq. NaHCO$_3$ (30 mL) and H$_2$O (30 mL). The aqueous layer was back-extracted with CHCl$_3$ (3×15 mL) and the combined organic layers dried over Na$_2$SO$_4$ and evaporated to dryness. The crude was purified by silica gel column chromatography (0-2.5% MeOH/CH$_2$Cl$_2$, v/v) to afford nucleoside 264 (445 mg, 88%) as a pale orange foam. R$_f$: 0.7 (10%, MeOH in CH$_2$Cl$_2$, v/v); MALDI-HRMS m/z 824.3319 ([M+Na]$^+$, C$_{50}$H$_{47}$N$_3$O$_7$.Na$^+$, Calc. 824.3306); $^1$H NMR (DMSO-d$_6$) δ 8.40 (d, 1H, J=9.33 Hz, Py), 8.24-8.30 (m, 2H, Py), 8.18 (d, 1H, J=7.96 Hz, Py), 8.14 (s, 2H, Py) 8.03-8.11 (m, 2H, Py), 7.99 (d, J=7.68 Hz, Py), 7.68 (d, 1H, J=7.68 Hz, H6), 7.19-7.39 (m, 9H, DMTr), 6.83-6.90 (m, 4H, DMTr), 6.32 (d, 1H, J=7.96 Hz, H1'), 5.59-5.64 (m, 2H, 3'-OH, H5), 4.51 (m, 2H, CH$_2$Py), 4.42-4.48 (m, 1H, H3'), 4.08-4.24 (m, 3H, H4', CH$_2$CH$_3$), 3.71 (s, 3H, OCH$_3$), 3.70 (s, 3H, OCH$_3$), 3.51-3.58 (m, 1H, H2'), 3.31-3.35 (m, 1H, H5'$_A$), 3.14-3.20 (m, 1H, H5'$_B$), 2.42 (s, 3H, NCH$_3$), 1.05 (t, 3H, CH$_2$CH$_3$); $^{13}$C NMR (DMSO-d$_6$) δ 169.2, 158.09, 158.08, 154.9, 144.5, 138.1 (C6), 135.3, 135.0, 132.6, 130.7, 130.2, 130.1, 129.7 (Ar), 129.6 (Ar), 129.0, 127.8 (Ar), 127.6 (Ar), 127.5 (Ar), 127.3 (Ar), 126.9 (Ar), 126.8 (Ar), 126.7 (Ar), 126.1 (Ar), 125.0 (Ar), 124.4 (Ar), 124.1, 123.9, 123.6 (Ar), 113.2 (Ar), 113.1 (Ar), 108.1 (C5), 85.9, 85.7 (C4'), 85.3 (C1'), 71.0 (C3'), 68.1 (C2'), 64.2 (CH₂CH₃), 63.9 (C5'), 57.1 (CH₂Py), 55.0 (OCH₃), 38.8 (NCH₃), 13.6 (CH₂CH₃).

Synthesis of 266.

Nucleoside 264 (435 mg, 0.54 mmol) was flushed with argon and cooled to 0° C. over a freezing bath. A solution of 1,1,3,3-tetramethylguanidine (TMG, 0.68 mL, 5.42 mmol) in anhydrous pyridine (10 mL) was flushed with argon and cooled to 0° C. over a freezing bath. After cooling, the pyridine solution was saturated with hydrogen sulfide for 1 h while maintaining the temperature of the bath below 0° C. The solution was then transferred to the pre-cooled flask containing nucleoside 264 and allowed to reach room temperature while stirring for 72 h whereupon the mixture was diluted with EtOAc (100 mL) and washed with conc. aq. NaHCO₃ (50 mL) and H₂O (50 mL). The aqueous layer was then back-extracted with CH₂Cl₂ (3×20 mL) and the combined organic layers were evaporated to dryness and co-evaporated with EtOH:toluene (2:1, 3×15 mL). The crude was then purified via silica gel column chromatography (0-70% EtOAc/petroleum ether, v/v) to afford nucleoside 268 (353 mg, 82%) as a white foam. $R_f$: 0.8 (80%, EtOAc in petroleum ether, v/v); MALDI-HRMS m/z 812.2765 ([M+Na]$^+$, $C_{48}H_{43}N_3O_6S.Na^+$, Calc. 812.2797); $^1$H NMR (DMSO-d₆) δ 12.76 (br d, 1H, ex, J=1.65 Hz, NH), 8.50 (d, 1H, J=9.33 Hz, Py), 8.01-8.30 (m, 8H, Py), 7.74 (d, 1H, J=8.23 Hz, H6), 7.18-7.41 (m, 10H, DMTr, H1'), 6.81-6.91 (m, 4H, DMTr), 5.61 (dd, 1H, J=1.65 Hz, 8.23 Hz, H5), 5.54 (d, 1H, ex, J=4.94, 3'-OH), 4.42-4.58 (m, 3H, CH₂Py, H3'), 4.06-4.11 (m, 1H, H4'), 3.71 (s, 3H, OCH₃), 3.70 (s, 3H, OCH₃), 3.45-3.53 (m, 1H, H2'), 3.30-3.37 (m, 1H, H5'$_A$), 3.15-3.24 (m, 1H, H5'$_B$), 2.43 (s, 3H, NCH₃); $^{13}$C NMR (DMSO-d₆) δ 176.6, 159.0, 158.1, 144.5, 140.8 (C6), 135.3, 135.0, 132.6, 130.7, 130.3, 130.2, 129.7 (Ar), 129.6 (Ar), 129.2, 128.0 (Ar), 127.9 (Ar), 127.6 (Ar), 127.3 (Ar), 126.9 (Ar), 126.8 (Ar), 126.7 (Ar), 126.1 (Ar), 125.0 (Ar), 124.9, 124.4 (Ar), 124.1, 123.9, 123.8, 113.24 (Ar), 113.21 (Ar), 106.9 (C5), 88.0 (C1'), 86.0, 85.3 (C4'), 70.9 (C3'), 68.6 (C2'), 63.9 (C5'), 57.6 (CH₂Py), 55.0 (OCH₃), 39.2 (NCH₃).

Synthesis of 268.

Nucleoside 266 (150 mg, 0.19 mmol) was added to a flame dried 10 mL round-bottom flask and dissolved in an. CH₂Cl₂ (2 mL) whereupon anhydrous diisopropylethylamine (DIPEA, 165 µL, 0.95 mmol) and 2-cyanoethyl diisopropylchlorophosphoramidite (PCl-reagent, 85 µL, 0.38 mmol) were added. The reaction mixture was stirred at ambient temperature under an argon atmosphere for 3.5 h whereupon it was quenched with 1 mL cold EtOH, evaporated to dryness, and purified by silica gel column chromatography (0-55% EtOAc/petroleum ether (v/v) followed by precipitation in cold petroleum ether to afford nucleoside 268 (153 mg, 81%) was a white foam. $R_f$: 0.6 (50%, EtOAc in Pet Ether, v/v); MALDI-HRMS m/z 1012.3843 ([M+Na]$^+$, $C_{57}H_{60}N_5O_7PS.Na^+$, Calc. 1012.3887); $^{31}$P NMR (CDCl₃) δ 150.9, 149.6.

Synthesis of Single-Stranded Probes Modified with Monomer 270.

Briefly, the monomer was introduced into probes using compound 268, MeCN as solvent and DCI as an activator (15 min hand-coupling, 90-99% yield). 10% tert-butylhydroperoxide (tBuOOH) in an. MeCN was used as an oxidizer (2×5 min oxidation, 10:87:3, tBuOOH, MeCN, H₂O) whereas 2,6-aminopurine 2'-deoxyriboside monomers were coupled using MeCN and 4,5-dicyanoimidazole activator, 15 min, 95-99%. Strands were cleaved from solid support 15-17 h, rt, NH₄OH. Purified via RP-HPLC, with DMT cleavage and precipitation overnight in freezer.

Probes Modified with Non-Pairing (or Bulged) Monomers 402-4, 402-N or 402-9.

Particular embodiments pertain to probes that are modified with monomers 402-4, 402-N or 402-9. These monomers were incorporated into probes (e.g., oligonucleotides) using 400-4, 400-N or 400-9 as suggested by commercial vendors. The composition of the probes was verified by MALDI-MS analysis (Table 67) whereas the purity (>80%, unless stated otherwise) was verified by ion-exchange HPLC using a LaChrom L-7000 system (VWR International) equipped with a Gen-Pak Fax column (100 mm×4.6 mm). A representative protocol involves the use of an isocratic hold of 95% A-buffer for 5 min, followed by a linear gradient to 70% B-buffer over 41 min at a flow rate of 0.75 mL/min (A-buffer: 25 mM Tris-Cl, 1 mM EDTA, pH 8.0; B-buffer: 1 M NaCl).

TABLE 67

MS-Data of Representative Probes Modified with Intercalator-Functionalized Monomers 120'Y, 120'W, 140'X and/or 140'Y and Non-Pairing (or Bulged) Monomers 402-4, 402-N Or 402-9.

| Probe | Calc. Mass | Exp. Mass |
|---|---|---|
| 5'-TC(140'X) AGA TAG TTG AC(140'X) ACC (SEQ ID NO: 220) | 5901.1 | 5901.7 |
| 3'-AGG (120'Y)CT ATC AAC TGG (120'Y)GG (SEQ ID NO: 221) | 5984.1 | 5984.2 |
| 5'-TC(140'X) AGA TAG (402-9) TTG AC(140'X) ACC (SEQ ID NO: 222) | 6206.2 | 6206.3 |
| 3'-AGG (120'Y)CT ATC (402-9) AAC TGG (120'Y)GG (SEQ ID NO: 223) | 6123.2 | 6123.5 |
| 5'-TC(140'X) AGA TAG (402-9)₃ TTG AC(140'X) ACC (SEQ ID NO: 224) | 6650.4 | 6650.6 |
| 3'-AGG (120'Y)CT ATC (402-9)₃ AAC TGG (120'Y)GG (SEQ ID NO: 225) | 6567.4 | 6567.7 |
| 5'-TC(140'X) AGA TAG (402-4) TTG AC(140'X) ACC (SEQ ID NO: 226) | 6136.1 | 6136.4 |
| 3'-AGG (120'Y)CT ATC (402-4) AAC TGG (120'Y)GG (SEQ ID NO: 227) | 6053.1 | 6053.3 |

TABLE 67-continued

MS-Data of Representative Probes Modified with
Intercalator-Functionalized Monomers 120Y,
120'W, 140'X and/or 140'Y and Non-Pairing
(or Bulged) Monomers 402-4, 402-N Or 402-9.

| Probe | Calc. Mass | Exp. Mass |
|---|---|---|
| 5'-TC(140'X) AGA TAG (402-4)₃ TTG AC(140'X) ACC (SEQ ID NO: 228) | 6440.1 | 6440.4 |
| 3'-AGG (120Y)CT ATC (402-4)₃ AAC TGG (120Y)GG (SEQ ID NO: 229) | 6357.2 | 6358.5 |
| 5'-TC(140'X) AGA TAG (402-N) TTG AC(140'X) ACC (SEQ ID NO: 230) | 6137.1 | 6137.4 |
| 3'-AGG (120Y)CT ATC (402-N) AAC TGG (120Y)GG (SEQ ID NO: 231) | 6054.1 | 6054.3 |
| 5'-TC(140'X) AGA TAG (402-N)₃ TTG AC(140'X) ACC (SEQ ID NO: 232) | 6360.1 | 6360.2 |
| 3'-AGG (120Y)CT ATC (402-N)₃ AAC TGG (120Y)GG (SEQ ID NO: 233) | 6443.1 | 6443.8 |

TABLE 68

MS-Data of Additional Single-Stranded Probes Modified with
Intercalator-Functionalized Monomers 120Y, 120'W and
140'X as well as Non-Pairing (or Bulged) Monomers
402-4, 402-N Or 402-9 as eell as a Cy3 Fluorophore

| Probe | Mass Calc. | Mass Obs. |
|---|---|---|
| 5'-Cy3 (120'W)GC CC(120Y) GTG 402-9 CC(140'X) TG (SEQ ID NO: 234) | 5619.6 | 5619.3 |
| 3'-T(140'X)G GGA (140'X)AC 402-9 GGG (120'W)C Cy3 (SEQ ID NO: 235) | 5731.7 | 5731.2 |
| 5'-Cy3 (120'W)GC CC(120Y) GTG 402-4 CC(140'X) TG (SEQ ID NO: 236) | 5549.5 | 5549.2 |
| 3'-T(140'X)G GGA (140'X)AC 402-4 GGG (120'W)C Cy3 (SEQ ID NO: 237) | 5661.6 | 5661.3 |
| 5'-Cy3 (120'W)GC CC(120Y) GTG 402-N CC(140'X) TG (SEQ ID NO: 238) | 5550.5 | 5550.0 |
| 3'-T(140'X)G GGA (140'X)AC 402-N GGG (120'W)C Cy3 (SEQ ID NO: 239) | 5662.6 | 5662.3 |

Experimental Protocol for Electrophoretic Mobility Shift Assays Used to Study Targeting of Nucleic Acid Targets, More Commonly, dsDNA, as Illustrated by FIGS. 24-26 and FIGS. 30-39:

100 pmol of hairpin oligonucleotide was labeled with digoxigenine-ddUTP following recommended protocol by Roche Applied Bioscience. Equal volumes of 100 nM solution of digoxigenine labeled target hairpin duplex and varying concentration (e.g., 0.5 µM, 1 µM, 5 µM, 10 µM, 50 µM) of stock probe duplex solution in 1xHEPES buffer (50 mM HEPES, 100 mM NaCl, 5 mM MgCl$_2$, pH 7.2, 10% sucrose, 1 mg/mL spermine tetrahydrochloride) were mixed and incubated for three hours before loading on 15% non-denaturing polyacrilamide gel. After 2-3 hrs of electrophoresis at 100V and 0° C. the oligonucleotide complexes were transferred to a positively charged nylon membrane by electroblotting, which was then processed according to recommended protocol for chemiluminescence detection by Roche Applied Bioscience. The chemiluminescence was captured on X-ray film and bands were quantified using Quantity One software.

Additional Working Examples of dsDNA-Targeting Via the Method Disclosed in FIG. 1 Using Modified Double-Stranded Probes.

Figure 34:
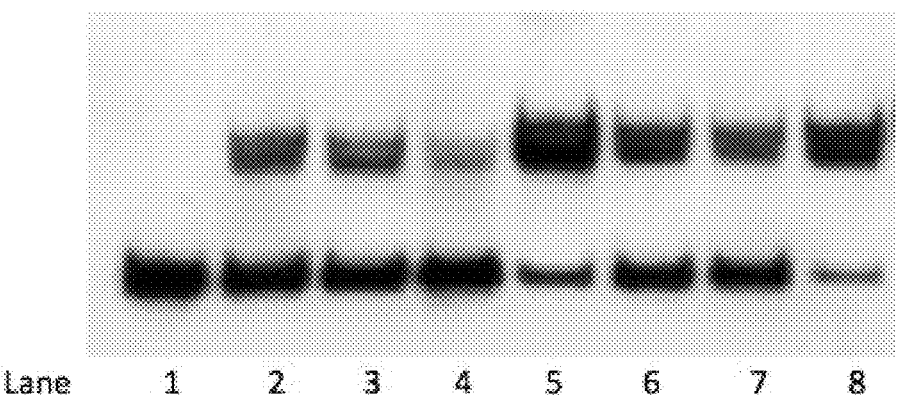
FIG. 34 illustrates targeting of structured dsDNA HP1 using different probes modified with monomer 120Y (200-fold molar excess) as monitored by the gel mobility shift assay (electrophoretic mobility shift assay; for concept see FIG. 30). HP1: (5'-GGTATATATAGGC-(T10)-GC-CTATATATACC (SEQ ID NO: 4)) (34.4 nM) incubated at room temperature. HP1 alone (lane 1); HP1 incubated with 200-excess of 120Y-P1 (lane 2), 120Y-P2 (lane 3), 120Y-P3 (lane 4), 120Y-P4 (lane 5), 120Y-P5 (lane 6), 120Y-P6 (lane 7) or 120Y-P7 (lane 8).

A central embodiment entails the use of probes, more commonly double-stranded probes, with certain interstrand zipper monomer arrangements, more commonly one or more +1 interstrand zipper arrangements, for targeting of nucleic acid targets, more commonly dsDNA, via the method shown in FIG. 1. FIG. 34 and Table 69 show the results from additional working examples hereof. Thus, various double-stranded probes with one or more +1 interstrand zipper arrangements of monomer 120Y were incubated at 200-fold excess (6.88 µM) with a structured dig-labeled model dsDNA target, i.e., a hairpin-loop (HP) with a double-stranded target stem region that is connected via a loop of ten thymidines [HP1: 5'-GGTATATATAGGC-(T10)-GCCTATATATACC (SEQ ID NO: 4)] at room temperature for 15 h. Hepes buffer (50 mM Hepes, 100 mM NaCl, 10 mM MgCl2, 20% sucrose, 2.9 mM spermine, pH 7.2) was used. FIG. 34 illustrates recognition as monitored by the formation of the probe:HP1 complex, which has retarded mobility on non-denaturing PAGE compared to HP1 (for related concept see FIG. 30). The degree of invasion (=recognition) is calculated from the ratio of the signal [100 (probe:HP1)/HP1] in FIG. 34 and tabulated in Table 69. The data demonstrate that probes with one or more +1 interstrand arrangements of the disclosed monomers recognize the double-stranded stem of the structured dsDNA target. Without being limited to a theory of operation, probes with two or more +1 interstrand arrangements of the disclosed monomers recognize dsDNA targets with similar or significantly greater efficiency (e.g., see entries 4-8) than probes with a single +1 interstrand arrangements of the disclosed monomers (e.g., see entries 1-3).

excess with structured dsDNAs (HP1-HP7; for sequences, see Table 70 below) that have an isosequential (HP1) or non-isosequential double-stranded DNA target region (HP2-HP7). Only when probe 120Y-P4 is incubated with its isosequential (correct) target, significant recognition is observed (Lane 1). Lanes 2-7 show no or scant levels of recognition. This demonstrates that targeting of dsDNA using the disclosed probes is highly specific.

TABLE 69

Recognition Efficiency of Double-Stranded Probes Modified with one or More +1 Interstrand Zipper Arrangements of Monomer 120Y

| Name | Probe | Invasion (%) |
|---|---|---|
| 120Y-P1 | 5'-GG(120Y) ATA TAT AGG C (SEQ ID NO: 38)<br>3'-CCA (120Y)AT ATA TCC G<br>(SEQ ID NO: 136) | 48 |
| 120Y-P2 | 5'-GGT A(120Y)A TAT AGG C (SEQ ID NO: 40)<br>3'-CCA TA(120Y) ATA TCC G<br>(SEQ ID NO: 137) | 46 |
| 120Y-P3 | 5'-GGT ATA TA(120Y) AGG C (SEQ ID NO: 44)<br>3'-CCA TAT ATA (120Y)CC G<br>(SEQ ID NO: 139) | 24 |
| 120Y-P4 | 5'-GG(120Y) A(120Y)A TAT AGG C<br>(SEQ ID NO: 46)<br>3'-CCA (120Y)A(120Y) ATA TCC G<br>(SEQ ID NO: 140) | 86 |
| 120Y-P5 | 5'-GG(120Y) ATA (120Y)AT AGG C<br>(SEQ ID NO: 48)<br>3'-CCA (120Y)AT A(120Y)A TCC G<br>(SEQ ID NO: 141) | 45 |
| 120Y-P6 | 5'-GG(120Y) ATA TA(120Y) AGG C<br>(SEQ ID NO: 50)<br>3'-CCA (120Y)AT ATA (120Y)CC G<br>(SEQ ID NO: 142) | 35 |
| 120Y-P7 | 5'-GGT A(120Y)A (120Y)AT AGG C<br>(SEQ ID NO: 52)<br>3'-CCA TA(120Y) A(120Y)A TCC G<br>(SEQ ID NO: 143) | 82 |
| 120Y-P8 | 5'-GG(120Y) A(120Y)A (120Y)A(120Y) AGG C<br>(SEQ ID NO: 56)<br>3'-CCA (120Y)A(120Y) A(120Y)A (120Y)CC G<br>(SEQ ID NO: 145) | 100 |

Figure 35:
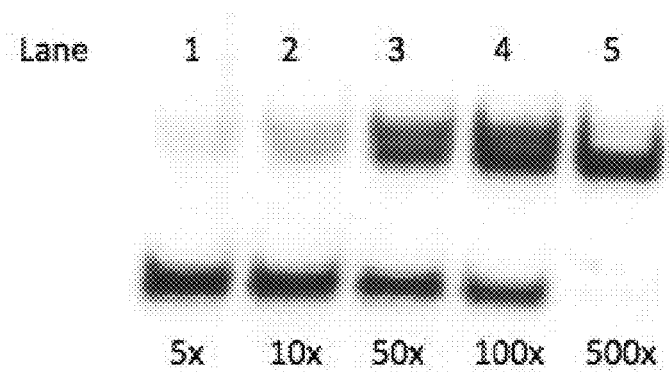
FIG. 35 illustrates targeting of structured dsDNA HP1 using various concentrations of a selected probe (120Y-P4).

FIG. 35 illustrates targeting of structured dsDNA HP1 using various concentrations of 120Y-P4. Addition of probes with two +1 interstrand arrangements of the disclosed monomers results in a dose-dependent recognition of the structured dsDNA target. At low probe excess (e.g., 5-10 fold relative to target HP1) little recognition is observed (as seen by the pale upper band). At higher probe excess (e.g., 50-500 fold relative to target HP1) significant (or complete) recognition is observed. Without being limited to a single mode of operation, and excess of 50-fold or greater fold probe excess (relative to target) may be needed to facilitate significant recognition.

Figure 36:
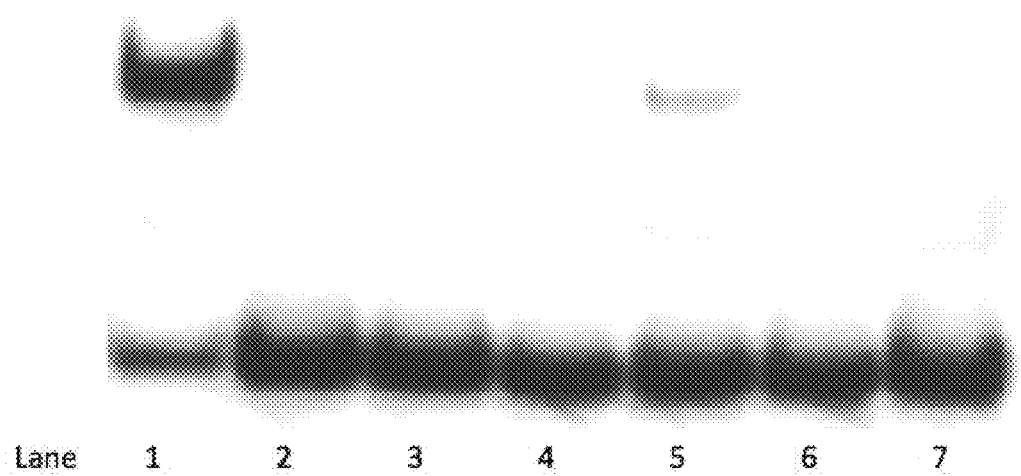
FIG. 36 illustrates the results of a control experiment demonstrating the recognition specificity of the disclosed probes.

FIG. 36 provides the results of a representative control experiment demonstrating the recognition specificity of the disclosed probes. Probe 120Y-P4 is incubated at 200-fold

TABLE 70

Sequence of Isosequential and Non-Isosequential dsDNA Targets used in FIGS. 34-36

| Target Sequence | |
|---|---|
| HP1 | 5'-GGT ATA TAT AGG C (T)$_{10}$ G CCT ATA TAT ACC (SEQ ID NO: 4) |
| HP2 | 5'-GGT ATT TAT AGG C (T)$_{10}$ G CCT ATA AAT ACC (SEQ ID NO: 240) |
| HP3 | 5'-GGT ATG TAT AGG C (T)$_{10}$ G CCT ATA CAT ACC (SEQ ID NO: 241) |

TABLE 70-continued

Sequence of Isosequential and Non-Isosequential dsDNA Targets used in FIGS. 34-36

Target Sequence

HP4  5'-GGT ATC TAT AGG C (T)$_{10}$ G CCT ATA GAT ACC (SEQ ID NO: 242)

HP5  5'-GGT ATA TAA AGG C (T)$_{10}$ G CCT TTA TAT ACC (SEQ ID NO: 243)

HP6  5'-GGT ATA TAG AGG C (T)$_{10}$ G CCT CTA TAT ACC (SEQ ID NO: 244)

HP7  5'-GGT ATA TAC AGG C (T)$_{10}$ G CCT GTA TAT ACC (SEQ ID NO: 245)

Figure 37:
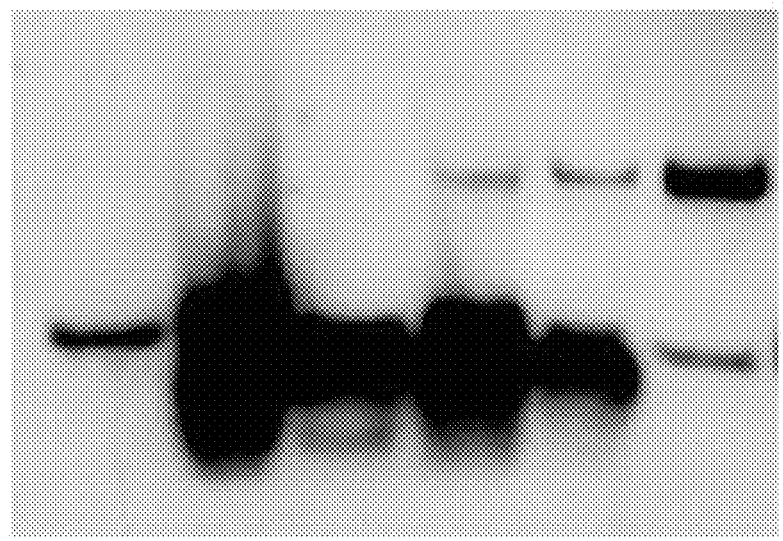
FIG. 37 provides proof for a proposed recognition mechanism, demonstrating the disclosed mode of nucleic acid targeting using disclosed probes. Lane 1: DIG-labeled HP1 only; lane 2: DIG-labeled 'upper' probe strand only (5'-GG (120Y)A(120Y)A TAT AGG C-DIG (SEQ ID NO: 46); lane 3: DIG-labeled 'lower' probe strand only (3'-DIG-CCA (120Y)A(120Y) ATA TCC G (SEQ ID NO: 6)); lane 4: probe with DIG-labeled upper strand (5'-GG(120Y)A (120Y)ATATAGGC-DIG (SEQ ID NO: 46)+3'-CCA(120Y)A(120Y)ATATCCG (SEQ ID NO: 140)) incubated with unlabeled structured target HP1; lane 5: probe with DIG-labeled lower strand (5'-GG(120Y)A(120Y)ATATAGGC (SEQ ID NO: 46)+3'-DIG-CCA(120Y)A(120Y)ATATCCG (SEQ ID NO: 140)) incubated with unlabeled structured target HP1; lane 6: unlabeled probe (5'-GG(120Y)A(120Y)ATATAGGC (SEQ ID NO: 46)+3'-CCA(120Y)A(120Y)ATATCCG (SEQ ID NO: 140)) incubated with labeled structured target HP1.

FIG. 37 demonstrates that the observed 'low mobility band' (upper band) truly is a recognition complex that is comprised of both probes strands and both target strands (see FIG. 1). In other words, FIG. 37 demonstrates that the mode of operation is as illustrated in FIG. 1. With reference to FIG. 37, lane 1: DIG-labeled HP1 only; lane 2: DIG-labeled 'upper' probe strand only (i.e., 5'-GG(120Y)A(120Y) ATATAGGC-DIG (SEQ ID NO: 46)); lane 3: DIG-labeled 'lower' probe strand only (3'-DIG-CCA(120Y)A(120Y) ATATCCG (SEQ ID NO: 140)); lane 4: probe with DIG-labeled upper strand (5'-GG(120Y)A(120Y)ATATAGGC-DIG (SEQ ID NO: 46)+3'-CCA(120Y)A(120Y)ATATCCG (SEQ ID NO: 140)) incubated with unlabeled HP1; lane 5: probe with DIG-labeled lower strand (5'-GG(120Y)A (120Y)ATATAGGC (SEQ ID NO: 46)+3'-DIG-CCA(120Y) A(120Y)ATATCCG (SEQ ID NO: 140)) incubated with unlabeled HP1; lane 6: unlabeled probe 120Y-P4 incubated with labeled structured target HP1. With continued reference to FIG. 37, lane 1: shows where unreacted target is located; Lane 2+3: shows where unreacted probes are located; Lanes 4-6 concern real recognition experiments and show the same 'low mobility band' (upper band) regardless if whether only the target or only one of the probe strands was labelled with digoxeginin (dig).

Figure 38:
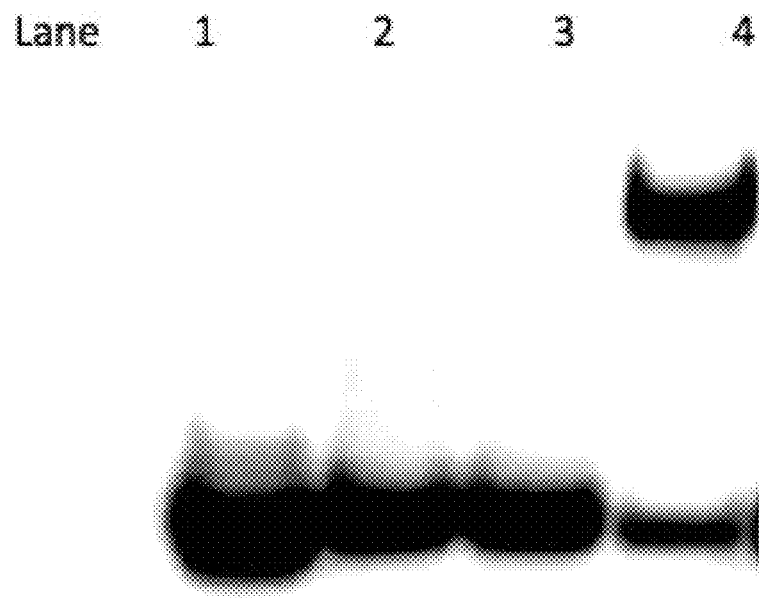
FIG. 38 provides information that both strands of a double-stranded probe facilitate recognition of dsDNA target regions. Lane 1: only HP1; lane 2: HP1+upper strand of 120Y-P4 (i.e., 5'-GG(120Y)A(120Y)ATATAGGC (SEQ ID NO: 46)); lane 3: HP1+lower strand of 120Y-P4 (i.e., 3'-CCA(120Y)A(120Y)ATATCCG (SEQ ID NO: 140)); lane 4: HP1+120Y-P4. Probes are used in 200-fold molar excess relative to structured target HP1. Incubated in Hepes buffer for 15 hours at room temperature.

FIG. 38 concerns a control experiment demonstrating that both probe strands are needed to facilitate recognition of double-stranded DNA. Incubation of structured dsDNA target HP1 with only the upper (lane 2; 5'-GG(120Y)A (120Y)ATATAGGC (SEQ ID NO: 46) or lower (lane 3; 3'-CCA(120Y)A(120Y)ATATCCG (SEQ ID NO: 140)) strand of 120Y-P4, does not result in formation of a recognition complex (note absence of upper spot). This demonstrates that both strands of the disclosed double-stranded probes are needed to facilitate recognition of dsDNA (lane 4). In lane 1, only dsDNA target HP1 is present. All probe strands are added at 200-fold excess.

Figure 39:
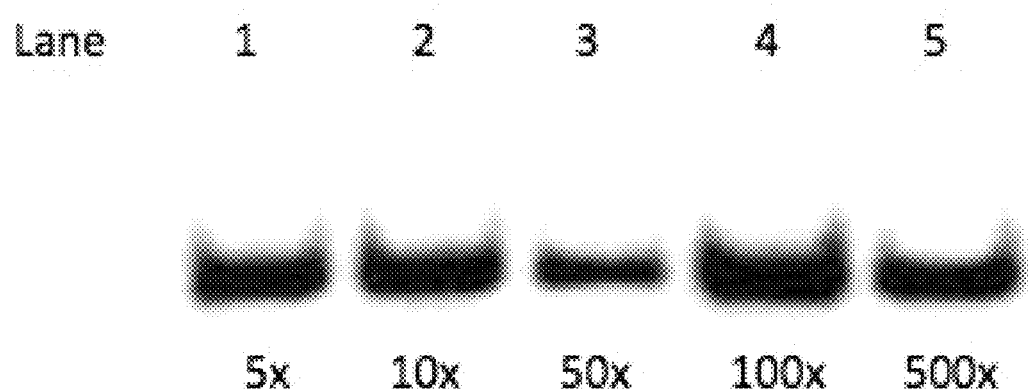
FIG. 39 is a gel illustrating the results of incubation of HP1 with increasing concentrations of an isosequential and unmodified dsDNA probe. 5×-500× refers to molar fold excess of dsDNA with respect to HP1

FIG. 39 illustrates the results of a control experiment demonstrating that an unmodified probe (i.e., without any incorporations of disclosed monomers) does not result in recognition of dsDNA.

Table 71 provides data from dose-response and time-course studies where the listed probes were incubated with structured dsDNA target HP1 at a) different concentrations but fixed time (dose-response, used to determine Kd 50%=probe concentration that results in 50% binding) or b) fixed concentration+varying time (time-course; used to determine TC 50%=time to accomplish 50% recognition). With reference to Table 71, probes with a greater number of +1 zipper monomer arrangements display more effective recognition (lower Kd-values, i.e., 120Q-based probes 1.72 vs 0.76 vs 0.30 uM; 120Y-based probes 10.30, 2.95, 0.34 uM). Without being limited to a single mode of theory, probes with +1 zipper arrangements of monomer 120Q are more efficient than monomer 120Y (lower Kd-values). Recognition is faster for probes with +1 zipper arrangements of monomer 120Q than monomer 120Y in some but not all cases

TABLE 71

Representative Results from Dose-Response and Time-Course Studies using Certain Disclosed Probes

| Sequence | KD 50% (µM) | TC 50% (min) |
|---|---|---|
| 5'-GG(120Q) ATA TAT AGG C (SEQ ID NO: 246) 3'-CCA (120Q)AT ATA TCC G (SEQ ID NO: 163) | 1.72 | 560 |
| 5'-GG(120Q) A(120Q)A TAT AGG C (SEQ ID NO: 248) 3'-CCA (120Q)A(120Q) ATA TCC G (SEQ ID NO: 165) | 0.76 | 205 |
| 5'-GG(120Q) A(120Q)A (120Q)A(120Q) AGG C (SEQ ID NO: 250) 3'-CCA (120Q)A(120Q) A(120Q)A (120Q) CC G (SEQ ID NO: 167) | 0.3 | 29 |
| 5'-GG(120Y) ATA TAT AGG C (SEQ ID NO: 38) 3'-CCA (120Y)AT ATA TCC G (SEQ ID NO: 136) | 10.3 | N/A |
| 5'-GG(120Y) A(120Y)A TAT AGG C (SEQ ID NO: 40) 3'-CCA (120Y)A(120Y) ATA TCC G (SEQ ID NO: 140) | 2.95 | 62 |
| 5'-GG(120Y) A(120Y)A (120Y)A(120Y) AGG C (SEQ ID NO: 56) 3'-CCA (120Y)A(120Y) A(120Y)A (120Y) CC G (SEQ ID NO: 145) | 0.34 | 6 |

Figure 40:
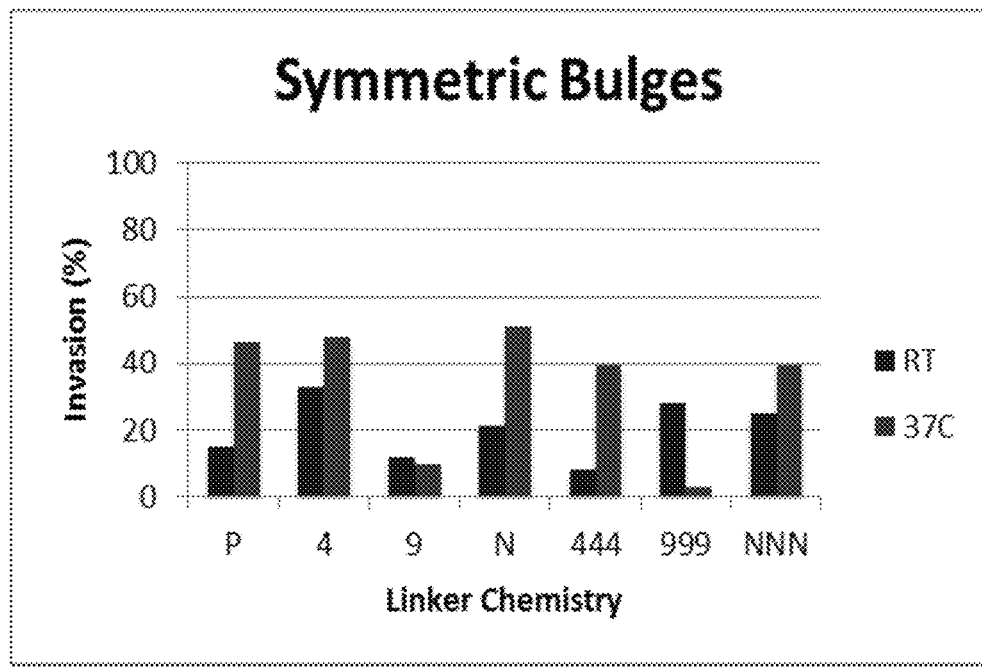
FIG. 40 is a graph of linker chemistry versus invastion % for symmetric bulges illustrating the results of targeting structured dsDNA (stem-loop) target using probe with one or more bulges, where Dig-labeled structured dsDNA target was incubated with 200-fold excess of probe in Hepes buffer for 15 hours followed by electrophoresis, imaging, and quantification.
Figure 41:
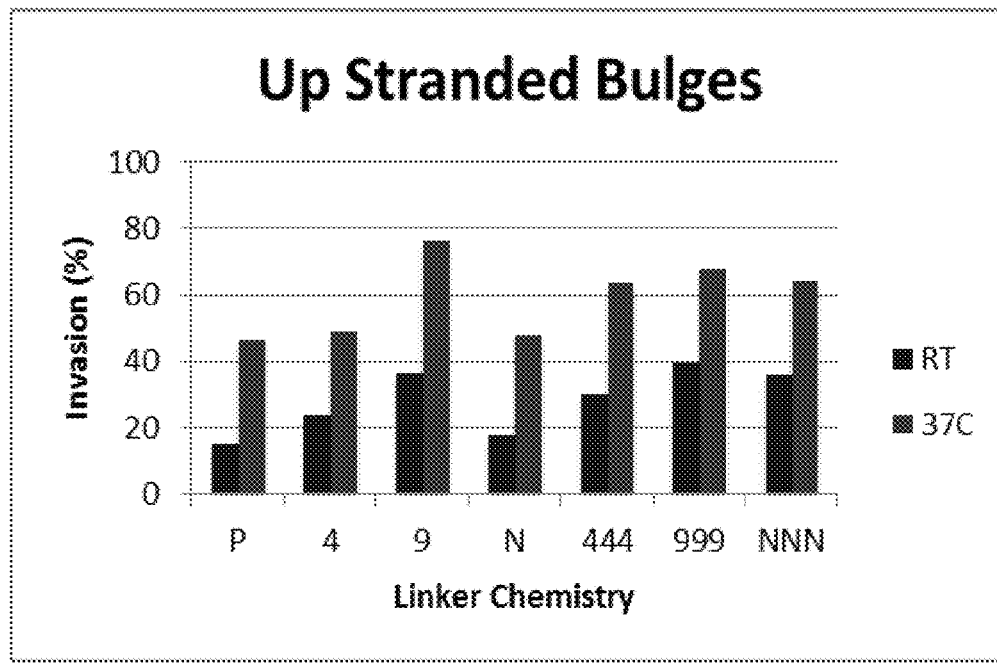
FIG. 41 is a graph of linker chemistry versus invastion % for an up stranded bulge illustrating the results of targeting structured dsDNA (stem-loop) target using probe with one or more bulges where Dig-labeled structured dsDNA target was incubated with 200-fold excess of probe in Hepes buffer for 15 hours followed by electrophoresis, imaging, and quantification.
Figure 42:
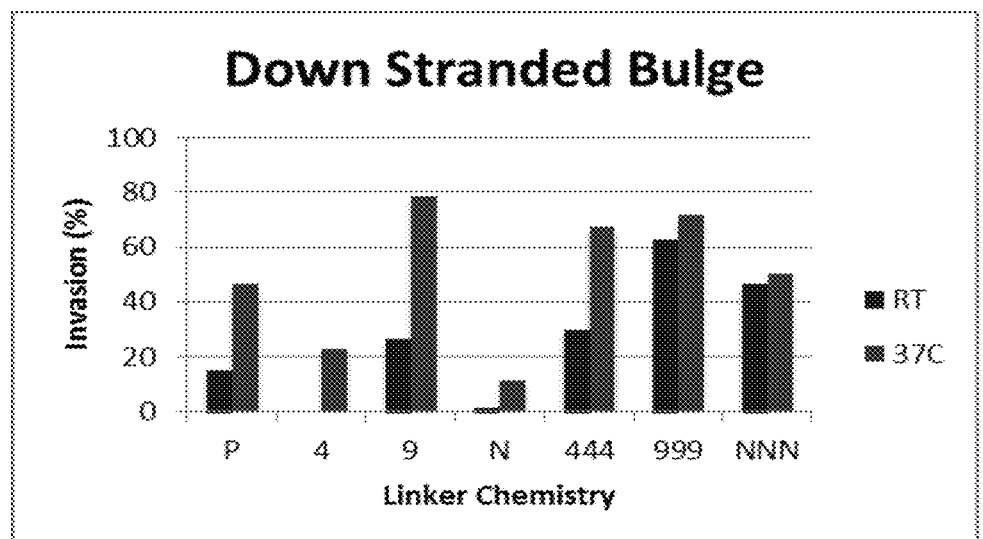
FIG. 42 is a graph of linker chemistry versus invastion % for a down stranded bulge illustrating the results of targeting structured dsDNA (stem-loop) target using probe with one or more bulges where Dig-labeled structured dsDNA target was incubated with 200-fold excess of probe in Hepes buffer for 15 hours followed by electrophoresis, imaging, and quantification.

FIGS. 40-42 illustrate the results of recognition experiments where probes modified with intercalator-functionalized monomers 120Y, 120'W, 140'X and/or 140'Y and non-pairing (or bulged) monomers 402-4, 402-N or 402-9 (for probes, see Table 67 above) are incubated with an isosequential structured dsDNA target (i.e., 5'-GGT GGT CAA CTA TCT GGA-(T10)-TCC AGA TAG TTG ACC ACC (SEQ ID NO: 11)) at room temperature or 37° C. These figures illustrate quantification results from a gel mobility shift assay (similar to FIG. 30), where a 200-fold excess of the listed double-stranded probes containing one (either in up or down strand) or two (=symmetric) 'bulges' (=positioned opposite of each other) were used.

The data show that some of probes with one or two bulges display dsDNA-recognition efficiencies that differ from the 'regular' probe (P; i.e., not containing such a bulged monomer) at both evaluated temperatures. More specifically, at 37° C.: probes with two +1 interstrand arrangements of 120Y and 140'X that are additionally modified with (402-4), (402-N), (402-4)$_3$ and (402-N)$_3$ in both strands (=symmetric bulges) display similar or more efficient dsDNA-targeting than the regular probe. At room temperature, all probes that are modified with 402-4, 402-9, 402-N, (402-4)$_3$, (402-9)$_3$ or (402-N)$_3$ in both strands display similar or more efficient dsDNA-targeting than the regular probe. A probe containing one bulge, in some cases, displays greater recognition efficiency than a regular probe (P) without the bulges Without being limited to one a theory of operation, introduction of one or more bulge monomers may be beneficial for the dsDNA-recognition events disclosed herein.

Table 72 shows the degree of recognition (based on gel electrophoresis assay; probes used at 200-fold excess) upon incubation of structured isosequential dsDNA target HP1 [=5'-GGTATATATAGGC-(T10)-GCCTATATATACC (SEQ ID NO: 4)] with probes that are modified with two +1 interstrand zipper arrangements of monomer 120Y and one or more non-pairing (bulged) monomers 402-9.

TABLE 72

Dsdna-Recognition Efficiency of Double-Stranded Probes that are Modified with +1 Interstrand Zipper Arrangements of Monomer 120Y and Non-Pairing (Bulged) Monomer 402-9

| Probe | Degree of recognition (%) | |
|---|---|---|
| | 8° C. | 20° C. |
| 5'-GGT A(120Y)A (120Y)AT AGG C (SEQ ID NO: 52) 3'-CCA TA(120Y) A(120Y)A TCC G (SEQ ID NO: 143) | 41 | 90 |
| 5'-GG(402-9)T A(120Y)A (120Y)ATAGG C (SEQ ID NO: 168) 3'-CC(402-9)ATA(120Y)A(120Y)ATCC G (SEQ ID NO: 169) | 57 | 96 |
| 5'-GGTA(120Y)A(120Y)AT AG(402-9)GC (SEQ ID NO: 170) 3'-CCATA(120Y)A(120Y)A TC(402-9)CG (SEQ ID NO: 171) | 71 | 91 |
| 5'-GG(402-9)TA(120Y)A(120Y)ATAG (402-9)GC (SEQ ID NO: 172) 3'-CC(402-9)ATA(120Y)A(120Y)ATC (402-9)CG (SEQ ID NO: 173) | 2 | 2 |
| 5'-GG(402-9)TA(120Y)A(120Y)ATAGGC (SEQ ID NO: 168) 3'-CCATA(120Y)A(120Y)ATC(402-9)CG (SEQ ID NO: 171) | 4 | 20 |
| 5'-GGT A(120Y)A(120Y)AT AG(402-9)GC (SEQ ID NO: 170) 3'-CC(402-9)ATA(120Y)A(120Y)A TCCG (SEQ ID NO: 169) | 13 | 43 |
| 5'-GG(402-9)TA(120Y)A (120Y)AT AGG C (SEQ ID NO: 168) 3'-CCATA(120Y) A(120Y)A TCC G (SEQ ID NO: 143) | 49 | 99 |
| 5'-GGTA(120Y)A (120Y)AT AG(402-9)GC (SEQ ID NO: 170) 3'-CCATA(120Y)A(120Y)ATCCG (SEQ ID NO: 143) | 49 | 99 |

TABLE 72-continued

Dsdna-Recognition Efficiency of Double-Stranded Probes that are Modified with +1 Interstrand Zipper Arrangements of Monomer 120Y and Non-Pairing (Bulged) Monomer 402-9

| Probe | Degree of recognition (%) | |
|---|---|---|
| | 8° C. | 20° C. |
| 5'-GGTA(120Y)A(120Y)ATAGGC (SEQ ID NO: 52) 3'-CC(402-9)ATA(120Y)A(120Y)ATCCG (SEQ ID NO: 169) | 37 | 100 |
| 5'-GGTA(120Y)A (120Y)AT AGG C (SEQ ID NO: 52) 3'-CCATA(120Y)A(120Y)ATC(402-9)CG (SEQ ID NO: 171) | 46 | 102 |
| 5'-GG(402-9)TA(120Y)A(120Y)ATAG (402-9)GC (SEQ ID NO: 172) 3'-CCATA(120Y)A(120Y)ATCCG (SEQ ID NO: 143) | 75 | 93 |
| 5'-GGT A(120Y)A (120Y)AT AGG C (SEQ ID NO: 52) 3'-CC(402-9)ATA(120Y)A(120Y)ATC (402-9)CG (SEQ ID NO: 173) | 66 | 92 |
| 5'-GG(402-9)TA(120Y)A (120Y)ATAG (402-9)GC (SEQ ID NO: 172) 3'-CC(402-9)ATA(120Y)A(120Y)ATCC G (SEQ ID NO: 169) | 19 | 3 |
| 5'-GG(402-9)TA(120Y)A (120Y)AT AG (402-9)GC (SEQ ID NO: 172) 3'-CCATA(120Y)A(120Y)ATC(402-9)CG (SEQ ID NO: 171) | 6 | 1 |

Figure 43:
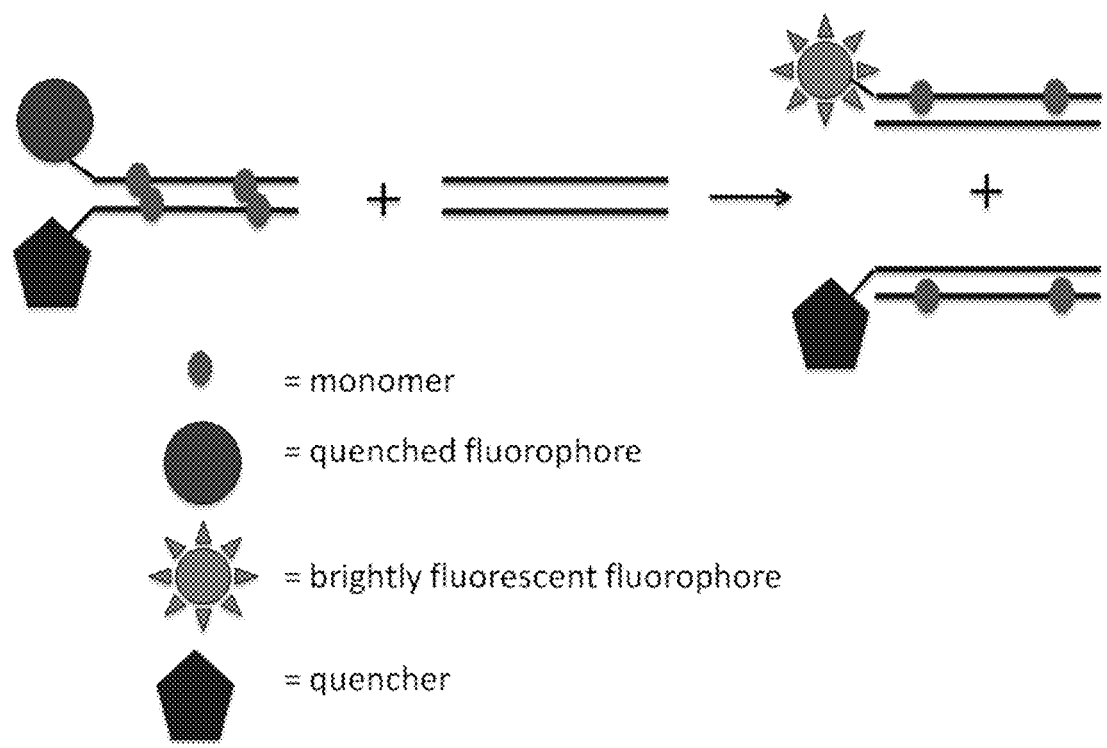
FIG. 43 is an illustration on the use of double-stranded probes with +1 interstrand zipper arrangements that are additionally modified with a fluorophore-quencher pair. Binding to the nucleic acid target results in generation of an optical signal, more commonly a fluorescent signal.

Particular embodiments involve the use of double-stranded probes with certain interstrand zipper monomer arrangements, more commonly one or more +1 interstrand zipper arrangements, that are additionally modified with fluorophore-quencher or fluorophore-fluorophore quencher pairs, and which enable targeting of nucleic acid targets, more commonly dsDNA, via the method shown in FIG. 43, under the simultaneous generation of an optical signal, more commonly a fluorescent signal. Table 73 below, provides working examples of this embodiment where Cy3 and BHQ2 (=Black Hole Quencher 2) are used as a representative fluorophore-quencher pair. With reference to Table 73, probe-target duplexes (products of recognition reaction) display significantly higher thermostability than the probe, which enables detection via the method illustrated by FIG. 43.

TABLE 73

MS Of Representative Examples of Double-Stranded Probes with +1 Interstrand Zipper Monomer Arrangements, which are Additionally Modified With Fluorophore-Quencher Pairs (BHQ2 = Black Hole Quencher 2)

| Sequence | Mass Calc. | Mass Obs. |
|---|---|---|
| 5'-Cy3 (120'W)GC CC(120Y) GTG CC(140'X) TG (SEQ ID NO: 128) | 5397.5 | 5396.0 |
| 3'-BHQ2 T(140'X)G GGA (140'X)AC GGG (120'W)C (SEQ ID NO: 127) | 5558.4 | 5558.9 |

TABLE 73-continued

MS Of Representative Examples of Double-Stranded Probes
with +1 Interstrand Zipper Monomer Arrangements, which
are Additionally Modified With Fluorophore-Quencher Pairs
(BHQ2 = Black Hole Quencher 2)

| Sequence | Mass Calc. | Mass Obs. |
| --- | --- | --- |
| 5'-(120'W)GC CC(120Y) GTG CC(140'X) TG BHQ2 (SEQ ID NO: 118) | 5446.4 | 5445.9 |
| 3'-T(140'X)G GGA (140'X)AC GGG (120'W)C Cy3 (SEQ ID NO: 119) | 5509.6 | 5508.6 |

Particular embodiments involve the use of double-stranded probes with certain interstrand zipper monomer arrangements, more commonly one or more +1 interstrand zipper arrangements, where the oligonucleotide backbone is chemically modified. Table 74 below, provides a working example hereof, where the backbone of double-stranded probe is fully modified with the phosphorthioate-DNA backbone modification.

TABLE 74

MS of Representative Examples of Double-Stranded Probes with +1 Interstrand Zipper Monomer Arrangements, where the Backbone of Double-Stranded Probe is Fully Modified with the Phosphorthioate-DNA [Ps-DNA] Backbone Modification.

| Probe | Mass Calc. | Mass Obs. |
| --- | --- | --- |
| 5'-[ps-DNA]-Cy3 (120'W)GC CC(120Y) GTG CC(140'X) TG (SEQ ID NO: 128) | 5621.5 | 5622.0 |

TABLE 74-continued

MS of Representative Examples of Double-Stranded Probes with +1 Interstrand Zipper Monomer Arrangements, where the Backbone of Double-Stranded Probe is Fully Modified with the Phosphorthioate-DNA [Ps-DNA] Backbone Modification.

| Probe | Mass Calc. | Mass Obs. |
| --- | --- | --- |
| 3'-[ps-DNA]-T(140'X)G GGA (140'X)AC GGG (120'W)C-Cy3-5' (SEQ ID NO: 127) | 5733.6 | 5734.0 |

Additional information concerning subject matter similar to that disclosed herein is provided by International Patent Application No. PCT/US2010/048520, which is incorporated herein by reference.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

I claim:

1. A double stranded probe, comprising:

a pair of monomers comprising a first monomer having a formula

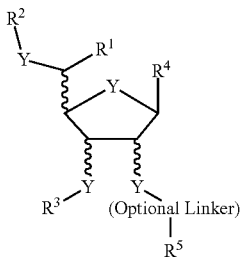

where each Y independently is selected from carbon, oxygen, sulfur, a triazole, oxazole, tetrazole, isoxazole, and $NR^b$, wherein $R^b$ is selected from hydrogen, aliphatic, aryl, heteroaliphatic, and heteroaryl; $R^1$ and $R^2$ are selected from hydrogen, aliphatic, aryl, aryl aliphatic, and a heteroatom-containing moiety, or $R^2$ is selected from a heteroatom-containing functional group; $R^3$ is a heteroatom-containing functional group; $R^4$ is selected from any natural or non-natural nucleobase; $R^5$ is selected from an intercalator suitable for intercalating within a nucleic acid; and "optional linker" is selected from linkers comprising alkyl linkers, amide linkers, carbamate linkers, carbonate linkers, urea linkers, and combinations thereof;

a second monomer having a formula

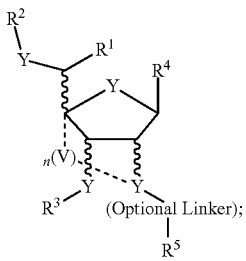

wherein Y, $R^1$, $R^2$ $R^3$, $R^4$, $R^5$, and "optional linker" are as stated for the first monomer; V is selected from carbon, oxygen, sulfur, and $NR^b$; and n ranges from 0 to 4;

at least one nucleotide selected from a natural nucleotide, a non-natural nucleotide, and combinations thereof; and a signal generating moiety capable of being detected and wherein the signal generating moiety is selected from a fluorophore, a member of a specific binding pair, a nanoparticle, or combinations thereof; one or more bulge monomers selected from

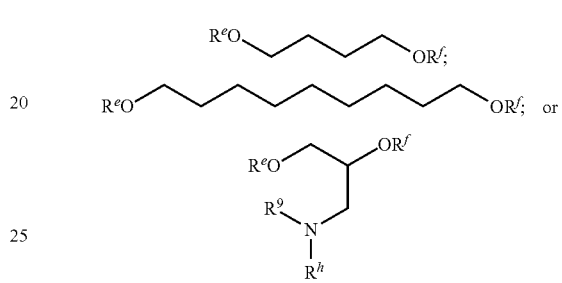

wherein $R^e$ is selected from H, DMTr, or phosphate, $R^f$ is selected from H, $(N(i-Pr)_2)P(OCH_2CH_2CN)$, or phosphate, and $R^g$ and $R^h$ independently selected from hydrogen, aliphatic, cyclic, heterocyclic, aromatic, heteroaromatic, amides, and carbamates; or a combination of the signal generating moiety and the one or more bulge monomers.

2. A double stranded probe, comprising:

a pair of monomers comprising a first monomer having a formula

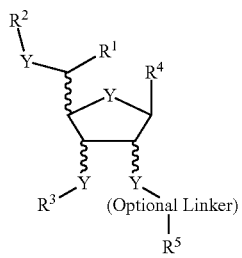

where each Y independently is selected from carbon, oxygen, sulfur, a triazole, oxazole, tetrazole, isoxazole, and $NR^b$, wherein $R^h$ is selected from hydrogen, aliphatic, aryl, heteroaliphatic, and heteroaryl; $R^1$ and $R^2$ are selected from hydrogen, aliphatic, aryl, aryl aliphatic, and a heteroatom-containing moiety, or $R^2$ is selected from a heteroatom-containing functional group; $R^3$ is a heteroatom-containing functional group; $R^4$ is selected from any natural or non-natural nucleobase; $R^5$ is selected from an intercalator suitable for intercalating within a nucleic acid; "optional linker" is selected from linkers comprising alkyl linkers, amide linkers, carbamate linkers, carbonate linkers, urea linkers, and combinations thereof;

a second monomer having a formula

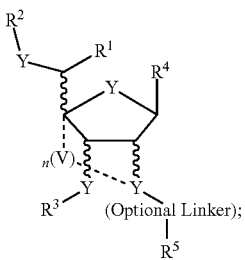

wherein Y, $R^1$, $R^2$ $R^3$, $R^4$, $R^5$, and "optional linker" are as stated for the first monomer; V is selected from carbon, oxygen, sulfur, and $NR^b$; and n ranges from 0 to 4; wherein the probe has a sequence selected from any one of SEQ ID Nos. 5-10, 12-33, 38-65, 72-85, 94-105, 112-129, 136-218, 220-239, or 246-253.

3. A method for associating a probe with a target, comprising:

selecting a double stranded probe comprising a pair of monomers comprising a first monomer having a formula

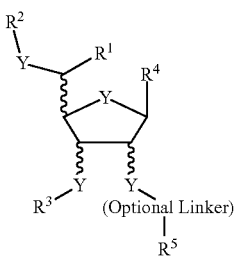

where each Y independently is selected from carbon, oxygen, sulfur, a triazole, oxazole, tetrazole, isoxazole, and $NR^b$, wherein $R^b$ is selected from hydrogen, aliphatic, aryl, heteroaliphatic, and heteroaryl; $R^1$ and $R^2$ are selected from hydrogen, aliphatic, aryl, aryl aliphatic, and a heteroatom-containing moiety, or $R^2$ is selected from a heteroatom-containing functional group; $R^3$ is a heteroatom-containing functional group; $R^4$ is selected from any natural or non-natural nucleobase; $R^5$ is selected from an intercalator suitable for intercalating within a nucleic acid; and "optional linker" is selected from linkers comprising alkyl linkers, amide linkers, carbamate linkers, carbonate linkers, urea linkers, and combinations thereof;

a second monomer having a formula

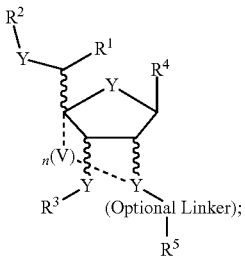

wherein Y, $R^1$, $R^2$ $R^3$, $R^4$, $R^5$, and "optional linker" are as stated for the first monomer; V is selected from carbon, oxygen, sulfur, and $NR^b$; and n ranges from 0 to 4; wherein the first monomer is positioned in a first strand of the double stranded probe and the second monomer is positioned in a second strand of the double stranded probe; at least one natural nucleotide, unnatural nucleotide, and combinations thereof; wherein the probe has a sequence selected from any one of SEQ ID Nos. 5-10, 12-33, 38-65, 72-85, 94-105, 112-129, 136-218, 220-239, or 246-253;

exposing a single stranded or double stranded nucleic acid target to the probe; and detecting the probe and/or a probe-target complex.

4. The probe according to claim 1 wherein the heteroatom-containing moiety is selected from ether ($R^aOR^b$), hydroxyl ($R^aOH$), silyl ether ($R^aR^bR^cSiOR^d$), phosphine ($PR^aR^bR^c$), thiol ($R^aSH$), thioether/sulfide ($R^aSR^b$), disulfide ($R^aSSR^b$), isothiocyanate ($R^aNCS$), isocyanate ($R^aNCO$), amine ($NH_2$, $NHR^a$, $NR^aR^b$), amide ($R^aNR^bC(O)R^c$), ester ($R^aOC(O)R^b$), halogen (I, Br, Cl, F), carbonate ($R^aOC(O)OR^b$), carboxyl ($R^aC(O)OH$), carboxylate ($R^a\text{-}COO^-$), ester ($R^aC(O)OR^b$), ketone ($R^aC(O)R^b$), phosphate ($R^aOP(O)OH_2$), phosphoryl ($R^aP(O)(OH)_2$), sulfinyl ($R^aS(O)R^b$), sulfonyl ($R^aSO_2R^b$), carbonothioyl ($R^aC(S)R^b$ or $R^aC(S)H$), sulfino ($R^aS(O)OH$), sulfo ($R^aSO_3H$), amide ($R^aC(O)NR^bR^c$), azide ($N_3$), nitrile ($R^aCN$), isonitrile ($R^aN^+C^-$), and nitro ($R^aNO_2$); $R^a$ represents the remaining monomer structure, which is attached to the abovementioned functional groups at the position indicated for $R^1$; and $R^b$, $R^c$, and $R^d$ independently are hydrogen, aliphatic, aryl, heteroaliphatic, heteroaryl, and any combination thereof.

5. The probe according to claim 1 wherein $R^2$ and $R^3$ independently are selected from a heteroatom-containing functional group comprising phosphorous, sulfur, nitrogen, oxygen, selenium, and/or a metal.

6. The probe according to claim 1 wherein $R^2$ and $R^3$ independently are selected from a phosphate group of a natural nucleotide, non-natural nucleotide, non-nucleosidic linker, or combinations thereof.

7. The probe according to claim 1 wherein $R^2$ and $R^3$ independently have a formula

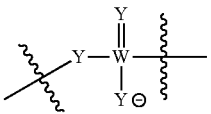

where each Y independently is selected from oxygen, sulfur, or $NR^b$ where $R^b$ is selected from hydrogen, aliphatic, aryl, heteroaliphatic, heteroaryl, and W is selected from phosphorus, SH, or SeH.

8. The probe according to claim 1 wherein $R^2$ and $R^3$ independently are

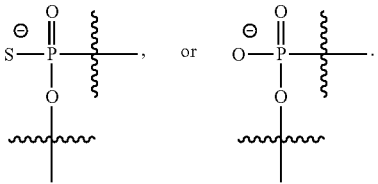 [SMILES: *OP(*)(=O)[S-] ; *OP(*)(=O)[O-]]

9. The probe according to claim 1 wherein $R^4$ is selected from adenine, guanine, cytosine, uracil, thymine, 2-thiouracil, 2,6-diaminopurine, inosine, or 3-pyrrolo-[2,3-d]-pyrimdine-2-(3H)-one.

10. The probe according to claim 1 wherein the intercalator is selected from pyrene, coronene, perylene, anthracene, naphthalene, a porphyrin, a nucleobase, a metal chelator, azapyrene, thiazole orange, ethidium, an indole, a pyrrole, or a benzimidizole.

11. The probe according to claim 1 wherein either the first monomer or the second monomer has a formula

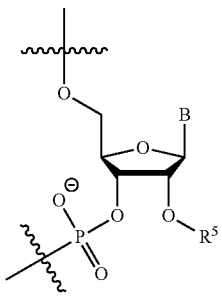

wherein B is selected from uracil, guanine, cytosine, adenine, thymine, 2-thiouracil, 2,6-diaminopurine, inosine, or 3-pyrrolo-[2,3-d]-pyrimdine-2-(3H)-one.

12. The probe according to claim 1 wherein either the first monomer or the second monomer has a formula

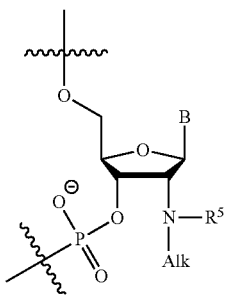

wherein B is selected from uracil, guanine, cytosine, adenine, thymine, 2-thiouracil, 2,6-diaminopurine, inosine, or 3-pyrrolo-[2,3-d]-pyrimdine-2-(3H)-one, and alk is C1-C10 alkyl.

13. The probe according to claim 1 wherein either the first monomer or the second monomer has any one of the following formulas:

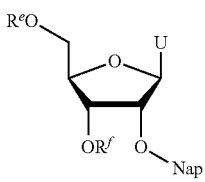 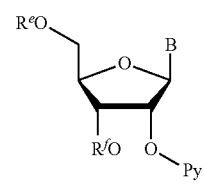

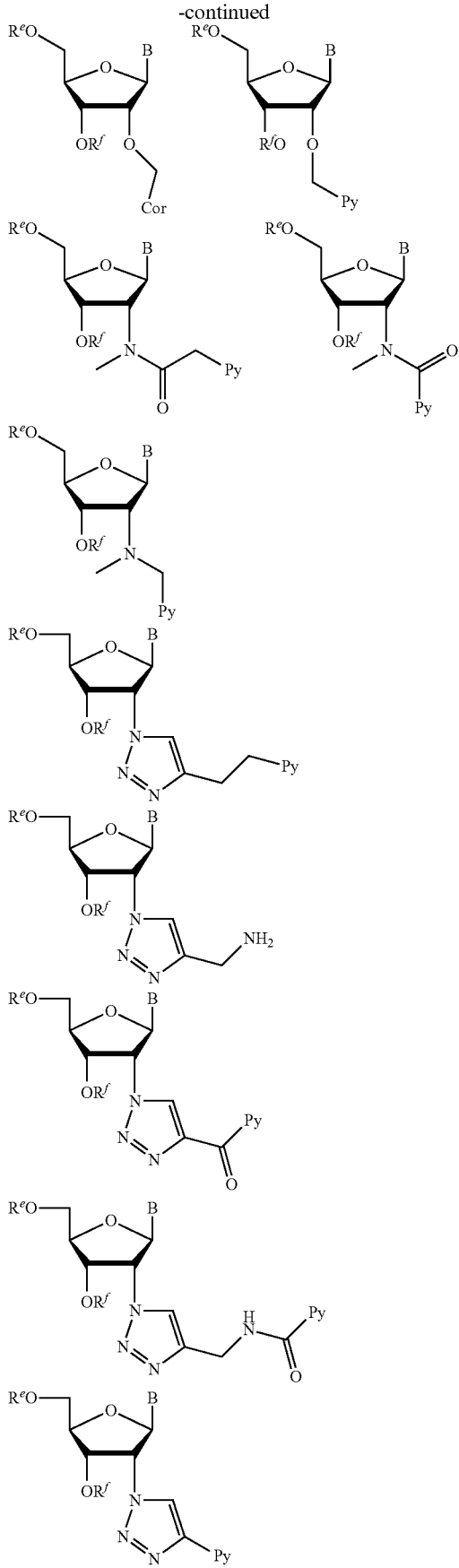

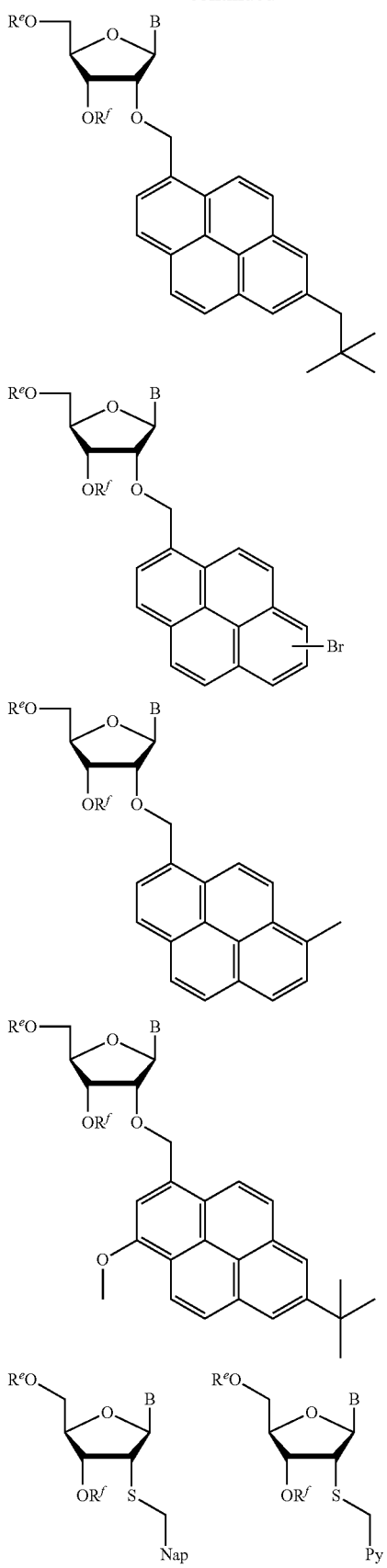

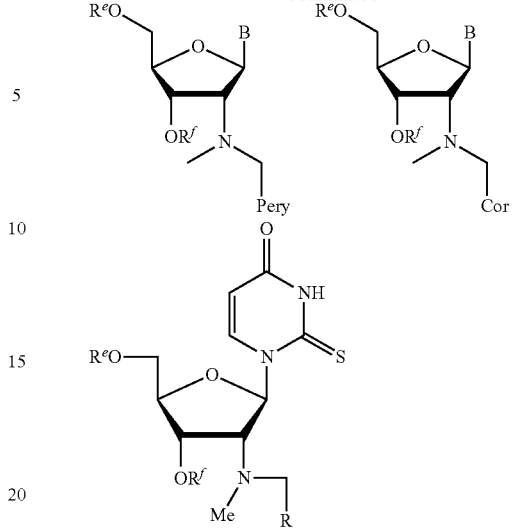

wherein B is selected from uracil, guanine, cytosine, adenine, thymine, 2-thiouracil, 2,6-diaminopurine, inosine, or 3-pyrrolo-[2,3-d]-pyrimdine-2-(3H)-one; $R^e$ is H, DMTr, or phosphate; R is peryleneyl or coronenyl; and $R^f$ is H, $(N(i-Pr)_2)P(OCH_2CH_2CN)$, or phosphate.

14. The probe according to claim 1 wherein the natural nucleotide is selected from adenine, guanine, cytosine, uracil, or thymine; and the non-natural nucleobase is selected from a C-5 functionalized pyrimidine, a C6-functionalized pyrimidine, a C7-functionalized 7-deazapurine, a C8-functionalized purine, 2,6-diaminopurine, 2-thiouracil, 4-thiouracil, deoxyinosine, or 3-(2'-deoxy-β-D-ribofuranosyl)pyrrolo-[2,3-d]-pyrimdine-2-(3H)-one.

15. The probe according to claim 1 having a formula

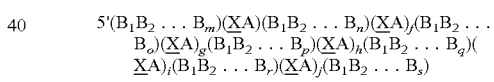

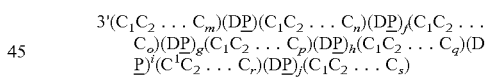

wherein $B_1$, $B_2$ and $B_{m-s}$ may be any natural, non-natural nucleotide, or a non-nucleosidic linker, wherein m-r ranges from zero to about 28; f g, h, i and j range from zero to 10; X is the first monomer; A is the complement Watson-Crick base pairing nucleotide of P; C is any natural or non-natural nucleotide capable of Watson-Crick base pairing with any one of $B_1$, $B_2$ and $B_{m-s}$; P is the second monomer, and D is the complement Watson-Crick base pairing nucleotide of X.

16. The probe according to claim 1 wherein the probe is selected to recognize a predetermined sequence of a single-stranded or double-stranded nucleic acid target.

17. The probe according to claim 2 comprising one or more bulge monomers selected from

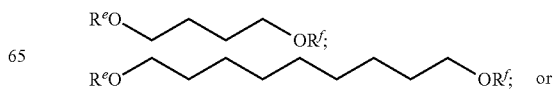

-continued

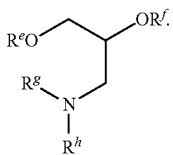

wherein $R^e$ is selected from H, DMTr, or phosphate; $R^f$ is selected from H, $(N(i\text{-}Pr)_2)P(OCH_2CH_2CN)$, or phosphate; and $R^g$ and $R^h$ independently selected from hydrogen, aliphatic, particularly alkyl, such as C1-C10 alkyl, cyclic, heterocyclic, aromatic, heteroaromatic, amides, and carbamates.

18. The probe according to claim 1 wherein the first monomer and the second monomer are arranged in a +n or −n zipper orientation, wherein n ranges from 0 to about 10.

19. The probe according to claim 2 further comprising a signal generating moiety capable of being detected and wherein the signal generating moiety is selected from a fluorophore, a member of a specific binding pair, a nanoparticle, or combinations thereof.

20. The probe according to claim 1 further comprising a secondary entity that facilitates cell-uptake; a quencher; a crosslinking reagent capable of forming bonds between the probe and nucleic acids, proteins, sugars, lipids or other biomolecules; a nucleic acid cargo moiety selected from single-stranded DNA, single-stranded RNA, double-stranded DNA, double-stranded RNA, plasmid, or gene; or combinations thereof.

21. The probe according to claim 1 wherein the probe is used in solution, on a solid surface, or in combination with a colloidal material.

22. The probe according to claim 1 wherein the probe is selected from any one of SEQ ID Nos. 124-126, 129, 169-179, 222-239, 252, or 253.

23. A method for associating a probe with a target, comprising:
selecting a double stranded probe comprising a pair of monomers comprising a first monomer having a formula

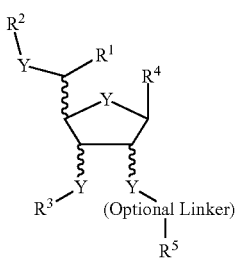

where each Y independently is selected from carbon, oxygen, sulfur, a triazole, oxazole, tetrazole, isoxazole, and $NR^b$, wherein $R^b$ is selected from hydrogen, aliphatic, aryl, heteroaliphatic, and heteroaryl; $R^1$ and $R^2$ are selected from hydrogen, aliphatic, aryl, aryl aliphatic, and a heteroatom-containing moiety, or $R^2$ is selected from a heteroatom-containing functional group; $R^3$ is a heteroatom-containing functional group; $R^4$ is selected from any natural or non-natural nucleobase; $R^5$ is selected from an intercalator suitable for intercalating within a nucleic acid; and "optional linker" is selected from linkers comprising alkyl linkers, amide linkers, carbamate linkers, carbonate linkers, urea linkers, and combinations thereof;

a second monomer having a formula

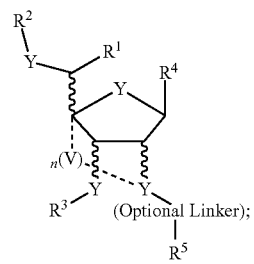

wherein Y, $R^1$, $R^2$ $R^3$, $R^4$, $R^5$, and "optional linker" are as stated for the first monomer; V is selected from carbon, oxygen, sulfur, and $NR^b$; and n ranges from 0 to 4; wherein the first monomer is positioned in a first strand of the double stranded probe and the second monomer is positioned in a second strand of the double stranded probe; at least one natural nucleotide, unnatural nucleotide, and combinations thereof; and a signal generating moiety capable of being detected and wherein the signal generating moiety is selected from a fluorophore, a member of a specific binding pair, a nanoparticle, or combinations thereof; one or more bulge monomers selected from

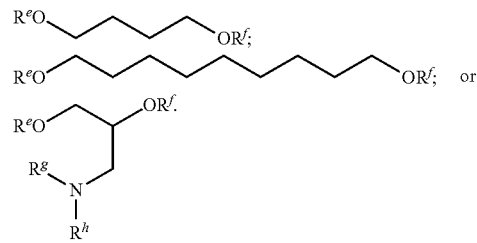

wherein $R^e$ is selected from H, DMTr, or phosphate, $R^f$ is selected from H, $(N(i\text{-}Pr)_2)P(OCH_2CH_2CN)$, or phosphate, and $R^g$ and $R^h$ independently selected from hydrogen, aliphatic, cyclic, heterocyclic, aromatic, heteroaromatic, amides, and carbamates; or a combination of the signal generating moiety and the one or more bulge monomers;

exposing a single stranded or double stranded nucleic acid target to the probe; and detecting the probe and/or a probe-target complex.

24. The method according to claim 23 wherein the first strand of the double stranded probe further comprises one or more additional first monomers and/or one or more second monomers and the second strand of the double stranded probe further comprises one or more additional second monomers.

25. The method according to claim 23 wherein the nucleic acid target comprises one or more polypurine units.

26. The method according to claim 23 wherein the nucleic acid target is a biologically-relevant, mixed-sequence hairpin nucleic acid target.

27. The method according to claim 23 wherein the nucleic acid target is isosequential with the probe.

28. The method according to claim 23 wherein the probe-target complex is detected by fluorescence spectroscopy, electrophoresis, absorption spectroscopy, flow cytometry, and combinations thereof.

29. The method according to claim 23 wherein the probe is used for gender determination in mammals selected from ungulates or ruminants.

30. The method according to claim 29 wherein the mammals are bovines, equines or porcines.

31. The method according to claim 23 wherein the target is selected from a stem of a molecular beacon; a target region embedded within PCR amplicons; a target region embedded within circular or linearized plasmids; a target region embedded within genomic DNA; a target region embedded within microorganisms; a nucleic acid sequence associated with B cell and T cell leukemias, lymphomas, breast cancer, colon cancer, and neurological cancers; a virus or other microorganism wherein the probe is used to detect and/or identify the microorganism; a genome of an oncogenic or pathogenic virus; a bacterium; an intracellular parasite selected from *Plasmodium* species, *Leishmania* (sp.), *Cryptosporidium parvum, Entamoeba histolytica, Giardia lamblia, Toxoplasma, Eimeria, Theileria*, and *Babesia*; a second insulin promoter; a PPAR gamma promoter; or a CEBP promoter.

32. A kit, comprising:
the double stranded nucleic acid probe of claim 1.

* * * * *

SEQUENCE LISTING

```
<160> NUMBER OF SEQ ID NOS: 264

<210> SEQ ID NO 1
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 1
gtgatatgct ttttttttg catatcac                                            28

<210> SEQ ID NO 2
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 2
gtgaaatgct ttttttttg catttcac                                            28

<210> SEQ ID NO 3
<211> LENGTH: 28
<212> TYPE: DNA
<213> ORGANISM: Artificial Sequence
```

```
<220> FEATURE:
<223> OTHER INFORMATION: Synthetic oligonucleotide

<400> SEQUENCE: 3
gtggtacgct tttttttttg cgtaccac                                              28

<210> SEQ ID NO 4
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 4
ggtatatata ggctttttttt tttgcctata tatacc                                    36

<210> SEQ ID NO 5
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: n is a, c, g, or t modified with monomer 120Y
<220> FEATURE:
<221> NAME/KEY: misc_feature
<222> LOCATION: (5)..(5)
<223> OTHER INFORMATION: n is a, c, g, or t modified with monomer 120Y

<400> SEQUENCE: 5
ggnanatata ggc                                                              13

<210> SEQ ID NO 6
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (8)..(8)
<223> OTHER INFORMATION: n is a, c, g, or t modified with monomer 120Y
<220> FEATURE:
<221> NAME/KEY: misc_feature
<222> LOCATION: (10)..(10)
<223> OTHER INFORMATION: n is a, c, g, or t modified with monomer 120Y

<400> SEQUENCE: 6
gcctatanan acc                                                              13

<210> SEQ ID NO 7
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (9)..(9)
<223> OTHER INFORMATION: n is a, c, g, or t modified with monomer 120Y

<400> SEQUENCE: 7
ggtatatana ggc                                                              13

<210> SEQ ID NO 8
<211> LENGTH: 13
<212> TYPE: DNA
```

<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (8)..(8)
<223> OTHER INFORMATION: n is a, c, g, or t modified with monomer 120Y

<400> SEQUENCE: 8
gcctatanat acc                                                           13

<210> SEQ ID NO 9
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (5)..(5)
<223> OTHER INFORMATION: n is a, c, g, or t modified with monomer 120Y

<400> SEQUENCE: 9
ggtanatata ggc                                                           13

<210> SEQ ID NO 10
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (4)..(4)
<223> OTHER INFORMATION: n is a, c, g, or t modified with monomer 120Y

<400> SEQUENCE: 10
gccnatatat acc                                                           13

<210> SEQ ID NO 11
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 11
ggtggtcaac tatctggatt ttttttttc cagatagttg accacc                        46

<210> SEQ ID NO 12
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: n is a, c, g, or t modified with a monomer

<400> SEQUENCE: 12
ggnatatata ggc                                                           13

<210> SEQ ID NO 13
<211> LENGTH: 13
<212> TYPE: DNA
<213> ORGANISM: Artificial Sequence
<220> FEATURE:
<223> OTHER INFORMATION: Synthetic oligonucleotide

```
<220> FEATURE:
<221> NAME/KEY: misc_feature
<222> LOCATION: (10)..(10)
<223> OTHER INFORMATION: n is a, c, g, or t modified with a monomer

<400> SEQUENCE: 13
gcctatatan acc                                                          13

<210> SEQ ID NO 14
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (5)..(5)
<223> OTHER INFORMATION: n is a, c, g, or t modified with a monomer

<400> SEQUENCE: 14
ggtanatata ggc                                                          13

<210> SEQ ID NO 15
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (8)..(8)
<223> OTHER INFORMATION: n is a, c, g, or t modified with a monomer

<400> SEQUENCE: 15
gcctatanat acc                                                          13

<210> SEQ ID NO 16
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (7)..(7)
<223> OTHER INFORMATION: n is a, c, g, or t modified with a monomer

<400> SEQUENCE: 16
ggtatanata ggc                                                          13

<210> SEQ ID NO 17
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (6)..(6)
<223> OTHER INFORMATION: n is a, c, g, or t modified with a monomer

<400> SEQUENCE: 17
gcctanatat acc                                                          13

<210> SEQ ID NO 18
<211> LENGTH: 13
<212> TYPE: DNA
<213> ORGANISM: Artificial Sequence
<220> FEATURE:
```

<223> OTHER INFORMATION: Synthetic oligonucleotide
<220> FEATURE:
<221> NAME/KEY: misc_feature
<222> LOCATION: (9)..(9)
<223> OTHER INFORMATION: n is a, c, g, or t modified with a monomer

<400> SEQUENCE: 18
ggtatatana ggc                                                              13

<210> SEQ ID NO 19
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (10)..(10)
<223> OTHER INFORMATION: n is a, c, g, or t modified with a monomer

<400> SEQUENCE: 19
gcctatatan acc                                                              13

<210> SEQ ID NO 20
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: n is a, c, g, or t modified with a monomer
<220> FEATURE:
<221> NAME/KEY: misc_feature
<222> LOCATION: (5)..(5)
<223> OTHER INFORMATION: n is a, c, g, or t modified with a monomer

<400> SEQUENCE: 20
ggnanatata ggc                                                              13

<210> SEQ ID NO 21
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (8)..(8)
<223> OTHER INFORMATION: n is a, c, g, or t modified with a monomer
<220> FEATURE:
<221> NAME/KEY: misc_feature
<222> LOCATION: (10)..(10)
<223> OTHER INFORMATION: n is a, c, g, or t modified with a monomer

<400> SEQUENCE: 21
gcctatanan acc                                                              13

<210> SEQ ID NO 22
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: n is a, c, g, or t modified with a monomer
<220> FEATURE:
<221> NAME/KEY: misc_feature

```
<222> LOCATION: (7)..(7)
<223> OTHER INFORMATION: n is a, c, g, or t modified with a monomer

<400> SEQUENCE: 22
ggnatanata ggc                                                        13

<210> SEQ ID NO 23
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (6)..(6)
<223> OTHER INFORMATION: n is a, c, g, or t modified with a monomer
<220> FEATURE:
<221> NAME/KEY: misc_feature
<222> LOCATION: (10)..(10)
<223> OTHER INFORMATION: n is a, c, g, or t modified with a monomer

<400> SEQUENCE: 23
gcctanatan acc                                                        13

<210> SEQ ID NO 24
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: n is a, c, g, or t modified with a monomer
<220> FEATURE:
<221> NAME/KEY: misc_feature
<222> LOCATION: (9)..(9)
<223> OTHER INFORMATION: n is a, c, g, or t modified with a monomer

<400> SEQUENCE: 24
ggnatatana ggc                                                        13

<210> SEQ ID NO 25
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (4)..(4)
<223> OTHER INFORMATION: n is a, c, g, or t modified with a monomer
<220> FEATURE:
<221> NAME/KEY: misc_feature
<222> LOCATION: (10)..(10)
<223> OTHER INFORMATION: n is a, c, g, or t modified with a monomer

<400> SEQUENCE: 25
gccnatatan acc                                                        13

<210> SEQ ID NO 26
<211> LENGTH: 14
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: n is a, c, g, or t modified with a monomer
<220> FEATURE:
```

<221> NAME/KEY: misc_feature
<222> LOCATION: (5)..(5)
<223> OTHER INFORMATION: n is a, c, g, or t modified with a monomer

<400> SEQUENCE: 26
ggnanataag cagc                                                                14

<210> SEQ ID NO 27
<211> LENGTH: 14
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (9)..(9)
<223> OTHER INFORMATION: n is a, c, g, or t modified with a monomer
<220> FEATURE:
<221> NAME/KEY: misc_feature
<222> LOCATION: (11)..(11)
<223> OTHER INFORMATION: n is a, c, g, or t modified with a monomer

<400> SEQUENCE: 27
gctgcttana nacc                                                                14

<210> SEQ ID NO 28
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (5)..(5)
<223> OTHER INFORMATION: n is a, c, g, or t modified with a monomer
<220> FEATURE:
<221> NAME/KEY: misc_feature
<222> LOCATION: (7)..(7)
<223> OTHER INFORMATION: n is a, c, g, or t modified with a monomer

<400> SEQUENCE: 28
ggtananata ggc                                                                 13

<210> SEQ ID NO 29
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (6)..(6)
<223> OTHER INFORMATION: n is a, c, g, or t modified with a monomer
<220> FEATURE:
<221> NAME/KEY: misc_feature
<222> LOCATION: (8)..(8)
<223> OTHER INFORMATION: n is a, c, g, or t modified with a monomer

<400> SEQUENCE: 29
gcctananat acc                                                                 13

<210> SEQ ID NO 30
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (7)..(7)
<223> OTHER INFORMATION: n is a, c, g, or t modified with a monomer -continued

```
<220> FEATURE:
<221> NAME/KEY: misc_feature
<222> LOCATION: (9)..(9)
<223> OTHER INFORMATION: n is a, c, g, or t modified with a monomer

<400> SEQUENCE: 30
ggtatanana ggc                                                              13

<210> SEQ ID NO 31
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (4)..(4)
<223> OTHER INFORMATION: n is a, c, g, or t modified with a monomer
<220> FEATURE:
<221> NAME/KEY: misc_feature
<222> LOCATION: (6)..(6)
<223> OTHER INFORMATION: n is a, c, g, or t modified with a monomer

<400> SEQUENCE: 31
gccnanatat acc                                                              13

<210> SEQ ID NO 32
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: n is a, c, g, or t modified with a monomer
<220> FEATURE:
<221> NAME/KEY: misc_feature
<222> LOCATION: (5)..(5)
<223> OTHER INFORMATION: n is a, c, g, or t modified with a monomer
<220> FEATURE:
<221> NAME/KEY: misc_feature
<222> LOCATION: (7)..(7)
<223> OTHER INFORMATION: n is a, c, g, or t modified with a monomer
<220> FEATURE:
<221> NAME/KEY: misc_feature
<222> LOCATION: (9)..(9)
<223> OTHER INFORMATION: n is a, c, g, or t modified with a monomer

<400> SEQUENCE: 32
ggnananana ggc                                                              13

<210> SEQ ID NO 33
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (4)..(4)
<223> OTHER INFORMATION: n is a, c, g, or t modified with a monomer
<220> FEATURE:
<221> NAME/KEY: misc_feature
<222> LOCATION: (6)..(6)
<223> OTHER INFORMATION: n is a, c, g, or t modified with a monomer
<220> FEATURE:
<221> NAME/KEY: misc_feature
<222> LOCATION: (8)..(8)
<223> OTHER INFORMATION: n is a, c, g, or t modified with a monomer
<220> FEATURE:
<221> NAME/KEY: misc_feature
<222> LOCATION: (10)..(10)
```

<223> OTHER INFORMATION: n is a, c, g, or t modified with a monomer

<400> SEQUENCE: 33
gccnananan acc        13

<210> SEQ ID NO 34
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 34
ggtatatata ggc        13

<210> SEQ ID NO 35
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 35
gcctatatat acc        13

<210> SEQ ID NO 36
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 36
ggtatataag cagc        14

<210> SEQ ID NO 37
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 37
gctgcttata tacc        14

<210> SEQ ID NO 38
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: n is a, c, g, or t modified with monomer 120Y

<400> SEQUENCE: 38
ggnatatata ggc        13

<210> SEQ ID NO 39
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (11)..(11)
<223> OTHER INFORMATION: n is a, c, g, or t modified with monomer 120Y

<400> SEQUENCE: 39
gcctatatat ncc                                                        13

<210> SEQ ID NO 40
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (5)..(5)
<223> OTHER INFORMATION: n is a, c, g, or t modified with monomer 120Y

<400> SEQUENCE: 40
ggtanatata ggc                                                        13

<210> SEQ ID NO 41
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (9)..(9)
<223> OTHER INFORMATION: n is a, c, g, or t modified with monomer 120Y

<400> SEQUENCE: 41
gcctatatnt acc                                                        13

<210> SEQ ID NO 42
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (7)..(7)
<223> OTHER INFORMATION: n is a, c, g, or t modified with monomer 120Y

<400> SEQUENCE: 42
ggtatanata ggc                                                        13

<210> SEQ ID NO 43
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (7)..(7)
<223> OTHER INFORMATION: n is a, c, g, or t modified with monomer 120Y

<400> SEQUENCE: 43
gcctatntat acc                                                        13

<210> SEQ ID NO 44
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:

```
<221> NAME/KEY: misc_feature
<222> LOCATION: (9)..(9)
<223> OTHER INFORMATION: n is a, c, g, or t modified with monomer 120Y

<400> SEQUENCE: 44
ggtatatana ggc                                                             13

<210> SEQ ID NO 45
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (5)..(5)
<223> OTHER INFORMATION: n is a, c, g, or t modified with monomer 120Y

<400> SEQUENCE: 45
gcctntatat acc                                                             13

<210> SEQ ID NO 46
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: n is a, c, g, or t modified with monomer 120Y
<220> FEATURE:
<221> NAME/KEY: misc_feature
<222> LOCATION: (5)..(5)
<223> OTHER INFORMATION: n is a, c, g, or t modified with monomer 120Y

<400> SEQUENCE: 46
ggnanatata ggc                                                             13

<210> SEQ ID NO 47
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (9)..(9)
<223> OTHER INFORMATION: n is a, c, g, or t modified with monomer 120Y
<220> FEATURE:
<221> NAME/KEY: misc_feature
<222> LOCATION: (11)..(11)
<223> OTHER INFORMATION: n is a, c, g, or t modified with monomer 120Y

<400> SEQUENCE: 47
gcctatatnt ncc                                                             13

<210> SEQ ID NO 48
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: n is a, c, g, or t modified with monomer 120Y
<220> FEATURE:
<221> NAME/KEY: misc_feature
<222> LOCATION: (7)..(7)
<223> OTHER INFORMATION: n is a, c, g, or t modified with monomer 120Y
```

<400> SEQUENCE: 48
ggnatanata ggc					13

<210> SEQ ID NO 49
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (7)..(7)
<223> OTHER INFORMATION: n is a, c, g, or t modified with monomer 120Y
<220> FEATURE:
<221> NAME/KEY: misc_feature
<222> LOCATION: (11)..(11)
<223> OTHER INFORMATION: n is a, c, g, or t modified with monomer 120Y

<400> SEQUENCE: 49
gcctatntat ncc					13

<210> SEQ ID NO 50
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: n is a, c, g, or t modified with monomer 120Y
<220> FEATURE:
<221> NAME/KEY: misc_feature
<222> LOCATION: (9)..(9)
<223> OTHER INFORMATION: n is a, c, g, or t modified with monomer 120Y

<400> SEQUENCE: 50
ggnatatana ggc					13

<210> SEQ ID NO 51
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (5)..(5)
<223> OTHER INFORMATION: n is a, c, g, or t modified with monomer 120Y
<220> FEATURE:
<221> NAME/KEY: misc_feature
<222> LOCATION: (11)..(11)
<223> OTHER INFORMATION: n is a, c, g, or t modified with monomer 120Y

<400> SEQUENCE: 51
gcctntatat ncc					13

<210> SEQ ID NO 52
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (5)..(5)
<223> OTHER INFORMATION: n is a, c, g, or t modified with monomer 120Y
<220> FEATURE:
<221> NAME/KEY: misc_feature
<222> LOCATION: (7)..(7)

<223> OTHER INFORMATION: n is a, c, g, or t modified with monomer 120Y

<400> SEQUENCE: 52
ggtananata ggc                                                                13

<210> SEQ ID NO 53
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (7)..(7)
<223> OTHER INFORMATION: n is a, c, g, or t modified with monomer 120Y
<220> FEATURE:
<221> NAME/KEY: misc_feature
<222> LOCATION: (9)..(9)
<223> OTHER INFORMATION: n is a, c, g, or t modified with monomer 120Y

<400> SEQUENCE: 53
gcctatntnt acc                                                                13

<210> SEQ ID NO 54
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (7)..(7)
<223> OTHER INFORMATION: n is a, c, g, or t modified with monomer 120Y
<220> FEATURE:
<221> NAME/KEY: misc_feature
<222> LOCATION: (9)..(9)
<223> OTHER INFORMATION: n is a, c, g, or t modified with monomer 120Y

<400> SEQUENCE: 54
ggtatanana ggc                                                                13

<210> SEQ ID NO 55
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (5)..(5)
<223> OTHER INFORMATION: n is a, c, g, or t modified with monomer 120Y
<220> FEATURE:
<221> NAME/KEY: misc_feature
<222> LOCATION: (7)..(7)
<223> OTHER INFORMATION: n is a, c, g, or t modified with monomer 120Y

<400> SEQUENCE: 55
gcctntntat acc                                                                13

<210> SEQ ID NO 56
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: n is a, c, g, or t modified with monomer 120Y
<220> FEATURE:
<221> NAME/KEY: misc_feature

```
<222> LOCATION: (5)..(5)
<223> OTHER INFORMATION: n is a, c, g, or t modified with monomer 120Y
<220> FEATURE:
<221> NAME/KEY: misc_feature
<222> LOCATION: (7)..(7)
<223> OTHER INFORMATION: n is a, c, g, or t modified with monomer 120Y
<220> FEATURE:
<221> NAME/KEY: misc_feature
<222> LOCATION: (9)..(9)
<223> OTHER INFORMATION: n is a, c, g, or t modified with monomer 120Y

<400> SEQUENCE: 56
ggnananana ggc                                                           13

<210> SEQ ID NO 57
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (5)..(5)
<223> OTHER INFORMATION: n is a, c, g, or t modified with monomer 120Y
<220> FEATURE:
<221> NAME/KEY: misc_feature
<222> LOCATION: (7)..(7)
<223> OTHER INFORMATION: n is a, c, g, or t modified with monomer 120Y
<220> FEATURE:
<221> NAME/KEY: misc_feature
<222> LOCATION: (9)..(9)
<223> OTHER INFORMATION: n is a, c, g, or t modified with monomer 120Y
<220> FEATURE:
<221> NAME/KEY: misc_feature
<222> LOCATION: (11)..(11)
<223> OTHER INFORMATION: n is a, c, g, or t modified with monomer 120Y

<400> SEQUENCE: 57
gcctntntnt ncc                                                           13

<210> SEQ ID NO 58
<211> LENGTH: 17
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: n is a, c, g, or t modified with monomer 120Y

<400> SEQUENCE: 58
ggnatataag cagcaca                                                       17

<210> SEQ ID NO 59
<211> LENGTH: 17
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (14)..(14)
<223> OTHER INFORMATION: n is a, c, g, or t modified with monomer 120Y

<400> SEQUENCE: 59
tgtgctgctt atanacc                                                       17

<210> SEQ ID NO 60
<211> LENGTH: 17
<212> TYPE: DNA
```

```
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: n is a, c, g, or t modified with monomer 120Y
<220> FEATURE:
<221> NAME/KEY: misc_feature
<222> LOCATION: (5)..(5)
<223> OTHER INFORMATION: n is a, c, g, or t modified with monomer 120Y

<400> SEQUENCE: 60
ggnanataag cagcaca                                                  17

<210> SEQ ID NO 61
<211> LENGTH: 17
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (12)..(12)
<223> OTHER INFORMATION: n is a, c, g, or t modified with monomer 120Y
<220> FEATURE:
<221> NAME/KEY: misc_feature
<222> LOCATION: (14)..(14)
<223> OTHER INFORMATION: n is a, c, g, or t modified with monomer 120Y

<400> SEQUENCE: 61
tgtgctgctt ananacc                                                  17

<210> SEQ ID NO 62
<211> LENGTH: 17
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (8)..(8)
<223> OTHER INFORMATION: n is a, c, g, or t modified with monomer 120Y
<220> FEATURE:
<221> NAME/KEY: misc_feature
<222> LOCATION: (10)..(10)
<223> OTHER INFORMATION: n is a, c, g, or t modified with monomer 120Y

<400> SEQUENCE: 62
aggaaggnan ataagca                                                  17

<210> SEQ ID NO 63
<211> LENGTH: 17
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (7)..(7)
<223> OTHER INFORMATION: n is a, c, g, or t modified with monomer 120Y
<220> FEATURE:
<221> NAME/KEY: misc_feature
<222> LOCATION: (9)..(9)
<223> OTHER INFORMATION: n is a, c, g, or t modified with monomer 120Y

<400> SEQUENCE: 63
tgcttanana ccttcct                                                  17

<210> SEQ ID NO 64
<211> LENGTH: 17
```

```
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: n is a, c, g, or t modified with monomer 120Y
<220> FEATURE:
<221> NAME/KEY: misc_feature
<222> LOCATION: (5)..(5)
<223> OTHER INFORMATION: n is a, c, g, or t modified with monomer 120Y

<400> SEQUENCE: 64
acnanagaat actcaag                                               17

<210> SEQ ID NO 65
<211> LENGTH: 17
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (12)..(12)
<223> OTHER INFORMATION: n is a, c, g, or t modified with monomer 120Y
<220> FEATURE:
<221> NAME/KEY: misc_feature
<222> LOCATION: (14)..(14)
<223> OTHER INFORMATION: n is a, c, g, or t modified with monomer 120Y

<400> SEQUENCE: 65
cttgagtatt cnanagt                                               17

<210> SEQ ID NO 66
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 66
ggtatataag cagcaca                                               17

<210> SEQ ID NO 67
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 67
tgtgctgctt atatacc                                               17

<210> SEQ ID NO 68
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 68
aggaaggtat ataagca                                               17

<210> SEQ ID NO 69
<211> LENGTH: 17
<212> TYPE: DNA
<213> ORGANISM: Artificial Sequence
<220> FEATURE:
```

<223> OTHER INFORMATION: Synthetic oligonucleotide

<400> SEQUENCE: 69
tgcttatata ccttcct        17

<210> SEQ ID NO 70
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 70
actatagaat actcaag        17

<210> SEQ ID NO 71
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 71
cttgagtatt ctatagt        17

<210> SEQ ID NO 72
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: n is a, c, g, or t modified with monomer 140'X
<220> FEATURE:
<221> NAME/KEY: misc_feature
<222> LOCATION: (8)..(8)
<223> OTHER INFORMATION: n is a, c, g, or t modified with monomer 120Y

<400> SEQUENCE: 72
ccnacgtnag cagtt        15

<210> SEQ ID NO 73
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (7)..(7)
<223> OTHER INFORMATION: n is a, c, g, or t modified with monomer 120Y
<220> FEATURE:
<221> NAME/KEY: misc_feature
<222> LOCATION: (12)..(12)
<223> OTHER INFORMATION: n is a, c, g, or t modified with monomer 120Y

<400> SEQUENCE: 73
aactgcnaac gnggg        15

<210> SEQ ID NO 74
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature

```
<222> LOCATION: (8)..(8)
<223> OTHER INFORMATION: n is a, c, g, or t modified with monomer 120Y
<220> FEATURE:
<221> NAME/KEY: misc_feature
<222> LOCATION: (11)..(11)
<223> OTHER INFORMATION: n is a, c, g, or t modified with monomer 140'X

<400> SEQUENCE: 74
cccacgtnag nagtt                                                          15

<210> SEQ ID NO 75
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (4)..(4)
<223> OTHER INFORMATION: n is a, c, g, or t modified with monomer 120Y
<220> FEATURE:
<221> NAME/KEY: misc_feature
<222> LOCATION: (7)..(7)
<223> OTHER INFORMATION: n is a, c, g, or t modified with monomer 120Y

<400> SEQUENCE: 75
aacngcnaac gtggg                                                          15

<210> SEQ ID NO 76
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (9)..(9)
<223> OTHER INFORMATION: n is a, c, g, or t modified with monomer 140'X
<220> FEATURE:
<221> NAME/KEY: misc_feature
<222> LOCATION: (12)..(12)
<223> OTHER INFORMATION: n is a, c, g, or t modified with monomer 140'X

<400> SEQUENCE: 76
agacaaaana cnagt                                                          15

<210> SEQ ID NO 77
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: n is a, c, g, or t modified with monomer 120Y
<220> FEATURE:
<221> NAME/KEY: misc_feature
<222> LOCATION: (6)..(6)
<223> OTHER INFORMATION: n is a, c, g, or t modified with monomer 120Y

<400> SEQUENCE: 77
acnggngttt tgtct                                                          15

<210> SEQ ID NO 78
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
```

```
<221> NAME/KEY: misc_feature
<222> LOCATION: (4)..(4)
<223> OTHER INFORMATION: n is a, c, g, or t modified with monomer 140'X
<220> FEATURE:
<221> NAME/KEY: misc_feature
<222> LOCATION: (9)..(9)
<223> OTHER INFORMATION: n is a, c, g, or t modified with monomer 140'X

<400> SEQUENCE: 78
aganaaaana ccagt                                                     15

<210> SEQ ID NO 79
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (6)..(6)
<223> OTHER INFORMATION: n is a, c, g, or t modified with monomer 120Y
<220> FEATURE:
<221> NAME/KEY: misc_feature
<222> LOCATION: (11)..(11)
<223> OTHER INFORMATION: n is a, c, g, or t modified with monomer 120Y

<400> SEQUENCE: 79
actggngttt ngtct                                                     15

<210> SEQ ID NO 80
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (4)..(4)
<223> OTHER INFORMATION: n is a, c, g, or t modified with monomer 140'X
<220> FEATURE:
<221> NAME/KEY: misc_feature
<222> LOCATION: (7)..(7)
<223> OTHER INFORMATION: n is a, c, g, or t modified with monomer 120Y

<400> SEQUENCE: 80
ctanatngtc tcgcc                                                     15

<210> SEQ ID NO 81
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (8)..(8)
<223> OTHER INFORMATION: n is a, c, g, or t modified with monomer 140'X
<220> FEATURE:
<221> NAME/KEY: misc_feature
<222> LOCATION: (11)..(11)
<223> OTHER INFORMATION: n is a, c, g, or t modified with monomer 120Y

<400> SEQUENCE: 81
ggcgaganaa ngtag                                                     15

<210> SEQ ID NO 82
<211> LENGTH: 15
<212> TYPE: DNA
<213> ORGANISM: Artificial Sequence
<220> FEATURE:
<223> OTHER INFORMATION: Synthetic oligonucleotide
```

```
<220> FEATURE:
<221> NAME/KEY: misc_feature
<222> LOCATION: (5)..(5)
<223> OTHER INFORMATION: n is a, c, g, or t modified with monomer 120'W
<220> FEATURE:
<221> NAME/KEY: misc_feature
<222> LOCATION: (7)..(7)
<223> OTHER INFORMATION: n is is a, c, g, or t modified with monomer
      120Y

<400> SEQUENCE: 82
ctacntngtc tcgcc                                                          15

<210> SEQ ID NO 83
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (8)..(8)
<223> OTHER INFORMATION: n is a, c, g, or t modified with monomer 140'X
<220> FEATURE:
<221> NAME/KEY: misc_feature
<222> LOCATION: (10)..(10)
<223> OTHER INFORMATION: n is a, c, g, or t modified with monomer 120'W

<400> SEQUENCE: 83
ggcgaganan tgtag                                                          15

<210> SEQ ID NO 84
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (4)..(4)
<223> OTHER INFORMATION: n is a, c, g, or t modified with monomer 140'X
<220> FEATURE:
<221> NAME/KEY: misc_feature
<222> LOCATION: (9)..(9)
<223> OTHER INFORMATION: n is is a, c, g, or t modified with monomer
      120Y

<400> SEQUENCE: 84
cgtnatcgng ctcgc                                                          15

<210> SEQ ID NO 85
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (6)..(6)
<223> OTHER INFORMATION: n is a, c, g, or t modified with monomer 140'X
<220> FEATURE:
<221> NAME/KEY: misc_feature
<222> LOCATION: (11)..(11)
<223> OTHER INFORMATION: n is a, c, g, or t modified with monomer 120Y

<400> SEQUENCE: 85
gcgagnacga ngacg                                                          15

<210> SEQ ID NO 86
<211> LENGTH: 15
<212> TYPE: DNA
```

```
<213> ORGANISM: Artificial Sequence
<220> FEATURE:
<223> OTHER INFORMATION: Synthetic oligonucleotide

<400> SEQUENCE: 86
cccacgttag cagtt                                                        15

<210> SEQ ID NO 87
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 87
aactgctaac gtggg                                                        15

<210> SEQ ID NO 88
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 88
agacaaaaca ccagt                                                        15

<210> SEQ ID NO 89
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 89
actggtgttt tgtct                                                        15

<210> SEQ ID NO 90
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 90
ctacattgtc tcgcc                                                        15

<210> SEQ ID NO 91
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 91
ggcgagacaa tgtag                                                        15

<210> SEQ ID NO 92
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 92
ctacattgtc tcgcc                                                        15
```

<210> SEQ ID NO 93
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 93
gcgagcacga tgacg                                                     15

<210> SEQ ID NO 94
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (10)..(10)
<223> OTHER INFORMATION: n is a, c, g, or t modified with monomer 120Y
<220> FEATURE:
<221> NAME/KEY: misc_feature
<222> LOCATION: (12)..(12)
<223> OTHER INFORMATION: n is a, c, g, or t modified with monomer 120Y

<400> SEQUENCE: 94
cggaccacgn gngtg                                                     15

<210> SEQ ID NO 95
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: n is a, c, g, or t modified with monomer 140'X
<220> FEATURE:
<221> NAME/KEY: misc_feature
<222> LOCATION: (5)..(5)
<223> OTHER INFORMATION: n is a, c, g, or t modified with monomer 140'X

<400> SEQUENCE: 95
cananacgtg gtccg                                                     15

<210> SEQ ID NO 96
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (6)..(6)
<223> OTHER INFORMATION: n is a, c, g, or t modified with monomer 140'X
<220> FEATURE:
<221> NAME/KEY: misc_feature
<222> LOCATION: (12)..(12)
<223> OTHER INFORMATION: n is a, c, g, or t modified with monomer 120Y

<400> SEQUENCE: 96
cggacnacgt gngtg                                                     15

<210> SEQ ID NO 97
<211> LENGTH: 15
<212> TYPE: DNA
<213> ORGANISM: Artificial Sequence
<220> FEATURE:

<223> OTHER INFORMATION: Synthetic oligonucleotide
<220> FEATURE:
<221> NAME/KEY: misc_feature
<222> LOCATION: (3)..(3)
<223> OTHER INFORMATION: n is a, c, g, or t modified with monomer 140'X
<220> FEATURE:
<221> NAME/KEY: misc_feature
<222> LOCATION: (9)..(9)
<223> OTHER INFORMATION: n is a, c, g, or t modified with monomer 120Y

<400> SEQUENCE: 97
canacacgng gtccg                                              15

<210> SEQ ID NO 98
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: n is a, c, g, or t modified with monomer 140'X
<220> FEATURE:
<221> NAME/KEY: misc_feature
<222> LOCATION: (6)..(6)
<223> OTHER INFORMATION: n is a, c, g, or t modified with monomer 120Y

<400> SEQUENCE: 98
gtnagngggc gttgc                                              15

<210> SEQ ID NO 99
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (9)..(9)
<223> OTHER INFORMATION: n is a, c, g, or t modified with monomer 140'X
<220> FEATURE:
<221> NAME/KEY: misc_feature
<222> LOCATION: (12)..(12)
<223> OTHER INFORMATION: n is a, c, g, or t modified with monomer 120Y

<400> SEQUENCE: 99
gcaacgccna cngac                                              15

<210> SEQ ID NO 100
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: n is a, c, g, or t modified with monomer 140'X
<220> FEATURE:
<221> NAME/KEY: misc_feature
<222> LOCATION: (6)..(6)
<223> OTHER INFORMATION: n is a, c, g, or t modified with monomer 120Y
<220> FEATURE:
<221> NAME/KEY: misc_feature
<222> LOCATION: (12)..(12)
<223> OTHER INFORMATION: n is a, c, g, or t modified with monomer 120Y

<400> SEQUENCE: 100
gtnagngggc gntgc                                              15

```
<210> SEQ ID NO 101
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: n is a, c, g, or t modified with monomer 120'W
<220> FEATURE:
<221> NAME/KEY: misc_feature
<222> LOCATION: (9)..(9)
<223> OTHER INFORMATION: n is a, c, g, or t modified with monomer 140'X
<220> FEATURE:
<221> NAME/KEY: misc_feature
<222> LOCATION: (12)..(12)
<223> OTHER INFORMATION: n is a, c, g, or t modified with monomer 120Y

<400> SEQUENCE: 101
gcnacgccna cngac                                                    15

<210> SEQ ID NO 102
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (5)..(5)
<223> OTHER INFORMATION: n is a, c, g, or t modified with monomer 120Y
<220> FEATURE:
<221> NAME/KEY: misc_feature
<222> LOCATION: (7)..(7)
<223> OTHER INFORMATION: n is a, c, g, or t modified with monomer 120Y

<400> SEQUENCE: 102
cctcnanaaa agcgg                                                    15

<210> SEQ ID NO 103
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (8)..(8)
<223> OTHER INFORMATION: n is a, c, g, or t modified with monomer 120Y
<220> FEATURE:
<221> NAME/KEY: misc_feature
<222> LOCATION: (10)..(10)
<223> OTHER INFORMATION: n is a, c, g, or t modified with monomer 120Y

<400> SEQUENCE: 103
ccgctttnan agagg                                                    15

<210> SEQ ID NO 104
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: n is a, c, g, or t modified with monomer 120Y
<220> FEATURE:
<221> NAME/KEY: misc_feature
<222> LOCATION: (5)..(5)
<223> OTHER INFORMATION: n is a, c, g, or t modified with monomer 120Y
<220> FEATURE:
```

```
<221> NAME/KEY: misc_feature
<222> LOCATION: (7)..(7)
<223> OTHER INFORMATION: n is a, c, g, or t modified with monomer 120Y

<400> SEQUENCE: 104
ccncnanaaa agcgg                                                        15

<210> SEQ ID NO 105
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (8)..(8)
<223> OTHER INFORMATION: n is a, c, g, or t modified with monomer 120Y
<220> FEATURE:
<221> NAME/KEY: misc_feature
<222> LOCATION: (10)..(10)
<223> OTHER INFORMATION: n is a, c, g, or t modified with monomer 120Y
<220> FEATURE:
<221> NAME/KEY: misc_feature
<222> LOCATION: (12)..(12)
<223> OTHER INFORMATION: n is a, c, g, or t modified with monomer 140'Y

<400> SEQUENCE: 105
ccgctttnan anagg                                                        15

<210> SEQ ID NO 106
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 106
cggaccacgt gtgtg                                                        15

<210> SEQ ID NO 107
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 107
cacacacgtg gtccg                                                        15

<210> SEQ ID NO 108
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 108
gtcagtgggc gttgc                                                        15

<210> SEQ ID NO 109
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 109
gcaacgccca ctgac                                                        15
```

<210> SEQ ID NO 110
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 110
cctctataaa agcgg                                                    15

<210> SEQ ID NO 111
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 111
ccgcttttat agagg                                                    15

<210> SEQ ID NO 112
<211> LENGTH: 14
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (6)..(6)
<223> OTHER INFORMATION: n is a, c, g, or t modified with monomer 120Y
<220> FEATURE:
<221> NAME/KEY: misc_feature
<222> LOCATION: (8)..(8)
<223> OTHER INFORMATION: n is a, c, g, or t modified with monomer 120Y

<400> SEQUENCE: 112
agcccngngc cctg                                                     14

<210> SEQ ID NO 113
<211> LENGTH: 14
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (6)..(6)
<223> OTHER INFORMATION: n is a, c, g, or t modified with monomer 140'X
<220> FEATURE:
<221> NAME/KEY: misc_feature
<222> LOCATION: (8)..(8)
<223> OTHER INFORMATION: n is a, c, g, or t modified with monomer 140'X

<400> SEQUENCE: 113
cagggnanag ggct                                                     14

<210> SEQ ID NO 114
<211> LENGTH: 11
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: n is a, c, g, or t modified with monomer 120Y
<220> FEATURE:
<221> NAME/KEY: misc_feature
<222> LOCATION: (5)..(5)

<223> OTHER INFORMATION: n is a, c, g, or t modified with monomer 120Y

<400> SEQUENCE: 114
ccngngccct g                                                        11

<210> SEQ ID NO 115
<211> LENGTH: 11
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (6)..(6)
<223> OTHER INFORMATION: n is a, c, g, or t modified with monomer 140'X
<220> FEATURE:
<221> NAME/KEY: misc_feature
<222> LOCATION: (8)..(8)
<223> OTHER INFORMATION: n is a, c, g, or t modified with monomer 140'X

<400> SEQUENCE: 115
cagggnanag g                                                        11

<210> SEQ ID NO 116
<211> LENGTH: 11
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: n is a, c, g, or t modified with monomer 120Y
<220> FEATURE:
<221> NAME/KEY: misc_feature
<222> LOCATION: (9)..(9)
<223> OTHER INFORMATION: n is a, c, g, or t modified with monomer 140'X

<400> SEQUENCE: 116
ccngtgccnt g                                                        11

<210> SEQ ID NO 117
<211> LENGTH: 11
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (2)..(2)
<223> OTHER INFORMATION: n is a, c, g, or t modified with monomer 120Y
<220> FEATURE:
<221> NAME/KEY: misc_feature
<222> LOCATION: (8)..(8)
<223> OTHER INFORMATION: n is a, c, g, or t modified with monomer 140'X

<400> SEQUENCE: 117
cngggcanag g                                                        11

<210> SEQ ID NO 118
<211> LENGTH: 14
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: n is a, c, g, or t modified with monomer 120'W
<220> FEATURE:
<221> NAME/KEY: misc_feature
<222> LOCATION: (6)..(6)
<223> OTHER INFORMATION: n is a, c, g, or t modified with monomer 120Y
<220> FEATURE:
<221> NAME/KEY: misc_feature
<222> LOCATION: (12)..(12)
<223> OTHER INFORMATION: n is a, c, g, or t modified with monomer 140'X

<400> SEQUENCE: 118
ngcccngtgc cntg                                                         14

<210> SEQ ID NO 119
<211> LENGTH: 14
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (2)..(2)
<223> OTHER INFORMATION: n is a, c, g, or t modified with monomer 120'W
<220> FEATURE:
<221> NAME/KEY: misc_feature
<222> LOCATION: (8)..(8)
<223> OTHER INFORMATION: n is a, c, g, or t modified with monomer 140'X
<220> FEATURE:
<221> NAME/KEY: misc_feature
<222> LOCATION: (13)..(13)
<223> OTHER INFORMATION: n is a, c, g, or t modified with monomer 140'X

<400> SEQUENCE: 119 cnggggcanag ggnt                                                        14

<210> SEQ ID NO 120
<211> LENGTH: 17
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (2)..(2)
<223> OTHER INFORMATION: n is a, c, g, or t modified with monomer 120Y
<220> FEATURE:
<221> NAME/KEY: misc_feature
<222> LOCATION: (4)..(4)
<223> OTHER INFORMATION: n is a, c, g, or t modified with monomer 120'W
<220> FEATURE:
<221> NAME/KEY: misc_feature
<222> LOCATION: (9)..(9)
<223> OTHER INFORMATION: n is a, c, g, or t modified with monomer 120Y
<220> FEATURE:
<221> NAME/KEY: misc_feature
<222> LOCATION: (11)..(11)
<223> OTHER INFORMATION: n is a, c, g, or t modified with monomer 120Y
<220> FEATURE:
<221> NAME/KEY: misc_feature
<222> LOCATION: (16)..(16)
<223> OTHER INFORMATION: n is a, c, g, or t modified with monomer 120Y

<400> SEQUENCE: 120
cngngcccng ngcccng                                                      17

<210> SEQ ID NO 121
<211> LENGTH: 17
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: n is a, c, g, or t modified with monomer 140'X
<220> FEATURE:

```
<221> NAME/KEY: misc_feature
<222> LOCATION: (6)..(6)
<223> OTHER INFORMATION: n is a, c, g, or t modified with monomer 140'X
<220> FEATURE:
<221> NAME/KEY: misc_feature
<222> LOCATION: (8)..(8)
<223> OTHER INFORMATION: n is a, c, g, or t modified with monomer 140'X
<220> FEATURE:
<221> NAME/KEY: misc_feature
<222> LOCATION: (13)..(13)
<223> OTHER INFORMATION: n is a, c, g, or t modified with monomer 140'X
<220> FEATURE:
<221> NAME/KEY: misc_feature
<222> LOCATION: (15)..(15)
<223> OTHER INFORMATION: n is a, c, g, or t modified with monomer 140'Y

<400> SEQUENCE: 121
nagggnanag ggntnag                                                    17

<210> SEQ ID NO 122
<211> LENGTH: 14
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: n is a, c, g, or t modified with monomer 120'W
<220> FEATURE:
<221> NAME/KEY: misc_feature
<222> LOCATION: (6)..(6)
<223> OTHER INFORMATION: n is a, c, g, or t modified with monomer 120Y
<220> FEATURE:
<221> NAME/KEY: misc_feature
<222> LOCATION: (8)..(8)
<223> OTHER INFORMATION: n is a, c, g, or t modified with monomer 120Y
<220> FEATURE:
<221> NAME/KEY: misc_feature
<222> LOCATION: (13)..(13)
<223> OTHER INFORMATION: n is a, c, g, or t modified with monomer 120Y

<400> SEQUENCE: 122
ngcccngngc ccng                                                       14

<210> SEQ ID NO 123
<211> LENGTH: 14
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: n is a, c, g, or t modified with monomer 140'X
<220> FEATURE:
<221> NAME/KEY: misc_feature
<222> LOCATION: (6)..(6)
<223> OTHER INFORMATION: n is a, c, g, or t modified with monomer 140'X
<220> FEATURE:
<221> NAME/KEY: misc_feature
<222> LOCATION: (8)..(8)
<223> OTHER INFORMATION: n is a, c, g, or t modified with monomer 140'X
<220> FEATURE:
<221> NAME/KEY: misc_feature
<222> LOCATION: (13)..(13)
<223> OTHER INFORMATION: n is a, c, g, or t modified with monomer 140'X

<400> SEQUENCE: 123
nagggnanag ggnt                                                       14

<210> SEQ ID NO 124
<211> LENGTH: 15
```

```
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: n is a, c, g, or t modified with monomer 120'W
<220> FEATURE:
<221> NAME/KEY: misc_feature
<222> LOCATION: (6)..(6)
<223> OTHER INFORMATION: n is a, c, g, or t modified with monomer 120Y
<220> FEATURE:
<221> NAME/KEY: misc_feature
<222> LOCATION: (10)..(10)
<223> OTHER INFORMATION: n is a, c, g, or t modified with a non-pairing
      monomer
<220> FEATURE:
<221> NAME/KEY: misc_feature
<222> LOCATION: (13)..(13)
<223> OTHER INFORMATION: n is a, c, g, or t modified with monomer 140'X

<400> SEQUENCE: 124
ngcccngtgn ccntg                                                    15

<210> SEQ ID NO 125
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (2)..(2)
<223> OTHER INFORMATION: n is a, c, g, or t modified with monomer 120'W
<220> FEATURE:
<221> NAME/KEY: misc_feature
<222> LOCATION: (6)..(6)
<223> OTHER INFORMATION: n is a, c, g, or t modified with a non-pairing
      monomer
<220> FEATURE:
<221> NAME/KEY: misc_feature
<222> LOCATION: (9)..(9)
<223> OTHER INFORMATION: n is a, c, g, or t modified with monomer 140'X
<220> FEATURE:
<221> NAME/KEY: misc_feature
<222> LOCATION: (14)..(14)
<223> OTHER INFORMATION: n is a, c, g, or t modified with monomer 140'X

<400> SEQUENCE: 125
cngggncana gggnt                                                    15

<210> SEQ ID NO 126
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: n is a, c, g, or t modified with monomer 120'W
<220> FEATURE:
<221> NAME/KEY: misc_feature
<222> LOCATION: (6)..(6)
<223> OTHER INFORMATION: n is a, c, g, or t modified with monomer 120Y
<220> FEATURE:
<221> NAME/KEY: misc_feature
<222> LOCATION: (10)..(10)
<223> OTHER INFORMATION: n is a, c, g, or t modified with a non-pairing
      monomer
<220> FEATURE:
<221> NAME/KEY: misc_feature
<222> LOCATION: (13)..(13)
<223> OTHER INFORMATION: n is a, c, g, or t modified with monomer 140'X
```

```
<400> SEQUENCE: 126
ngcccngtgn ccntg                                                     15

<210> SEQ ID NO 127
<211> LENGTH: 14
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (2)..(2)
<223> OTHER INFORMATION: n is a, c, g, or t modified with monomer 120'W
<220> FEATURE:
<221> NAME/KEY: misc_feature
<222> LOCATION: (8)..(8)
<223> OTHER INFORMATION: n is a, c, g, or t modified with monomer 140'X
<220> FEATURE:
<221> NAME/KEY: misc_feature
<222> LOCATION: (13)..(13)
<223> OTHER INFORMATION: n is a, c, g, or t modified with monomer 140'X

<400> SEQUENCE: 127
cngggcanag ggnt                                                      14

<210> SEQ ID NO 128
<211> LENGTH: 14
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: n is a, c, g, or t modified with monomer 120'W
<220> FEATURE:
<221> NAME/KEY: misc_feature
<222> LOCATION: (6)..(6)
<223> OTHER INFORMATION: n is a, c, g, or t modified with monomer 120Y
<220> FEATURE:
<221> NAME/KEY: misc_feature
<222> LOCATION: (12)..(12)
<223> OTHER INFORMATION: n is a, c, g, or t modified with monomer 140'X

<400> SEQUENCE: 128
ngcccngtgc cntg                                                      14

<210> SEQ ID NO 129
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (2)..(2)
<223> OTHER INFORMATION: n is a, c, g, or t modified with monomer 120'W
<220> FEATURE:
<221> NAME/KEY: misc_feature
<222> LOCATION: (6)..(6)
<223> OTHER INFORMATION: n is a, c, g, or t modified with a non-pairing
      monomer
<220> FEATURE:
<221> NAME/KEY: misc_feature
<222> LOCATION: (9)..(9)
<223> OTHER INFORMATION: n is a, c, g, or t modified with monomer 140'X
<220> FEATURE:
<221> NAME/KEY: misc_feature
<222> LOCATION: (14)..(14)
<223> OTHER INFORMATION: n is a, c, g, or t modified with monomer 140'X

<400> SEQUENCE: 129
```
cngggncana gggnt                                             15

<210> SEQ ID NO 130
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 130
agccctgtgc cctg                                              14

<210> SEQ ID NO 131
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 131
tcgggacacg ggac                                              14

<210> SEQ ID NO 132
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 132
cctgtgccct g                                                 11

<210> SEQ ID NO 133
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 133
ggacacggga c                                                 11

<210> SEQ ID NO 134
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 134
ctgagccctg tgccctg                                           17

<210> SEQ ID NO 135
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 135
gagtcgggac acgggac                                           17

<210> SEQ ID NO 136
<211> LENGTH: 13
<212> TYPE: DNA

```
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (10)..(10)
<223> OTHER INFORMATION: n is a, c, g, or t modified with monomer 120Y

<400> SEQUENCE: 136
gcctatatan acc                                                          13

<210> SEQ ID NO 137
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (8)..(8)
<223> OTHER INFORMATION: n is a, c, g, or t modified with monomer 120Y

<400> SEQUENCE: 137
gcctatanat acc                                                          13

<210> SEQ ID NO 138
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (6)..(6)
<223> OTHER INFORMATION: n is a, c, g, or t modified with monomer 120Y

<400> SEQUENCE: 138
gcctanatat acc                                                          13

<210> SEQ ID NO 139
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (4)..(4)
<223> OTHER INFORMATION: n is a, c, g, or t modified with monomer 120Y

<400> SEQUENCE: 139
gccnatatat acc                                                          13

<210> SEQ ID NO 140
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (8)..(8)
<223> OTHER INFORMATION: n is a, c, g, or t modified with monomer 120Y
<220> FEATURE:
<221> NAME/KEY: misc_feature
<222> LOCATION: (10)..(10)
<223> OTHER INFORMATION: n is a, c, g, or t modified with monomer 120Y

<400> SEQUENCE: 140
gcctatanan acc                                                          13
```

```
<210> SEQ ID NO 141
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (6)..(6)
<223> OTHER INFORMATION: n is a, c, g, or t modified with monomer 120Y
<220> FEATURE:
<221> NAME/KEY: misc_feature
<222> LOCATION: (10)..(10)
<223> OTHER INFORMATION: n is a, c, g, or t modified with monomer 120Y

<400> SEQUENCE: 141
gcctanatan acc                                                           13

<210> SEQ ID NO 142
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (4)..(4)
<223> OTHER INFORMATION: n is a, c, g, or t modified with monomer 120Y
<220> FEATURE:
<221> NAME/KEY: misc_feature
<222> LOCATION: (10)..(10)
<223> OTHER INFORMATION: n is a, c, g, or t modified with monomer 120Y

<400> SEQUENCE: 142
gccnatatan acc                                                           13

<210> SEQ ID NO 143
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (6)..(6)
<223> OTHER INFORMATION: n is a, c, g, or t modified with monomer 120Y
<220> FEATURE:
<221> NAME/KEY: misc_feature
<222> LOCATION: (8)..(8)
<223> OTHER INFORMATION: n is a, c, g, or t modified with monomer 120Y

<400> SEQUENCE: 143
gcctananat acc                                                           13

<210> SEQ ID NO 144
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (4)..(4)
<223> OTHER INFORMATION: n is a, c, g, or t modified with monomer 120Y
<220> FEATURE:
<221> NAME/KEY: misc_feature
<222> LOCATION: (6)..(6)
<223> OTHER INFORMATION: n is a, c, g, or t modified with monomer 120Y

<400> SEQUENCE: 144
```
gccnanatat acc                                                          13

<210> SEQ ID NO 145
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (4)..(4)
<223> OTHER INFORMATION: n is a, c, g, or t modified with monomer 120Y
<220> FEATURE:
<221> NAME/KEY: misc_feature
<222> LOCATION: (6)..(6)
<223> OTHER INFORMATION: n is a, c, g, or t modified with monomer 120Y
<220> FEATURE:
<221> NAME/KEY: misc_feature
<222> LOCATION: (8)..(8)
<223> OTHER INFORMATION: n is a, c, g, or t modified with monomer 120Y
<220> FEATURE:
<221> NAME/KEY: misc_feature
<222> LOCATION: (10)..(10)
<223> OTHER INFORMATION: n is a, c, g, or t modified with monomer 120Y

<400> SEQUENCE: 145
gccnananan acc                                                          13

<210> SEQ ID NO 146
<211> LENGTH: 17
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: n is a, c, g, or t modified with monomer 120Y

<400> SEQUENCE: 146
ggnatataag cagcaca                                                      17

<210> SEQ ID NO 147
<211> LENGTH: 17
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (14)..(14)
<223> OTHER INFORMATION: n is a, c, g, or t modified with monomer 120Y

<400> SEQUENCE: 147
tgtgctgctt atanacc                                                      17

<210> SEQ ID NO 148
<211> LENGTH: 17
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: n is a, c, g, or t modified with monomer 120Y
<220> FEATURE:
<221> NAME/KEY: misc_feature
<222> LOCATION: (5)..(5)
<223> OTHER INFORMATION: n is a, c, g, or t modified with monomer 120Y

<400> SEQUENCE: 148
ggnanataag cagcaca                                                17

<210> SEQ ID NO 149
<211> LENGTH: 17
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (12)..(12)
<223> OTHER INFORMATION: n is a, c, g, or t modified with monomer 120Y
<220> FEATURE:
<221> NAME/KEY: misc_feature
<222> LOCATION: (14)..(14)
<223> OTHER INFORMATION: n is a, c, g, or t modified with monomer 120Y

<400> SEQUENCE: 149
tgtgctgctt ananacc                                                17

<210> SEQ ID NO 150
<211> LENGTH: 17
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (8)..(8)
<223> OTHER INFORMATION: n is a, c, g, or t modified with monomer 120Y
<220> FEATURE:
<221> NAME/KEY: misc_feature
<222> LOCATION: (10)..(10)
<223> OTHER INFORMATION: n is a, c, g, or t modified with monomer 120Y

<400> SEQUENCE: 150
aggaaggnan ataagca                                                17

<210> SEQ ID NO 151
<211> LENGTH: 17
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (7)..(7)
<223> OTHER INFORMATION: n is a, c, g, or t modified with monomer 120Y
<220> FEATURE:
<221> NAME/KEY: misc_feature
<222> LOCATION: (9)..(9)
<223> OTHER INFORMATION: n is a, c, g, or t modified with monomer 120Y

<400> SEQUENCE: 151
tgcttanana ccttcct                                                17

<210> SEQ ID NO 152
<211> LENGTH: 17
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: n is a, c, g, or t modified with monomer 120Y
<220> FEATURE:
<221> NAME/KEY: misc_feature
<222> LOCATION: (5)..(5)
<223> OTHER INFORMATION: n is a, c, g, or t modified with monomer 120Y

<400> SEQUENCE: 152
acnanagaat actcaag					17

<210> SEQ ID NO 153
<211> LENGTH: 17
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (12)..(12)
<223> OTHER INFORMATION: n is a, c, g, or t modified with monomer 120Y
<220> FEATURE:
<221> NAME/KEY: misc_feature
<222> LOCATION: (14)..(14)
<223> OTHER INFORMATION: n is a, c, g, or t modified with monomer 120Y

<400> SEQUENCE: 153
cttgagtatt cnanagt					17

<210> SEQ ID NO 154
<211> LENGTH: 17
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: n is a, c, g, or t modified with monomer 120Q

<400> SEQUENCE: 154
ggnatataag cagcaca					17

<210> SEQ ID NO 155
<211> LENGTH: 17
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (14)..(14)
<223> OTHER INFORMATION: n is a, c, g, or t modified with monomer 120Q

<400> SEQUENCE: 155
tgtgctgctt atanacc					17

<210> SEQ ID NO 156
<211> LENGTH: 17
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: n is a, c, g, or t modified with monomer 120Q
<220> FEATURE:
<221> NAME/KEY: misc_feature
<222> LOCATION: (5)..(5)
<223> OTHER INFORMATION: n is a, c, g, or t modified with monomer 120Q

<400> SEQUENCE: 156
ggnanataag cagcaca					17

<210> SEQ ID NO 157
<211> LENGTH: 17

```
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (12)..(12)
<223> OTHER INFORMATION: n is a, c, g, or t modified with monomer 120Q
<220> FEATURE:
<221> NAME/KEY: misc_feature
<222> LOCATION: (14)..(14)
<223> OTHER INFORMATION: n is a, c, g, or t modified with monomer 120Q

<400> SEQUENCE: 157
tgtgctgctt ananacc                                                    17

<210> SEQ ID NO 158
<211> LENGTH: 17
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (8)..(8)
<223> OTHER INFORMATION: n is a, c, g, or t modified with monomer 120Q
<220> FEATURE:
<221> NAME/KEY: misc_feature
<222> LOCATION: (10)..(10)
<223> OTHER INFORMATION: n is a, c, g, or t modified with monomer 120Q

<400> SEQUENCE: 158
aggaaggnan ataagca                                                    17

<210> SEQ ID NO 159
<211> LENGTH: 17
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (7)..(7)
<223> OTHER INFORMATION: n is a, c, g, or t modified with monomer 120Q
<220> FEATURE:
<221> NAME/KEY: misc_feature
<222> LOCATION: (9)..(9)
<223> OTHER INFORMATION: n is a, c, g, or t modified with monomer 120Q

<400> SEQUENCE: 159
tgcttanana ccttcct                                                    17

<210> SEQ ID NO 160
<211> LENGTH: 17
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: n is a, c, g, or t modified with monomer 120Q
<220> FEATURE:
<221> NAME/KEY: misc_feature
<222> LOCATION: (5)..(5)
<223> OTHER INFORMATION: n is a, c, g, or t modified with monomer 120Q

<400> SEQUENCE: 160
acnanagaat actcaag                                                    17

<210> SEQ ID NO 161
```

```
<211> LENGTH: 17
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (12)..(12)
<223> OTHER INFORMATION: n is a, c, g, or t modified with monomer 120Q
<220> FEATURE:
<221> NAME/KEY: misc_feature
<222> LOCATION: (14)..(14)
<223> OTHER INFORMATION: n is a, c, g, or t modified with monomer 120Q

<400> SEQUENCE: 161
cttgagtatt cnanagt                                                    17

<210> SEQ ID NO 162
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: n is a, c, g, or t modified with monomer 120Q

<400> SEQUENCE: 162
ggnatatata ggc                                                        13

<210> SEQ ID NO 163
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (10)..(10)
<223> OTHER INFORMATION: n is a, c, g, or t modified with monomer 120Q

<400> SEQUENCE: 163
gcctatatan acc                                                        13

<210> SEQ ID NO 164
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: n is a, c, g, or t modified with monomer 120Q
<220> FEATURE:
<221> NAME/KEY: misc_feature
<222> LOCATION: (5)..(5)
<223> OTHER INFORMATION: n is a, c, g, or t modified with monomer 120Q

<400> SEQUENCE: 164
ggnanatata ggc                                                        13

<210> SEQ ID NO 165
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
```

<222> LOCATION: (8)..(8)
<223> OTHER INFORMATION: n is a, c, g, or t modified with monomer 120Q
<220> FEATURE:
<221> NAME/KEY: misc_feature
<222> LOCATION: (10)..(10)
<223> OTHER INFORMATION: n is a, c, g, or t modified with monomer 120Q

<400> SEQUENCE: 165
gcctatanan acc                                                        13

<210> SEQ ID NO 166
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: n is a, c, g, or t modified with monomer 120Q
<220> FEATURE:
<221> NAME/KEY: misc_feature
<222> LOCATION: (5)..(5)
<223> OTHER INFORMATION: n is a, c, g, or t modified with monomer 120Q
<220> FEATURE:
<221> NAME/KEY: misc_feature
<222> LOCATION: (7)..(7)
<223> OTHER INFORMATION: n is a, c, g, or t modified with monomer 120Q
<220> FEATURE:
<221> NAME/KEY: misc_feature
<222> LOCATION: (9)..(9)
<223> OTHER INFORMATION: n is a, c, g, or t modified with monomer 120Q

<400> SEQUENCE: 166
ggnananana ggc                                                        13

<210> SEQ ID NO 167
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (4)..(4)
<223> OTHER INFORMATION: n is a, c, g, or t modified with monomer 120Q
<220> FEATURE:
<221> NAME/KEY: misc_feature
<222> LOCATION: (6)..(6)
<223> OTHER INFORMATION: n is a, c, g, or t modified with monomer 120Q
<220> FEATURE:
<221> NAME/KEY: misc_feature
<222> LOCATION: (8)..(8)
<223> OTHER INFORMATION: n is a, c, g, or t modified with monomer 120Q
<220> FEATURE:
<221> NAME/KEY: misc_feature
<222> LOCATION: (10)..(10)
<223> OTHER INFORMATION: n is a, c, g, or t modified with monomer 120Q

<400> SEQUENCE: 167
gccnananan acc                                                        13

<210> SEQ ID NO 168
<211> LENGTH: 14
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: n is a, c, g, or t modified with monomer 402-9
<220> FEATURE:

```
<221> NAME/KEY: misc_feature
<222> LOCATION: (6)..(6)
<223> OTHER INFORMATION: n is a, c, g, or t modified with monomer 120Y
<220> FEATURE:
<221> NAME/KEY: misc_feature
<222> LOCATION: (8)..(8)
<223> OTHER INFORMATION: n is a, c, g, or t modified with monomer 120Y

<400> SEQUENCE: 168
ggntananat aggc                                                         14

<210> SEQ ID NO 169
<211> LENGTH: 14
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (6)..(6)
<223> OTHER INFORMATION: n is a, c, g, or t modified with monomer 120Y
<220> FEATURE:
<221> NAME/KEY: misc_feature
<222> LOCATION: (8)..(8)
<223> OTHER INFORMATION: n is a, c, g, or t modified with monomer 120Y
<220> FEATURE:
<221> NAME/KEY: misc_feature
<222> LOCATION: (12)..(12)
<223> OTHER INFORMATION: n is a, c, g, or t modified with monomer 402-9

<400> SEQUENCE: 169
gcctananat ancc                                                         14

<210> SEQ ID NO 170
<211> LENGTH: 14
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (5)..(5)
<223> OTHER INFORMATION: n is a, c, g, or t modified with monomer 120Y
<220> FEATURE:
<221> NAME/KEY: misc_feature
<222> LOCATION: (7)..(7)
<223> OTHER INFORMATION: n is a, c, g, or t modified with monomer 120Y
<220> FEATURE:
<221> NAME/KEY: misc_feature
<222> LOCATION: (12)..(12)
<223> OTHER INFORMATION: n is a, c, g, or t modified with monomer 402-9

<400> SEQUENCE: 170
ggtananata gngc                                                         14

<210> SEQ ID NO 171
<211> LENGTH: 14
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: n is a, c, g, or t modified with monomer 402-9
<220> FEATURE:
<221> NAME/KEY: misc_feature
<222> LOCATION: (7)..(7)
<223> OTHER INFORMATION: n is a, c, g, or t modified with monomer 120Y
<220> FEATURE:
<221> NAME/KEY: misc_feature
<222> LOCATION: (9)..(9)
<223> OTHER INFORMATION: n is a, c, g, or t modified with monomer 120Y
```

<400> SEQUENCE: 171
gcnctanana tacc                                                       14

<210> SEQ ID NO 172
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: n is a, c, g, or t modified with monomer 402-9
<220> FEATURE:
<221> NAME/KEY: misc_feature
<222> LOCATION: (6)..(6)
<223> OTHER INFORMATION: n is a, c, g, or t modified with monomer 120Y
<220> FEATURE:
<221> NAME/KEY: misc_feature
<222> LOCATION: (8)..(8)
<223> OTHER INFORMATION: n is a, c, g, or t modified with monomer 120Y
<220> FEATURE:
<221> NAME/KEY: misc_feature
<222> LOCATION: (13)..(13)
<223> OTHER INFORMATION: n is a, c, g, or t modified with monomer 402-9

<400> SEQUENCE: 172
ggntananat agngc                                                      15

<210> SEQ ID NO 173
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: n is a, c, g, or t modified with monomer 402-9
<220> FEATURE:
<221> NAME/KEY: misc_feature
<222> LOCATION: (7)..(7)
<223> OTHER INFORMATION: n is a, c, g, or t modified with monomer 120Y
<220> FEATURE:
<221> NAME/KEY: misc_feature
<222> LOCATION: (9)..(9)
<223> OTHER INFORMATION: n is a, c, g, or t modified with monomer 120Y
<220> FEATURE:
<221> NAME/KEY: misc_feature
<222> LOCATION: (13)..(13)
<223> OTHER INFORMATION: n is a, c, g, or t modified with monomer 402-9

<400> SEQUENCE: 173
gcnctanana tancc                                                      15

<210> SEQ ID NO 174
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: n is a, c, g, or t modified with monomer 120'W
<220> FEATURE:
<221> NAME/KEY: misc_feature
<222> LOCATION: (6)..(6)
<223> OTHER INFORMATION: n is a, c, g, or t modified with monomer 120Y
<220> FEATURE:
<221> NAME/KEY: misc_feature
<222> LOCATION: (10)..(10)

<223> OTHER INFORMATION: n is a, c, g, or t modified with monomer 402-9
<220> FEATURE:
<221> NAME/KEY: misc_feature
<222> LOCATION: (13)..(13)
<223> OTHER INFORMATION: n is a, c, g, or t modified with monomer 140'X

<400> SEQUENCE: 174
ngcccngtgn ccntg                                                    15

<210> SEQ ID NO 175
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (2)..(2)
<223> OTHER INFORMATION: n is a, c, g, or t modified with monomer 120'W
<220> FEATURE:
<221> NAME/KEY: misc_feature
<222> LOCATION: (6)..(6)
<223> OTHER INFORMATION: n is a, c, g, or t modified with monomer 402-9
<220> FEATURE:
<221> NAME/KEY: misc_feature
<222> LOCATION: (9)..(9)
<223> OTHER INFORMATION: n is a, c, g, or t modified with monomer 140'X
<220> FEATURE:
<221> NAME/KEY: misc_feature
<222> LOCATION: (14)..(14)
<223> OTHER INFORMATION: n is a, c, g, or t modified with monomer 140'X

<400> SEQUENCE: 175
cngggncana gggnt                                                    15

<210> SEQ ID NO 176
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (2)..(2)
<223> OTHER INFORMATION: n is a, c, g, or t modified with monomer 120'W
<220> FEATURE:
<221> NAME/KEY: misc_feature
<222> LOCATION: (7)..(7)
<223> OTHER INFORMATION: n is a, c, g, or t modified with monomer 120Y
<220> FEATURE:
<221> NAME/KEY: misc_feature
<222> LOCATION: (10)..(10)
<223> OTHER INFORMATION: n is a, c, g, or t modified with monomer 402-4
<220> FEATURE:
<221> NAME/KEY: misc_feature
<222> LOCATION: (14)..(14)
<223> OTHER INFORMATION: n is a, c, g, or t modified with monomer 140'X

<400> SEQUENCE: 176
tnggganacn gggnc                                                    15

<210> SEQ ID NO 177
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (2)..(2)
<223> OTHER INFORMATION: n is a, c, g, or t modified with monomer 120'W
<220> FEATURE:
<221> NAME/KEY: misc_feature

```
<222> LOCATION: (6)..(6)
<223> OTHER INFORMATION: n is a, c, g, or t modified with monomer 402-4
<220> FEATURE:
<221> NAME/KEY: misc_feature
<222> LOCATION: (9)..(9)
<223> OTHER INFORMATION: n is a, c, g, or t modified with monomer 140'X
<220> FEATURE:
<221> NAME/KEY: misc_feature
<222> LOCATION: (14)..(14)
<223> OTHER INFORMATION: n is a, c, g, or t modified with monomer 140'X

<400> SEQUENCE: 177
cngggncana gggnt                                                    15

<210> SEQ ID NO 178
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: n is a, c, g, or t modified with monomer 120'W
<220> FEATURE:
<221> NAME/KEY: misc_feature
<222> LOCATION: (6)..(6)
<223> OTHER INFORMATION: n is a, c, g, or t modified with monomer 120Y
<220> FEATURE:
<221> NAME/KEY: misc_feature
<222> LOCATION: (10)..(10)
<223> OTHER INFORMATION: n is a, c, g, or t modified with monomer 402-N
<220> FEATURE:
<221> NAME/KEY: misc_feature
<222> LOCATION: (13)..(13)
<223> OTHER INFORMATION: n is a, c, g, or t modified with monomer 140'X

<400> SEQUENCE: 178
ngcccngtgn ccntg                                                    15

<210> SEQ ID NO 179
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (2)..(2)
<223> OTHER INFORMATION: n is a, c, g, or t modified with monomer 120'W
<220> FEATURE:
<221> NAME/KEY: misc_feature
<222> LOCATION: (6)..(6)
<223> OTHER INFORMATION: n is a, c, g, or t modified with monomer 402-N
<220> FEATURE:
<221> NAME/KEY: misc_feature
<222> LOCATION: (9)..(9)
<223> OTHER INFORMATION: n is a, c, g, or t modified with monomer 140'X
<220> FEATURE:
<221> NAME/KEY: misc_feature
<222> LOCATION: (14)..(14)
<223> OTHER INFORMATION: n is a, c, g, or t modified with monomer 140'X

<400> SEQUENCE: 179
cngggncana gggnt                                                    15

<210> SEQ ID NO 180
<211> LENGTH: 14
<212> TYPE: DNA
<213> ORGANISM: Artificial Sequence
<220> FEATURE:
<223> OTHER INFORMATION: Synthetic oligonucleotide
<220> FEATURE:
```

```
<221> NAME/KEY: misc_feature
<222> LOCATION: (3)..(3)
<223> OTHER INFORMATION: n is a, c, g, or t modified with monomer 120Y
<220> FEATURE:
<221> NAME/KEY: misc_feature
<222> LOCATION: (5)..(5)
<223> OTHER INFORMATION: n is a, c, g, or t modified with monomer 120Y

<400> SEQUENCE: 180
ggnanataag cagc                                                        14

<210> SEQ ID NO 181
<211> LENGTH: 14
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (9)..(9)
<223> OTHER INFORMATION: n is a, c, g, or t modified with monomer 120Y
<220> FEATURE:
<221> NAME/KEY: misc_feature
<222> LOCATION: (11)..(11)
<223> OTHER INFORMATION: n is a, c, g, or t modified with monomer 120Y

<400> SEQUENCE: 181
gctgcttana nacc                                                        14

<210> SEQ ID NO 182
<211> LENGTH: 14
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: n is a, c, g, or t modified with monomer 120Y
<220> FEATURE:
<221> NAME/KEY: misc_feature
<222> LOCATION: (5)..(5)
<223> OTHER INFORMATION: n is a, c, g, or t modified with monomer 120Y

<400> SEQUENCE: 182
acnanagaat actc                                                        14

<210> SEQ ID NO 183
<211> LENGTH: 14
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (9)..(9)
<223> OTHER INFORMATION: n is a, c, g, or t modified with monomer 120Y
<220> FEATURE:
<221> NAME/KEY: misc_feature
<222> LOCATION: (11)..(11)
<223> OTHER INFORMATION: n is a, c, g, or t modified with monomer 120Y

<400> SEQUENCE: 183
gagtattcna nagt                                                        14

<210> SEQ ID NO 184
<211> LENGTH: 13
<212> TYPE: DNA
<213> ORGANISM: Artificial Sequence
<220> FEATURE:
<223> OTHER INFORMATION: Synthetic oligonucleotide
```

```
<220> FEATURE:
<221> NAME/KEY: misc_feature
<222> LOCATION: (3)..(3)
<223> OTHER INFORMATION: n is a, c, g, or t modified with monomer 120Q

<400> SEQUENCE: 184
ggnatatata ggc                                                          13

<210> SEQ ID NO 185
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (10)..(10)
<223> OTHER INFORMATION: n is a, c, g, or t modified with monomer 120Q

<400> SEQUENCE: 185
gcctatatan acc                                                          13

<210> SEQ ID NO 186
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: n is a, c, g, or t modified with monomer 120Q
<220> FEATURE:
<221> NAME/KEY: misc_feature
<222> LOCATION: (5)..(5)
<223> OTHER INFORMATION: n is a, c, g, or t modified with monomer 120Q

<400> SEQUENCE: 186
ggnanatata ggc                                                          13

<210> SEQ ID NO 187
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (8)..(8)
<223> OTHER INFORMATION: n is a, c, g, or t modified with monomer 120Q
<220> FEATURE:
<221> NAME/KEY: misc_feature
<222> LOCATION: (10)..(10)
<223> OTHER INFORMATION: n is a, c, g, or t modified with monomer 120Q

<400> SEQUENCE: 187
gcctatanan acc                                                          13

<210> SEQ ID NO 188
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (5)..(5)
<223> OTHER INFORMATION: n is a, c, g, or t modified with monomer 120Q
<220> FEATURE:
<221> NAME/KEY: misc_feature
<222> LOCATION: (7)..(7)
```

<223> OTHER INFORMATION: n is a, c, g, or t modified with monomer 120Q

<400> SEQUENCE: 188
ggtananata ggc                                                            13

<210> SEQ ID NO 189
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (6)..(6)
<223> OTHER INFORMATION: n is a, c, g, or t modified with monomer 120Q
<220> FEATURE:
<221> NAME/KEY: misc_feature
<222> LOCATION: (8)..(8)
<223> OTHER INFORMATION: n is a, c, g, or t modified with monomer 120Q

<400> SEQUENCE: 189
gcctananat acc                                                            13

<210> SEQ ID NO 190
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: n is a, c, g, or t modified with monomer 120Q
<220> FEATURE:
<221> NAME/KEY: misc_feature
<222> LOCATION: (5)..(5)
<223> OTHER INFORMATION: n is a, c, g, or t modified with monomer 120Q
<220> FEATURE:
<221> NAME/KEY: misc_feature
<222> LOCATION: (7)..(7)
<223> OTHER INFORMATION: n is a, c, g, or t modified with monomer 120Q
<220> FEATURE:
<221> NAME/KEY: misc_feature
<222> LOCATION: (9)..(9)
<223> OTHER INFORMATION: n is a, c, g, or t modified with monomer 120Q

<400> SEQUENCE: 190
ggnananana ggc                                                            13

<210> SEQ ID NO 191
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (7)..(7)
<223> OTHER INFORMATION: n is t, or t modified with monomer 122W, 122X,
      122Y or 122Z

<400> SEQUENCE: 191
cgcaaanaaa cgc                                                            13

<210> SEQ ID NO 192
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:

```
<221> NAME/KEY: misc_feature
<222> LOCATION: (7)..(7)
<223> OTHER INFORMATION: n is t, or t modified with monomer 122W, 122X,
      122Y or 122Z

<400> SEQUENCE: 192
cgcaacncaa cgc                                                        13

<210> SEQ ID NO 193
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (7)..(7)
<223> OTHER INFORMATION: n is t, or t modified with monomer 122W, 122X,
      122Y or 122Z

<400> SEQUENCE: 193
cgcaagngaa cgc                                                        13

<210> SEQ ID NO 194
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (7)..(7)
<223> OTHER INFORMATION: n is t, or t modified with monomer 122W, 122X,
      122Y or 122Z

<400> SEQUENCE: 194
cgcaatntaa cgc                                                        13

<210> SEQ ID NO 195
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (6)..(6)
<223> OTHER INFORMATION: n is a, c, g, or t modified with monomer 122W,
      122X, 122Y or 122Z

<400> SEQUENCE: 195
gcgttnattt gcg                                                        13

<210> SEQ ID NO 196
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (8)..(8)
<223> OTHER INFORMATION: n is a, c, g, or t modified with monomer 122W,
      122X, 122Y or 122Z

<400> SEQUENCE: 196
gcgtttantt gcg                                                        13

<210> SEQ ID NO 197
```

```
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (6)..(6)
<223> OTHER INFORMATION: n is a, c, g, or t modified with monomer 122W,
      122X, 122Y or 122Z
<220> FEATURE:
<221> NAME/KEY: misc_feature
<222> LOCATION: (8)..(8)
<223> OTHER INFORMATION: n is a, c, g, or t modified with monomer 122W,
      122X, 122Y or 122Z

<400> SEQUENCE: 197
gcgttnantt gcg                                                            13

<210> SEQ ID NO 198
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (7)..(7)
<223> OTHER INFORMATION: n is a, c, g, or t modified with monomer 122X,
      122Y or 122Z

<400> SEQUENCE: 198
cgcaaanaaa cgc                                                            13

<210> SEQ ID NO 199
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (7)..(7)
<223> OTHER INFORMATION: n is a, c, g, or t modified with monomer 122X,
      122Y or 122Z

<400> SEQUENCE: 199
cgcaacncaa cgc                                                            13

<210> SEQ ID NO 200
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (7)..(7)
<223> OTHER INFORMATION: n is a, c, g, or t modified with monomer 122X,
      122Y or 122Z

<400> SEQUENCE: 200
cgcaagngaa cgc                                                            13

<210> SEQ ID NO 201
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
```

```
<221> NAME/KEY: misc_feature
<222> LOCATION: (7)..(7)
<223> OTHER INFORMATION: n is a, c, g, or t modified with monomer 122X,
      122Y or 122Z

<400> SEQUENCE: 201
cgcaatntaa cgc                                                        13

<210> SEQ ID NO 202
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (6)..(6)
<223> OTHER INFORMATION: n is a, c, g, or t modified with monomer 122X

<400> SEQUENCE: 202
gcgttnattt gcg                                                        13

<210> SEQ ID NO 203
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (8)..(8)
<223> OTHER INFORMATION: n is a, c, g, or t modified with monomer 122X

<400> SEQUENCE: 203
gcgtttantt gcg                                                        13

<210> SEQ ID NO 204
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (6)..(6)
<223> OTHER INFORMATION: n is a, c, g, or t modified with monomer 122X
<220> FEATURE:
<221> NAME/KEY: misc_feature
<222> LOCATION: (8)..(8)
<223> OTHER INFORMATION: n is a, c, g, or t modified with monomer 122X

<400> SEQUENCE: 204
gcgttnantt gcg                                                        13

<210> SEQ ID NO 205
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (7)..(7)
<223> OTHER INFORMATION: n is a, c, g, or t modified with monomer 122Y

<400> SEQUENCE: 205
cgcaaanaaa cgc                                                        13

<210> SEQ ID NO 206
```

```
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (7)..(7)
<223> OTHER INFORMATION: n is a, c, g, or t modified with monomer 122Y

<400> SEQUENCE: 206
cgcaacncaa cgc                                                        13

<210> SEQ ID NO 207
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (7)..(7)
<223> OTHER INFORMATION: n is a, c, g, or t modified with monomer 122Y

<400> SEQUENCE: 207
cgcaagngaa cgc                                                        13

<210> SEQ ID NO 208
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (7)..(7)
<223> OTHER INFORMATION: n is a, c, g, or t modified with monomer 122Y

<400> SEQUENCE: 208
cgcaatntaa cgc                                                        13

<210> SEQ ID NO 209
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (6)..(6)
<223> OTHER INFORMATION: n is a, c, g, or t modified with monomer 122Y

<400> SEQUENCE: 209
gcgttnattt gcg                                                        13

<210> SEQ ID NO 210
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (8)..(8)
<223> OTHER INFORMATION: n is a, c, g, or t modified with monomer 122Y

<400> SEQUENCE: 210
gcgtttantt gcg                                                        13
```

```
<210> SEQ ID NO 211
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (6)..(6)
<223> OTHER INFORMATION: n is a, c, g, or t modified with monomer 122Y
<220> FEATURE:
<221> NAME/KEY: misc_feature
<222> LOCATION: (8)..(8)
<223> OTHER INFORMATION: n is a, c, g, or t modified with monomer 122Y

<400> SEQUENCE: 211
gcgttnantt gcg                                                          13

<210> SEQ ID NO 212
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (7)..(7)
<223> OTHER INFORMATION: n is a, c, g, or t modified with monomer 122Z

<400> SEQUENCE: 212
cgcaaanaaa cgc                                                          13

<210> SEQ ID NO 213
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (7)..(7)
<223> OTHER INFORMATION: n is a, c, g, or t modified with monomer 122Z

<400> SEQUENCE: 213
cgcaacncaa cgc                                                          13

<210> SEQ ID NO 214
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (7)..(7)
<223> OTHER INFORMATION: n is a, c, g, or t modified with monomer 122Z

<400> SEQUENCE: 214
cgcaagngaa cgc                                                          13

<210> SEQ ID NO 215
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (7)..(7)
<223> OTHER INFORMATION: n is a, c, g, or t modified with monomer 122Z
```

```
<400> SEQUENCE: 215
cgcaatntaa cgc                                                      13

<210> SEQ ID NO 216
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (6)..(6)
<223> OTHER INFORMATION: n is a, c, g, or t modified with monomer 122Z

<400> SEQUENCE: 216
gcgttnattt gcg                                                      13

<210> SEQ ID NO 217
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (8)..(8)
<223> OTHER INFORMATION: n is a, c, g, or t modified with monomer 122Z

<400> SEQUENCE: 217
gcgtttantt gcg                                                      13

<210> SEQ ID NO 218
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (6)..(6)
<223> OTHER INFORMATION: n is a, c, g, or t modified with monomer 122Z
<220> FEATURE:
<221> NAME/KEY: misc_feature
<222> LOCATION: (8)..(8)
<223> OTHER INFORMATION: n is a, c, g, or t modified with monomer 122Z

<400> SEQUENCE: 218
gcgttnantt gcg                                                      13

<210> SEQ ID NO 219
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 219
gcgtttattt gcg                                                      13

<210> SEQ ID NO 220
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: n is a, c, g, or t modified with monomer 140'X
```

```
<220> FEATURE:
<221> NAME/KEY: misc_feature
<222> LOCATION: (15)..(15)
<223> OTHER INFORMATION: n is a, c, g, or t modified with monomer 140'X

<400> SEQUENCE: 220
tcnagatagt tgacnacc                                                        18

<210> SEQ ID NO 221
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: n is a, c, g, or t modified with monomer 120Y
<220> FEATURE:
<221> NAME/KEY: misc_feature
<222> LOCATION: (15)..(15)
<223> OTHER INFORMATION: n is a, c, g, or t modified with monomer 120Y

<400> SEQUENCE: 221
ggnggtcaac tactngga                                                        18

<210> SEQ ID NO 222
<211> LENGTH: 19
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: n is a, c, g, or t modified with monomer 140'X
<220> FEATURE:
<221> NAME/KEY: misc_feature
<222> LOCATION: (10)..(10)
<223> OTHER INFORMATION: n is a, c, g, or t modified with monomer 402-9
<220> FEATURE:
<221> NAME/KEY: misc_feature
<222> LOCATION: (16)..(16)
<223> OTHER INFORMATION: n is a, c, g, or t modified with monomer 140'X

<400> SEQUENCE: 222
tcnagatagn ttgacnacc                                                       19

<210> SEQ ID NO 223
<211> LENGTH: 19
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: n is a, c, g, or t modified with monomer 120Y
<220> FEATURE:
<221> NAME/KEY: misc_feature
<222> LOCATION: (10)..(10)
<223> OTHER INFORMATION: n is a, c, g, or t modified with monomer 402-9
<220> FEATURE:
<221> NAME/KEY: misc_feature
<222> LOCATION: (16)..(16)
<223> OTHER INFORMATION: n is a, c, g, or t modified with monomer 120Y

<400> SEQUENCE: 223
ggnggtcaan ctatcngga                                                       19

<210> SEQ ID NO 224
```

```
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: n is a, c, g, or t modified with monomer 140'X
<220> FEATURE:
<221> NAME/KEY: misc_feature
<222> LOCATION: (10)..(12)
<223> OTHER INFORMATION: n is a, c, g, or t modified with monomer 402-9
<220> FEATURE:
<221> NAME/KEY: misc_feature
<222> LOCATION: (18)..(18)
<223> OTHER INFORMATION: n is a, c, g, or t modified with monomer 140'X

<400> SEQUENCE: 224
tcnagatagn nnttgacnac c                                              21

<210> SEQ ID NO 225
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: n is a, c, g, or t modified with monomer 120Y
<220> FEATURE:
<221> NAME/KEY: misc_feature
<222> LOCATION: (10)..(12)
<223> OTHER INFORMATION: n is a, c, g, or t modified with monomer 402-9
<220> FEATURE:
<221> NAME/KEY: misc_feature
<222> LOCATION: (18)..(18)
<223> OTHER INFORMATION: n is a, c, g, or t modified with monomer 120Y

<400> SEQUENCE: 225
ggnggtcaan nnctatcngg a                                              21

<210> SEQ ID NO 226
<211> LENGTH: 19
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: n is a, c, g, or t modified with monomer 140'X
<220> FEATURE:
<221> NAME/KEY: misc_feature
<222> LOCATION: (10)..(10)
<223> OTHER INFORMATION: n is a, c, g, or t modified with monomer 402-4
<220> FEATURE:
<221> NAME/KEY: misc_feature
<222> LOCATION: (16)..(16)
<223> OTHER INFORMATION: n is a, c, g, or t modified with monomer 140'X

<400> SEQUENCE: 226
tcnagatagn ttgacnacc                                                 19

<210> SEQ ID NO 227
<211> LENGTH: 19
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
```

```
<222> LOCATION: (3)..(3)
<223> OTHER INFORMATION: n is a, c, g, or t modified with monomer 120Y
<220> FEATURE:
<221> NAME/KEY: misc_feature
<222> LOCATION: (10)..(10)
<223> OTHER INFORMATION: n is a, c, g, or t modified with monomer 402-4
<220> FEATURE:
<221> NAME/KEY: misc_feature
<222> LOCATION: (16)..(16)
<223> OTHER INFORMATION: n is a, c, g, or t modified with monomer 120Y

<400> SEQUENCE: 227
ggnggtcaan ctatcngga                                                  19

<210> SEQ ID NO 228
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: n is a, c, g, or t modified with monomer 140'X
<220> FEATURE:
<221> NAME/KEY: misc_feature
<222> LOCATION: (10)..(12)
<223> OTHER INFORMATION: n is a, c, g, or t modified with monomer 402-4
<220> FEATURE:
<221> NAME/KEY: misc_feature
<222> LOCATION: (18)..(18)
<223> OTHER INFORMATION: n is a, c, g, or t modified with monomer 140'X

<400> SEQUENCE: 228
tcnagatagn nnttgacnac c                                               21

<210> SEQ ID NO 229
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: n is a, c, g, or t modified with monomer 120Y
<220> FEATURE:
<221> NAME/KEY: misc_feature
<222> LOCATION: (10)..(12)
<223> OTHER INFORMATION: n is a, c, g, or t modified with monomer 402-4
<220> FEATURE:
<221> NAME/KEY: misc_feature
<222> LOCATION: (18)..(18)
<223> OTHER INFORMATION: n is a, c, g, or t modified with monomer 120Y

<400> SEQUENCE: 229
ggnggtcaan nnctatcngg a                                               21

<210> SEQ ID NO 230
<211> LENGTH: 19
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: n is a, c, g, or t modified with monomer 140'X
<220> FEATURE:
<221> NAME/KEY: misc_feature
<222> LOCATION: (10)..(10)
<223> OTHER INFORMATION: n is a, c, g, or t modified with monomer 402-N
<220> FEATURE:
```

```
<221> NAME/KEY: misc_feature
<222> LOCATION: (16)..(16)
<223> OTHER INFORMATION: n is a, c, g, or t modified with monomer 140'X

<400> SEQUENCE: 230
tcnagatagn ttgacnacc                                              19

<210> SEQ ID NO 231
<211> LENGTH: 19
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: n is a, c, g, or t modified with monomer 120Y
<220> FEATURE:
<221> NAME/KEY: misc_feature
<222> LOCATION: (10)..(10)
<223> OTHER INFORMATION: n is a, c, g, or t modified with monomer 402-N
<220> FEATURE:
<221> NAME/KEY: misc_feature
<222> LOCATION: (16)..(16)
<223> OTHER INFORMATION: n is a, c, g, or t modified with monomer 120Y

<400> SEQUENCE: 231
ggnggtcaan ctatcngga                                              19

<210> SEQ ID NO 232
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: n is a, c, g, or t modified with monomer 140'X
<220> FEATURE:
<221> NAME/KEY: misc_feature
<222> LOCATION: (10)..(12)
<223> OTHER INFORMATION: n is a, c, g, or t modified with monomer 402-N
<220> FEATURE:
<221> NAME/KEY: misc_feature
<222> LOCATION: (18)..(18)
<223> OTHER INFORMATION: n is a, c, g, or t modified with monomer 140'X

<400> SEQUENCE: 232
tcnagatagn nnttgacnac c                                           21

<210> SEQ ID NO 233
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: n is a, c, g, or t modified with monomer 120Y
<220> FEATURE:
<221> NAME/KEY: misc_feature
<222> LOCATION: (10)..(12)
<223> OTHER INFORMATION: n is a, c, g, or t modified with monomer 402-N
<220> FEATURE:
<221> NAME/KEY: misc_feature
<222> LOCATION: (18)..(18)
<223> OTHER INFORMATION: n is a, c, g, or t modified with monomer 120Y

<400> SEQUENCE: 233
ggnggtcaan nnctatcngg a                                           21
```

<210> SEQ ID NO 234
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: n is a, c, g, or t modified with monomer 120'W
<220> FEATURE:
<221> NAME/KEY: misc_feature
<222> LOCATION: (6)..(6)
<223> OTHER INFORMATION: n is a, c, g, or t modified with monomer 120Y
<220> FEATURE:
<221> NAME/KEY: misc_feature
<222> LOCATION: (10)..(10)
<223> OTHER INFORMATION: n is a, c, g, or t modified with monomer 402-9
<220> FEATURE:
<221> NAME/KEY: misc_feature
<222> LOCATION: (13)..(13)
<223> OTHER INFORMATION: n is a, c, g, or t modified with monomer 140'X

<400> SEQUENCE: 234
ngcccngtgn ccntg                                                    15

<210> SEQ ID NO 235
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (2)..(2)
<223> OTHER INFORMATION: n is a, c, g, or t modified with monomer 120'W
<220> FEATURE:
<221> NAME/KEY: misc_feature
<222> LOCATION: (6)..(6)
<223> OTHER INFORMATION: n is a, c, g, or t modified with monomer 402-9
<220> FEATURE:
<221> NAME/KEY: misc_feature
<222> LOCATION: (9)..(9)
<223> OTHER INFORMATION: n is a, c, g, or t modified with monomer 140'X
<220> FEATURE:
<221> NAME/KEY: misc_feature
<222> LOCATION: (14)..(14)
<223> OTHER INFORMATION: n is a, c, g, or t modified with monomer 140'X

<400> SEQUENCE: 235
cngggncana gggnt                                                    15

<210> SEQ ID NO 236
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: n is a, c, g, or t modified with monomer 120'W
<220> FEATURE:
<221> NAME/KEY: misc_feature
<222> LOCATION: (6)..(6)
<223> OTHER INFORMATION: n is a, c, g, or t modified with monomer 120Y
<220> FEATURE:
<221> NAME/KEY: misc_feature
<222> LOCATION: (10)..(10)
<223> OTHER INFORMATION: n is na, c, g, or t modified with monomer 402-4
<220> FEATURE:
<221> NAME/KEY: misc_feature
<222> LOCATION: (13)..(13)

<223> OTHER INFORMATION: n is a, c, g, or t modified with monomer 140'X

<400> SEQUENCE: 236
ngcccngtgn ccntg                                                    15

<210> SEQ ID NO 237
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (2)..(2)
<223> OTHER INFORMATION: n is a, c, g, or t modified with monomer 120'W
<220> FEATURE:
<221> NAME/KEY: misc_feature
<222> LOCATION: (6)..(6)
<223> OTHER INFORMATION: n is a, c, g, or t modified with monomer 402-4
<220> FEATURE:
<221> NAME/KEY: misc_feature
<222> LOCATION: (9)..(9)
<223> OTHER INFORMATION: n is a, c, g, or t modified with monomer 140'X
<220> FEATURE:
<221> NAME/KEY: misc_feature
<222> LOCATION: (14)..(14)
<223> OTHER INFORMATION: n is a, c, g, or t modified with monomer 140'X

<400> SEQUENCE: 237
cngggncana gggnt                                                    15

<210> SEQ ID NO 238
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: n is a, c, g, or t modified with monomer 120'W
<220> FEATURE:
<221> NAME/KEY: misc_feature
<222> LOCATION: (6)..(6)
<223> OTHER INFORMATION: n is a, c, g, or t modified with monomer 120Y
<220> FEATURE:
<221> NAME/KEY: misc_feature
<222> LOCATION: (10)..(10)
<223> OTHER INFORMATION: n is a, c, g, or t modified with monomer 402-N
<220> FEATURE:
<221> NAME/KEY: misc_feature
<222> LOCATION: (13)..(13)
<223> OTHER INFORMATION: n is a, c, g, or t modified with monomer 140'X

<400> SEQUENCE: 238
ngcccngtgn ccntg                                                    15

<210> SEQ ID NO 239
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (2)..(2)
<223> OTHER INFORMATION: n is a, c, g, or t modified with monomer 120'W
<220> FEATURE:
<221> NAME/KEY: misc_feature
<222> LOCATION: (6)..(6)
<223> OTHER INFORMATION: n is a, c, g, or t modified with monomer 402-N
<220> FEATURE:
<221> NAME/KEY: misc_feature

```
<222> LOCATION: (9)..(9)
<223> OTHER INFORMATION: n is a, c, g, or t modified with monomer 140'X
<220> FEATURE:
<221> NAME/KEY: misc_feature
<222> LOCATION: (14)..(14)
<223> OTHER INFORMATION: n is a, c, g, or t modified with monomer 140'X

<400> SEQUENCE: 239
cngggncana gggnt                                                    15

<210> SEQ ID NO 240
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 240
ggtatttata ggcttttttt tttgcctata aatacc                             36

<210> SEQ ID NO 241
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 241
ggtatgtata ggcttttttt tttgcctata catacc                             36

<210> SEQ ID NO 242
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 242
ggtatctata ggcttttttt tttgcctata gatacc                             36

<210> SEQ ID NO 243
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 243
ggtatataaa ggcttttttt tttgccttta tatacc                             36

<210> SEQ ID NO 244
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 244
ggtatataga ggcttttttt tttgcctcta tatacc                             36

<210> SEQ ID NO 245
<211> LENGTH: 36
<212> TYPE: DNA
<213> ORGANISM: Artificial Sequence
<220> FEATURE:
<223> OTHER INFORMATION: Synthetic oligonucleotide
```

```
<400> SEQUENCE: 245
ggtatataca ggcttttttt tttgcctgta tatacc                                36

<210> SEQ ID NO 246
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: n is a, c, g, or t modified with monomer 120Q

<400> SEQUENCE: 246
ggnatatata ggc                                                         13

<210> SEQ ID NO 247
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (10)..(10)
<223> OTHER INFORMATION: n is a, c, g, or t modified with monomer 120Q

<400> SEQUENCE: 247
gcctatatan acc                                                         13

<210> SEQ ID NO 248
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: n is a, c, g, or t modified with monomer 120Q
<220> FEATURE:
<221> NAME/KEY: misc_feature
<222> LOCATION: (5)..(5)
<223> OTHER INFORMATION: n is a, c, g, or t modified with monomer 120Q

<400> SEQUENCE: 248
ggnanatata ggc                                                         13

<210> SEQ ID NO 249
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (8)..(8)
<223> OTHER INFORMATION: n is a, c, g, or t modified with monomer 120Q
<220> FEATURE:
<221> NAME/KEY: misc_feature
<222> LOCATION: (10)..(10)
<223> OTHER INFORMATION: n is a, c, g, or t modified with monomer 120Q

<400> SEQUENCE: 249
gcctatanan acc                                                         13

<210> SEQ ID NO 250
<211> LENGTH: 13
```

```
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: n is a, c, g, or t modified with monomer 120Q
<220> FEATURE:
<221> NAME/KEY: misc_feature
<222> LOCATION: (5)..(5)
<223> OTHER INFORMATION: n is a, c, g, or t modified with monomer 120Q
<220> FEATURE:
<221> NAME/KEY: misc_feature
<222> LOCATION: (7)..(7)
<223> OTHER INFORMATION: n is a, c, g, or t modified with monomer 120Q
<220> FEATURE:
<221> NAME/KEY: misc_feature
<222> LOCATION: (9)..(9)
<223> OTHER INFORMATION: n is a, c, g, or t modified with monomer 120Q

<400> SEQUENCE: 250
ggnananana ggc                                                      13

<210> SEQ ID NO 251
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (4)..(4)
<223> OTHER INFORMATION: n is a, c, g, or t modified with monomer 120Q
<220> FEATURE:
<221> NAME/KEY: misc_feature
<222> LOCATION: (6)..(6)
<223> OTHER INFORMATION: n is a, c, g, or t modified with monomer 120Q
<220> FEATURE:
<221> NAME/KEY: misc_feature
<222> LOCATION: (8)..(8)
<223> OTHER INFORMATION: n is a, c, g, or t modified with monomer 120Q
<220> FEATURE:
<221> NAME/KEY: misc_feature
<222> LOCATION: (10)..(10)
<223> OTHER INFORMATION: n is a, c, g, or t modified with monomer 120Q

<400> SEQUENCE: 251
gccnananan acc                                                      13

<210> SEQ ID NO 252
<211> LENGTH: 19
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: n is a, c, g, or t modified with monomer 120Y
<220> FEATURE:
<221> NAME/KEY: misc_feature
<222> LOCATION: (10)..(10)
<223> OTHER INFORMATION: n is a, c, g, or t modified with a non-pairing
      monomer
<220> FEATURE:
<221> NAME/KEY: misc_feature
<222> LOCATION: (16)..(16)
<223> OTHER INFORMATION: n is a, c, g, or t modified with monomer 120Q

<400> SEQUENCE: 252
ggnggtcaan ctatcngga                                                19
```

-continued

```
<210> SEQ ID NO 253
<211> LENGTH: 19
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: n is a, c, g, or t modified with monomer 140'X
<220> FEATURE:
<221> NAME/KEY: misc_feature
<222> LOCATION: (10)..(10)
<223> OTHER INFORMATION: n is a, c, g, or t modified with a non-pairing
      monomer
<220> FEATURE:
<221> NAME/KEY: misc_feature
<222> LOCATION: (16)..(16)
<223> OTHER INFORMATION: n is a, c, g, or t modified with monomer 140'X

<400> SEQUENCE: 253
tcnagatagn tggacnacc                                                    19

<210> SEQ ID NO 254
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (4)..(4)
<223> OTHER INFORMATION: n is a, c, g, or t modified with monomer 120Q
<220> FEATURE:
<221> NAME/KEY: misc_feature
<222> LOCATION: (6)..(6)
<223> OTHER INFORMATION: n is a, c, g, or t modified with monomer 120Q
<220> FEATURE:
<221> NAME/KEY: misc_feature
<222> LOCATION: (8)..(8)
<223> OTHER INFORMATION: n is a, c, g, or t modified with monomer 120Q
<220> FEATURE:
<221> NAME/KEY: misc_feature
<222> LOCATION: (10)..(10)
<223> OTHER INFORMATION: n is a, c, g, or t modified with monomer 120Q

<400> SEQUENCE: 254
gccnananan acc                                                          13

<210> SEQ ID NO 255
<211> LENGTH: 13
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (11)..(11)
<223> OTHER INFORMATION: n is a, c, g, or t modified with monomer 120'W

<400> SEQUENCE: 255
gcctatatat ncc                                                          13

<210> SEQ ID NO 256
<211> LENGTH: 13
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (9)..(9)
<223> OTHER INFORMATION: n is a, c, g, or t modified with monomer 120'W
```

```
<400> SEQUENCE: 256
gcctatatnt acc                                                              13

<210> SEQ ID NO 257
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (7)..(7)
<223> OTHER INFORMATION: n is a, c, g, or t modified with monomer 120'W

<400> SEQUENCE: 257
gcctatntat acc                                                              13

<210> SEQ ID NO 258
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (5)..(5)
<223> OTHER INFORMATION: n is a, c, g, or t modified with monomer 120'W

<400> SEQUENCE: 258
gcctntatat acc                                                              13

<210> SEQ ID NO 259
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (9)..(9)
<223> OTHER INFORMATION: n is a, c, g, or t modified with monomer 120'W
<220> FEATURE:
<221> NAME/KEY: misc_feature
<222> LOCATION: (11)..(11)
<223> OTHER INFORMATION: n is a, c, g, or t modified with monomer 120'W

<400> SEQUENCE: 259
gcctatatnt ncc                                                              13

<210> SEQ ID NO 260
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (7)..(7)
<223> OTHER INFORMATION: n is a, c, g, or t modified with monomer 120'W
<220> FEATURE:
<221> NAME/KEY: misc_feature
<222> LOCATION: (11)..(11)
<223> OTHER INFORMATION: n is a, c, g, or t modified with monomer 120'W

<400> SEQUENCE: 260
gcctatntat ncc                                                              13

<210> SEQ ID NO 261
```

```
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (5)..(5)
<223> OTHER INFORMATION: n is a, c, g, or t modified with monomer 120'W
<220> FEATURE:
<221> NAME/KEY: misc_feature
<222> LOCATION: (11)..(11)
<223> OTHER INFORMATION: n is a, c, g, or t modified with monomer 120'W

<400> SEQUENCE: 261
gcctntatat ncc                                                          13

<210> SEQ ID NO 262
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: Misc_feature
<222> LOCATION: (7)..(7)
<223> OTHER INFORMATION: n is a, c, g, or t modified with monomer 120'W
<220> FEATURE:
<221> NAME/KEY: Misc_feature
<222> LOCATION: (9)..(9)
<223> OTHER INFORMATION: n is a, c, g, or t modified with monomer 120'W

<400> SEQUENCE: 262
gcctatntnt acc                                                          13

<210> SEQ ID NO 263
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (5)..(5)
<223> OTHER INFORMATION: n is a, c, g, or t modified with monomer 120'W
<220> FEATURE:
<221> NAME/KEY: misc_feature
<222> LOCATION: (7)..(7)
<223> OTHER INFORMATION: n is a, c, g, or t modified with monomer 120'W

<400> SEQUENCE: 263
gcctntntat acc                                                          13

<210> SEQ ID NO 264
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (5)..(5)
<223> OTHER INFORMATION: n is a, c, g, or t modified with monomer 120'W
<220> FEATURE:
<221> NAME/KEY: misc_feature
<222> LOCATION: (7)..(7)
<223> OTHER INFORMATION: n is a, c, g, or t modified with monomer 120'W
<220> FEATURE:
<221> NAME/KEY: misc_feature
<222> LOCATION: (9)..(9)
<223> OTHER INFORMATION: n is a, c, g, or t modified with monomer 120'W
<220> FEATURE:
<221> NAME/KEY: misc_feature
```

```
<222> LOCATION: (11)..(11)
<223> OTHER INFORMATION: n is a, c, g, or t modified with monomer 120'W

<400> SEQUENCE: 264
gcctntntnt ncc                                                   13
```